United States Patent
Powers

(10) Patent No.: US 11,732,263 B2
(45) Date of Patent: Aug. 22, 2023

(54) COMPOUNDS AND METHODS FOR MODULATING PLP1

(71) Applicant: Ionis Pharmaceuticals, Inc., Carlsbad, CA (US)

(72) Inventor: Berit Elissa Powers, San Marcos, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 17/362,567

(22) Filed: Jun. 29, 2021

(65) Prior Publication Data

US 2022/0056445 A1 Feb. 24, 2022

Related U.S. Application Data

(60) Provisional application No. 63/124,476, filed on Dec. 11, 2020, provisional application No. 63/045,740, filed on Jun. 29, 2020.

(51) Int. Cl.
*C12N 15/113* (2010.01)

(52) U.S. Cl.
CPC ........ *C12N 15/113* (2013.01); *C12N 2310/11* (2013.01); *C12N 2310/315* (2013.01); *C12N 2310/322* (2013.01); *C12N 2310/3341* (2013.01); *C12N 2310/341* (2013.01)

(58) Field of Classification Search
CPC combination set(s) only.
See application file for complete search history.

(56) References Cited

U.S. PATENT DOCUMENTS

| | | | |
|---|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Camthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |

(Continued)

FOREIGN PATENT DOCUMENTS

| | | |
|---|---|---|
| WO | WO 2004/045543 | 6/2004 |
| WO | WO 2005/116204 | 12/2005 |

(Continued)

OTHER PUBLICATIONS

Lucchinetti CF, Mandler RN, McGavern D, Bruck W, Gleich G, Ransohoff RM, Trebst C, Weinshenker B, Wingerchuk D, Parisi JE, Lassmann H. A role for humoral mechanisms in the pathogenesis of Devic's neuromyelitis optica. Brain. Jul. 2002;125(Pt 7):1450-61. (Year: 2002).*

(Continued)

*Primary Examiner* — J. E. Angell
*Assistant Examiner* — Keyur A Vyas
(74) *Attorney, Agent, or Firm* — McNeill Baur PLLC

(57) ABSTRACT

Provided are compounds, methods, and pharmaceutical compositions for reducing the amount or activity of PLP1 RNA in a cell or subject, and in certain instances reducing the amount of proteolipid protein 1 in a cell or subject. Such compounds, methods, and pharmaceutical compositions are useful to ameliorate at least one symptom or hallmark of a leukodystrophy. Such symptoms and hallmarks include hypotonia, nystagmus, optic atrophy, respiratory distress, motor delays, cognitive dysfunction, speech dysfunction, spasticity, ataxia, seizures, choreiform movements, and death. Such leukodystrophies include Pelizaeus-Merzbacher disease.

61 Claims, No Drawings

Specification includes a Sequence Listing.

(56) References Cited

U.S. PATENT DOCUMENTS

| | | |
|---|---|---|
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,770,748 B2 | 8/2004 | Imanishi et al. |
| 7,015,315 B1 | 3/2006 | Cook et al. |
| 7,053,207 B2 | 5/2006 | Wengel et al. |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,655,785 B1 | 2/2010 | Bentwich |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,875,733 B2 | 1/2011 | Bhat et al. |
| 7,884,260 B2 | 2/2011 | Popko et al. |
| 7,888,497 B2 | 2/2011 | Bentwich et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,178,503 B2 | 5/2012 | Rigoutsos et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,415,106 B2 | 4/2013 | Popko et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,290,760 B2 | 3/2016 | Rajeev et al. |
| 2001/0053519 A1 | 12/2001 | Fodor et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0171570 A1 | 9/2004 | Allerson et al. |
| 2005/0130923 A1 | 6/2005 | Bhat et al. |
| 2006/0148740 A1 | 7/2006 | Platenburg |
| 2007/0031844 A1 | 2/2007 | Khvorova et al. |
| 2008/0039618 A1 | 2/2008 | Allerson et al. |
| 2010/0190837 A1 | 7/2010 | Migawa et al. |
| 2010/0197762 A1 | 8/2010 | Swayze et al. |
| 2011/0178283 A1 | 7/2011 | Rigoutsos et al. |
| 2013/0130378 A1 | 5/2013 | Manoharan et al. |
| 2014/0107330 A1 | 4/2014 | Freier et al. |
| 2015/0018540 A1 | 1/2015 | Prakash et al. |
| 2015/0184153 A1 | 7/2015 | Freier et al. |
| 2015/0191727 A1 | 7/2015 | Migawa et al. |
| 2015/0267195 A1 | 9/2015 | Seth et al. |
| 2015/0275212 A1 | 10/2015 | Albaek et al. |
| 2020/0040345 A1 | 2/2020 | Tesar et al. |

FOREIGN PATENT DOCUMENTS

| | | |
|---|---|---|
| WO | WO 2006/006948 | 1/2006 |
| WO | WO 2008/020435 | 2/2008 |
| WO | WO 2013/173637 | 11/2013 |
| WO | WO 2016/203262 | 12/2016 |
| WO | WO 2018/106782 | 6/2018 |

(56) References Cited

FOREIGN PATENT DOCUMENTS

| WO | WO 2019/156115 | 8/2019 |
|---|---|---|
| WO | WO 2022/006134 | 1/2022 |
| WO | 2022031847 A2 | 2/2022 |

OTHER PUBLICATIONS

Rangachari and Kuchroo, Using EAE to better understand principles of immune function and autoimmune pathology, 2013, J. of Autoimmunity, 45, 31-39. (Year: 2013).*
Khalaf et al. Mutation of proteolipid protein 1 gene: from severe hypomyelinating leukodystrophy to inherited spastic paraplegia, 2022, Biomedicines, 10, 1709, 1-20. (Year: 2022).*
GenBank Accession NC_000023.11 *Homo sapiens* chromosome X, GRCh38.p13 Primary Assembly (May 29, 2020) [online], [Retrieved on Oct. 5, 2021], Retrieved from the Internet: <URL: https://www.ncbi.nlm.nih.gov/nuccore/568815575?sat-48&satkey=93022424 >; nucleotides 103776824-103776805, 100% identity to SEQ ID No. 20.
GenBank Accession M95057.1 Human proteolipid protein (PLP) gene, upstream region and 5' end of exon 1 (1995) [online], (Retrieved on Oct. 4, 2021], Retrieved from the Internet: <URL: https://www.ncbi.nlm.nih.gov/nuccore/M95057.1/ >];in entirety; nucleotides 303-284, 100% complementary to SEQ ID No. 20.
International Search Report for PCT/US21/039651 dated Dec. 22, 2021.
Barrie et al., "Modulation of Rumpshaker Phenotype with Wild-Type PLP/DM20 Suggests Several Pathogenic Mechanisms" J Neurosci Res (2010) 88: 2135-2145.
Bijland et al., "An in vitro model for studying CNS white matter: functional properties and experimental approaches" F1000Research (2019) 8: 1-27.
Branch et al., "A good antisense molecule is hard to find," IIBS (1998) 23:45-50.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke et al., "Basic Principles of Antisense Therapeutics" Antisense Research and Application (1998) Chapter 1:1-50.
Crooke, St., et al., "Antisense Drug Technology" Second Edition, CRC Press (2008) Chapters 1-28.
Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.
Elitt et al., "Therapeutic suppression of proteolipid protein rescues Pelizaeus-Merzbacher Disease in mice" bioRxiv (2018) 1-52.
Elitt et al., "Suppression ofproteolipid protein rescues Pelizaeus-Merzbacher Disease" Nature (2020) 585: 397-403.
Elitt et al., "Therapeutic Suppression of proteolipid protein rescues Pelizaeus-Merzbacher Disease in mice" Poster for Keystone: From Rare to Care: Discovery, Modeling and Translation of Rare Diseases Conference (Nov. 11-14, 2018) Vienna, Austria.
Garbern et al., "The molecular pathogenesis of Pelizaeus-Merzbacher disease" Arch Neurol (1999) 56: 1210-1214.
Gautschi et al., "Activity of a novel bcl-2/bcl-xLbispecific antisense oligonucleotide against tumors of diverse histologic origins" J. Natl. Cancer Inst. (2001) 93:463-471.
Hobson et al., "Pelizaeus-Merzbacher Disease, Pelizaeus-Merzbacher-Like Disease 1, and Related Hypomyelinating Disorders" Semin Neurol (2012) 32: 62-67.
Karim et al., "PLP/DM20 Expression and Turnover in a Transgenic Mouse Model of Pelizaeus-Merzbacher Disease" GLIA (2010) 58: 1727-1738.
Lane et al., "Antisense Oligonucleotide (ASO) Approach to the Treatment of Pelizaeus-Merzbacher Disease (PMD)" Presentation for Global Leukodystrophy Initiative Conference (GLIA) (May 1-3, 2019).
Li et al., "Gene suppressing therapy for Pelizaeus-Merzbacher disease using artificial microRNA" JCI Insight (2019) 4: 1-20.
Madhavan "Modeling and Therapy for Pelizaeus-Merzbacher Disease" Presentation for American Society of Neurochemistry Annual Meeting (virtual) Jun. 27-Jul. 1, 2021.
Maher et al., "Comparative hybrid arrest by tandem antisense oligodeoxyribonucleotides or oligodeoxyribonucleoside methylpbosphonates in a cell-free system" Nucl. Acid. Res. (1988) 16(8):3341-3358.
New England Biolabs 1998/99 Catalog (cover page and pp. 121 and 284).
Osorio et al., "Concise Review: Stem Cell-Based Treatment of Pelizaeus-Merzbacher Disease" Stem Cells (2017) 35:311-315.
Powers et al., "Antisense oligonucleotides (ASOs) effeciently target glial cells and provide a novel therapeutic platform for demyelinating disorders" Presentation for Society of Neuroscience (Nov. 7, 2018).
Powers et al., "Antisense oligonucleotides (ASOs) efficiently target glial cells and provide a novel therapeutic platform for demyelinating disorders" Society for Neuroscience 48th Annual Meeting (Nov. 3-7, 2018) San Diego, CA.
Regis et al., "Restoration of the normal splicing pattern of the PLP1 gene by means of an antisense oligonucleotide directed against an exonic mutation" PLoS One (2013) 8: e73633.
Reynolds et al., "Rational siRNA design for RNA interference" Nature Biotechnology (2004) 22(3):326-330.
Sanghvi et al., "Heterocyclic Base Modifications in Nucleic Acids and Their Applications in Antisense Oligonucleotides" Antisense Research and Applications (1993) pp. 273-288.
Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.
Tantzer et al., "Morpholino Antisense Oligomers as a Potential Therapeutic Option for the Correction of Alternative Splicing in PMD, SPG2, and HEMS" Mol Ther Nucleic Acids (2018) 12: 420-432.
Taymans et al., "LRRK2 Kinase Inhibition as a Therapeutic Strategy for Parkinson's Disease, Where Do We Stand" Current Neurophannacology (2016) 14: 214-225.
Wang et al., "Epileptic Seizures and Electioencephalographic Evolution in Genetic Leukodystrophies" J Clin Neurophysiology (2001) 18: 25-32.
Wolf et al., "PLP1 Disorders" Gene Reviews (1999) 1-22.
Woolf et al., "Specificity of antisense oligonucleotides in vivo" PNAS (1992) 89: 7305-7309.
Yang et al., "Proteolipid Protein Regulates the Survival and Differentiation of Oligodendrocytes" J Nerosc (1997) 17(6): 2056-2070.

* cited by examiner

COMPOUNDS AND METHODS FOR MODULATING PLP1

SEQUENCE LISTING

The present application is being filed along with a Sequence Listing in electronic format. The Sequence Listing is provided as a file entitled BIOL0382USSEQ_ST25.txt, created on Jun. 25, 2021, which is 456 Kb in size. The information in the electronic format of the sequence listing is incorporated herein by reference in its entirety.

FIELD

Provided are compounds, methods, and pharmaceutical compositions for reducing the amount or activity of proteolipid protein 1 (PLP1) RNA in a cell or subject, and in certain instances reducing the amount of proteolipid protein 1 in a cell or subject. Such compounds, methods, and pharmaceutical compositions are useful to ameliorate at least one symptom or hallmark of a leukodystrophy. Such symptoms and hallmarks include hypotonia, nystagmus, optic atrophy, respiratory distress, motor delays, cognitive dysfunction, speech dysfunction, spasticity, ataxia, seizures, choreiform movements, and death. Such leukodystrophies include Pelizaeus-Merzbacher disease.

BACKGROUND

Pelizaeus-Merzbacher disease (PMD) is a severe and fatal childhood X-linked leukodystrophy, associated with an extensive loss or lack of myelination of the central nervous system, and is caused by duplications or sequence variations in the gene encoding proteolipid protein 1 (PLP1). Hundreds of mutations in PLP1 have been identified, and lead to a toxic gain-of-function due to PLP1 misfolding and dysmyelination (Hobson, G., 2012, Semin. Neurol. 32, 62-67; Nevin, Z. S., 2017, American J. Hum. Genetics 100, 617-634; Sima, A. A. F., et al., 2009, Acta Neuropathologica 118, 431-439). The majority of PMD cases are due to overexpression of otherwise normal PLP1 protein, as a result of duplications or triplications of PLP1 (Inoue, K., 2005, Neurogenetics 6, 1-16; Karim, S. A., 2010, Glia 58, 1727-1738). PLP1 is expressed in myelinating oligodendrocytes and oligodendrocyte progenitor cells (OPCs) in the central nervous system (CNS), where it is responsible for about 50% of the total protein content of myelin and in Schwann cells in the peripheral nervous system (PNS) (Klugman, W., et al., 1997, Neuron 18, 59-70; Harlow, D. E., et al., 2014, J. Neurosci. 34, 1333-1343; Baumann, N., et al., 2001, Physiol. Rev. 81, 871-927).

Because of the genetic heterogeneity associated with PMD, symptoms and hallmarks vary and have been grouped into two main categories: connatal and classic. The connatal form (severe/early onset) of PMD is caused by mutations in PLP1, leading to dysmyelination. This most severe form of PMD leads to mortality in early childhood, typically within the first few years of life, and presents symptoms such as nystagmus and respiratory distress, extrapyramidal signs, laryngeal stridor, feeding difficulties, optic atrophy, seizures, and extreme neonatal hypotonia. The classic form, associated with PLP1 overexpression due to PLP1 duplication or triplication, presents before the first year of age with a constellation of motor delays, hypotonia, nystagmus, and/or motor delay in early childhood, with the development of progressive spasticity, ataxia, and/or choreiform movements through adolescence and early adulthood. Other PMD phenotypes include the transitional form of PMD, associated with PLP1 overexpression or with PLP1 mutations, which combines clinical features of both the classic and connatal forms. A less severe phenotype, Spastic paraplegia type 2 (SPG2), has a later onset than classic PMD, and is associated with a mild, late-onset spasticity in the legs or assorted mild peripheral neuropathies with minimal CNS deficits. Patients with PLP1 deletions ("null" patients) have significantly milder symptoms than patients with PLP1 mutations or duplications, and can live until 40-60 years old. There are no approved therapies for PMD, with current therapy mainly being limited to palliative symptom management (Nevin, 2017; Inoue, 2005; Madry, J., et al., 2010, Neurol. Neurochir. Pol. 44, 511-515; Osorio, M. J., et al., 2017, Stem Cells 35, 311-315; Wang, P-J, et al., 2001, J. Clin. Neurophys. 18, 25-32).

Currently there is a lack of acceptable options for treating leukodystrophies such as PMD. It is therefore an object herein to provide compounds, methods, and pharmaceutical compositions for the treatment of such diseases.

SUMMARY OF THE INVENTION

Provided herein are compounds, methods and pharmaceutical compositions for reducing the amount or activity of PLP1 RNA, and in certain embodiments reducing the expression of proteolipid protein 1 in a cell or animal. In certain embodiments, the subject has a disease or disorder associated with overexpression of PLP1 or a mutation in PLP1. In certain embodiments, the subject has a leukodystrophy. In certain embodiments, the subject has Pelizaeus-Merzbacher disease. In certain embodiments, compounds useful for reducing the amount or activity of PLP1 RNA are oligomeric compounds. In certain embodiments, compounds useful for reducing the amount or activity of PLP1 RNA are modified oligonucleotides. In certain embodiments, compounds useful for decreasing expression of proteolipid protein 1 are oligomeric compounds. In certain embodiments, compounds useful for decreasing expression of proteolipid protein 1 are modified oligonucleotides.

Also provided are methods useful for ameliorating at least one symptom or hallmark of a leukodystrophy. In certain embodiments, the leukodystrophy is Pelizaeus-Merzbacher disease. In certain embodiments, the symptom or hallmark includes hypotonia, nystagmus, optic atrophy, respiratory distress, motor delays, cognitive dysfunction, speech dysfunction, spasticity, ataxia, seizures, or choreiform movements.

DETAILED DESCRIPTION OF THE INVENTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included" is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, treatises, and GenBank, ENSEMBL, and NCBI reference sequence records, are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well-known and commonly used in the art. Where permitted, all patents, applications, published applications and other publications and other data referred to throughout in the disclosure are incorporated by reference herein in their entirety.

Unless otherwise indicated, the following terms have the following meanings:

Definitions

As used herein, "2'-deoxynucleoside" means a nucleoside comprising a 2'-H(H) deoxyfuranosyl sugar moiety. In certain embodiments, a 2'-deoxynucleoside is a 2'-β-D-deoxynucleoside and comprises a 2'-β-D-deoxyribosyl sugar moiety, which has the β-D ribosyl configuration as found in naturally occurring deoxyribonucleic acids (DNA). In certain embodiments, a 2'-deoxynucleoside may comprise a modified nucleobase or may comprise an RNA nucleobase (uracil).

As used herein, "2'-MOE" means a 2'-OCH$_2$CH$_2$OCH$_3$ group in place of the 2'-OH group of a furanosyl sugar moiety. A "2'-MOE sugar moiety" means a sugar moiety with a 2'-OCH$_2$CH$_2$OCH$_3$ group in place of the 2'-OH group of a furanosyl sugar moiety. Unless otherwise indicated, a 2'-MOE sugar moiety is in the β-D-ribosyl configuration. "MOE" means O-methoxyethyl.

As used herein, "2'-MOE nucleoside" means a nucleoside comprising a 2'-MOE sugar moiety.

As used herein, "2'-OMe" means a 2'-OCH$_3$ group in place of the 2'-OH group of a furanosyl sugar moiety. A "2'-O-methyl sugar moiety" or "2'-OMe sugar moiety" means a sugar moiety with a 2'-OCH$_3$ group in place of the 2'-OH group of a furanosyl sugar moiety. Unless otherwise indicated, a 2'-OMe sugar moiety is in the β-D-ribosyl configuration.

As used herein, "2'-OMe nucleoside" means a nucleoside comprising a 2'-OMe sugar moiety.

As used herein, "2'-substituted nucleoside" means a nucleoside comprising a 2'-substituted sugar moiety. As used herein, "2'-substituted" in reference to a sugar moiety means a sugar moiety comprising at least one 2'-substituent group other than H or OH.

As used herein, "5-methyl cytosine" means a cytosine modified with a methyl group attached to the 5 position. A 5-methyl cytosine is a modified nucleobase.

As used herein, "administering" means providing a pharmaceutical agent to a subject.

As used herein, "antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound.

As used herein, "antisense compound" means an oligomeric compound capable of achieving at least one antisense activity.

As used herein, "ameliorate" in reference to a treatment means improvement in at least one symptom or hallmark relative to the same symptom or hallmark in the absence of the treatment. In certain embodiments, amelioration is the reduction in the severity or frequency of a symptom or hallmark or the delayed onset or slowing of progression in the severity or frequency of a symptom or hallmark. In certain embodiments, the symptom or hallmark is one or more of hypotonia, nystagmus, optic atrophy, respiratory distress, motor delays, cognitive dysfunction, speech dysfunction, spasticity, ataxia, seizures, choreiform movements, and death.

As used herein, "bicyclic nucleoside" or "BNA" means a nucleoside comprising a bicyclic sugar moiety.

As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the furanosyl sugar moiety is a ribosyl moiety. In certain embodiments, the bicyclic sugar moiety does not comprise a furanosyl moiety.

As used herein, "cerebrospinal fluid" or "CSF" means the fluid filling the space around the brain and spinal cord. "Artificial cerebrospinal fluid" or "aCSF" means a prepared or manufactured fluid that has certain properties of cerebrospinal fluid.

As used herein, "cleavable moiety" means a bond or group of atoms that is cleaved under physiological conditions, for example, inside a cell, an animal, or a human.

As used herein, "complementary" in reference to an oligonucleotide means that at least 70% of the nucleobases of the oligonucleotide or one or more portions thereof and the nucleobases of another nucleic acid or one or more portions thereof are capable of hydrogen bonding with one another when the nucleobase sequence of the oligonucleotide and the other nucleic acid are aligned in opposing directions. As used herein, "complementary nucleobases" means nucleobases that are capable of forming hydrogen bonds with one another. Complementary nucleobase pairs include adenine (A) and thymine (T), adenine (A) and uracil (U), cytosine (C) and guanine (G), 5-methyl cytosine ($^m$C) and guanine (G). Complementary oligonucleotides and/or target nucleic acids need not have nucleobase complementarity at each nucleoside. Rather, some mismatches are tolerated. As used herein, "fully complementary" or "100% complementary" in reference to an oligonucleotide, or a portion thereof, means that the oligonucleotide, or portion thereof, is complementary to another oligonucleotide or target nucleic acid at each nucleobase of the shorter of the two oligonucleotides, or at each nucleoside if the oligonucleotides are the same length.

As used herein, "conjugate group" means a group of atoms that is directly or indirectly attached to an oligonucleotide. Conjugate groups include a conjugate moiety and a conjugate linker that attaches the conjugate moiety to the oligonucleotide.

As used herein, "conjugate linker" means a single bond or a group of atoms comprising at least one bond that connects a conjugate moiety to an oligonucleotide.

As used herein, "conjugate moiety" means a group of atoms that is attached to an oligonucleotide via a conjugate linker.

As used herein, "contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

As used herein, "cEt" means a 4' to 2' bridge in place of the 2'OH-group of a ribosyl sugar moiety, wherein the bridge has the formula of 4'-CH(CH$_3$)—O-2', and wherein the methyl group of the bridge is in the S configuration. A "cEt sugar moiety" is a bicyclic sugar moiety with a 4' to 2' bridge in place of the 2'OH-group of a ribosyl sugar moiety, wherein the bridge has the formula of 4'-CH(CH$_3$)—O-2', and wherein the methyl group of the bridge is in the S configuration. "cEt" means constrained ethyl.

As used herein, "cEt nucleoside" means a nucleoside comprising a cEt sugar moiety.

As used herein, "chirally enriched population" means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom. Chirally enriched populations of molecules having multiple chiral centers within each molecule may contain one or more stereorandom chiral centers. In certain embodiments, the molecules are modified oligonucleotides. In certain embodiments, the molecules are compounds comprising modified oligonucleotides.

As used herein, "chirally controlled" in reference to an internucleoside linkage means chirality at that linkage is enriched for a particular stereochemical configuration.

As used herein, "deoxy region" means a region of 5-12 contiguous nucleotides, wherein at least 70% of the nucleosides are 2'-β-D-deoxynucleosides. In certain embodiments, each nucleoside is selected from a 2'-β-D-deoxynucleoside, a bicyclic nucleoside, and a 2'-substituted nucleoside. In certain embodiments, a deoxy region supports RNase H activity. In certain embodiments, a deoxy region is the gap or internal region of a gapmer.

As used herein, "gapmer" means a modified oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings" or "wing segments." In certain embodiments, the internal region is a deoxy region. The positions of the internal region or gap refer to the order of the nucleosides of the internal region and are counted starting from the 5'-end of the internal region. Unless otherwise indicated, "gapmer" refers to a sugar motif. In certain embodiments, each nucleoside of the gap is a 2'-β-D-deoxynucleoside. In certain embodiments, the gap comprises one 2'-substituted nucleoside at position 1, 2, 3, 4, or 5 of the gap, and the remainder of the nucleosides of the gap are 2'-β-D-deoxynucleosides. As used herein, the term "MOE gapmer" indicates a gapmer having a gap comprising 2'-β-D-deoxynucleosides and wings comprising 2'-MOE nucleosides. As used herein, the term "mixed wing gapmer" indicates a gapmer having wings comprising modified nucleosides comprising at least two different sugar modifications. Unless otherwise indicated, a gapmer may comprise one or more modified internucleoside linkages and/or modified nucleobases and such modifications do not necessarily follow the gapmer pattern of the sugar modifications.

As used herein, "hotspot region" is a range of nucleobases on a target nucleic acid that is amenable to oligomeric compound-mediated reduction of the amount or activity of the target nucleic acid.

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, "internucleoside linkage" means the covalent linkage between contiguous nucleosides in an oligonucleotide. As used herein, "modified internucleoside linkage" means any internucleoside linkage other than a phosphodiester internucleoside linkage. "Phosphorothioate internucleoside linkage or "PS internucleoside linkage" is a modified internucleoside linkage in which one of the non-bridging oxygen atoms of a phosphodiester internucleoside linkage is replaced with a sulfur atom.

As used herein, "leukodystrophy" means a disorder due to abnormalities in the myelin sheath of neurons.

As used herein, "linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, "non-bicyclic modified sugar moiety" means a modified sugar moiety that comprises a modification, such as a substituent, that does not form a bridge between two atoms of the sugar to form a second ring.

As used herein, "mismatch" or "non-complementary" means a nucleobase of a first oligonucleotide that is not complementary with the corresponding nucleobase of a second oligonucleotide or target nucleic acid when the first and second oligonucleotide are aligned.

As used herein, "motif" means the pattern of unmodified and/or modified sugar moieties, nucleobases, and/or internucleoside linkages, in an oligonucleotide.

As used herein, "nucleobase" means an unmodified nucleobase or a modified nucleobase. As used herein an "unmodified nucleobase" is adenine (A), thymine (T), cytosine (C), uracil (U), or guanine (G). As used herein, a "modified nucleobase" is a group of atoms other than unmodified A, T, C, U, or G capable of pairing with at least one unmodified nucleobase. A "5-methyl cytosine" is a modified nucleobase. A universal base is a modified nucleobase that can pair with any one of the five unmodified nucleobases. As used herein, "nucleobase sequence" means the order of contiguous nucleobases in a nucleic acid or oligonucleotide independent of any sugar or internucleoside linkage modification.

As used herein, "nucleoside" means a compound, or a fragment of a compound, comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase. "Linked nucleosides" are nucleosides that are connected in a contiguous sequence (i.e., no additional nucleosides are presented between those that are linked).

As used herein, "oligomeric compound" means an oligonucleotide and optionally one or more additional features, such as a conjugate group or terminal group. An oligomeric compound may be paired with a second oligomeric compound that is complementary to the first oligomeric compound or may be unpaired. A "singled-stranded oligomeric compound" is an unpaired oligomeric compound. The term "oligomeric duplex" means a duplex formed by two oligomeric compounds having complementary nucleobase sequences. Each oligomeric compound of an oligomeric duplex may be referred to as a "duplexed oligomeric compound."

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "pharmaceutically acceptable carrier or diluent" means any substance suitable for use in administering to a subject. Certain such carriers enable pharmaceutical compositions to be formulated as, for example, tablets, pills, dragees, capsules, liquids, gels, symps, slurries, suspension and lozenges for the oral ingestion by a subject. In certain embodiments, a pharmaceutically acceptable carrier or diluent is sterile water, sterile saline, sterile buffer solution or sterile artificial cerebrospinal fluid.

As used herein, "pharmaceutically acceptable salts" means physiologically and pharmaceutically acceptable salts of compounds. Pharmaceutically acceptable salts retain the desired biological activity of the parent compound and do not impart undesired toxicological effects thereto.

As used herein, "pharmaceutical composition" means a mixture of substances suitable for administering to a subject. For example, a pharmaceutical composition may comprise an oligomeric compound and a sterile aqueous solution. In certain embodiments, a pharmaceutical composition shows activity in free uptake assay in certain cell lines.

As used herein, "prodrug" means a therapeutic agent in a form outside the body that is converted to a different form within a subject or cells thereof. Typically, conversion of a prodrug within the subject is facilitated by the action of an enzymes (e.g., endogenous or viral enzyme) or chemicals present in cells or tissues and/or by physiologic conditions.

As used herein, "reducing the amount or activity" refers to a reduction or blockade of the transcriptional expression or activity relative to the transcriptional expression or activity in an untreated or control sample and does not necessarily indicate a total elimination of transcriptional expression or activity.

As used herein, "RNA" means an RNA transcript and includes pre-mRNA and mature mRNA unless otherwise specified.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense compounds that act through RNase H.

As used herein, "self-complementary" in reference to an oligonucleotide means an oligonucleotide that at least partially hybridizes to itself.

As used herein, "standard in vitro assay" means the assay described in Example 1 and reasonable variations thereof.

As used herein, "standard in vivo assay" means the assay described in Example 5 and reasonable variations thereof.

As used herein, "stereorandom chiral center" in the context of a population of molecules of identical molecular formula means a chiral center having a random stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the result of a synthetic method that is not designed to control the stereochemical configuration. In certain embodiments, a stereorandom chiral center is a stereorandom phosphorothioate internucleoside linkage.

As used herein, "subject" means a human or non-human animal. The terms "subject" and "individual" are used interchangeably.

As used herein, "sugar moiety" means an unmodified sugar moiety or a modified sugar moiety. As used herein, "unmodified sugar moiety" means a 2'-OH(H) β-D-ribosyl sugar moiety, as found in RNA (an "unmodified RNA sugar moiety"), or a 2'-H(H) β-D-deoxyribosyl sugar moiety, as found in DNA (an "unmodified DNA sugar moiety"). Unmodified sugar moieties have one hydrogen at each of the V, 3', and 4' positions, an oxygen at the 3' position, and two hydrogens at the 5' position. As used herein, "modified sugar moiety" or "modified sugar" means a modified furanosyl sugar moiety or a sugar surrogate.

As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or target nucleic acids.

As used herein, "symptom or hallmark" means any physical feature or test result that indicates the existence or extent of a disease or disorder. In certain embodiments, a symptom is apparent to a subject or to a medical professional examining or testing said subject. In certain embodiments, a hallmark is apparent upon invasive diagnostic testing, including, but not limited to, post-mortem tests. In certain embodiments, a hallmark is apparent on a brain MRI scan.

As used herein, "target nucleic acid" and "target RNA" mean a nucleic acid that an antisense compound is designed to affect. Target RNA means an RNA transcript and includes pre-mRNA and mature mRNA unless otherwise specified.

As used herein, "target region" means a portion of a target nucleic acid to which an oligomeric compound is designed to hybridize.

As used herein, "terminal group" means a chemical group or group of atoms that is covalently linked to a terminus of an oligonucleotide.

As used herein, "therapeutically effective amount" means an amount of a pharmaceutical agent that provides a therapeutic benefit to a subject. For example, a therapeutically effective amount improves a symptom or hallmark of a disease or disorder.

As used herein, "treating" means improving a subject's disease or disorder by administering an oligomeric agent or oligomeric compound described herein. In certain embodiments, treating a subject improves a symptom relative to the same symptom in the absence of the treatment. In certain embodiments, treatment reduces in the severity or frequency of a symptom, or delays the onset of a symptom, slows the progression of a symptom, or slows the severity or frequency of a symptom.

CERTAIN EMBODIMENTS

The present disclosure provides the following non-limiting numbered embodiments:

Embodiment 1. An oligomeric compound comprising a modified oligonucleotide consisting of 12 to 30 linked nucleosides wherein the nucleobase sequence of the modified oligonucleotide is at least 85% complementary to an equal length portion of a PLP1 nucleic acid, and wherein the modified oligonucleotide comprises at least one modification selected from a modified sugar moiety and a modified internucleoside linkage.

Embodiment 2. An oligomeric compound comprising a modified oligonucleotide consisting of 12 to 30 linked nucleosides and having a nucleobase sequence comprising at least 12, at least 13, at least 14, at least 15, at least 16, at least 17, at least 18, at least 19, or 20 contiguous nucleobases of any of the nucleobase sequences of SEQ ID NOs: 20-2155, wherein the modified oligonucleotide comprises at least one modification selected from a modified sugar moiety and a modified internucleoside linkage.

Embodiment 3. An oligomeric compound comprising a modified oligonucleotide consisting of 12 to 30 linked nucleosides and having a nucleobase sequence comprising at least 8, at least 9, at least 10, at least 11, at least 12, at least 13, at least 14, at least 15, at least 16, at least 17, at least 18, at least 19, or at least 20 contiguous nucleobases complementary to:
  an equal length portion of nucleobases 9198-9222 of SEQ ID NO: 2;
  an equal length portion of nucleobases 13702-13766 of SEQ ID NO: 2;
  an equal length portion of nucleobases 14037-14062 of SEQ ID NO: 2;
  an equal length portion of nucleobases 16761-16800 of SEQ ID NO: 2;
  an equal length portion of nucleobases 17558-17602 of SEQ ID NO: 2;
  an equal length portion of nucleobases 17615-17667 of SEQ ID NO: 2;
  an equal length portion of nucleobases 17853-17883 of SEQ ID NO: 2;
  an equal length portion of nucleobases 18097-18160 of SEQ ID NO: 2;
  an equal length portion of nucleobases 18206-18237 of SEQ ID NO: 2;
  an equal length portion of nucleobases 18237-18340 of SEQ ID NO: 2;
  an equal length portion of nucleobases 18350-18387 of SEQ ID NO: 2;
  an equal length portion of nucleobases 18412-18469 of SEQ ID NO: 2;
  an equal length portion of nucleobases 18461-18506 of SEQ ID NO: 2;
  an equal length portion of nucleobases 18539-18579 of SEQ ID NO: 2;
  an equal length portion of nucleobases 18697-18727 of SEQ ID NO: 2;
  an equal length portion of nucleobases 18755-18793 of SEQ ID NO: 2;
  an equal length portion of nucleobases 18797-18819 of SEQ ID NO: 2;
  an equal length portion of nucleobases 18839-18862 of SEQ ID NO: 2;
  an equal length portion of nucleobases 18974-19021 of SEQ ID NO: 2;
  an equal length portion of nucleobases 19028-19080 of SEQ ID NO: 2;
  an equal length portion of nucleobases 19146-19173 of SEQ ID NO: 2;
  an equal length portion of nucleobases 19228-19253 of SEQ ID NO: 2;
  an equal length portion of nucleobases 19347-19393 of SEQ ID NO: 2;
  an equal length portion of nucleobases 19500-19523 of SEQ ID NO: 2; or
  an equal length portion of nucleobases 19512-19534 of SEQ ID NO: 2,
  wherein the modified oligonucleotide comprises at least one modification selected from a modified sugar moiety and a modified internucleoside linkage.

Embodiment 4. An oligomeric compound comprising a modified oligonucleotide consisting of 12 to 30 linked nucleosides and having a nucleobase sequence comprising at least 8, at least 9, at least 10, at least 11, at least 12, at least 13, at least 14, at least 15, at least 16, at least 17, or at least 18 contiguous nucleobases of a sequence selected from:
  SEQ ID NOs: 1050, 1124, 2145, 2151, 2152, 2153;
  SEQ ID NOs: 36, 86, 114, 164, 191, 242, 269, 426, 523, 602, 691, 780;
  SEQ ID NOs: 89, 167, 245, 322, 323;
  SEQ ID NOs: 720, 808, 904, 937, 1058, 1097, 1184, 1278, 1340;
  SEQ ID NOs: 40, 41, 117, 118, 195, 196, 273, 274, 588, 690;
  SEQ ID NOs: 42, 43, 119, 120, 197, 198, 275, 276, 373, 460, 1431, 1542, 1645, 1850, 1965, 2109;
  SEQ ID NOs: 1451, 1499, 1543, 1654, 1733, 2154, 2155;
  SEQ ID NOs: 200, 420, 504, 620, 646, 709, 823, 980, 1029, 1149, 1196, 1253, 1323, 1423, 1476, 1605, 1613, 1728, 1832;
  SEQ ID NOs: 45, 46, 123, 124, 201, 202, 279, 280, 538, 562, 2091;
  SEQ ID NOs: 48, 49, 50, 51, 52, 53, 125, 126, 127, 128, 129, 130, 131, 203, 204, 205, 206, 207, 208, 281, 282, 283, 284, 285, 286, 414, 459, 485, 503, 579, 580, 693, 724, 840, 873, 911, 1034, 1081, 1125, 1159, 1318, 1413, 1513, 1548, 1672, 1701, 1794, 1868, 1958, 2002;
  SEQ ID NOs: 209, 287, 335, 439, 506, 606, 659, 1922, 2033, 2104;
  SEQ ID NOs: 784, 842, 869, 978, 1082, 1131, 1218, 1250, 1320, 1453, 1529, 1538, 1616, 1712, 1821;
  SEQ ID NOs: 54, 55, 132, 133, 210, 288, 419, 499, 564, 665, 764, 800, 881, 993, 1059, 1200, 1295, 1354, 1422, 1465, 1544, 1705, 1802, 2149;
  SEQ ID NOs: 338, 438, 525, 604, 658, 758, 813, 887, 977, 1043, 1108, 1199, 1258, 1336, 1395, 1514, 1557, 1668, 1697, 2089;
  SEQ ID NOs: 875, 934, 1047, 1110, 1229, 1243, 1373, 1438, 2146, 2147;

SEQ ID NOs: 761, 798, 890, 946, 1022, 1120, 1198, 1293, 1358, 1398, 1463;
SEQ ID NOs: 56, 134, 683, 718;
SEQ ID NOs: 1610, 1663, 1702, 1786;
SEQ ID NOs: 212, 1060, 1090, 1181, 1277, 1446, 1510, 1589, 1646, 1693, 1772, 2148;
SEQ ID NOs: 57, 586, 666, 714, 812, 914, 951, 1052, 1138, 1162, 1248, 1363, 1455;
SEQ ID NOs: 385, 416, 545, 621, 682, 1968, 2055, 2101, 2150;
SEQ ID NOs: 363, 467, 541, 2008, 2111;
SEQ ID NOs: 58, 59, 136, 213, 214, 291, 292, 383, 417, 519, 612, 671, 730, 900, 986, 1019, 1136, 1353, 1457, 1504, 1546, 2093;
SEQ ID NOs: 398, 435, 2095, 2010, 2144; or
SEQ ID NOs: 1201, 1238, 1341, 1435,
wherein the modified oligonucleotide comprises at least one modification selected from a modified sugar moiety and a modified internucleoside linkage.

Embodiment 5. The oligomeric compound of any of embodiments 1-4, wherein the modified oligonucleotide has a nucleobase sequence that is at least 80%, at least 85%, at least 90%, at least 95%, or 100% complementary to the nucleobase sequence of SEQ ID NO: 1 or SEQ ID NO: 2 when measured across the entire nucleobase sequence of the modified oligonucleotide.

Embodiment 6. The oligomeric compound of any of embodiments 1-5, wherein the modified oligonucleotide comprises at least one modified nucleoside comprising a modified sugar moiety.

Embodiment 7. The oligomeric compound of embodiment 6, wherein the modified oligonucleotide comprises at least one modified nucleoside comprising a bicyclic sugar moiety.

Embodiment 8. The oligomeric compound of embodiment 7, wherein the bicyclic sugar moiety comprises a 4'-2' bridge, wherein the 4'-2' bridge is selected from —CH$_2$—O—; and —CH(CH$_3$)—O—.

Embodiment 9. The oligomeric compound of any of embodiments 6-8, wherein the modified oligonucleotide comprises at least one modified nucleoside comprising a non-bicyclic modified sugar moiety.

Embodiment 10. The oligomeric compound of embodiment 9, wherein the non-bicyclic modified sugar moiety is a 2'-MOE sugar moiety or a 2'-OMe sugar moiety.

Embodiment 11. The oligomeric compound of any of embodiments 6-10, wherein the modified oligonucleotide comprises at least one modified nucleoside comprising a sugar surrogate.

Embodiment 12. The oligomeric compound of embodiment 11, wherein the sugar surrogate is any of morpholino, modified morpholino, PNA, THP, and F-HNA.

Embodiment 13. The oligomeric compound of any of embodiments 1-6 or 9-12, wherein the modified oligonucleotide does not comprise a bicyclic sugar moiety.

Embodiment 14. The oligomeric compound of any of embodiments 1-13, wherein the modified oligonucleotide is a gapmer.

Embodiment 15. The oligomeric compound of any of embodiments 1-14, wherein the modified oligonucleotide comprises:
a 5'-region consisting of 1-7 linked 5'-region nucleosides;
a central region consisting of 6-10 linked central region nucleosides; and
a 3'-region consisting of 1-7 linked 3'-region nucleosides; wherein
each of the 5'-region nucleosides and each of the 3'-region nucleosides comprises a modified sugar moiety and each of the central region nucleosides comprises a 2'-deoxyfuranosyl sugar moiety.

Embodiment 16. The oligomeric compound of embodiment 15, wherein the modified oligonucleotide comprises: a 5'-region consisting of 5 linked 5'-region nucleosides;
a central region consisting of 10 linked central region nucleosides; and
a 3'-region consisting of 5 linked 3'-region nucleosides; wherein
each of the 5'-region nucleosides and each of the 3'-region nucleosides is a 2'-MOE nucleoside, and each of the central region nucleosides is a 2'-β-D-deoxynucleoside.

Embodiment 17. The oligomeric compound of embodiment 15, wherein the modified oligonucleotide comprises: a 5'-region consisting of 6 linked 5'-region nucleosides;
a central region consisting of 10 linked central region nucleosides; and
a 3'-region consisting of 4 linked 3'-region nucleosides; wherein
each of the 5'-region nucleosides and each of the 3'-region nucleosides is a 2'-MOE nucleoside, and each of the central region nucleosides is a 2'-β-D-deoxynucleoside.

Embodiment 18. The oligomeric compound of any of embodiments 1-17, wherein the modified oligonucleotide comprises at least one modified internucleoside linkage.

Embodiment 19. The oligomeric compound of embodiment 18, wherein each internucleoside linkage of the modified oligonucleotide is a modified internucleoside linkage.

Embodiment 20. The oligomeric compound of embodiment 18 or embodiment 19, wherein at least one internucleoside linkage is a phosphorothioate internucleoside linkage.

Embodiment 21. The oligomeric compound of embodiment 18 or embodiment 20 wherein the modified oligonucleotide comprises at least one phosphodiester internucleoside linkage.

Embodiment 22. The oligomeric compound of any of embodiments 18, 20, or 21, wherein each internucleoside linkage is either a phosphodiester internucleoside linkage or a phosphorothioate internucleoside linkage.

Embodiment 23. The oligomeric compound of embodiment 19, wherein each internucleoside linkage is a phosphorothioate internucleoside linkage.

Embodiment 24. The oligomeric compound of any of embodiments 1-18 or 20-22, wherein the modified oligonucleotide has an internucleoside linkage motif of sooooossssssssssooss or sooooossssssssssoss; wherein,
s=a phosphorothioate internucleoside linkage and o=a phosphodiester internucleoside linkage.

Embodiment 25. The oligomeric compound of any of embodiments 1-24, wherein the modified oligonucleotide comprises at least one modified nucleobase.

Embodiment 26. The oligomeric compound of embodiment 25, wherein the modified nucleobase is a 5-methyl cytosine.

Embodiment 27. The oligomeric compound of any of embodiments 1-26, wherein the modified oligonucleotide consists of 12-30, 12-22, 12-20, 14-18, 14-20, 15-17, 15-25, 16-18, 16-20, 17-20, 18-20 or 18-22 linked nucleosides.

Embodiment 28. The oligomeric compound of any of embodiments 1-26, wherein the modified oligonucleotide consists of 16, 17, 18, 19, or 20 linked nucleosides.

Embodiment 29. The oligomeric compound of embodiment 28, wherein the modified oligonucleotide consists of 20 linked nucleosides.

Embodiment 30. The oligomeric compound of embodiment 28, wherein the modified oligonucleotide consists of 18 linked nucleosides.

Embodiment 31. An oligomeric compound comprising a modified oligonucleotide according to any of the following chemical notations:

(SEQ ID NO: 134)
$^mC_{es}{}^mC_{eo}{}^mC_{eo}A_{eo}A_{eo}T_{ds}A_{ds}G_{ds}A_{ds}T_{ds}T_{ds}$ $^mC_{ds}A_{ds}A_{ds}{}^mC_{ds}T_{eo}A_{eo}G_{es}{}^mC_{es}{}^mC_e;$ (SEQ ID NO: 411)
$A_{es}{}^mC_{eo}A_{eo}{}^mC_{eo}A_{eo}A_{ds}{}^mC_{ds}T_{ds}{}^mC_{ds}T_{ds}T_{ds}$ $T_{ds}A_{ds}{}^mC_{ds}A_{ds}A_{eo}{}^mC_{eo}A_{es}A_{es}A_e;$ (SEQ ID NO: 934)
$T_{es}{}^mC_{eo}T_{eo}{}^mC_{eo}{}^mC_{eo}A_{ds}G_{ds}A_{ds}{}^mC_{ds}A_{ds}T_{ds}$ $T_{ds}T_{ds}{}^mC_{ds}T_{ds}G_{eo}A_{eo}T_{es}G_{es}{}^mC_e;$ (SEQ ID NO: 1238)
$G_{es}T_{eo}G_{eo}T_{eo}G_{eo}T_{ds}T_{ds}A_{ds}A_{ds}A_{ds}A_{ds}T_{ds}$ $T_{ds}G_{ds}{}^mC_{ds}A_{eo}A_{eo}T_{es}T_{es}{}^mC_e;$ (SEQ ID NO: 2010)
$A_{es}T_{eo}T_{eo}G_{eo}{}^mC_{eo}A_{ds}A_{ds}T_{ds}T_{ds}{}^mC_{ds}T_{ds}$ $A_{ds}T_{ds}A_{ds}T_{ds}{}^mC_{eo}A_{eo}G_{es}A_{es}A_e;$ (SEQ ID NO: 1772)
$A_{es}T_{eo}G_{eo}T_{eo}G_{eo}A_{ds}T_{ds}{}^mC_{ds}T_{ds}A_{ds}T_{ds}$ $A_{ds}T_{ds}{}^mC_{ds}A_{ds}G_{eo}G_{eo}A_{es}G_{es}A_e;$
or (SEQ ID NO: 881)
$A_{es}{}^mC_{eo}{}^mC_{eo}A_{eo}G_{eo}A_{ds}G_{ds}G_{ds}G_{ds}{}^mC_{ds}$ $^mC_{ds}A_{ds}T_{ds}{}^mC_{ds}T_{ds}{}^mC_{eo}A_{eo}G_{es}G_{es}T_e$ (SEQ ID NO: 2101)
$T_{es}G_{eo}T_{eo}A_{eo}G_{eo}T_{ds}A_{ds}{}^mC_{ds}A_{ds}A_{ds}A_{ds}$ $T_{ds}{}^mC_{ds}T_{ds}T_{ds}T_{eo}{}^mC_{eo}{}^mC_{es}T_{es}T_e;$ (SEQ ID NO: 1050)
$G_{e}S^mC_{eo}A_{eo}T_{eo}{}^mC_{eo}A_{ds}G_{ds}A_{ds}T_{ds}G_{ds}T_{ds}$ $T_{ds}{}^mC_{ds}A_{ds}T_{ds}{}^mC_{eo}T_{eo}{}^mC_{es}T_{es}T_e;$ (SEQ ID NO: 1449)
$^mC_{es}{}^mC_{eo}T_{eo}{}^mC_{eo}{}^mC_{eo}A_{ds}T_{ds}T_{ds}{}^mC_{ds}$ $^mC_{ds}T_{ds}T_{ds}T_{ds}G_{ds}T_{ds}G_{eo}A_{eo}{}^mC_{es}T_{es}T_e,$ wherein:
  A=an adenine nucleobase,
  $^m$C=a 5-methyl cytosine nucleobase,
  G=a guanine nucleobase,
  T=a thymine nucleobase,
  e=a 2'-MOE sugar moiety,
  d=a 2'-β-D-deoxyribosyl sugar moiety,
  s=a phosphorothioate internucleoside linkage, and
  o=a phosphodiester internucleoside linkage.

Embodiment 32. An oligomeric compound comprising a modified oligonucleotide according to the following chemical notation:

(SEQ ID NO: 2101)
$T_{es}G_{eo}T_{eo}A_{eo}G_{eo}T_{ds}A_{ds}{}^mC_{ds}A_{ds}A_{ds}A_{ds}$ $T_{ds}{}^mC_{ds}T_{ds}T_{ds}T_{eo}{}^mC_{eo}{}^mC_{es}T_{es}T_e,$ wherein:
  A=an adenine nucleobase,
  $^m$C=a 5-methyl cytosine nucleobase,
  G=a guanine nucleobase,
  T=a thymine nucleobase,
  e=a 2'-MOE sugar moiety,
  d=a 2'-β-D-deoxyribosyl sugar moiety,
  s=a phosphorothioate internucleoside linkage, and
  o=a phosphodiester internucleoside linkage.

Embodiment 33. An oligomeric compound comprising a modified oligonucleotide according to the following chemical notation:

(SEQ ID NO: 682)
$A_{es}{}^mC_{eo}A_{eo}A_{eo}A_{eo}T_{eo}{}^mC_{ds}T_{ds}T_{ds}T_{ds}{}^mC_{ds}$ $^mC_{ds}T_{ds}T_{ds}{}^mC_{ds}A_{ds}A_{eo}T_{es}T_{es}A_e,$ wherein:
  A=an adenine nucleobase,
  $^m$C=a 5-methyl cytosine nucleobase,
  G=a guanine nucleobase,
  T=a thymine nucleobase,
  e=a 2'-MOE sugar moiety,
  d=a 2'-β-D-deoxyribosyl sugar moiety,
  s=a phosphorothioate internucleoside linkage, and
  o=a phosphodiester internucleoside linkage.

Embodiment 34. An oligomeric compound comprising a modified oligonucleotide according to the following chemical notation:

(SEQ ID NO: 1124)
$^mC_{es}A_{eo}G_{eo}A_{eo}T_{eo}G_{eo}T_{ds}T_{ds}{}^mC_{ds}A_{ds}T_{ds}$ $^mC_{ds}T_{ds}{}^mC_{ds}T_{ds}T_{ds}{}^mC_{eo}A_{es}{}^mC_{es}A_e,$ wherein:
  A=an adenine nucleobase,
  $^m$C=a 5-methyl cytosine nucleobase,
  G=a guanine nucleobase,
  T=a thymine nucleobase,
  e=a 2'-MOE sugar moiety,
  d=a 2'-β-D-deoxyribosyl sugar moiety,
  s=a phosphorothioate internucleoside linkage, and
  o=a phosphodiester internucleoside linkage.

Embodiment 35. An oligomeric compound comprising a modified oligonucleotide according to the following chemical notation:

(SEQ ID NO: 2145)
$^mC_{es}A_{eo}T_{eo}{}^mC_{eo}A_{eo}G_{eo}A_{ds}T_{ds}G_{ds}T_{ds}T_{ds}$ $^mC_{ds}A_{ds}T_{ds}{}^mC_{ds}T_{ds}{}^mC_{eo}T_{es}T_{es}{}^mC_e,$ wherein:
  A=an adenine nucleobase,
  $^m$C=a 5-methyl cytosine nucleobase,
  G=a guanine nucleobase,
  T=a thymine nucleobase,
  e=a 2'-MOE sugar moiety,
  d=a 2'-β-D-deoxyribosyl sugar moiety,
  s=a phosphorothioate internucleoside linkage, and
  o=a phosphodiester internucleoside linkage.

Embodiment 36. The oligomeric compound of any of embodiments 1-35 wherein the oligomeric compound is a singled-stranded oligomeric compound.

Embodiment 37. The oligomeric compound of any of embodiments 1-36, consisting of the modified oligonucleotide.

Embodiment 38. The oligomeric compound of any of embodiments 1-36, further comprising a conjugate group.

Embodiment 39. The oligomeric compound of embodiment 38, wherein the conjugate group comprises a conjugate moiety and a conjugate linker.

Embodiment 40. The oligomeric compound of embodiment 38, wherein the conjugate group comprises a GalNAc cluster comprising 1-3 GalNAc ligands.

Embodiment 41. The oligomeric compound of embodiment 38 or embodiment 39, wherein the conjugate linker consists of a single bond.

Embodiment 42. The oligomeric compound of and of embodiments 39 or embodiment 41, wherein the conjugate linker is cleavable.

Embodiment 43. The oligomeric compound of embodiment 39 or embodiment 42, wherein the conjugate linker comprises 1-3 linker-nucleosides.

Embodiment 44. The oligomeric compound of any of embodiments 38-43, wherein the conjugate group is attached to the modified oligonucleotide at the 5'-end of the modified oligonucleotide.

Embodiment 45. The oligomeric compound of any of embodiments 38-43, wherein the conjugate group is attached to the modified oligonucleotide at the 3'-end of the modified oligonucleotide.

Embodiment 46. The oligomeric compound of any of embodiments 1-36 or 38-45 further comprising a terminal group.

Embodiment 47. The oligomeric compound of any of embodiments 1-42 or 44-46, wherein the oligomeric compound does not comprise linker-nucleosides.

Embodiment 48. The oligomeric compound of any of embodiments 1-47, wherein the modified oligonucleotide of the oligomeric compound is a salt, and wherein the salt is a sodium salt or a potassium salt.

Embodiment 49. The oligomeric compound of any of embodiments 1-48, wherein the modified oligonucleotide is an RNAi compound.

Embodiment 50. An oligomeric duplex comprising an oligomeric compound of any of embodiments 1-35 or 37-49.

Embodiment 51. An antisense compound comprising or consisting of an oligomeric compound of any of embodiments 1-49 or an oligomeric duplex of embodiment 50.

Embodiment 52. A modified oligonucleotide according to the following chemical structure:

(SEQ ID NO: 2101)
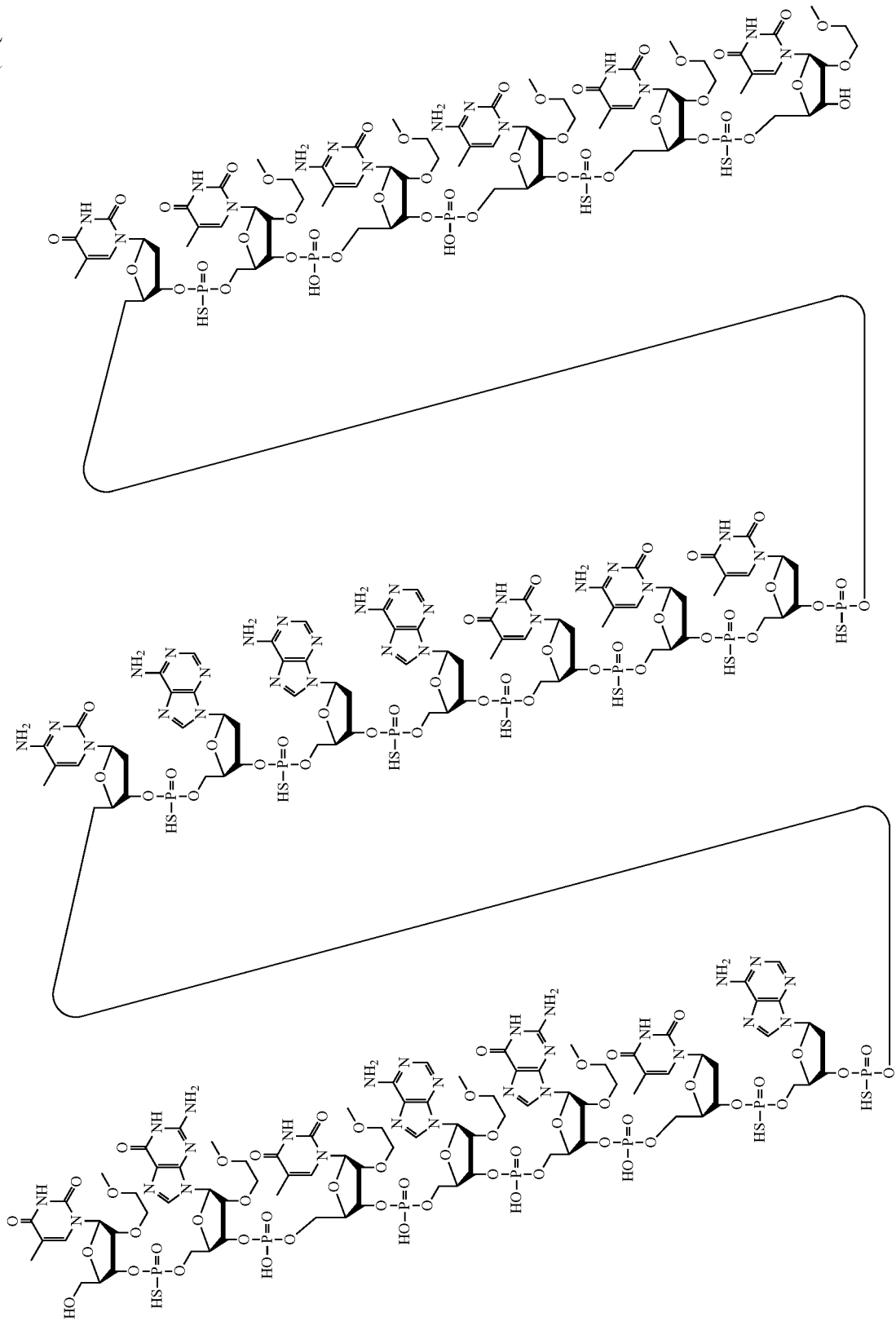

or a salt thereof.

Embodiment 53. The modified oligonucleotide of embodiment 52, which is the sodium salt or the potassium salt.

Embodiment 54. A modified oligonucleotide according to the following chemical structure:

(SEQ ID NO: 2101)
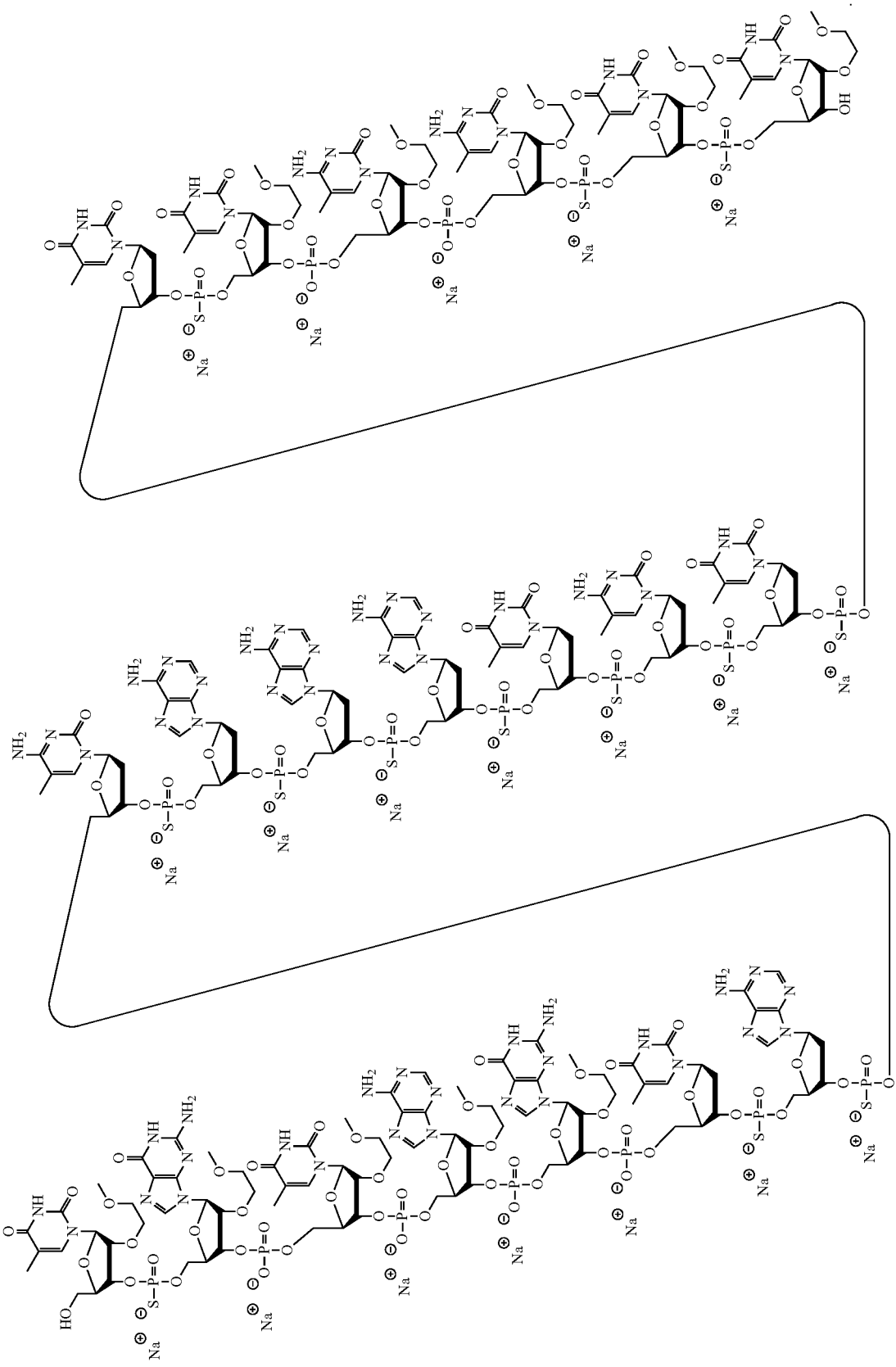

Embodiment 55. A modified oligonucleotide according to the following chemical structure:

(SEQ ID NO: 682)
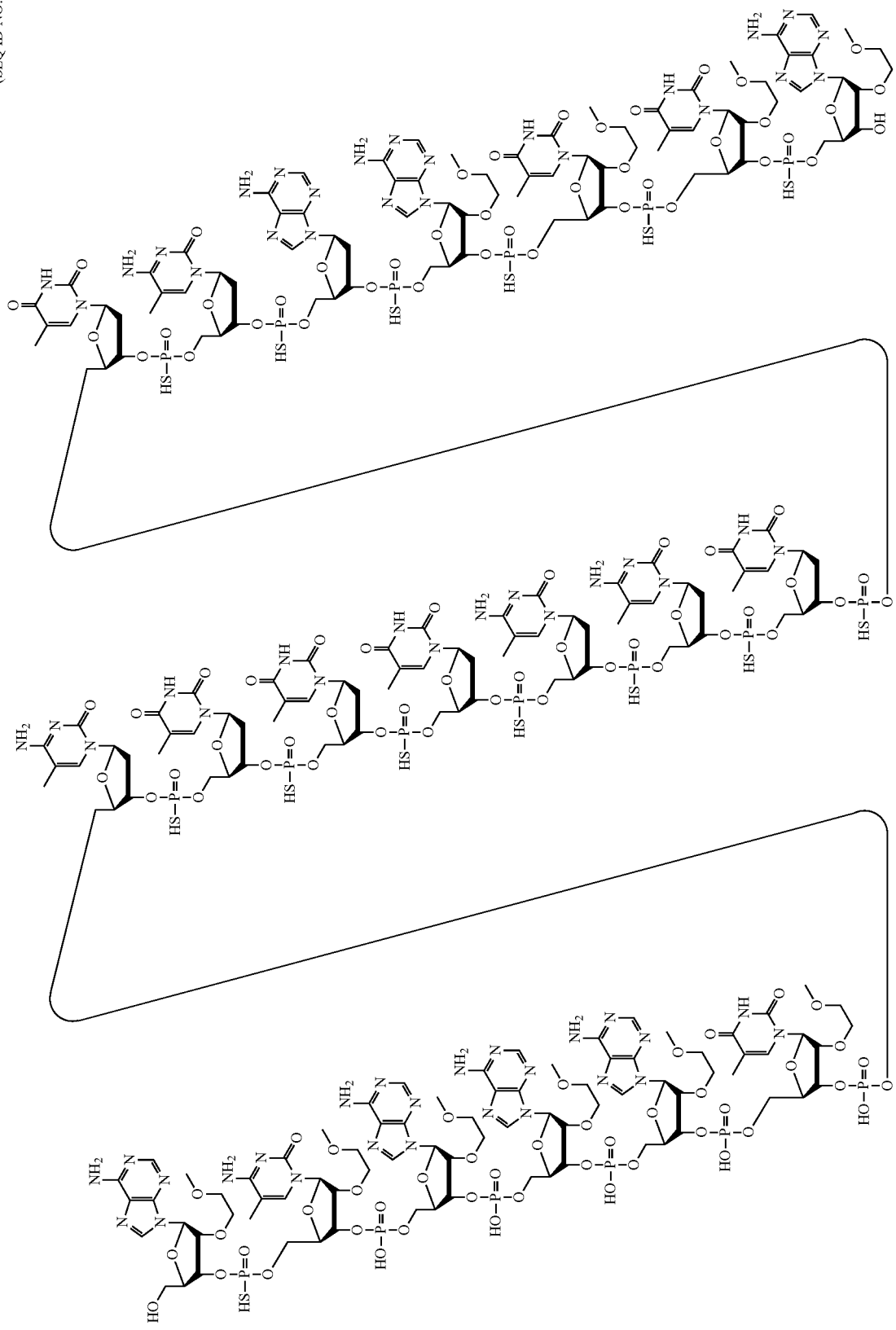

or a salt thereof.
Embodiment 56. The modified oligonucleotide of embodiment 55, which is the sodium salt or the potassium salt.
Embodiment 57. A modified oligonucleotide according to the following chemical structure:
(SEQ ID NO: 682)
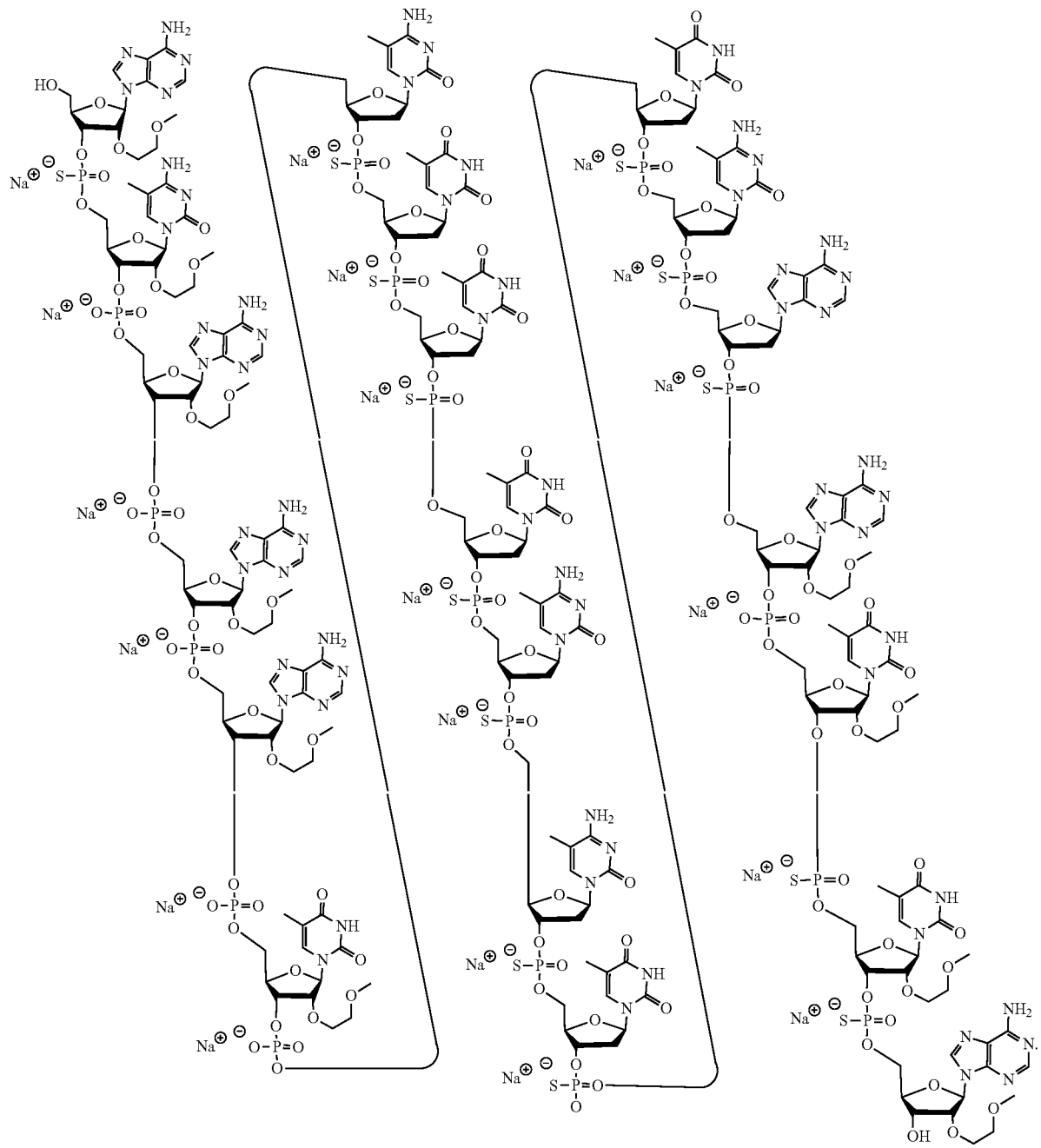
Embodiment 58. A modified oligonucleotide according to the following chemical structure:

(SEQ ID NO: 1124)
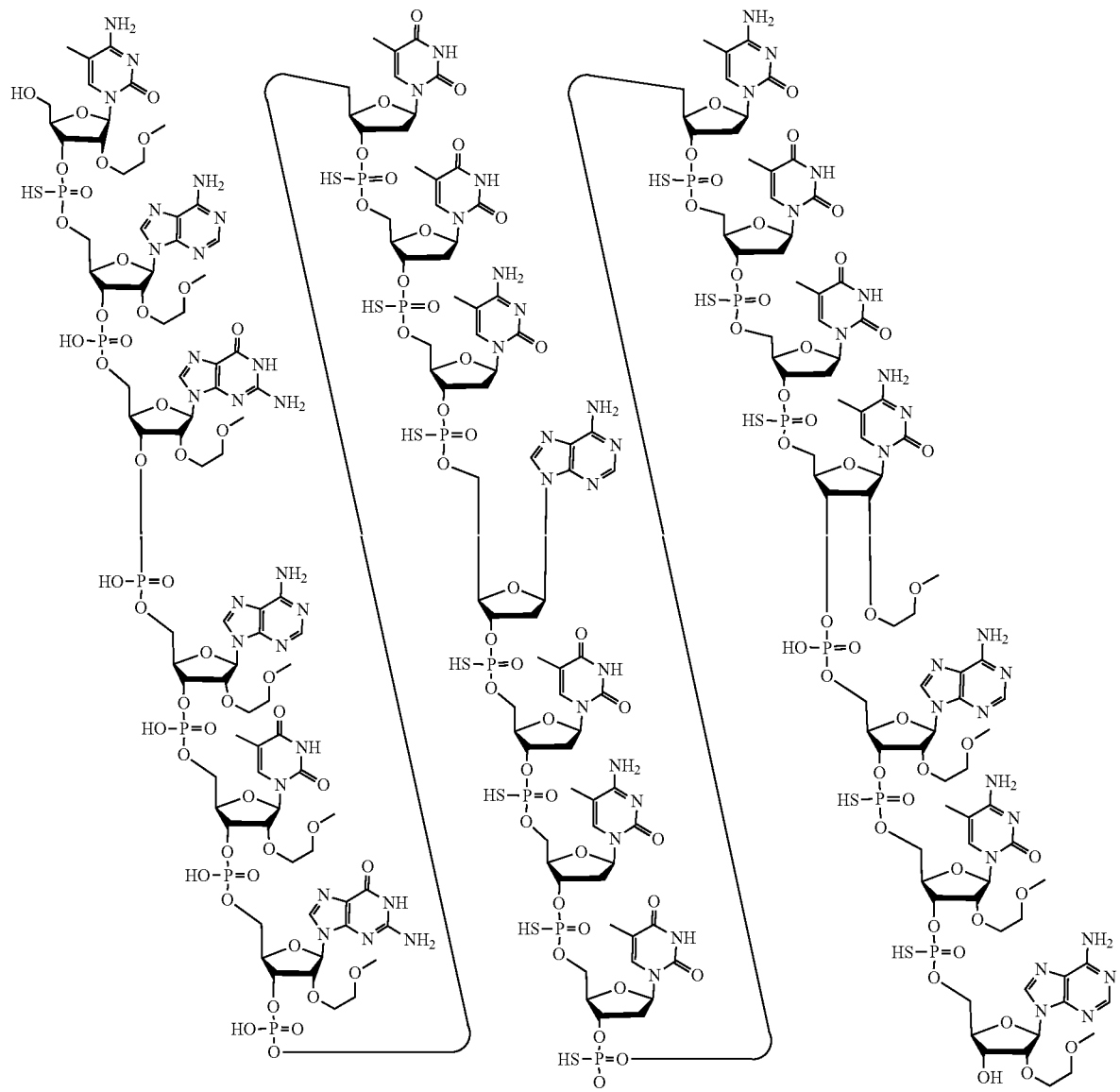
or a salt thereof.
Embodiment 59. The modified oligonucleotide of embodiment 58, which is the sodium salt or the potassium salt.
Embodiment 60. A modified oligonucleotide according to the following chemical structure:

(SEQ ID NO: 1124)
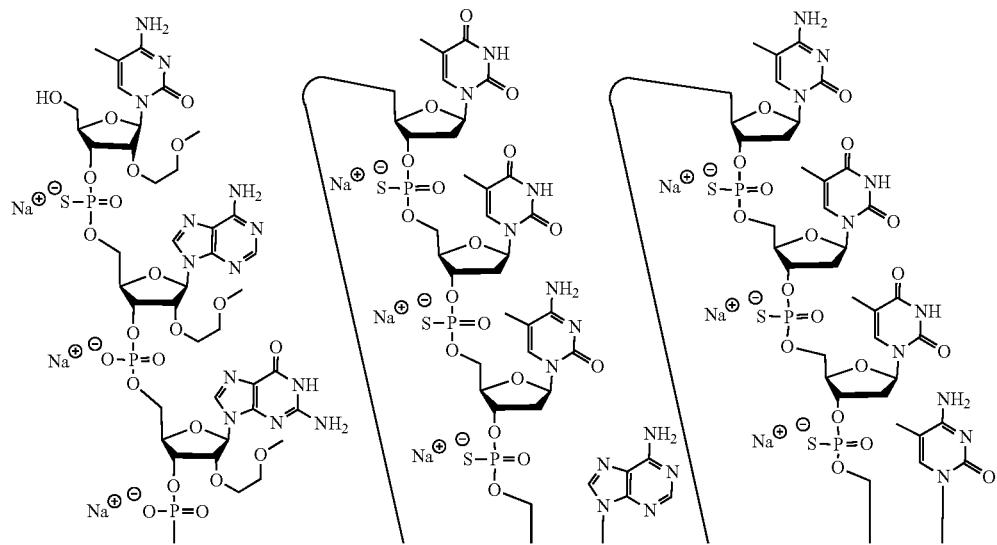
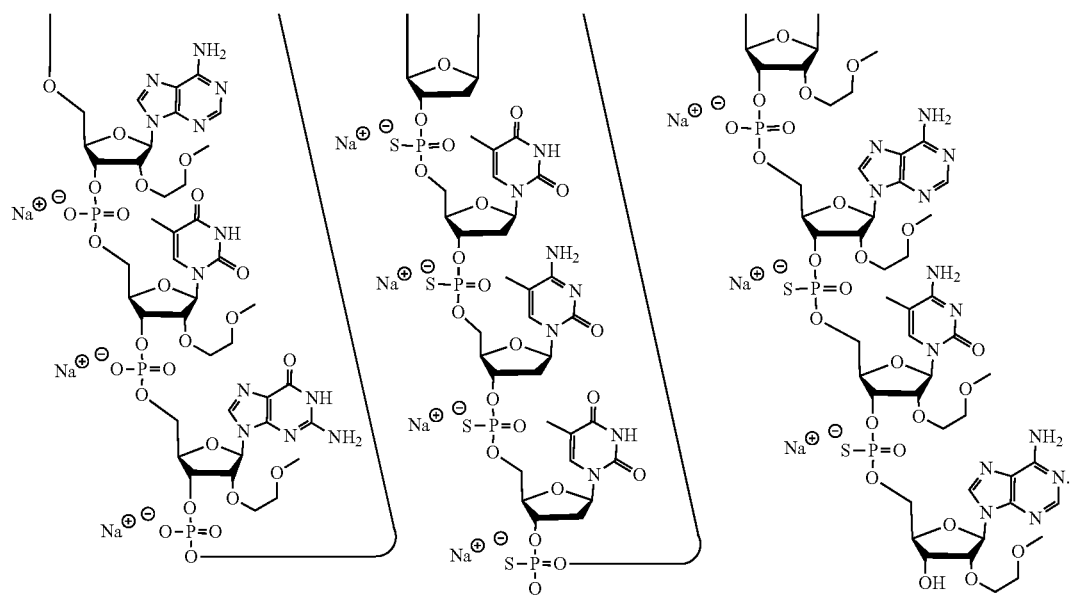

Embodiment 61. A modified oligonucleotide according to the following chemical structure:
(SEQ ID NO: 2145)
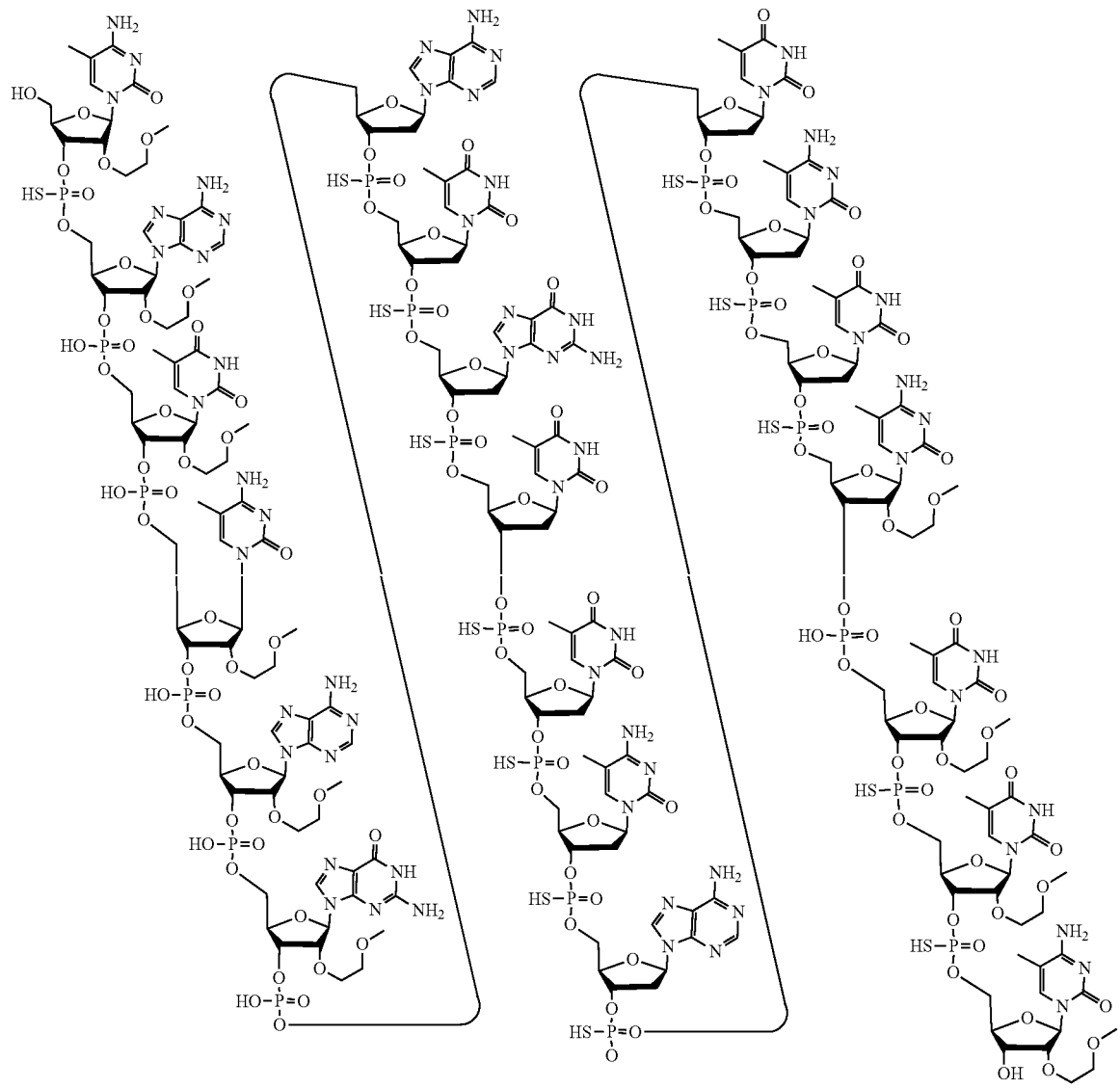
or a salt thereof.
Embodiment 62. The modified oligonucleotide of embodiment 61, which is the sodium salt or the potassium salt.
Embodiment 63. A modified oligonucleotide according to the following chemical structure:

(SEQ ID NO: 2145)

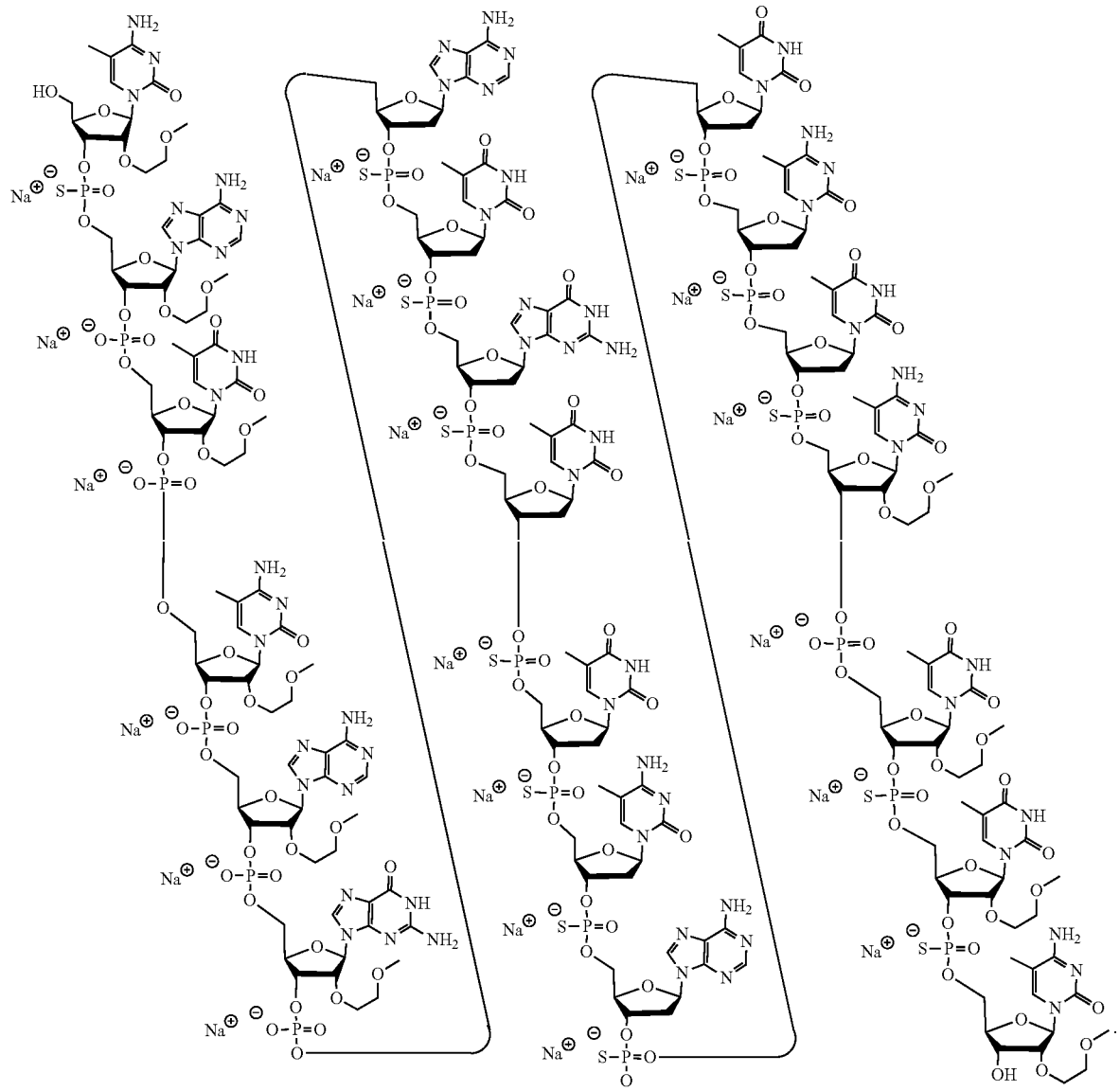

Embodiment 64. A pharmaceutical composition comprising the oligomeric compound of any of embodiments 1-49, the oligomeric duplex of embodiment 50, the antisense compound of embodiment 51, or the modified oligonucleotide of any of embodiments 52-63 and a pharmaceutically acceptable diluent or carrier.

Embodiment 65. The pharmaceutical composition of embodiment 64, comprising a pharmaceutically acceptable diluent and wherein the pharmaceutically acceptable diluent is artificial cerebrospinal fluid (aCSF) or phosphate-buffered saline (PBS).

Embodiment 66. The pharmaceutical composition of embodiment 65, wherein the pharmaceutical composition consists essentially of the oligomeric compound or the modified oligonucleotide and aCSF.

Embodiment 67. The pharmaceutical composition of embodiment 65, wherein the pharmaceutical composition consists essentially of the oligomeric compound or the modified oligonucleotide and PBS.

Embodiment 68. A pharmaceutical composition comprising a modified oligonucleotide of any of embodiments 52-63 and a pharmaceutically acceptable diluent.

Embodiment 69. The pharmaceutical composition of embodiment 68, wherein the pharmaceutically acceptable diluent is artificial cerebrospinal fluid (aCSF) or phosphate-buffered saline (PBS).

Embodiment 70. The pharmaceutical composition of embodiment 69, wherein the pharmaceutical composition consists essentially of the modified oligonucleotide and aCSF.

Embodiment 71. The pharmaceutical composition of embodiment 69, wherein the pharmaceutical composition consists essentially of the modified oligonucleotide and PBS.

Embodiment 72. A pharmaceutical composition comprising an oligomeric compound of any of embodiments 32-35 and a pharmaceutically acceptable diluent.

Embodiment 73. The pharmaceutical composition of embodiment 72, wherein the pharmaceutically acceptable diluent is artificial cerebrospinal fluid (aCSF) or phosphate-buffered saline (PBS).

Embodiment 74. The pharmaceutical composition of embodiment 73, wherein the pharmaceutical composition consists essentially of the oligomeric compound and aCSF.

Embodiment 75. The pharmaceutical composition of embodiment 73, wherein the pharmaceutical composition consists essentially of the oligomeric compound and PBS.

Embodiment 76. A chirally enriched population of modified oligonucleotides of any of embodiments 52-63, wherein the population is enriched for modified oligonucleotides comprising at least one particular phosphorothioate internucleoside linkage having a particular stereochemical configuration.

Embodiment 77. The chirally enriched population of embodiment 76, wherein the population is enriched for modified oligonucleotides comprising at least one particular phosphorothioate internucleoside linkage having the (Sp) configuration.

Embodiment 78. The chirally enriched population of embodiment 76, wherein the population is enriched for modified oligonucleotides comprising at least one particular phosphorothioate internucleoside linkage having the (Rp) configuration.

Embodiment 79. The chirally enriched population of embodiment 76, wherein the population is enriched for modified oligonucleotides having a particular, independently selected stereochemical configuration at each phosphorothioate internucleoside linkage.

Embodiment 80. The chirally enriched population of embodiment 79, wherein the population is enriched for modified oligonucleotides having the (Sp) configuration at each phosphorothioate internucleoside linkage or for modified oligonucleotides having the (Rp) configuration at each phosphorothioate internucleoside linkage.

Embodiment 81. The chirally enriched population of embodiment 79, wherein the population is enriched for modified oligonucleotides having the (Rp) configuration at one particular phosphorothioate internucleoside linkage and the (Sp) configuration at each of the remaining phosphorothioate internucleoside linkages.

Embodiment 82. The chirally enriched population of embodiment 79, wherein the population is enriched for modified oligonucleotides having at least 3 contiguous phosphorothioate internucleoside linkages in the Sp, Sp, and Rp configurations, in the 5' to 3' direction.

Embodiment 83. A population of modified oligonucleotides of any of embodiments 52-63, wherein all of the phosphorothioate internucleoside linkages of the modified oligonucleotide are stereorandom.

Embodiment 84. A chirally enriched population of oligomeric compounds of any of embodiments 32-35, wherein the population is enriched for oligomeric compounds comprising at least one particular phosphorothioate internucleoside linkage having a particular stereochemical configuration.

Embodiment 85. The chirally enriched population of embodiment 84, wherein the population is enriched for oligomeric compounds comprising at least one particular phosphorothioate internucleoside linkage having the (Sp) configuration.

Embodiment 86. The chirally enriched population of embodiment 84, wherein the population is enriched for oligomeric compounds comprising at least one particular phosphorothioate internucleoside linkage having the (Rp) configuration.

Embodiment 87. The chirally enriched population of embodiment 84, wherein the population is enriched for oligomeric compounds having a particular, independently selected stereochemical configuration at each phosphorothioate internucleoside linkage.

Embodiment 88. The chirally enriched population of embodiment 87, wherein the population is enriched for oligomeric compounds having the (Sp) configuration at each phosphorothioate internucleoside linkage or for modified oligonucleotides having the (Rp) configuration at each phosphorothioate internucleoside linkage.

Embodiment 89. The chirally enriched population of embodiment 87, wherein the population is enriched for oligomeric compounds having the (Rp) configuration at one particular phosphorothioate internucleoside linkage and the (Sp) configuration at each of the remaining phosphorothioate internucleoside linkages.

Embodiment 90. The chirally enriched population of embodiment 87, wherein the population is enriched for oligomeric compounds having at least 3 contiguous phosphorothioate internucleoside linkages in the Sp, Sp, and Rp configurations, in the 5' to 3' direction.

Embodiment 91. A population of oligomeric compounds of any of embodiments 32-35, wherein all of the phosphorothioate internucleoside linkages of the modified oligonucleotide are stereorandom.

Embodiment 92. A pharmaceutical composition comprising the chirally enriched population of any of embodiments 76-82 or 84-90, the population of claim 83, or the population of claim 91 and a pharmaceutically acceptable diluent.

Embodiment 93. The pharmaceutical composition of claim 92, wherein the pharmaceutically acceptable diluent is artificial CSF (aCSF) or phosphate-buffered saline (PBS).

Embodiment 94. The pharmaceutical composition of claim 93, wherein the pharmaceutical composition consists essentially of the oligomeric compounds or the modified oligonucleotides and artificial CSF (aCSF).

Embodiment 95. The pharmaceutical composition of embodiment 93, wherein the pharmaceutical composition consists essentially of the oligomeric compounds or the modified oligonucleotides and PBS.

Embodiment 96. A method comprising administering to an animal the pharmaceutical composition of any of embodiments 64-75 or 92-95.

Embodiment 97. A method of treating a disease or disorder associated with PLP1, comprising administering to a subject having or at risk for developing a disease or disorder associated with PLP1 a therapeutically effective amount of a pharmaceutical composition according to any of embodiments 64-75 or 92-95, and thereby treating the disease or disorder associated with PLP1.

Embodiment 98. A method of reducing PLP1 protein in the CSF of a subject having or at risk for developing a disease or disorder associated with PLP1 a therapeutically effective amount of a pharmaceutical composition according any of embodiments 64-75 or 92-95, and thereby reducing PLP1 protein in the CSF.

Embodiment 99. The method of embodiment 97 or embodiment 98, wherein the disease or disorder associated with PLP1 is a neurodegenerative disease.

Embodiment 100. The method of any of embodiments 97-99, wherein the disease or disorder associated with PLP1 is a leukodystrophy.

Embodiment 101. The method of embodiment 100, wherein the leukodystrophy is PMD.

Embodiment 102. The method of embodiment 101, wherein the PMD is any of connatal PMD, classic PMD, transitional PMD.

Embodiment 103. The method of embodiment 101, wherein the PMD is caused by overexpression of PLP1 protein.

Embodiment 104. The method of embodiment 101, wherein the PMD is caused by multiple copies of the PLP1 gene.

Embodiment 105. The method of embodiment 101, wherein the PMD is caused by the expression of duplicate copies of the PLP1 gene.

Embodiment 106. The method of any of embodiments 100-105, wherein at least one symptom or hallmark of the leukodystrophy is ameliorated.

Embodiment 107. The method of embodiment 97 or embodiment 98, wherein the disease or disorder associated with PLP1 is SPG2.

Embodiment 108. The method of embodiment 107, wherein at least one symptom or hallmark of SPG2 is ameliorated.

Embodiment 109. The method of embodiment 106 or embodiment 108, wherein the symptom or hallmark is any of hypotonia, nystagmus, optic atrophy, respiratory distress, motor delays, cognitive dysfunction, speech dysfunction, spasticity, ataxia, seizures, choreiform movements, and death.

Embodiment 110. The method of any of embodiments 96-109 wherein administering the modified oligonucleotide reduces hypotonia, nystagmus, optic atrophy, respiratory distress, motor delays, cognitive dysfunction, speech dysfunction, spasticity, ataxia, seizures, or choreiform movements, or delays death in the subject.

Embodiment 111. The method of any of embodiments 96-110, wherein the pharmaceutical composition is administered to the central nervous system or systemically.

Embodiment 112. The method of embodiment 111, wherein the pharmaceutical composition is administered to the central nervous system and systemically.

Embodiment 113. The method of any of embodiments 96-110, wherein the pharmaceutical composition is administered any of intrathecally, systemically, subcutaneously, or intramuscularly.

Embodiment 114. A method of reducing PLP1 RNA in a cell comprising contacting the cell with an oligomeric compound of any of embodiments 1-49, an oligomeric duplex according to embodiment 50, an antisense compound according to embodiment 51, or a modified oligonucleotide of any of embodiments 52-63, and thereby reducing PLP1 RNA in the cell.

Embodiment 115. A method of reducing PLP1 protein in a cell comprising contacting the cell with an oligomeric compound of any of embodiments 1-49, an oligomeric duplex according to embodiment 50, an antisense compound according to embodiment 51, or a modified oligonucleotide of any of embodiments 52-63, and thereby reducing PLP1 protein in the cell.

Embodiment 116. The method of embodiment 114 or embodiment 115, wherein the cell is an oligodendrocyte or an oligodendrocyte progenitor cell.

Embodiment 117. The method of embodiment 114 or embodiment 115, wherein the cell is a Schwann cell or a Schwann cell progenitor.

Embodiment 118. The method of any of embodiments 114-117, wherein the cell is in an animal.

Embodiment 119. The method of embodiment 96 or embodiment 118, wherein the animal is human.

Embodiment 120. A method comprising administering to a subject a pharmaceutical composition of any of embodiments 68-71.

Embodiment 121. A method of treating a disease or disorder associated with PLP1, comprising administering to an subject having or at risk for developing a disease or disorder associated with PLP1 a therapeutically effective amount of a pharmaceutical composition according to any of embodiments 68-71 and thereby treating the disease or disorder associated with PLP1.

Embodiment 122. The method of embodiment 121, wherein the disease associated with PLP1 is a neurodegenerative disease.

Embodiment 123. The method of embodiment 122, wherein the neurodegenerative disease is a leukodystrophy.

Embodiment 124. The method of embodiment 123, wherein the leukodystrophy is PMD.

Embodiment 125. The method of embodiment 124, wherein the PMD is any of connatal PMD, classic PMD, transitional PMD.

Embodiment 126. The method of embodiment 124, wherein the PMD is caused by overexpression of PLP1 protein.

Embodiment 127. The method of embodiment 124, wherein the PMD is caused by multiple copies of the PLP1 gene.

Embodiment 128. The method of embodiment 124, wherein the PMD is caused by the expression of duplicate copies of the PLP1 gene.

Embodiment 129. The method of any of embodiments 122-128, wherein at least one symptom or hallmark of the neurodegenerative disease is ameliorated.

Embodiment 130. The method of embodiment 129, wherein the symptom or hallmark is any of hypotonia, nystagmus, optic atrophy, respiratory distress, motor delays, cognitive dysfunction, speech dysfunction, spasticity, ataxia, seizures, choreiform movements, and death.

Embodiment 131. The method of any of embodiments 121-130 wherein administering the pharmaceutical composition reduces hypotonia, nystagmus, optic atrophy, respiratory distress, motor delays, cognitive dysfunction, speech dysfunction, spasticity, ataxia, seizures, or choreiform movements, or delays death in the subject.

Embodiment 132. The method of any of embodiments 120-131, wherein the subject is human.

Embodiment 133. A method of reducing expression of PLP1 in a cell comprising contacting the cell with a modified oligonucleotide of any of embodiments 52-63.

Embodiment 134. The method of embodiment 133, wherein the cell is a human cell.

Embodiment 135. Use of an oligomeric compound any of embodiments 1-49, an oligomeric duplex according to embodiment 50, an antisense compound according to embodiment 51, or a modified oligonucleotide of any of embodiments 52-63 for reducing PLP1 expression in a cell.

Embodiment 136. The use of embodiment 135, wherein the level of PLP1 RNA in the cell is reduced.

Embodiment 137. The use of embodiment 135, wherein the level of PLP1 protein in the cell is reduced.

Embodiment 138. The use of any of embodiments 133-137, wherein the cell is an oligodendrocyte or an oligodendrocyte progenitor cell.

Embodiment 139. The use of any of embodiments 133-137, wherein the cell is a Schwann cell or a Schwann cell progenitor.

Certain Oligonucleotides

In certain embodiments, provided herein are oligomeric compounds comprising oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA. That is, modified oligonucleotides comprise at least one modified nucleoside (comprising a modified sugar moiety and/or a modified nucleobase) and/or at least one modified internucleoside linkage.

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more substituent groups none of which bridges two atoms of the furanosyl ring to form a bicyclic structure. Such non bridging substituents may be at any position of the furanosyl, including but not limited to substituents at the 2', 4', and/or 5' positions. In certain embodiments one or more non-bridging substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE" or "O-methoxyethyl"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the T-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl(R or S), 5'-vinyl, and 5'-methoxy. In certain embodiments, non-bicyclic modified sugar moieties comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.

In certain embodiments, a 2'-substituted non-bicyclic modified nucleoside comprises a sugar moiety comprising a non-bridging 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted non-bicyclic modified nucleoside comprises a sugar moiety comprising a non-bridging 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted non-bicyclic modified nucleoside comprises a sugar moiety comprising a non-bridging 2'-substituent group selected from: F, OCH$_3$, and OCH$_2$CH$_2$OCH$_3$.

In certain embodiments, modified furanosyl sugar moieties and nucleosides incorporating such modified furanosyl sugar moieties are further defined by isomeric configuration. For example, a 2'-deoxyfuranosyl sugar moiety may be in seven isomeric configurations other than the naturally occurring β-D-deoxyribosyl configuration. Such modified sugar moieties are described in, e.g., WO 2019/157531, incorporated by reference herein. A 2'-modified sugar moiety has an additional stereocenter at the 2'-position relative to a 2'-deoxyfuranosyl sugar moiety; therefore, such sugar moieties have a total of sixteen possible isomeric configurations. 2'-modified sugar moieties described herein are in the β-D-ribosyl isomeric configuration unless otherwise specified.

Certain modified sugar moieties comprise a substituent that bridges two atoms of the furanosyl ring to form a second ring, resulting in a bicyclic sugar moiety. Nucleosides comprising such bicyclic sugar moieties have been referred to as bicyclic nucleosides (BNAs), locked nucleosides, or conformationally restricted nucleotides (CRN). Certain such compounds are described in US Patent Publication No. 2013/0190383; and PCT publication WO 2013/036868. In certain such embodiments, the bicyclic sugar moiety comprises a bridge between the 4' and the 2' furanose ring atoms. In certain such embodiments, the furanose ring is a ribose ring. Examples of such 4' to 2' bridging sugar substituents include but are not limited to: 4'-CH$_2$-2', 4'-(CH$_2$)$_2$-2', 4'-(CH$_2$)$_3$-2', 4'-CH$_2$—O-2' ("LNA"), 4'-CH$_2$—S-2', 4'-(CH$_2$)$_2$—O-2' ("ENA"), 4'-CH(CH$_3$)—O-2' (referred to as "constrained ethyl" or "cEt" when in the S configuration), 4'-CH$_2$—O—CH$_2$-2', 4'-CH$_2$—N(R)-2', 4'-CH(CH$_2$OCH$_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N(OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g, Zhou, et al, J. Org. Chem., 2009, 74, 118-134), 4'-CH$_2$—C(=CH$_2$)-2' and analogs thereof (see e.g., Seth et al., U.S. Pat. No. 8,278,426), 4'-C(R$_a$R$_b$)—N(R)—O-2', 4'-C(R$_a$R$_b$)—O—N(R)-2', 4'-CH$_2$—O—N(R)-2', and 4'-CH$_2$—N(R)—O-2', wherein each R, R$_a$, and R$_b$ is, independently, H, a protecting group, or C$_1$-C$_{12}$ alkyl (see, e.g. Imanishi et al., U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C($R_a$)=C($R_b$)—, —C($R_a$)=N—, —C(=N$R_a$)—, —C(=O)—, —C(=S)—, —O—, —Si($R_a$)$_2$—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each L and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Additional bicyclic sugar moieties are known in the art, see, for example: Freier et al., Nucleic Acids Research, 1997, 25(22), 4429-4443, Albaek et al., J. Org. Chem., 2006, 71, 7731-7740, Singh et al., Chem. Common, 1998, 4, 455-456; Koshkin et al., Tetrahedron, 1998, 54, 3607-3630; Wahlestedt et al., Proc. Natl. Acad. Sci. U.S.A, 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 2007, 129, 8362-8379; Elayadi et al., Curr. Opinion Invens. Drugs, 2001, 2, 558-561; Braasch et al., Chem. Biol., 2001, 8, 1-7; Omm et al., Curr. Opinion Mol. Ther., 2001, 3, 239-243; Wengel et al., U.S. Pat. No. 7,053,207, Imanishi et al., U.S. Pat. No. 6,268,490, Imanishi et al. U.S. Pat. No. 6,770,748, Imanishi et al., U.S. RE44,779; Wengel et al., U.S. Pat. No. 6,794,499, Wengel et al., U.S. Pat. No. 6,670,461; Wengel et al., U.S. Pat. No. 7,034,133, Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191, Torsten et al., WO 2004/106356, Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; Allerson et al., US2008/0039618; and Migawa et al., US2015/0191727. In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

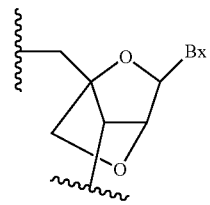

LNA (β-D-configuration)
bridge = 4'-CH$_2$—O-2'

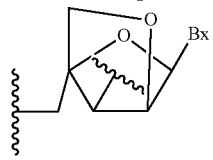

α-L-LNA (α-L-configuration)
bridge = 4'-CH$_2$—O-2'

α-L-methyleneoxy (4'-CH$_2$—O-2') or α-L-LNA bicyclic nucleosides have been incorporated into oligonucleotides that showed antisense activity (Frieden et al., Nucleic Acids Research, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. Bioorg. & Med. Chem. 2002, 10, 841-854), fluoro HNA:

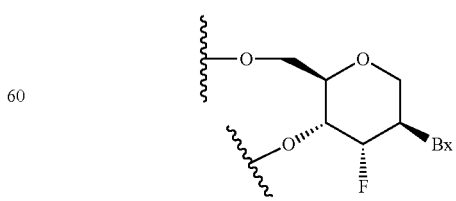

F—HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

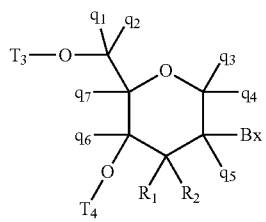

wherein, independently, for each of the modified THP nucleosides:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or NT, and each T, $J_2$, and $J_3$ is, independently, H or $C_1$-$C_6$ alkyl.

In certain embodiments, modified THP nucleosides are provided wherein $q_6$ $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 47, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

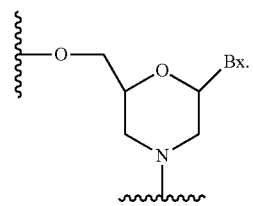

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., Org. Biomol. Chem., 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides.

2. Certain Modified Nucleobases

In certain embodiments, modified oligonucleotides comprise one or more nucleosides comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and 0-6 substituted purines. In certain embodiments, modified nucleobases are selected from: 5-methyl cytosine, 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in The Concise Encyclopedia Of Polymer Science And Engineering, Kroschwitz, J. I., Ed., John Wiley & Sons, 1990, 858-859; Englisch et al., Angewandte Chemie, International Edition, 1991, 30, 613; Sanghvi, Y. S., Chapter 15, Antisense Research and Applications, Crooke, S. T. and Lebleu, B., Eds., CRC Press, 1993, 273-288; and those disclosed in Chapters 6 and 15, Antisense Drug Technology, Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

3. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphodiesters, which contain a phosphodiester bond ("P(O$_2$)=O") (also referred to as unmodified or naturally occurring linkages), phosphotriesters, methylphosphonates, phosphoramidates, phosphorothioates ("P(O$_2$)=S"), and phosphorodithioates ("HS—P=S"). Representative non-phosphorus containing internucleoside linking groups include but are not limited to methylenemethylimino (—CH$_2$—N(CH$_3$)—O—CH$_2$—), thiodiester, thionocarbamate (—O—C(=O)(NH)—S—); siloxane (—O—SiH$_2$—O—); and N,N'-dimethylhydrazine (—CH$_2$—N(CH$_3$)—N(CH$_3$)—). Modified internucleoside linkages, compared to naturally occurring phosphodiester internucleoside linkages, can be used to alter, typically increase, nuclease resistance of the oligonucleotide. In certain embodiments, internucleoside linkages having a chiral atom can be prepared as a racemic mixture, or as separate enantiomers. Methods of preparation of phosphorous-containing and non-phosphorous-containing internucleoside linkages are well known to those skilled in the art.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate internucleoside linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate internucleoside linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkage in a particular, independently selected stereochemical configuration. In certain embodiments, the particular configuration of the particular phosphorothioate internucleoside linkage is present in at least 65% of the molecules in the population. In certain embodiments, the particular configuration of the particular phosphorothioate internucleoside linkage is present in at least 70% of the molecules in the population. In certain embodiments, the particular configuration of the particular phosphorothioate internucleoside linkage is present in at least 80% of the molecules in the population. In certain embodiments, the particular configuration of the particular phosphorothioate internucleoside linkage is present in at least 90% of the molecules in the population. In certain embodiments, the particular configuration of the particular phosphorothioate internucleoside linkage is present in at least 99% of the molecules in the population. Such chirally enriched populations of modified oligonucleotides can be generated using synthetic methods known in the art, e.g., methods described in Oka et al., *JACS*, 2003, 125, 8307, Wan et al., *Nuc. Acid. Res.*, 2014, 42, 13456, and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

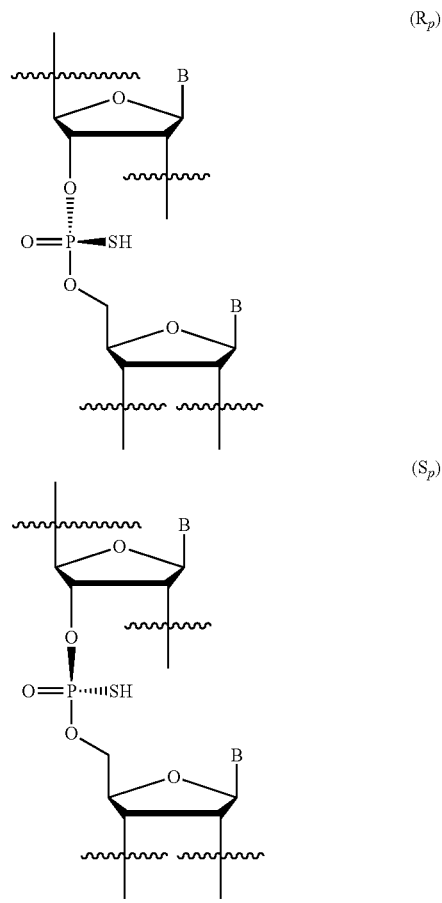

Unless otherwise indicated, chiral internucleoside linkages of modified oligonucleotides described herein can be stereorandom or in a particular stereochemical configuration.

Neutral internucleoside linkages include, without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), methoxypropyl (MOP), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (see, for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

B. Certain Motifs

In certain embodiments, modified oligonucleotides comprise one or more modified nucleosides comprising a modified sugar moiety. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or portion thereof in a defined pattern or sugar motif. In certain instances, such sugar motifs include but are not limited to any of the sugar modifications discussed herein.

In certain embodiments, modified oligonucleotides have a gapmer motif, which is defined by two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-6 nucleosides. In certain embodiments, each nucleoside of each wing of a gapmer comprises a modified sugar moiety. In certain embodiments, at least one nucleoside of each wing of a gapmer comprises a modified sugar moiety. In certain embodiments, at least two nucleosides of each wing of a gapmer comprises a modified sugar moiety. In certain embodiments, at least three nucleosides of each wing of a gapmer comprises a modified sugar moiety. In certain embodiments, at least four nucleosides of each wing of a gapmer comprises a modified sugar moiety. In certain embodiments, at least five nucleosides of each wing of a gapmer comprises a modified sugar moiety.

In certain embodiments, the gap of a gapmer comprises 7-12 nucleosides. In certain embodiments, each nucleoside of the gap of a gapmer comprises a 2'-deoxyribosyl sugar moiety. In certain embodiments, at least six nucleosides of the gap of a gapmer comprise a 2'-β-D-deoxyribosyl sugar moiety. In certain embodiments, each nucleoside of the gap of a gapmer comprises a 2'-β-D-deoxyribosyl sugar moiety. In certain embodiments, at least one nucleoside of the gap of a gapmer comprises a modified sugar moiety. In certain embodiments, at least one nucleoside of the gap of a gapmer comprises a 2'-OMe sugar moiety.

In certain embodiments, the gapmer is a deoxy gapmer. In certain embodiments, the nucleosides on the gap side of each wing/gap junction comprise 2'-deoxyribosyl sugar moieties and the nucleosides on the wing sides of each wing/gap junction comprise modified sugar moieties. In certain embodiments, at least six nucleosides of the gap of a gapmer comprise a 2'-β-D-deoxyribosyl sugar moiety. In certain embodiments, each nucleoside of the gap of a gapmer comprises a 2'-deoxyribosyl sugar moiety. In certain embodiments, each nucleoside of each wing of a gapmer comprises a modified sugar moiety. In certain embodiments, one nucleoside of the gap comprises a modified sugar moiety and each remaining nucleoside of the gap comprises a 2'-deoxyribosyl sugar moiety.

In certain embodiments, modified oligonucleotides comprise or consist of a portion having a fully modified sugar motif. In such embodiments, each nucleoside of the fully modified portion of the modified oligonucleotide comprises a modified sugar moiety. In certain embodiments, each nucleoside of the entire modified oligonucleotide comprises a modified sugar moiety. In certain embodiments, modified oligonucleotides comprise or consist of a portion having a fully modified sugar motif, wherein each nucleoside within the fully modified portion comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified oligonucleotide comprises the same 2'-modification.

Herein, the lengths (number of nucleosides) of the three regions of a gapmer may be provided using the notation [# of nucleosides in the 5'-wing]-[# of nucleosides in the gap]-[# of nucleosides in the 3'-wing], Thus, a 5-10-5 gapmer consists of 5 linked nucleosides in each wing and 10 linked nucleosides in the gap. Where such nomenclature is followed by a specific modification, that modification is the modification in each sugar moiety of each wing and the gap nucleosides comprises a 2'-β-D-deoxyribosyl sugar moiety. Thus, a 5-10-5 MOE gapmer consists of 5 linked 2'-MOE nucleosides in the 5'-wing, 10 linked 2'-β-D-deoxynucleosides in the gap, and 5 linked 2'-MOE nucleosides in the 3'-wing. A 3-10-3 cEt gapmer consists of 3 linked cEt nucleosides in the 5'-wing, 10 linked 2'-β-D-deoxynucleosides in the gap, and 3 linked cEt nucleosides in the 3'-wing. A 5-8-5 gapmer consists of 5 linked nucleosides comprising a modified sugar moiety in the 5'-wing, 8 linked a 2'-β-D-deoxynucleosides in the gap, and 5 linked nucleosides comprising a modified sugar moiety in the 3'-wing. A mixed wing gapmer has at least two different modified sugar moieties in the 5' and/or the 3' wing. A 5-8-5 or 5-8-4 mixed wing gapmer has at least two different modified sugar moieties in the 5'- and/or the 3'-wing.

In certain embodiments, modified oligonucleotides are 5-10-5 MOE gapmers. In certain embodiments, modified oligonucleotides are 6-10-4 MOE gapmers. In certain embodiments, modified oligonucleotides are 4-10-6 MOE gapmers. In certain embodiments, modified oligonucleotides are 4-8-6 MOE gapmers. In certain embodiments, modified oligonucleotides are 6-8-4 MOE gapmers. In certain embodiments, modified oligonucleotides are 5-8-4 MOE gapmers. In certain embodiments, modified oligonucleotides are 3-10-7 MOE gapmers. In certain embodiments, modified oligonucleotides are 7-10-3 MOE gapmers. In certain embodiments, modified oligonucleotides are 5-8-5 MOE gapmers. In certain embodiments, modified oligonucleotides are 5-9-5 MOE gapmers. In certain embodiments, modified oligonucleotides are X—Y—Z MOE gapmers, wherein X and Z are independently selected from 1, 2, 3, 4, 5, 6, or 7 linked 2'-MOE nucleosides and Y is selected from 7, 8, 9, 10, or 11 linked deoxynucleosides.

In certain embodiments, modified oligonucleotides have the following sugar motif (5' to 3'): eeeeedddddddddeeeee, eeeeeedddddddddeeee, or eeeeedydddddddeeeee, wherein 'd' represents a 2'-deoxyribosyl sugar moiety, 'e' represents a 2'-MOE sugar moiety, and 'y' represents a 2'-OMe sugar moiety.

2. Certain Nucleobase Motifs

In certain embodiments, oligonucleotides comprise modified and/or unmodified nucleobases arranged along the oligonucleotide or portion thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methyl cytosines. In certain embodiments, all of the cytosine nucleobases are 5-methyl cytosines and all of the other nucleobases of the modified oligonucleotide are unmodified nucleobases.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of the nucleoside is a 2'-deoxyribosyl sugar moiety. In certain embodiments, the modified nucleobase is selected from: a 2-thiopyrimidine and a 5-propynepyrimidine.

3. Certain Internucleoside Linkage Motifs

In certain embodiments, oligonucleotides comprise modified and/or unmodified internucleoside linkages arranged along the oligonucleotide or portion thereof in a defined pattern or motif. In certain embodiments, each internucleoside linking group is a phosphodiester internucleoside linkage (P=O). In certain embodiments, each internucleoside linking group of a modified oligonucleotide is a phosphorothioate internucleoside linkage (P=S). In certain embodiments, each internucleoside linkage of a modified oligonucleotide is independently selected from a phosphorothioate internucleoside linkage and phosphodiester internucleoside linkage. In certain embodiments, each phosphorothioate internucleoside linkage is independently selected from a stereorandom phosphorothioate, a (Sp) phosphorothioate, and a (Rp) phosphorothioate. In certain embodiments, the sugar motif of a modified oligonucleotide is a gapmer and the internucleoside linkages within the gap are all modified. In certain such embodiments, some or all of the internucleoside linkages in the wings are unmodified phosphodiester internucleoside linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester internucleoside linkage is not a terminal internucleoside linkage, and the remaining internucleoside linkages are phosphorothioate internucleoside linkages. In certain such embodiments, all of the phosphorothioate internucleoside linkages are stereorandom. In certain embodiments, all of the phosphorothioate internucleoside linkages in the wings are (Sp) phosphorothioates, and the gap comprises at least one Sp, Sp, Rp motif. In certain embodiments, populations of modified oligonucleotides are enriched for modified oligonucleotides comprising such internucleoside linkage motifs.

In certain embodiments, modified oligonucleotides have an internucleoside linkage motif of sooooosssssssssoooss or sooooossssssssssosss wherein each "s" represents a phosphorothioate internucleoside linkage and each "o" represents a phosphodiester internucleoside linkage.

C. Certain Lengths

It is possible to increase or decrease the length of an oligonucleotide without eliminating activity. For example, in Woolf et al., *Proc. Natl. Acad. Sci. USA,* 1992, SP, 7305-7309, 1992), a series of oligonucleotides 13-25 nucleobases in length were tested for their ability to induce cleavage of a target nucleic acid in an oocyte injection model. Oligonucleotides 25 nucleobases in length with 8 or 11 mismatch bases near the ends of the oligonucleotides were able to direct specific cleavage of the target nucleic acid, albeit to a lesser extent than the oligonucleotides that contained no mismatches. Similarly, target specific cleavage was achieved using 13 nucleobase oligonucleotides, including those with 1 or 3 mismatches.

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides.

In certain embodiments, oligonucleotides consist of 16 linked nucleosides. In certain embodiments, oligonucleotides consist of 17 linked nucleosides. In certain embodiments, oligonucleotides consist of 18 linked nucleosides. In certain embodiments, oligonucleotides consist of 19 linked nucleosides. In certain embodiments, oligonucleotides consist of 20 linked nucleosides.

D. Certain Modified Oligonucleotides

In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Unless otherwise indicated, all modifications are independent of nucleobase sequence.

E. Certain Populations of Modified Oligonucleotides

Populations of modified oligonucleotides in which all of the modified oligonucleotides of the population have the same molecular formula can be stereorandom populations or chirally enriched populations. All of the chiral centers of all of the modified oligonucleotides are stereorandom in a stereorandom population. In a chirally enriched population, at least one particular chiral center is not stereorandom in the modified oligonucleotides of the population. In certain embodiments, the modified oligonucleotides of a chirally enriched population are enriched for β-D ribosyl sugar moieties, and all of the phosphorothioate internucleoside linkages are stereorandom. In certain embodiments, the modified oligonucleotides of a chirally enriched population are enriched for both β-D ribosyl sugar moieties and at least one, particular phosphorothioate internucleoside linkage in a particular stereochemical configuration.

F. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a portion of an oligonucleotide has a nucleobase sequence that is complementary to a second oligonucleotide or an identified reference nucleic acid, such as a target nucleic acid. In certain embodiments, the nucleobase sequence of a portion or entire length of an oligonucleotide is at least 50%, at least 60%, at least 70%, at least 80%, at least 85%, at least 90%, at least 95%, or 100% complementary to the second oligonucleotide or nucleic acid, such as a target nucleic acid.

I. Certain Oligomeric Compounds

In certain embodiments, provided herein are oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, abasic nucleosides, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., *Bioorg. Med. Chem. Lett.*, 1994, 4, 1053-1060), a thioether, e.g., hexyl-S-tritylthiol (Manoharan et al., *Ann. N. Y. Acad. Sci.*, 1992, 660, 306-309; Manoharan et al., *Bioorg. Med. Chem. Lett.*, 1993, 3, 2765-2770), a thiocholesterol (Oberhauser et al., *Nucl. Acids Res.*, 1992, 20, 533-538), an aliphatic chain, e.g., do-decan-diol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid a palmityl moiety (Mishra et al., *Biochim. Biophys. Acta*, 1995, 1264, 229-237), an octadecylamine or hexylamino-carbonyl-oxycholesterol moiety (Crooke et al., *J. Pharmacol. Exp. Ther.*, 1996, 277, 923-937), a tocopherol group (Nishina et A., *Molecular Therapy Nucleic Acids*, 2015, 4, e220; and Nishina et al., *Molecular Therapy*, 2008, 16, 734-740), or a N-acetylgalactosamine (GalNAc) cluster (e.g., WO2014/179620).

In certain embodiments, conjugate groups may be selected from any of a C22 alkyl, C20 alkyl, C16 alkyl, C10 alkyl, C21 alkyl, C19 alkyl, C18 alkyl, C15 alkyl, C14 alkyl, C13 alkyl, C12 alkyl, C11 alkyl, C9 alkyl, C8 alkyl, C7 alkyl, C6 alkyl, C5 alkyl, C22 alkenyl, C20 alkenyl, C16 alkenyl, C10 alkenyl, C21 alkenyl, C19 alkenyl, C18 alkenyl, C15 alkenyl, C14 alkenyl, C13 alkenyl, C12 alkenyl, C11 alkenyl, C9 alkenyl, C8 alkenyl, C7 alkenyl, C6 alkenyl, or C5 alkenyl.

In certain embodiments, conjugate groups may be selected from any of C22 alkyl, C20 alkyl, C16 alkyl, C10 alkyl, C21 alkyl, C19 alkyl, C18 alkyl, C15 alkyl, C14 alkyl, C13 alkyl, C12 alkyl, C11 alkyl, C9 alkyl, C8 alkyl, C7 alkyl, C6 alkyl, and C5 alkyl, where the alkyl chain has one or more unsaturated bonds.

1. Conjugate Moieties

Conjugate moieties include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, lipophilic groups, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofcn, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain oligomeric compounds, a conjugate moiety is attached to an oligonucleotide via a more complex conjugate linker comprising one or more conjugate linker moieties, which are sub-units making up a conjugate linker. In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methyl cytosine, 4-N-benzoyl-5-methyl cytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate or phosphodiester linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxynucleoside that is attached to either the 3' or 5'-terminal nucleoside of an oligonucleotide by a phosphodiester internucleoside linkage and covalently attached to the remainder of the conjugate linker or conjugate moiety by a phosphate or phosphorothioate internucleoside linkage. In certain such embodiments, the cleavable moiety is 2'-deoxyadenosine.

3. Cell-Targeting Moieties

In certain embodiments, a conjugate group comprises a cell-targeting moiety. In certain embodiments, a conjugate group has the general formula:

wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group. In certain embodiments, cell-targeting moieties comprise three tethered ligands covalently attached to a branching group.

B. Certain Terminal Groups

In certain embodiments, oligomeric compounds comprise one or more terminal groups. In certain such embodiments, oligomeric compounds comprise a stabilized 5'-phosphate. Stabilized 5'-phosphates include, but are not limited to 5'-phosphonates, including, but not limited to 5'-vinylphosphonates. In certain embodiments, terminal groups comprise one or more abasic nucleosides and/or inverted nucleosides. In certain embodiments, terminal groups comprise one or more 2'-linked nucleosides. In certain such embodiments, the 2'-linked nucleoside is an abasic nucleoside.

III. Oligomeric Duplexes

In certain embodiments, oligomeric compounds described herein comprise an oligonucleotide, having a nucleobase sequence complementary to that of a target nucleic acid. In certain embodiments, an oligomeric compound is paired with a second oligomeric compound to form an oligomeric duplex. Such oligomeric duplexes comprise a first oligomeric compound having a portion complementary to a target nucleic acid and a second oligomeric compound having a portion complementary to the first oligomeric compound. In certain embodiments, the first oligomeric compound of an oligomeric duplex comprises or consists of (1) a modified or unmodified oligonucleotide and optionally a conjugate group and (2) a second modified or unmodified oligonucleotide and optionally a conjugate group. Either or both oligomeric compounds of an oligomeric duplex may comprise a conjugate group. The oligonucleotides of each oligomeric compound of an oligomeric duplex may include non-complementary overhanging nucleosides.

IV. Antisense Activity

In certain embodiments, oligomeric compounds and oligomeric duplexes are capable of hybridizing to a target nucleic acid, resulting in at least one antisense activity; such oligomeric compounds and oligomeric duplexes are antisense compounds. In certain embodiments, antisense compounds have antisense activity when they reduce the amount or activity of a target nucleic acid by 25% or more in the standard cell assay. In certain embodiments, antisense com-

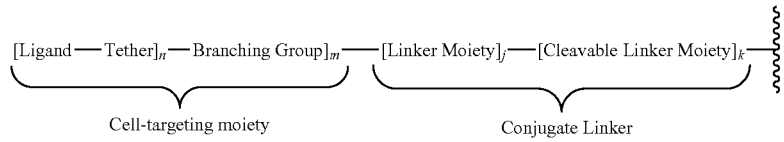

pounds selectively affect one or more target nucleic acid. Such antisense compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, described herein are antisense compounds that are sufficiently "DNA-like" to elicit RNase H activity. In certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute. Antisense compounds that are loaded into RISC are RNAi compounds. RNAi compounds may be double-stranded (siRNA) or single-stranded (ssRNA).

In certain embodiments, hybridization of an antisense compound to a target nucleic acid does not result in recruitment of a protein that cleaves that target nucleic acid. In certain embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein and/or a phenotypic change in a cell or subject.

V. Certain Target Nucleic Acids

In certain embodiments, oligomeric compounds comprise or consist of an oligonucleotide comprising a portion that is complementary to a target nucleic acid. In certain embodiments, the target nucleic acid is an endogenous RNA molecule. In certain embodiments, the target nucleic acid encodes a protein. In certain such embodiments, the target nucleic acid is selected from: a mature mRNA and a pre-mRNA, including intronic, exonic and untranslated regions. In certain embodiments, the target nucleic acid is a mature mRNA. In certain embodiments, the target nucleic acid is a pre-mRNA. In certain embodiments, the target region is entirely within an intron. In certain embodiments, the target region spans an intron/exon junction. In certain embodiments, the target region is at least 50% within an intron.

A. Complementarity/Mismatches to the Target Nucleic Acid

It is possible to introduce mismatch bases without eliminating activity. For example, Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo. Maher and Dolnick (Nuc. Acid. Res. 16:3341-3358, 1988) tested a series of tandem 14 nucleobase oligonucleotides, and a 28 and 42 nucleobase oligonucleotides comprised of the sequence of two or three of the tandem oligonucleotides, respectively, for their ability to arrest translation of human DHFR in a rabbit reticulocyte assay. Each of the three 14 nucleobase oligonucleotides alone was able to inhibit translation, albeit at a more modest level than the 28 or 42 nucleobase oligonucleotides.

In certain embodiments, oligonucleotides are complementary to the target nucleic acid over the entire length of the oligonucleotide. In certain embodiments, oligonucleotides are 99%, 95%, 90%, 85%, or 80% complementary to the target nucleic acid. In certain embodiments, oligonucleotides are at least 80% complementary to the target nucleic acid over the entire length of the oligonucleotide and comprise a portion that is 100% or fully complementary to a target nucleic acid. In certain embodiments, the portion of full complementarity is 6, 7, 8, 9, 10, 11, 12, 13, 14, 15, 16, 17, 18, 19, 20, 21, 22, 23, or 24 nucleobases in length.

In certain embodiments, oligonucleotides comprise one or more mismatched nucleobases relative to the target nucleic acid. In certain embodiments, antisense activity against the target is reduced by such mismatch, but activity against a non-target is reduced by a greater amount. Thus, in certain embodiments selectivity of the oligonucleotide is improved. In certain embodiments, the mismatch is specifically positioned within an oligonucleotide having a gapmer motif. In certain embodiments, the mismatch is at position 1, 2, 3, 4, 5, 6, 7, 8, 9, 10, or 11 from the 5'-end of the gap region. In certain embodiments, the mismatch is at position 1, 2, 3, 4, 5, or 6 from the 5'-end of the 5' wing region or the 3' wing region.

B. PLP1

In certain embodiments, oligomeric compounds comprise or consist of an oligonucleotide that is complementary to a target nucleic acid, wherein the target nucleic acid is a PLP1 nucleic acid. In certain embodiments, the PLP1 nucleic acid has the sequence set forth in SEQ ID NO: 1 (GENBANK Accession No. NM_001128834.2) or SEQ ID NO: 2 (GENBANK Accession No. NC_000023.11 truncated from nucleotides 103773001 to 103795000).

In certain embodiments, contacting a cell with an oligomeric compound complementary to SEQ ID NO: 1 or SEQ ID NO: 2 reduces the amount of PLP1 RNA in a cell, and in certain embodiments reduces the amount of PLP1 protein in a cell. In certain embodiments, contacting a cell with a modified oligonucleotide complementary to SEQ ID NO: 1 or SEQ ID NO: 2 reduces the amount of PLP1 RNA in a cell, and in certain embodiments reduces the amount of PLP1 protein in a cell. In certain embodiments, the cell is in vitro. In certain embodiments, the cell is in a subject. In certain embodiments, contacting a cell in a subject with an oligomeric compound complementary to SEQ ID NO: 1 or SEQ ID NO: 2 ameliorates one or more symptom or hallmark of a leukodystrophy. In certain embodiments, the leukodystrophy is PMD. In certain embodiments, the symptom or hallmark is selected from hypotonia, nystagmus, optic atrophy, respiratory distress, motor delays, cognitive dysfunction, speech dysfunction, spasticity, ataxia, seizures, and choreiform movements. In certain embodiments, the oligomeric compound consists of a modified oligonucleotide.

In certain embodiments, an oligomeric compound complementary to SEQ ID NO: 1 or SEQ ID NO: 2 is capable of reducing the detectable amount of PLP1 RNA in vitro by at least 10%, at least 20%, at least 30%, at least 40%, at least 50%, at least 60%, at least 70%, at least 80%, or at least 90% in the standard in vitro assay. In certain embodiments, an oligomeric compound complementary to SEQ ID NO: 1 or SEQ ID NO: 2 is capable of reducing the detectable amount of PLP1 protein in vitro by at least 10%, at least 20%, at least 30%, at least 40%, at least 50%, at least 60%, at least 70%, at least 80%, or at least 90% in the standard in vitro assay. In certain embodiments, an oligomeric compound complementary to SEQ ID NO: 1 or SEQ ID NO: 2 is capable of reducing the detectable amount of PLP1 RNA in vivo by at least 10%, at least 20%, at least 30%, at least 40%, at least 50%, at least 60%, at least 70%, at least 80%, or at least 90% when administered according to the standard in vivo assay. In certain embodiments, an oligomeric compound complementary to SEQ ID NO: 1 or SEQ ID NO: 2 is capable of reducing the detectable amount of PLP1 protein in vivo by at least 10%, at least 20%, at least 30%, at least 40%, at least 50%, at least 60%, at least 70%, at least 80%, or at least 90% when administered according to the standard in vivo assay. In certain embodiments, an oligomeric compound complementary to SEQ ID NO: 1 or SEQ ID NO: 2, is capable of reducing the detectable amount of PLP1 RNA in the CSF of a subject by at least 10%, at least 20%, at least 30%, at least 40%, at least 50%, at least 60%, at least 70%, at least 80%, or at least 90%. In certain embodiments, an oligomeric compound complementary to SEQ ID NO: 1 or SEQ ID NO: 2, is capable of reducing the detectable amount of PLP1 protein in the CSF of a subject by at least 10%, at least 20%, at least 30%, at least 40%, at least 50%, at least 60%, at least 70%, at least 80%, or at least 90%.

C. Certain Target Nucleic Acids in Certain Tissues

In certain embodiments, oligomeric compounds comprise or consist of an oligonucleotide comprising a region that is complementary to a target nucleic acid, wherein the target nucleic acid is expressed in a pharmacologically relevant tissue. In certain embodiments, the pharmacologically relevant tissues are the cells and tissues that comprise the central nervous system (CNS). Such tissues include the brain and spinal cord. In certain embodiments, the pharmacologically relevant tissues include white matter tracts across the brain and spinal cord, such tissues include the corpus callosum, cortex, cerebellum, hippocampus, brain stem, striatum, and spinal cord. In certain embodiments, the pharmacologically relevant tissues include the cortex, cerebellum, hippocampus, brain stem, and spinal cord. In certain embodiments, the pharmacologically relevant cells are oligodendrocytes and oligodendrocyte progenitor cells. In certain embodiments, the pharmacologically relevant cells are Schwann cells or Schwann cell progenitors.

VI. Certain Pharmaceutical Compositions

In certain embodiments, described herein are pharmaceutical compositions comprising one or more oligomeric compounds. In certain embodiments, the one or more oligomeric compounds each consists of a modified oligonucleotide. In certain embodiments, the pharmaceutical composition comprises a pharmaceutically acceptable diluent or carrier. In certain embodiments, a pharmaceutical composition comprises or consists of a sterile saline solution and one or more oligomeric compound. In certain embodiments, the sterile saline is pharmaceutical grade saline. In certain embodiments, a pharmaceutical composition comprises or consists of one or more oligomeric compound and sterile water. In certain embodiments, the sterile water is pharmaceutical grade water. In certain embodiments, a pharmaceutical composition comprises or consists of one or more oligomeric compound and phosphate-buffered saline (PBS). In certain embodiments, the sterile PBS is pharmaceutical grade PBS. In certain embodiments, a pharmaceutical composition comprises or consists of one or more oligomeric compound and artificial cerebrospinal fluid ("artificial CSF" or "aCSF"). In certain embodiments, the artificial cerebrospinal fluid is pharmaceutical grade.

In certain embodiments, a pharmaceutical composition comprises a modified oligonucleotide and artificial cerebrospinal fluid. In certain embodiments, a pharmaceutical composition consists of a modified oligonucleotide and artificial cerebrospinal fluid. In certain embodiments, a pharmaceutical composition consists essentially of a modified oligonucleotide and artificial cerebrospinal fluid. In certain embodiments, the artificial cerebrospinal fluid is pharmaceutical grade.

In certain embodiments, pharmaceutical compositions comprise one or more oligomeric compound and one or more excipients. In certain embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, oligomeric compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an oligomeric compound encompass any pharmaceutically acceptable salts of the oligomeric compound, esters of the oligomeric compound, or salts of such esters. In certain embodiments, pharmaceutical compositions comprising oligomeric compounds comprising one or more oligonucleotide, upon administration to a subject, including a human, are capable of providing (directly or indirectly) the biologically active metabolite or residue thereof. Accordingly, for example, the disclosure is also drawn to pharmaceutically acceptable salts of oligomeric compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an oligomeric compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents comprising an oligomeric compound provided herein to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, intrathecal (IT), intracerebroventricular (ICV), intraneural, perineural, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes.

Under certain conditions, certain compounds disclosed herein act as acids. Although such compounds may be drawn or described in protonated (free acid) form, or ionized and in association with a cation (salt) form, aqueous solutions of such compounds exist in equilibrium among such forms. For example, a phosphate linkage of an oligonucleotide in aqueous solution exists in equilibrium among free acid, anion and salt forms. Unless otherwise indicated, compounds described herein are intended to include all such forms. Moreover, certain oligonucleotides have several such linkages, each of which is in equilibrium. Thus, oligonucleotides in solution exist in an ensemble of forms at multiple positions all at equilibrium. The term "oligonucleotide" is intended to include all such forms. Drawn structures necessarily depict a single form. Nevertheless, unless otherwise indicated, such drawings are likewise intended to include corresponding forms. Herein, a structure depicting the free acid of a compound followed by the term "or salt thereof" expressly includes all such forms that may be fully or partially protonated/de-protonated/in association with a cation. In certain instances, one or more specific cation is identified.

In certain embodiments, modified oligonucleotides or oligomeric compounds are in aqueous solution with sodium. In certain embodiments, modified oligonucleotides or oligomeric compounds are in aqueous solution with potassium. In certain embodiments, modified oligonucleotides or oligomeric compounds are in PBS. In certain embodiments, modified oligonucleotides or oligomeric compounds are in water. In certain such embodiments, the pH of the solution is adjusted with NaOH and/or HCl to achieve a desired pH.

Herein, certain specific doses are described. A dose may be in the form of a dosage unit. For clarity, a dose (or dosage unit) of a modified oligonucleotide or an oligomeric compound in milligrams indicates the mass of the free acid form of the modified oligonucleotide or oligomeric compound. As described above, in aqueous solution, the free acid is in equilibrium with anionic and salt forms. However, for the purpose of calculating dose, it is assumed that the modified oligonucleotide or oligomeric compound exists as a solvent-free, sodium-acetate free, anhydrous, free acid. For example, where a modified oligonucleotide or an oligomeric compound is in solution comprising sodium (e.g., saline), the modified oligonucleotide or oligomeric compound may be partially or fully de-protonated and in association with Na+ ions. However, the mass of the protons are nevertheless counted toward the weight of the dose, and the mass of the Na+ ions are not counted toward the weight of the dose. Thus, for example, a dose, or dosage unit, of 10 mg of Compound No. 1362458 equals the number of fully protonated molecules that weighs 10 mg. This would be equivalent to 10.47 mg of solvent-free, sodium acetate-free, anhydrous sodiated Compound No. 1362458. And, for example, a dose, or dosage unit, of 10 mg of Compound No. 1523605 equals the number of fully protonated molecules that weighs 10 mg. This would be equivalent to 10.59 mg of solvent-free, sodium acetate-free, anhydrous sodiated Compound No. 1523605. When an oligomeric compound comprises a conjugate group, the mass of the conjugate group is included in calculating the dose of such oligomeric compound. If the conjugate group also has an acid, the conjugate group is likewise assumed to be fully protonated for the purpose of calculating dose.

VII. Certain Compositions

1. Compound No. 1363235

In certain embodiments, Compound No. 1363235 is characterized as a 5-10-5 MOE gapmer having a sequence (from 5' to 3') of TGTAGTACAAATCTTTCCTT (SEQ ID NO: 2101), wherein each of nucleosides 1-5 and 16-20 (from 5' to 3') are 2'-MOE nucleosides and each of nucleosides 6-15 are 2'-β-D-deoxynucleosides, wherein the internucleoside linkages between nucleosides 2 to 3, 3 to 4, 4 to 5, 5 to 6, 16 to 17, and 17 to 18 are phosphodiester internucleoside linkages, the internucleoside linkages between nucleosides 1 to 2, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

In certain embodiments, Compound No. 1363235 is represented by the following chemical notation:

(SEQ ID NO: 2101)
$T_{es}G_{eo}T_{eo}A_{eo}G_{eo}T_{ds}A_{ds}{}^{m}C_{ds}A_{ds}A_{ds}A_{ds}T_{ds}{}^{m}C_{ds}T_{ds}T_{ds}T_{eo}$ ${}^{m}C_{eo}{}^{m}C_{es}T_{es}T_{e'}$ wherein:
A=an adenine nucleobase,
$^m$C=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

In certain embodiments, Compound No. 1363235 is represented by the following chemical structure:

Structure 1. Compound No. 1363235

(SEQ ID NO: 2101)

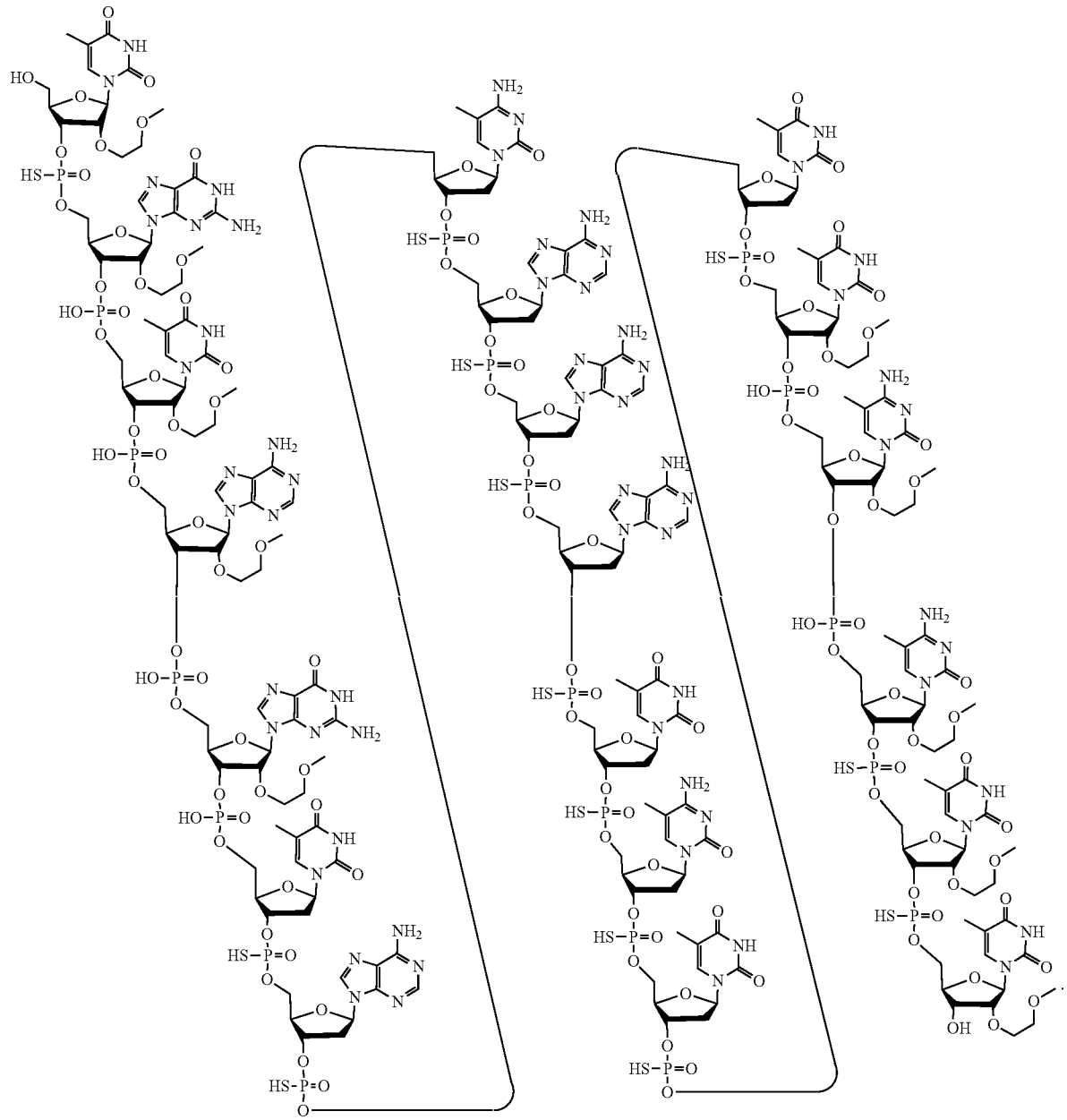

In certain embodiments, the sodium salt of Compound No. 1363235 is represented by the following chemical structure:

Structure 2. The sodium salt of Compound No. 1363235

(SEQ ID NO: 2101)

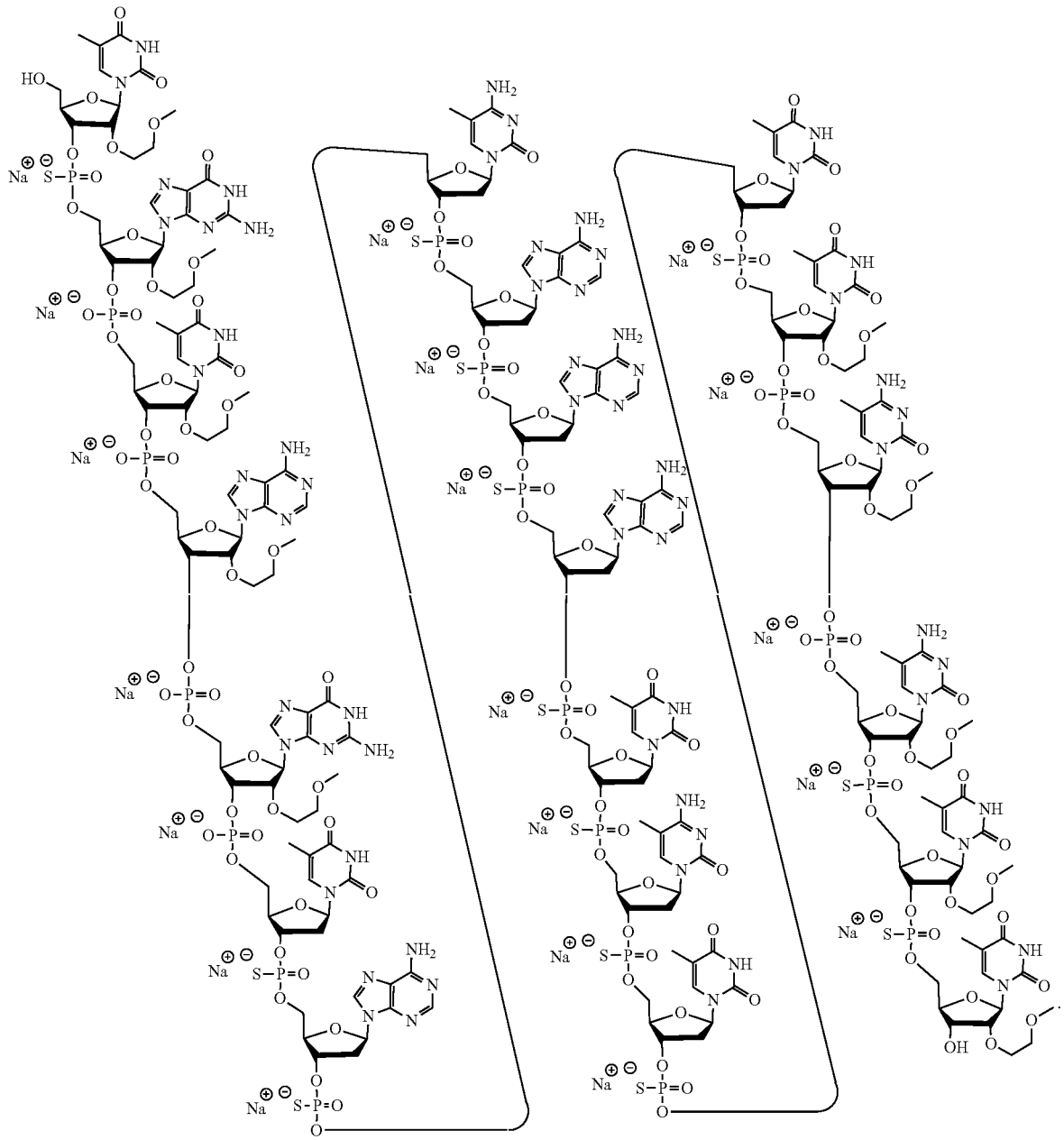

2. Compound No. 1523601

In certain embodiments, Compound No. 1523601 is characterized as a 6-10-4 MOE gapmer having a sequence (from 5' to 3') of ACAAATCTTTCCTTCAATTA (SEQ ID NO: 682), wherein each of nucleosides 1-6 and 17-20 (from 5' to 3') are 2'-MOE nucleosides and each of nucleosides 7-16 are 2'-β-D-deoxynucleosides, wherein the internucleoside linkages between nucleosides 2 to 3, 3 to 4, 4 to 5, 5 to 6, 6 to 7, and 17 to 18 are phosphodiester internucleoside linkages, the internucleoside linkages between nucleosides 1 to 2, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate internucleoside linkages, and wherein each cytosine is a 5-methyl cytosine.

In certain embodiments, Compound No. 1523601 is represented by the following chemical notation:

(SEQ ID NO: 682)

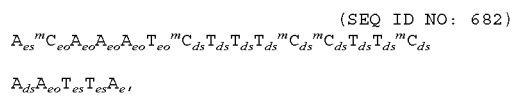

wherein:

A=an adenine nucleobase, PGP-122 DNA
$^{m}$C=a 5-methyl cytosine nucleobase,

G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

In certain embodiments, Compound No. 1523601 is represented by the following chemical structure:

Structure 3. Compound No. 1523601

(SEQ ID NO: 682)

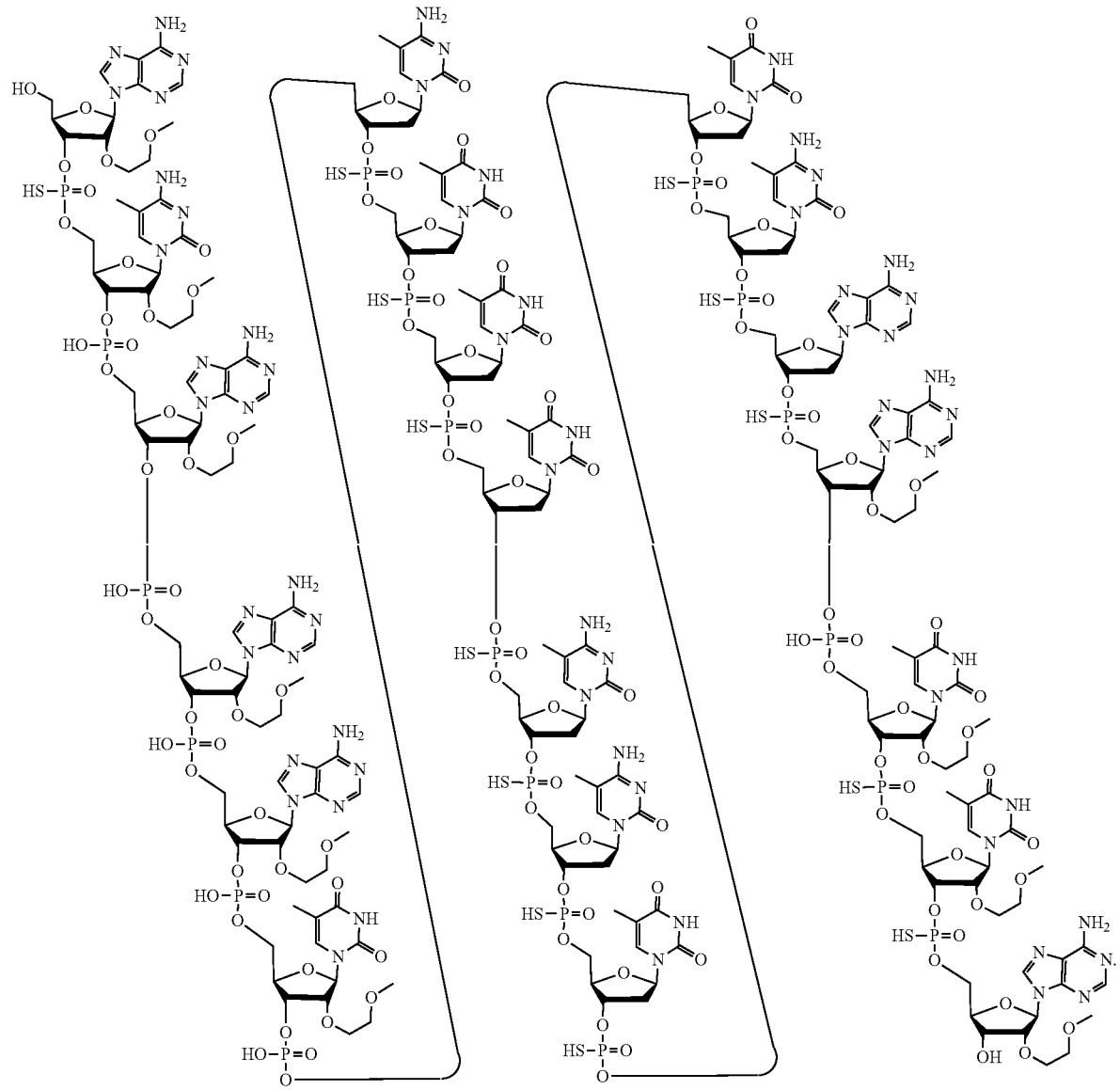

In certain embodiments, the sodium salt of Compound No. 1523601 is represented by the following chemical structure:

Structure 4. The sodium salt of Compound No. 1523601

(SEQ ID NO: 682)

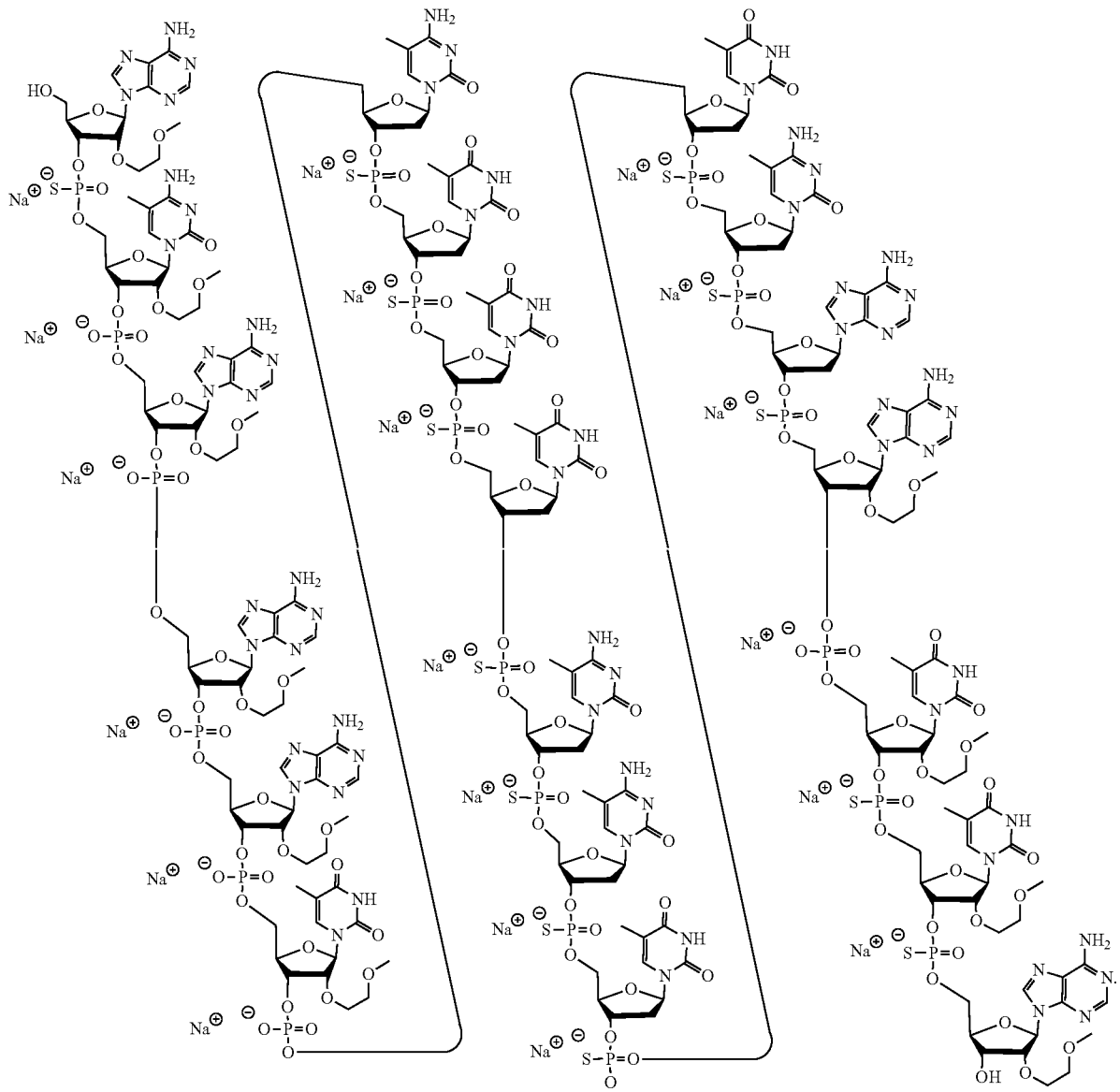

3. Compound No. 1523605

In certain embodiments, Compound No. 1523605 is characterized as a 6-10-4 MOE gapmer having a sequence (from 5' to 3') of CAGATGTTCATCTCTTCACA (SEQ ID NO: 1124), wherein each of nucleosides 1-6 and 17-20 (from 5' to 3') are 2'-MOE nucleosides and each of nucleosides 7-16 are 2'-β-D-deoxynucleosides, wherein the internucleoside linkages between nucleosides 2 to 3, 3 to 4, 4 to 5, 5 to 6, 6 to 7, and 17 to 18 are phosphodiester internucleoside linkages, the internucleoside linkages between nucleosides 1 to 2, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate internucleoside linkages, and wherein each cytosine is a 5-methyl cytosine.

In certain embodiments, Compound No. 1523605 is represented by the following chemical notation:

(SEQ ID NO: 1124)

$^{m}C_{es}A_{eo}G_{eo}A_{eo}T_{eo}G_{eo}T_{ds}T_{ds}{}^{m}C_{ds}A_{ds}T_{ds}{}^{m}C_{ds}T_{ds}{}^{m}C_{ds}T_{ds}$
$T_{ds}{}^{m}C_{eo}A_{es}{}^{m}C_{es}A_{e}$, wherein:
A=an adenine nucleobase, PGP-123 DNA
$^{m}$C=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

In certain embodiments, Compound No. 1523605 is represented by the following chemical structure:

Structure 5. Compound No. 1523605
(SEQ ID NO: 1124)
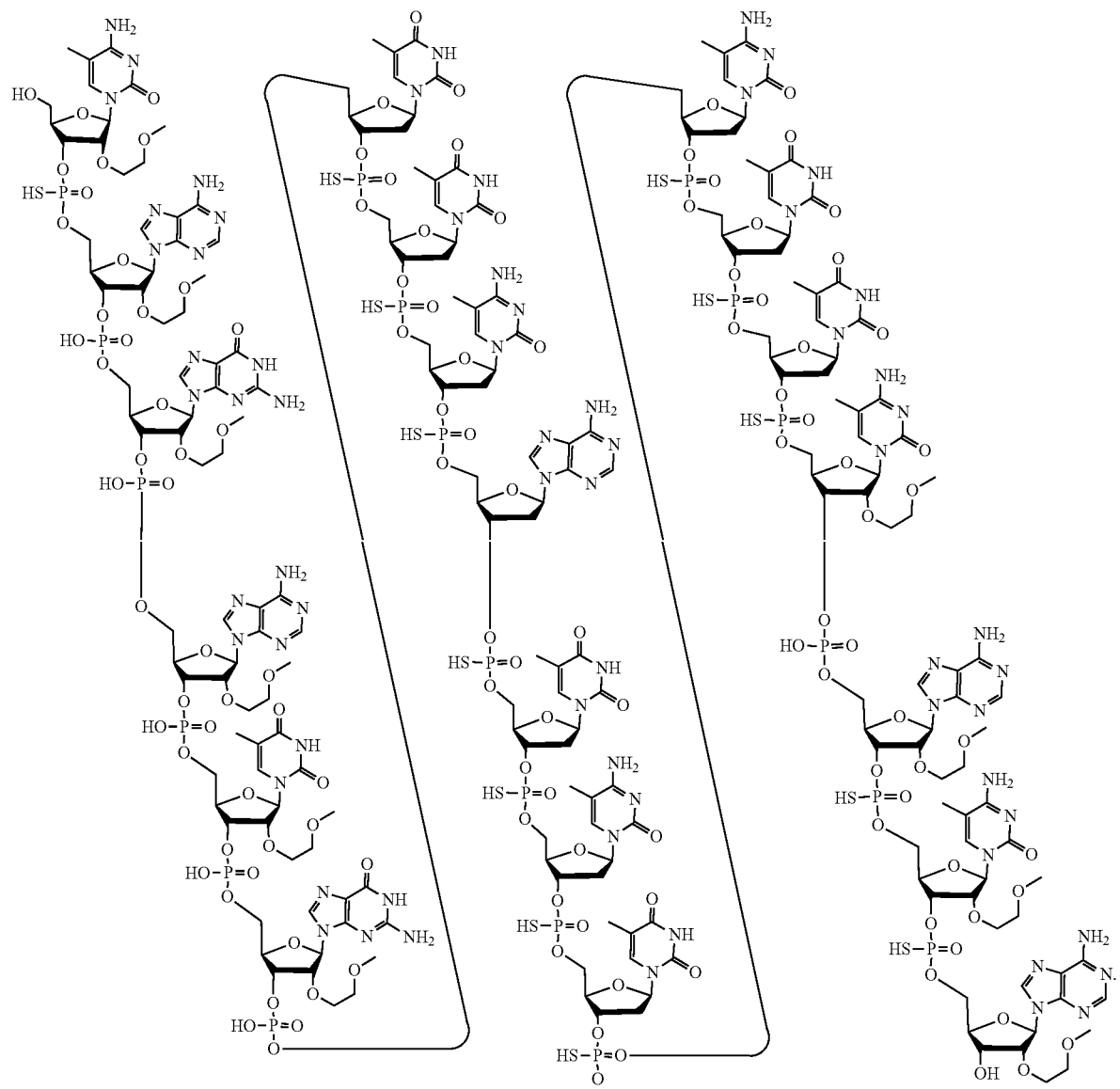
In certain embodiments, the sodium salt of Compound No. 1523605 is represented by the following chemical structure:

Structure 6. The sodium salt of Compound No. 1523605

(SEQ ID NO: 1124)

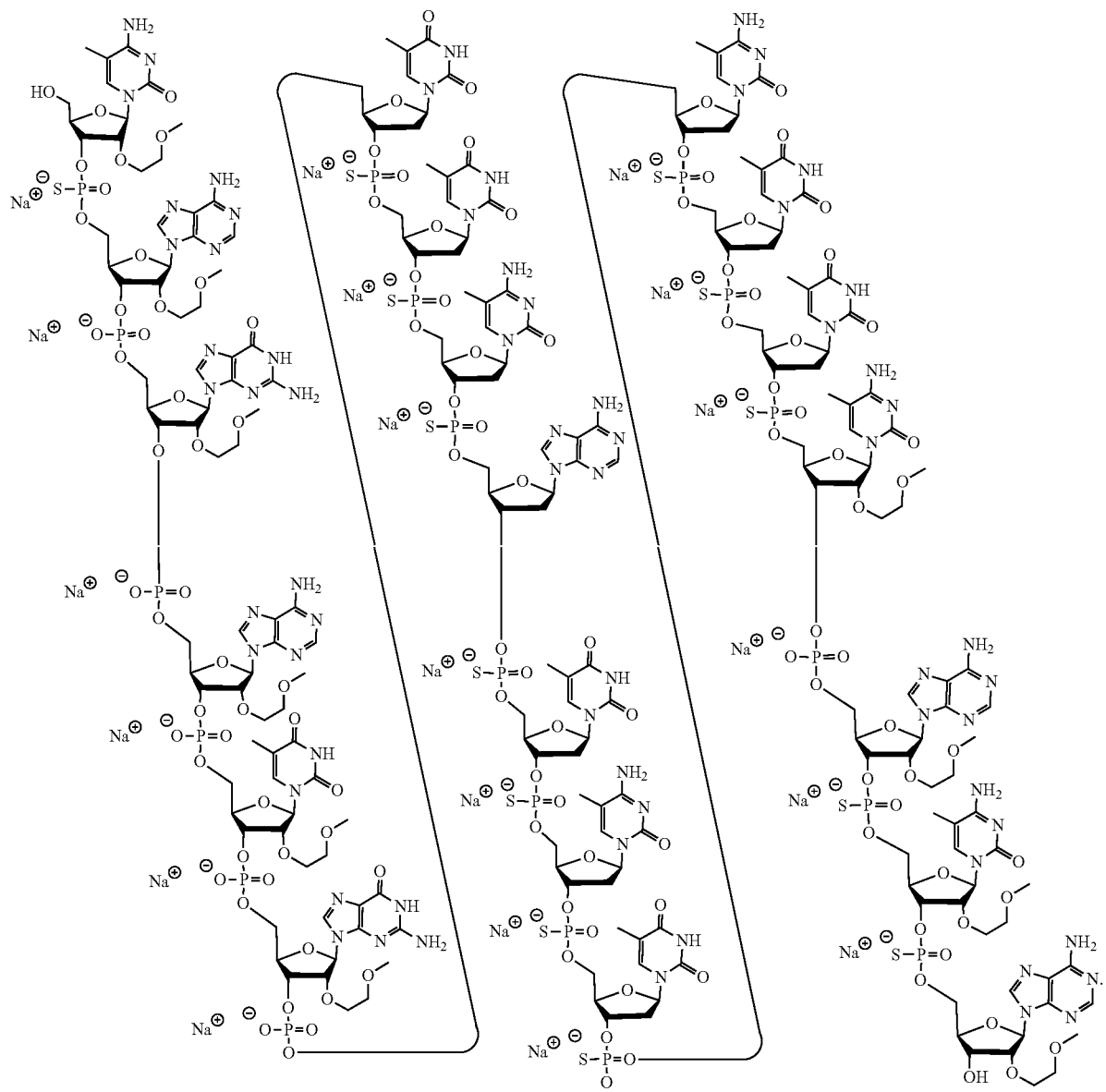

4. Compound No. 1523608

In certain embodiments, Compound No. 1523608 is characterized as a 6-10-4 MOE gapmer having a sequence (from 5' to 3') of CATCAGATGTTCATCTCTTC (SEQ ID NO: 2145), wherein each of nucleosides 1-6 and 17-20 (from 5' to 3') are 2'-MOE nucleosides and each of nucleosides 7-16 are 2'-β-D-deoxynucleosides, wherein the internucleoside linkages between nucleosides 2 to 3, 3 to 4, 4 to 5, 5 to 6, 6 to 7, and 17 to 18 are phosphodiester internucleoside linkages, the internucleoside linkages between nucleosides 1 to 2, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate internucleoside linkages, and wherein each cytosine is a 5-methyl cytosine.

In certain embodiments, Compound No. 1523608 is represented by the following chemical notation:

(SEQ ID NO: 2145)
$^mC_{es}A_{eo}T_{eo}{}^mC_{eo}A_{eo}G_{eo}A_{ds}T_{ds}G_{ds}T_{ds}T_{ds}{}^mC_{ds}A_{ds}T_{ds}{}^mC_{ds}$
$T_{ds}{}^mC_{eo}T_{es}T_{es}{}^mC_{e'}$ wherein:
A=an adenine nucleobase,
$^mC$=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

In certain embodiments, Compound No. 1523608 is represented by the following chemical structure:

Structure 7. Compound No. 1523608
(SEQ ID NO: 2145)
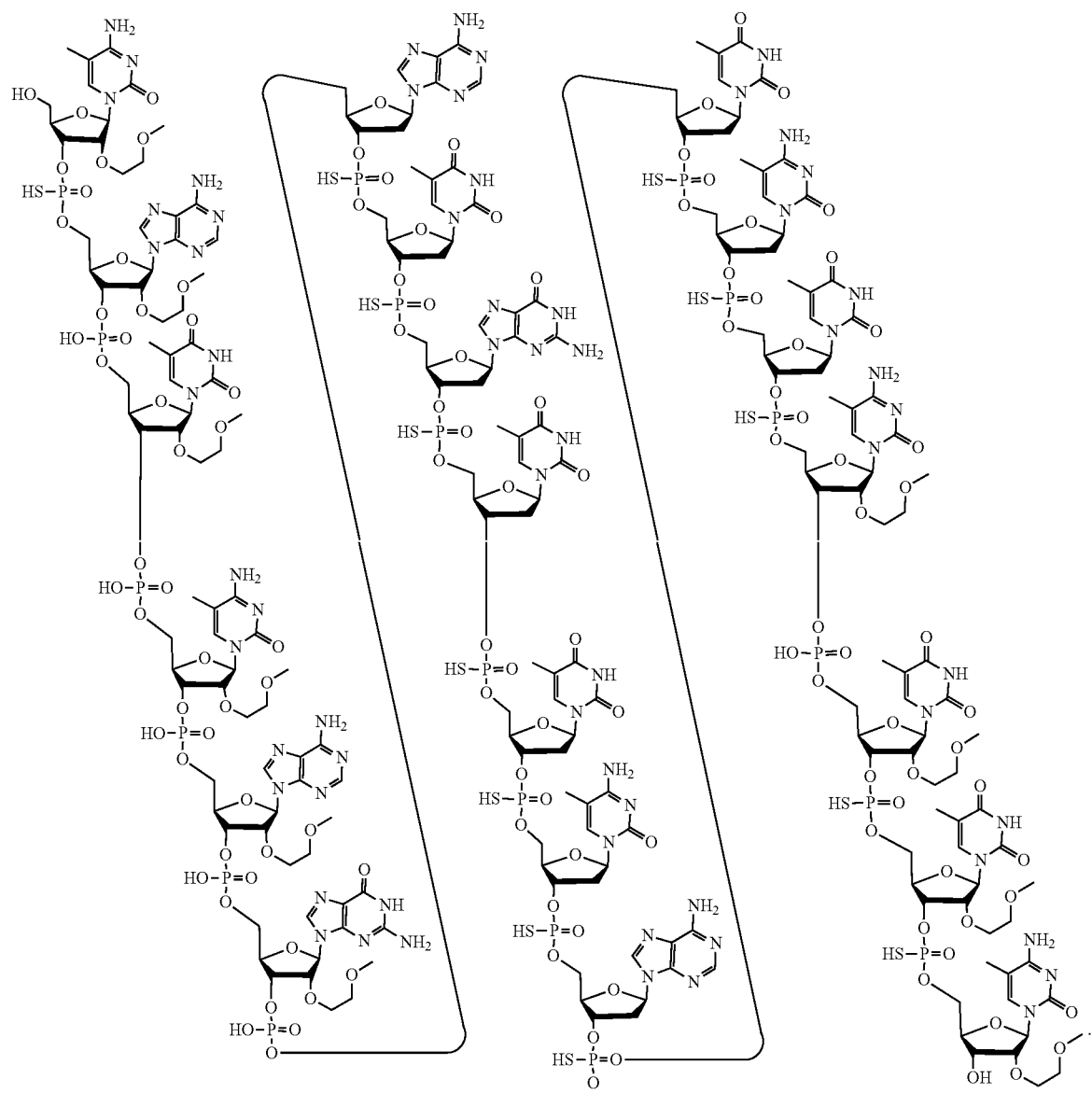
In certain embodiments, the sodium salt of Compound No. 1523608 is represented by the following chemical structure:

Structure 8. The sodium salt of Compound No. 1523608

(SEQ ID NO: 2145)

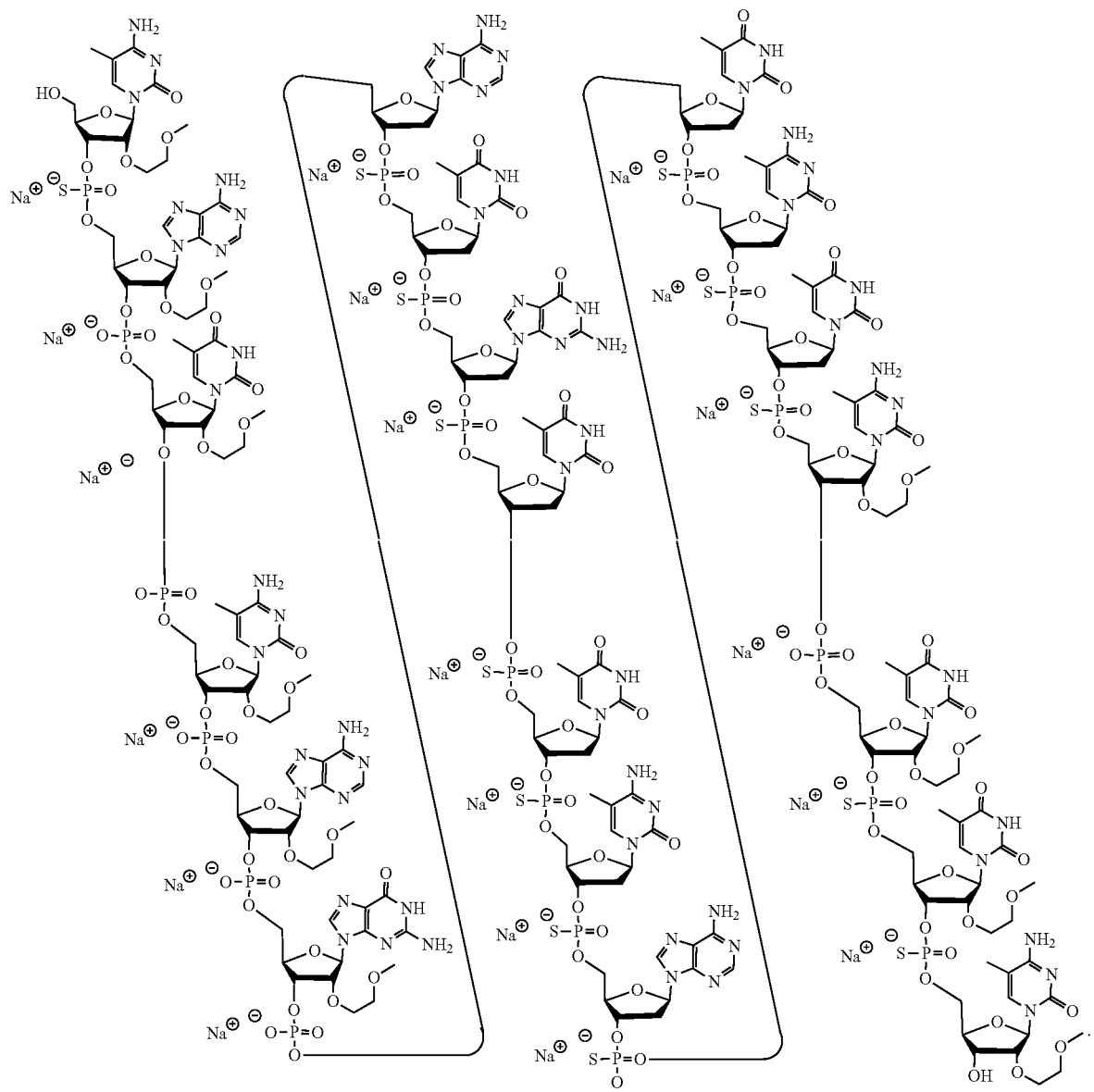

5. Compound No. 1362445

In certain embodiments, Compound No. 1362445 is characterized as a 5-10-5 MOE gapmer having a sequence (from 5' to 3') of CCCAATAGATTCAACTAGCC (SEQ ID NO: 134), wherein each of nucleosides 1-5 and 16-20 (from 5' to 3') are 2'-MOE nucleosides and each of nucleosides 6-15 are 2'-β-D-deoxynucleosides, wherein the internucleoside linkages between nucleosides 2 to 3, 3 to 4, 4 to 5, 5 to 6, 16 to 17, and 17 to 18 are phosphodiester internucleoside linkages, the internucleoside linkages between nucleosides 1 to 2, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

In certain embodiments, Compound No. 1362445 is represented by the following chemical notation:

(SEQ ID NO: 134)
$^{m}C_{es}{}^{m}C_{eo}{}^{m}C_{eo}A_{eo}A_{eo}T_{ds}A_{ds}G_{ds}A_{ds}T_{ds}T_{ds}{}^{m}C_{ds}A_{ds}A_{ds}{}^{m}C_{ds}$ $T_{eo}A_{eo}G_{es}{}^{m}C_{es}{}^{m}C_{e}$, wherein:
A=an adenine nucleobase,
$^{m}$C=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

6. Compound No. 1362449

In certain embodiments, Compound No. 1362449 is characterized as a 5-10-5 MOE gapmer having a sequence (from 5' to 3') of ACACAACTCTTTACAACAAA (SEQ ID NO: 411), wherein each of nucleosides 1-5 and 16-20 (from 5' to 3') are 2'-MOE nucleosides and each of nucleosides 6-15 are 2'-β-D-deoxynucleosides, wherein the internucleoside linkages between nucleosides 2 to 3, 3 to 4, 4 to 5, 5 to 6, 16 to 17, and 17 to 18 are phosphodiester internucleoside linkages, the internucleoside linkages between nucleosides 1 to 2, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

In certain embodiments, Compound No, 1362449 is represented by the following chemical notation:

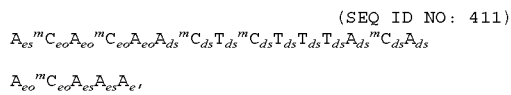
(SEQ ID NO: 411)

wherein:
A=an adenine nucleobase,
$^m$C=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

7. Compound No. 1362458

In certain embodiments, Compound No. 1362458 is characterized as a 5-10-5 MOE gapmer having a sequence (from 5' to 3') of TCTCCAGACATTTCTGATGC (SEQ ID NO: 934), wherein each of nucleosides 1-5 and 16-20 (from 5' to 3') are 2'-MOE nucleosides and each of nucleosides 6-15 are 2'-β-D-deoxynucleosides, wherein the internucleoside linkages between nucleosides 2 to 3, 3 to 4, 4 to 5, 5 to 6, 16 to 17, and 17 to 18 are phosphodiester internucleoside linkages, the internucleoside linkages between nucleosides 1 to 2, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

In certain embodiments, Compound No. 1362458 is represented by the following chemical notation:

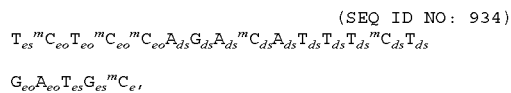
(SEQ ID NO: 934)

wherein:
A=an adenine nucleobase,
$^m$C=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

8. Compound No. 1362602

In certain embodiments, Compound No. 1362602 is characterized as a 5-10-5 MOE gapmer having a sequence (from 5' to 3') of GTGTGTTAAAATTGCAATTC (SEQ ID NO: 1238), wherein each of nucleosides 1-5 and 16-20 (from 5' to 3') are 2'-MOE nucleosides and each of nucleosides 6-15 are 2'-β-D-deoxynucleosides, wherein the internucleoside linkages between nucleosides 2 to 3, 3 to 4, 4 to 5, 5 to 6, 16 to 17, and 17 to 18 are phosphodiester internucleoside linkages, the internucleoside linkages between nucleosides 1 to 2, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

In certain embodiments, Compound No. 1362602 is represented by the following chemical notation:

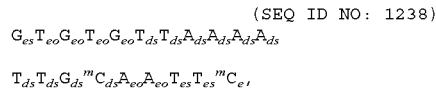
(SEQ ID NO: 1238)

wherein:
A=an adenine nucleobase,
$^m$C=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

9. Compound No. 1362842

In certain embodiments, Compound No. 1362842 is characterized as a 5-10-5 MOE gapmer having a sequence (from 5' to 3') of ATTGCAATTCTATATCAGAA (SEQ ID NO: 2010), wherein each of nucleosides 1-5 and 16-20 (from 5' to 3') are 2'-MOE nucleosides and each of nucleosides 6-15 are 2'-β-D-deoxynucleosides, wherein the internucleoside linkages between nucleosides 2 to 3, 3 to 4, 4 to 5, 5 to 6, 16 to 17, and 17 to 18 are phosphodiester internucleoside linkages, the internucleoside linkages between nucleosides 1 to 2, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

In certain embodiments, Compound No. 1362842 is represented by the following chemical notation:

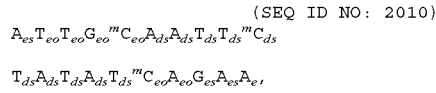
(SEQ ID NO: 2010)

wherein:
A=an adenine nucleobase,
$^m$C=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

10. Compound No. 1362892

In certain embodiments, Compound No. 1362892 is characterized as a 5-10-5 MOE gapmer having a sequence (from 5' to 3') of ATGTGATCTATATCAGGAGA (SEQ ID NO: 1772), wherein each of nucleosides 1-5 and 16-20 (from 5' to 3') are 2'-MOE nucleosides and each of nucleosides 6-15 are 2'-β-D-deoxynucleosides, wherein the internucleoside linkages between nucleosides 2 to 3, 3 to 4, 4 to 5, 5 to 6, 16 to 17, and 17 to 18 are phosphodiester internucleoside linkages, the internucleoside linkages between nucleosides 1 to 2, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

In certain embodiments, Compound No. 1362892 is represented by the following chemical notation:

(SEQ ID NO: 1772)
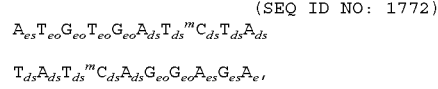

wherein:
A=an adenine nucleobase,
$^{m}$C=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

11. Compound No. 1363013

In certain embodiments, Compound No. 1363013 is characterized as a 5-10-5 MOE gapmer having a sequence (from 5' to 3') of ACCAGAGGGCCATCTCAGGT (SEQ ID NO: 881), wherein each of nucleosides 1-5 and 16-20 (from 5' to 3') are 2'-MOE nucleosides and each of nucleosides 6-15 are 2'-β-D-deoxynucleosides, wherein the internucleoside linkages between nucleosides 2 to 3, 3 to 4, 4 to 5, 5 to 6, 16 to 17, and 17 to 18 are phosphodiester internucleoside linkages, the internucleoside linkages between nucleosides 1 to 2, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

In certain embodiments, Compound No, 1363013 is represented by the following chemical notation:

(SEQ ID NO: 881)
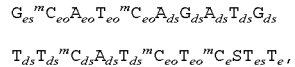

$^{m}C_{ds}A_{ds}T_{ds}{}^{m}C_{ds}T_{ds}{}^{m}C_{eo}A_{eo}G_{es}G_{es}T_{e}$, wherein:
A=an adenine nucleobase,
$^{m}$C=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

12. Compound No. 1363398

In certain embodiments, Compound No. 1363398 is characterized as a 5-10-5 MOE gapmer having a sequence (from 5' to 3') of GCATCAGATGTTCATCTCTT (SEQ ID NO: 1050), wherein each of nucleosides 1-5 and 16-20 (from 5' to 3') are 2'-MOE nucleosides and each of nucleosides 6-15 are 2'-β-D-deoxynucleosides, wherein the internucleoside linkages between nucleosides 2 to 3, 3 to 4, 4 to 5, 5 to 6, 16 to 17, and 17 to 18 are phosphodiester internucleoside linkages, the internucleoside linkages between nucleosides 1 to 2, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

In certain embodiments. Compound No. 1363398 is represented by the following chemical notation:

(SEQ ID NO: 1050)
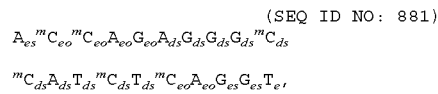

wherein:
A=an adenine nucleobase,
$^{m}$C=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

13. Compound No. 1363557

In certain embodiments, Compound No. 1363557 is characterized as a 5-10-5 MOE gapmer having a sequence (from 5' to 3') of CCTCCATTCCTTTGTGACTT (SEQ ID NO: 1449), wherein each of nucleosides 1-5 and 16-20 (from 5' to 3') are 2'-MOE nucleosides and each of nucleosides 6-15 are 2'-β-D-deoxynucleosides, wherein the internucleoside linkages between nucleosides 2 to 3, 3 to 4, 4 to 5, 5 to 6, 16 to 17, and 17 to 18 are phosphodiester internucleoside linkages, the internucleoside linkages between nucleosides 1 to 2, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

In certain embodiments, Compound No. 1363557 is represented by the following chemical notation:

(SEQ ID NO: 1449)
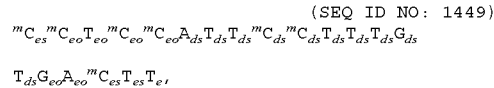

$T_{ds}G_{eo}A_{eo}{}^{m}C_{es}T_{es}T_{e}$, wherein:
A=an adenine nucleobase,
$^{m}$C=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

VIII. Certain Hotspot Regions

In certain embodiments, nucleobases in the ranges specified below comprise a hotspot region of PLP1 nucleic acid. In certain embodiments, modified oligonucleotides that are complementary to a portion of a hotspot region of PLP1 nucleic acid achieve an average of 50% or greater reduction of PLP1 RNA in vitro in the standard in vitro assay. In certain embodiments, modified oligonucleotides that are complementary to a portion of a hotspot region of PLP1 nucleic acid achieve an average of 50% or greater reduction of PLP1 RNA in vivo in the standard in vivo assay.

1. Nucleobases 9198-9222 of SEQ ID NO: 2

In certain embodiments, nucleobases 9198-9222 of SEQ ID NO: 2 comprise a hotspot region. In certain embodiments, modified oligonucleotides are complementary to a portion of nucleobases 9198-9222 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': sooooossssssssssooss or sooooosssssssssssoss, wherein each "s" represents a phosphorothioate internucleoside linkage and each "o" represents a phosphodiester internucleoside linkage.

The nucleobase sequences of SEQ ID NOs: 1050, 1124, 2145, 2151, 2152, and 2153 are complementary to a portion of nucleobases 9198-9222 of SEQ ID NO: 2.

The nucleobase sequences of Compound Nos.: 1363398, 1363516, 1523604, 1523605, 1523606, 1523607, 1523608, and 1523609 are complementary to a portion of nucleobases 9198-9222 of SEQ ID NO: 2.

In certain embodiments, modified oligonucleotides complementary to a portion of nucleobases 9198-9222 of SEQ ID NO: 2 achieve at least 65% reduction of PLP1 RNA in the standard in vitro assay. In certain embodiments, modified oligonucleotides complementary to a portion of nucleobases 9198-9222 of SEQ ID NO: 2 achieve an average of 71.5% reduction of PLP1 RNA in the standard in vitro assay.

2. Nucleobases 13702-13766 of SEQ ID NO: 2

In certain embodiments, nucleobases 13702-13766 of SEQ ID NO: 2 comprise a hotspot region. In certain embodiments, modified oligonucleotides are complementary to a portion of nucleobases 13702-13766 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': sooooossssssssssooss or sooooosssssssssssoss, wherein each "s" represents a phosphorothioate internucleoside linkage and each "o" represents a phosphodiester internucleoside linkage.

The nucleobase sequences of SEQ ID NOs: 36, 86, 114, 164, 191, 242, 269, 426, 523, 602, 691, and 780 are complementary to a portion of nucleobases 13702-13766 of SEQ ID NO: 2.

The nucleobase sequences of Compound Nos.: 1218139, 1218140, 1218141, 1218142, 1218341, 1218342, 1218343, 1362839, 1363565, 1363589, 1363758, and 1364150 are complementary to a portion of nucleobases 13702-13766 of SEQ ID NO: 2.

In certain embodiments, modified oligonucleotides complementary to a portion of nucleobases 13702-13766 of SEQ ID NO: 2 achieve at least 60% reduction of PLP1 RNA in the standard in vitro assay. In certain embodiments, modified oligonucleotides complementary to a portion of nucleobases 13702-13766 of SEQ ID NO: 2 achieve an average of 68.6% reduction of PLP1 RNA in the standard in vitro assay.

3. Nucleobases 14037-14062 of SEQ ID NO: 2

In certain embodiments, nucleobases 14037-14062 of SEQ ID NO: 2 comprise a hotspot region. In certain embodiments, modified oligonucleotides are complementary to a portion of nucleobases 14037-14062 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': sooooosssssssssssooss or sooooosssssssssssoss, wherein each "s" represents a phosphorothioate internucleoside linkage and each "o" represents a phosphodiester internucleoside linkage.

The nucleobase sequences of SEQ ID NOs: 89, 167, 245, 322, and 323 are complementary to a portion of nucleobases 14037-14062 of SEQ ID NO: 2.

The nucleobase sequences of Compound Nos.: 1218352, 1218353, 1218354, 1362909, 1362866, 1218355, and 1218356 are complementary to a portion of nucleobases 14037-14062 of SEQ ID NO: 2.

In certain embodiments, modified oligonucleotides complementary to a portion of nucleobases 14037-14062 of SEQ ID NO: 2 achieve at least 64% reduction of PLP1 RNA in the standard in vitro assay. In certain embodiments, modified oligonucleotides complementary to a portion of nucleobases 14037-14062 of SEQ ID NO: 2 achieve an average of 79.9% reduction of PLP1 RNA in the standard in vitro assay.

4. Nucleobases 16761-16800 of SEQ ID NO: 2

In certain embodiments, nucleobases 16761-16800 of SEQ ID NO: 2 comprise a hotspot region. In certain embodiments, modified oligonucleotides are complementary to a portion of nucleobases 16761-16800 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': sooooosssssssssssooss or sooooosssssssssssoss, wherein each "s" represents a phosphorothioate internucleoside linkage and each "o" represents a phosphodiester internucleoside linkage.

The nucleobase sequences of SEQ ID NOs: 720, 808, 904, 937, 1058, 1097, 1184, 1278, and 1340 are complementary to a portion of nucleobases 16761-16800 of SEQ ID NO: 2.

The nucleobase sequences of Compound Nos.: 1362547, 1362649, 1362825, 1363052, 1363131, 1363205, 1363559, 1363590, and 1363607 are complementary to a portion of nucleobases 16761-16800 of SEQ ID NO: 2.

In certain embodiments, modified oligonucleotides complementary to a portion of nucleobases 16761-16800 of SEQ ID NO: 2 achieve at least 60% reduction of PLP1 RNA in the standard in vitro assay. In certain embodiments, modified oligonucleotides complementary to a portion of nucleobases 16761-16800 of SEQ ID NO: 2 achieve an average of 70.7% reduction of PLP1 RNA in the standard in vitro assay.

5. Nucleobases 17558-17602 of SEQ ID NO: 2

In certain embodiments, nucleobases 17558-17602 of SEQ ID NO: 2 comprise a hotspot region. In certain embodiments, modified oligonucleotides are complementary to a portion of nucleobases 17558-17602 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': sooooosssssssssssooss or sooooosssssssssssoss, wherein each "s" represents a phosphorothioate internucleoside linkage and each "o" represents a phosphodiester internucleoside linkage.

The nucleobase sequences of SEQ ID NOs: 40, 41, 117, 118, 195, 196, 273, 274, 588, 690 are complementary to a portion of nucleobases 17558-17602 of SEQ ID NO: 2.

The nucleobase sequence of Compound Nos.: 1218154, 1218155, 1218156, 1218157, 1218158, 1218159, 1218160, 1218161, 1363257, 1363439, and 1363756 are complementary to a portion of nucleobases 17558-17602 of SEQ ID NO: 2.

In certain embodiments, modified oligonucleotides complementary to a portion of nucleobases 17558-17602 of SEQ ID NO: 2 achieve at least 62% reduction of PLP1 RNA in the standard in vitro assay. In certain embodiments, modified oligonucleotides complementary to a portion of nucleobases 17558-17602 of SEQ ID NO: 2 achieve an average of 74.6% reduction of PLP1 RNA in the standard in vitro assay.

6. Nucleobases 17615-17667 of SEQ ID NO: 2

In certain embodiments, nucleobases 17615-17667 of SEQ ID NO: 2 comprise a hotspot region. In certain embodiments, modified oligonucleotides are complementary to a portion of nucleobases 17615-17667 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': soooosssssssssssooss or sooooosssssssssssoss, wherein each "s" represents a phosphorothioate internucleoside linkage and each "o" represents a phosphodiester internucleoside linkage.

The nucleobase sequences of SEQ ID NOs: 42, 43, 119, 120, 197, 198, 275, 276, 373, 460, 1431, 1542, 1645, 1850, 1965, and 2109 are complementary to a portion of nucleobases 17615-17667 of SEQ ID NO: 2.

The nucleobase sequences of Compound Nos.: 1218162, 1218163, 1218164, 1218165, 1218166, 1218167, 1218168, 1218169, 1362484, 1362497, 1362517, 1362591, 1362749, 1362970, 1363246, 1363342, 1363415, 1363474, 1363544, 1363725, and 1363736 are complementary to a portion of nucleobases 17615-17667 of SEQ ID NO: 2.

In certain embodiments, modified oligonucleotides complementary to a portion of nucleobases 17615-17667 of SEQ ID NO: 2 achieve at least 28% reduction of PLP1 RNA in the standard in vitro assay. In certain embodiments, modified oligonucleotides complementary to a portion of nucleobases 17615-17667 of SEQ ID NO: 2 achieve an average of 74.4% reduction of PLP1 RNA in the standard in vitro assay.

7. Nucleobases 17853-17883 of SEQ ID NO: 2

In certain embodiments, nucleobases 17853-17883 of SEQ ID NO: 2 comprise a hotspot region. In certain embodiments, modified oligonucleotides are complementary to a portion of nucleobases 17853-17883 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': soooosssssssssssooss or sooooosssssssssssoss, wherein each "s" represents a phosphorothioate internucleoside linkage and each "o" represents a phosphodiester internucleoside linkage.

The nucleobase sequences of SEQ ID NOs: 1451, 1499, 1543, 1654, 1733, 2154, and 2155 are complementary to a portion of nucleobases 17853-17883 of SEQ ID NO: 2.

The nucleobase sequences of Compound Nos.: 1362611, 1363392, 1363557, 1363795, 1364094, 1523610, 1523611, 1523612, and 1523613 are complementary to a portion of nucleobases 17853-17883 of SEQ ID NO: 2.

In certain embodiments, modified oligonucleotides complementary to a portion of nucleobases 17853-17883 of SEQ ID NO: 2 achieve at least 65% reduction of PLP1 RNA in the standard in vitro assay. In certain embodiments, modified oligonucleotides complementary to a portion of nucleobases 17853-17883 of SEQ ID NO: 2 achieve an average of 73.5% reduction of PLP1 RNA in the standard in vitro assay.

8. Nucleobases 18097-18160 of SEQ ID NO: 2

In certain embodiments, nucleobases 18097-18160 of SEQ ID NO: 2 comprise a hotspot region. In certain embodiments, modified oligonucleotides are complementary to a portion of nucleobases 18097-18160 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': soooosssssssssssooss or soooooossssssssssoss, wherein each "s" represents a phosphorothioate internucleoside linkage and each "o" represents a phosphodiester internucleoside linkage.

The nucleobase sequences of SEQ ID NOs: 200, 420, 504, 620, 646, 709, 823, 980, 1029, 1149, 1196, 1253, 1323, 1423, 1476, 1605, 1613, 1728, and 1832 are complementary to a portion of nucleobases 18097-18160 of SEQ ID NO: 2.

The nucleobase sequences of Compound Nos.: 1218175, 1362441, 1362447, 1362750, 1362769, 1362774, 1362926, 1362945, 1362957, 1362963, 1362967, 1363191, 1363253, 1363427, 1363489, 1363691, 1363993, 1364083, 1364097, and 1364099 are complementary to a portion of nucleobases 18097-18160 of SEQ ID NO: 2.

In certain embodiments, modified oligonucleotides complementary to a portion of nucleobases 18097-18160 of SEQ ID NO: 2 achieve at least 53% reduction of PLP1 RNA in the standard in vitro assay. In certain embodiments, modified oligonucleotides complementary to a portion of nucleobases 18097-18160 of SEQ ID NO: 2 achieve an average of 70.1% reduction of PLP1 RNA in the standard in vitro assay.

9. Nucleobases 18206-18237 of SEQ ID NO: 2

In certain embodiments, nucleobases 18206-18237 of SEQ ID NO: 2 comprise a hotspot region. In certain embodiments, modified oligonucleotides are complementary to a portion of nucleobases 18206-18237 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': soooosssssssssssooss or soooooossssssssssoss, wherein each "s" represents a phosphorothioate internucleoside linkage and each "o" represents a phosphodiester internucleoside linkage.

The nucleobase sequences of 45, 46, 123, 124, 201, 202, 279, 280, 538, 562, and 2091 are complementary to a portion of nucleobases 18206-18237 of SEQ ID NO: 2.

The nucleobase sequences of Compound Nos.: 1218177, 1218178, 1218179, 1218180, 1218181, 1218182, 1218183, 1218184, 1362490, 1362584, 1362927, 1363103, 1363121, 1363314, and 1363983 are complementaty to a portion of nucleobases 18206-18237 of SEQ ID NO: 2.

In certain embodiments, modified oligonucleotides complementary to a portion of nucleobases 18206-18237 of SEQ ID NO: 2 achieve at least 64% reduction of PLP1 RNA in the standard in vitro assay. In certain embodiments, modified oligonucleotides complementary to a portion of nucleobases 18206-18237 of SEQ ID NO: 2 achieve an average of 81.8% reduction of PLP1 RNA in the standard in vitro assay.

10. Nucleobases 18237-18340 of SEQ ID NO: 2

In certain embodiments, nucleobases 18237-18340 of SEQ ID NO: 2 comprise a hotspot region. In certain embodiments, modified oligonucleotides are complementary to a portion of nucleobases 18237-18340 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': soooosssssssssssooss or sooooosssssssssssoss, wherein each "s" represents a phosphorothioate internucleoside linkage and each "o" represents a phosphodiester internucleoside linkage.

The nucleobase sequences of SEQ ID NOs: 48, 49, 50, 51, 52, 53, 125, 126, 127, 128, 129, 130, 131, 203, 204, 205, 206, 207, 208, 281, 282, 283, 284, 285, 286, 414, 459, 485, 503, 579, 580, 693, 724, 840, 873, 911, 1034, 1081, 1125, 1159, 1318, 1413, 1513, 1548, 1672, 1701, 1794, 1868, 1958, and 2002 are complementary to a portion of nucleobases 18237-18340 of SEQ ID NO: 2.

The nucleobase sequences of Compound Nos.: 1218186, 1218187, 1218188, 1218189, 1218190, 1218191, 1218192, 1218193, 1218194, 1218195, 1218196, 1218197, 1218198, 1218199, 1218200, 1218201, 1218202, 1218203, 1218204, 1218205, 1218206, 1218207, 1218208, 1218209, 1218210, 1362429, 1362468, 1362571, 1362623, 1362659, 1362697, 1362699, 1362710, 1362714, 1362723, 1362734, 1362821, 1362902, 1362924, 1362955, 1362977, 1363036, 1363051, 1363069, 1363149, 1363206, 1363269, 1363286, 1363355, 1363429, 1363518, 1363687, 1363748, 1363790, 1363856, 1363872, 1363884, 1364129, 1364227, and 1364246 are complementary to a portion of nucleobases 18237-18340 of SEQ ID NO: 2.

In certain embodiments, modified oligonucleotides complementary to a portion of nucleobases 18237-18340 of SEQ ID NO: 2 achieve at least 44% reduction of PLP1 RNA in the standard in vitro assay. In certain embodiments, modified oligonucleotides complementary to a portion of nucleobases 18237-18340 of SEQ ID NO: 2 achieve an average of 70.9% reduction of PLP1 RNA in the standard in vitro assay.

11. Nucleobases 18350-18387 of SEQ ID NO: 2

In certain embodiments, nucleobases 18350-18387 of SEQ ID NO: 2 comprise a hotspot region. In certain embodiments, modified oligonucleotides are complementary to a portion of nucleobases 18350-18387 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': soooosssssssssssooss or sooooosssssssssssoss, wherein each "s" represents a phosphorothioate internucleoside linkage and each "o" represents a phosphodiester internucleoside linkage.

The nucleobase sequences of SEQ ID NOs: 209, 287, 335, 439, 506, 606, 659, 1922, 2033, and 2104 are complementary to a portion of nucleobases 18350-18387 of SEQ ID NO: 2.

The nucleobase sequences of Compound Nos.: 1218211, 1218212, 1362567, 1362579, 1362987, 1363166, 1363184, 1363310, 1363502, and 1363644 are complementary to a portion of nucleobases 18350-18387 of SEQ ID NO: 2.

In certain embodiments, modified oligonucleotides complementary to a portion of nucleobases 18350-18387 of SEQ ID NO: 2 achieve at least 64% reduction of PLP1 RNA in the standard in vitro assay. In certain embodiments, modified oligonucleotides complementary to a portion of nucleobases 18350-18387 of SEQ ID NO: 2 achieve an average of 76.2% reduction of PLP1 RNA in the standard in vitro assay.

12. Nucleobases 18412-18469 of SEQ ID NO: 2

In certain embodiments, nucleobases 18412-18469 of SEQ ID NO: 2 comprise a hotspot region. In certain embodiments, modified oligonucleotides are complementary to a portion of nucleobases 18412-18469 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': soooosssssssssssooss or sooooosssssssssssoss, wherein each "s" represents a phosphorothioate internucleoside linkage and each "o" represents a phosphodiester internucleoside linkage.

The nucleobase sequences of SEQ ID NOs: 784, 842, 869, 978, 1082, 1131, 1218, 1250, 1320, 1453, 1529, 1538, 1616, 1712, and 1821 are complementary to a portion of nucleobases 18412-18469 of SEQ ID NO: 2.

The nucleobase sequences of Compound Nos.: 1362519, 1362535, 1362684, 1362724, 1362885, 1363026, 1363457, 1363648, 1363838, 1363887, 1363933, 1364125, 1364192, 1364197, and 1364255 are complementaty to a portion of nucleobases 18412-18469 of SEQ ID NO: 2.

In certain embodiments, modified oligonucleotides complementary to a portion of nucleobases 18412-18469 of SEQ ID NO: 2 achieve at least 67% reduction of PLP1 RNA in the standard in vitro assay. In certain embodiments, modified oligonucleotides complementary to a portion of nucleobases 18412-18469 of SEQ ID NO: 2 achieve an average of 75% reduction of PLP1 RNA in the standard in vitro assay.

13. Nucleobases 18461-18506 of SEQ ID NO: 2

In certain embodiments, nucleobases 18461-18506 of SEQ ID NO: 2 comprise a hotspot region. In certain embodiments, modified oligonucleotides are complementary to a portion of nucleobases 18461-18506 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': sooooossssssssssooss or sooooosssssssssssoss, wherein each "s" represents a phosphorothioate internucleoside linkage and each "o" represents a phosphodiester internucleoside linkage.

The nucleobase sequences of SEQ ID NOs: 54, 55, 132, 133, 210, 288, 419, 499, 564, 665, 764, 800, 881, 993, 1059, 1200, 1295, 1354, 1422, 1465, 1544, 1705, 1802, and 2149 are complementary to a portion of nucleobases 18461-18506 of SEQ ID NO: 2.

The nucleobase sequences of Compound Nos.: 1218213, 1218214, 1218215, 1218216, 1218217, 1218218, 1362618, 1362620, 1362632, 1362704, 1362718, 1362815, 1363013, 1363023, 1363128, 1363328, 1363400, 1363431, 1363519, 1363533, 1363570, 1363709, 1363762, 1363975, 1364180, 1523591, 1523592, and 1523593 are complementary to a portion of nucleobases 18461-18506 of SEQ ID NO: 2.

In certain embodiments, modified oligonucleotides complementary to a portion of nucleobases 18461-18506 of SEQ ID NO: 2 achieve at least 40% reduction of PLP1 RNA in the standard in vitro assay. In certain embodiments, modified oligonucleotides complementary to a portion of nucleobases 18461-18506 of SEQ ID NO: 2 achieve an average of 69.7% reduction of PLP1 RNA in the standard in vitro assay.

14. Nucleobases 18539-18579 of SEQ ID NO: 2

In certain embodiments, nucleobases 18539-18579 of SEQ ID NO: 2 comprise a hotspot region. In certain embodiments, modified oligonucleotides are complementary to a portion of nucleobases 18539-18579 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': sooooossssssssssooss or sooooosssssssssssoss, wherein each "s" represents a phosphorothioate internucleoside linkage and each "o" represents a phosphodiester internucleoside linkage.

The nucleobase sequences of SEQ ID NOs: 338, 438, 525, 604, 658, 758, 813, 887, 977, 1043, 1108, 1199, 1258, 1336, 1395, 1514, 1557, 1668, 1697, and 2089 are complementary to a portion of nucleobases 18539-18579 of SEQ ID NO: 2.

The nucleobase sequences of Compound Nos.: 1362619, 1362637, 1362652, 1362830, 1362901, 1363079, 1363118, 1363143, 1363145, 1363146, 1363176, 1363193, 1363287, 1363422, 1363451, 1363569, 1363592, 1363611, 1363796, and 1363860 are complementary to a portion of nucleobases 18539-18579 of SEQ ID NO: 2.

In certain embodiments, modified oligonucleotides complementary to a portion of nucleobases 18539-18579 of SEQ ID NO: 2 achieve at least 62% reduction of PLP1 RNA in the standard in vitro assay. In certain embodiments, modified oligonucleotides complementary to a portion of nucleobases 18539-18579 of SEQ ID NO: 2 achieve an average of 68.8% reduction of PLP1 RNA in the standard in vitro assay.

15. Nucleobases 18697-18727 of SEQ ID NO: 2

In certain embodiments, nucleobases 18697-18727 of SEQ ID NO: 2 comprise a hotspot region. In certain embodiments, modified oligonucleotides are complementary to a portion of nucleobases 18697-18727 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': sooooossssssssssooss or sooooossssssssssoss, wherein each "s" represents a phosphorothioate internucleoside linkage and each "o" represents a phosphodiester internucleoside linkage.

The nucleobase sequences of SEQ ID NOs: 875, 934, 1047, 1110, 1229, 1243, 1373, 1438, 2146, and 2147 are complementary to a portion of nucleobases 18697-18727 of SEQ ID NO: 2.

The nucleobase sequences of Compound Nos.: 1362458, 1362696, 1362878, 1363179, 1363351, 1363697, 1364107, 1364147, 1523584, 1523586, and 1523587 are complementary to a portion of nucleobases 18697-18727 of SEQ ID NO: 2.

In certain embodiments, modified oligonucleotides complementary to a portion of nucleobases 18697-18727 of SEQ ID NO: 2 achieve at least 66% reduction of PLP1 RNA in the standard in vitro assay. In certain embodiments, modified oligonucleotides complementary to a portion of nucleobases 18697-18727 of SEQ ID NO: 2 achieve an average of 77.7% reduction of PLP1 RNA in the standard in vitro assay.

16. Nucleobases 18755-18793 of SEQ ID NO: 2

In certain embodiments, nucleobases 18755-18793 of SEQ ID NO: 2 comprise a hotspot region. In certain embodiments, modified oligonucleotides are complementary to a portion of nucleobases 18755-18793 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': sooooossssssssssooss or sooooossssssssssoss, wherein each "s" represents a phosphorothioate internucleoside linkage and each "o" represents a phosphodiester internucleoside linkage.

The nucleobase sequences of SEQ ID NOs: 761, 798, 890, 946, 1022, 1120, 1198, 1293, 1358, 1398, and 1463 are complementary to a portion of nucleobases 18755-18793 of SEQ ID NO: 2.

The nucleobase sequences of Compound Nos.: 1362575, 1362680, 1362689, 1362856, 1363019, 1363172, 1363357, 1363391, 1363591, 1363639, and 1363889 are complementary to a portion of nucleobases 18755-18793 of SEQ ID NO: 2.

In certain embodiments, modified oligonucleotides complementary to a portion of nucleobases 18755-18793 of SEQ ID NO: 2 achieve at least 65% reduction of PLP1 RNA in the standard in vitro assay. In certain embodiments, modified oligonucleotides complementary to a portion of nucleobases 18755-18793 of SEQ ID NO: 2 achieve an average of 77.7% reduction of PLP1 RNA in the standard in vitro assay.

17. Nucleobases 18797-18819 of SEQ ID NO: 2

In certain embodiments, nucleobases 18797-18819 of SEQ ID NO: 2 comprise a hotspot region. In certain embodiments, modified oligonucleotides are complementary to a portion of nucleobases 18797-18819 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': soooosssssssssssooss or sooooosssssssssssoss, wherein each "s" represents a phosphorothioate internucleoside linkage and each "o" represents a phosphodiester internucleoside linkage.

The nucleobase sequences of SEQ ID NOs: 56, 134, 683, and 718 are complementary to a portion of nucleobases 18797-18819 of SEQ ID NO: 2.

The nucleobase sequences of Compound Nos.: 1218221, 1218222, 1362445, 1362612, 1363487, and 1363656 are complementary to a portion of nucleobases 18797-18819 of SEQ ID NO: 2.

In certain embodiments, modified oligonucleotides complementary to a portion of nucleobases 18797-18819 of SEQ ID NO: 2 achieve at least 65% reduction of PLP1 RNA in the standard in vitro assay. In certain embodiments, modified oligonucleotides complementary to a portion of nucleobases 18797-18819 of SEQ ID NO: 2 achieve an average of 75.4% reduction of PLP1 RNA in the standard in vitro assay.

18. Nucleobases 18839-18862 of SEQ ID NO: 2

In certain embodiments, nucleobases 18839-18862 of SEQ ID NO: 2 comprise a hotspot region. In certain embodiments, modified oligonucleotides are complementary to a portion of nucleobases 18839-18862 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': soooosssssssssssooss or sooooosssssssssssoss, wherein each "s" represents a phosphorothioate internucleoside linkage and each "o" represents a phosphodiester internucleoside linkage.

The nucleobase sequences of SEQ ID NOs: 1610, 1663, 1702, and 1786 are complementary to a portion of nucleobases 18839-18862 of SEQ ID NO: 2.

The nucleobase sequences of Compound Nos.: 1363076, 1362712, 1363649, and 1364195 are complementary to a portion of nucleobases 18839-18862 of SEQ ID NO: 2.

In certain embodiments, modified oligonucleotides complementary to a portion of nucleobases 18839-18862 of SEQ ID NO: 2 achieve at least 66% reduction of PLP1 RNA in the standard in vitro assay. In certain embodiments, modified oligonucleotides complementary to a portion of nucleobases 18839-18862 of SEQ ID NO: 2 achieve an average of 72.8% reduction of PLP1 RNA in the standard in vitro assay.

19. Nucleobases 18974-19021 of SEQ ID NO: 2

In certain embodiments, nucleobases 18974-19021 of SEQ ID NO: 2 comprise a hotspot region. In certain embodiments, modified oligonucleotides are complementary to a portion of nucleobases 18974-19021 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': soooosssssssssssooss or sooooossssssssssssoss, wherein each "s" represents a phosphorothioate internucleoside linkage and each "o" represents a phosphodiester internucleoside linkage.

The nucleobase sequences of SEQ ID NOs: 212, 1060, 1090, 1181, 1277, 1446, 1510, 1589, 1646, 1693, 1772, and 2148 are complementary to a portion of nucleobases 18974-19021 of SEQ ID NO: 2.

The nucleobase sequences of Compound Nos.: 1218223, 1362460, 1362600, 1362805, 1362892, 1363007, 1363316, 1363581, 1363642, 1363664, 1363773, 1363984, 1523588, 1523589, and 1523590 are complementary to a portion of nucleobases 18974-19021 of SEQ ID NO: 2.

In certain embodiments, modified oligonucleotides complementary to a portion of nucleobases 18974-19021 of SEQ ID NO: 2 achieve at least 54% reduction of PLP1 RNA in the standard in vitro assay. In certain embodiments, modified oligonucleotides complementary to a portion of nucleobases 18974-19021 of SEQ ID NO: 2 achieve an average of 71.5% reduction of PLP1 RNA in the standard in vitro assay.

20. Nucleobases 19028-19080 of SEQ ID NO: 2

In certain embodiments, nucleobases 19028-19080 of SEQ ID NO: 2 comprise a hotspot region. In certain embodiments, modified oligonucleotides are complementary to a portion of nucleobases 19028-19080 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': soooosssssssssssooss or sooooossssssssssssoss, wherein each "s" represents a phosphorothioate internucleoside linkage and each "o" represents a phosphodiester internucleoside linkage.

The nucleobase sequences of SEQ ID NOs: 57, 586, 666, 714, 812, 914, 951, 1052, 1138, 1162, 1248, 1363, and 1455 are complementary to a portion of nucleobases 19028-19080 of SEQ ID NO: 2.

The nucleobase sequences of Compound Nos.: 1218225, 1362492, 1362565, 1362817, 1362846, 1363141, 1363160, 1363346, 1363453, 1363550, 1363765, 1363835, 1363883, and 1364201 are complementary to a portion of nucleobases 19028-19080 of SEQ ID NO: 2.

In certain embodiments, modified oligonucleotides complementary to a portion of nucleobases 19028-19080 of SEQ ID NO: 2 achieve at least 58% reduction of PLP1 RNA in the standard in vitro assay. In certain embodiments, modified oligonucleotides complementary to a portion of nucleobases 19028-19080 of SEQ ID NO: 2 achieve an average of 73.5% reduction of PLP1 RNA in the standard in vitro assay.

21. Nucleobases 19146-19173 of SEQ ID NO: 2

In certain embodiments, nucleobases 19146-19173 of SEQ ID NO: 2 comprise a hotspot region. In certain embodiments, modified oligonucleotides are complementary to a portion of nucleobases 19146-19173 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': soooosssssssssssooss or sooooossssssssssssoss, wherein each "s" represents a phosphorothioate internucleoside linkage and each "o" represents a phosphodiester internucleoside linkage.

The nucleobase sequences of SEQ ID NOs: 385, 416, 545, 621, 682, 1968, 2055, 2101, and 2150 are complementary to a portion of nucleobases 19146-19173 of SEQ ID NO: 2.

The nucleobase sequences of Compound Nos.: 1362670, 1363235, 1363627, 1363734, 1363940, 1364008, 1364066, 1523601, 1523602, and 1523603 are complementary to a portion of nucleobases 19146-19173 of SEQ ID NO: 2.

In certain embodiments, modified oligonucleotides complementary to a portion of nucleobases 19148-19173 of SEQ ID NO: 2 achieve at least 54% reduction of PLP1 RNA in the standard in vitro assay. In certain embodiments, modified oligonucleotides complementary to a portion of nucleobases 19146-19173 of SEQ ID NO: 2 achieve an average of 77.3% reduction of PLP1 RNA in the standard in vitro assay.

22. Nucleobases 19228-19253 of SEQ ID NO: 2

In certain embodiments, nucleobases 19228-19253 of SEQ ID NO: 2 comprise a hotspot region. In certain embodiments, modified oligonucleotides are complementary to a portion of nucleobases 19228-19253 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': sooooossssssssssooss or sooooossssssssssoss, wherein each "s" represents a phosphorothioate internucleoside linkage and each "o" represents a phosphodiester internucleoside linkage.

The nucleobase sequences of SEQ ID NOs: 363, 467, 541, 2008, and 2111 are complementary to a portion of nucleobases 19228-19253 of SEQ ID NO: 2.

The nucleobase sequences of Compound Nos.: 1364015, 1363882, 1363157, 1363485, and 1362808 are complementary to a portion of nucleobases 19228-19253 of SEQ ID NO: 2.

In certain embodiments, modified oligonucleotides complementary to a portion of nucleobases 19228-19253 of SEQ ID NO: 2 achieve at least 69% reduction of PLP1 RNA in the standard in vitro assay. In certain embodiments, modified oligonucleotides complementary to a portion of nucleobases 19228-19253 of SEQ ID NO: 2 achieve an average of 77.4% reduction of PLP1 RNA in the standard in vitro assay.

23. Nucleobases 19347-19393 of SEQ ID NO: 2

In certain embodiments, nucleobases 19347-19393 of SEQ ID NO: 2 comprise a hotspot region. In certain embodiments, modified oligonucleotides are complementary to a portion of nucleobases 19347-19393 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': sooooossssssssssooss or sooooossssssssssoss, wherein each "s" represents a phosphorothioate internucleoside linkage and each "o" represents a phosphodiester internucleoside linkage.

The nucleobase sequences of SEQ ID NOs: 58, 59, 136, 213, 214, 291, 292, 383, 417, 519, 612, 671, 730, 900, 986, 1019, 1136, 1353, 1457, 1504, 1546, and 2093 are complementary to a portion of nucleobases 19347-19393 of SEQ ID NO: 2.

The nucleobase sequences of Compound Nos.: 1218227, 1218228, 1218229, 1218230, 1218231, 1218232, 1218233, 1362526, 1362624, 1362677, 1362685, 1362799, 1362806, 1363094, 1363419, 1363425, 1363472, 1363499, 1363597, 1363628, 1363681, 1363744, 1363759, 1363800, and 1364257 are complementary to a portion of nucleobases 19347-19393 of SEQ ID NO: 2.

In certain embodiments, modified oligonucleotides complementary to a portion of nucleobases 19347-19393 of SEQ ID NO: 2 achieve at least 52% reduction of PLP1 RNA in the standard in vitro assay. In certain embodiments, modified oligonucleotides complementary to a portion of nucleobases 19347-19393 of SEQ ID NO: 2 achieve an average of 71.6% reduction of PLP1 RNA in the standard in vitro assay.

24. Nucleobases 19500-19523 of SEQ ID NO: 2

In certain embodiments, nucleobases 19500-19523 of SEQ ID NO: 2 comprise a hotspot region. In certain embodiments, modified oligonucleotides are complementary to a portion of nucleobases 19500-19523 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': soooosssssssssssooss or sooooosssssssssssoss, wherein each "s" represents a phosphorothioate internucleoside linkage and each "o" represents a phosphodiester internucleoside linkage.

The nucleobase sequences of SEQ ID NOs: 398, 435, 2095, 2010, and 2144 are complementary to a portion of nucleobases 19500-19523 of SEQ ID NO: 2.

The nucleobase sequences of Compound Nos.: 1362842, 1363110, 1363153, 1363982, 1523594, and 1523595 are complementary to a portion of nucleobases 19500-19523 of SEQ ID NO: 2.

In certain embodiments, modified oligonucleotides complementary to a portion of nucleobases 19500-19523 of SEQ ID NO: 2 achieve at least 62% reduction of PLP1 RNA in the standard in vitro assay. In certain embodiments, modified oligonucleotides complementary to a portion of nucleobases 19500-19523 of SEQ ID NO: 2 achieve an average of 69.5% reduction of PLP1 RNA in the standard in vitro assay.

25. Nucleobases 19512-19534 of SEQ ID NO: 2

In certain embodiments, nucleobases 19512-19534 of SEQ ID NO: 2 comprise a hotspot region. In certain embodiments, modified oligonucleotides are complementary to a portion of nucleobases 19512-19534 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are 16, 17, 18, 19, 20, 21, or 22 nucleobases in length. In certain embodiments, modified oligonucleotides consist of 17-19 or 21-30 linked nucleosides. In certain embodiments, modified oligonucleotides are gapmers. In certain embodiments, the gapmers are MOE gapmers. In certain embodiments, the gapmers are 5-10-5 MOE gapmers. In certain embodiments, the gapmers are 6-10-4 MOE gapmers. In certain embodiments, the gapmers are 4-10-6 MOE gapmers. In certain embodiments, the gapmers are 4-8-6 MOE gapmers. In certain embodiments, the gapmers are 6-8-4 MOE gapmers. In certain embodiments, the gapmers are 5-8-5 MOE gapmers. In certain embodiments, the gapmers have the sugar motif in order from 5' to 3': eeeeedddddddddeeeee or eeeeeedddddddddeeeee, wherein 'd' represents a 2'-β-D-deoxyribosyl sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3').

In certain embodiments, all of the internucleoside linkages of the modified oligonucleotides are phosphorothioate internucleoside linkages. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in the order from 5' to 3': soooosssssssssssooss or sooooosssssssssssoss, wherein each "s" represents a phosphorothioate internucleoside linkage and each "o" represents a phosphodiester internucleoside linkage.

The nucleobase sequences of SEQ ID NOs: 1201, 1238, 1341, and 1435 are complementary to a portion of nucleobases 19512-19534 of SEQ ID NO: 2.

The nucleobase sequences of Compound Nos.: 1362602, 1363268, 1363452, and 1363678 are complementary to a portion of nucleobases 19512-19534 of SEQ ID NO: 2.

In certain embodiments, modified oligonucleotides complementary to a portion of nucleobases 19512-19534 of SEQ ID NO: 2 achieve at least 63% reduction of PLP1 RNA in the standard in vitro assay. In certain embodiments, modified oligonucleotides complementary to a portion of nucleobases 19512-19534 of SEQ ID NO: 2 achieve an average of 80% reduction of PLP1 RNA in the standard in vitro assay.

Nonlimiting Disclosure and Incorporation by Reference

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar moiety (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^m$CGAUCG," wherein $^m$C indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as a α or β (such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms, unless specified otherwise. Likewise, all cis- and trans-isomers and tautomeric forms of the compounds herein are also included unless otherwise indicated. Oligomeric compounds described herein include chirally pure or enriched mixtures as well as racemic mixtures. For example, oligomeric compounds having a plurality of phosphorothioate internucleoside linkages include such compounds in which chirality of the phosphorothioate internucleoside linkages is controlled or is random. Unless otherwise indicated, compounds described herein are intended to include corresponding salt forms.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^1$H hydrogen atoms. Isotopic substitutions encompassed by the compounds herein include but are not limited to: $^2$H or $^3$H in place of $^1$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1: Effect of 5-10-5 MOE Gapmer Modified Oligonucleotides on Human PLP1 RNA In Vitro, Single Dose Modified oligonucleotides complementary to human PLP1 nucleic acid were designed and tested for their single dose effects on PLP1 RNA in vitro. The modified oligonucleotides were tested in a series of experiments that had the same culture conditions, and the results for each experiment are presented in separate tables below.

The modified oligonucleotides in the tables below are 5-10-5 MOE gapmers. The gapmers are 20 nucleosides in length, wherein the central gap segment consists of ten 2'-β-D-deoxynucleosides and the 5' and 3' wing segments each consists of five 2'-MOE modified nucleosides. The sugar motif for the gapmers is (from 5' to 3'): eeeeeddddddddddeeeee; wherein 'd' represents a 2'-β-D-deoxyribosyl sugar moiety, and 'e' represents a 2'-MOE sugar moiety. The internucleoside linkages throughout each modified oligonucleotide are phosphorothioate internucleoside linkages. Each cytosine residue is a 5-methyl cytosine.

"Start site" indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence. Each modified oligonucleotide listed in the Tables below is 100% complementary to either human PLP1 mRNA, designated herein as SEQ ID NO: 1 (GENBANK Accession No. NM_001128834.2) or to the human PLP1 genomic sequence, designated herein as SEQ ID NO: 2 (GENBANK Accession No. NC_000023.11 truncated from nucleotides 103773001 to 103795000), or to both. 'N/A' indicates that the modified oligonucleotide is not 100% complementary to that particular target nucleic acid sequence.

Cultured SK-MEL-28 cells were treated with modified oligonucleotide at a concentration of 7,000 nM using electroporation at a density of 20,000 cells per well. After a treatment period of approximately 24 hours, total RNA was isolated from the cells and PLP1 RNA levels were measured by quantitative real-time RTPCR. PLP1 RNA levels were measured by Human PLP1 primer probe set RTS35092 (forward sequence CTGATGCCAGAATGTATGGTGT, designated herein as SEQ ID NO: 11; reverse sequence AGGTGGAAGGTCATTTGGAAC, designated herein as SEQ ID NO: 12; probe sequence TGCAGATGGACAGAAGGTTGGAGC, designated herein as SEQ ID NO: 13). PLP1 RNA levels were normalized to total RNA content, as measured by RIBOGREEN®. Reduction of PLP1 RNA is presented in the tables below as percent PLP1 RNA relative to the amount in untreated control cells (% UTC). Each table represents results from an individual assay plate. The values marked with an "†" indicate that the modified oligonucleotide is complementary to the amplicon region of the primer probe set. Additional assays may be used to measure the potency and efficacy of the modified oligonucleotides complementary to the amplicon region.

TABLE 1

Reduction of PLP1 RNA by 5-10-5 MOE gapmers with phosphorothioate internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1218077 | N/A | N/A | 3805 | 3824 | AGCCAACCCCCTTAAAGGGA | 96 | 20 |

TABLE 1-continued

Reduction of PLP1 RNA by 5-10-5 MOE gapmers with phosphorothioate internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1218081 | N/A | N/A | 3815 | 3834 | TCTGATTGACAGCCAACCCC | 92 | 21 |
| 1218085 | 238 | 257 | 3948 | 3967 | CCGGCTGGCTAGTCTGCTTT | 43 | 22 |
| 1218089 | 249 | 268 | 3959 | 3978 | TCCAATTGTAGCCGGCTGGC | 62 | 23 |
| 1218093 | 305 | 324 | 12597 | 12616 | CCCTACCAGACATCTTGCAC | 39 | 24 |
| 1218097 | 551 | 570 | 13539 | 13558 | GCCGGTGGTGTAGAAGCCCT | 67 | 25 |
| 1218101 | 564 | 583 | 13552 | 13571 | TCTGCCTGACTGCGCCGGTG | 31 | 26 |
| 1218105 | 577 | 596 | 13565 | 13584 | TAGTCGCCAAAGATCTGCCT | 50 | 27 |
| 1218109 | 589 | 608 | 13577 | 13596 | ATGGTGGTCTTGTAGTCGCC | 47 | 28 |
| 1218113 | 600 | 619 | 13588 | 13607 | CCTTGCCGCAGATGGTGGTC | 54 | 29 |
| 1218117 | 604 | 623 | 13592 | 13611 | AGGCCCTTGCCGCAGATGGT | 51 | 30 |
| 1218121 | 614 | 633 | 13602 | 13621 | CGTTGCGCTCAGGCCCTTGC | 70 | 31 |
| 1218125 | 620 | 639 | 13608 | 13627 | TGTTACCGTTGCGCTCAGGC | 64 | 32 |
| 1218129 | 624 | 643 | 13612 | 13631 | CCCCTGTTACCGTTGCGCTC | 76 | 33 |
| 1218133 | 656 | 675 | 13644 | 13663 | ATGTTGGCCTCTGGAACCCC | 51 | 34 |
| 1218137 | 689 | 708 | 13677 | 13696 | ACAATGACACACCCGCTCCA | 75 | 35 |
| 1218141 | 717 | 736 | 13705 | 13724 | TGTCGGGATGTCCTAGCCAT | 31 | 36 |

TABLE 1-continued

Reduction of PLP1 RNA by 5-10-5 MOE gapmers with phosphorothioate internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1218145 | 757 | 776 | 14816 | 14835 | AGCCACACAACGGTCAGGGC | 25 | 37 |
| 1218149 | 815 | 834 | 14874 | 14893 | GGTGGTCCAGGTGTTGAAGT | 75 | 38 |
| 1218153 | 907 | 926 | 15436 | 15455 | GCATTCCATGGGAGAACACC | 29† | 39 |
| 1218157 | 1099 | 1118 | 17578 | 17597 | CAGAACTTGGTGCCTCGGCC | 16 | 40 |
| 1218161 | 1104 | 1123 | 17583 | 17602 | GGGATCAGAACTTGGTGCCT | 38 | 41 |
| 1218165 | 1151 | 1170 | 17630 | 17649 | GCTGTGTGGTTAGAGCCTCG | 19 | 42 |
| 1218169 | 1169 | 1188 | 17648 | 17667 | GGAGACGCAGCATTGTAGGC | 36 | 43 |
| 1218173 | 1528 | 1547 | 18007 | 18026 | GGCCCCTATAGATGGCAAGA | 46 | 44 |
| 1218177 | 1727 | 1746 | 18206 | 18225 | CAGTAGTCCATCGCCATCGG | 28 | 45 |
| 1218181 | 1734 | 1753 | 18213 | 18232 | AGGGCTTCAGTAGTCCATCG | 12 | 46 |
| 1218185 | 1747 | 1766 | 18226 | 18245 | GGTTGGCTGAGTTAGGGCTT | 25 | 47 |
| 1218189 | 1764 | 1783 | 18243 | 18262 | CCTTATGCTGTAAGTAAGGT | 24 | 48 |
| 1218193 | 1770 | 1789 | 18249 | 18268 | ACGCTCCCTTATGCTGTAAG | 11 | 49 |
| 1218197 | 1774 | 1793 | 18253 | 18272 | TTCTACGCTCCCTTATGCTG | 40 | 50 |
| 1218201 | 1782 | 1801 | 18261 | 18280 | TACACAGATTCTACGCTCCC | 29 | 51 |
| 1218205 | 1807 | 1826 | 18286 | 18305 | TGTAAGGCCAGATGCCCCT | 34 | 52 |

TABLE 1-continued

Reduction of PLP1 RNA by 5-10-5 MOE gapmers with phosphorothioate internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1218209 | 1824 | 1843 | 18303 | 18322 | TCTCTTCCCTAACGAGGTGT | 9 | 53 |
| 1218213 | 1983 | 2002 | 18462 | 18481 | AGGTTACACCATTAGCCACC | 25 | 54 |
| 1218217 | 2005 | 2024 | 18484 | 18503 | GTGTCTACCAGAGGGCCATC | 27 | 55 |
| 1218221 | 2318 | 2337 | 18797 | 18816 | CCAATAGATTCAACTAGCCA | 22 | 56 |
| 1218225 | 2582 | 2601 | 19061 | 19080 | GGAGCTATTCAGGTCTCAAA | 12 | 57 |
| 1218229 | 2880 | 2899 | 19359 | 19378 | TACGGATTACTTCACTGTCC | 18 | 58 |
| 1218233 | 2888 | 2907 | 19367 | 19386 | ACACAAGGTACGGATTACTT | 23 | 59 |
| 1218237 | 36 | 55 | 3541 | 3560 | TCCTTGGGTCTAATTGGTGT | 93 | 60 |
| 1218241 | 115 | 134 | 3620 | 3639 | TCGCTTTGCTGCAGAGACAT | 88 | 61 |
| 1218245 | N/A | N/A | 1120 | 1139 | TGGGCCCCTTGATCATGGC | 90 | 62 |
| 1218249 | N/A | N/A | 1412 | 1431 | GCTCCCTACAGACCTCATAG | 93 | 63 |
| 1218253 | N/A | N/A | 2172 | 2191 | GGTCCTAGAGCCCCTCGCCC | 94 | 64 |
| 1218257 | N/A | N/A | 2814 | 2833 | CCTGCCTTAGCAATAAGCTA | 91 | 65 |
| 1218261 | N/A | N/A | 3457 | 3476 | AACCTAGATATTAGCTCCCA | 91 | 66 |
| 1218265 | N/A | N/A | 4445 | 4464 | GCCCGATCCCCAGCTCCTA | 78 | 67 |
| 1218269 | N/A | N/A | 5257 | 5276 | GTTGTTATAGATCTTGCCCA | 38 | 68 |

TABLE 1-continued

Reduction of PLP1 RNA by 5-10-5 MOE gapmers with phosphorothioate internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1218273 | N/A | N/A | 5479 | 5498 | TGCACAACCTATCCAGTCAG | 65 | 69 |
| 1218277 | N/A | N/A | 5871 | 5890 | CCAATCCCGGATTCCATGAT | 55 | 70 |
| 1218281 | N/A | N/A | 5994 | 6013 | GTTGAAGTAGTAAGTCCCT | 34 | 71 |
| 1218285 | N/A | N/A | 6371 | 6390 | GCCGCCACACTTTTTGCCTG | 45 | 72 |
| 1218289 | N/A | N/A | 7095 | 7114 | AGGGCCATTTTGCCGTAGGC | 46 | 73 |
| 1218293 | N/A | N/A | 7523 | 7542 | CGATTTAGTATTACCACGGC | 24 | 74 |
| 1218297 | N/A | N/A | 7663 | 7682 | GATATCAGCACTTATATACC | 86 | 75 |
| 1218301 | N/A | N/A | 8082 | 8101 | ACCAATTGTACCCTGCACAA | 65 | 76 |
| 1218305 | N/A | N/A | 8355 | 8374 | TTAAGCCCTTCTCACCAGCG | 49 | 77 |
| 1218309 | N/A | N/A | 9005 | 9024 | CCATTGGGCTCCCTTTGATT | 49 | 78 |
| 1218313 | N/A | N/A | 9645 | 9664 | GTGCTTGTGCAGGTATGGTC | 26 | 79 |
| 1218317 | N/A | N/A | 9713 | 9732 | TCCACCCTAGCAAGTGACCA | 68 | 80 |
| 1218321 | N/A | N/A | 10517 | 10536 | GAGTCCTATTACCCACCATC | 47 | 81 |
| 1218325 | N/A | N/A | 10523 | 10542 | AGGAGTGAGTCCTATTACCC | 56 | 82 |
| 1218329 | N/A | N/A | 11359 | 11378 | CCCTCAGTTATACGCTGAGA | 43 | 83 |
| 1218333 | N/A | N/A | 11465 | 11484 | AGGAGGTTTGATATTACTCC | 64 | 84 |

TABLE 1-continued

Reduction of PLP1 RNA by 5-10-5 MOE gapmers with phosphorothioate internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1218337 | N/A | N/A | 13224 | 13243 | ACCTTGCTTACCCTGGGACC | 50 | 85 |
| 1218341 | N/A | N/A | 13709 | 13728 | ACCTTGTCGGGATGTCCTAG | 39 | 86 |
| 1218345 | N/A | N/A | 13766 | 13785 | ACTCGCGCCCAATTTTCCCC | 50 | 87 |
| 1218349 | N/A | N/A | 13777 | 13796 | CGAGGCCACAGACTCGCGCC | 49 | 88 |
| 1218353 | N/A | N/A | 14039 | 14058 | CCAGTTAGATCCACTCTTGT | 29 | 89 |
| 1218357 | N/A | N/A | 14083 | 14102 | GGTGCCCAAGTCTCAATCAC | 43 | 90 |
| 1218361 | N/A | N/A | 14608 | 14627 | TCTACTAGATAACTGGCCCC | 64 | 91 |
| 1218365 | N/A | N/A | 14964 | 14983 | CCCGTACCCTAACTCACCAT | 77† | 92 |
| 1218369 | N/A | N/A | 15536 | 15555 | GGTATTAGCTACTCCCTTGT | 40 | 93 |
| 1218373 | N/A | N/A | 15765 | 15784 | CCATTAGGCTCTATCTTTAC | 52 | 94 |
| 1218377 | N/A | N/A | 16150 | 16169 | TCAGTGTACACCATAGCACC | 37 | 95 |
| 1218381 | N/A | N/A | 16531 | 16550 | AAGTACGGAGCCTCCACCCT | 74 | 96 |
| 1218385 | N/A | N/A | 17129 | 17148 | CAGTAGAGCTCTCCCCTGGT | 66 | 97 |

TABLE 2

Reduction of PLP1 RNA by 5-10-5 MOE gapmers with phosphorothioate internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1218078 | N/A | N/A | 3806 | 3825 | CAGCCAACCCCCTTAAGGG | 102 | 98 |
| 1218082 | N/A | N/A | 3816 | 3835 | TTCTGATTGACAGCCAACCC | 111 | 99 |

TABLE 2-continued

Reduction of PLP1 RNA by 5-10-5 MOE gapmers with phosphorothioate internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1218086 | 241 | 260 | 3951 | 3970 | TAGCCGGCTGGCTAGTCTGC | 45 | 100 |
| 1218090 | 251 | 270 | 3961 | 3980 | ACTCCAATTGTAGCCGGCTG | 67 | 101 |
| 1218094 | 307 | 326 | 12599 | 12618 | GCCCCTACCAGACATCTTGC | 34 | 102 |
| 1218098 | 557 | 576 | 13545 | 13564 | GACTGCGCCGGTGGTGTAGA | 66 | 103 |
| 1218102 | 566 | 585 | 13554 | 13573 | GATCTGCCTGACTGCGCCGG | 53 | 104 |
| 1218106 | 578 | 597 | 13566 | 13585 | GTAGTCGCCAAAGATCTGCC | 58 | 105 |
| 1218110 | 590 | 609 | 13578 | 13597 | GATGGTGGTCTTGTAGTCGC | 77 | 106 |
| 1218114 | 601 | 620 | 13589 | 13608 | CCCTTGCCGCAGATGGTGT | 48 | 107 |
| 1218118 | 609 | 628 | 13597 | 13616 | CGCTCAGGCCCTTGCCGCAG | 21 | 108 |
| 1218122 | 617 | 636 | 13605 | 13624 | TACCGTTGCGCTCAGGCCCT | 71 | 109 |
| 1218126 | 621 | 640 | 13609 | 13628 | CTGTTACCGTTGCGCTCAGG | 90 | 110 |
| 1218130 | 625 | 644 | 13613 | 13632 | CCCCCTGTTACCGTTGCGCT | 76 | 111 |
| 1218134 | 657 | 676 | 13645 | 13664 | GATGTTGGCCTCTGGAACCC | 50 | 112 |
| 1218138 | 693 | 712 | 13681 | 13700 | CCAAACAATGACACACCCGC | 71 | 113 |
| 1218142 | 718 | 737 | 13706 | 13725 | TTGTCGGGATGTCCTAGCCA | 40 | 114 |
| 1218146 | 759 | 778 | 14818 | 14837 | GGAGCCACACAACGGTCAGG | 62 | 115 |
| 1218150 | 860 | 879 | 14919 | 14938 | GCCTATACTGGCAGAGGTCT | 38 | 116 |

TABLE 2-continued

Reduction of PLP1 RNA by 5-10-5 MOE gapmers with phosphorothioate internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1218154 | 1080 | 1099 | 17559 | 17578 | CCATGAGTTAAGGACGGCA | 24 | 117 |
| 1218158 | 1100 | 1119 | 17579 | 17598 | TCAGAACTTGGTGCCTCGGC | 31 | 118 |
| 1218162 | 1144 | 1163 | 17623 | 17642 | GGTTAGAGCCTCGCTATTAG | 20 | 119 |
| 1218166 | 1164 | 1183 | 17643 | 17662 | CGCAGCATTGTAGGCTGTGT | 18 | 120 |
| 1218170 | 1180 | 1199 | 17659 | 17678 | GAGTTAAGATGGGAGACGCA | 46 | 121 |
| 1218174 | 1531 | 1550 | 18010 | 18029 | TTTGGCCCCTATAGATGGCA | 41 | 122 |
| 1218178 | 1728 | 1747 | 18207 | 18226 | TCAGTAGTCCATCGCCATCG | 21 | 123 |
| 1218182 | 1737 | 1756 | 18216 | 18235 | GTTAGGGCTTCAGTAGTCCA | 24 | 124 |
| 1218186 | 1758 | 1777 | 18237 | 18256 | GCTGTAAGTAAGGTTGGCTG | 17 | 125 |
| 1218190 | 1765 | 1784 | 18244 | 18263 | CCCTTATGCTGTAAGTAAGG | 20 | 126 |
| 1218194 | 1771 | 1790 | 18250 | 18269 | TACGCTCCCTTATGCTGTAA | 22 | 127 |
| 1218198 | 1778 | 1797 | 18257 | 18276 | CAGATTCTACGCTCCCTTAT | 52 | 128 |
| 1218202 | 1783 | 1802 | 18262 | 18281 | CTACACAGATTCTACGCTCC | 36 | 129 |
| 1218206 | 1808 | 1827 | 18287 | 18306 | GTGTAAGGCCAGATGCCCCC | 38 | 130 |
| 1218210 | 1825 | 1844 | 18304 | 18323 | TTCTCTTCCCTAACGAGGTG | 25 | 131 |
| 1218214 | 1985 | 2004 | 18464 | 18483 | TCAGGTTACACCATTAGCCA | 23 | 132 |
| 1218218 | 2006 | 2025 | 18485 | 18504 | TGTGTCTACCAGAGGGCCAT | 26 | 133 |
| 1218222 | 2319 | 2338 | 18798 | 18817 | CCCAAT | 16 | 134 |

TABLE 2-continued

Reduction of PLP1 RNA by 5-10-5 MOE gapmers with phosphorothioate internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1218226 | 2583 | 2602 | 19062 | 19081 | AGATTCAACTAGCC GGGAGCTATTCAGGTCTCAA | 16 | 135 |
| 1218230 | 2881 | 2900 | 19360 | 19379 | GTACGGATTACTTCACTGTC | 31 | 136 |
| 1218234 | 17 | 36 | 3522 | 3541 | TGGGATATGCAGCACAAGCG | 61 | 137 |
| 1218238 | 37 | 56 | 3542 | 3561 | ATCCTTGGGTCTAATTGGTG | 104 | 138 |
| 1218242 | 121 | 140 | 3626 | 3645 | GGAATTCGCTTTGCTGCAG | 98 | 139 |
| 1218246 | N/A | N/A | 1121 | 1140 | CTGGGCCCCTTGATCATGG | 107 | 140 |
| 1218250 | N/A | N/A | 1468 | 1487 | GCTCTGTACATCCCGACACT | 91 | 141 |
| 1218254 | N/A | N/A | 2246 | 2265 | CTGCCCCTTGCAAAACGGTA | 90 | 142 |
| 1218258 | N/A | N/A | 3019 | 3038 | AGGTAGTCAGTATTCTATCC | 101 | 143 |
| 1218262 | N/A | N/A | 3630 | 3649 | GCCTGGAATTCGCTTTGCT | 102 | 144 |
| 1218266 | N/A | N/A | 4450 | 4469 | AGCTTGCCCGATCCCCAGCT | 55 | 145 |
| 1218270 | N/A | N/A | 5258 | 5277 | AGTTGTTATAGATCTTGCCC | 41 | 146 |
| 1218274 | N/A | N/A | 5642 | 5661 | CGTGCCCTTATCTGTGGCAC | 93 | 147 |
| 1218278 | N/A | N/A | 5880 | 5899 | AAGTTCCTTCCAATCCCGGA | 44 | 148 |
| 1218282 | N/A | N/A | 6231 | 6250 | GCTTGCAGACAATGTTTTGC | 54 | 149 |
| 1218286 | N/A | N/A | 6416 | 6435 | ACTCAGTTAGTCTTCGGGCA | 32 | 150 |
| 1218290 | N/A | N/A | 7164 | 7183 | GGGACTCTTTTC | 55 | 151 |

TABLE 2-continued

Reduction of PLP1 RNA by 5-10-5 MOE gapmers with phosphorothioate internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1218294 | N/A | N/A | 7527 | 7546 | GACACGATTTAGAGCCCTAGTATTACCA | 50 | 152 |
| 1218298 | N/A | N/A | 7859 | 7878 | GCAGTAGTTGACAAGGCCGA | 63 | 153 |
| 1218302 | N/A | N/A | 8084 | 8103 | AGACCAATTGTACCCTGCAC | 58 | 154 |
| 1218306 | N/A | N/A | 8367 | 8386 | GATACTCCAACTTTAAGCCC | 67 | 155 |
| 1218310 | N/A | N/A | 9421 | 9440 | GAGTCACCAGATCATAGCCT | 46 | 156 |
| 1218314 | N/A | N/A | 9691 | 9710 | TTGGGCCTACTCACTCATCC | 75 | 157 |
| 1218318 | N/A | N/A | 9750 | 9769 | GCAGGACTGTTTGTTTAGCC | 51 | 158 |
| 1218322 | N/A | N/A | 10518 | 10537 | TGAGTCCTATTACCCACCAT | 68 | 159 |
| 1218326 | N/A | N/A | 11020 | 11039 | CCTCTCGGCCAGATCCCTAA | 92 | 160 |
| 1218330 | N/A | N/A | 11378 | 11397 | AGCTTGGCTAATGTCCCCAC | 59 | 161 |
| 1218334 | N/A | N/A | 12872 | 12891 | CGGGAATCCGGTCTGGCTCC | 72 | 162 |
| 1218338 | N/A | N/A | 13226 | 13245 | ACACCTTGCTTACCCTGGGA | 47 | 163 |
| 1218342 | N/A | N/A | 13719 | 13738 | GAGGATGATCACCTTGTCGG | 35 | 164 |
| 1218346 | N/A | N/A | 13767 | 13786 | GACTCGCGCCAATTTTCCC | 64 | 165 |
| 1218350 | N/A | N/A | 13780 | 13799 | GGACGAGGCCACAGACTCGC | 69 | 166 |
| 1218354 | N/A | N/A | 14041 | 14060 | GTCCAGTTAGATCCACTCTT | 16 | 167 |

TABLE 2-continued

Reduction of PLP1 RNA by 5-10-5 MOE gapmers with phosphorothioate internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1218358 | N/A | N/A | 14181 | 14200 | CCTCTGGGACCTCGAACTGT | 88 | 168 |
| 1218362 | N/A | N/A | 14793 | 14812 | GGTGATGCCCACAAACTAAA | 91 | 169 |
| 1218366 | N/A | N/A | 14965 | 14984 | ACCCGTACCCTAACTCACCA | 91† | 170 |
| 1218370 | N/A | N/A | 15540 | 15559 | GTATGGTATTAGCTACTCCC | 24 | 171 |
| 1218374 | N/A | N/A | 15985 | 16004 | CCCCGGATTTACTTTTATTC | 55 | 172 |
| 1218378 | N/A | N/A | 16154 | 16173 | GTCTTCAGTGTACACCATAG | 37 | 173 |
| 1218382 | N/A | N/A | 16689 | 16708 | ACCGTAATTTATGACTGCAA | 24 | 174 |
| 1218386 | N/A | N/A | 17183 | 17202 | TCCGAGTGACTTAGAGTCAT | 32 | 175 |

TABLE 3

Reduction of PLP1 RNA by 5-10-5 MOE gapmers with phosphorothioate internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1218079 | N/A | N/A | 3813 | 3832 | TGATTGACAGCCAACCCCT | 104 | 176 |
| 1218083 | 235 | 254 | 3945 | 3964 | GCTGGCTAGTCTGCTTTGTG | 34 | 177 |
| 1218087 | 244 | 263 | 3954 | 3973 | TTGTAGCCGGCTGGCTAGTC | 47 | 178 |
| 1218091 | 252 | 271 | 3962 | 3981 | GACTCCAATTGTAGCCGGCT | 62 | 179 |
| 1218095 | 309 | 328 | 12601 | 12620 | GGGCCCCTACCAGACATCTT | 75 | 180 |
| 1218099 | 561 | 580 | 13549 | 13568 | GCCTGACTGCGCCGGTGGTG | 34 | 181 |
| 1218103 | 575 | 594 | 13563 | 13582 | GTCGCCAAAGATCTGCCTGA | 56 | 182 |
| 1218107 | 584 | 603 | 13572 | 13591 | GGTCTTGTAGTCGCCAAAGA | 62 | 183 |
| 1218111 | 593 | 612 | 13581 | 13600 | GCAGATGGTGGTCTT | 68 | 184 |

TABLE 3-continued

Reduction of PLP1 RNA by 5-10-5 MOE gapmers with phosphorothioate internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1218115 | 602 | 621 | 13590 | 13609 | GTAGTGCCCTTGCCGCAGATGGTGG | 30 | 185 |
| 1218119 | 610 | 629 | 13598 | 13617 | GCGCTCAGGCCCTTGCCGCA | 40 | 186 |
| 1218123 | 618 | 637 | 13606 | 13625 | TTACCGTTGCGCTCAGGCCC | 53 | 187 |
| 1218127 | 622 | 641 | 13610 | 13629 | CCTGTTACCGTTGCGCTCAG | 76 | 188 |
| 1218131 | 629 | 648 | 13617 | 13636 | CTGGCCCCTGTTACCGTTG | 53 | 189 |
| 1218135 | 677 | 696 | 13665 | 13684 | CCGCTCCAAAGAATGAGCTT | 32 | 190 |
| 1218139 | 714 | 733 | 13702 | 13721 | CGGGATGTCCTAGCCATTTT | 26 | 191 |
| 1218143 | 739 | 758 | 14798 | 14817 | GCATAGGTGATGCCCACAAA | 77 | 192 |
| 1218147 | 762 | 781 | 14821 | 14840 | CCAGGAGCCACAACGGTC | 43 | 193 |
| 1218151 | 861 | 880 | 14920 | 14939 | TGCCTATACTGGCAGAGGTC | 41 | 194 |
| 1218155 | 1091 | 1110 | 17570 | 17589 | GGTGCCTCGGCCCATGAGTT | 18 | 195 |
| 1218159 | 1102 | 1121 | 17581 | 17600 | GATCAGAACTTGGTGCCTCG | 34 | 196 |
| 1218163 | 1148 | 1167 | 17627 | 17646 | GTGTGGTTAGAGCCTCGCTA | 14 | 197 |
| 1218167 | 1165 | 1184 | 17644 | 17663 | ACGCAGCATTGTAGGCTGTG | 17 | 198 |
| 1218171 | 1450 | 1469 | 17929 | 17948 | AGTGGAAGTACCCTTTGAGA | 39 | 199 |
| 1218175 | 1650 | 1669 | 18129 | 18148 | TGCAATAGGCAGATTTGGGC | 14 | 200 |
| 1218179 | 1731 | 1750 | 18210 | 18229 | GCTTCAGTAGTCCATCGCCA | 7 | 201 |

TABLE 3-continued

Reduction of PLP1 RNA by 5-10-5 MOE gapmers with phosphorothioate internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1218183 | 1738 | 1757 | 18217 | 18236 | AGTTAGGGCTTCAGTAGTCC | 19 | 202 |
| 1218187 | 1759 | 1778 | 18238 | 18257 | TGCTGTAAGTAAGGTTGGCT | 22 | 203 |
| 1218191 | 1768 | 1787 | 18247 | 18266 | GCTCCCTTATGCTGTAAGTA | 14 | 204 |
| 1218195 | 1772 | 1791 | 18251 | 18270 | CTACGCTCCCTTATGCTGTA | 23 | 205 |
| 1218199 | 1779 | 1798 | 18258 | 18277 | ACAGATTCTACGCTCCCTTA | 36 | 206 |
| 1218203 | 1784 | 1803 | 18263 | 18282 | TCTACACAGATTCTACGCTC | 17 | 207 |
| 1218207 | 1809 | 1828 | 18288 | 18307 | GGTGTAAGGCCAGATGCCCC | 22 | 208 |
| 1218211 | 1885 | 1904 | 18364 | 18383 | GGTTGTCATGGTAGCTGTTA | 22 | 209 |
| 1218215 | 1986 | 2005 | 18465 | 18484 | CTCAGGTTACACCATTAGCC | 16 | 210 |
| 1218219 | 2120 | 2139 | 18599 | 18618 | GACTGAATGGATAATACCCC | 9 | 211 |
| 1218223 | 2515 | 2534 | 18994 | 19013 | GATGACTGGTGCATTCTGTT | 17 | 212 |
| 1218227 | 2878 | 2897 | 19357 | 19376 | CGGATTACTTCACTGTCCTT | 27 | 213 |
| 1218231 | 2882 | 2901 | 19361 | 19380 | GGTACGGATTACTTCACTGT | 23 | 214 |
| 1218235 | 21 | 40 | 3526 | 3545 | GGTGTGGGATATGCAGCACA | 91 | 215 |
| 1218239 | 38 | 57 | 3543 | 3562 | GATCCTTGGGTCTAATTGGT | 53 | 216 |
| 1218243 | N/A | N/A | 900 | 919 | AAGTGCCCAATCTAGTGGCC | 58 | 217 |
| 1218247 | N/A | N/A | 1359 | 1378 | ATCTACATACCCCCACCTAT | 90 | 218 |

TABLE 3-continued

Reduction of PLP1 RNA by 5-10-5 MOE gapmers with phosphorothioate internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1218251 | N/A | N/A | 1537 | 1556 | GGTGACCGTGTCTCACTCAT | 98 | 219 |
| 1218255 | N/A | N/A | 2308 | 2327 | TACTAGAACTCTAGATCCTT | 101 | 220 |
| 1218259 | N/A | N/A | 3070 | 3089 | CCAAGAAGGATAATCGACTT | 72 | 221 |
| 1218263 | N/A | N/A | 4083 | 4102 | CGACTCATTTAAACCATGGA | 51 | 222 |
| 1218267 | N/A | N/A | 4974 | 4993 | CCAGCTCAGTATAATTGCAA | 23 | 223 |
| 1218271 | N/A | N/A | 5443 | 5462 | TAGGATTCCTGATGTTACCC | 47 | 224 |
| 1218275 | N/A | N/A | 5668 | 5687 | CCTGGGACCAATGTGCATC | 27 | 225 |
| 1218279 | N/A | N/A | 5947 | 5966 | GTACGAACATTTAATTGGTT | 39 | 226 |
| 1218283 | N/A | N/A | 6249 | 6268 | GTTCTCAGACGACAACAGGC | 43 | 227 |
| 1218287 | N/A | N/A | 6716 | 6735 | TGTTATTACTCAGATCGCTC | 45 | 228 |
| 1218291 | N/A | N/A | 7261 | 7280 | GTAGCCATACCTTGTTCCTC | 33 | 229 |
| 1218295 | N/A | N/A | 7587 | 7606 | GCTGGATAGTCAAATCATGT | 45 | 230 |
| 1218299 | N/A | N/A | 7911 | 7930 | AACCCACCCCTTAACCTTAC | 91 | 231 |
| 1218303 | N/A | N/A | 8189 | 8208 | TGGGCCCGCCTCAAGGACCA | 71 | 232 |
| 1218307 | N/A | N/A | 8814 | 8833 | CCAGTCTAAGTACAGACTGC | 91 | 233 |
| 1218311 | N/A | N/A | 9519 | 9538 | AGTGTATCTGATCCCTCAAT | 65 | 234 |
| 1218315 | N/A | N/A | 9694 | 9713 | ATCTTGGGCTACTCACTCA | 75 | 235 |
| 1218319 | N/A | N/A | 9861 | 9880 | TCCCCC | 50 | 236 |

TABLE 3-continued

Reduction of PLP1 RNA by 5-10-5 MOE gapmers with phosphorothioate internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| | | | | | GGACAAAGAAGCCT | | |
| 1218323 | N/A | N/A | 10520 | 10539 | AGTGAGTCCTATTACCCACC | 45 | 237 |
| 1218327 | N/A | N/A | 11121 | 11140 | TCCAAGTACTAGTCCCATGC | 27 | 238 |
| 1218331 | N/A | N/A | 11463 | 11482 | GAGGTTTGATATTACTCCCA | 29 | 239 |
| 1218335 | N/A | N/A | 13022 | 13041 | GCAATATGAACCACACCTAG | 42 | 240 |
| 1218339 | N/A | N/A | 13230 | 13249 | CGCCACACCTTGCTTACCCT | 55 | 241 |
| 1218343 | N/A | N/A | 13747 | 13766 | CCACCCCTTGTTATTGCCAC | 40 | 242 |
| 1218347 | N/A | N/A | 13769 | 13788 | CAGACTCGCGCCCAATTTTC | 62 | 243 |
| 1218351 | N/A | N/A | 13969 | 13988 | GGTCTGATTGTACAAAGCAT | 22 | 244 |
| 1218355 | N/A | N/A | 14042 | 14061 | TGTCCAGTTAGATCCACTCT | 8 | 245 |
| 1218359 | N/A | N/A | 14289 | 14308 | CGCCAAAGGATCTTTAACTC | 30 | 246 |
| 1218363 | N/A | N/A | 14962 | 14981 | CGTACCCTAACTCACCATAC | 77† | 247 |
| 1218367 | N/A | N/A | 14966 | 14985 | CACCCGTACCTAACTCACC | 64† | 248 |
| 1218371 | N/A | N/A | 15541 | 15560 | TGTATGGTATTAGCTACTCC | 23 | 249 |
| 1218375 | N/A | N/A | 15992 | 16011 | CTGTCTCCCCGGATTTACT | 46 | 250 |
| 1218379 | N/A | N/A | 16434 | 16453 | TACCCACACTATCTCAGGCC | 23 | 251 |
| 1218383 | N/A | N/A | 16938 | 16957 | GCACACTACATTCACAGGGC | 17 | 252 |
| 1218387 | N/A | N/A | 17196 | 17215 | CCACATCAATAT | 12 | 253 |

TABLE 3-continued

Reduction of PLP1 RNA by 5-10-5 MOE gapmers with phosphorothioate internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| | | | | | GTCCGAGT | | |

TABLE 4

Reduction of PLP1 RNA by 5-10-5 MOE gapmers with phosphorothioate internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1218080 | N/A | N/A | 3814 | 3833 | CTGATTGACAGCAACCCCC | 98 | 254 |
| 1218084 | 236 | 255 | 3946 | 3965 | GGCTGGCTAGTCTGCTTTGT | 41 | 255 |
| 1218088 | 248 | 267 | 3958 | 3977 | CCAATTGTAGCCGGCTGGCT | 62 | 256 |
| 1218092 | 253 | 272 | 3963 | 3982 | TGACTCCAATTGTAGCCGGC | 80 | 257 |
| 1218096 | 550 | 569 | 13538 | 13557 | CCGGTGGTGTAGAAGCCCTC | 65 | 258 |
| 1218100 | 562 | 581 | 13550 | 13569 | TGCCTGACTGCGCCGGTGGT | 37 | 259 |
| 1218104 | 576 | 595 | 13564 | 13583 | AGTCGCCAAAGATCTGCCTG | 51 | 260 |
| 1218108 | 587 | 606 | 13575 | 13594 | GGTGGTCTTGTAGTCGCCAA | 44 | 261 |
| 1218112 | 595 | 614 | 13583 | 13602 | CCGCAGATGGTGGTCTTGTA | 50 | 262 |
| 1218116 | 603 | 622 | 13591 | 13610 | GGCCCTGCCGCAGATGGTG | 52 | 263 |
| 1218120 | 612 | 631 | 13600 | 13619 | TTGCGCTCAGGCCCTGCCG | 60 | 264 |
| 1218124 | 619 | 638 | 13607 | 13626 | GTTACCGTTGCGCTCAGGCC | 51 | 265 |
| 1218128 | 623 | 642 | 13611 | 13630 | CCCTGTTACCGTTGCGCTCA | 92 | 266 |
| 1218132 | 632 | 651 | 13620 | 13639 | CTTCTGGCCCCTGTTACCG | 82 | 267 |

TABLE 4-continued

Reduction of PLP1 RNA by 5-10-5 MOE gapmers with phosphorothioate internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1218136 | 679 | 698 | 13667 | 13686 | ACCCGCTCCAAAGAATGAGC | 50 | 268 |
| 1218140 | 715 | 734 | 13703 | 13722 | TCGGGATGTCCTAGCCATTT | 31 | 269 |
| 1218144 | 755 | 774 | 14814 | 14833 | CCACACAACGGTCAGGGCAT | 41 | 270 |
| 1218148 | 763 | 782 | 14822 | 14841 | ACCAGGAGCCACACAACGGT | 54 | 271 |
| 1218152 | 866 | 885 | 14925 | 14944 | GAGACTGCCTATACTGGCAG | 83 | 272 |
| 1218156 | 1096 | 1115 | 17575 | 17594 | AACTTGGTGCCTCGGCCCAT | 23 | 273 |
| 1218160 | 1103 | 1122 | 17582 | 17601 | GGATCAGAACTTGGTGCCTC | 22 | 274 |
| 1218164 | 1149 | 1168 | 17628 | 17647 | TGTGTGGTTAGAGCCTCGCT | 21 | 275 |
| 1218168 | 1168 | 1187 | 17647 | 17666 | GAGACGCAGCATTGTAGGCT | 17 | 276 |
| 1218172 | 1452 | 1471 | 17931 | 17950 | TCAGTGGAAGTACCCTTTGA | 69 | 277 |
| 1218176 | 1681 | 1700 | 18160 | 18179 | AAGATCCTTGCTTTGACCCC | 61 | 278 |
| 1218180 | 1732 | 1751 | 18211 | 18230 | GGCTTCAGTAGTCCATCGCC | 16 | 279 |
| 1218184 | 1739 | 1758 | 18218 | 18237 | GAGTTAGGGCTTCAGTAGTC | 21 | 280 |
| 1218188 | 1760 | 1779 | 18239 | 18258 | ATGCTGTAAGTAAGGTTGGC | 19 | 281 |
| 1218192 | 1769 | 1788 | 18248 | 18267 | CGCTCCCTTATGCTGTAAGT | 17 | 282 |
| 1218196 | 1773 | 1792 | 18252 | 18271 | TCTACGCTCCCTTATGCTGT | 32 | 283 |
| 1218200 | 1781 | 1800 | 18260 | 18279 | ACACAGATTCTACGCTCCCT | 24 | 284 |
| 1218204 | 1785 | 1804 | 18264 | 18283 | GTCTAC | 19 | 285 |

TABLE 4-continued

Reduction of PLP1 RNA by 5-10-5 MOE gapmers with phosphorothioate internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1218208 | 1818 | 1837 | 18297 | 18316 | ACAGATTCTACGCTCCCTAACGAGGTGTAAGGCC | 8 | 286 |
| 1218212 | 1887 | 1906 | 18366 | 18385 | AGGGTTGTCATGGTAGCTGT | 22 | 287 |
| 1218216 | 1994 | 2013 | 18473 | 18492 | AGGGCCATCTCAGGTACAC | 13 | 288 |
| 1218220 | 2141 | 2160 | 18620 | 18639 | GACCTTCAAATCACCTACGA | 17 | 289 |
| 1218224 | 2541 | 2560 | 19020 | 19039 | CCTGGAAGCTTACCAACTGA | 25 | 290 |
| 1218228 | 2879 | 2898 | 19358 | 19377 | ACGGATTACTTCACTGTCCT | 14 | 291 |
| 1218232 | 2883 | 2902 | 19362 | 19381 | AGGTACGGATTACTTCACTG | 20 | 292 |
| 1218236 | 30 | 49 | 3535 | 3554 | GGTCTAATTGGTGTGGGATA | 90 | 293 |
| 1218240 | 114 | 133 | 3619 | 3638 | CGCTTTGCTGCAGAGACATC | 93 | 294 |
| 1218244 | N/A | N/A | 974 | 993 | TCATTGTGTAGACTGAACTC | 91 | 295 |
| 1218248 | N/A | N/A | 1400 | 1419 | CCTCATAGGGTATCTTCCCA | 105 | 296 |
| 1218252 | N/A | N/A | 2020 | 2039 | ATCGCCAAATGTGTCTCCTC | 100 | 297 |
| 1218256 | N/A | N/A | 2563 | 2582 | GGTATGGTCTCCTGGAACTT | 104 | 298 |
| 1218260 | N/A | N/A | 3444 | 3463 | GCTCCCAAAGTCCTTCCGAA | 104 | 299 |
| 1218264 | N/A | N/A | 4366 | 4385 | GGCTAGACAGTGCTCAGTGG | 40 | 300 |
| 1218268 | N/A | N/A | 5141 | 5160 | GGTGATTCAGTGACCTGTCC | 39 | 301 |
| 1218272 | N/A | N/A | 5473 | 5492 | ACCTATCCAGTC | 85 | 302 |

TABLE 4-continued

Reduction of PLP1 RNA by 5-10-5 MOE gapmers with phosphorothioate internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1218276 | N/A | N/A | 5793 | 5812 | GTCCAGTACCTTGTTAGAGA | 29 | 303 |
| 1218280 | N/A | N/A | 5956 | 5975 | GCAGAGGCTGTACGAACATT | 29 | 304 |
| 1218284 | N/A | N/A | 6350 | 6369 | GCTACACCCACTTACTGCAA | 45 | 305 |
| 1218288 | N/A | N/A | 6780 | 6799 | GAGTTCTACCTTAATGGGTT | 57 | 306 |
| 1218292 | N/A | N/A | 7468 | 7487 | CACTCCTCTTCAGACGCGCA | 69 | 307 |
| 1218296 | N/A | N/A | 7636 | 7655 | AGTGCTGGAAAACAGTCCCG | 69 | 308 |
| 1218300 | N/A | N/A | 7949 | 7968 | GGTCTCGAATCTGCACTACA | 50 | 309 |
| 1218304 | N/A | N/A | 8273 | 8292 | TCAAGGGACTGTGTTGATCC | 63 | 310 |
| 1218308 | N/A | N/A | 8959 | 8978 | GGTATGTGTGAACAATAGCC | 56 | 311 |
| 1218312 | N/A | N/A | 9521 | 9540 | TGAGTGTATCTGATCCCTCA | 45 | 312 |
| 1218316 | N/A | N/A | 9709 | 9728 | CCCTAGCAAGTGACCATCTT | 90 | 313 |
| 1218320 | N/A | N/A | 9868 | 9887 | CCATAGCTCCCCGGACAAA | 77 | 314 |
| 1218324 | N/A | N/A | 10522 | 10541 | GGAGTGAGTCCTATTACCCA | 49 | 315 |
| 1218328 | N/A | N/A | 11125 | 11144 | GTGTTCCAAGTACTAGTCCC | 58 | 316 |
| 1218332 | N/A | N/A | 11464 | 11483 | GGAGGTTTGATATTACTCCC | 50 | 317 |
| 1218336 | N/A | N/A | 13056 | 13075 | CTCCATACCTACTACGCTGG | 48 | 318 |

TABLE 4-continued

Reduction of PLP1 RNA by 5-10-5 MOE gapmers with phosphorothioate internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1218340 | N/A | N/A | 13361 | 13380 | CCAGAGCGAGCACCTTAACA | 55 | 319 |
| 1218344 | N/A | N/A | 13762 | 13781 | GCGCCCAATTTTCCCCCACC | 46 | 320 |
| 1218348 | N/A | N/A | 13776 | 13795 | GAGGCCACAGACTCGCGCCC | 55 | 321 |
| 1218352 | N/A | N/A | 14037 | 14056 | AGTTAGATCCACTCTTGTGG | 36 | 322 |
| 1218356 | N/A | N/A | 14043 | 14062 | TTGTCCAGTTAGATCCACTC | 23 | 323 |
| 1218360 | N/A | N/A | 14402 | 14421 | TGTTCCCTAGCCATTGAACA | 67 | 324 |
| 1218364 | N/A | N/A | 14963 | 14982 | CCGTACCCTAACTCACCATA | 94† | 325 |
| 1218368 | N/A | N/A | 15173 | 15192 | GTAGGCCAATGTGAATGGCC | 95 | 326 |
| 1218372 | N/A | N/A | 15542 | 15561 | TTGTATGGTATTAGCTACTC | 45 | 327 |
| 1218376 | N/A | N/A | 16130 | 16149 | TGGCCCATTAACACCCAGAT | 49 | 328 |
| 1218380 | N/A | N/A | 16529 | 16548 | GTACGGAGCCTCCACCCTTT | 50 | 329 |
| 1218384 | N/A | N/A | 17128 | 17147 | AGTAGAGCTCTCCCCTGGTT | 66 | 330 |
| 1218388 | N/A | N/A | 17329 | 17348 | AGTCCGATGTCTCTGAGGCA | 42 | 331 |

Example 2: Effect of 5-10-5 MOE Gapmer Modified Oligonucleotides on Human PLP1 RNA In Vitro, Single Dose Modified oligonucleotides complementary to human PLP1 nucleic acid were designed and tested for their single dose effects on PLP1 RNA in vitro. The modified oligonucleotides were tested in a series of experiments that had the same culture conditions, and the results for each experiment are presented in separate tables below.

The modified oligonucleotides in the tables below are 5-10-5 MOE gapmers. The gapmers are 20 nucleosides in length, wherein the central gap segment consists of ten 2'-β-D-deoxynucleosides and the 5' and 3' wing segments each consists of five 2'-MOE modified nucleosides. The sugar motif for the gapmers is (from 5' to 3'): eeeeedddddddddeeeee; wherein 'd' represents a 2'-β-D-deoxyribosyl sugar moiety, and 'e' represents a 2'-MOE sugar moiety. The internucleoside linkage motif for the gapmers is (from 5' to 3'): "soooossssssssssooss"; wherein each 'o' represents a phosphodiester internucleoside linkage and each 's' represents a phosphorothioate internucleoside linkage. Each cytosine residue is a 5-methyl cytosine.

"Start site" indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence. Each modified oligonucleotide listed in the Tables below is 100% complementary to either human PLP1 mRNA (SEQ ID NO: 1) or to the human PLP1 genomic sequence (SEQ ID NO: 2), or to both. 'N/A' indicates that the modified oligonucleotide is not 100% complementary to that particular target nucleic acid sequence.

Cultured SK-MEL-28 cells were treated with modified oligonucleotide at a concentration of 4,000 nM using electroporation at a density of 20,000 cells per well. After a treatment period of approximately 24 hours, total RNA was isolated from the cells and PLP1 RNA levels were measured by quantitative real-time RTPCR. PLP1 RNA levels were measured by Human PLP1 primer probe set RTS35092, described in Example 1 above. PLP1 RNA levels were normalized to total RNA content, as measured by RIBOGREEN®. Reduction of PLP1 RNA is presented in the tables below as percent PLP1 RNA relative to the amount in untreated control cells (% UTC). Each table represents results from an individual assay plate. The values marked with an "†" indicate that the modified oligonucleotide is complementary to the amplicon region of the primer probe set. Additional assays may be used to measure the potency and efficacy of the modified oligonucleotides complementary to the amplicon region.

TABLE 5

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362432 | N/A | N/A | 8998 | 9017 | GCTCCCTTTGATTTTCACA | 37 | 332 |
| 1362464 | 2489 | 2508 | 18968 | 18987 | TCTATATCAGGAGAAATAA | 62 | 333 |
| 1362490 | 1731 | 1750 | 18210 | 18229 | GCTTCAGTAGTCCATCGCCA | 20 | 201 |
| 1362496 | 1917 | 1936 | 18396 | 18415 | TCCTTCTATTCTCAGCTCCT | 15 | 334 |
| 1362567 | 1879 | 1898 | 18358 | 18377 | CATGGTAGCTGTTATCAAGG | 21 | 335 |
| 1362568 | 2408 | 2427 | 18887 | 18906 | CATTAGCTAGAAAGAACGAT | 33 | 336 |
| 1362595 | N/A | N/A | 16249 | 16268 | CATGAATACAGCTTTCTGAA | 47 | 337 |
| 1362652 | 2080 | 2099 | 18559 | 18578 | AAGATATGACAGAGGCCAGA | 30 | 338 |
| 1362658 | 1217 | 1236 | 17696 | 17715 | TCAAGTAAGAAGAGGGCCAG | 56 | 339 |
| 1362661 | N/A | N/A | 10078 | 10097 | AGATTCAGCCTATAAGTCAA | 53 | 340 |
| 1362687 | N/A | N/A | 9225 | 9244 | CAATTCAGTAATATCAGCAT | 55 | 341 |
| 1362731 | 2016 | 2035 | 18495 | 18514 | TTATCTATCCTGTGTCTACC | 49 | 342 |
| 1362740 | 2300 | 2319 | 18779 | 18798 | CAATTTTTAATATCATTTGT | 57 | 343 |

TABLE 5-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362755 | 2844 | 2863 | 19323 | 19342 | TCTTACAAAACATTTTCCCT | 40 | 344 |
| 1362763 | 2350 | 2369 | 18829 | 18848 | TTTCTGCAAAGGCAGAATAC | 58 | 345 |
| 1362775 | 2325 | 2344 | 18804 | 18823 | GAAAATCCCAATAGATTCAA | 49 | 346 |
| 1362803 | 2159 | 2178 | 18638 | 18657 | CATTCTAAAACAAATCAAGA | 68 | 347 |
| 1362827 | N/A | N/A | 11747 | 11766 | CTAACAATTCAGGCAGCCAA | 57 | 348 |
| 1362850 | N/A | N/A | 17152 | 17171 | TGTAGACACACAGCCACATC | 57 | 349 |
| 1362884 | 1439 | 1458 | 17918 | 17937 | CCTTTGAGAAGAAATTACTT | 70 | 350 |
| 1362923 | 1254 | 1273 | 17733 | 17752 | TTAATCACTGCAAGACTCTC | 51 | 351 |
| 1362925 | N/A | N/A | 16906 | 16925 | TCAGCAAGACCTGGGACATA | 39 | 352 |
| 1362979 | N/A | N/A | 8166 | 8185 | CCATGATGGAAATTCAGTGT | 58 | 353 |
| 1363002 | 2699 | 2718 | 19178 | 19197 | AACACAACTCTTTACAACAA | 49 | 354 |
| 1363018 | N/A | N/A | 13294 | 13313 | TCACCTTATCTTTGTTGAAA | 55 | 355 |
| 1363035 | 1052 | 1071 | 17531 | 17550 | AGTGGCAGCAATCATGAAGG | 35 | 356 |
| 1363043 | N/A | N/A | 4770 | 4789 | TCTGAGTAGAAACTACCACC | 32 | 357 |
| 1363080 | 1843 | 1862 | 18322 | 18341 | ATGCTGACAACACCCTGTTT | 46 | 358 |
| 1363081 | N/A | N/A | 10740 | 10759 | GCCACACTCACTTTTCTATA | 48 | 359 |
| 1363103 | 1734 | 1753 | 18213 | 18232 | AGGGCTTCAGTAGTCATCG | 11 | 46 |
| 1363134 | 1481 | 1500 | 17960 | 17979 | TGAGCA | 14 | 360 |

TABLE 5-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363136 | 1520 | 1539 | 17999 | 18018 | TCTTTCCTTCCACT TAGATGGCAAGAGGACCAAA | 70 | 361 |
| 1363137 | 2793 | 2812 | 19272 | 19291 | TTGTATACTGGTTTGAAAAC | 62 | 362 |
| 1363157 | 2752 | 2771 | 19231 | 19250 | AAAGCTCTTACATCTCCTTA | 27 | 363 |
| 1363158 | 2436 | 2455 | 18915 | 18934 | GATAACATTGCTAAGTAAAA | 42 | 364 |
| 1363161 | 3121 | 3140 | 19600 | 19619 | TTTGATTGAGAACATTCTTA | 43 | 365 |
| 1363177 | N/A | N/A | 5117 | 5136 | TCACATAGTTCATAAGTAGC | 40 | 366 |
| 1363206 | 1784 | 1803 | 18263 | 18282 | TCTACACAGATTCTACGCTC | 25 | 207 |
| 1363219 | 2135 | 2154 | 18614 | 18633 | CAAATCACCTACGATGACTG | 51 | 367 |
| 1363230 | N/A | N/A | 7394 | 7413 | CATTCCAATTTATGTGCAAG | 48 | 368 |
| 1363240 | 2237 | 2256 | 18716 | 18735 | TCAAAGAATTATTCTCCAGA | 42 | 369 |
| 1363259 | 2381 | 2400 | 18860 | 18879 | CTCAAATTGAGATTCAAATT | 59 | 370 |
| 1363272 | 2994 | 3013 | 19473 | 19492 | ACTTTCAGTTGATTAACTCT | 37 | 371 |
| 1363291 | N/A | N/A | 13758 | 13777 | CCAATTTTCCCCACCCCTT | 56 | 372 |
| 1363342 | 1137 | 1156 | 17616 | 17635 | GCCTCGCTATTAGAGAAAGG | 34 | 373 |
| 1363383 | 1298 | 1317 | 17777 | 17796 | TGACTAAAAGAGGTACATAA | 52 | 374 |
| 1363396 | N/A | N/A | 15298 | 15317 | CCAACAATCAGGATCCTCTT | 73 | 375 |
| 1363437 | N/A | N/A | 11123 | 11142 | GTTCCAAGTACT | 40 | 376 |

TABLE 5-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363466 | N/A | N/A | 14343 | 14362 | CTAAGCTAACTGCTGGCCAC | 45 | 377 |
| 1363495 | 2262 | 2281 | 18741 | 18760 | TTCCTAGTTTAAAAACAGT | 59 | 378 |
| 1363529 | N/A | N/A | 5830 | 5849 | TTGAACAGCAGTGCACTCCA | 69 | 379 |
| 1363539 | 1554 | 1573 | 18033 | 18052 | TTTTGTACACCAAAGAGAAT | 62 | 380 |
| 1363641 | N/A | N/A | 16661 | 16680 | GCAACATTACATGTTCTATA | 11 | 381 |
| 1363679 | N/A | N/A | 11910 | 11929 | CTTATTTTAGTCATTCATCA | 47 | 382 |
| 1363681 | 2894 | 2913 | 19373 | 19392 | AACAAAACACAAGGTACGGA | 20 | 383 |
| 1363730 | 1363 | 1382 | 17842 | 17861 | TGCAGTTGGGAAGTCATCTT | 36 | 384 |
| 1363734 | 2672 | 2691 | 19151 | 19170 | GTAGTACAAATCTTTCCTTC | 15 | 385 |
| 1363751 | 2624 | 2643 | 19103 | 19122 | TTTAACCCAAAGTTAACAAA | 50 | 386 |
| 1363767 | 2107 | 2126 | 18586 | 18605 | ATACCCCATGAAATGAGCAC | 23 | 387 |
| 1363797 | 1403 | 1422 | 17882 | 17901 | TGCTTGAAAATTCAATTAGA | 45 | 388 |
| 1363843 | N/A | N/A | 8643 | 8662 | CAGTACAAGAATTAAGCACA | 41 | 389 |
| 1363858 | 1185 | 1204 | 17664 | 17683 | GCAAAGAGTTAAGATGGGAG | 27 | 390 |
| 1363892 | 1976 | 1995 | 18455 | 18474 | ACCATTAGCCACCAGCAACT | 47 | 391 |
| 1363900 | 2586 | 2605 | 19065 | 19084 | TCTGGGAGCTATTCAGGTCT | 19 | 392 |

TABLE 5-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363907 | 3060 | 3079 | 19539 | 19558 | AAGTTTCTAAAAGTTTATCC | 29 | 393 |
| 1363921 | 1593 | 1612 | 18072 | 18091 | CTATCTTCAGTGGTAATAGA | 35 | 394 |
| 1363922 | N/A | N/A | 15670 | 15689 | GGTGTTTTACCTTCTATGCT | 73 | 395 |
| 1363937 | 1664 | 1683 | 18143 | 18162 | CCCCTTCTCCCAGCTGCAAT | 44 | 396 |
| 1363951 | 2535 | 2554 | 19014 | 19033 | AGCTTACCAACTGAATAGCT | 33 | 397 |
| 1363982 | 3022 | 3041 | 19501 | 19520 | GCAATTCTATATCAGAAATG | 21 | 398 |
| 1363998 | N/A | N/A | 7041 | 7060 | TTGATGTAAGTTTGGCACTG | 35 | 399 |
| 1364032 | 1324 | 1343 | 17803 | 17822 | TAGCAGGAACCAGCTATGAA | 56 | 400 |
| 1364046 | 2202 | 2221 | 18681 | 18700 | CCCAAATAAGTAATAAACAA | 46 | 401 |
| 1364111 | N/A | N/A | 6222 | 6241 | CAATGTTTTGCTGTTCAATA | 50 | 402 |
| 1364117 | 2053 | 2072 | 18532 | 18551 | ACTAATTAACAGAAAAAAAG | 74 | 403 |
| 1364223 | N/A | N/A | 5446 | 5465 | AGATAGGATTCCTGATGTTA | 62 | 404 |
| 1364232 | 2462 | 2481 | 18941 | 18960 | GTTAAACCTAACTCTTAACA | 49 | 405 |
| 1364251 | N/A | N/A | 6414 | 6433 | TCAGTTAGTCTTCGGGCATT | 34 | 406 |

TABLE 6

Reduction of PLP1 RNA by 5-10-5 MOE gapmers with mixed
PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 805577 | 1253 | 1272 | 17732 | 17751 | TAATCACTGCAAGACTCTCC | 35 | 407 |
| 1362428 | N/A | N/A | 7391 | 7410 | TCCAATTTATGTGCAAGCAT | 24 | 408 |
| 1362431 | 2488 | 2507 | 18967 | 18986 | CTATATCAGGAGAAAATAAC | 50 | 409 |
| 1362443 | N/A | N/A | 6215 | 6234 | TTGCTGTTCAATAATGGCAT | 26 | 410 |
| 1362449 | 2698 | 2717 | 19177 | 19196 | ACACAACTCTTTACAACAAA | 16 | 411 |
| 1362490 | 1731 | 1750 | 18210 | 18229 | GCTTCAGTAGTCCATCGCCA | 13 | 201 |
| 1362498 | N/A | N/A | 5445 | 5464 | GATAGGATTCCTGATGTTAC | 48 | 412 |
| 1362508 | N/A | N/A | 5115 | 5134 | ACATAGTTCATAAGTAGCAG | 29 | 413 |
| 1362623 | 1780 | 1799 | 18259 | 18278 | CACAGATTCTACGCTCCCTT | 16 | 414 |
| 1362629 | N/A | N/A | 13281 | 13300 | GTTGAAATAAGTGAAGACAG | 53 | 415 |
| 1362670 | 2671 | 2690 | 19150 | 19169 | TAGTACAAATCTTTCCTTCA | 18 | 416 |
| 1362677 | 2893 | 2912 | 19372 | 19391 | ACAAAACACAAGGTACGGAT | 21 | 417 |
| 1362711 | 2435 | 2454 | 18914 | 18933 | ATAACATTGCTAAGTAAAAT | 77 | 418 |
| 1362718 | 2008 | 2027 | 18487 | 18506 | CCTGTGTCTACCAGAGGGCC | 21 | 419 |
| 1362750 | 1662 | 1681 | 18141 | 18160 | CCTTCTCCCAGCTGCAATAG | 30 | 420 |
| 1362756 | N/A | N/A | 16905 | 16924 | CAGCAAGACCTGGGACATAG | 33 | 421 |
| 1362765 | N/A | N/A | 5828 | 5847 | GAACAGCAGTGCACTCCACA | 36 | 422 |
| 1362766 | 1323 | 1342 | 17802 | 17821 | AGCAGGAACCAGCTATGAAG | 33 | 423 |
| 1362809 | 2236 | 2255 | 18715 | 18734 | CAAAGAATTATTCTCCAGAC | 23 | 424 |
| 1362812 | 3119 | 3138 | 19598 | 19617 | TGATTGAGAACATTCTTAAT | 48 | 425 |
| 1362839 | N/A | N/A | 13743 | 13762 | CCCTTGTTATTGCCACAAAA | 32 | 426 |
| 1362880 | 2843 | 2862 | 19322 | 19341 | CTTACAAAACATTTTCCCTC | 30 | 427 |
| 1362922 | 2461 | 2480 | 18940 | 18959 | TTAAACCTAACTCTTAACAC | 50 | 428 |
| 1362933 | 1553 | 1572 | 18032 | 18051 | TTTGTACACCAAAGAGAATA | 50 | 429 |
| 1362995 | 1591 | 1610 | 18070 | 18089 | ATCTTCAGTGGTAATAGAGA | 34 | 430 |
| 1363011 | N/A | N/A | 4769 | 4788 | CTGAGTAGAAACTACCACCA | 27 | 431 |
| 1363046 | N/A | N/A | 16597 | 16616 | TCCTCATACCACTTTTCTTG | 87 | 432 |
| 1363055 | 1216 | 1235 | 17695 | 17714 | CAAGTAAGAAGAGGGCCAGT | 69 | 433 |
| 1363058 | 2380 | 2399 | 18859 | 18878 | TCAAATTGAGATTCAAATTC | 63 | 434 |
| 1363110 | 3021 | 3040 | 19500 | 19519 | CAATTCTATATCAGAAATGA | 35 | 435 |
| 1363121 | 1732 | 1751 | 18211 | 18230 | GGCTTCAGTAGTCCATCGCC | 11 | 279 |
| 1363140 | 1361 | 1380 | 17840 | 17859 | CAGTTGGGAAGTCATCTTCT | 27 | 436 |
| 1363170 | 2534 | 2553 | 19013 | 19032 | GCTTACCAACTGAATAGCTG | 18 | 437 |
| 1363176 | 2079 | 2098 | 18558 | 18577 | AGATATGACAGAGGCCAGAG | 32 | 438 |
| 1363184 | 1874 | 1893 | 18353 | 18372 | TAGCTGTTATCAAGGAGAAG | 11 | 439 |
| 1363188 | 1519 | 1538 | 17998 | 18017 | AGATGGCAAGAGGACCAAAG | 34 | 440 |

TABLE 6-continued

Reduction of PLP1 RNA by 5-10-5 MOE gapmers with mixed
PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363209 | 1051 | 1070 | 17530 | 17549 | GTGGCAGCAATCATGAAGGT | 23 | 441 |
| 1363223 | 1297 | 1316 | 17776 | 17795 | GACTAAAAGAGGTACATAAG | 39 | 442 |
| 1363224 | N/A | N/A | 9224 | 9243 | AATTCAGTAATATCAGCATA | 71 | 443 |
| 1363225 | N/A | N/A | 16248 | 16267 | ATGAATACAGCTTTCTGAAT | 64 | 444 |
| 1363244 | 3059 | 3078 | 19538 | 19557 | AGTTTCTAAAAGTTTATCCT | 19 | 445 |
| 1363263 | 2261 | 2280 | 18740 | 18759 | TCCTAGTTTAAAAACAGTC | 21 | 446 |
| 1363264 | N/A | N/A | 6399 | 6418 | GCATTTTATAAAACTGGACC | 40 | 447 |
| 1363279 | 2158 | 2177 | 18637 | 18656 | ATTCTAAAACAAATCAAGAC | 63 | 448 |
| 1363331 | 1436 | 1455 | 17915 | 17934 | TTGAGAAGAAATTACTTTCT | 64 | 449 |
| 1363332 | 2583 | 2602 | 19062 | 19081 | GGGAGCTATTCAGGTCTCAA | 88 | 135 |
| 1363350 | N/A | N/A | 10033 | 10052 | ACTGCCATTTTCCTTCTCTG | 34 | 450 |
| 1363354 | 1184 | 1203 | 17663 | 17682 | CAAAGAGTTAAGATGGGAGA | 44 | 451 |
| 1363362 | N/A | N/A | 7027 | 7046 | GCACTGAGTAGGCTCTGAAA | 18 | 452 |
| 1363388 | N/A | N/A | 15221 | 15240 | TGTTATTGAAATGTGCTGCT | 47 | 453 |
| 1363416 | N/A | N/A | 15669 | 15688 | GTGTTTTACCTTCTATGCTC | 27 | 454 |
| 1363510 | 2407 | 2426 | 18886 | 18905 | ATTAGCTAGAAAGAACGATC | 19 | 455 |
| 1363545 | 1975 | 1994 | 18454 | 18473 | CCATTAGCCACCAGCAACTG | 40 | 456 |
| 1363634 | N/A | N/A | 11120 | 11139 | CCAAGTACTAGTCCCATGCT | 48 | 457 |
| 1363645 | 2623 | 2642 | 19102 | 19121 | TTAACCCAAAGTTAACAAAA | 56 | 458 |
| 1363687 | 1842 | 1861 | 18321 | 18340 | TGCTGACAACACCCTGTTTC | 28 | 459 |
| 1363736 | 1136 | 1155 | 17615 | 17634 | CCTCGCTATTAGAGAAAGGG | 13 | 460 |
| 1363755 | 2201 | 2220 | 18680 | 18699 | CCAAATAAGTAATAAACAAA | 60 | 461 |
| 1363761 | 1402 | 1421 | 17881 | 17900 | GCTTGAAAATTCAATTAGAG | 17 | 462 |
| 1363798 | N/A | N/A | 8641 | 8660 | GTACAAGAATTAAGCACACT | 38 | 463 |
| 1363806 | 2349 | 2368 | 18828 | 18847 | TTCTGCAAAGGCAGAATACT | 63 | 464 |
| 1363823 | 2134 | 2153 | 18613 | 18632 | AAATCACCTACGATGACTGA | 45 | 465 |
| 1363851 | N/A | N/A | 8994 | 9013 | CCTTTGATTTTTCACAGTCC | 28 | 466 |
| 1363882 | 2750 | 2769 | 19229 | 19248 | AGCTCTTACATCTCCTTAAA | 16 | 467 |
| 1363930 | 2324 | 2343 | 18803 | 18822 | AAAATCCCAATAGATTCAAC | 29 | 468 |
| 1363932 | 2792 | 2811 | 19271 | 19290 | TGTATACTGGTTTGAAAACA | 32 | 469 |
| 1363934 | N/A | N/A | 8160 | 8179 | TGGAAATTCAGTGTGAATCT | 37 | 470 |
| 1363959 | 2106 | 2125 | 18585 | 18604 | TACCCCATGAAATGAGCACC | 13 | 471 |
| 1364007 | 1916 | 1935 | 18395 | 18414 | CCTTCTATTCTCAGCTCCTT | 14 | 472 |
| 1364041 | N/A | N/A | 14308 | 14327 | GAACCCACACATGTTCAGCC | 17 | 473 |
| 1364067 | N/A | N/A | 11746 | 11765 | TAACAATTCAGGCAGCCAAG | 38 | 474 |

TABLE 6-continued

Reduction of PLP1 RNA by 5-10-5 MOE gapmers with mixed
PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1364100 | N/A | N/A | 17151 | 17170 | GTAGACACACAGCCACATCA | 31 | 475 |
| 1364146 | 2052 | 2071 | 18531 | 18550 | CTAATTAACAGAAAAAAAGA | 107 | 476 |
| 1364156 | 2299 | 2318 | 18778 | 18797 | AATTTTTAATATCATTTGTG | 71 | 477 |
| 1364174 | N/A | N/A | 10688 | 10707 | TTCTGTTAACATTAGTTACA | 30 | 478 |
| 1364235 | 1478 | 1497 | 17957 | 17976 | GCATCTTTCCTTCCACTTTG | 13 | 479 |
| 1364240 | N/A | N/A | 11907 | 11926 | ATTTTAGTCATTCATCAACT | 43 | 480 |
| 1364269 | 2993 | 3012 | 19472 | 19491 | CTTTCAGTTGATTAACTCTC | 17 | 481 |

TABLE 7

Reduction of PLP1 RNA by 5-10-5 MOE gapmers with mixed PO/PS
internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362427 | N/A | N/A | 7390 | 7409 | CCAATTTATGTGCAAGCATT | 34 | 482 |
| 1362453 | 1551 | 1570 | 18030 | 18049 | TGTACACCAAAGAGAATATA | 43 | 483 |
| 1362467 | N/A | N/A | 4548 | 4567 | CTACCCATATCTGTTTCCCA | 60 | 484 |
| 1362468 | 1841 | 1860 | 18320 | 18339 | GCTGACAACACCCTGTTTCT | 21 | 485 |
| 1362481 | N/A | N/A | 5826 | 5845 | ACAGCAGTGCACTCCACATC | 59 | 486 |
| 1362490 | 1731 | 1750 | 18210 | 18229 | GCTTCAGTAGTCCATCGCCA | 11 | 201 |
| 1362500 | 1049 | 1068 | 17528 | 17547 | GGCAGCAATCATGAAGGTGA | 19 | 487 |
| 1362524 | N/A | N/A | 7024 | 7043 | CTGAGTAGGCTCTGAAAGCA | 66 | 488 |
| 1362566 | 2460 | 2479 | 18939 | 18958 | TAAACCTAACTCTTAACACA | 51 | 489 |
| 1362577 | 1913 | 1932 | 18392 | 18411 | TCTATTCTCAGCTCCTTGGA | 38 | 490 |
| 1362578 | 1473 | 1492 | 17952 | 17971 | TTTCCTTCCACTTTGTTTCC | 60 | 491 |
| 1362604 | N/A | N/A | 16191 | 16210 | TAACTAAGTTTTCACTTCCC | 88 | 492 |
| 1362613 | N/A | N/A | 16540 | 16559 | TGCAAGTAGAAGTACGGAGC | 34 | 493 |
| 1362621 | N/A | N/A | 9221 | 9240 | TCAGTAATATCAGCATAAGC | 43 | 494 |
| 1362636 | 1215 | 1234 | 17694 | 17713 | AAGTAAGAAGAGGGCCAGTT | 63 | 495 |
| 1362641 | 2791 | 2810 | 19270 | 19289 | GTATACTGGTTTGAAAACAA | 14 | 496 |
| 1362650 | 1183 | 1202 | 17662 | 17681 | AAAGAGTTAAGATGGGAGAC | 61 | 497 |
| 1362690 | N/A | N/A | 9918 | 9937 | CCACTGTTCCCTTTCTCCCC | 94 | 498 |
| 1362704 | 2007 | 2026 | 18486 | 18505 | CTGTGTCTACCAGAGGGCCA | 24 | 499 |
| 1362706 | N/A | N/A | 11119 | 11138 | CAAGTACTAGTCCCATGCTC | 62 | 500 |
| 1362822 | 3058 | 3077 | 19537 | 19556 | GTTTCTAAAAGTTTATCCTT | 26 | 501 |
| 1362831 | 2433 | 2452 | 18912 | 18931 | AACATTGCTAAGTAAAATCA | 43 | 502 |

TABLE 7-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362955 | 1777 | 1796 | 18256 | 18275 | AGATTCTACGCTCCCTTATG | 53 | 503 |
| 1362957 | 1661 | 1680 | 18140 | 18159 | CTTCTCCCAGCTGCAATAGG | 36 | 504 |
| 1362980 | N/A | N/A | 10680 | 10699 | ACATTAGTTACAGTTTGTTT | 48 | 505 |
| 1362987 | 1873 | 1892 | 18352 | 18371 | AGCTGTTATCAAGGAGAAGG | 16 | 506 |
| 1363016 | N/A | N/A | 5114 | 5133 | CATAGTTCATAAGTAGCAGA | 37 | 507 |
| 1363061 | N/A | N/A | 15220 | 15239 | GTTATTGAAATGTGCTGCTT | 62 | 508 |
| 1363071 | N/A | N/A | 11738 | 11757 | CAGGCAGCCAAGTAAGTGGT | 36 | 509 |
| 1363121 | 1732 | 1751 | 18211 | 18230 | GGCTTCAGTAGTCCATCGCC | 13 | 279 |
| 1363165 | 1518 | 1537 | 17997 | 18016 | GATGGCAAGAGGACCAAAGA | 39 | 510 |
| 1363174 | 2379 | 2398 | 18858 | 18877 | CAAATTGAGATTCAAATTCA | 80 | 511 |
| 1363182 | 1296 | 1315 | 17775 | 17794 | ACTAAAAGAGGTACATAAGA | 82 | 512 |
| 1363243 | N/A | N/A | 14287 | 14306 | CCAAAGGATCTTTAACTCCA | 42 | 513 |
| 1363276 | 1322 | 1341 | 17801 | 17820 | GCAGGAACCAGCTATGAAGC | 50 | 514 |
| 1363300 | 3020 | 3039 | 19499 | 19518 | AATTCTATATCAGAAATGAA | 84 | 515 |
| 1363308 | N/A | N/A | 11904 | 11923 | TTAGTCATTCATCAACTATT | 36 | 516 |
| 1363344 | N/A | N/A | 16863 | 16882 | TTCTAATAATGTTAGGAGGT | 27 | 517 |
| 1363410 | 2105 | 2124 | 18584 | 18603 | ACCCCATGAAATGAGCACCA | 14 | 518 |
| 1363425 | 2892 | 2911 | 19371 | 19390 | CAAAACACAAGGTACGGATT | 48 | 519 |
| 1363434 | N/A | N/A | 15661 | 15680 | CCTTCTATGCTCATTGGCTC | 65 | 520 |
| 1363439 | 1099 | 1118 | 17578 | 17597 | CAGAACTTGGTGCCTCGGCC | 15 | 40 |
| 1363443 | N/A | N/A | 5441 | 5460 | GGATTCCTGATGTTACCCAG | 41 | 521 |
| 1363542 | N/A | N/A | 6211 | 6230 | TGTTCAATAATGGCATTGTG | 50 | 522 |
| 1363550 | 2582 | 2601 | 19061 | 19080 | GGAGCTATTCAGGTCTCAAA | 20 | 57 |
| 1363589 | N/A | N/A | 13739 | 13758 | TGTTATTGCCACAAAATCCT | 40 | 523 |
| 1363610 | 2842 | 2861 | 19321 | 19340 | TTACAAAACATTTTCCCTCT | 53 | 524 |
| 1363611 | 2078 | 2097 | 18557 | 18576 | GATATGACAGAGGCCAGAGT | 30 | 525 |
| 1363631 | 1974 | 1993 | 18453 | 18472 | CATTAGCCACCAGCAACTGC | 50 | 526 |
| 1363711 | N/A | N/A | 6368 | 6387 | GCCACACTTTTTGCCTGGGC | 27 | 527 |
| 1363746 | 1435 | 1454 | 17914 | 17933 | TGAGAAGAAATTACTTTCTG | 101 | 528 |
| 1363825 | 2622 | 2641 | 19101 | 19120 | TAACCCAAAGTTAACAAAAA | 74 | 529 |
| 1363829 | 2235 | 2254 | 18714 | 18733 | AAAGAATTATTCTCCAGACA | 37 | 530 |
| 1363888 | 2406 | 2425 | 18885 | 18904 | TTAGCTAGAAAGAACGATCA | 29 | 531 |
| 1363891 | 2298 | 2317 | 18777 | 18796 | ATTTTTAATATCATTTGTGA | 78 | 532 |
| 1363897 | 2157 | 2176 | 18636 | 18655 | TTCTAAAACAAATCAAGACC | 55 | 533 |
| 1363899 | 2487 | 2506 | 18966 | 18985 | TATATCAGGAGAAAATAACC | 63 | 534 |

TABLE 7-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363968 | N/A | N/A | 8085 | 8104 | GAGACCAATTGTACCCTGCA | 59 | 535 |
| 1363969 | 2260 | 2279 | 18739 | 18758 | CCTAGTTTAAAAAACAGTCA | 38 | 536 |
| 1363980 | 1401 | 1420 | 17880 | 17899 | CTTGAAAATTCAATTAGAGC | 62 | 537 |
| 1363983 | 1730 | 1749 | 18209 | 18228 | CTTCAGTAGTCCATCGCCAT | 21 | 538 |
| 1364000 | N/A | N/A | 12823 | 12842 | CTGAAGAGTTCTCTATCTCC | 59 | 539 |
| 1364002 | 3118 | 3137 | 19597 | 19616 | GATTGAGAACATTCTTAATT | 57 | 540 |
| 1364015 | 2749 | 2768 | 19228 | 19247 | GCTCTTACATCTCCTTAAAT | 28 | 541 |
| 1364024 | 2133 | 2152 | 18612 | 18631 | AATCACCTACGATGACTGAA | 33 | 542 |
| 1364047 | N/A | N/A | 8993 | 9012 | CTTTGATTTTTCACAGTCCA | 43 | 543 |
| 1364052 | 1360 | 1379 | 17839 | 17858 | AGTTGGGAAGTCATCTTCTT | 53 | 544 |
| 1364066 | 2670 | 2689 | 19149 | 19168 | AGTACAAATCTTTCCTTCAA | 16 | 545 |
| 1364084 | N/A | N/A | 17150 | 17169 | TAGACACACAGCCACATCAT | 67 | 546 |
| 1364089 | N/A | N/A | 8640 | 8659 | TACAAGAATTAAGCACACTA | 77 | 547 |
| 1364093 | 2051 | 2070 | 18530 | 18549 | TAATTAACAGAAAAAAAGAC | 103 | 548 |
| 1364155 | 2323 | 2342 | 18802 | 18821 | AAATCCCAATAGATTCAACT | 44 | 549 |
| 1364158 | 1252 | 1271 | 17731 | 17750 | AATCACTGCAAGACTCTCCT | 36 | 550 |
| 1364162 | 1590 | 1609 | 18069 | 18088 | TCTTCAGTGGTAATAGAGAG | 43 | 551 |
| 1364178 | 2197 | 2216 | 18676 | 18695 | ATAAGTAATAAACAAACTGG | 79 | 552 |
| 1364181 | 2348 | 2367 | 18827 | 18846 | TCTGCAAAGGCAGAATACTT | 73 | 553 |
| 1364189 | 2532 | 2551 | 19011 | 19030 | TTACCAACTGAATAGCTGAT | 32 | 554 |
| 1364248 | 2989 | 3008 | 19468 | 19487 | CAGTTGATTAACTCTCTTTG | 21 | 555 |
| 1364262 | 2696 | 2715 | 19175 | 19194 | ACAACTCTTTACAACAAAAG | 49 | 556 |

TABLE 8

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362437 | 2156 | 2175 | 18635 | 18654 | TCTAAAACAAATCAAGACCT | 45 | 557 |
| 1362490 | 1731 | 1750 | 18210 | 18229 | GCTTCAGTAGTCCATCGCCA | 13 | 201 |
| 1362518 | 2621 | 2640 | 19100 | 19119 | AACCCAAAGTTAACAAAAAC | 62 | 558 |
| 1362534 | 1470 | 1489 | 17949 | 17968 | CCTTCCACTTTGTTTCCATC | 64 | 559 |
| 1362548 | 2790 | 2809 | 19269 | 19288 | TATACTGGTTTGAAAACAAG | 55 | 560 |
| 1362580 | 1912 | 1931 | 18391 | 18410 | CTATTCTCAGCTCCTTGGAA | 36 | 561 |
| 1362584 | 1729 | 1748 | 18208 | 18227 | TTCAGTAGTCCATCGCCATC | 36 | 562 |

TABLE 8-continued

Reduction of PLP1 RNA by 5-10-5 MOE gapmers with mixed
PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362597 | 2378 | 2397 | 18857 | 18876 | AAATTGAGATTCAAATTCAC | 59 | 563 |
| 1362632 | 2004 | 2023 | 18483 | 18502 | TGTCTACCAGAGGGCCATCT | 25 | 564 |
| 1362664 | 2347 | 2366 | 18826 | 18845 | CTGCAAAGGCAGAATACTTG | 38 | 565 |
| 1362691 | 2322 | 2341 | 18801 | 18820 | AATCCCAATAGATTCAACTA | 45 | 566 |
| 1362735 | 2531 | 2550 | 19010 | 19029 | TACCAACTGAATAGCTGATG | 32 | 567 |
| 1362748 | N/A | N/A | 7382 | 7401 | TGTGCAAGCATTGGGAAGCT | 36 | 568 |
| 1362791 | N/A | N/A | 9728 | 9747 | GGGTAAGAAGAGCCATCCAC | 68 | 569 |
| 1362826 | N/A | N/A | 17523 | 17542 | CAATCATGAAGGTGAGCTGT | 72 | 570 |
| 1362849 | N/A | N/A | 6986 | 7005 | GCTCCATTCACCTACCATGG | 38 | 571 |
| 1362860 | 2405 | 2424 | 18884 | 18903 | TAGCTAGAAAGAACGATCAG | 51 | 572 |
| 1362900 | 2104 | 2123 | 18583 | 18602 | CCCCATGAAATGAGCACCAT | 19 | 573 |
| 1362913 | 2259 | 2278 | 18738 | 18757 | CTAGTTTAAAAAACAGTCAT | 41 | 574 |
| 1362961 | 1295 | 1314 | 17774 | 17793 | CTAAAAGAGGTACATAAGAG | 76 | 575 |
| 1362962 | 1973 | 1992 | 18452 | 18471 | ATTAGCCACCAGCAACTGCT | 39 | 576 |
| 1362965 | 1589 | 1608 | 18068 | 18087 | CTTCAGTGGTAATAGAGAGA | 32 | 577 |
| 1363027 | N/A | N/A | 11067 | 11086 | GCCAAGTAGATGACTGACTA | 33 | 578 |
| 1363036 | 1776 | 1795 | 18255 | 18274 | GATTCTACGCTCCCTTATGC | 54 | 579 |
| 1363069 | 1840 | 1859 | 18319 | 18338 | CTGACAACACCCTGTTTCTC | 32 | 580 |
| 1363077 | N/A | N/A | 11656 | 11675 | TTGTCAGACAGGATTTTAGC | 45 | 581 |
| 1363082 | N/A | N/A | 4537 | 4556 | TGTTTCCCATGGTCAAGCCA | 51 | 582 |
| 1363091 | N/A | N/A | 8053 | 8072 | TGTCCCTTGAATCCAGCTGA | 67 | 583 |
| 1363121 | 1732 | 1751 | 18211 | 18230 | GGCTTCAGTAGTCCATCGCC | 12 | 279 |
| 1363123 | 2132 | 2151 | 18611 | 18630 | ATCACCTACGATGACTGAAT | 36 | 584 |
| 1363126 | 3117 | 3136 | 19596 | 19615 | ATTGAGAACATTCTTAATTT | 75 | 585 |
| 1363141 | 2581 | 2600 | 19060 | 19079 | GAGCTATTCAGGTCTCAAAC | 21 | 586 |
| 1363200 | 2432 | 2451 | 18911 | 18930 | ACATTGCTAAGTAAAATCAT | 50 | 587 |
| 1363257 | 1081 | 1100 | 17560 | 17579 | CCCATGAGTTTAAGGACGGC | 22 | 588 |
| 1363295 | 2045 | 2064 | 18524 | 18543 | ACAGAAAAAAAGACATGCTA | 63 | 589 |
| 1363323 | 2486 | 2505 | 18965 | 18984 | ATATCAGGAGAAAATAACCT | 49 | 590 |
| 1363333 | 1400 | 1419 | 17879 | 17898 | TTGAAAATTCAATTAGAGCC | 47 | 591 |
| 1363340 | N/A | N/A | 6184 | 6203 | GCAGAGAATAATCAGCTACT | 62 | 592 |
| 1363367 | 1517 | 1536 | 17996 | 18015 | ATGGCAAGAGGACCAAAGAC | 65 | 593 |
| 1363436 | N/A | N/A | 8990 | 9009 | TGATTTTCACAGTCCAAGA | 55 | 594 |
| 1363441 | 2297 | 2316 | 18776 | 18795 | TTTTTAATATCATTTGTGAT | 84 | 595 |
| 1363454 | N/A | N/A | 5435 | 5454 | CTGATGTTACCCAGGGCAGG | 44 | 596 |

TABLE 8-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363455 | N/A | N/A | 14282 | 14301 | GGATCTTTAACTCCAGAGAC | 26 | 597 |
| 1363491 | N/A | N/A | 5817 | 5836 | CACTCCACATCAGAAGTAGT | 65 | 598 |
| 1363493 | 1550 | 1569 | 18029 | 18048 | GTACACCAAAGAGAATATAT | 18 | 599 |
| 1363504 | N/A | N/A | 5111 | 5130 | AGTTCATAAGTAGCAGATCT | 32 | 600 |
| 1363506 | 2987 | 3006 | 19466 | 19485 | GTTGATTAACTCTCTTTGTG | 33 | 601 |
| 1363565 | N/A | N/A | 13734 | 13753 | TTGCCACAAAATCCTGAGGA | 21 | 602 |
| 1363568 | 2234 | 2253 | 18713 | 18732 | AAGAATTATTCTCCAGACAT | 26 | 603 |
| 1363592 | 2077 | 2096 | 18556 | 18575 | ATATGACAGAGGCCAGAGTA | 38 | 604 |
| 1363623 | 3055 | 3074 | 19534 | 19553 | TCTAAAAGTTTATCCTTTAT | 37 | 605 |
| 1363644 | 1872 | 1891 | 18351 | 18370 | GCTGTTATCAAGGAGAAGGG | 23 | 606 |
| 1363650 | 2459 | 2478 | 18938 | 18957 | AAACCTAACTCTTAACACAC | 45 | 607 |
| 1363688 | N/A | N/A | 16190 | 16209 | AACTAAGTTTTCACTTCCCT | 72 | 608 |
| 1363704 | 1321 | 1340 | 17800 | 17819 | CAGGAACCAGCTATGAAGCA | 37 | 609 |
| 1363776 | 2194 | 2213 | 18673 | 18692 | AGTAATAAACAAACTGGAAT | 68 | 610 |
| 1363783 | 1359 | 1378 | 17838 | 17857 | GTTGGGAAGTCATCTTCTTA | 45 | 611 |
| 1363800 | 2891 | 2910 | 19370 | 19389 | AAAACACAAGGTACGGATTA | 38 | 612 |
| 1363852 | N/A | N/A | 10586 | 10605 | AAATTATCTCTGTCATGGGA | 55 | 613 |
| 1363865 | 3019 | 3038 | 19498 | 19517 | ATTCTATATCAGAAATGAAG | 64 | 614 |
| 1363879 | 2841 | 2860 | 19320 | 19339 | TACAAAACATTTTCCCTCTC | 59 | 615 |
| 1363901 | N/A | N/A | 16498 | 16517 | AGAAGCTTCCCTCCAGCATT | 84 | 616 |
| 1363953 | 1214 | 1233 | 17693 | 17712 | AGTAAGAAGAGGGCCAGTTG | 75 | 617 |
| 1363956 | N/A | N/A | 15143 | 15162 | CCACCACTTCCAAGTTCCCT | 69 | 618 |
| 1363972 | N/A | N/A | 6367 | 6386 | CCACACTTTTTGCCTGGGCT | 25 | 619 |
| 1363993 | 1655 | 1674 | 18134 | 18153 | CCAGCTGCAATAGGCAGATT | 21 | 620 |
| 1364008 | 2668 | 2687 | 19147 | 19166 | TACAAATCTTTCCTTCAATT | 43 | 621 |
| 1364009 | N/A | N/A | 8638 | 8657 | CAAGAATTAAGCACACTAGC | 77 | 622 |
| 1364035 | 1434 | 1453 | 17913 | 17932 | GAGAAGAAATTACTTTCTGA | 113 | 623 |
| 1364039 | 1182 | 1201 | 17661 | 17680 | AAGAGTTAAGATGGGAGACG | 66 | 624 |
| 1364042 | N/A | N/A | 17149 | 17168 | AGACACACAGCCACATCATG | 57 | 625 |
| 1364065 | N/A | N/A | 11896 | 11915 | TCATCAACTATTTATGGAAT | 67 | 626 |
| 1364073 | N/A | N/A | 9220 | 9239 | CAGTAATATCAGCATAAGCA | 23 | 627 |
| 1364112 | N/A | N/A | 12817 | 12836 | AGTTCTCTATCTCCAGGATG | 56 | 628 |
| 1364128 | 1250 | 1269 | 17729 | 17748 | TCACTGCAAGACTCTCCTTT | 45 | 629 |
| 1364159 | 2695 | 2714 | 19174 | 19193 | CAACTCTTTACAACAAAAGA | 75 | 630 |

TABLE 8-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1364171 | 2748 | 2767 | 19227 | 19246 | CTCTTACATCTCCTTAAATA | 43 | 631 |
| 1364185 | N/A | N/A | 16858 | 16877 | ATAATGTTAGGAGGTCCTCC | 33 | 632 |
| 1364187 | N/A | N/A | 15658 | 15677 | TCTATGCTCATTGGCTCAGG | 70 | 633 |

TABLE 9

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362479 | 3115 | 3134 | 19594 | 19613 | TGAGAACATTCTTAATTTTA | 84 | 634 |
| 1362490 | 1731 | 1750 | 18210 | 18229 | GCTTCAGTAGTCCATCGCCA | 14 | 201 |
| 1362499 | 1469 | 1488 | 17948 | 17967 | CTTCCACTTTGTTTCCATCA | 70 | 635 |
| 1362545 | N/A | N/A | 11653 | 11672 | TCAGACAGGATTTTAGCATG | 65 | 636 |
| 1362561 | N/A | N/A | 16189 | 16208 | ACTAAGTTTTCACTTCCCTA | 72 | 637 |
| 1362586 | N/A | N/A | 6181 | 6200 | GAGAATAATCAGCTACTGCT | 76 | 638 |
| 1362634 | N/A | N/A | 7948 | 7967 | GTCTCGAATCTGCACTACAG | 57 | 639 |
| 1362635 | 1516 | 1535 | 17995 | 18014 | TGGCAAGAGGACCAAAGACA | 62 | 640 |
| 1362638 | 2985 | 3004 | 19464 | 19483 | TGATTAACTCTCTTTGTGTG | 49 | 641 |
| 1362669 | 2840 | 2859 | 19319 | 19338 | ACAAAACATTTTCCCTCTCC | 57 | 642 |
| 1362681 | 1294 | 1313 | 17773 | 17792 | TAAAAGAGGTACATAAGAGG | 84 | 643 |
| 1362695 | 2155 | 2174 | 18634 | 18653 | CTAAAACAAATCAAGACCTT | 62 | 644 |
| 1362737 | 2746 | 2765 | 19225 | 19244 | CTTACATCTCCTTAAATATT | 38 | 645 |
| 1362769 | 1654 | 1673 | 18133 | 18152 | CAGCTGCAATAGGCAGATTT | 41 | 646 |
| 1362802 | N/A | N/A | 10560 | 10579 | AGGTAGAGGCATTTGCCTCT | 85 | 647 |
| 1362852 | N/A | N/A | 17360 | 17379 | GCTTGGCTTTCTCCATATAC | 34 | 648 |
| 1362863 | 2377 | 2396 | 18856 | 18875 | AATTGAGATTCAAATTCACC | 46 | 649 |
| 1362872 | N/A | N/A | 7378 | 7397 | CAAGCATTGGGAAGCTGAGG | 42 | 650 |
| 1362893 | N/A | N/A | 5108 | 5127 | TCATAAGTAGCAGATCTGGG | 44 | 651 |
| 1362939 | 2346 | 2365 | 18825 | 18844 | TGCAAAGGCAGAATACTTGT | 60 | 652 |
| 1362942 | 1399 | 1418 | 17878 | 17897 | TGAAAATTCAATTAGAGCCT | 43 | 653 |
| 1362943 | 2044 | 2063 | 18523 | 18542 | CAGAAAAAAGACATGCTAT | 78 | 654 |
| 1363003 | 1181 | 1200 | 17660 | 17679 | AGAGTTAAGATGGGAGACGC | 52 | 655 |
| 1363075 | N/A | N/A | 15624 | 15643 | ATGTTGTAGAAGGCAATCGG | 59 | 656 |
| 1363093 | 2296 | 2315 | 18775 | 18794 | TTTTAATATCATTTGTGATG | 73 | 657 |
| 1363121 | 1732 | 1751 | 18211 | 18230 | GGCTTCAGTAGTCCATCGCC | 15 | 279 |

TABLE 9-continued

Reduction of PLP1 RNA by 5-10-5 MOE gapmers with mixed
PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363146 | 2076 | 2095 | 18555 | 18574 | TATGACAGAGGCCAGAGTAC | 22 | 658 |
| 1363166 | 1871 | 1890 | 18350 | 18369 | CTGTTATCAAGGAGAAGGGA | 24 | 659 |
| 1363178 | N/A | N/A | 15110 | 15129 | ACCTCTCTGGTTTCAGTAGG | 67 | 660 |
| 1363185 | 2485 | 2504 | 18964 | 18983 | TATCAGGAGAAAATAACCTT | 44 | 661 |
| 1363201 | 1249 | 1268 | 17728 | 17747 | CACTGCAAGACTCTCCTTTC | 34 | 662 |
| 1363251 | 2103 | 2122 | 18582 | 18601 | CCCATGAAATGAGCACCATT | 43 | 663 |
| 1363285 | N/A | N/A | 17148 | 17167 | GACACACAGCCACATCATGC | 57 | 664 |
| 1363314 | 1728 | 1747 | 18207 | 18226 | TCAGTAGTCCATCGCCATCG | 23 | 123 |
| 1363328 | 2002 | 2021 | 18481 | 18500 | TCTACCAGAGGGCCATCTCA | 50 | 665 |
| 1363346 | 2580 | 2599 | 19059 | 19078 | AGCTATTCAGGTCTCAAACT | 39 | 666 |
| 1363347 | 2404 | 2423 | 18883 | 18902 | AGCTAGAAAGAACGATCAGA | 38 | 667 |
| 1363364 | N/A | N/A | 4532 | 4551 | CCCATGGTCAAGCCATTGAG | 63 | 668 |
| 1363380 | N/A | N/A | 14246 | 14265 | CCTCACTCAAAGCATGGATA | 26 | 669 |
| 1363406 | N/A | N/A | 9219 | 9238 | AGTAATATCAGCATAAGCAT | 46 | 670 |
| 1363419 | 2890 | 2909 | 19369 | 19388 | AAACACAAGGTACGGATTAC | 40 | 671 |
| 1363448 | 2620 | 2639 | 19099 | 19118 | ACCCAAAGTTAACAAAAACA | 52 | 672 |
| 1363462 | N/A | N/A | 5421 | 5440 | GGCAGGAATTGAGTTCCTCC | 35 | 673 |
| 1363480 | N/A | N/A | 11894 | 11913 | ATCAACTATTTATGGAATAC | 62 | 674 |
| 1363507 | 2193 | 2212 | 18672 | 18691 | GTAATAAACAAACTGGAATA | 88 | 675 |
| 1363527 | N/A | N/A | 8637 | 8656 | AAGAATTAAGCACACTAGCA | 80 | 676 |
| 1363551 | 2233 | 2252 | 18712 | 18731 | AGAATTATTCTCCAGACATT | 35 | 677 |
| 1363604 | 3054 | 3073 | 19533 | 19552 | CTAAAAGTTTATCCTTTATG | 60 | 678 |
| 1363608 | 1213 | 1232 | 17692 | 17711 | GTAAGAAGAGGGCCAGTTGG | 80 | 679 |
| 1363613 | 1433 | 1452 | 17912 | 17931 | AGAAGAAATTACTTTCTGAT | 115 | 680 |
| 1363636 | N/A | N/A | 6979 | 6998 | TCACCTACCATGGCTGCTGT | 66 | 681 |
| 1363654 | 2667 | 2686 | 19146 | 19165 | ACAAATCTTTCCTTCAATTA | 59 | 682 |
| 1363656 | 2321 | 2340 | 18800 | 18819 | ATCCCAATAGATTCAACTAG | 35 | 683 |
| 1363676 | 2258 | 2277 | 18737 | 18756 | TAGTTTAAAAAACAGTCATA | 94 | 684 |
| 1363686 | 2530 | 2549 | 19009 | 19028 | ACCAACTGAATAGCTGATGA | 27 | 685 |
| 1363706 | 342 | 361 | 12634 | 12653 | AACACAATCCAGTGGCCACC | 67 | 686 |
| 1363721 | 2131 | 2150 | 18610 | 18629 | TCACCTACGATGACTGAATG | 56 | 687 |
| 1363732 | N/A | N/A | 8983 | 9002 | TCACAGTCCAAGAAATGTCC | 62 | 688 |
| 1363742 | N/A | N/A | 9634 | 9653 | GGTATGGTCAGGGATGGAGG | 55 | 689 |
| 1363756 | 1079 | 1098 | 17558 | 17577 | CATGAGTTTAAGGACGGCAA | 36 | 690 |
| 1363758 | N/A | N/A | 13732 | 13751 | GCCACAAAATCCTGAGGATG | 14 | 691 |
| 1363814 | 1320 | 1339 | 17799 | 17818 | AGGAACCAGCTATGAAGCAA | 26 | 692 |

TABLE 9-continued

Reduction of PLP1 RNA by 5-10-5 MOE gapmers with mixed
PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363856 | 1839 | 1858 | 18318 | 18337 | TGACAACACCCTGTTTCTCT | 24 | 693 |
| 1363876 | N/A | N/A | 6330 | 6349 | GCCAGCCAAAACTACACTGC | 53 | 694 |
| 1363991 | 2431 | 2450 | 18910 | 18929 | CATTGCTAAGTAAAATCATT | 47 | 695 |
| 1364012 | 1588 | 1607 | 18067 | 18086 | TTCAGTGGTAATAGAGAGAC | 64 | 696 |
| 1364018 | 2458 | 2477 | 18937 | 18956 | AACCTAACTCTTAACACACC | 34 | 697 |
| 1364028 | 1972 | 1991 | 18451 | 18470 | TTAGCCACCAGCAACTGCTG | 43 | 698 |
| 1364071 | 1911 | 1930 | 18390 | 18409 | TATTCTCAGCTCCTTGGAAA | 72 | 699 |
| 1364081 | 1358 | 1377 | 17837 | 17856 | TTGGGAAGTCATCTTCTTAG | 61 | 700 |
| 1364139 | 2693 | 2712 | 19172 | 19191 | ACTCTTTACAACAAAAGAAC | 48 | 701 |
| 1364163 | N/A | N/A | 16489 | 16508 | CCTCCAGCATTTCAAGGATG | 79 | 702 |
| 1364196 | 3018 | 3037 | 19497 | 19516 | TTCTATATCAGAAATGAAGG | 49 | 703 |
| 1364213 | N/A | N/A | 10960 | 10979 | TGTCTTAATTCATATGTATG | 61 | 704 |
| 1364246 | 1770 | 1789 | 18249 | 18268 | ACGCTCCCTTATGCTGTAAG | 13 | 49 |
| 1364249 | N/A | N/A | 16791 | 16810 | GGATTCATATTGATAGTATA | 76 | 705 |
| 1364260 | 1549 | 1568 | 18028 | 18047 | TACACCAAAGAGAATATATT | 79 | 706 |
| 1364263 | N/A | N/A | 5816 | 5835 | ACTCCACATCAGAAGTAGTG | 53 | 707 |
| 1364272 | 2789 | 2808 | 19268 | 19287 | ATACTGGTTTGAAAACAAGT | 35 | 708 |

TABLE 10

Reduction of PLP1 RNA by 5-10-5 MOE gapmers with mixed
PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362447 | 1652 | 1671 | 18131 | 18150 | GCTGCAATAGGCAGATTTGG | 29 | 709 |
| 1362477 | N/A | N/A | 5416 | 5435 | GAATTGAGTTCCTCCAACAT | 73 | 710 |
| 1362490 | 1731 | 1750 | 18210 | 18229 | GCTTCAGTAGTCCATCGCCA | 16 | 201 |
| 1362491 | N/A | N/A | 6303 | 6322 | ACAGCCACTTTTGGATGGAG | 55 | 711 |
| 1362533 | 2129 | 2148 | 18608 | 18627 | ACCTACGATGACTGAATGGA | 49 | 712 |
| 1362559 | 2376 | 2395 | 18855 | 18874 | ATTGAGATTCAAATTCACCA | 18 | 713 |
| 1362565 | 2578 | 2597 | 19057 | 19076 | CTATTCAGGTCTCAAACTCT | 30 | 714 |
| 1362569 | N/A | N/A | 15623 | 15642 | TGTTGTAGAAGGCAATCGGC | 75 | 715 |
| 1362588 | N/A | N/A | 16065 | 16084 | GGTTCCCTACAGTTGTGCCC | 37 | 716 |
| 1362599 | 1355 | 1374 | 17834 | 17853 | GGAAGTCATCTTCTTAGGCA | 44 | 717 |
| 1362612 | 2320 | 2339 | 18799 | 18818 | TCCCAATAGATTCAACTAGC | 22 | 718 |
| 1362642 | 2666 | 2685 | 19145 | 19164 | CAAATCTTTCCTTCAATTAA | 72 | 719 |
| 1362649 | N/A | N/A | 16781 | 16800 | TGATAGTATATAGAATTCCA | 23 | 720 |

TABLE 10-continued

Reduction of PLP1 RNA by 5-10-5 MOE gapmers with mixed
PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362651 | N/A | N/A | 8627 | 8646 | CACACTAGCAGTGACATAGA | 75 | 721 |
| 1362665 | 3114 | 3133 | 19593 | 19612 | GAGAACATTCTTAATTTTAT | 68 | 722 |
| 1362707 | 2484 | 2503 | 18963 | 18982 | ATCAGGAGAAAATAACCTTT | 30 | 723 |
| 1362714 | 1838 | 1857 | 18317 | 18336 | GACAACACCCTGTTTCTCTT | 30 | 724 |
| 1362715 | 2430 | 2449 | 18909 | 18928 | ATTGCTAAGTAAAATCATTT | 50 | 725 |
| 1362744 | N/A | N/A | 7940 | 7959 | TCTGCACTACAGTCTTACCC | 67 | 726 |
| 1362747 | 2745 | 2764 | 19224 | 19243 | TTACATCTCCTTAAATATTG | 56 | 727 |
| 1362757 | 2619 | 2638 | 19098 | 19117 | CCCAAAGTTAACAAAAACAG | 36 | 728 |
| 1362761 | N/A | N/A | 4531 | 4550 | CCATGGTCAAGCCATTGAGG | 61 | 729 |
| 1362799 | 2889 | 2908 | 19368 | 19387 | AACACAAGGTACGGATTACT | 41 | 730 |
| 1362874 | 2042 | 2061 | 18521 | 18540 | GAAAAAAGACATGCTATCC | 64 | 731 |
| 1362906 | 2102 | 2121 | 18581 | 18600 | CCATGAAATGAGCACCATTG | 26 | 732 |
| 1362924 | 1769 | 1788 | 18248 | 18267 | CGCTCCCTTATGCTGTAAGT | 21 | 282 |
| 1362985 | 3053 | 3072 | 19532 | 19551 | TAAAAGTTTATCCTTTATGT | 85 | 733 |
| 1363066 | N/A | N/A | 5814 | 5833 | TCCACATCAGAAGTAGTGGC | 59 | 734 |
| 1363074 | 1248 | 1267 | 17727 | 17746 | ACTGCAAGACTCTCCTTTCT | 38 | 735 |
| 1363108 | 1432 | 1451 | 17911 | 17930 | GAAGAAATTACTTTCTGATC | 111 | 736 |
| 1363113 | N/A | N/A | 10892 | 10911 | AAACACAGTATACACATGCA | 71 | 737 |
| 1363116 | 2403 | 2422 | 18882 | 18901 | GCTAGAAAGAACGATCAGAT | 39 | 738 |
| 1363121 | 1732 | 1751 | 18211 | 18230 | GGCTTCAGTAGTCCATCGCC | 21 | 279 |
| 1363169 | 1870 | 1889 | 18349 | 18368 | TGTTATCAAGGAGAAGGGAG | 43 | 739 |
| 1363197 | N/A | N/A | 6179 | 6198 | GAATAATCAGCTACTGCTCT | 89 | 740 |
| 1363207 | N/A | N/A | 11650 | 11669 | GACAGGATTTTAGCATGAAG | 66 | 741 |
| 1363213 | 1398 | 1417 | 17877 | 17896 | GAAAATTCAATTAGAGCCTC | 43 | 742 |
| 1363270 | N/A | N/A | 6925 | 6944 | TCTTCTTTAGACCTGAAGTG | 74 | 743 |
| 1363280 | 1909 | 1928 | 18388 | 18407 | TTCTCAGCTCCTTGGAAACC | 52 | 744 |
| 1363303 | 1179 | 1198 | 17658 | 17677 | AGTTAAGATGGGAGACGCAG | 47 | 745 |
| 1363326 | 1467 | 1486 | 17946 | 17965 | TCCACTTTGTTTCCATCAGT | 72 | 746 |
| 1363438 | 2956 | 2975 | 19435 | 19454 | GTGTATGTATGCATGTGAGG | 29 | 747 |
| 1363440 | 1293 | 1312 | 17772 | 17791 | AAAAGAGGTACATAAGAGGG | 68 | 748 |
| 1363449 | N/A | N/A | 5046 | 5065 | TCCTGTTTTACCTGAACACA | 66 | 749 |
| 1363473 | 2192 | 2211 | 18671 | 18690 | TAATAAACAAACTGGAATAC | 90 | 750 |
| 1363482 | N/A | N/A | 16486 | 16505 | CCAGCATTTCAAGGATGGAA | 55 | 751 |
| 1363488 | N/A | N/A | 15073 | 15092 | AGACCCAATCATTCATCATC | 70 | 752 |
| 1363496 | 1708 | 1727 | 18187 | 18206 | GGGTCAGTGCTCTCTTTCTG | 37 | 753 |
| 1363509 | 1211 | 1230 | 17690 | 17709 | AAGAAGAGGGCCAGTTGGTG | 77 | 754 |

TABLE 10-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363525 | 2692 | 2711 | 19171 | 19190 | CTCTTTACAACAAAAGAACT | 78 | 755 |
| 1363543 | 2528 | 2547 | 19007 | 19026 | CAACTGAATAGCTGATGACT | 58 | 756 |
| 1363556 | N/A | N/A | 9617 | 9636 | AGGAACTTGAACTCTTGCTA | 47 | 757 |
| 1363569 | 2075 | 2094 | 18554 | 18573 | ATGACAGAGGCCAGAGTACA | 44 | 758 |
| 1363605 | 1587 | 1606 | 18066 | 18085 | TCAGTGGTAATAGAGAGACC | 54 | 759 |
| 1363620 | 2257 | 2276 | 18736 | 18755 | AGTTTAAAAAACAGTCATAA | 96 | 760 |
| 1363639 | 2295 | 2314 | 18774 | 18793 | TTTAATATCATTTGTGATGC | 30 | 761 |
| 1363661 | 3017 | 3036 | 19496 | 19515 | TCTATATCAGAAATGAAGGA | 47 | 762 |
| 1363677 | N/A | N/A | 17147 | 17166 | ACACACAGCCACATCATGCA | 61 | 763 |
| 1363709 | 2001 | 2020 | 18480 | 18499 | CTACCAGAGGGCCATCTCAG | 51 | 764 |
| 1363754 | 2788 | 2807 | 19267 | 19286 | TACTGGTTTGAAAACAAGTA | 38 | 765 |
| 1363771 | 2154 | 2173 | 18633 | 18652 | TAAAACAAATCAAGACCTTC | 55 | 766 |
| 1363781 | N/A | N/A | 11893 | 11912 | TCAACTATTTATGGAATACT | 69 | 767 |
| 1363799 | 1078 | 1097 | 17557 | 17576 | ATGAGTTTAAGGACGGCAAA | 55 | 768 |
| 1363810 | 1515 | 1534 | 17994 | 18013 | GGCAAGAGGACCAAAGACAT | 40 | 769 |
| 1363864 | N/A | N/A | 8958 | 8977 | GTATGTGTGAACAATAGCCT | 56 | 770 |
| 1363895 | N/A | N/A | 14243 | 14262 | CACTCAAAGCATGGATAACC | 54 | 771 |
| 1363931 | 2838 | 2857 | 19317 | 19336 | AAAACATTTTCCCTCTCCTC | 58 | 772 |
| 1363950 | 340 | 359 | 12632 | 12651 | CACAATCCAGTGGCCACCAG | 72 | 773 |
| 1363997 | 2232 | 2251 | 18711 | 18730 | GAATTATTCTCCAGACATTT | 42 | 774 |
| 1363999 | 1319 | 1338 | 17798 | 17817 | GGAACCAGCTATGAAGCAAA | 32 | 775 |
| 1364010 | 2345 | 2364 | 18824 | 18843 | GCAAAGGCAGAATACTTGTA | 50 | 776 |
| 1364104 | 2457 | 2476 | 18936 | 18955 | ACCTAACTCTTAACACACCA | 32 | 777 |
| 1364114 | N/A | N/A | 17351 | 17370 | TCTCCATATACACTTGACTG | 46 | 778 |
| 1364130 | N/A | N/A | 10367 | 10386 | GCTGCCAGGAAACTTGGCCT | 41 | 779 |
| 1364150 | N/A | N/A | 13731 | 13750 | CCACAAAATCCTGAGGATGA | 28 | 780 |
| 1364153 | N/A | N/A | 9218 | 9237 | GTAATATCAGCATAAGCATC | 57 | 781 |
| 1364169 | N/A | N/A | 7343 | 7362 | TAAAACTTATCCTTGGCACA | 93 | 782 |
| 1364252 | 1548 | 1567 | 18027 | 18046 | ACACCAAAGAGAATATATTT | 71 | 783 |
| 1364255 | 1971 | 1990 | 18450 | 18469 | TAGCCACCAGCAACTGCTGC | 31 | 784 |

TABLE 11

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362445 | 2319 | 2338 | 18798 | 18817 | CCCAATAGATTCAACTAGCC | 24 | 134 |
| 1362482 | N/A | N/A | 16485 | 16504 | CAGCATTTCAAGGATGGAAG | 51 | 785 |
| 1362490 | 1731 | 1750 | 18210 | 18229 | GCTTCAGTAGTCCATCGCCA | 30 | 201 |
| 1362513 | 1869 | 1888 | 18348 | 18367 | GTTATCAAGGAGAAGGGAGT | 37 | 786 |
| 1362549 | N/A | N/A | 5045 | 5064 | CCTGTTTTACCTGAACACAT | 53 | 787 |
| 1362550 | 2041 | 2060 | 18520 | 18539 | AAAAAAAGACATGCTATCCA | 63 | 788 |
| 1362560 | 2455 | 2474 | 18934 | 18953 | CTAACTCTTAACACACCAAG | 49 | 789 |
| 1362564 | N/A | N/A | 9215 | 9234 | ATATCAGCATAAGCATCAGA | 73 | 790 |
| 1362603 | N/A | N/A | 7337 | 7356 | TTATCCTTGGCACATTGTCT | 74 | 791 |
| 1362617 | 2344 | 2363 | 18823 | 18842 | CAAAGGCAGAATACTTGTAG | 53 | 792 |
| 1362699 | 1768 | 1787 | 18247 | 18266 | GCTCCCTTATGCTGTAAGTA | 35 | 204 |
| 1362804 | 1318 | 1337 | 17797 | 17816 | GAACCAGCTATGAAGCAAAA | 40 | 793 |
| 1362835 | 2618 | 2637 | 19097 | 19116 | CCAAAGTTAACAAAAACAGG | 63 | 794 |
| 1362840 | 2256 | 2275 | 18735 | 18754 | GTTTAAAAAACAGTCATAAT | 97 | 795 |
| 1362844 | N/A | N/A | 10891 | 10910 | AACACAGTATACACATGCAC | 48 | 796 |
| 1362996 | 2483 | 2502 | 18962 | 18981 | TCAGGAGAAAATAACCTTTA | 28 | 797 |
| 1363019 | 2294 | 2313 | 18773 | 18792 | TTAATATCATTTGTGATGCT | 25 | 798 |
| 1363020 | 1466 | 1485 | 17945 | 17964 | CCACTTTGTTTCCATCAGTG | 64 | 799 |
| 1363023 | 2000 | 2019 | 18479 | 18498 | TACCAGAGGGCCATCTCAGG | 53 | 800 |
| 1363032 | 3016 | 3035 | 19495 | 19514 | CTATATCAGAAATGAAGGAA | 56 | 801 |
| 1363037 | 2189 | 2208 | 18668 | 18687 | TAAACAAACTGGAATACATG | 93 | 802 |
| 1363086 | 2787 | 2806 | 19266 | 19285 | ACTGGTTTGAAAACAAGTAT | 49 | 803 |
| 1363090 | N/A | N/A | 17146 | 17165 | CACACAGCCACATCATGCAG | 89 | 804 |
| 1363095 | N/A | N/A | 4528 | 4547 | TGGTCAAGCCATTGAGGACT | 41 | 805 |
| 1363097 | N/A | N/A | 16064 | 16083 | GTTCCCTACAGTTGTGCCCA | 41 | 806 |
| 1363109 | 2375 | 2394 | 18854 | 18873 | TTGAGATTCAAATTCACCAA | 44 | 807 |
| 1363121 | 1732 | 1751 | 18211 | 18230 | GGCTTCAGTAGTCCATCGCC | 22 | 279 |
| 1363131 | N/A | N/A | 16780 | 16799 | GATAGTATATAGAATTCCAG | 40 | 808 |
| 1363135 | 304 | 323 | 12596 | 12615 | CCTACCAGACATCTTGCACA | 44 | 809 |
| 1363147 | 1547 | 1566 | 18026 | 18045 | CACCAAAGAGAATATATTTG | 58 | 810 |
| 1363148 | 1431 | 1450 | 17910 | 17929 | AAGAAATTACTTTCTGATCC | 79 | 811 |
| 1363160 | 2577 | 2596 | 19056 | 19075 | TATTCAGGTCTCAAACTCTT | 42 | 812 |
| 1363193 | 2074 | 2093 | 18553 | 18572 | TGACAGAGGCCAGAGTACAC | 43 | 813 |
| 1363217 | 1908 | 1927 | 18387 | 18406 | TCTCAGCTCCTTGGAAACCA | 38 | 814 |
| 1363250 | N/A | N/A | 11542 | 11561 | CTTCTTAGTTTACATATGGG | 40 | 815 |
| 1363256 | 3089 | 3108 | 19568 | 19587 | TTAATTTTATAAAATACACT | 99 | 816 |

TABLE 11-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363271 | 2665 | 2684 | 19144 | 19163 | AAATCTTTCCTTCAATTAAA | 80 | 817 |
| 1363296 | N/A | N/A | 6302 | 6321 | CAGCCACTTTTGGATGGAGG | 54 | 818 |
| 1363343 | 1178 | 1197 | 17657 | 17676 | GTTAAGATGGGAGACGCAGC | 46 | 819 |
| 1363363 | 2402 | 2421 | 18881 | 18900 | CTAGAAAGAACGATCAGATT | 69 | 820 |
| 1363376 | N/A | N/A | 8952 | 8971 | GTGAACAATAGCCTAAAGCC | 59 | 821 |
| 1363386 | N/A | N/A | 15072 | 15091 | GACCCAATCATTCATCATCT | 60 | 822 |
| 1363427 | 1651 | 1670 | 18130 | 18149 | CTGCAATAGGCAGATTTGGG | 24 | 823 |
| 1363469 | 2230 | 2249 | 18709 | 18728 | ATTATTCTCCAGACATTTCT | 66 | 824 |
| 1363579 | N/A | N/A | 9615 | 9634 | GAACTTGAACTCTTGCTAGC | 69 | 825 |
| 1363583 | 1586 | 1605 | 18065 | 18084 | CAGTGGTAATAGAGAGACCA | 24 | 826 |
| 1363586 | 2153 | 2172 | 18632 | 18651 | AAAACAAATCAAGACCTTCA | 57 | 827 |
| 1363609 | 2100 | 2119 | 18579 | 18598 | ATGAAATGAGCACCATTGTG | 45 | 828 |
| 1363614 | N/A | N/A | 7936 | 7955 | CACTACAGTCTTACCCTCCT | 83 | 829 |
| 1363632 | 2837 | 2856 | 19316 | 19335 | AAACATTTTCCCTCTCCTCC | 57 | 830 |
| 1363652 | 2691 | 2710 | 19170 | 19189 | TCTTTACAACAAAAGAACTG | 73 | 831 |
| 1363660 | 3052 | 3071 | 19531 | 19550 | AAAAGTTTATCCTTTATGTG | 69 | 832 |
| 1363665 | 1275 | 1294 | 17754 | 17773 | GGGAGAGTCCAAAGAGAGAC | 77 | 833 |
| 1363668 | 1695 | 1714 | 18174 | 18193 | CTTTCTGTGGGTGAAAGATC | 70 | 834 |
| 1363715 | 1246 | 1265 | 17725 | 17744 | TGCAAGACTCTCCTTTCTTG | 51 | 835 |
| 1363727 | N/A | N/A | 8625 | 8644 | CACTAGCAGTGACATAGACA | 71 | 836 |
| 1363759 | 2888 | 2907 | 19367 | 19386 | ACACAAGGTACGGATTACTT | 42 | 59 |
| 1363775 | N/A | N/A | 5812 | 5831 | CACATCAGAAGTAGTGGCAG | 66 | 837 |
| 1363805 | 2954 | 2973 | 19433 | 19452 | GTATGTATGCATGTGAGGTT | 60 | 838 |
| 1363811 | N/A | N/A | 17349 | 17368 | TCCATATACACTTGACTGGA | 50 | 839 |
| 1363872 | 1834 | 1853 | 18313 | 18332 | ACACCCTGTTTCTCTTCCCT | 39 | 840 |
| 1363917 | N/A | N/A | 15622 | 15641 | GTTGTAGAAGGCAATCGGCT | 63 | 841 |
| 1363933 | 1969 | 1988 | 18448 | 18467 | GCCACCAGCAACTGCTGCTC | 29 | 842 |
| 1363947 | N/A | N/A | 6003 | 6022 | TTCTATATGGTTGAAGTAGT | 61 | 843 |
| 1363957 | 2743 | 2762 | 19222 | 19241 | ACATCTCCTTAAATATTGCT | 33 | 844 |
| 1364023 | N/A | N/A | 5411 | 5430 | GAGTTCCTCCAACATTCACC | 39 | 845 |
| 1364038 | 1077 | 1096 | 17556 | 17575 | TGAGTTTAAGGACGGCAAAG | 80 | 846 |
| 1364060 | 1397 | 1416 | 17876 | 17895 | AAAATTCAATTAGAGCCTCC | 49 | 847 |
| 1364098 | 1210 | 1229 | 17689 | 17708 | AGAAGAGGGCCAGTTGGTGG | 69 | 848 |
| 1364106 | 1350 | 1369 | 17829 | 17848 | TCATCTTCTTAGGCATTTCC | 45 | 849 |
| 1364119 | 1514 | 1533 | 17993 | 18012 | GCAAGAGGACCAAAGACATT | 77 | 850 |

TABLE 11-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1364123 | 2527 | 2546 | 19006 | 19025 | AACTGAATAGCTGATGACTG | 55 | 851 |
| 1364138 | N/A | N/A | 14242 | 14261 | ACTCAAAGCATGGATAACCC | 38 | 852 |
| 1364145 | 609 | 628 | 13597 | 13616 | CGCTCAGGCCCTTGCCGCAG | 43 | 108 |
| 1364170 | 2428 | 2447 | 18907 | 18926 | TGCTAAGTAAAATCATTTTC | 47 | 853 |
| 1364193 | 2128 | 2147 | 18607 | 18626 | CCTACGATGACTGAATGGAT | 49 | 854 |
| 1364202 | N/A | N/A | 10364 | 10383 | GCCAGGAAACTTGGCCTCTA | 22 | 855 |
| 1364204 | N/A | N/A | 11892 | 11911 | CAACTATTTATGGAATACTC | 59 | 856 |
| 1364210 | N/A | N/A | 6923 | 6942 | TTCTTTAGACCTGAAGTGCT | 85 | 857 |

TABLE 12

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362483 | N/A | N/A | 17145 | 17164 | ACACAGCCACATCATGCAGT | 59 | 858 |
| 1362490 | 1731 | 1750 | 18210 | 18229 | GCTTCAGTAGTCCATCGCCA | 10 | 201 |
| 1362505 | N/A | N/A | 17348 | 17367 | CCATATACACTTGACTGGAA | 42 | 859 |
| 1362507 | 582 | 601 | 13570 | 13589 | TCTTGTAGTCGCCAAAGATC | 75 | 860 |
| 1362538 | N/A | N/A | 9212 | 9231 | TCAGCATAAGCATCAGATGT | 46 | 861 |
| 1362539 | 1274 | 1293 | 17753 | 17772 | GGAGAGTCCAAAGAGAGACC | 61 | 862 |
| 1362556 | 2482 | 2501 | 18961 | 18980 | CAGGAGAAAATAACCTTTAT | 15 | 863 |
| 1362557 | 1243 | 1262 | 17722 | 17741 | AAGACTCTCCTTTCTTGTTA | 52 | 864 |
| 1362558 | 3015 | 3034 | 19494 | 19513 | TATATCAGAAATGAAGGAAA | 73 | 865 |
| 1362622 | N/A | N/A | 7890 | 7909 | CCATGAACAGAGGCCTCCTT | 84 | 866 |
| 1362647 | 2152 | 2171 | 18631 | 18650 | AAACAAATCAAGACCTTCAA | 38 | 867 |
| 1362678 | 1464 | 1483 | 17943 | 17962 | ACTTTGTTTCCATCAGTGGA | 47 | 868 |
| 1362684 | 1968 | 1987 | 18447 | 18466 | CCACCAGCAACTGCTGCTCC | 24 | 869 |
| 1362692 | 1429 | 1448 | 17908 | 17927 | GAAATTACTTTCTGATCCTC | 70 | 870 |
| 1362741 | N/A | N/A | 9613 | 9632 | ACTTGAACTCTTGCTAGCCA | 44 | 871 |
| 1362782 | N/A | N/A | 15070 | 15089 | CCCAATCATTCATCATCTTA | 55 | 872 |
| 1362821 | 1766 | 1785 | 18245 | 18264 | TCCCTTATGCTGTAAGTAAG | 32 | 873 |
| 1362829 | 303 | 322 | 12595 | 12614 | CTACCAGACATCTTGCACAG | 53 | 874 |
| 1362878 | 2229 | 2248 | 18708 | 18727 | TTATTCTCCAGACATTTCTG | 36 | 875 |
| 1362895 | 2617 | 2636 | 19096 | 19115 | CAAAGTTAACAAAAACAGGA | 71 | 876 |
| 1362911 | N/A | N/A | 6914 | 6933 | CCTGAAGTGCTGTGGGCAGG | 78 | 877 |

TABLE 12-continued

Reduction of PLP1 RNA by 5-10-5 MOE gapmers with mixed
PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362938 | 2255 | 2274 | 18734 | 18753 | TTTAAAAAACAGTCATAATC | 81 | 878 |
| 1362967 | 1650 | 1669 | 18129 | 18148 | TGCAATAGGCAGATTTGGGC | 22 | 200 |
| 1362973 | 1546 | 1565 | 18025 | 18044 | ACCAAAGAGAATATATTTGG | 49 | 879 |
| 1363004 | N/A | N/A | 16483 | 16502 | GCATTTCAAGGATGGAAGCA | 53 | 880 |
| 1363013 | 1999 | 2018 | 18478 | 18497 | ACCAGAGGGCCATCTCAGGT | 15 | 881 |
| 1363073 | N/A | N/A | 5811 | 5830 | ACATCAGAAGTAGTGGCAGT | 66 | 882 |
| 1363084 | 1316 | 1335 | 17795 | 17814 | ACCAGCTATGAAGCAAAATG | 30 | 883 |
| 1363104 | 2040 | 2059 | 18519 | 18538 | AAAAAGACATGCTATCCAA | 51 | 884 |
| 1363106 | 1396 | 1415 | 17875 | 17894 | AAATTCAATTAGAGCCTCCA | 40 | 885 |
| 1363114 | 1209 | 1228 | 17688 | 17707 | GAAGAGGGCCAGTTGGTGGC | 44 | 886 |
| 1363121 | 1732 | 1751 | 18211 | 18230 | GGCTTCAGTAGTCCATCGCC | 16 | 279 |
| 1363143 | 2073 | 2092 | 18552 | 18571 | GACAGAGGCCAGAGTACACA | 10 | 887 |
| 1363159 | N/A | N/A | 10303 | 10322 | AGTTTACTCAGCATGAACTT | 85 | 888 |
| 1363168 | 1513 | 1532 | 17992 | 18011 | CAAGAGGACCAAAGACATTC | 85 | 889 |
| 1363172 | 2293 | 2312 | 18772 | 18791 | TAATATCATTTGTGATGCTT | 25 | 890 |
| 1363220 | 2662 | 2681 | 19141 | 19160 | TCTTTCCTTCAATTAAAACC | 27 | 891 |
| 1363231 | 2454 | 2473 | 18933 | 18952 | TAACTCTTAACACACCAAGA | 40 | 892 |
| 1363293 | N/A | N/A | 6299 | 6318 | CCACTTTTGGATGGAGGCAT | 38 | 893 |
| 1363294 | 2690 | 2709 | 19169 | 19188 | CTTTACAACAAAAGAACTGT | 39 | 894 |
| 1363305 | 2374 | 2393 | 18853 | 18872 | TGAGATTCAAATTCACCAAA | 22 | 895 |
| 1363306 | N/A | N/A | 16061 | 16080 | CCCTACAGTTGTGCCCAGGG | 47 | 896 |
| 1363322 | 2427 | 2446 | 18906 | 18925 | GCTAAGTAAAATCATTTTCC | 13 | 897 |
| 1363356 | 2953 | 2972 | 19432 | 19451 | TATGTATGCATGTGAGGTTT | 58 | 898 |
| 1363421 | N/A | N/A | 8590 | 8609 | GGGAATTAAAAGGCCAGTCC | 57 | 899 |
| 1363472 | 2887 | 2906 | 19366 | 19385 | CACAAGGTACGGATTACTTC | 26 | 900 |
| 1363475 | 2786 | 2805 | 19265 | 19284 | CTGGTTTGAAAACAAGTATC | 25 | 901 |
| 1363487 | 2318 | 2337 | 18797 | 18816 | CCAATAGATTCAACTAGCCA | 29 | 56 |
| 1363528 | N/A | N/A | 11540 | 11559 | TCTTAGTTTACATATGGGAG | 38 | 902 |
| 1363577 | 2188 | 2207 | 18667 | 18686 | AAACAAACTGGAATACATGA | 53 | 903 |
| 1363590 | N/A | N/A | 16778 | 16797 | TAGTATATAGAATTCCAGGC | 23 | 904 |
| 1363601 | N/A | N/A | 5929 | 5948 | TTGTTGTAAAATGAATCCC | 48 | 905 |
| 1363630 | 3050 | 3069 | 19529 | 19548 | AAGTTTATCCTTTATGTGTG | 36 | 906 |
| 1363666 | 2127 | 2146 | 18606 | 18625 | CTACGATGACTGAATGGATA | 44 | 907 |
| 1363675 | 3086 | 3105 | 19565 | 19584 | ATTTTATAAAATACACTTTG | 78 | 908 |
| 1363682 | N/A | N/A | 5407 | 5426 | TCCTCCAACATTCACCTCTC | 43 | 909 |
| 1363722 | 2526 | 2545 | 19005 | 19024 | ACTGAATAGCTGATGACTGG | 44 | 910 |

TABLE 12-continued

Reduction of PLP1 RNA by 5-10-5 MOE gapmers with mixed
PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363748 | 1827 | 1846 | 18306 | 18325 | GTTTCTCTTCCCTAACGAGG | 27 | 911 |
| 1363826 | 2836 | 2855 | 19315 | 19334 | AACATTTTCCCTCTCCTCCT | 31 | 912 |
| 1363847 | 2401 | 2420 | 18880 | 18899 | TAGAAAGAACGATCAGATTA | 66 | 913 |
| 1363883 | 2573 | 2592 | 19052 | 19071 | CAGGTCTCAAACTCTTTCTG | 18 | 914 |
| 1363902 | 2742 | 2761 | 19221 | 19240 | CATCTCCTTAAATATTGCTG | 20 | 915 |
| 1363904 | N/A | N/A | 15616 | 15635 | GAAGGCAATCGGCTAATTCA | 54 | 916 |
| 1363929 | 2343 | 2362 | 18822 | 18841 | AAAGGCAGAATACTTGTAGA | 58 | 917 |
| 1363958 | N/A | N/A | 7332 | 7351 | CTTGGCACATTGTCTCCACC | 79 | 918 |
| 1363965 | N/A | N/A | 8924 | 8943 | TCCATTTCAGAACCCCTCCT | 55 | 919 |
| 1363976 | 1585 | 1604 | 18064 | 18083 | AGTGGTAATAGAGAGACCAG | 25 | 920 |
| 1364070 | 1906 | 1925 | 18385 | 18404 | TCAGCTCCTTGGAAACCACA | 19 | 921 |
| 1364109 | 1868 | 1887 | 18347 | 18366 | TTATCAAGGAGAAGGGAGTG | 67 | 922 |
| 1364132 | N/A | N/A | 11891 | 11910 | AACTATTTATGGAATACTCA | 71 | 923 |
| 1364134 | 1694 | 1713 | 18173 | 18192 | TTTCTGTGGGTGAAAGATCC | 56 | 924 |
| 1364141 | 1347 | 1366 | 17826 | 17845 | TCTTCTTAGGCATTTCCCAT | 30 | 925 |
| 1364191 | N/A | N/A | 10875 | 10894 | GCACACACACAAATACTCAG | 34 | 926 |
| 1364208 | N/A | N/A | 14236 | 14255 | AGCATGGATAACCCTCAGGC | 18 | 927 |
| 1364218 | N/A | N/A | 5044 | 5063 | CTGTTTTACCTGAACACATG | 64 | 928 |
| 1364225 | 1076 | 1095 | 17555 | 17574 | GAGTTTAAGGACGGCAAAGT | 30 | 929 |
| 1364243 | 1177 | 1196 | 17656 | 17675 | TTAAGATGGGAGACGCAGCA | 39 | 930 |
| 1364245 | 2099 | 2118 | 18578 | 18597 | TGAAATGAGCACCATTGTGA | 42 | 931 |
| 1364247 | N/A | N/A | 4470 | 4489 | CCATAGCCAAGCCTGAGTCC | 72 | 932 |

TABLE 13

Reduction of PLP1 RNA by 5-10-5 MOE gapmers with mixed
PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362426 | 2661 | 2680 | 19140 | 19159 | CTTTCCTTCAATTAAAACCA | 49 | 933 |
| 1362458 | 2225 | 2244 | 18704 | 18723 | TCTCCAGACATTTCTGATGC | 18 | 934 |
| 1362490 | 1731 | 1750 | 18210 | 18229 | GCTTCAGTAGTCCATCGCCA | 25 | 201 |
| 1362510 | 2098 | 2117 | 18577 | 18596 | GAAATGAGCACCATTGTGAA | 72 | 935 |
| 1362528 | 1241 | 1260 | 17720 | 17739 | GACTCTCCTTTCTTGTTACA | 38 | 936 |
| 1362547 | N/A | N/A | 16777 | 16796 | AGTATATAGAATTCCAGGCT | 30 | 937 |
| 1362573 | 2614 | 2633 | 19093 | 19112 | AGTTAACAAAAACAGGAAAA | 89 | 938 |
| 1362587 | N/A | N/A | 17343 | 17362 | TACACTTGACTGGAAGTCCG | 43 | 939 |

TABLE 13-continued

Reduction of PLP1 RNA by 5-10-5 MOE gapmers with mixed
PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362590 | 1175 | 1194 | 17654 | 17673 | AAGATGGGAGACGCAGCATT | 55 | 940 |
| 1362606 | 2342 | 2361 | 18821 | 18840 | AAGGCAGAATACTTGTAGAA | 61 | 941 |
| 1362625 | 2946 | 2965 | 19425 | 19444 | GCATGTGAGGTTTTCAGGGA | 30 | 942 |
| 1362626 | N/A | N/A | 10872 | 10891 | CACACACAAATACTCAGCAA | 53 | 943 |
| 1362644 | 2785 | 2804 | 19264 | 19283 | TGGTTTGAAAACAAGTATCA | 47 | 944 |
| 1362671 | N/A | N/A | 8923 | 8942 | CCATTTCAGAACCCCTCCTG | 81 | 945 |
| 1362680 | 2292 | 2311 | 18771 | 18790 | AATATCATTTGTGATGCTTA | 18 | 946 |
| 1362694 | N/A | N/A | 16481 | 16500 | ATTTCAAGGATGGAAGCAGT | 88 | 947 |
| 1362720 | N/A | N/A | 5761 | 5780 | CAAAGTACTTTAGATACTCT | 71 | 948 |
| 1362779 | 1545 | 1564 | 18024 | 18043 | CCAAAGAGAATATATTTGGC | 65 | 949 |
| 1362810 | 2317 | 2336 | 18796 | 18815 | CAATAGATTCAACTAGCCAA | 44 | 950 |
| 1362817 | 2571 | 2590 | 19050 | 19069 | GGTCTCAAACTCTTTCTGCC | 21 | 951 |
| 1362833 | 2740 | 2759 | 19219 | 19238 | TCTCCTTAAATATTGCTGAA | 27 | 952 |
| 1362836 | N/A | N/A | 11392 | 11411 | TCCTCCTATAATGCAGCTTG | 39 | 953 |
| 1362858 | 2125 | 2144 | 18604 | 18623 | ACGATGACTGAATGGATAAT | 41 | 954 |
| 1362902 | 1765 | 1784 | 18244 | 18263 | CCCTTATGCTGTAAGTAAGG | 27 | 126 |
| 1362936 | 3042 | 3061 | 19521 | 19540 | CCTTTATGTGTGTTAAAATT | 41 | 955 |
| 1362946 | 3081 | 3100 | 19560 | 19579 | ATAAAATACACTTTGTAAGA | 86 | 956 |
| 1362975 | N/A | N/A | 15615 | 15634 | AAGGCAATCGGCTAATTCAA | 54 | 957 |
| 1363012 | 1584 | 1603 | 18063 | 18082 | GTGGTAATAGAGAGACCAGA | 26 | 958 |
| 1363025 | 1208 | 1227 | 17687 | 17706 | AAGAGGGCCAGTTGGTGGCA | 37 | 959 |
| 1363033 | N/A | N/A | 8458 | 8477 | GCAAAATGTAAGCAAAGGGA | 60 | 960 |
| 1363105 | 1428 | 1447 | 17907 | 17926 | AAATTACTTTCTGATCCTCA | 91 | 961 |
| 1363121 | 1732 | 1751 | 18211 | 18230 | GGCTTCAGTAGTCCATCGCC | 18 | 279 |
| 1363183 | 1075 | 1094 | 17554 | 17573 | AGTTTAAGGACGGCAAAGTT | 58 | 962 |
| 1363189 | N/A | N/A | 15954 | 15973 | TTGTATATAATATCTGTTCT | 61 | 963 |
| 1363192 | 2689 | 2708 | 19168 | 19187 | TTTACAACAAAAGAACTGTA | 76 | 964 |
| 1363211 | N/A | N/A | 6295 | 6314 | TTTTGGATGGAGGCATCACA | 72 | 965 |
| 1363214 | N/A | N/A | 14235 | 14254 | GCATGGATAACCCTCAGGCA | 27 | 966 |
| 1363215 | 2400 | 2419 | 18879 | 18898 | AGAAAGAACGATCAGATTAC | 65 | 967 |
| 1363239 | 2151 | 2170 | 18630 | 18649 | AACAAATCAAGACCTTCAAA | 63 | 968 |
| 1363255 | 1904 | 1923 | 18383 | 18402 | AGCTCCTTGGAAACCACAGG | 20 | 969 |
| 1363261 | 2187 | 2206 | 18666 | 18685 | AACAAACTGGAATACATGAA | 54 | 970 |
| 1363288 | N/A | N/A | 5403 | 5422 | CCAACATTCACCTCTCATCT | 59 | 971 |
| 1363298 | 2481 | 2500 | 18960 | 18979 | AGGAGAAAATAACCTTTATG | 40 | 972 |
| 1363355 | 1824 | 1843 | 18303 | 18322 | TCTCTTCCCTAACGAGGTGT | 36 | 53 |

TABLE 13-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363359 | 2453 | 2472 | 18932 | 18951 | AACTCTTAACACACCAAGAT | 41 | 973 |
| 1363382 | 2524 | 2543 | 19003 | 19022 | TGAATAGCTGATGACTGGTG | 49 | 974 |
| 1363445 | 1463 | 1482 | 17942 | 17961 | CTTTGTTTCCATCAGTGGAA | 71 | 975 |
| 1363450 | N/A | N/A | 7773 | 7792 | AACAACAATTATCAAGAGGT | 60 | 976 |
| 1363451 | 2071 | 2090 | 18550 | 18569 | CAGAGGCCAGAGTACACAAC | 31 | 977 |
| 1363457 | 1967 | 1986 | 18446 | 18465 | CACCAGCAACTGCTGCTCCT | 29 | 978 |
| 1363476 | 3013 | 3032 | 19492 | 19511 | TATCAGAAATGAAGGAAACA | 78 | 979 |
| 1363489 | 1649 | 1668 | 18128 | 18147 | GCAATAGGCAGATTTGGGCA | 31 | 980 |
| 1363490 | N/A | N/A | 15068 | 15087 | CAATCATTCATCATCTTATA | 68 | 981 |
| 1363546 | 1273 | 1292 | 17752 | 17771 | GAGAGTCCAAAGAGAGACCT | 50 | 982 |
| 1363575 | 2828 | 2847 | 19307 | 19326 | CCCTCTCCTCCTTCTATGCA | 54 | 983 |
| 1363578 | N/A | N/A | 6800 | 6819 | GAAAGTGATGTTACTGGCTG | 52 | 984 |
| 1363595 | N/A | N/A | 5928 | 5947 | TGTTGTAAAAATGAATCCCG | 48 | 985 |
| 1363597 | 2886 | 2905 | 19365 | 19384 | ACAAGGTACGGATTACTTCA | 45 | 986 |
| 1363626 | 301 | 320 | 12593 | 12612 | ACCAGACATCTTGCACAGCA | 39 | 987 |
| 1363640 | 1315 | 1334 | 17794 | 17813 | CCAGCTATGAAGCAAAATGA | 24 | 988 |
| 1363680 | 2254 | 2273 | 18733 | 18752 | TTAAAAAACAGTCATAATCA | 86 | 989 |
| 1363685 | 2426 | 2445 | 18905 | 18924 | CTAAGTAAAATCATTTTCCA | 18 | 990 |
| 1363694 | 1346 | 1365 | 17825 | 17844 | CTTCTTAGGCATTTCCCATT | 40 | 991 |
| 1363720 | 1692 | 1711 | 18171 | 18190 | TCTGTGGGTGAAAGATCCTT | 33 | 992 |
| 1363762 | 1998 | 2017 | 18477 | 18496 | CCAGAGGGCCATCTCAGGTT | 22 | 993 |
| 1363841 | N/A | N/A | 5041 | 5060 | TTTTACCTGAACACATGCTT | 85 | 994 |
| 1363885 | 573 | 592 | 13561 | 13580 | CGCCAAAGATCTGCCTGACT | 61 | 995 |
| 1364003 | N/A | N/A | 9601 | 9620 | GCTAGCCAAAAGAGAACTCC | 86 | 996 |
| 1364031 | N/A | N/A | 17018 | 17037 | TGTCTGATCACTGCTTATAA | 44 | 997 |
| 1364043 | N/A | N/A | 9206 | 9225 | TAAGCATCAGATGTTCATCT | 42 | 998 |
| 1364044 | N/A | N/A | 11881 | 11900 | GGAATACTCACTATATGCCC | 49 | 999 |
| 1364049 | 1866 | 1885 | 18345 | 18364 | ATCAAGGAGAAGGGAGTGAG | 50 | 1000 |
| 1364101 | 2039 | 2058 | 18518 | 18537 | AAAAAGACATGCTATCCAAA | 57 | 1001 |
| 1364131 | N/A | N/A | 10296 | 10315 | TCAGCATGAACTTTGCAAAC | 76 | 1002 |
| 1364136 | N/A | N/A | 4469 | 4488 | CATAGCCAAGCCTGAGTCCA | 88 | 1003 |
| 1364175 | 1512 | 1531 | 17991 | 18010 | AAGAGGACCAAAGACATTCC | 59 | 1004 |
| 1364182 | 2373 | 2392 | 18852 | 18871 | GAGATTCAAATTCACCAAAT | 16 | 1005 |
| 1364188 | N/A | N/A | 7288 | 7307 | GGGAAGTAACTGGTACTAGA | 57 | 1006 |
| 1364265 | 1395 | 1414 | 17874 | 17893 | AATTCAATTAGAGCCTCCAT | 48 | 1007 |

TABLE 14

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362486 | 2827 | 2846 | 19306 | 19325 | CCTCTCCTCCTTCTATGCAG | 30 | 1008 |
| 1362490 | 1731 | 1750 | 18210 | 18229 | GCTTCAGTAGTCCATCGCCA | 12 | 201 |
| 1362511 | N/A | N/A | 8895 | 8914 | GGTGTGAGTTTGATTCAAGA | 64 | 1009 |
| 1362514 | 2038 | 2057 | 18517 | 18536 | AAAAGACATGCTATCCAAAG | 68 | 1010 |
| 1362521 | 2150 | 2169 | 18629 | 18648 | ACAAATCAAGACCTTCAAAT | 57 | 1011 |
| 1362527 | N/A | N/A | 15952 | 15971 | GTATATAATATCTGTTCTCA | 39 | 1012 |
| 1362582 | 2372 | 2391 | 18851 | 18870 | AGATTCAAATTCACCAAATC | 38 | 1013 |
| 1362630 | 2945 | 2964 | 19424 | 19443 | CATGTGAGGTTTTCAGGGAA | 36 | 1014 |
| 1362683 | 1544 | 1563 | 18023 | 18042 | CAAAGAGAATATATTTGGCC | 69 | 1015 |
| 1362703 | 1207 | 1226 | 17686 | 17705 | AGAGGGCCAGTTGGTGGCAA | 55 | 1016 |
| 1362758 | 2784 | 2803 | 19263 | 19282 | GGTTTGAAAACAAGTATCAA | 35 | 1017 |
| 1362792 | 1865 | 1884 | 18344 | 18363 | TCAAGGAGAAGGGAGTGAGA | 45 | 1018 |
| 1362806 | 2885 | 2904 | 19364 | 19383 | CAAGGTACGGATTACTTCAC | 36 | 1019 |
| 1362843 | 2425 | 2444 | 18904 | 18923 | TAAGTAAAATCATTTTCCAT | 56 | 1020 |
| 1362854 | 2452 | 2471 | 18931 | 18950 | ACTCTTAACACACCAAGATA | 52 | 1021 |
| 1362856 | 2289 | 2308 | 18768 | 18787 | ATCATTTGTGATGCTTAATG | 11 | 1022 |
| 1362877 | N/A | N/A | 4403 | 4422 | GTTTGCATCAAGCAAGCAGT | 40 | 1023 |
| 1362887 | 2688 | 2707 | 19167 | 19186 | TTACAACAAAAGAACTGTAG | 65 | 1024 |
| 1362908 | 1462 | 1481 | 17941 | 17960 | TTTGTTTCCATCAGTGGAAG | 72 | 1025 |
| 1362932 | N/A | N/A | 5927 | 5946 | GTTGTAAAATGAATCCCGC | 35 | 1026 |
| 1362934 | N/A | N/A | 10871 | 10890 | ACACACAAATACTCAGCAAA | 58 | 1027 |
| 1362953 | N/A | N/A | 6796 | 6815 | GTGATGTTACTGGCTGGAGT | 52 | 1028 |
| 1362963 | 1648 | 1667 | 18127 | 18146 | CAATAGGCAGATTTGGGCAA | 47 | 1029 |
| 1362966 | N/A | N/A | 15608 | 15627 | TCGGCTAATTCAAAATCCAG | 37 | 1030 |
| 1362978 | N/A | N/A | 16478 | 16497 | TCAAGGATGGAAGCAGTCTA | 77 | 1031 |
| 1362983 | 299 | 318 | 12591 | 12610 | CAGACATCTTGCACAGCACT | 34 | 1032 |
| 1363008 | 3079 | 3098 | 19558 | 19577 | AAAATACACTTTGTAAGATA | 80 | 1033 |
| 1363051 | 1822 | 1841 | 18301 | 18320 | TCTTCCCTAACGAGGTGTAA | 31 | 1034 |
| 1363064 | N/A | N/A | 11880 | 11899 | GAATACTCACTATATGCCCA | 65 | 1035 |
| 1363101 | 1903 | 1922 | 18382 | 18401 | GCTCCTTGGAAACCACAGGG | 23 | 1036 |
| 1363115 | N/A | N/A | 14089 | 14108 | AGATCAGGTGCCCAAGTCTC | 43 | 1037 |
| 1363121 | 1732 | 1751 | 18211 | 18230 | GGCTTCAGTAGTCCATCGCC | 12 | 279 |
| 1363129 | N/A | N/A | 7771 | 7790 | CAACAATTATCAAGAGGTGC | 40 | 1038 |
| 1363144 | 2253 | 2272 | 18732 | 18751 | TAAAAACAGTCATAATCAA | 107 | 1039 |
| 1363167 | 2097 | 2116 | 18576 | 18595 | AAATGAGCACCATTGTGAAG | 68 | 1040 |
| 1363187 | 1583 | 1602 | 18062 | 18081 | TGGTAATAGAGAGACCAGAA | 29 | 1041 |

TABLE 14-continued

Reduction of PLP1 RNA by 5-10-5 MOE gapmers with mixed
PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363283 | 1314 | 1333 | 17793 | 17812 | CAGCTATGAAGCAAAATGAC | 50 | 1042 |
| 1363287 | 2070 | 2089 | 18549 | 18568 | AGAGGCCAGAGTACACAACT | 18 | 1043 |
| 1363290 | 1394 | 1413 | 17873 | 17892 | ATTCAATTAGAGCCTCCATT | 60 | 1044 |
| 1363311 | 1272 | 1291 | 17751 | 17770 | AGAGTCCAAAGAGAGACCTT | 51 | 1045 |
| 1363320 | N/A | N/A | 5038 | 5057 | TACCTGAACACATGCTTCAA | 87 | 1046 |
| 1363351 | 2224 | 2243 | 18703 | 18722 | CTCCAGACATTTCTGATGCA | 20 | 1047 |
| 1363389 | 1174 | 1193 | 17653 | 17672 | AGATGGGAGACGCAGCATTG | 50 | 1048 |
| 1363395 | N/A | N/A | 5758 | 5777 | AGTACTTTAGATACTCTGTT | 24 | 1049 |
| 1363398 | N/A | N/A | 9203 | 9222 | GCATCAGATGTTCATCTCTT | 22 | 1050 |
| 1363408 | N/A | N/A | 10147 | 10166 | AAATCGATTGTTGTTCTCAG | 60 | 1051 |
| 1363453 | 2569 | 2588 | 19048 | 19067 | TCTCAAACTCTTTCTGCCTG | 24 | 1052 |
| 1363460 | 872 | 891 | 14931 | 14950 | AGCACAGAGACTGCCTATAC | 67† | 1053 |
| 1363467 | 2124 | 2143 | 18603 | 18622 | CGATGACTGAATGGATAATA | 28 | 1054 |
| 1363513 | 572 | 591 | 13560 | 13579 | GCCAAAGATCTGCCTGACTG | 45 | 1055 |
| 1363534 | 2399 | 2418 | 18878 | 18897 | GAAAGAACGATCAGATTACT | 53 | 1056 |
| 1363558 | 1427 | 1446 | 17906 | 17925 | AATTACTTTCTGATCCTCAG | 88 | 1057 |
| 1363559 | N/A | N/A | 16776 | 16795 | GTATATAGAATTCCAGGCTA | 32 | 1058 |
| 1363570 | 1997 | 2016 | 18476 | 18495 | CAGAGGGCCATCTCAGGTTA | 45 | 1059 |
| 1363642 | 2523 | 2542 | 19002 | 19021 | GAATAGCTGATGACTGGTGC | 23 | 1060 |
| 1363651 | 1239 | 1258 | 17718 | 17737 | CTCTCCTTTCTTGTTACACT | 36 | 1061 |
| 1363716 | 2480 | 2499 | 18959 | 18978 | GGAGAAAATAACCTTTATGT | 33 | 1062 |
| 1363735 | 2184 | 2203 | 18663 | 18682 | AAACTGGAATACATGAAATG | 73 | 1063 |
| 1363737 | N/A | N/A | 11389 | 11408 | TCCTATAATGCAGCTTGGCT | 60 | 1064 |
| 1363760 | 2316 | 2335 | 18795 | 18814 | AATAGATTCAACTAGCCAAT | 48 | 1065 |
| 1363809 | 3041 | 3060 | 19520 | 19539 | CTTTATGTGTGTTAAAATTG | 72 | 1066 |
| 1363812 | 2739 | 2758 | 19218 | 19237 | CTCCTTAAATATTGCTGAAA | 32 | 1067 |
| 1363817 | N/A | N/A | 5402 | 5421 | CAACATTCACCTCTCATCTG | 77 | 1068 |
| 1363831 | N/A | N/A | 9597 | 9616 | GCCAAAAGAGAACTCCACTT | 49 | 1069 |
| 1363836 | 3012 | 3031 | 19491 | 19510 | ATCAGAAATGAAGGAAACAC | 61 | 1070 |
| 1363846 | 2341 | 2360 | 18820 | 18839 | AGGCAGAATACTTGTAGAAA | 58 | 1071 |
| 1363848 | 1691 | 1710 | 18170 | 18189 | CTGTGGGTGAAAGATCCTTG | 29 | 1072 |
| 1363854 | N/A | N/A | 7272 | 7291 | TAGAGACAATAGTAGCCATA | 73 | 1073 |
| 1363886 | N/A | N/A | 16994 | 17013 | ACTTCAGATAAATCACTTCA | 53 | 1074 |
| 1364056 | N/A | N/A | 17340 | 17359 | ACTTGACTGGAAGTCCGATG | 29 | 1075 |
| 1364078 | 2613 | 2632 | 19092 | 19111 | GTTAACAAAAACAGGAAAAG | 79 | 1076 |

TABLE 14-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1364079 | 1511 | 1530 | 17990 | 18009 | AGAGGACCAAAGACATTCCT | 48 | 1077 |
| 1364086 | N/A | N/A | 8419 | 8438 | GCTACATTTGTATACAAACT | 36 | 1078 |
| 1364091 | 1074 | 1093 | 17553 | 17572 | GTTTAAGGACGGCAAAGTTG | 55 | 1079 |
| 1364126 | N/A | N/A | 6291 | 6310 | GGATGGAGGCATCACAGTCT | 47 | 1080 |
| 1364129 | 1762 | 1781 | 18241 | 18260 | TTATGCTGTAAGTAAGGTTG | 42 | 1081 |
| 1364192 | 1966 | 1985 | 18445 | 18464 | ACCAGCAACTGCTGCTCCTC | 33 | 1082 |
| 1364205 | 2658 | 2677 | 19137 | 19156 | TCCTTCAATTAAAACCAATC | 38 | 1083 |
| 1364244 | 1345 | 1364 | 17824 | 17843 | TTCTTAGGCATTTCCCATTT | 52 | 1084 |

TABLE 15

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362433 | 296 | 315 | 12588 | 12607 | ACATCTTGCACAGCACTCTA | 34 | 1085 |
| 1362442 | N/A | N/A | 5303 | 5322 | CTGTATACACATTATTGTCT | 46 | 1086 |
| 1362446 | 1864 | 1883 | 18343 | 18362 | CAAGGAGAAGGGAGTGAGAA | 60 | 1087 |
| 1362448 | 1234 | 1253 | 17713 | 17732 | CTTTCTTGTTACACTCATCA | 28 | 1088 |
| 1362450 | 2783 | 2802 | 19262 | 19281 | GTTTGAAAACAAGTATCAAG | 29 | 1089 |
| 1362460 | 2520 | 2539 | 18999 | 19018 | TAGCTGATGACTGGTGCATT | 26 | 1090 |
| 1362485 | 2738 | 2757 | 19217 | 19236 | TCCTTAAATATTGCTGAAAC | 40 | 1091 |
| 1362490 | 1731 | 1750 | 18210 | 18229 | GCTTCAGTAGTCCATCGCCA | 13 | 201 |
| 1362516 | N/A | N/A | 10143 | 10162 | CGATTGTTGTTCTCAGAAAA | 49 | 1092 |
| 1362738 | 2183 | 2202 | 18662 | 18681 | AACTGGAATACATGAAATGT | 78 | 1093 |
| 1362745 | N/A | N/A | 8416 | 8435 | ACATTTGTATACAAACTCCC | 46 | 1094 |
| 1362767 | N/A | N/A | 17254 | 17273 | CCTCTGTTTGATCTAGCACT | 31 | 1095 |
| 1362816 | 2657 | 2676 | 19136 | 19155 | CCTTCAATTAAAACCAATCA | 39 | 1096 |
| 1362825 | N/A | N/A | 16765 | 16784 | TCCAGGCTATAGCAAGTCAT | 23 | 1097 |
| 1362857 | 1073 | 1092 | 17552 | 17571 | TTTAAGGACGGCAAAGTTGT | 66 | 1098 |
| 1362866 | N/A | N/A | 14042 | 14061 | TGTCCAGTTAGATCCACTCT | 16 | 245 |
| 1362899 | N/A | N/A | 10870 | 10889 | CACACAAATACTCAGCAAAT | 66 | 1099 |
| 1362916 | 1205 | 1224 | 17684 | 17703 | AGGGCCAGTTGGTGGCAAAG | 34 | 1100 |
| 1362951 | 3039 | 3058 | 19518 | 19537 | TTATGTGTGTTAAAATTGCA | 55 | 1101 |
| 1362982 | N/A | N/A | 11388 | 11407 | CCTATAATGCAGCTTGGCTA | 54 | 1102 |
| 1363000 | N/A | N/A | 5037 | 5056 | ACCTGAACACATGCTTCAAA | 59 | 1103 |

TABLE 15-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363031 | N/A | N/A | 5728 | 5747 | TGAAAACTCAGTGGCTGCTC | 47 | 1104 |
| 1363039 | 2315 | 2334 | 18794 | 18813 | ATAGATTCAACTAGCCAATT | 61 | 1105 |
| 1363059 | 2037 | 2056 | 18516 | 18535 | AAAGACATGCTATCCAAAGA | 46 | 1106 |
| 1363100 | 1543 | 1562 | 18022 | 18041 | AAAGAGAATATATTTGGCCC | 58 | 1107 |
| 1363121 | 1732 | 1751 | 18211 | 18230 | GGCTTCAGTAGTCCATCGCC | 15 | 279 |
| 1363145 | 2069 | 2088 | 18548 | 18567 | GAGGCCAGAGTACACAACTA | 15 | 1108 |
| 1363151 | 2371 | 2390 | 18850 | 18869 | GATTCAAATTCACCAAATCT | 28 | 1109 |
| 1363179 | 2223 | 2242 | 18702 | 18721 | TCCAGACATTTCTGATGCAA | 14 | 1110 |
| 1363199 | N/A | N/A | 16993 | 17012 | CTTCAGATAAATCACTTCAC | 40 | 1111 |
| 1363216 | N/A | N/A | 7714 | 7733 | TGGTCAGACAATGCCCTGCC | 56 | 1112 |
| 1363221 | N/A | N/A | 16474 | 16493 | GGATGGAAGCAGTCTACCTT | 44 | 1113 |
| 1363234 | 1343 | 1362 | 17822 | 17841 | CTTAGGCATTTCCCATTTCT | 47 | 1114 |
| 1363237 | 3011 | 3030 | 19490 | 19509 | TCAGAAATGAAGGAAACACT | 51 | 1115 |
| 1363248 | 1425 | 1444 | 17904 | 17923 | TTACTTTCTGATCCTCAGGA | 66 | 1116 |
| 1363273 | 1459 | 1478 | 17938 | 17957 | GTTTCCATCAGTGGAAGTAC | 16 | 1117 |
| 1363292 | 2929 | 2948 | 19408 | 19427 | GGAAGGGTTGGTTATTTGTT | 41 | 1118 |
| 1363338 | N/A | N/A | 7271 | 7290 | AGAGACAATAGTAGCCATAC | 69 | 1119 |
| 1363357 | 2286 | 2305 | 18765 | 18784 | ATTTGTGATGCTTAATGTCC | 30 | 1120 |
| 1363361 | 1901 | 1920 | 18380 | 18399 | TCCTTGGAAACCACAGGGTT | 49 | 1121 |
| 1363424 | N/A | N/A | 9511 | 9530 | TGATCCCTCAATCATCATCC | 56 | 1122 |
| 1363486 | N/A | N/A | 15607 | 15626 | CGGCTAATTCAAAATCCAGC | 19 | 1123 |
| 1363516 | N/A | N/A | 9199 | 9218 | CAGATGTTCATCTCTTCACA | 35 | 1124 |
| 1363518 | 1821 | 1840 | 18300 | 18319 | CTTCCCTAACGAGGTGTAAG | 33 | 1125 |
| 1363519 | 1994 | 2013 | 18473 | 18492 | AGGGCCATCTCAGGTTACAC | 10 | 288 |
| 1363521 | N/A | N/A | 5912 | 5931 | CCCGCATTGAAGGTTGGCTC | 32 | 1126 |
| 1363584 | 2398 | 2417 | 18877 | 18896 | AAAGAACGATCAGATTACTC | 28 | 1127 |
| 1363598 | 2122 | 2141 | 18601 | 18620 | ATGACTGAATGGATAATACC | 37 | 1128 |
| 1363638 | 2823 | 2842 | 19302 | 19321 | TCCTCCTTCTATGCAGCCTG | 21 | 1129 |
| 1363646 | N/A | N/A | 6282 | 6301 | CATCACAGTCTGGTTACCAG | 68 | 1130 |
| 1363648 | 1965 | 1984 | 18444 | 18463 | CCAGCAACTGCTGCTCCTCA | 17 | 1131 |
| 1363655 | 871 | 890 | 14930 | 14949 | GCACAGAGACTGCCTATACT | 77† | 1132 |
| 1363663 | 478 | 497 | 13466 | 13485 | ACATACTGGAAGGCATGGAT | 36 | 1133 |
| 1363693 | N/A | N/A | 8893 | 8912 | TGTGAGTTTGATTCAAGAAG | 52 | 1134 |
| 1363714 | 1393 | 1412 | 17872 | 17891 | TTCAATTAGAGCCTCCATTC | 50 | 1135 |
| 1363744 | 2884 | 2903 | 19363 | 19382 | AAGGTACGGATTACTTCACT | 26 | 1136 |
| 1363764 | 1271 | 1290 | 17750 | 17769 | GAGTCCAAAGAGAGACCTTA | 43 | 1137 |

TABLE 15-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
| --- | --- | --- | --- | --- | --- | --- | --- |
| 1363835 | 2566 | 2585 | 19045 | 19064 | CAAACTCTTTCTGCCTGTCC | 31 | 1138 |
| 1363866 | 3078 | 3097 | 19557 | 19576 | AAATACACTTTGTAAGATAA | 55 | 1139 |
| 1363920 | N/A | N/A | 6767 | 6786 | ATGGGTTTGGAGACTATATT | 61 | 1140 |
| 1363945 | 2612 | 2631 | 19091 | 19110 | TTAACAAAAACAGGAAAAGA | 86 | 1141 |
| 1363952 | 2687 | 2706 | 19166 | 19185 | TACAACAAAAGAACTGTAGT | 49 | 1142 |
| 1363971 | 1582 | 1601 | 18061 | 18080 | GGTAATAGAGAGACCAGAAT | 21 | 1143 |
| 1363996 | 2451 | 2470 | 18930 | 18949 | CTCTTAACACACCAAGATAA | 58 | 1144 |
| 1364006 | N/A | N/A | 15913 | 15932 | AAATGTACTTATTTTACCTC | 65 | 1145 |
| 1364054 | 1313 | 1332 | 17792 | 17811 | AGCTATGAAGCAAAATGACT | 41 | 1146 |
| 1364059 | 2424 | 2443 | 18903 | 18922 | AAGTAAAATCATTTTCCATT | 47 | 1147 |
| 1364082 | 2096 | 2115 | 18575 | 18594 | AATGAGCACCATTGTGAAGA | 44 | 1148 |
| 1364083 | 1647 | 1666 | 18126 | 18145 | AATAGGCAGATTTGGGCAAA | 36 | 1149 |
| 1364135 | N/A | N/A | 11875 | 11894 | CTCACTATATGCCCAGCATT | 66 | 1150 |
| 1364140 | 2479 | 2498 | 18958 | 18977 | GAGAAAATAACCTTTATGTT | 56 | 1151 |
| 1364160 | N/A | N/A | 4399 | 4418 | GCATCAAGCAAGCAGTTATT | 23 | 1152 |
| 1364161 | 2340 | 2359 | 18819 | 18838 | GGCAGAATACTTGTAGAAAA | 28 | 1153 |
| 1364217 | 2149 | 2168 | 18628 | 18647 | CAAATCAAGACCTTCAAATC | 68 | 1154 |
| 1364224 | 1173 | 1192 | 17652 | 17671 | GATGGGAGACGCAGCATTGT | 58 | 1155 |
| 1364227 | 1760 | 1779 | 18239 | 18258 | ATGCTGTAAGTAAGGTTGGC | 24 | 281 |
| 1364229 | 1689 | 1708 | 18168 | 18187 | GTGGGTGAAAGATCCTTGCT | 26 | 1156 |
| 1364242 | 1510 | 1529 | 17989 | 18008 | GAGGACCAAAGACATTCCTT | 49 | 1157 |
| 1364264 | 2252 | 2271 | 18731 | 18750 | AAAAAACAGTCATAATCAAA | 118 | 1158 |

TABLE 16

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
| --- | --- | --- | --- | --- | --- | --- | --- |
| 1362429 | 1820 | 1839 | 18299 | 18318 | TTCCCTAACGAGGTGTAAGG | 34 | 1159 |
| 1362430 | 863 | 882 | 14922 | 14941 | ACTGCCTATACTGGCAGAGG | 70 | 1160 |
| 1362465 | 2181 | 2200 | 18660 | 18679 | CTGGAATACATGAAATGTGC | 30 | 1161 |
| 1362490 | 1731 | 1750 | 18210 | 18229 | GCTTCAGTAGTCCATCGCCA | 15 | 201 |
| 1362492 | 2565 | 2584 | 19044 | 19063 | AAACTCTTTCTGCCTGTCCT | 26 | 1162 |
| 1362515 | 2370 | 2389 | 18849 | 18868 | ATTCAAATTCACCAAATCTG | 45 | 1163 |
| 1362526 | 2880 | 2899 | 19359 | 19378 | TACGGATTACTTCACTGTCC | 27 | 58 |
| 1362676 | 2478 | 2497 | 18957 | 18976 | AGAAAATAACCTTTATGTTA | 83 | 1164 |

TABLE 16-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362682 | N/A | N/A | 8412 | 8431 | TTGTATACAAACTCCCAAAA | 69 | 1165 |
| 1362701 | 3010 | 3029 | 19489 | 19508 | CAGAAATGAAGGAAACACTT | 34 | 1166 |
| 1362725 | N/A | N/A | 4382 | 4401 | ATTTTGTACATCTGAGGGCT | 72 | 1167 |
| 1362726 | 2397 | 2416 | 18876 | 18895 | AAGAACGATCAGATTACTCA | 34 | 1168 |
| 1362770 | 1688 | 1707 | 18167 | 18186 | TGGGTGAAAGATCCTTGCTT | 32 | 1169 |
| 1362796 | N/A | N/A | 17246 | 17265 | TGATCTAGCACTGAGTTTTC | 69 | 1170 |
| 1362801 | N/A | N/A | 6275 | 6294 | GTCTGGTTACCAGGGTAACA | 28 | 1171 |
| 1362814 | N/A | N/A | 16992 | 17011 | TTCAGATAAATCACTTCACC | 62 | 1172 |
| 1362864 | 2035 | 2054 | 18514 | 18533 | AGACATGCTATCCAAAGAGT | 53 | 1173 |
| 1362909 | N/A | N/A | 14041 | 14060 | GTCCAGTTAGATCCACTCTT | 13 | 167 |
| 1362976 | N/A | N/A | 11326 | 11345 | GCTACAAACAGACTTTATAC | 69 | 1174 |
| 1362984 | N/A | N/A | 10139 | 10158 | TGTTGTTCTCAGAAAACATT | 70 | 1175 |
| 1362986 | 1458 | 1477 | 17937 | 17956 | TTTCCATCAGTGGAAGTACC | 66 | 1176 |
| 1362994 | 1204 | 1223 | 17683 | 17702 | GGGCCAGTTGGTGGCAAAGG | 36 | 1177 |
| 1362997 | N/A | N/A | 8889 | 8908 | AGTTTGATTCAAGAAGGCTG | 52 | 1178 |
| 1362999 | 2095 | 2114 | 18574 | 18593 | ATGAGCACCATTGTGAAGAT | 32 | 1179 |
| 1363005 | N/A | N/A | 9425 | 9444 | TTCTGAGTCACCAGATCATA | 78 | 1180 |
| 1363007 | 2517 | 2536 | 18996 | 19015 | CTGATGACTGGTGCATTCTG | 24 | 1181 |
| 1363009 | N/A | N/A | 12528 | 12547 | CCAGTAGGTAGCTCATGCCA | 93 | 1182 |
| 1363029 | 1312 | 1331 | 17791 | 17810 | GCTATGAAGCAAAATGACTA | 39 | 1183 |
| 1363052 | N/A | N/A | 16764 | 16783 | CCAGGCTATAGCAAGTCATG | 33 | 1184 |
| 1363060 | 2782 | 2801 | 19261 | 19280 | TTTGAAAACAAGTATCAAGT | 60 | 1185 |
| 1363068 | N/A | N/A | 13455 | 13474 | GGCATGGATCCTGCATTAAC | 73 | 1186 |
| 1363083 | 1423 | 1442 | 17902 | 17921 | ACTTTCTGATCCTCAGGAGA | 87 | 1187 |
| 1363121 | 1732 | 1751 | 18211 | 18230 | GGCTTCAGTAGTCCATCGCC | 22 | 279 |
| 1363127 | N/A | N/A | 10862 | 10881 | TACTCAGCAAATGTACTGGG | 46 | 1188 |
| 1363139 | 3077 | 3096 | 19556 | 19575 | AATACACTTTGTAAGATAAG | 70 | 1189 |
| 1363154 | 1270 | 1289 | 17749 | 17768 | AGTCCAAAGAGAGACCTTAA | 70 | 1190 |
| 1363196 | 2819 | 2838 | 19298 | 19317 | CCTTCTATGCAGCCTGGAAG | 13 | 1191 |
| 1363204 | 1072 | 1091 | 17551 | 17570 | TTAAGGACGGCAAAGTTGTA | 78 | 1192 |
| 1363227 | 2928 | 2947 | 19407 | 19426 | GAAGGGTTGGTTATTTGTTA | 55 | 1193 |
| 1363245 | 1392 | 1411 | 17871 | 17890 | TCAATTAGAGCCTCCATTCC | 64 | 1194 |
| 1363247 | 2314 | 2333 | 18793 | 18812 | TAGATTCAACTAGCCAATTT | 71 | 1195 |
| 1363253 | 1646 | 1665 | 18125 | 18144 | ATAGGCAGATTTGGGCAAAC | 42 | 1196 |
| 1363337 | 1542 | 1561 | 18021 | 18040 | AAGAGAATATATTTGGCCCC | 62 | 1197 |
| 1363391 | 2285 | 2304 | 18764 | 18783 | TTTGTGATGCTTAATGTCCA | 20 | 1198 |

TABLE 16-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363422 | 2067 | 2086 | 18546 | 18565 | GGCCAGAGTACACAACTAAT | 32 | 1199 |
| 1363429 | 1758 | 1777 | 18237 | 18256 | GCTGTAAGTAAGGTTGGCTG | 15 | 125 |
| 1363431 | 1993 | 2012 | 18472 | 18491 | GGGCCATCTCAGGTTACACC | 17 | 1200 |
| 1363452 | 3036 | 3055 | 19515 | 19534 | TGTGTGTTAAAATTGCAATT | 20 | 1201 |
| 1363479 | 2423 | 2442 | 18902 | 18921 | AGTAAAATCATTTTCCATTA | 44 | 1202 |
| 1363501 | 2251 | 2270 | 18730 | 18749 | AAAAACAGTCATAATCAAAG | 77 | 1203 |
| 1363523 | 2148 | 2167 | 18627 | 18646 | AAATCAAGACCTTCAAATCA | 71 | 1204 |
| 1363524 | 2450 | 2469 | 18929 | 18948 | TCTTAACACACCAAGATAAC | 79 | 1205 |
| 1363531 | 2609 | 2628 | 19088 | 19107 | ACAAAAACAGGAAAAGACTG | 91 | 1206 |
| 1363566 | 1900 | 1919 | 18379 | 18398 | CCTTGGAAACCACAGGGTTG | 46 | 1207 |
| 1363580 | 1861 | 1880 | 18340 | 18359 | GGAGAAGGGAGTGAGAAGAT | 56 | 1208 |
| 1363622 | 1172 | 1191 | 17651 | 17670 | ATGGGAGACGCAGCATTGTA | 56 | 1209 |
| 1363635 | 2737 | 2756 | 19216 | 19235 | CCTTAAATATTGCTGAAACC | 44 | 1210 |
| 1363647 | N/A | N/A | 5036 | 5055 | CCTGAACACATGCTTCAAAG | 73 | 1211 |
| 1363729 | N/A | N/A | 5727 | 5746 | GAAAACTCAGTGGCTGCTCC | 41 | 1212 |
| 1363733 | N/A | N/A | 9155 | 9174 | GGGCATTTAAGTTCAGCAGA | 45 | 1213 |
| 1363768 | 1342 | 1361 | 17821 | 17840 | TTAGGCATTTCCCATTTCTA | 40 | 1214 |
| 1363770 | N/A | N/A | 11874 | 11893 | TCACTATATGCCCAGCATTA | 103 | 1215 |
| 1363794 | N/A | N/A | 7270 | 7289 | GAGACAATAGTAGCCATACC | 68 | 1216 |
| 1363840 | 1581 | 1600 | 18060 | 18079 | GTAATAGAGAGACCAGAATG | 55 | 1217 |
| 1363887 | 1961 | 1980 | 18440 | 18459 | CAACTGCTGCTCCTCAGGCC | 23 | 1218 |
| 1363903 | N/A | N/A | 15907 | 15926 | ACTTATTTTACCTCTCATTT | 57 | 1219 |
| 1363915 | N/A | N/A | 7700 | 7719 | CCTGCCTATAATCTTGTCTT | 72 | 1220 |
| 1363935 | 2121 | 2140 | 18600 | 18619 | TGACTGAATGGATAATACCC | 25 | 1221 |
| 1363964 | N/A | N/A | 6763 | 6782 | GTTTGGAGACTATATTTCCC | 67 | 1222 |
| 1363994 | 1232 | 1251 | 17711 | 17730 | TTCTTGTTACACTCATCAAG | 45 | 1223 |
| 1364048 | N/A | N/A | 16470 | 16489 | GGAAGCAGTCTACCTTCTTG | 52 | 1224 |
| 1364063 | N/A | N/A | 5302 | 5321 | TGTATACACATTATTGTCTA | 71 | 1225 |
| 1364105 | 2686 | 2705 | 19165 | 19184 | ACAACAAAGAACTGTAGTA | 61 | 1226 |
| 1364113 | N/A | N/A | 5905 | 5924 | TGAAGGTTGGCTCAGACAAC | 51 | 1227 |
| 1364115 | N/A | N/A | 15606 | 15625 | GGCTAATTCAAAATCCAGCA | 20 | 1228 |
| 1364147 | 2222 | 2241 | 18701 | 18720 | CCAGACATTTCTGATGCAAC | 13 | 1229 |
| 1364177 | 1509 | 1528 | 17988 | 18007 | AGGACCAAAGACATTCCTTC | 35 | 1230 |
| 1364179 | 2656 | 2675 | 19135 | 19154 | CTTCAATTAAACCAATCAG | 53 | 1231 |
| 1364261 | 2338 | 2357 | 18817 | 18836 | CAGAATACTTGTAGAAAATC | 78 | 1232 |

TABLE 17

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362451 | N/A | N/A | 15605 | 15624 | GCTAATTCAAAATCCAGCAA | 39 | 1233 |
| 1362466 | N/A | N/A | 8393 | 8412 | ACAAGTCTAATCAATCTGTG | 102 | 1234 |
| 1362476 | N/A | N/A | 16991 | 17010 | TCAGATAAATCACTTCACCC | 44 | 1235 |
| 1362490 | 1731 | 1750 | 18210 | 18229 | GCTTCAGTAGTCCATCGCCA | 16 | 201 |
| 1362509 | N/A | N/A | 11863 | 11882 | CCAGCATTATGCTGGGTGTT | 102 | 1236 |
| 1362531 | 2422 | 2441 | 18901 | 18920 | GTAAAATCATTTTCCATTAG | 61 | 1237 |
| 1362571 | 1818 | 1837 | 18297 | 18316 | CCCTAACGAGGTGTAAGGCC | 32 | 286 |
| 1362602 | 3035 | 3054 | 19514 | 19533 | GTGTGTTAAAATTGCAATTC | 14 | 1238 |
| 1362615 | 1421 | 1440 | 17900 | 17919 | TTTCTGATCCTCAGGAGATG | 87 | 1239 |
| 1362624 | 2879 | 2898 | 19358 | 19377 | ACGGATTACTTCACTGTCCT | 27 | 291 |
| 1362653 | 862 | 881 | 14921 | 14940 | CTGCCTATACTGGCAGAGGT | 72 | 1240 |
| 1362660 | 2917 | 2936 | 19396 | 19415 | TATTTGTTATGTTATTAAAT | 126 | 1241 |
| 1362686 | N/A | N/A | 11317 | 11336 | AGACTTTATACAAAGTCAGC | 101 | 1242 |
| 1362696 | 2221 | 2240 | 18700 | 18719 | CAGACATTTCTGATGCAACC | 28 | 1243 |
| 1362776 | 2147 | 2166 | 18626 | 18645 | AATCAAGACCTTCAAATCAC | 79 | 1244 |
| 1362794 | N/A | N/A | 5033 | 5052 | GAACACATGCTTCAAAGTGT | 45 | 1245 |
| 1362823 | 2685 | 2704 | 19164 | 19183 | CAACAAAGAACTGTAGTAC | 57 | 1246 |
| 1362838 | 1269 | 1288 | 17748 | 17767 | GTCCAAAGAGAGACCTTAAT | 61 | 1247 |
| 1362846 | 2553 | 2572 | 19032 | 19051 | CCTGTCCTTTTTCCTGGAAG | 41 | 1248 |
| 1362875 | 3009 | 3028 | 19488 | 19507 | AGAAATGAAGGAAACACTTT | 87 | 1249 |
| 1362885 | 1958 | 1977 | 18437 | 18456 | CTGCTGCTCCTCAGGCCAGT | 31 | 1250 |
| 1362928 | 1340 | 1359 | 17819 | 17838 | AGGCATTTCCCATTTCTAGC | 18 | 1251 |
| 1362940 | 2449 | 2468 | 18928 | 18947 | CTTAACACACCAAGATAACA | 66 | 1252 |
| 1362945 | 1645 | 1664 | 18124 | 18143 | TAGGCAGATTTGGGCAAACG | 39 | 1253 |
| 1362950 | 1508 | 1527 | 17987 | 18006 | GGACCAAAGACATTCCTTCT | 47 | 1254 |
| 1363030 | 1860 | 1879 | 18339 | 18358 | GAGAAGGGAGTGAGAAGATG | 70 | 1255 |
| 1363038 | N/A | N/A | 7655 | 7674 | CACTTATATACCACATTCAA | 79 | 1256 |
| 1363063 | N/A | N/A | 5724 | 5743 | AACTCAGTGGCTGCTCCATC | 89 | 1257 |
| 1363079 | 2066 | 2085 | 18545 | 18564 | GCCAGAGTACACAACTAATT | 23 | 1258 |
| 1363092 | 1171 | 1190 | 17650 | 17669 | TGGGAGACGCAGCATTGTAG | 57 | 1259 |
| 1363121 | 1732 | 1751 | 18211 | 18230 | GGCTTCAGTAGTCCATCGCC | 13 | 279 |
| 1363142 | N/A | N/A | 10856 | 10875 | GCAAATGTACTGGGAAGCTG | 61 | 1260 |
| 1363212 | 2736 | 2755 | 19215 | 19234 | CTTAAATATTGCTGAAACCA | 62 | 1261 |
| 1363252 | N/A | N/A | 9422 | 9441 | TGAGTCACCAGATCATAGCC | 77 | 1262 |
| 1363281 | 1231 | 1250 | 17710 | 17729 | TCTTGTTACACTCATCAAGT | 56 | 1263 |
| 1363289 | 1311 | 1330 | 17790 | 17809 | CTATGAAGCAAAATGACTAA | 84 | 1264 |

TABLE 17-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363307 | N/A | N/A | 4251 | 4270 | GGACACATGACCACATCCAT | 38 | 1265 |
| 1363309 | N/A | N/A | 15889 | 15908 | TTGAGATAAAGAAGTTCCAA | 57 | 1266 |
| 1363319 | N/A | N/A | 9153 | 9172 | GCATTTAAGTTCAGCAGAAG | 71 | 1267 |
| 1363349 | N/A | N/A | 7268 | 7287 | GACAATAGTAGCCATACCTT | 76 | 1268 |
| 1363405 | 2477 | 2496 | 18956 | 18975 | GAAAATAACCTTTATGTTAA | 67 | 1269 |
| 1363428 | N/A | N/A | 6757 | 6776 | AGACTATATTTCCCCTCCCA | 78 | 1270 |
| 1363446 | N/A | N/A | 13454 | 13473 | GCATGGATCCTGCATTAACA | 93 | 1271 |
| 1363464 | 1203 | 1222 | 17682 | 17701 | GGCCAGTTGGTGGCAAAGGC | 46 | 1272 |
| 1363492 | N/A | N/A | 16466 | 16485 | GCAGTCTACCTTCTTGCCTT | 58 | 1273 |
| 1363500 | 3074 | 3093 | 19553 | 19572 | ACACTTTGTAAGATAAGTTT | 29 | 1274 |
| 1363536 | 1899 | 1918 | 18378 | 18397 | CTTGGAAACCACAGGGTTGT | 82 | 1275 |
| 1363553 | 1456 | 1475 | 17935 | 17954 | TCCATCAGTGGAAGTACCCT | 27 | 1276 |
| 1363581 | 2516 | 2535 | 18995 | 19014 | TGATGACTGGTGCATTCTGT | 34 | 1277 |
| 1363607 | N/A | N/A | 16763 | 16782 | CAGGCTATAGCAAGTCATGT | 30 | 1278 |
| 1363674 | 2369 | 2388 | 18848 | 18867 | TTCAAATTCACCAAATCTGT | 43 | 1279 |
| 1363698 | N/A | N/A | 10136 | 10155 | TGTTCTCAGAAAACATTCCA | 48 | 1280 |
| 1363703 | 2180 | 2199 | 18659 | 18678 | TGGAATACATGAAATGTGCA | 38 | 1281 |
| 1363718 | 2250 | 2269 | 18729 | 18748 | AAAACAGTCATAATCAAAGA | 70 | 1282 |
| 1363728 | N/A | N/A | 6274 | 6293 | TCTGGTTACCAGGGTAACAG | 43 | 1283 |
| 1363782 | 1391 | 1410 | 17870 | 17889 | CAATTAGAGCCTCCATTCCT | 75 | 1284 |
| 1363786 | 2313 | 2332 | 18792 | 18811 | AGATTCAACTAGCCAATTTT | 61 | 1285 |
| 1363789 | 2034 | 2053 | 18513 | 18532 | GACATGCTATCCAAAGAGTT | 48 | 1286 |
| 1363803 | 1070 | 1089 | 17549 | 17568 | AAGGACGGCAAAGTTGTAAG | 37 | 1287 |
| 1363804 | N/A | N/A | 5901 | 5920 | GGTTGGCTCAGACAACTTCT | 44 | 1288 |
| 1363816 | 2094 | 2113 | 18573 | 18592 | TGAGCACCATTGTGAAGATA | 51 | 1289 |
| 1363857 | 1687 | 1706 | 18166 | 18185 | GGGTGAAAGATCCTTGCTTT | 52 | 1290 |
| 1363871 | N/A | N/A | 8854 | 8873 | GAGAAGTTCCTTGGCTCTCT | 56 | 1291 |
| 1363875 | 1541 | 1560 | 18020 | 18039 | AGAGAATATATTTGGCCCCT | 52 | 1292 |
| 1363889 | 2282 | 2301 | 18761 | 18780 | GTGATGCTTAATGTCCAATT | 20 | 1293 |
| 1363946 | 2655 | 2674 | 19134 | 19153 | TTCAATTAAAACCAATCAGA | 75 | 1294 |
| 1363975 | 1991 | 2010 | 18470 | 18489 | GCCATCTCAGGTTACACCAT | 25 | 1295 |
| 1364016 | N/A | N/A | 13995 | 14014 | GGGATACCAACAGATGGCTT | 43 | 1296 |
| 1364017 | N/A | N/A | 17242 | 17261 | CTAGCACTGAGTTTTCCTCA | 49 | 1297 |
| 1364020 | 1580 | 1599 | 18059 | 18078 | TAATAGAGAGACCAGAATGA | 88 | 1298 |
| 1364021 | 2602 | 2621 | 19081 | 19100 | CAGGAAAAGACTGAAATCTG | 52 | 1299 |
| 1364061 | 1757 | 1776 | 18236 | 18255 | CTGTAAGTAAGGTTGGCTGA | 38 | 1300 |

TABLE 17-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1364085 | N/A | N/A | 5301 | 5320 | GTATACACATTATTGTCTAA | 53 | 1301 |
| 1364116 | 2120 | 2139 | 18599 | 18618 | GACTGAATGGATAATACCCC | 20 | 211 |
| 1364118 | 2781 | 2800 | 19260 | 19279 | TTGAAAACAAGTATCAAGTG | 39 | 1302 |
| 1364124 | 2818 | 2837 | 19297 | 19316 | CTTCTATGCAGCCTGGAAGC | 62 | 1303 |
| 1364165 | 2337 | 2356 | 18816 | 18835 | AGAATACTTGTAGAAAATCC | 70 | 1304 |
| 1364166 | N/A | N/A | 12527 | 12546 | CAGTAGGTAGCTCATGCCAC | 90 | 1305 |
| 1364230 | 2396 | 2415 | 18875 | 18894 | AGAACGATCAGATTACTCAA | 36 | 1306 |

TABLE 18

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362454 | 2684 | 2703 | 19163 | 19182 | AACAAAAGAACTGTAGTACA | 52 | 1307 |
| 1362473 | 2179 | 2198 | 18658 | 18677 | GGAATACATGAAATGTGCAT | 8 | 1308 |
| 1362490 | 1731 | 1750 | 18210 | 18229 | GCTTCAGTAGTCCATCGCCA | 15 | 201 |
| 1362503 | N/A | N/A | 10840 | 10859 | GCTGCTATTTTGAATAAGC | 24 | 1309 |
| 1362517 | 1168 | 1187 | 17647 | 17666 | GAGACGCAGCATTGTAGGCT | 9 | 276 |
| 1362543 | N/A | N/A | 5898 | 5917 | TGGCTCAGACAACTTCTAAA | 36 | 1310 |
| 1362551 | N/A | N/A | 17239 | 17258 | GCACTGAGTTTTCCTCAGGG | 23 | 1311 |
| 1362593 | 1418 | 1437 | 17897 | 17916 | CTGATCCTCAGGAGATGCTT | 26 | 1312 |
| 1362609 | 2735 | 2754 | 19214 | 19233 | TTAAATATTGCTGAAACCAC | 43 | 1313 |
| 1362610 | 2312 | 2331 | 18791 | 18810 | GATTCAACTAGCCAATTTTT | 48 | 1314 |
| 1362656 | N/A | N/A | 9142 | 9161 | CAGCAGAAGTGAAGAATCTC | 54 | 1315 |
| 1362657 | N/A | N/A | 6756 | 6775 | GACTATATTTCCCCTCCCAC | 81 | 1316 |
| 1362662 | N/A | N/A | 5298 | 5317 | TACACATTATTGTCTAATAG | 66 | 1317 |
| 1362697 | 1817 | 1836 | 18296 | 18315 | CCTAACGAGGTGTAAGGCCA | 23 | 1318 |
| 1362709 | 1507 | 1526 | 17986 | 18005 | GACCAAAGACATTCCTTCTC | 37 | 1319 |
| 1362724 | 1955 | 1974 | 18434 | 18453 | CTGCTCCTCAGGCCAGTCTG | 17 | 1320 |
| 1362733 | 2421 | 2440 | 18900 | 18919 | TAAAATCATTTTCCATTAGC | 54 | 1321 |
| 1362752 | 2654 | 2673 | 19133 | 19152 | TCAATTAAAACCAATCAGAC | 53 | 1322 |
| 1362774 | 1644 | 1663 | 18123 | 18142 | AGGCAGATTTGGGCAAACGC | 15 | 1323 |
| 1362795 | 2033 | 2052 | 18512 | 18531 | ACATGCTATCCAAAGAGTTA | 47 | 1324 |
| 1362797 | 1310 | 1329 | 17789 | 17808 | TATGAAGCAAAATGACTAAA | 82 | 1325 |
| 1362805 | 2515 | 2534 | 18994 | 19013 | GATGACTGGTGCATTCTGTT | 16 | 212 |
| 1362819 | 3073 | 3092 | 19552 | 19571 | CACTTTGTAAGATAAGTTTC | 28 | 1326 |

TABLE 18-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362873 | 1390 | 1409 | 17869 | 17888 | AATTAGAGCCTCCATTCCTT | 49 | 1327 |
| 1362890 | 2448 | 2467 | 18927 | 18946 | TTAACACACCAAGATAACAT | 56 | 1328 |
| 1362897 | 1268 | 1287 | 17747 | 17766 | TCCAAAGAGAGACCTTAATC | 72 | 1329 |
| 1362905 | N/A | N/A | 10135 | 10154 | GTTCTCAGAAAACATTCCAG | 39 | 1330 |
| 1362974 | N/A | N/A | 13446 | 13465 | CCTGCATTAACAGGTAGACA | 83 | 1331 |
| 1363045 | 2915 | 2934 | 19394 | 19413 | TTTGTTATGTTATTAAATCA | 80 | 1332 |
| 1363049 | N/A | N/A | 16458 | 16477 | CCTTCTTGCCTTTCAGAATA | 60 | 1333 |
| 1363107 | N/A | N/A | 11316 | 11335 | GACTTTATACAAAGTCAGCA | 71 | 1334 |
| 1363117 | N/A | N/A | 4961 | 4980 | ATTGCAAATTGATCTCTGTG | 37 | 1335 |
| 1363118 | 2065 | 2084 | 18544 | 18563 | CCAGAGTACACAACTAATTA | 19 | 1336 |
| 1363121 | 1732 | 1751 | 18211 | 18230 | GGCTTCAGTAGTCCATCGCC | 13 | 279 |
| 1363130 | 1756 | 1775 | 18235 | 18254 | TGTAAGTAAGGTTGGCTGAG | 52 | 1337 |
| 1363175 | 1455 | 1474 | 17934 | 17953 | CCATCAGTGGAAGTACCCTT | 26 | 1338 |
| 1363198 | 1202 | 1221 | 17681 | 17700 | GCCAGTTGGTGGCAAAGGCA | 37 | 1339 |
| 1363205 | N/A | N/A | 16761 | 16780 | GGCTATAGCAAGTCATGTTT | 30 | 1340 |
| 1363268 | 3034 | 3053 | 19513 | 19532 | TGTGTTAAAATTGCAATTCT | 27 | 1341 |
| 1363329 | N/A | N/A | 4250 | 4269 | GACACATGACCCACATCCATC | 52 | 1342 |
| 1363374 | 2091 | 2110 | 18570 | 18589 | GCACCATTGTGAAGATATGA | 21 | 1343 |
| 1363399 | 1230 | 1249 | 17709 | 17728 | CTTGTTACACTCATCAAGTA | 44 | 1344 |
| 1363404 | 804 | 823 | 14863 | 14882 | TGTTGAAGTAAATGTACACA | 65 | 1345 |
| 1363407 | 1068 | 1087 | 17547 | 17566 | GGACGGCAAAGTTGTAAGTG | 26 | 1346 |
| 1363414 | 2601 | 2620 | 19080 | 19099 | AGGAAAAGACTGAAATCTGG | 34 | 1347 |
| 1363435 | 1859 | 1878 | 18338 | 18357 | AGAAGGGAGTGAGAAGATGC | 45 | 1348 |
| 1363442 | 1897 | 1916 | 18376 | 18395 | TGGAAACCACAGGGTTGTCA | 34 | 1349 |
| 1363458 | 2249 | 2268 | 18728 | 18747 | AAACAGTCATAATCAAAGAA | 66 | 1350 |
| 1363470 | 2779 | 2798 | 19258 | 19277 | GAAAACAAGTATCAAGTGTC | 32 | 1351 |
| 1363484 | 3008 | 3027 | 19487 | 19506 | GAAATGAAGGAAACACTTTC | 70 | 1352 |
| 1363499 | 2877 | 2896 | 19356 | 19375 | GGATTACTTCACTGTCCTTT | 19 | 1353 |
| 1363533 | 1990 | 2009 | 18469 | 18488 | CCATCTCAGGTTACACCATT | 25 | 1354 |
| 1363549 | N/A | N/A | 15852 | 15871 | AAACCTATGAATGCCTCTG | 60 | 1355 |
| 1363564 | N/A | N/A | 12423 | 12442 | TTGGCTTTCAGCATGTGAGA | 46 | 1356 |
| 1363585 | 1338 | 1357 | 17817 | 17836 | GCATTTCCCATTTCTAGCAG | 35 | 1357 |
| 1363591 | 2281 | 2300 | 18760 | 18779 | TGATGCTTAATGTCCAATTT | 14 | 1358 |
| 1363662 | N/A | N/A | 7267 | 7286 | ACAATAGTAGCCATACCTTG | 80 | 1359 |
| 1363673 | 2119 | 2138 | 18598 | 18617 | ACTGAATGGATAATACCCCA | 18 | 1360 |
| 1363683 | 2336 | 2355 | 18815 | 18834 | GAATACTTGTAGAAAATCCC | 28 | 1361 |

TABLE 18-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363750 | 1685 | 1704 | 18164 | 18183 | GTGAAAGATCCTTGCTTTGA | 82 | 1362 |
| 1363765 | 2552 | 2571 | 19031 | 19050 | CTGTCCTTTTCCTGGAAGC | 25 | 1363 |
| 1363778 | 2146 | 2165 | 18625 | 18644 | ATCAAGACCTTCAAATCACC | 51 | 1364 |
| 1363788 | 2395 | 2414 | 18874 | 18893 | GAACGATCAGATTACTCAAA | 21 | 1365 |
| 1363819 | N/A | N/A | 8391 | 8410 | AAGTCTAATCAATCTGTGAT | 70 | 1366 |
| 1363822 | 1540 | 1559 | 18019 | 18038 | GAGAATATATTTGGCCCCTA | 47 | 1367 |
| 1363912 | N/A | N/A | 16985 | 17004 | AAATCACTTCACCCTTCAGT | 102 | 1368 |
| 1363916 | 2475 | 2494 | 18954 | 18973 | AAATAACCTTTATGTTAAAC | 81 | 1369 |
| 1363943 | N/A | N/A | 13994 | 14013 | GGATACCAACAGATGGCTTA | 53 | 1370 |
| 1363990 | N/A | N/A | 15538 | 15557 | ATGGTATTAGCTACTCCCTT | 26 | 1371 |
| 1364069 | 2368 | 2387 | 18847 | 18866 | TCAAATTCACCAAATCTGTT | 30 | 1372 |
| 1364107 | 2219 | 2238 | 18698 | 18717 | GACATTTCTGATGCAACCCC | 15 | 1373 |
| 1364183 | N/A | N/A | 5709 | 5728 | CCATCATATGTACCTGGCCC | 48 | 1374 |
| 1364216 | 2816 | 2835 | 19295 | 19314 | TCTATGCAGCCTGGAAGCTT | 35 | 1375 |
| 1364220 | N/A | N/A | 6271 | 6290 | GGTTACCAGGGTAACAGCCA | 39 | 1376 |
| 1364228 | N/A | N/A | 11799 | 11818 | GAGTCTTTAATTTCCTGAGG | 50 | 1377 |
| 1364238 | N/A | N/A | 9418 | 9437 | TCACCAGATCATAGCCTTTC | 43 | 1378 |
| 1364250 | N/A | N/A | 7654 | 7673 | ACTTATATACCACATTCAAG | 88 | 1379 |
| 1364256 | 1579 | 1598 | 18058 | 18077 | AATAGAGAGACCAGAATGAA | 85 | 1380 |
| 1364271 | N/A | N/A | 8838 | 8857 | CTCTCAAGAGACATTCTCAC | 70 | 1381 |

TABLE 19

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362435 | 1578 | 1597 | 18057 | 18076 | ATAGAGAGACCAGAATGAAT | 81 | 1382 |
| 1362461 | 2683 | 2702 | 19162 | 19181 | ACAAAAGAACTGTAGTACAA | 36 | 1383 |
| 1362474 | N/A | N/A | 9141 | 9160 | AGCAGAAGTGAAGAATCTCA | 55 | 1384 |
| 1362478 | N/A | N/A | 16950 | 16969 | TCTGCACAATGAGCACACTA | 41 | 1385 |
| 1362490 | 1731 | 1750 | 18210 | 18229 | GCTTCAGTAGTCCATCGCCA | 15 | 201 |
| 1362493 | N/A | N/A | 5264 | 5283 | ATTTACAGTTGTTATAGATC | 44 | 1386 |
| 1362512 | 2117 | 2136 | 18596 | 18615 | TGAATGGATAATACCCCATG | 33 | 1387 |
| 1362532 | 1896 | 1915 | 18375 | 18394 | GGAAACCACAGGGTTGTCAT | 26 | 1388 |
| 1362541 | N/A | N/A | 4131 | 4150 | ATCTAACTGAATGTTAAGGA | 41 | 1389 |

TABLE 19-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362544 | 1755 | 1774 | 18234 | 18253 | GTAAGTAAGGTTGGCTGAGT | 32 | 1390 |
| 1362553 | 3072 | 3091 | 19551 | 19570 | ACTTTGTAAGATAAGTTTCT | 39 | 1391 |
| 1362555 | N/A | N/A | 10134 | 10153 | TTCTCAGAAAACATTCCAGA | 62 | 1392 |
| 1362562 | 2734 | 2753 | 19213 | 19232 | TAAATATTGCTGAAACCACT | 36 | 1393 |
| 1362583 | N/A | N/A | 7260 | 7279 | TAGCCATACCTTGTTCCTCA | 39 | 1394 |
| 1362619 | 2064 | 2083 | 18543 | 18562 | CAGAGTACACAACTAATTAA | 45 | 1395 |
| 1362640 | 803 | 822 | 14862 | 14881 | GTTGAAGTAAATGTACACAG | 62 | 1396 |
| 1362655 | 1228 | 1247 | 17707 | 17726 | TGTTACACTCATCAAGTAAG | 32 | 1397 |
| 1362689 | 2280 | 2299 | 18759 | 18778 | GATGCTTAATGTCCAATTTT | 17 | 1398 |
| 1362702 | N/A | N/A | 4959 | 4978 | TGCAAATTGATCTCTGTGGA | 29 | 1399 |
| 1362716 | 2367 | 2386 | 18846 | 18865 | CAAATTCACCAAATCTGTTT | 56 | 1400 |
| 1362732 | N/A | N/A | 8835 | 8854 | TCAAGAGACATTCTCACATT | 82 | 1401 |
| 1362736 | 2032 | 2051 | 18511 | 18530 | CATGCTATCCAAAGAGTTAT | 41 | 1402 |
| 1362742 | N/A | N/A | 16690 | 16709 | AACCGTAATTTATGACTGCA | 26 | 1403 |
| 1362789 | 2600 | 2619 | 19079 | 19098 | GGAAAAGACTGAAATCTGGG | 24 | 1404 |
| 1362800 | 2653 | 2672 | 19132 | 19151 | CAATTAAAACCAATCAGACT | 74 | 1405 |
| 1362811 | 1506 | 1525 | 17985 | 18004 | ACCAAAGACATTCCTTCTCT | 45 | 1406 |
| 1362832 | 2420 | 2439 | 18899 | 18918 | AAAATCATTTTCCATTAGCT | 32 | 1407 |
| 1362883 | 1684 | 1703 | 18163 | 18182 | TGAAAGATCCTTGCTTTGAC | 88 | 1408 |
| 1362910 | N/A | N/A | 13993 | 14012 | GATACCAACAGATGGCTTAG | 52 | 1409 |
| 1362930 | 2311 | 2330 | 18790 | 18809 | ATTCAACTAGCCAATTTTTA | 66 | 1410 |
| 1362944 | N/A | N/A | 5706 | 5725 | TCATATGTACCTGGCCCAAG | 83 | 1411 |
| 1362958 | N/A | N/A | 9417 | 9436 | CACCAGATCATAGCCTTTCT | 37 | 1412 |
| 1362977 | 1816 | 1835 | 18295 | 18314 | CTAACGAGGTGTAAGGCCAG | 44 | 1413 |
| 1362981 | N/A | N/A | 16455 | 16474 | TCTTGCCTTTCAGAATAGCT | 37 | 1414 |
| 1362991 | N/A | N/A | 7650 | 7669 | ATATACCACATTCAAGTGCT | 69 | 1415 |
| 1362992 | N/A | N/A | 6270 | 6289 | GTTACCAGGGTAACAGCCAC | 41 | 1416 |
| 1363040 | 2335 | 2354 | 18814 | 18833 | AATACTTGTAGAAAATCCCA | 30 | 1417 |
| 1363042 | N/A | N/A | 8362 | 8381 | TCCAACTTTAAGCCCTTCTC | 51 | 1418 |
| 1363078 | 1538 | 1557 | 18017 | 18036 | GAATATATTTGGCCCCTATA | 91 | 1419 |
| 1363085 | 1267 | 1286 | 17746 | 17765 | CCAAAGAGAGACCTTAATCA | 57 | 1420 |
| 1363096 | 2172 | 2191 | 18651 | 18670 | ATGAAATGTGCATCATTCTA | 44 | 1421 |
| 1363121 | 1732 | 1751 | 18211 | 18230 | GGCTTCAGTAGTCCATCGCC | 17 | 279 |
| 1363128 | 1989 | 2008 | 18468 | 18487 | CATCTCAGGTTACACCATTA | 37 | 1422 |
| 1363191 | 1628 | 1647 | 18107 | 18126 | ACGCTCTTATTGTTTTCTG | 15 | 1423 |
| 1363208 | 2248 | 2267 | 18727 | 18746 | AACAGTCATAATCAAAGAAT | 60 | 1424 |

TABLE 19-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363228 | 3007 | 3026 | 19486 | 19505 | AAATGAAGGAAACACTTTCA | 61 | 1425 |
| 1363301 | 1417 | 1436 | 17896 | 17915 | TGATCCTCAGGAGATGCTTG | 37 | 1426 |
| 1363313 | N/A | N/A | 6755 | 6774 | ACTATATTTCCCCTCCCACC | 89 | 1427 |
| 1363370 | 1309 | 1328 | 17788 | 17807 | ATGAAGCAAAATGACTAAAA | 70 | 1428 |
| 1363423 | 1067 | 1086 | 17546 | 17565 | GACGGCAAAGTTGTAAGTGG | 34 | 1429 |
| 1363433 | 1200 | 1219 | 17679 | 17698 | CAGTTGGTGGCAAAGGCAAA | 42 | 1430 |
| 1363544 | 1167 | 1186 | 17646 | 17665 | AGACGCAGCATTGTAGGCTG | 13 | 1431 |
| 1363573 | N/A | N/A | 13445 | 13464 | CTGCATTAACAGGTAGACAA | 83 | 1432 |
| 1363576 | 1337 | 1356 | 17816 | 17835 | CATTTCCCATTTCTAGCAGG | 54 | 1433 |
| 1363643 | 1454 | 1473 | 17933 | 17952 | CATCAGTGGAAGTACCCTTT | 49 | 1434 |
| 1363678 | 3033 | 3052 | 19512 | 19531 | GTGTTAAAATTGCAATTCTA | 19 | 1435 |
| 1363684 | N/A | N/A | 15510 | 15529 | ACCCAAATAACCCACTCACC | 91† | 1436 |
| 1363692 | 1858 | 1877 | 18337 | 18356 | GAAGGGAGTGAGAAGATGCT | 42 | 1437 |
| 1363697 | 2218 | 2237 | 18697 | 18716 | ACATTTCTGATGCAACCCCA | 34 | 1438 |
| 1363705 | 2393 | 2412 | 18872 | 18891 | ACGATCAGATTACTCAAATT | 24 | 1439 |
| 1363763 | 2815 | 2834 | 19294 | 19313 | CTATGCAGCCTGGAAGCTTA | 28 | 1440 |
| 1363824 | N/A | N/A | 5897 | 5916 | GGCTCAGACAACTTCTAAAG | 39 | 1441 |
| 1363833 | N/A | N/A | 15851 | 15870 | AAACCTATGAATGCCTCTGT | 69 | 1442 |
| 1363834 | 2090 | 2109 | 18569 | 18588 | CACCATTGTGAAGATATGAC | 23 | 1443 |
| 1363868 | N/A | N/A | 10837 | 10856 | GCTATTTTGAATAAGCAGG | 41 | 1444 |
| 1363949 | 2145 | 2164 | 18624 | 18643 | TCAAGACCTTCAAATCACCT | 49 | 1445 |
| 1363984 | 2513 | 2532 | 18992 | 19011 | TGACTGGTGCATTCTGTTAT | 30 | 1446 |
| 1363988 | 2474 | 2493 | 18953 | 18972 | AATAACCTTTATGTTAAACC | 54 | 1447 |
| 1364051 | N/A | N/A | 17220 | 17239 | GAAGTGAACAATATTTGGGC | 57 | 1448 |
| 1364055 | N/A | N/A | 11315 | 11334 | ACTTTATACAAAGTCAGCAA | 67 | 1449 |
| 1364090 | N/A | N/A | 12420 | 12439 | GCTTTCAGCATGTGAGATTG | 42 | 1450 |
| 1364094 | 1383 | 1402 | 17862 | 17881 | GCCTCCATTCCTTTGTGACT | 41 | 1451 |
| 1364095 | 2778 | 2797 | 19257 | 19276 | AAAACAAGTATCAAGTGTCT | 31 | 1452 |
| 1364197 | 1951 | 1970 | 18430 | 18449 | TCCTCAGGCCAGTCTGTTCT | 28 | 1453 |
| 1364198 | N/A | N/A | 11796 | 11815 | TCTTTAATTTCCTGAGGAAG | 92 | 1454 |
| 1364201 | 2549 | 2568 | 19028 | 19047 | TCCTTTTTCCTGGAAGCTTA | 21 | 1455 |
| 1364239 | 2447 | 2466 | 18926 | 18945 | TAACACACCAAGATAACATT | 44 | 1456 |
| 1364257 | 2876 | 2895 | 19355 | 19374 | GATTACTTCACTGTCCTTTA | 17 | 1457 |
| 1364258 | 2913 | 2932 | 19392 | 19411 | TGTTATGTTATTAAATCAAA | 72 | 1458 |

TABLE 20

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362436 | 2912 | 2931 | 19391 | 19410 | GTTATGTTATTAAATCAAAA | 73 | 1459 |
| 1362487 | N/A | N/A | 11309 | 11328 | TACAAAGTCAGCAAAGCATG | 110 | 1460 |
| 1362490 | 1731 | 1750 | 18210 | 18229 | GCTTCAGTAGTCCATCGCCA | 21 | 201 |
| 1362506 | 802 | 821 | 14861 | 14880 | TTGAAGTAAATGTACACAGG | 97 | 1461 |
| 1362542 | 2365 | 2384 | 18844 | 18863 | AATTCACCAAATCTGTTTCT | 57 | 1462 |
| 1362575 | 2276 | 2295 | 18755 | 18774 | CTTAATGTCCAATTTTCCTA | 35 | 1463 |
| 1362581 | N/A | N/A | 13443 | 13462 | GCATTAACAGGTAGACAAAC | 103 | 1464 |
| 1362618 | 1988 | 2007 | 18467 | 18486 | ATCTCAGGTTACACCATTAG | 60 | 1465 |
| 1362639 | 3071 | 3090 | 19550 | 19569 | CTTTGTAAGATAAGTTTCTA | 56 | 1466 |
| 1362688 | N/A | N/A | 4924 | 4943 | GCTACATTTGATAGGGAATA | 26 | 1467 |
| 1362705 | 2419 | 2438 | 18898 | 18917 | AAATCATTTTCCATTAGCTA | 48 | 1468 |
| 1362781 | N/A | N/A | 5888 | 5907 | AACTTCTAAAGTTCCTTCCA | 57 | 1469 |
| 1362783 | N/A | N/A | 6729 | 6748 | CCAGGGTTGAGGTTGTTATT | 74 | 1470 |
| 1362859 | 2652 | 2671 | 19131 | 19150 | AATTAAAACCAATCAGACTT | 75 | 1471 |
| 1362867 | N/A | N/A | 4094 | 4113 | GTGCCAAAACACGACTCATT | 28 | 1472 |
| 1362868 | N/A | N/A | 8361 | 8380 | CCAACTTTAAGCCCTTCTCA | 67 | 1473 |
| 1362888 | 2116 | 2135 | 18595 | 18614 | GAATGGATAATACCCCATGA | 34 | 1474 |
| 1362914 | 2446 | 2465 | 18925 | 18944 | AACACACCAAGATAACATTG | 34 | 1475 |
| 1362926 | 1626 | 1645 | 18105 | 18124 | GCTCTTATTGTTTTTCTGAC | 18 | 1476 |
| 1362948 | 1227 | 1246 | 17706 | 17725 | GTTACACTCATCAAGTAAGA | 19 | 1477 |
| 1362968 | 2392 | 2411 | 18871 | 18890 | CGATCAGATTACTCAAATTG | 47 | 1478 |
| 1363041 | N/A | N/A | 11765 | 11784 | TAGACCTAATATTTTCAACT | 69 | 1479 |
| 1363062 | 3032 | 3051 | 19511 | 19530 | TGTTAAAATTGCAATTCTAT | 49 | 1480 |
| 1363099 | N/A | N/A | 12413 | 12432 | GCATGTGAGATTGACCCAGA | 54 | 1481 |
| 1363121 | 1732 | 1751 | 18211 | 18230 | GGCTTCAGTAGTCCATCGCC | 11 | 279 |
| 1363122 | N/A | N/A | 13990 | 14009 | ACCAACAGATGGCTTAGAAA | 66 | 1482 |
| 1363150 | N/A | N/A | 16688 | 16707 | CCGTAATTTATGACTGCAAA | 31 | 1483 |
| 1363155 | N/A | N/A | 10123 | 10142 | CATTCCAGAAATTGATCTTC | 60 | 1484 |
| 1363190 | 2777 | 2796 | 19256 | 19275 | AAACAAGTATCAAGTGTCTT | 27 | 1485 |
| 1363202 | N/A | N/A | 8826 | 8845 | ATTCTCACATTTCCAGTCTA | 87 | 1486 |
| 1363318 | 2247 | 2266 | 18726 | 18745 | ACAGTCATAATCAAAGAATT | 45 | 1487 |
| 1363358 | 1266 | 1285 | 17745 | 17764 | CAAAGAGAGACCTTAATCAC | 70 | 1488 |
| 1363385 | 2334 | 2353 | 18813 | 18832 | ATACTTGTAGAAAATCCCAA | 34 | 1489 |
| 1363387 | 1537 | 1556 | 18016 | 18035 | AATATATTTGGCCCCTATAG | 88 | 1490 |
| 1363390 | 1451 | 1470 | 17930 | 17949 | CAGTGGAAGTACCCTTTGAG | 53 | 1491 |
| 1363412 | 1308 | 1327 | 17787 | 17806 | TGAAGCAAAATGACTAAAAG | 102 | 1492 |

TABLE 20-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363498 | 2310 | 2329 | 18789 | 18808 | TTCAACTAGCCAATTTTTAA | 69 | 1493 |
| 1363514 | 2473 | 2492 | 18952 | 18971 | ATAACCTTTATGTTAAACCT | 44 | 1494 |
| 1363520 | 1683 | 1702 | 18162 | 18181 | GAAAGATCCTTGCTTTGACC | 65 | 1495 |
| 1363530 | 2546 | 2565 | 19025 | 19044 | TTTTTCCTGGAAGCTTACCA | 41 | 1496 |
| 1363532 | 1334 | 1353 | 17813 | 17832 | TTCCCATTTCTAGCAGGAAC | 48 | 1497 |
| 1363541 | 1196 | 1215 | 17675 | 17694 | TGGTGGCAAAGGCAAAGAGT | 47 | 1498 |
| 1363557 | 1382 | 1401 | 17861 | 17880 | CCTCCATTCCTTTGTGACTT | 21 | 1499 |
| 1363596 | N/A | N/A | 17217 | 17236 | GTGAACAATATTTGGGCTTT | 23 | 1500 |
| 1363599 | 2731 | 2750 | 19210 | 19229 | ATATTGCTGAAACCACTTTG | 53 | 1501 |
| 1363602 | 2812 | 2831 | 19291 | 19310 | TGCAGCCTGGAAGCTTATCT | 18 | 1502 |
| 1363621 | 3006 | 3025 | 19485 | 19504 | AATGAAGGAAACACTTTCAG | 69 | 1503 |
| 1363628 | 2872 | 2891 | 19351 | 19370 | ACTTCACTGTCCTTTATCTT | 24 | 1504 |
| 1363653 | 2030 | 2049 | 18509 | 18528 | TGCTATCCAAAGAGTTATCT | 30 | 1505 |
| 1363671 | 1895 | 1914 | 18374 | 18393 | GAAACCACAGGGTTGTCATG | 38 | 1506 |
| 1363700 | 1754 | 1773 | 18233 | 18252 | TAAGTAAGGTTGGCTGAGTT | 63 | 1507 |
| 1363725 | 1164 | 1183 | 17643 | 17662 | CGCAGCATTGTAGGCTGTGT | 52 | 120 |
| 1363741 | N/A | N/A | 16948 | 16967 | TGCACAATGAGCACACTACA | 55 | 1508 |
| 1363757 | N/A | N/A | 15509 | 15528 | CCCAAATAACCCACTCACCT | 75† | 1509 |
| 1363773 | 2503 | 2522 | 18982 | 19001 | ATTCTGTTATGTGATCTATA | 27 | 1510 |
| 1363785 | N/A | N/A | 16449 | 16468 | CTTTCAGAATAGCTGTACCC | 82 | 1511 |
| 1363787 | N/A | N/A | 7649 | 7668 | TATACCACATTCAAGTGCTG | 84 | 1512 |
| 1363790 | 1815 | 1834 | 18294 | 18313 | TAACGAGGTGTAAGGCCAGA | 55 | 1513 |
| 1363796 | 2063 | 2082 | 18542 | 18561 | AGAGTACACAACTAATTAAC | 47 | 1514 |
| 1363820 | 2682 | 2701 | 19161 | 19180 | CAAAGAACTGTAGTACAAA | 85 | 1515 |
| 1363837 | N/A | N/A | 7253 | 7272 | ACCTTGTTCCTCAGGTCAGT | 49 | 1516 |
| 1363844 | N/A | N/A | 15848 | 15867 | CCTATGAATGCCTCTGTGCA | 67 | 1517 |
| 1363878 | 1066 | 1085 | 17545 | 17564 | ACGGCAAAGTTGTAAGTGGC | 27 | 1518 |
| 1363905 | N/A | N/A | 6262 | 6281 | GGTAACAGCCACTGTTCTCA | 64 | 1519 |
| 1363913 | 1857 | 1876 | 18336 | 18355 | AAGGGAGTGAGAAGATGCTG | 51 | 1520 |
| 1363919 | 2599 | 2618 | 19078 | 19097 | GAAAAGACTGAAATCTGGGA | 44 | 1521 |
| 1363924 | N/A | N/A | 5263 | 5282 | TTTACAGTTGTTATAGATCT | 53 | 1522 |
| 1363954 | 1505 | 1524 | 17984 | 18003 | CCAAAGACATTCCTTCTCTG | 44 | 1523 |
| 1363970 | N/A | N/A | 10836 | 10855 | CTATTTTGAATAAGCAGGT | 51 | 1524 |
| 1363995 | 2089 | 2108 | 18568 | 18587 | ACCATTGTGAAGATATGACA | 28 | 1525 |
| 1364005 | N/A | N/A | 5664 | 5683 | GGACCCAATGTGCATCCTCA | 60 | 1526 |
| 1364026 | 2171 | 2190 | 18650 | 18669 | TGAAATGTGCATCATTCTAA | 63 | 1527 |

TABLE 20-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1364074 | N/A | N/A | 9397 | 9416 | TTTTACATCCATTTTTCCTC | 58 | 1528 |
| 1364125 | 1947 | 1966 | 18426 | 18445 | CAGGCCAGTCTGTTCTCATG | 14 | 1529 |
| 1364164 | 1415 | 1434 | 17894 | 17913 | ATCCTCAGGAGATGCTTGAA | 59 | 1530 |
| 1364207 | 2212 | 2231 | 18691 | 18710 | CTGATGCAACCCCAAATAAG | 49 | 1531 |
| 1364215 | 1577 | 1596 | 18056 | 18075 | TAGAGAGACCAGAATGAATT | 67 | 1532 |
| 1364233 | N/A | N/A | 9140 | 9159 | GCAGAAGTGAAGAATCTCAG | 62 | 1533 |
| 1364253 | 2144 | 2163 | 18623 | 18642 | CAAGACCTTCAAATCACCTA | 26 | 1534 |

TABLE 21

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362456 | N/A | N/A | 7246 | 7265 | TCCTCAGGTCAGTCTCCCAC | 54 | 1535 |
| 1362459 | 1449 | 1468 | 17928 | 17947 | GTGGAAGTACCCTTTGAGAA | 43 | 1536 |
| 1362489 | 2115 | 2134 | 18594 | 18613 | AATGGATAATACCCCATGAA | 55 | 1537 |
| 1362490 | 1731 | 1750 | 18210 | 18229 | GCTTCAGTAGTCCATCGCCA | 29 | 201 |
| 1362519 | 1942 | 1961 | 18421 | 18440 | CAGTCTGTTCTCATGTAAGC | 20 | 1538 |
| 1362529 | 2143 | 2162 | 18622 | 18641 | AAGACCTTCAAATCACCTAC | 41 | 1539 |
| 1362536 | N/A | N/A | 5887 | 5906 | ACTTCTAAAGTTCCTTCCAA | 96 | 1540 |
| 1362570 | N/A | N/A | 6719 | 6738 | GGTTGTTATTACTCAGATCG | 69 | 1541 |
| 1362591 | 1160 | 1179 | 17639 | 17658 | GCATTGTAGGCTGTGTGGTT | 18 | 1542 |
| 1362611 | 1379 | 1398 | 17858 | 17877 | CCATTCCTTTGTGACTTGCA | 25 | 1543 |
| 1362620 | 1987 | 2006 | 18466 | 18485 | TCTCAGGTTACACCATTAGC | 49 | 1544 |
| 1362645 | 2088 | 2107 | 18567 | 18586 | CCATTGTGAAGATATGACAG | 73 | 1545 |
| 1362685 | 2868 | 2887 | 19347 | 19366 | CACTGTCCTTTATCTTGATT | 30 | 1546 |
| 1362722 | 3070 | 3089 | 19549 | 19568 | TTTGTAAGATAAGTTTCTAA | 61 | 1547 |
| 1362723 | 1813 | 1832 | 18292 | 18311 | ACGAGGTGTAAGGCCAGATG | 24 | 1548 |
| 1362729 | 1195 | 1214 | 17674 | 17693 | GGTGGCAAAGGCAAAGAGTT | 45 | 1549 |
| 1362730 | 2598 | 2617 | 19077 | 19096 | AAAAGACTGAAATCTGGGAG | 59 | 1550 |
| 1362771 | 1414 | 1433 | 17893 | 17912 | TCCTCAGGAGATGCTTGAAA | 66 | 1551 |
| 1362778 | 801 | 820 | 14860 | 14879 | TGAAGTAAATGTACACAGGC | 89 | 1552 |
| 1362780 | N/A | N/A | 7646 | 7665 | ACCACATTCAAGTGCTGGAA | 66 | 1553 |
| 1362784 | 2029 | 2048 | 18508 | 18527 | GCTATCCAAAGAGTTATCTA | 21 | 1554 |
| 1362785 | 1225 | 1244 | 17704 | 17723 | TACACTCATCAAGTAAGAAG | 53 | 1555 |
| 1362788 | 1064 | 1083 | 17543 | 17562 | GGCAAAGTTGTAAGTGGCAG | 31 | 1556 |

TABLE 21-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362830 | 2062 | 2081 | 18541 | 18560 | GAGTACACAACTAATTAACA | 34 | 1557 |
| 1362855 | 2472 | 2491 | 18951 | 18970 | TAACCTTTATGTTAAACCTA | 50 | 1558 |
| 1362912 | N/A | N/A | 15503 | 15522 | TAACCCACTCACCTCAGCTG | 104† | 1559 |
| 1362952 | N/A | N/A | 16447 | 16466 | TTCAGAATAGCTGTACCCAC | 82 | 1560 |
| 1362956 | N/A | N/A | 8311 | 8330 | TCAACAGAACCAATGTGACT | 85 | 1561 |
| 1362969 | N/A | N/A | 5255 | 5274 | TGTTATAGATCTTGCCCATT | 54 | 1562 |
| 1363048 | 2309 | 2328 | 18788 | 18807 | TCAACTAGCCAATTTTTAAT | 52 | 1563 |
| 1363056 | N/A | N/A | 9128 | 9147 | AATCTCAGTCAGTCTGTCCA | 69 | 1564 |
| 1363089 | 1894 | 1913 | 18373 | 18392 | AAACCACAGGGTTGTCATGG | 60 | 1565 |
| 1363121 | 1732 | 1751 | 18211 | 18230 | GGCTTCAGTAGTCCATCGCC | 22 | 279 |
| 1363173 | 2911 | 2930 | 19390 | 19409 | TTATGTTATTAAATCAAAAC | 106 | 1566 |
| 1363222 | 2729 | 2748 | 19208 | 19227 | ATTGCTGAAACCACTTTGGG | 49 | 1567 |
| 1363232 | 2811 | 2830 | 19290 | 19309 | GCAGCCTGGAAGCTTATCTT | 20 | 1568 |
| 1363254 | 1753 | 1772 | 18232 | 18251 | AAGTAAGGTTGGCTGAGTTA | 81 | 1569 |
| 1363265 | 1856 | 1875 | 18335 | 18354 | AGGGAGTGAGAAGATGCTGA | 36 | 1570 |
| 1363278 | 2545 | 2564 | 19024 | 19043 | TTTTCCTGGAAGCTTACCAA | 49 | 1571 |
| 1363299 | N/A | N/A | 9393 | 9412 | ACATCCATTTTTCCTCTATT | 62 | 1572 |
| 1363341 | N/A | N/A | 17216 | 17235 | TGAACAATATTTGGGCTTTG | 66 | 1573 |
| 1363348 | 2445 | 2464 | 18924 | 18943 | ACACACCAAGATAACATTGC | 43 | 1574 |
| 1363381 | 1307 | 1326 | 17786 | 17805 | GAAGCAAATGACTAAAAGA | 81 | 1575 |
| 1363384 | N/A | N/A | 8822 | 8841 | TCACATTTCCAGTCTAAGTA | 83 | 1576 |
| 1363426 | 1504 | 1523 | 17983 | 18002 | CAAAGACATTCCTTCTCTGT | 99 | 1577 |
| 1363447 | 2275 | 2294 | 18754 | 18773 | TTAATGTCCAATTTTCCTAG | 67 | 1578 |
| 1363494 | N/A | N/A | 4086 | 4105 | ACACGACTCATTTAAACCAT | 60 | 1579 |
| 1363508 | N/A | N/A | 5547 | 5566 | TCCTCAGGGATTTCATCCCC | 104 | 1580 |
| 1363552 | 1536 | 1555 | 18015 | 18034 | ATATATTTGGCCCCTATAGA | 88 | 1581 |
| 1363554 | 2651 | 2670 | 19130 | 19149 | ATTAAAACCAATCAGACTTT | 88 | 1582 |
| 1363555 | 2681 | 2700 | 19160 | 19179 | AAAAGAACTGTAGTACAAAT | 83 | 1583 |
| 1363567 | 2391 | 2410 | 18870 | 18889 | GATCAGATTACTCAAATTGA | 32 | 1584 |
| 1363582 | 2170 | 2189 | 18649 | 18668 | GAAATGTGCATCATTCTAAA | 50 | 1585 |
| 1363593 | N/A | N/A | 12410 | 12429 | TGTGAGATTGACCCAGAATC | 80 | 1586 |
| 1363606 | N/A | N/A | 16947 | 16966 | GCACAATGAGCACACTACAT | 62 | 1587 |
| 1363618 | N/A | N/A | 11294 | 11313 | GCATGAAACATCTTTCTGGC | 50 | 1588 |
| 1363664 | 2499 | 2518 | 18978 | 18997 | TGTTATGTGATCTATATCAG | 46 | 1589 |
| 1363699 | N/A | N/A | 15847 | 15866 | CTATGAATGCCTCTGTGCAC | 69 | 1590 |
| 1363707 | 3005 | 3024 | 19484 | 19503 | ATGAAGGAAACACTTTCAGT | 60 | 1591 |

TABLE 21-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363710 | N/A | N/A | 13379 | 13398 | ACATAAGTGAGGTATACACC | 79 | 1592 |
| 1363753 | 1332 | 1351 | 17811 | 17830 | CCCATTTCTAGCAGGAACCA | 35 | 1593 |
| 1363777 | N/A | N/A | 10122 | 10141 | ATTCCAGAAATTGATCTTCC | 76 | 1594 |
| 1363808 | 1265 | 1284 | 17744 | 17763 | AAAGAGAGACCTTAATCACT | 100 | 1595 |
| 1363827 | N/A | N/A | 16687 | 16706 | CGTAATTTATGACTGCAAAG | 45 | 1596 |
| 1363877 | 2776 | 2795 | 19255 | 19274 | AACAAGTATCAAGTGTCTTT | 31 | 1597 |
| 1363894 | 2246 | 2265 | 18725 | 18744 | CAGTCATAATCAAAGAATTA | 62 | 1598 |
| 1363981 | N/A | N/A | 6261 | 6280 | GTAACAGCCACTGTTCTCAG | 85 | 1599 |
| 1363987 | 2417 | 2436 | 18896 | 18915 | ATCATTTTCCATTAGCTAGA | 25 | 1600 |
| 1364001 | 1576 | 1595 | 18055 | 18074 | AGAGAGACCAGAATGAATTC | 82 | 1601 |
| 1364011 | N/A | N/A | 13962 | 13981 | TTGTACAAAGCATCCCACAA | 63 | 1602 |
| 1364050 | 1680 | 1699 | 18159 | 18178 | AGATCCTTGCTTTGACCCCC | 48 | 1603 |
| 1364088 | N/A | N/A | 4897 | 4916 | CAACTGAGTCTCATTTCATT | 81 | 1604 |
| 1364099 | 1624 | 1643 | 18103 | 18122 | TCTTATTGTTTTCTGACAT | 32 | 1605 |
| 1364102 | 3031 | 3050 | 19510 | 19529 | GTTAAAATTGCAATTCTATA | 59 | 1606 |
| 1364103 | 2333 | 2352 | 18812 | 18831 | TACTTGTAGAAAATCCCAAT | 27 | 1607 |
| 1364133 | 2211 | 2230 | 18690 | 18709 | TGATGCAACCCCAAATAAGT | 44 | 1608 |
| 1364144 | N/A | N/A | 10829 | 10848 | TGAATAAGCAGGTTGTGACA | 65 | 1609 |
| 1364195 | 2364 | 2383 | 18843 | 18862 | ATTCACCAAATCTGTTTCTG | 34 | 1610 |
| 1364200 | N/A | N/A | 11764 | 11783 | AGACCTAATATTTTCAACTA | 78 | 1611 |

TABLE 22

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362439 | N/A | N/A | 4053 | 4072 | CCCAAAGTTGGAAATTCTCT | 74 | 1612 |
| 1362441 | 1622 | 1641 | 18101 | 18120 | TTATTGTTTTCTGACATTC | 34 | 1613 |
| 1362471 | 2114 | 2133 | 18593 | 18612 | ATGGATAATACCCCATGAAA | 77 | 1614 |
| 1362490 | 1731 | 1750 | 18210 | 18229 | GCTTCAGTAGTCCATCGCCA | 27 | 201 |
| 1362525 | 1448 | 1467 | 17927 | 17946 | TGGAAGTACCCTTTGAGAAG | 65 | 1615 |
| 1362535 | 1939 | 1958 | 18418 | 18437 | TCTGTTCTCATGTAAGCTAG | 19 | 1616 |
| 1362554 | 2244 | 2263 | 18723 | 18742 | GTCATAATCAAAGAATTATT | 33 | 1617 |
| 1362598 | 800 | 819 | 14859 | 14878 | GAAGTAAATGTACACAGGCA | 89 | 1618 |
| 1362643 | 2910 | 2929 | 19389 | 19408 | TATGTTATTAAATCAAACA | 112 | 1619 |

TABLE 22-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362679 | 1264 | 1283 | 17743 | 17762 | AAGAGAGACCTTAATCACTG | 49 | 1620 |
| 1362693 | N/A | N/A | 11762 | 11781 | ACCTAATATTTTCAACTAAC | 69 | 1621 |
| 1362708 | 1893 | 1912 | 18372 | 18391 | AACCACAGGGTTGTCATGGT | 26 | 1622 |
| 1362739 | 1331 | 1350 | 17810 | 17829 | CCATTTCTAGCAGGAACCAG | 50 | 1623 |
| 1362787 | N/A | N/A | 16937 | 16956 | CACACTACATTCACAGGGCA | 52 | 1624 |
| 1362828 | 2471 | 2490 | 18950 | 18969 | AACCTTTATGTTAAACCTAA | 37 | 1625 |
| 1362841 | 2308 | 2327 | 18787 | 18806 | CAACTAGCCAATTTTTAATA | 52 | 1626 |
| 1362851 | 2142 | 2161 | 18621 | 18640 | AGACCTTCAAATCACCTACG | 31 | 1627 |
| 1362865 | 1676 | 1695 | 18155 | 18174 | CCTTGCTTTGACCCCCTTCT | 56 | 1628 |
| 1362871 | 2597 | 2616 | 19076 | 19095 | AAAGACTGAAATCTGGGAGC | 31 | 1629 |
| 1362896 | N/A | N/A | 5546 | 5565 | CCTCAGGGATTTCATCCCCT | 100 | 1630 |
| 1362898 | 1063 | 1082 | 17542 | 17561 | GCAAAGTTGTAAGTGGCAGC | 52 | 1631 |
| 1362921 | 2332 | 2351 | 18811 | 18830 | ACTTGTAGAAAATCCCAATA | 40 | 1632 |
| 1362949 | 3030 | 3049 | 19509 | 19528 | TTAAAATTGCAATTCTATAT | 104 | 1633 |
| 1362954 | N/A | N/A | 15502 | 15521 | AACCCACTCACCTCAGCTGT | 104† | 1634 |
| 1363001 | N/A | N/A | 16413 | 16432 | ATTTACTTGCCAAGATCATT | 95 | 1635 |
| 1363010 | N/A | N/A | 15830 | 15849 | CACAGCCCATTTTCTTGATA | 55 | 1636 |
| 1363021 | 3069 | 3088 | 19548 | 19567 | TTGTAAGATAAGTTTCTAAA | 76 | 1637 |
| 1363028 | N/A | N/A | 17213 | 17232 | ACAATATTTGGGCTTTGCCA | 62 | 1638 |
| 1363044 | N/A | N/A | 7242 | 7261 | CAGGTCAGTCTCCCACCATT | 59 | 1639 |
| 1363067 | N/A | N/A | 13953 | 13972 | GCATCCCACAAAACTCATGC | 37 | 1640 |
| 1363121 | 1732 | 1751 | 18211 | 18230 | GGCTTCAGTAGTCCATCGCC | 15 | 279 |
| 1363125 | N/A | N/A | 5218 | 5237 | TTATTGTTACTTGATTCTCA | 61 | 1641 |
| 1363162 | 2028 | 2047 | 18507 | 18526 | CTATCCAAAGAGTTATCTAT | 44 | 1642 |
| 1363180 | 2168 | 2187 | 18647 | 18666 | AATGTGCATCATTCTAAAAC | 65 | 1643 |
| 1363181 | N/A | N/A | 6258 | 6277 | ACAGCCACTGTTCTCAGACG | 68 | 1644 |
| 1363246 | 1159 | 1178 | 17638 | 17657 | CATTGTAGGCTGTGTGGTTA | 72 | 1645 |
| 1363316 | 2498 | 2517 | 18977 | 18996 | GTTATGTGATCTATATCAGG | 31 | 1646 |
| 1363317 | 3004 | 3023 | 19483 | 19502 | TGAAGGAAACACTTTCAGTT | 56 | 1647 |
| 1363321 | N/A | N/A | 8306 | 8325 | AGAACCAATGTGACTTACAC | 95 | 1648 |
| 1363339 | 1854 | 1873 | 18333 | 18352 | GGAGTGAGAAGATGCTGACA | 56 | 1649 |
| 1363353 | N/A | N/A | 16678 | 16697 | TGACTGCAAAGTACTTGGCA | 62 | 1650 |
| 1363371 | 2775 | 2794 | 19254 | 19273 | ACAAGTATCAAGTGTCTTTT | 36 | 1651 |
| 1363372 | 2544 | 2563 | 19023 | 19042 | TTTCCTGGAAGCTTACCAAC | 51 | 1652 |
| 1363373 | N/A | N/A | 10828 | 10847 | GAATAAGCAGGTTGTGACAG | 68 | 1653 |
| 1363392 | 1378 | 1397 | 17857 | 17876 | CATTCCTTTGTGACTTGCAG | 25 | 1654 |

TABLE 22-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363417 | N/A | N/A | 11292 | 11311 | ATGAAACATCTTTCTGGCAC | 76 | 1655 |
| 1363478 | 2710 | 2729 | 19189 | 19208 | GGGAAAAGAACAACACAACT | 56 | 1656 |
| 1363483 | 2860 | 2879 | 19339 | 19358 | TTTATCTTGATTGGTTTCTT | 51 | 1657 |
| 1363522 | 2444 | 2463 | 18923 | 18942 | CACACCAAGATAACATTGCT | 44 | 1658 |
| 1363535 | 1306 | 1325 | 17785 | 17804 | AAGCAAAATGACTAAAAGAG | 91 | 1659 |
| 1363547 | 2679 | 2698 | 19158 | 19177 | AAGAACTGTAGTACAAATCT | 50 | 1660 |
| 1363633 | 2808 | 2827 | 19287 | 19306 | GCCTGGAAGCTTATCTTGTA | 22 | 1661 |
| 1363637 | N/A | N/A | 4872 | 4891 | TGTGTTTAAGCTGCTATCTT | 47 | 1662 |
| 1363649 | 2363 | 2382 | 18842 | 18861 | TTCACCAAATCTGTTTCTGC | 25 | 1663 |
| 1363659 | 2274 | 2293 | 18753 | 18772 | TAATGTCCAATTTTCCTAGT | 56 | 1664 |
| 1363702 | N/A | N/A | 9389 | 9408 | CCATTTTCCTCTATTTTCT | 74 | 1665 |
| 1363738 | 1224 | 1243 | 17703 | 17722 | ACACTCATCAAGTAAGAAGA | 32 | 1666 |
| 1363813 | 1413 | 1432 | 17892 | 17911 | CCTCAGGAGATGCTTGAAAA | 46 | 1667 |
| 1363860 | 2061 | 2080 | 18540 | 18559 | AGTACACAACTAATTAACAG | 48 | 1668 |
| 1363869 | N/A | N/A | 9124 | 9143 | TCAGTCAGTCTGTCCAAGCA | 62 | 1669 |
| 1363870 | 2415 | 2434 | 18894 | 18913 | CATTTTCCATTAGCTAGAAA | 40 | 1670 |
| 1363873 | 2390 | 2409 | 18869 | 18888 | ATCAGATTACTCAAATTGAG | 37 | 1671 |
| 1363884 | 1812 | 1831 | 18291 | 18310 | CGAGGTGTAAGGCCAGATGC | 32 | 1672 |
| 1363909 | 1503 | 1522 | 17982 | 18001 | AAAGACATTCCTTCTCTGTA | 86 | 1673 |
| 1363974 | N/A | N/A | 10121 | 10140 | TTCCAGAAATTGATCTTCCT | 71 | 1674 |
| 1363985 | N/A | N/A | 5884 | 5903 | TCTAAAGTTCCTTCCAATCC | 86 | 1675 |
| 1364019 | 1534 | 1553 | 18013 | 18032 | ATATTTGGCCCCTATAGATG | 77 | 1676 |
| 1364029 | 1194 | 1213 | 17673 | 17692 | GTGGCAAAGGCAAAGAGTTA | 63 | 1677 |
| 1364030 | N/A | N/A | 12407 | 12426 | GAGATTGACCCAGAATCCTT | 52 | 1678 |
| 1364036 | 2650 | 2669 | 19129 | 19148 | TTAAAACCAATCAGACTTTT | 74 | 1679 |
| 1364072 | N/A | N/A | 13378 | 13397 | CATAAGTGAGGTATACACCA | 64 | 1680 |
| 1364077 | N/A | N/A | 6717 | 6736 | TTGTTATTACTCAGATCGCT | 64 | 1681 |
| 1364152 | N/A | N/A | 8820 | 8839 | ACATTTCCAGTCTAAGTACA | 87 | 1682 |
| 1364157 | 2087 | 2106 | 18566 | 18585 | CATTGTGAAGATATGACAGA | 55 | 1683 |
| 1364180 | 1986 | 2005 | 18465 | 18484 | CTCAGGTTACACCATTAGCC | 29 | 210 |
| 1364206 | 1575 | 1594 | 18054 | 18073 | GAGAGACCAGAATGAATTCC | 33 | 1684 |
| 1364209 | N/A | N/A | 7645 | 7664 | CCACATTCAAGTGCTGGAAA | 61 | 1685 |
| 1364221 | 2210 | 2229 | 18689 | 18708 | GATGCAACCCCAAATAAGTA | 48 | 1686 |
| 1364270 | 1751 | 1770 | 18230 | 18249 | GTAAGGTTGGCTGAGTTAGG | 39 | 1687 |

TABLE 23

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362463 | N/A | N/A | 16936 | 16955 | ACACTACATTCACAGGGCAC | 57 | 1688 |
| 1362472 | N/A | N/A | 10789 | 10808 | TTGTATTAATTACTTAGGCT | 98 | 1689 |
| 1362488 | N/A | N/A | 12406 | 12425 | AGATTGACCCAGAATCCTTA | 53 | 1690 |
| 1362490 | 1731 | 1750 | 18210 | 18229 | GCTTCAGTAGTCCATCGCCA | 18 | 201 |
| 1362497 | 1151 | 1170 | 17630 | 17649 | GCTGTGTGGTTAGAGCCTCG | 23 | 42 |
| 1362530 | N/A | N/A | 6255 | 6274 | GCCACTGTTCTCAGACGACA | 37 | 1691 |
| 1362589 | N/A | N/A | 7584 | 7603 | GGATAGTCAAATCATGTGGA | 55 | 1692 |
| 1362600 | 2497 | 2516 | 18976 | 18995 | TTATGTGATCTATATCAGGA | 40 | 1693 |
| 1362607 | 2596 | 2615 | 19075 | 19094 | AAGACTGAAATCTGGGAGCT | 35 | 1694 |
| 1362631 | 3068 | 3087 | 19547 | 19566 | TGTAAGATAAGTTTCTAAAA | 70 | 1695 |
| 1362633 | N/A | N/A | 5883 | 5902 | CTAAAGTTCCTTCCAATCCC | 73 | 1696 |
| 1362637 | 2060 | 2079 | 18539 | 18558 | GTACACAACTAATTAACAGA | 31 | 1697 |
| 1362648 | 1412 | 1431 | 17891 | 17910 | CTCAGGAGATGCTTGAAAAT | 72 | 1698 |
| 1362663 | 3003 | 3022 | 19482 | 19501 | GAAGGAAACACTTTCAGTTG | 50 | 1699 |
| 1362675 | 2086 | 2105 | 18565 | 18584 | ATTGTGAAGATATGACAGAG | 46 | 1700 |
| 1362710 | 1811 | 1830 | 18290 | 18309 | GAGGTGTAAGGCCAGATGCC | 44 | 1701 |
| 1362712 | 2362 | 2381 | 18841 | 18860 | TCACCAAATCTGTTTCTGCA | 22 | 1702 |
| 1362746 | 2773 | 2792 | 19252 | 19271 | AAGTATCAAGTGTCTTTTTG | 41 | 1703 |
| 1362764 | 2678 | 2697 | 19157 | 19176 | AGAACTGTAGTACAAATCTT | 50 | 1704 |
| 1362815 | 1984 | 2003 | 18463 | 18482 | CAGGTTACACCATTAGCCAC | 44 | 1705 |
| 1362886 | 2389 | 2408 | 18868 | 18887 | TCAGATTACTCAAATTGAGA | 38 | 1706 |
| 1362889 | 1892 | 1911 | 18371 | 18390 | ACCACAGGGTTGTCATGGTA | 45 | 1707 |
| 1362918 | 3029 | 3048 | 19508 | 19527 | TAAAATTGCAATTCTATATC | 114 | 1708 |
| 1362960 | 797 | 816 | 14856 | 14875 | GTAAATGTACACAGGCACAG | 50 | 1709 |
| 1362971 | N/A | N/A | 16677 | 16696 | GACTGCAAAGTACTTGGCAA | 39 | 1710 |
| 1362988 | N/A | N/A | 9337 | 9356 | GCTCCACTACAGCTCAAAGC | 56 | 1711 |
| 1363026 | 1935 | 1954 | 18414 | 18433 | TTCTCATGTAAGCTAGTTTC | 33 | 1712 |
| 1363034 | 1675 | 1694 | 18154 | 18173 | CTTGCTTTGACCCCCTTCTC | 70 | 1713 |
| 1363112 | 1330 | 1349 | 17809 | 17828 | CATTTCTAGCAGGAACCAGC | 59 | 1714 |
| 1363121 | 1732 | 1751 | 18211 | 18230 | GGCTTCAGTAGTCCATCGCC | 20 | 279 |
| 1363195 | N/A | N/A | 4052 | 4071 | CCAAAGTTGGAAATTCTCTT | 63 | 1715 |
| 1363345 | N/A | N/A | 13374 | 13393 | AGTGAGGTATACACCAGAGC | 40 | 1716 |
| 1363393 | 1744 | 1763 | 18223 | 18242 | TGGCTGAGTTAGGGCTTCAG | 23 | 1717 |
| 1363394 | N/A | N/A | 11753 | 11772 | TTTCAACTAACAATTCAGGC | 52 | 1718 |
| 1363397 | 2414 | 2433 | 18893 | 18912 | ATTTTCCATTAGCTAGAAAG | 47 | 1719 |
| 1363401 | 1501 | 1520 | 17980 | 17999 | AGACATTCCTTCTCTGTACC | 50 | 1720 |

TABLE 23-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363409 | 2443 | 2462 | 18922 | 18941 | ACACCAAGATAACATTGCTA | 35 | 1721 |
| 1363413 | N/A | N/A | 15756 | 15775 | TCTATCTTTACCTAAAGCTA | 58 | 1722 |
| 1363503 | 2908 | 2927 | 19387 | 19406 | TGTTATTAAATCAAAACAAA | 89 | 1723 |
| 1363511 | 2709 | 2728 | 19188 | 19207 | GGAAAAGAACAACACAACTC | 56 | 1724 |
| 1363563 | N/A | N/A | 15333 | 15352 | ATCTCTAATTATCCTGGCTG | 70 | 1725 |
| 1363571 | N/A | N/A | 11290 | 11309 | GAAACATCTTTCTGGCACTA | 54 | 1726 |
| 1363603 | 2141 | 2160 | 18620 | 18639 | GACCTTCAAATCACCTACGA | 37 | 289 |
| 1363619 | 2470 | 2489 | 18949 | 18968 | ACCTTTATGTTAAACCTAAC | 46 | 1727 |
| 1363691 | 1620 | 1639 | 18099 | 18118 | ATTGTTTTCTGACATTCTT | 38 | 1728 |
| 1363696 | 1574 | 1593 | 18053 | 18072 | AGAGACCAGAATGAATTCCA | 18 | 1729 |
| 1363708 | 2243 | 2262 | 18722 | 18741 | TCATAATCAAAGAATTATTC | 75 | 1730 |
| 1363747 | 2272 | 2291 | 18751 | 18770 | ATGTCCAATTTTCCTAGTTT | 28 | 1731 |
| 1363792 | 1533 | 1552 | 18012 | 18031 | TATTTGGCCCCTATAGATGG | 90 | 1732 |
| 1363795 | 1374 | 1393 | 17853 | 17872 | CCTTTGTGACTTGCAGTTGG | 35 | 1733 |
| 1363815 | 2113 | 2132 | 18592 | 18611 | TGGATAATACCCCATGAAAT | 40 | 1734 |
| 1363818 | 2307 | 2326 | 18786 | 18805 | AACTAGCCAATTTTTAATAT | 52 | 1735 |
| 1363842 | 1192 | 1211 | 17671 | 17690 | GGCAAAGGCAAAGAGTTAAG | 28 | 1736 |
| 1363850 | 1262 | 1281 | 17741 | 17760 | GAGAGACCTTAATCACTGCA | 24 | 1737 |
| 1363863 | N/A | N/A | 17212 | 17231 | CAATATTTGGGCTTTGCCAC | 60 | 1738 |
| 1363881 | 2331 | 2350 | 18810 | 18829 | CTTGTAGAAAATCCCAATAG | 45 | 1739 |
| 1363890 | 2167 | 2186 | 18646 | 18665 | ATGTGCATCATTCTAAAACA | 41 | 1740 |
| 1363914 | 1447 | 1466 | 17926 | 17945 | GGAAGTACCCTTTGAGAAGA | 64 | 1741 |
| 1363938 | N/A | N/A | 16410 | 16429 | TACTTGCCAAGATCATTCAA | 98 | 1742 |
| 1363948 | N/A | N/A | 5214 | 5233 | TGTTACTTGATTCTCACAAC | 45 | 1743 |
| 1363960 | 2649 | 2668 | 19128 | 19147 | TAAAACCAATCAGACTTTTT | 65 | 1744 |
| 1363967 | 1223 | 1242 | 17702 | 17721 | CACTCATCAAGTAAGAAGAG | 53 | 1745 |
| 1363978 | 2856 | 2875 | 19335 | 19354 | TCTTGATTGGTTTCTTACAA | 27 | 1746 |
| 1364013 | N/A | N/A | 4871 | 4890 | GTGTTTAAGCTGCTATCTTT | 38 | 1747 |
| 1364022 | N/A | N/A | 5527 | 5546 | TGAGGAAGTAATATTCAACA | 86 | 1748 |
| 1364025 | N/A | N/A | 10093 | 10112 | ACAGGTTAAGATACTAGATT | 59 | 1749 |
| 1364034 | 1062 | 1081 | 17541 | 17560 | CAAAGTTGTAAGTGGCAGCA | 38 | 1750 |
| 1364045 | 2805 | 2824 | 19284 | 19303 | TGGAAGCTTATCTTGTATAC | 43 | 1751 |
| 1364062 | N/A | N/A | 8815 | 8834 | TCCAGTCTAAGTACAGACTG | 98 | 1752 |
| 1364064 | N/A | N/A | 13950 | 13969 | TCCCACAAAACTCATGCTTT | 40 | 1753 |
| 1364092 | N/A | N/A | 6532 | 6551 | GCTGCACTTGATTATTTTAG | 47 | 1754 |
| 1364121 | 2543 | 2562 | 19022 | 19041 | TTCCTGGAAGCTTACCAACT | 40 | 1755 |

TABLE 23-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1364137 | 1853 | 1872 | 18332 | 18351 | GAGTGAGAAGATGCTGACAA | 48 | 1756 |
| 1364142 | 1305 | 1324 | 17784 | 17803 | AGCAAAATGACTAAAAGAGG | 56 | 1757 |
| 1364151 | 2208 | 2227 | 18687 | 18706 | TGCAACCCCAAATAAGTAAT | 33 | 1758 |
| 1364176 | 2027 | 2046 | 18506 | 18525 | TATCCAAAGAGTTATCTATC | 53 | 1759 |
| 1364219 | N/A | N/A | 9114 | 9133 | TGTCCAAGCAAGAATCAGAT | 69 | 1760 |
| 1364234 | N/A | N/A | 8297 | 8316 | GTGACTTACACAGATCCAGG | 51 | 1761 |
| 1364236 | N/A | N/A | 7230 | 7249 | CCACCATTTCCTCCTCTCTC | 53 | 1762 |

TABLE 24

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362462 | N/A | N/A | 10090 | 10109 | GGTTAAGATACTAGATTCAG | 76 | 1763 |
| 1362490 | 1731 | 1750 | 18210 | 18229 | GCTTCAGTAGTCCATCGCCA | 30 | 201 |
| 1362495 | N/A | N/A | 13949 | 13968 | CCCACAAAACTCATGCTTTC | 52 | 1764 |
| 1362520 | 2085 | 2104 | 18564 | 18583 | TTGTGAAGATATGACAGAGG | 37 | 1765 |
| 1362601 | N/A | N/A | 5841 | 5860 | TACTGCAATTGTTGAACAGC | 90 | 1766 |
| 1362666 | 1260 | 1279 | 17739 | 17758 | GAGACCTTAATCACTGCAAG | 43 | 1767 |
| 1362672 | 1329 | 1348 | 17808 | 17827 | ATTTCTAGCAGGAACCAGCT | 49 | 1768 |
| 1362674 | 1191 | 1210 | 17670 | 17689 | GCAAAGGCAAAGAGTTAAGA | 66 | 1769 |
| 1362818 | 1891 | 1910 | 18370 | 18389 | CCACAGGGTTGTCATGGTAG | 44 | 1770 |
| 1362870 | N/A | N/A | 5490 | 5509 | TCTGTTTTTAATGCACAACC | 66 | 1771 |
| 1362892 | 2495 | 2514 | 18974 | 18993 | ATGTGATCTATATCAGGAGA | 28 | 1772 |
| 1362907 | 2242 | 2261 | 18721 | 18740 | CATAATCAAAGAATTATTCT | 85 | 1773 |
| 1362917 | 2271 | 2290 | 18750 | 18769 | TGTCCAATTTTCCTAGTTTA | 34 | 1774 |
| 1362920 | N/A | N/A | 16935 | 16954 | CACTACATTCACAGGGCACT | 60 | 1775 |
| 1362935 | 795 | 814 | 14854 | 14873 | AAATGTACACAGGCACAGCA | 72 | 1776 |
| 1362941 | 2306 | 2325 | 18785 | 18804 | ACTAGCCAATTTTTAATATC | 53 | 1777 |
| 1362947 | 2899 | 2918 | 19378 | 19397 | ATCAAAACAAAACACAAGGT | 57 | 1778 |
| 1362970 | 1148 | 1167 | 17627 | 17646 | GTGTGGTTAGAGCCTCGCTA | 23 | 197 |
| 1363006 | N/A | N/A | 11241 | 11260 | GTGTCTTAAAGTGCTAAGAG | 37 | 1779 |
| 1363014 | 3028 | 3047 | 19507 | 19526 | AAAATTGCAATTCTATATCA | 64 | 1780 |
| 1363015 | 2677 | 2696 | 19156 | 19175 | GAACTGTAGTACAAATCTTT | 51 | 1781 |
| 1363017 | 1573 | 1592 | 18052 | 18071 | GAGACCAGAATGAATTCCAT | 33 | 1782 |
| 1363057 | N/A | N/A | 15306 | 15325 | GGATTCTACCAACAATCAGG | 66 | 1783 |

TABLE 24-continued

Reduction of PLP1 RNA by 5-10-5 MOE gapmers with mixed
PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363065 | N/A | N/A | 9336 | 9355 | CTCCACTACAGCTCAAAGCA | 73 | 1784 |
| 1363072 | N/A | N/A | 8760 | 8779 | TAATAACATTTCTCAATGCA | 87 | 1785 |
| 1363076 | 2360 | 2379 | 18839 | 18858 | ACCAAATCTGTTTCTGCAAA | 28 | 1786 |
| 1363088 | 2026 | 2045 | 18505 | 18524 | ATCCAAAGAGTTATCTATCC | 45 | 1787 |
| 1363098 | 2853 | 2872 | 19332 | 19351 | TGATTGGTTTCTTACAAAAC | 49 | 1788 |
| 1363102 | N/A | N/A | 17196 | 17215 | CCACATCAATATGTCCGAGT | 19 | 253 |
| 1363120 | N/A | N/A | 7184 | 7203 | GGAACCTTATTCTCTTCCTT | 37 | 1789 |
| 1363121 | 1732 | 1751 | 18211 | 18230 | GGCTTCAGTAGTCCATCGCC | 17 | 279 |
| 1363133 | 2442 | 2461 | 18921 | 18940 | CACCAAGATAACATTGCTAA | 39 | 1790 |
| 1363152 | 2166 | 2185 | 18645 | 18664 | TGTGCATCATTCTAAAACAA | 30 | 1791 |
| 1363203 | 2140 | 2159 | 18619 | 18638 | ACCTTCAAATCACCTACGAT | 57 | 1792 |
| 1363266 | 2112 | 2131 | 18591 | 18610 | GGATAATACCCCATGAAATG | 28 | 1793 |
| 1363269 | 1810 | 1829 | 18289 | 18308 | AGGTGTAAGGCCAGATGCCC | 39 | 1794 |
| 1363275 | N/A | N/A | 4800 | 4819 | ACAAAGACCCTTGTGCTCTG | 81 | 1795 |
| 1363282 | 2759 | 2778 | 19238 | 19257 | TTTTTGTAAAGCTCTTACAT | 62 | 1796 |
| 1363297 | N/A | N/A | 15752 | 15771 | TCTTTACCTAAAGCTACAAA | 91 | 1797 |
| 1363304 | 2059 | 2078 | 18538 | 18557 | TACACAACTAATTAACAGAA | 75 | 1798 |
| 1363315 | 2804 | 2823 | 19283 | 19302 | GGAAGCTTATCTTGTATACT | 21 | 1799 |
| 1363360 | 1499 | 1518 | 17978 | 17997 | ACATTCCTTCTCTGTACCTG | 38 | 1800 |
| 1363378 | N/A | N/A | 11752 | 11771 | TTCAACTAACAATTCAGGCA | 42 | 1801 |
| 1363400 | 1982 | 2001 | 18461 | 18480 | GGTTACACCATTAGCCACCA | 25 | 1802 |
| 1363403 | 1304 | 1323 | 17783 | 17802 | GCAAAATGACTAAAAGAGGT | 61 | 1803 |
| 1363456 | 2595 | 2614 | 19074 | 19093 | AGACTGAAATCTGGGAGCTA | 49 | 1804 |
| 1363459 | 1222 | 1241 | 17701 | 17720 | ACTCATCAAGTAAGAAGAGG | 29 | 1805 |
| 1363463 | 1444 | 1463 | 17923 | 17942 | AGTACCCTTTGAGAAGAAAT | 48 | 1806 |
| 1363517 | 2207 | 2226 | 18686 | 18705 | GCAACCCCAAATAAGTAATA | 23 | 1807 |
| 1363526 | N/A | N/A | 16675 | 16694 | CTGCAAAGTACTTGGCAACA | 34 | 1808 |
| 1363537 | N/A | N/A | 8295 | 8314 | GACTTACACAGATCCAGGTT | 67 | 1809 |
| 1363587 | 2468 | 2487 | 18947 | 18966 | CTTTATGTTAAACCTAACTC | 45 | 1810 |
| 1363625 | 1060 | 1079 | 17539 | 17558 | AAGTTGTAAGTGGCAGCAAT | 92 | 1811 |
| 1363667 | 3067 | 3086 | 19546 | 19565 | GTAAGATAAGTTTCTAAAAG | 71 | 1812 |
| 1363670 | 1527 | 1546 | 18006 | 18025 | GCCCCTATAGATGGCAAGAG | 53 | 1813 |
| 1363672 | 1674 | 1693 | 18153 | 18172 | TTGCTTTGACCCCCTTCTCC | 74 | 1814 |
| 1363701 | 1743 | 1762 | 18222 | 18241 | GGCTGAGTTAGGGCTTCAGT | 21 | 1815 |
| 1363712 | N/A | N/A | 6244 | 6263 | CAGACGACAACAGGCTTGCA | 88 | 1816 |
| 1363713 | 2413 | 2432 | 18892 | 18911 | TTTTCCATTAGCTAGAAAGA | 50 | 1817 |

TABLE 24-continued

Reduction of PLP1 RNA by 5-10-5 MOE gapmers with mixed
PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
| --- | --- | --- | --- | --- | --- | --- | --- |
| 1363731 | 3002 | 3021 | 19481 | 19500 | AAGGAAACACTTTCAGTTGA | 62 | 1818 |
| 1363772 | N/A | N/A | 16409 | 16428 | ACTTGCCAAGATCATTCAAA | 86 | 1819 |
| 1363830 | 2388 | 2407 | 18867 | 18886 | CAGATTACTCAAATTGAGAT | 39 | 1820 |
| 1363838 | 1933 | 1952 | 18412 | 18431 | CTCATGTAAGCTAGTTTCCT | 27 | 1821 |
| 1363849 | N/A | N/A | 7581 | 7600 | TAGTCAAATCATGTGGACAA | 52 | 1822 |
| 1363861 | 2330 | 2349 | 18809 | 18828 | TTGTAGAAAATCCCAATAGA | 51 | 1823 |
| 1363874 | N/A | N/A | 4001 | 4020 | GCTAAAGTTTTTGAAACTTA | 124 | 1824 |
| 1363918 | N/A | N/A | 13373 | 13392 | GTGAGGTATACACCAGAGCG | 55 | 1825 |
| 1363927 | 1411 | 1430 | 17890 | 17909 | TCAGGAGATGCTTGAAAATT | 62 | 1826 |
| 1363936 | 1852 | 1871 | 18331 | 18350 | AGTGAGAAGATGCTGACAAC | 40 | 1827 |
| 1363955 | 2648 | 2667 | 19127 | 19146 | AAAACCAATCAGACTTTTTT | 53 | 1828 |
| 1363962 | N/A | N/A | 5213 | 5232 | GTTACTTGATTCTCACACCC | 29 | 1829 |
| 1364037 | N/A | N/A | 12401 | 12420 | GACCCAGAATCCTTACTTTG | 64 | 1830 |
| 1364058 | 1370 | 1389 | 17849 | 17868 | TGTGACTTGCAGTTGGGAAG | 47 | 1831 |
| 1364097 | 1618 | 1637 | 18097 | 18116 | TGTTTTTCTGACATTCTTTT | 34 | 1832 |
| 1364173 | N/A | N/A | 9112 | 9131 | TCCAAGCAAGAATCAGATTT | 77 | 1833 |
| 1364203 | N/A | N/A | 10788 | 10807 | TGTATTAATTACTTAGGCTT | 74 | 1834 |
| 1364226 | 2708 | 2727 | 19187 | 19206 | GAAAAGAACAACACAACTCT | 60 | 1835 |
| 1364259 | N/A | N/A | 6527 | 6546 | ACTTGATTATTTTAGTCAGT | 44 | 1836 |
| 1364267 | 2542 | 2561 | 19021 | 19040 | TCCTGGAAGCTTACCAACTG | 42 | 1837 |

TABLE 25

Reduction of PLP1 RNA by 5-10-5 MOE gapmers with mixed
PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
| --- | --- | --- | --- | --- | --- | --- | --- |
| 805563 | 1058 | 1077 | 17537 | 17556 | GTTGTAAGTGGCAGCAATCA | 55 | 1838 |
| 1362438 | 2647 | 2666 | 19126 | 19145 | AAACCAATCAGACTTTTTTT | 54 | 1839 |
| 1362452 | N/A | N/A | 13369 | 13388 | GGTATACACCAGAGCGAGCA | 67 | 1840 |
| 1362490 | 1731 | 1750 | 18210 | 18229 | GCTTCAGTAGTCCATCGCCA | 16 | 201 |
| 1362494 | 1890 | 1909 | 18369 | 18388 | CACAGGGTTGTCATGGTAGC | 58 | 1841 |
| 1362523 | 2139 | 2158 | 18618 | 18637 | CCTTCAAATCACCTACGATG | 50 | 1842 |
| 1362563 | N/A | N/A | 5488 | 5507 | TGTTTTTAATGCACAACCTA | 114 | 1843 |
| 1362572 | N/A | N/A | 6524 | 6543 | TGATTATTTTAGTCAGTGTC | 73 | 1844 |
| 1362608 | 2387 | 2406 | 18866 | 18885 | AGATTACTCAAATTGAGATT | 72 | 1845 |

TABLE 25-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362628 | 2898 | 2917 | 19377 | 19396 | TCAAAACAAAACACAAGGTA | 65 | 1846 |
| 1362698 | 265 | 284 | 3975 | 3994 | TCTTTGGGACTCTGACTCCA | 100 | 1847 |
| 1362713 | 2164 | 2183 | 18643 | 18662 | TGCATCATTCTAAAACAAAT | 48 | 1848 |
| 1362728 | N/A | N/A | 15742 | 15761 | AAGCTACAAACTTCTCTTTT | 91 | 1849 |
| 1362749 | 1147 | 1166 | 17626 | 17645 | TGTGGTTAGAGCCTCGCTAT | 34 | 1850 |
| 1362759 | 2706 | 2725 | 19185 | 19204 | AAAGAACAACACAACTCTTT | 71 | 1851 |
| 1362786 | N/A | N/A | 7067 | 7086 | TTAATCAATCAGTACTTGCT | 107 | 1852 |
| 1362793 | 1410 | 1429 | 17889 | 17908 | CAGGAGATGCTTGAAAATTC | 54 | 1853 |
| 1362798 | 2676 | 2695 | 19155 | 19174 | AACTGTAGTACAAATCTTTC | 65 | 1854 |
| 1362807 | N/A | N/A | 10089 | 10108 | GTTAAGATACTAGATTCAGC | 101 | 1855 |
| 1362813 | 2852 | 2871 | 19331 | 19350 | GATTGGTTTCTTACAAAACA | 19 | 1856 |
| 1362824 | 1981 | 2000 | 18460 | 18479 | GTTACACCATTAGCCACCAG | 79 | 1857 |
| 1362847 | 1608 | 1627 | 18087 | 18106 | ACATTCTTTTTCTTCTATC | 56 | 1858 |
| 1362861 | 2539 | 2558 | 19018 | 19037 | TGGAAGCTTACCAACTGAAT | 81 | 1859 |
| 1362876 | 1851 | 1870 | 18330 | 18349 | GTGAGAAGATGCTGACAACA | 35 | 1860 |
| 1362929 | N/A | N/A | 16934 | 16953 | ACTACATTCACAGGGCACTG | 68 | 1861 |
| 1362931 | N/A | N/A | 15305 | 15324 | GATTCTACCAACAATCAGGA | 134 | 1862 |
| 1362989 | 2441 | 2460 | 18920 | 18939 | ACCAAGATAACATTGCTAAG | 57 | 1863 |
| 1363047 | N/A | N/A | 8758 | 8777 | ATAACATTTCTCAATGCAAC | 61 | 1864 |
| 1363054 | N/A | N/A | 13905 | 13924 | GGAACCTTTGAAAGGTGAGG | 46 | 1865 |
| 1363087 | N/A | N/A | 6243 | 6262 | AGACGACAACAGGCTTGCAG | 88 | 1866 |
| 1363111 | N/A | N/A | 12395 | 12414 | GAATCCTTACTTTGTTTCAT | 65 | 1867 |
| 1363121 | 1732 | 1751 | 18211 | 18230 | GGCTTCAGTAGTCCATCGCC | 34 | 279 |
| 1363149 | 1806 | 1825 | 18285 | 18304 | GTAAGGCCAGATGCCCCCTT | 56 | 1868 |
| 1363164 | N/A | N/A | 14681 | 14700 | AAACCAGGTTCCAGGGCTCT | 61 | 1869 |
| 1363241 | 1328 | 1347 | 17807 | 17826 | TTTCTAGCAGGAACCAGCTA | 67 | 1870 |
| 1363260 | 1742 | 1761 | 18221 | 18240 | GCTGAGTTAGGGCTTCAGTA | 45 | 1871 |
| 1363277 | 1221 | 1240 | 17700 | 17719 | CTCATCAAGTAAGAAGAGGG | 34 | 1872 |
| 1363324 | 2329 | 2348 | 18808 | 18827 | TGTAGAAAATCCCAATAGAT | 60 | 1873 |
| 1363325 | 2241 | 2260 | 18720 | 18739 | ATAATCAAAGAATTATTCTC | 76 | 1874 |
| 1363335 | 1443 | 1462 | 17922 | 17941 | GTACCCTTTGAGAAGAAATT | 53 | 1875 |
| 1363369 | N/A | N/A | 4796 | 4815 | AGACCCTTGTGCTCTGCACA | 43 | 1876 |
| 1363379 | N/A | N/A | 11751 | 11770 | TCAACTAACAATTCAGGCAG | 72 | 1877 |
| 1363418 | N/A | N/A | 9103 | 9122 | GAATCAGATTTTAGATTCTA | 118 | 1878 |
| 1363430 | 1491 | 1510 | 17970 | 17989 | TCTCTGTACCTGAGCATCTT | 37 | 1879 |
| 1363465 | 2206 | 2225 | 18685 | 18704 | CAACCCCAAATAAGTAATAA | 66 | 1880 |

TABLE 25-continued

Reduction of PLP1 RNA by 5-10-5 MOE gapmers with mixed
PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363538 | 1572 | 1591 | 18051 | 18070 | AGACCAGAATGAATTCCATT | 44 | 1881 |
| 1363588 | 2758 | 2777 | 19237 | 19256 | TTTTGTAAAGCTCTTACATC | 74 | 1882 |
| 1363594 | 2467 | 2486 | 18946 | 18965 | TTTATGTTAAACCTAACTCT | 87 | 1883 |
| 1363658 | N/A | N/A | 10771 | 10790 | CTTGGATTTTTGTATTCAAG | 73 | 1884 |
| 1363745 | 1526 | 1545 | 18005 | 18024 | CCCCTATAGATGGCAAGAGG | 83 | 1885 |
| 1363769 | 2305 | 2324 | 18784 | 18803 | CTAGCCAATTTTTAATATCA | 35 | 1886 |
| 1363780 | 1190 | 1209 | 17669 | 17688 | CAAAGGCAAAGAGTTAAGAT | 77 | 1887 |
| 1363791 | 2412 | 2431 | 18891 | 18910 | TTTCCATTAGCTAGAAAGAA | 46 | 1888 |
| 1363801 | 3000 | 3019 | 19479 | 19498 | GGAAACACTTTCAGTTGATT | 21 | 1889 |
| 1363802 | 2803 | 2822 | 19282 | 19301 | GAAGCTTATCTTGTATACTG | 26 | 1890 |
| 1363807 | 2359 | 2378 | 18838 | 18857 | CCAAATCTGTTTCTGCAAAG | 52 | 1891 |
| 1363828 | N/A | N/A | 5211 | 5230 | TACTTGATTCTCACAACCCT | 83 | 1892 |
| 1363839 | 3027 | 3046 | 19506 | 19525 | AAATTGCAATTCTATATCAG | 100 | 1893 |
| 1363867 | 1673 | 1692 | 18152 | 18171 | TGCTTTGACCCCCTTCTCCC | 76 | 1894 |
| 1363893 | N/A | N/A | 16673 | 16692 | GCAAAGTACTTGGCAACATT | 50 | 1895 |
| 1363911 | N/A | N/A | 5840 | 5859 | ACTGCAATTGTTGAACAGCA | 58 | 1896 |
| 1363923 | N/A | N/A | 9335 | 9354 | TCCACTACAGCTCAAAGCAA | 82 | 1897 |
| 1363942 | 2111 | 2130 | 18590 | 18609 | GATAATACCCCATGAAATGA | 82 | 1898 |
| 1363963 | N/A | N/A | 17177 | 17196 | TGACTTAGAGTCATAGGGTG | 81 | 1899 |
| 1364033 | N/A | N/A | 16326 | 16345 | AGGTCATTTGGAACTGCAGG | 59† | 1900 |
| 1364040 | 2493 | 2512 | 18972 | 18991 | GTGATCTATATCAGGAGAAA | 44 | 1901 |
| 1364068 | 1302 | 1321 | 17781 | 17800 | AAAATGACTAAAAGAGGTAC | 106 | 1902 |
| 1364075 | N/A | N/A | 7579 | 7598 | GTCAAATCATGTGGACAAGG | 72 | 1903 |
| 1364096 | 2025 | 2044 | 18504 | 18523 | TCCAAAGAGTTATCTATCCT | 43 | 1904 |
| 1364108 | 3066 | 3085 | 19545 | 19564 | TAAGATAAGTTTCTAAAAGT | 93 | 1905 |
| 1364110 | 2594 | 2613 | 19073 | 19092 | GACTGAAATCTGGGAGCTAT | 38 | 1906 |
| 1364149 | N/A | N/A | 11158 | 11177 | GCACACAAGAAGTCACAGGC | 41 | 1907 |
| 1364154 | 2269 | 2288 | 18748 | 18767 | TCCATTTTCCTAGTTTAAA | 59 | 1908 |
| 1364167 | 2058 | 2077 | 18537 | 18556 | ACACAACTAATTAACAGAAA | 103 | 1909 |
| 1364184 | N/A | N/A | 8294 | 8313 | ACTTACACAGATCCAGGTTC | 98 | 1910 |
| 1364186 | 2084 | 2103 | 18563 | 18582 | TGTGAAGATATGACAGAGGC | 59 | 1911 |
| 1364212 | 1369 | 1388 | 17848 | 17867 | GTGACTTGCAGTTGGGAAGT | 47 | 1912 |
| 1364222 | 1259 | 1278 | 17738 | 17757 | AGACCTTAATCACTGCAAGA | 60 | 1913 |
| 1364266 | 1932 | 1951 | 18411 | 18430 | TCATGTAAGCTAGTTTCCTT | 46 | 1914 |

TABLE 26

Reduction of PLP1 RNA by 5-10-5 MOE gapmers with mixed
PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362434 | 2897 | 2916 | 19376 | 19395 | CAAAACAAAACACAAGGTAC | 80 | 1915 |
| 1362470 | N/A | N/A | 11750 | 11769 | CAACTAACAATTCAGGCAGC | 88 | 1916 |
| 1362480 | N/A | N/A | 13904 | 13923 | GAACCTTTGAAAGGTGAGGC | 77 | 1917 |
| 1362490 | 1731 | 1750 | 18210 | 18229 | GCTTCAGTAGTCCATCGCCA | 23 | 201 |
| 1362504 | 2304 | 2323 | 18783 | 18802 | TAGCCAATTTTTAATATCAT | 99 | 1918 |
| 1362537 | 2057 | 2076 | 18536 | 18555 | CACAACTAATTAACAGAAAA | 122 | 1919 |
| 1362540 | N/A | N/A | 14679 | 14698 | ACCAGGTTCCAGGGCTCTCC | 39 | 1920 |
| 1362576 | N/A | N/A | 5836 | 5855 | CAATTGTTGAACAGCAGTGC | 82 | 1921 |
| 1362579 | 1889 | 1908 | 18368 | 18387 | ACAGGGTTGTCATGGTAGCT | 36 | 1922 |
| 1362596 | 2591 | 2610 | 19070 | 19089 | TGAAATCTGGGAGCTATTCA | 102 | 1923 |
| 1362614 | 1220 | 1239 | 17699 | 17718 | TCATCAAGTAAGAAGAGGGC | 73 | 1924 |
| 1362627 | 2328 | 2347 | 18807 | 18826 | GTAGAAAATCCCAATAGATT | 49 | 1925 |
| 1362646 | N/A | N/A | 9334 | 9353 | CCACTACAGCTCAAAGCAAG | 117 | 1926 |
| 1362743 | N/A | N/A | 6241 | 6260 | ACGACAACAGGCTTGCAGAC | 91 | 1927 |
| 1362753 | N/A | N/A | 8290 | 8309 | ACACAGATCCAGGTTCATCA | 80 | 1928 |
| 1362754 | 2411 | 2430 | 18890 | 18909 | TTCCATTAGCTAGAAAGAAC | 54 | 1929 |
| 1362773 | 1741 | 1760 | 18220 | 18239 | CTGAGTTAGGGCTTCAGTAG | 39 | 1930 |
| 1362777 | N/A | N/A | 16291 | 16310 | GAACTGTTTCTTGCAACAGC | 98 | 1931 |
| 1362834 | 1850 | 1869 | 18329 | 18348 | TGAGAAGATGCTGACAACAC | 92 | 1932 |
| 1362848 | 2850 | 2869 | 19329 | 19348 | TTGGTTTCTTACAAAACATT | 57 | 1933 |
| 1362853 | 1258 | 1277 | 17737 | 17756 | GACCTTAATCACTGCAAGAC | 61 | 1934 |
| 1362862 | N/A | N/A | 17175 | 17194 | ACTTAGAGTCATAGGGTGCT | 38 | 1935 |
| 1362869 | N/A | N/A | 16672 | 16691 | CAAAGTACTTGGCAACATTA | 87 | 1936 |
| 1362882 | 1366 | 1385 | 17845 | 17864 | ACTTGCAGTTGGGAAGTCAT | 61 | 1937 |
| 1362904 | 2757 | 2776 | 19236 | 19255 | TTTGTAAAGCTCTTACATCT | 39 | 1938 |
| 1362915 | 2163 | 2182 | 18642 | 18661 | GCATCATTCTAAAACAAATC | 36 | 1939 |
| 1362919 | 2024 | 2043 | 18503 | 18522 | CCAAAGAGTTATCTATCCTG | 50 | 1940 |
| 1362937 | N/A | N/A | 5210 | 5229 | ACTTGATTCTCACAACCCTG | 40 | 1941 |
| 1362959 | N/A | N/A | 7484 | 7503 | TGTTTCCTATACTCCCCACT | 66 | 1942 |
| 1362964 | N/A | N/A | 10086 | 10105 | AAGATACTAGATTCAGCCTA | 111 | 1943 |
| 1362990 | 1301 | 1320 | 17780 | 17799 | AAATGACTAAAAGAGGTACA | 87 | 1944 |
| 1362998 | 2268 | 2287 | 18747 | 18766 | CCAATTTTCCTAGTTTAAAA | 63 | 1945 |
| 1363050 | 2357 | 2376 | 18836 | 18855 | AAATCTGTTTCTGCAAAGGC | 55 | 1946 |
| 1363070 | 1672 | 1691 | 18151 | 18170 | GCTTTGACCCCCTTCTCCCA | 63 | 1947 |
| 1363119 | 2083 | 2102 | 18562 | 18581 | GTGAAGATATGACAGAGGCC | 49 | 1948 |
| 1363121 | 1732 | 1751 | 18211 | 18230 | GGCTTCAGTAGTCCATCGCC | 18 | 279 |

TABLE 26-continued

Reduction of PLP1 RNA by 5-10-5 MOE gapmers with mixed
PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363124 | 2386 | 2405 | 18865 | 18884 | GATTACTCAAATTGAGATTC | 40 | 1949 |
| 1363138 | N/A | N/A | 15302 | 15321 | TCTACCAACAATCAGGATCC | 84 | 1950 |
| 1363163 | 2798 | 2817 | 19277 | 19296 | TTATCTTGTATACTGGTTTG | 32 | 1951 |
| 1363218 | N/A | N/A | 16932 | 16951 | TACATTCACAGGGCACTGTA | 89 | 1952 |
| 1363236 | 1602 | 1621 | 18081 | 18100 | TTTTTTCTTCTATCTTCAGT | 75 | 1953 |
| 1363238 | 247 | 266 | 3957 | 3976 | CAATTGTAGCCGGCTGGCTA | 99 | 1954 |
| 1363262 | N/A | N/A | 4784 | 4803 | TCTGCACACATTACTCTGAG | 79 | 1955 |
| 1363274 | 1327 | 1346 | 17806 | 17825 | TTCTAGCAGGAACCAGCTAT | 58 | 1956 |
| 1363284 | 2466 | 2485 | 18945 | 18964 | TTATGTTAAACCTAACTCTT | 98 | 1957 |
| 1363286 | 1804 | 1823 | 18283 | 18302 | AAGGCCAGATGCCCCCTTCG | 38 | 1958 |
| 1363302 | 1407 | 1426 | 17886 | 17905 | GAGATGCTTGAAAATTCAAT | 55 | 1959 |
| 1363352 | 2205 | 2224 | 18684 | 18703 | AACCCCAAATAAGTAATAAA | 48 | 1960 |
| 1363366 | 1189 | 1208 | 17668 | 17687 | AAAGGCAAAGAGTTAAGATG | 98 | 1961 |
| 1363420 | N/A | N/A | 5454 | 5473 | CTGACATTAGATAGGATTCC | 107 | 1962 |
| 1363432 | 2999 | 3018 | 19478 | 19497 | GAAACACTTTCAGTTGATTA | 75 | 1963 |
| 1363461 | N/A | N/A | 11157 | 11176 | CACACAAGAAGTCACAGGCT | 82 | 1964 |
| 1363474 | 1146 | 1165 | 17625 | 17644 | GTGGTTAGAGCCTCGCTATT | 28 | 1965 |
| 1363477 | 1442 | 1461 | 17921 | 17940 | TACCCTTTGAGAAGAAATTA | 86 | 1966 |
| 1363515 | 2110 | 2129 | 18589 | 18608 | ATAATACCCCATGAAATGAG | 70 | 1967 |
| 1363627 | 2675 | 2694 | 19154 | 19173 | ACTGTAGTACAAATCTTTCC | 23 | 1968 |
| 1363657 | 3026 | 3045 | 19505 | 19524 | AATTGCAATTCTATATCAGA | 84 | 1969 |
| 1363690 | 2138 | 2157 | 18617 | 18636 | CTTCAAATCACCTACGATGA | 73 | 1970 |
| 1363724 | 1571 | 1590 | 18050 | 18069 | GACCAGAATGAATTCCATTT | 31 | 1971 |
| 1363739 | N/A | N/A | 11990 | 12009 | TCAGCAATTCAAATAGCAAG | 89 | 1972 |
| 1363743 | 1980 | 1999 | 18459 | 18478 | TTACACCATTAGCCACCAGC | 61 | 1973 |
| 1363774 | N/A | N/A | 6518 | 6537 | TTTTAGTCAGTGTCTCCAGG | 76 | 1974 |
| 1363845 | 1929 | 1948 | 18408 | 18427 | TGTAAGCTAGTTTCCTTCTA | 52 | 1975 |
| 1363880 | 2492 | 2511 | 18971 | 18990 | TGATCTATATCAGGAGAAAA | 75 | 1976 |
| 1363896 | 1525 | 1544 | 18004 | 18023 | CCCTATAGATGGCAAGAGGA | 74 | 1977 |
| 1363906 | 3065 | 3084 | 19544 | 19563 | AAGATAAGTTTCTAAAAGTT | 81 | 1978 |
| 1363910 | N/A | N/A | 7066 | 7085 | TAATCAATCAGTACTTGCTG | 77 | 1979 |
| 1363928 | 2240 | 2259 | 18719 | 18738 | TAATCAAAGAATTATTCTCC | 90 | 1980 |
| 1363941 | 2440 | 2459 | 18919 | 18938 | CCAAGATAACATTGCTAAGT | 44 | 1981 |
| 1363966 | N/A | N/A | 9099 | 9118 | CAGATTTAGATTCTAACTG | 118 | 1982 |
| 1363986 | 2646 | 2665 | 19125 | 19144 | AACCAATCAGACTTTTTTTT | 67 | 1983 |
| 1364004 | N/A | N/A | 15711 | 15730 | GGTTGGAAAGGAAGTCTTTC | 65 | 1984 |

TABLE 26-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1364014 | N/A | N/A | 13368 | 13387 | GTATACACCAGAGCGAGCAC | 67 | 1985 |
| 1364053 | 2538 | 2557 | 19017 | 19036 | GGAAGCTTACCAACTGAATA | 75 | 1986 |
| 1364087 | 2705 | 2724 | 19184 | 19203 | AAGAACAACACAACTCTTTA | 85 | 1987 |
| 1364143 | 1487 | 1506 | 17966 | 17985 | TGTACCTGAGCATCTTTCCT | 37 | 1988 |
| 1364168 | 1057 | 1076 | 17536 | 17555 | TTGTAAGTGGCAGCAATCAT | 61 | 1989 |
| 1364194 | N/A | N/A | 10768 | 10787 | GGATTTTGTATTCAAGCAT | 99 | 1990 |
| 1364211 | N/A | N/A | 8755 | 8774 | ACATTTCTCAATGCAACTCA | 60 | 1991 |

TABLE 27

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362457 | 2384 | 2403 | 18863 | 18882 | TTACTCAAATTGAGATTCAA | 48 | 1992 |
| 1362469 | N/A | N/A | 9235 | 9254 | AAGCTATAAACAATTCAGTA | 78 | 1993 |
| 1362475 | 1978 | 1997 | 18457 | 18476 | ACACCATTAGCCACCAGCAA | 53 | 1994 |
| 1362484 | 1144 | 1163 | 17623 | 17642 | GGTTAGAGCCTCGCTATTAG | 32 | 119 |
| 1362490 | 1731 | 1750 | 18210 | 18229 | GCTTCAGTAGTCCATCGCCA | 20 | 201 |
| 1362501 | 184 | 203 | 3894 | 3913 | CTCTCCAGCCTCCTTCTTCG | 76 | 1995 |
| 1362546 | 2356 | 2375 | 18835 | 18854 | AATCTGTTTCTGCAAAGGCA | 38 | 1996 |
| 1362552 | 2796 | 2815 | 19275 | 19294 | ATCTTGTATACTGGTTTGAA | 47 | 1997 |
| 1362574 | 2847 | 2866 | 19326 | 19345 | GTTTCTTACAAAACATTTTC | 32 | 1998 |
| 1362592 | N/A | N/A | 16910 | 16929 | ACTATCAGCAAGACCTGGGA | 77 | 1999 |
| 1362594 | 2109 | 2128 | 18588 | 18607 | TAATACCCCATGAAATGAGC | 50 | 2000 |
| 1362616 | 1300 | 1319 | 17779 | 17798 | AATGACTAAAAGAGGTACAT | 61 | 2001 |
| 1362659 | 1786 | 1805 | 18265 | 18284 | CGTCTACACAGATTCTACGC | 28 | 2002 |
| 1362700 | 1927 | 1946 | 18406 | 18425 | TAAGCTAGTTTCCTTCTATT | 53 | 2003 |
| 1362719 | 2239 | 2258 | 18718 | 18737 | AATCAAAGAATTATTCTCCA | 40 | 2004 |
| 1362721 | 2439 | 2458 | 18918 | 18937 | CAAGATAACATTGCTAAGTA | 67 | 2005 |
| 1362751 | N/A | N/A | 13364 | 13383 | ACACCAGAGCGAGCACCTTA | 65 | 2006 |
| 1362768 | 2896 | 2915 | 19375 | 19394 | AAAACAAAACACAAGGTACG | 75 | 2007 |
| 1362808 | 2755 | 2774 | 19234 | 19253 | TGTAAAGCTCTTACATCTCC | 31 | 2008 |
| 1362820 | N/A | N/A | 7404 | 7423 | ATGATGTACACATTCCAATT | 67 | 2009 |
| 1362842 | 3025 | 3044 | 19504 | 19523 | ATTGCAATTCTATATCAGAA | 28 | 2010 |
| 1362879 | N/A | N/A | 11156 | 11175 | ACACAAGAAGTCACAGGCTC | 65 | 2011 |
| 1362881 | N/A | N/A | 8272 | 8291 | CAAGGGACTGTGTTGATCCT | 67 | 2012 |

TABLE 27-continued

Reduction of PLP1 RNA by 5-10-5 MOE gapmers with mixed
PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362993 | 1056 | 1075 | 17535 | 17554 | TGTAAGTGGCAGCAATCATG | 36 | 2013 |
| 1363022 | 1569 | 1588 | 18048 | 18067 | CCAGAATGAATTCCATTTTG | 25 | 2014 |
| 1363024 | 1441 | 1460 | 17920 | 17939 | ACCCTTTGAGAAGAAATTAC | 60 | 2015 |
| 1363053 | 1326 | 1345 | 17805 | 17824 | TCTAGCAGGAACCAGCTATG | 63 | 2016 |
| 1363121 | 1732 | 1751 | 18211 | 18230 | GGCTTCAGTAGTCCATCGCC | 29 | 279 |
| 1363171 | 2704 | 2723 | 19183 | 19202 | AGAACAACACAACTCTTTAC | 57 | 2017 |
| 1363186 | 2327 | 2346 | 18806 | 18825 | TAGAAAATCCCAATAGATTC | 52 | 2018 |
| 1363229 | 2204 | 2223 | 18683 | 18702 | ACCCCAAATAAGTAATAAAC | 39 | 2019 |
| 1363242 | 2162 | 2181 | 18641 | 18660 | CATCATTCTAAAACAAATCA | 52 | 2020 |
| 1363258 | N/A | N/A | 6500 | 6519 | GGAAGACTAGGTGAACATGC | 67 | 2021 |
| 1363327 | N/A | N/A | 8656 | 8675 | GTTTATGTGAATTCAGTACA | 54 | 2022 |
| 1363330 | N/A | N/A | 14525 | 14544 | GCTTCAGAGGATGTTTTTGG | 27 | 2023 |
| 1363365 | 2265 | 2284 | 18744 | 18763 | ATTTTCCTAGTTTAAAAAAC | 77 | 2024 |
| 1363368 | 1365 | 1384 | 17844 | 17863 | CTTGCAGTTGGGAAGTCATC | 64 | 2025 |
| 1363375 | 1740 | 1759 | 18219 | 18238 | TGAGTTAGGGCTTCAGTAGT | 50 | 2026 |
| 1363377 | N/A | N/A | 9016 | 9035 | TGAGAAAAGATCCATTGGGC | 70 | 2027 |
| 1363411 | N/A | N/A | 5453 | 5472 | TGACATTAGATAGGATTCCT | 88 | 2028 |
| 1363444 | N/A | N/A | 11749 | 11768 | AACTAACAATTCAGGCAGCC | 57 | 2029 |
| 1363468 | 2465 | 2484 | 18944 | 18963 | TATGTTAAACCTAACTCTTA | 77 | 2030 |
| 1363481 | N/A | N/A | 5835 | 5854 | AATTGTTGAACAGCAGTGCA | 97 | 2031 |
| 1363497 | N/A | N/A | 6239 | 6258 | GACAACAGGCTTGCAGACAA | 43 | 2032 |
| 1363502 | 1881 | 1900 | 18360 | 18379 | GTCATGGTAGCTGTTATCAA | 28 | 2033 |
| 1363505 | N/A | N/A | 15301 | 15320 | CTACCAACAATCAGGATCCT | 75 | 2034 |
| 1363512 | 2491 | 2510 | 18970 | 18989 | GATCTATATCAGGAGAAAAT | 50 | 2035 |
| 1363548 | N/A | N/A | 16255 | 16274 | GTAAATCATGAATACAGCTT | 43 | 2036 |
| 1363560 | 1671 | 1690 | 18150 | 18169 | CTTTGACCCCCTTCTCCCAG | 73 | 2037 |
| 1363572 | 1257 | 1276 | 17736 | 17755 | ACCTTAATCACTGCAAGACT | 58 | 2038 |
| 1363574 | N/A | N/A | 5150 | 5169 | TGAGGAAGTGGTGATTCAGT | 100 | 2039 |
| 1363612 | 2590 | 2609 | 19069 | 19088 | GAAATCTGGGAGCTATTCAG | 46 | 2040 |
| 1363616 | 3064 | 3083 | 19543 | 19562 | AGATAAGTTTCTAAAAGTTT | 68 | 2041 |
| 1363617 | N/A | N/A | 16670 | 16689 | AAGTACTTGGCAACATTACA | 45 | 2042 |
| 1363624 | 2023 | 2042 | 18502 | 18521 | CAAAGAGTTATCTATCCTGT | 83 | 2043 |
| 1363629 | 1406 | 1425 | 17885 | 17904 | AGATGCTTGAAAATTCAATT | 47 | 2044 |
| 1363695 | 1188 | 1207 | 17667 | 17686 | AAGGCAAAGAGTTAAGATGG | 63 | 2045 |
| 1363723 | 1486 | 1505 | 17965 | 17984 | GTACCTGAGCATCTTTCCTT | 29 | 2046 |
| 1363726 | N/A | N/A | 11989 | 12008 | CAGCAATTCAAATAGCAAGC | 39 | 2047 |

TABLE 27-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363766 | 2410 | 2429 | 18889 | 18908 | TCCATTAGCTAGAAAGAACG | 45 | 2048 |
| 1363779 | N/A | N/A | 10767 | 10786 | GATTTTTGTATTCAAGCATT | 73 | 2049 |
| 1363793 | 2627 | 2646 | 19106 | 19125 | TTTTTTAACCCAAAGTTAAC | 80 | 2050 |
| 1363821 | N/A | N/A | 13886 | 13905 | GCTAAGCCAGCTGGGCACCA | 61 | 2051 |
| 1363855 | 1849 | 1868 | 18328 | 18347 | GAGAAGATGCTGACAACACC | 47 | 2052 |
| 1363859 | N/A | N/A | 10085 | 10104 | AGATACTAGATTCAGCCTAT | 85 | 2053 |
| 1363925 | 2302 | 2321 | 18781 | 18800 | GCCAATTTTTAATATCATTT | 36 | 2054 |
| 1363940 | 2674 | 2693 | 19153 | 19172 | CTGTAGTACAAATCTTTCCT | 28 | 2055 |
| 1363961 | 2082 | 2101 | 18561 | 18580 | TGAAGATATGACAGAGGCCA | 44 | 2056 |
| 1363977 | 2997 | 3016 | 19476 | 19495 | AACACTTTCAGTTGATTAAC | 59 | 2057 |
| 1363979 | N/A | N/A | 4782 | 4801 | TGCACACATTACTCTGAGTA | 72 | 2058 |
| 1363992 | 2137 | 2156 | 18616 | 18635 | TTCAAATCACCTACGATGAC | 76 | 2059 |
| 1364027 | 2056 | 2075 | 18535 | 18554 | ACAACTAATTAACAGAAAAA | 102 | 2060 |
| 1364080 | 1595 | 1614 | 18074 | 18093 | TTCTATCTTCAGTGGTAATA | 47 | 2061 |
| 1364172 | N/A | N/A | 15707 | 15726 | GGAAAGGAAGTCTTTCTATG | 52 | 2062 |
| 1364199 | 1219 | 1238 | 17698 | 17717 | CATCAAGTAAGAAGAGGGCC | 61 | 2063 |
| 1364214 | N/A | N/A | 7063 | 7082 | TCAATCAGTACTTGCTGAGC | 51 | 2064 |
| 1364237 | N/A | N/A | 17174 | 17193 | CTTAGAGTCATAGGGTGCTT | 63 | 2065 |
| 1364254 | 1524 | 1543 | 18003 | 18022 | CCTATAGATGGCAAGAGGAC | 72 | 2066 |
| 1364268 | 2537 | 2556 | 19016 | 19035 | GAAGCTTACCAACTGAATAG | 43 | 2067 |

TABLE 28

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362440 | 2996 | 3015 | 19475 | 19494 | ACACTTTCAGTTGATTAACT | 35 | 2068 |
| 1362444 | N/A | N/A | 15299 | 15318 | ACCAACAATCAGGATCCTCT | 70 | 2069 |
| 1362455 | 2409 | 2428 | 18888 | 18907 | CCATTAGCTAGAAAGAACGA | 50 | 2070 |
| 1362490 | 1731 | 1750 | 18210 | 18229 | GCTTCAGTAGTCCATCGCCA | 13 | 201 |
| 1362502 | 1299 | 1318 | 17778 | 17797 | ATGACTAAAAGAGGTACATA | 84 | 2071 |
| 1362522 | N/A | N/A | 14521 | 14540 | CAGAGGATGTTTTTGGGCAG | 40 | 2072 |
| 1362585 | 2301 | 2320 | 18780 | 18799 | CCAATTTTTAATATCATTTG | 67 | 2073 |
| 1362605 | N/A | N/A | 11987 | 12006 | GCAATTCAAATAGCAAGCCA | 31 | 2074 |
| 1362654 | N/A | N/A | 11128 | 11147 | GCTGTGTTCCAAGTACTAGT | 66 | 2075 |

TABLE 28-continued

Reduction of PLP1 RNA by 5-10-5 MOE gapmers with mixed PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1362667 | N/A | N/A | 7062 | 7081 | CAATCAGTACTTGCTGAGCT | 38 | 2076 |
| 1362668 | N/A | N/A | 10763 | 10782 | TTTGTATTCAAGCATTTCTC | 70 | 2077 |
| 1362673 | N/A | N/A | 10084 | 10103 | GATACTAGATTCAGCCTATA | 72 | 2078 |
| 1362717 | N/A | N/A | 5120 | 5139 | AGGTCACATAGTTCATAAGT | 88 | 2079 |
| 1362727 | 1053 | 1072 | 17532 | 17551 | AAGTGGCAGCAATCATGAAG | 50 | 2080 |
| 1362734 | 1785 | 1804 | 18264 | 18283 | GTCTACACAGATTCTACGCT | 30 | 285 |
| 1362760 | 2795 | 2814 | 19274 | 19293 | TCTTGTATACTGGTTTGAAA | 55 | 2081 |
| 1362762 | N/A | N/A | 17170 | 17189 | GAGTCATAGGGTGCTTGCTG | 54 | 2082 |
| 1362772 | N/A | N/A | 16909 | 16928 | CTATCAGCAAGACCTGGGAC | 66 | 2083 |
| 1362790 | 1924 | 1943 | 18403 | 18422 | GCTAGTTTCCTTCTATTCTC | 15 | 2084 |
| 1362837 | 1364 | 1383 | 17843 | 17862 | TTGCAGTTGGGAAGTCATCT | 41 | 2085 |
| 1362845 | 2464 | 2483 | 18943 | 18962 | ATGTTAAACCTAACTCTTAA | 53 | 2086 |
| 1362891 | N/A | N/A | 6438 | 6457 | GCATTCTTGCCATTTTGATG | 51 | 2087 |
| 1362894 | N/A | N/A | 13759 | 13778 | CCCAATTTTCCCCCACCCCT | 63 | 2088 |
| 1362901 | 2081 | 2100 | 18560 | 18579 | GAAGATATGACAGAGGCCAG | 36 | 2089 |
| 1362903 | 1977 | 1996 | 18456 | 18475 | CACCATTAGCCACCAGCAAC | 36 | 2090 |
| 1362927 | 1735 | 1754 | 18214 | 18233 | TAGGGCTTCAGTAGTCCATC | 12 | 2091 |
| 1362972 | 1405 | 1424 | 17884 | 17903 | GATGCTTGAAAATTCAATTA | 34 | 2092 |
| 1363094 | 2895 | 2914 | 19374 | 19393 | AAACAAAACACAAGGTACGG | 27 | 2093 |
| 1363121 | 1732 | 1751 | 18211 | 18230 | GGCTTCAGTAGTCCATCGCC | 25 | 279 |
| 1363132 | 2536 | 2555 | 19015 | 19034 | AAGCTTACCAACTGAATAGC | 47 | 2094 |
| 1363153 | 3023 | 3042 | 19502 | 19521 | TGCAATTCTATATCAGAAAT | 38 | 2095 |
| 1363156 | N/A | N/A | 15705 | 15724 | AAAGGAAGTCTTTCTATGCA | 60 | 2096 |
| 1363194 | 2108 | 2127 | 18587 | 18606 | AATACCCCATGAAATGAGCA | 33 | 2097 |
| 1363210 | 1256 | 1275 | 17735 | 17754 | CCTTAATCACTGCAAGACTC | 37 | 2098 |
| 1363226 | 2018 | 2037 | 18497 | 18516 | AGTTATCTATCCTGTGTCTA | 51 | 2099 |
| 1363233 | 2589 | 2608 | 19068 | 19087 | AAATCTGGGAGCTATTCAGG | 50 | 2100 |
| 1363235 | 2673 | 2692 | 19152 | 19171 | TGTAGTACAAATCTTTCCTT | 16 | 2101 |
| 1363249 | 2160 | 2179 | 18639 | 18658 | TCATTCTAAAACAAATCAAG | 80 | 2102 |
| 1363267 | N/A | N/A | 7403 | 7422 | TGATGTACACATTCCAATTT | 54 | 2103 |
| 1363310 | 1880 | 1899 | 18359 | 18378 | TCATGGTAGCTGTTATCAAG | 35 | 2104 |
| 1363312 | 1187 | 1206 | 17666 | 17685 | AGGCAAAGAGTTAAGATGGG | 40 | 2105 |
| 1363334 | 2845 | 2864 | 19324 | 19343 | TTCTTACAAAACATTTTCCC | 42 | 2106 |
| 1363336 | N/A | N/A | 8169 | 8188 | GCTCCATGATGGAAATTCAG | 68 | 2107 |
| 1363402 | 2625 | 2644 | 19104 | 19123 | TTTTAACCCAAAGTTAACAA | 64 | 2108 |
| 1363415 | 1141 | 1160 | 17620 | 17639 | TAGAGCCTCGCTATTAGAGA | 24 | 2109 |

TABLE 28-continued

Reduction of PLP1 RNA by 5-10-5 MOE gapmers with mixed
PO/PS internucleoside linkages in SK-MEL-28 cells

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | PLP1 (% UTC) | SEQ ID No. |
|---|---|---|---|---|---|---|---|
| 1363471 | N/A | N/A | 9013 | 9032 | GAAAAGATCCATTGGGCTCC | 56 | 2110 |
| 1363485 | 2754 | 2773 | 19233 | 19252 | GTAAAGCTCTTACATCTCCT | 11 | 2111 |
| 1363540 | 2136 | 2155 | 18615 | 18634 | TCAAATCACCTACGATGACT | 71 | 2112 |
| 1363561 | 2203 | 2222 | 18682 | 18701 | CCCCAAATAAGTAATAAACA | 36 | 2113 |
| 1363562 | N/A | N/A | 5833 | 5852 | TTGTTGAACAGCAGTGCACT | 85 | 2114 |
| 1363600 | N/A | N/A | 6230 | 6249 | CTTGCAGACAATGTTTTGCT | 40 | 2115 |
| 1363615 | 1325 | 1344 | 17804 | 17823 | CTAGCAGGAACCAGCTATGA | 36 | 2116 |
| 1363669 | N/A | N/A | 5452 | 5471 | GACATTAGATAGGATTCCTG | 93 | 2117 |
| 1363689 | 2263 | 2282 | 18742 | 18761 | TTTCCTAGTTTAAAAAACAG | 72 | 2118 |
| 1363717 | 2055 | 2074 | 18534 | 18553 | CAACTAATTAACAGAAAAAA | 92 | 2119 |
| 1363719 | 1844 | 1863 | 18323 | 18342 | GATGCTGACAACACCCTGTT | 40 | 2120 |
| 1363740 | 2490 | 2509 | 18969 | 18988 | ATCTATATCAGGAGAAAATA | 68 | 2121 |
| 1363749 | N/A | N/A | 16665 | 16684 | CTTGGCAACATTACATGTTC | 38 | 2122 |
| 1363752 | 1218 | 1237 | 17697 | 17716 | ATCAAGTAAGAAGAGGGCCA | 50 | 2123 |
| 1363784 | 1440 | 1459 | 17919 | 17938 | CCCTTTGAGAAGAAATTACT | 48 | 2124 |
| 1363832 | 2437 | 2456 | 18916 | 18935 | AGATAACATTGCTAAGTAAA | 60 | 2125 |
| 1363853 | 2238 | 2257 | 18717 | 18736 | ATCAAAGAATTATTCTCCAG | 38 | 2126 |
| 1363862 | 1555 | 1574 | 18034 | 18053 | ATTTTGTACACCAAAGAGAA | 70 | 2127 |
| 1363898 | N/A | N/A | 9227 | 9246 | AACAATTCAGTAATATCAGC | 54 | 2128 |
| 1363908 | 1485 | 1504 | 17964 | 17983 | TACCTGAGCATCTTTCCTTC | 38 | 2129 |
| 1363926 | N/A | N/A | 13301 | 13320 | CATGCTTTCACCTTATCTTT | 47 | 2130 |
| 1363939 | 1523 | 1542 | 18002 | 18021 | CTATAGATGGCAAGAGGACC | 67 | 2131 |
| 1363944 | N/A | N/A | 16251 | 16270 | ATCATGAATACAGCTTTCTG | 74 | 2132 |
| 1363973 | 2326 | 2345 | 18805 | 18824 | AGAAAATCCCAATAGATTCA | 37 | 2133 |
| 1363989 | 1594 | 1613 | 18073 | 18092 | TCTATCTTCAGTGGTAATAG | 29 | 2134 |
| 1364057 | N/A | N/A | 11748 | 11767 | ACTAACAATTCAGGCAGCCA | 47 | 2135 |
| 1364076 | 3063 | 3082 | 19542 | 19561 | GATAAGTTTCTAAAAGTTTA | 56 | 2136 |
| 1364120 | N/A | N/A | 8651 | 8670 | TGTGAATTCAGTACAAGAAT | 62 | 2137 |
| 1364122 | 2351 | 2370 | 18830 | 18849 | GTTTCTGCAAAGGCAGAATA | 83 | 2138 |
| 1364127 | 2703 | 2722 | 19182 | 19201 | GAACAACACAACTCTTTACA | 40 | 2139 |
| 1364148 | N/A | N/A | 4780 | 4799 | CACACATTACTCTGAGTAGA | 36 | 2140 |
| 1364190 | 1668 | 1687 | 18147 | 18166 | TGACCCCTTCTCCCAGCTG | 49 | 2141 |
| 1364231 | 149 | 168 | 3859 | 3878 | TCTCTGAGTATCTTTGTCCT | 75 | 2142 |
| 1364241 | 2383 | 2402 | 18862 | 18881 | TACTCAAATTGAGATTCAAA | 54 | 2143 |

Example 3: Effect of Modified Oligonucleotides on Human PLP1 RNA In Vitro, Multiple Doses Modified oligonucleotides selected from the examples above were tested at various doses in SK-MEL-28 cells. Cultured SK-MEL-28 cells at a density of 20,000 cells per well were transfected using electroporation with concentrations of modified oligonucleotides as specified in the tables below. After a treatment period of approximately 24 hours, total RNA was isolated from the cells and PLP1 RNA levels were measured by quantitative real-time RTPCR. Human PLP1 primer probe set RTS35092 was used to measure RNA levels, as described above. PLP1 RNA levels were normalized to total RNA content, as measured by RIBOGREEN®. The modified oligonucleotides were tested in a series of experiments using the same culture conditions, and the results for each experiment are presented in separate tables below. Reduction of PLP1 RNA is presented in the tables below as percent PLP1 RNA relative to the amount in untreated control cells (% UTC).

The half maximal inhibitory concentration ($IC_{50}$) of each modified oligonucleotide was calculated using a linear regression on a log/linear plot of the data in Excel and is also presented in the tables below.

TABLE 29

Dose-dependent reduction of human PLP1 RNA in SK-MEL-28 cells by modified oligonucleotides

| Compound ID | PLP1 (% UTC) | | | | $IC_{50}$ (μM) |
|---|---|---|---|---|---|
| | 556 nM | 1667 nM | 5000 nM | 15000 nM | |
| 1218118 | 89 | 66 | 35 | 22 | 3.3 |
| 1218157 | 69 | 45 | 21 | 15 | 1.4 |
| 1218162 | 74 | 54 | 28 | 18 | 2.0 |
| 1218165 | 73 | 51 | 23 | 9 | 1.6 |
| 1218166 | 79 | 55 | 41 | 21 | 2.7 |
| 1218178 | 83 | 56 | 34 | 18 | 2.6 |
| 1218179 | 55 | 24 | 12 | 10 | <0.6 |
| 1218181 | 57 | 41 | 23 | 15 | 0.8 |
| 1218186 | 67 | 44 | 23 | 25 | 1.3 |
| 1218190 | 80 | 55 | 34 | 20 | 2.5 |
| 1218193 | 67 | 38 | 20 | 9 | 1.1 |
| 1218209 | 60 | 33 | 19 | 6 | 0.8 |
| 1218221 | 79 | 56 | 32 | 13 | 2.3 |
| 1218222 | 71 | 44 | 32 | 21 | 1.7 |
| 1218225 | 70 | 45 | 23 | 7 | 1.4 |
| 1218226 | 78 | 53 | 29 | 17 | 2.1 |
| 1218229 | 70 | 44 | 21 | 9 | 1.4 |
| 1218233 | 82 | 61 | 31 | 13 | 2.5 |
| 1218354 | 71 | 43 | 22 | 18 | 1.4 |

TABLE 30

Dose-dependent reduction of human PLP1 RNA in SK-MEL-28 cells by modified oligonucleotides

| Compound ID | PLP1 (% UTC) | | | | $IC_{50}$ (μM) |
|---|---|---|---|---|---|
| | 556 nM | 1667 nM | 5000 nM | 15000 nM | |
| 1218163 | 61 | 31 | 13 | 7 | 0.8 |
| 1218168 | 69 | 46 | 26 | 18 | 1.5 |
| 1218175 | 64 | 36 | 22 | 14 | 1.0 |
| 1218180 | 72 | 52 | 25 | 15 | 1.8 |
| 1218188 | 72 | 45 | 29 | 24 | 1.7 |
| 1218191 | 75 | 51 | 26 | 13 | 1.8 |
| 1218192 | 75 | 47 | 23 | 11 | 1.7 |
| 1218203 | 74 | 50 | 22 | 7 | 1.6 |
| 1218204 | 50 | 57 | 31 | 31 | 1.0 |
| 1218208 | 63 | 34 | 17 | 10 | 0.9 |
| 1218209 | 61 | 33 | 27 | 10 | 0.8 |
| 1218215 | 75 | 47 | 17 | 5 | 1.5 |
| 1218216 | 68 | 47 | 36 | 18 | 1.7 |
| 1218219 | 61 | 31 | 19 | 8 | 0.8 |
| 1218220 | 85 | 65 | 37 | 16 | 3.0 |
| 1218223 | 60 | 34 | 23 | 10 | 0.8 |
| 1218228 | 67 | 44 | 22 | 13 | 1.3 |
| 1218355 | 75 | 46 | 21 | 9 | 1.6 |
| 1218387 | 62 | 33 | 21 | 19 | 0.8 |

TABLE 31

Dose-dependent reduction of human PLP1 RNA in SK-MEL-28 cells by modified oligonucleotides

| Compound ID | PLP1 (% UTC) | | | | $IC_{50}$ (μM) |
|---|---|---|---|---|---|
| | 94 nM | 375 nM | 1500 nM | 6000 nM | |
| 1362449 | 107 | 88 | 67 | 28 | 2.5 |
| 1362490 | 82 | 45 | 21 | 10 | 0.4 |
| 1362496 | 81 | 49 | 21 | 11 | 0.4 |
| 1362641 | 92 | 65 | 30 | 14 | 0.8 |
| 1362987 | 89 | 78 | 43 | 29 | 1.4 |
| 1363103 | 123 | 81 | 35 | 10 | 1.2 |
| 1363134 | 75 | 57 | 26 | 10 | 0.5 |
| 1363184 | 104 | 78 | 59 | 16 | 1.5 |
| 1363410 | 100 | 66 | 27 | 12 | 0.8 |
| 1363439 | 91 | 63 | 40 | 21 | 0.9 |
| 1363641 | 80 | 48 | 18 | 10 | 0.4 |
| 1363734 | 80 | 59 | 19 | 14 | 0.5 |
| 1363736 | 90 | 73 | 39 | 12 | 0.9 |
| 1363900 | 91 | 58 | 25 | 8 | 0.6 |
| 1363959 | 84 | 65 | 34 | 15 | 0.7 |
| 1364007 | 78 | 59 | 27 | 12 | 0.5 |
| 1364235 | 109 | 86 | 41 | 14 | 1.3 |

TABLE 32

Dose-dependent reduction of human PLP1 RNA in SK-MEL-28 cells by modified oligonucleotides

| Compound ID | PLP1 (% UTC) | | | | $IC_{50}$ (μM) |
|---|---|---|---|---|---|
| | 94 nM | 375 nM | 1500 nM | 6000 nM | |
| 1362468 | 90 | 67 | 24 | 6 | 0.6 |
| 1362490 | 83 | 41 | 13 | 5 | 0.3 |
| 1362500 | 106 | 83 | 43 | 10 | 1.2 |
| 1362900 | 115 | 78 | 30 | 6 | 1.0 |
| 1363141 | 99 | 63 | 31 | 13 | 0.8 |
| 1363257 | 118 | 82 | 40 | 12 | 1.2 |
| 1363493 | 139 | 93 | 48 | 9 | 1.5 |
| 1363550 | 72 | 54 | 21 | 5 | 0.4 |
| 1363565 | 88 | 52 | 29 | 14 | 0.6 |
| 1363644 | 103 | 91 | 36 | 12 | 1.2 |
| 1363758 | 84 | 49 | 16 | 5 | 0.4 |
| 1363983 | 74 | 71 | 30 | 9 | 0.6 |
| 1363993 | 78 | 60 | 36 | 10 | 0.6 |
| 1364066 | 103 | 78 | 34 | 8 | 1.0 |
| 1364073 | 107 | 82 | 56 | 17 | 1.5 |
| 1364246 | 125 | 70 | 17 | 11 | 0.9 |
| 1364248 | 80 | 62 | 30 | 9 | 0.6 |

TABLE 33

Dose-dependent reduction of human PLP1 RNA in SK-MEL-28 cells by modified oligonucleotides

| Compound ID | PLP1 (% UTC) | | | | IC$_{50}$ (µM) |
|---|---|---|---|---|---|
| | 94 nM | 375 nM | 1500 nM | 6000 nM | |
| 1362445 | 72 | 55 | 24 | 8 | 0.4 |
| 1362490 | 69 | 33 | 11 | 4 | 0.2 |
| 1362556 | 81 | 58 | 30 | 14 | 0.6 |
| 1362612 | 86 | 79 | 56 | 26 | 1.6 |
| 1362649 | 92 | 64 | 37 | 10 | 0.8 |
| 1362924 | 87 | 80 | 55 | 26 | 1.7 |
| 1362996 | 79 | 62 | 32 | 8 | 0.6 |
| 1363013 | 103 | 67 | 38 | 15 | 1.0 |
| 1363019 | 79 | 59 | 20 | 6 | 0.5 |
| 1363143 | 74 | 47 | 16 | 5 | 0.3 |
| 1363146 | 110 | 101 | 59 | 24 | 2.2 |
| 1363322 | 70 | 52 | 19 | 6 | 0.3 |
| 1363583 | 98 | 65 | 34 | 7 | 0.8 |
| 1364202 | 113 | 88 | 73 | 31 | 3.0 |

TABLE 34

Dose-dependent reduction of human PLP1 RNA in SK-MEL-28 cells by modified oligonucleotides

| Compound ID | PLP1 (% UTC) | | | | IC$_{50}$ (µM) |
|---|---|---|---|---|---|
| | 94 nM | 375 nM | 1500 nM | 6000 nM | |
| 1362458 | 95 | 67 | 37 | 20 | 1.0 |
| 1362490 | 76 | 41 | 21 | 7 | 0.3 |
| 1362680 | 91 | 50 | 28 | 7 | 0.6 |
| 1362817 | 94 | 76 | 31 | 13 | 0.9 |
| 1362856 | 77 | 57 | 34 | 8 | 0.5 |
| 1363012 | 90 | 74 | 48 | 17 | 1.1 |
| 1363101 | 76 | 45 | 26 | 10 | 0.4 |
| 1363255 | 102 | 77 | 39 | 8 | 1.0 |
| 1363287 | 99 | 69 | 39 | 13 | 0.9 |
| 1363351 | 103 | 74 | 40 | 11 | 1.0 |
| 1363398 | 85 | 66 | 45 | 18 | 0.9 |
| 1363640 | 96 | 82 | 54 | 23 | 1.6 |
| 1363685 | 86 | 67 | 43 | 10 | 0.8 |
| 1363762 | 77 | 57 | 23 | 7 | 0.5 |
| 1363883 | 103 | 60 | 23 | 18 | 0.8 |
| 1364182 | 86 | 64 | 35 | 8 | 0.7 |
| 1364208 | 77 | 57 | 30 | 16 | 0.5 |

TABLE 35

Dose-dependent reduction of human PLP1 RNA in SK-MEL-28 cells by modified oligonucleotides

| Compound ID | PLP1 (% UTC) | | | | IC$_{50}$ (µM) |
|---|---|---|---|---|---|
| | 94 nM | 375 nM | 1500 nM | 6000 nM | |
| 1362490 | 72 | 42 | 19 | 5 | 0.3 |
| 1362866 | 82 | 50 | 25 | 12 | 0.5 |
| 1362909 | 91 | 53 | 24 | 18 | 0.6 |
| 1363145 | 86 | 66 | 39 | 10 | 0.8 |
| 1363179 | 87 | 55 | 20 | 7 | 0.5 |
| 1363196 | 110 | 85 | 47 | 18 | 1.5 |
| 1363273 | 82 | 72 | 34 | 12 | 0.7 |
| 1363391 | 87 | 71 | 37 | 21 | 0.9 |
| 1363429 | 81 | 59 | 23 | 9 | 0.5 |
| 1363431 | 92 | 51 | 20 | 5 | 0.5 |
| 1363452 | 100 | 72 | 41 | 16 | 1.1 |
| 1363486 | 90 | 80 | 37 | 14 | 1.0 |
| 1363519 | 78 | 53 | 15 | 5 | 0.4 |
| 1363638 | 81 | 56 | 23 | 7 | 0.5 |
| 1363642 | 97 | 84 | 39 | 17 | 1.2 |
| 1363648 | 107 | 72 | 35 | 14 | 1.0 |
| 1363971 | 101 | 79 | 46 | 20 | 1.3 |
| 1364147 | 75 | 66 | 24 | 7 | 0.5 |

TABLE 36

Dose-dependent reduction of human PLP1 RNA in SK-MEL-28 cells by modified oligonucleotides

| Compound ID | PLP1 (% UTC) | | | | IC$_{50}$ (µM) |
|---|---|---|---|---|---|
| | 94 nM | 375 nM | 1500 nM | 6000 nM | |
| 1362473 | 93 | 73 | 28 | 8 | 0.8 |
| 1362490 | 80 | 48 | 15 | 6 | 0.4 |
| 1362517 | 78 | 42 | 12 | 3 | 0.3 |
| 1362602 | 80 | 68 | 20 | 8 | 0.5 |
| 1362689 | 90 | 61 | 28 | 8 | 0.6 |
| 1362724 | 112 | 78 | 46 | 12 | 1.2 |
| 1362774 | 93 | 70 | 41 | 11 | 0.9 |
| 1362805 | 94 | 85 | 38 | 11 | 1.0 |
| 1362928 | 84 | 69 | 26 | 10 | 0.7 |
| 1363191 | 91 | 48 | 18 | 6 | 0.5 |
| 1363544 | 87 | 50 | 17 | 4 | 0.4 |
| 1363591 | 74 | 50 | 19 | 6 | 0.4 |
| 1363673 | 89 | 70 | 32 | 13 | 0.8 |
| 1363889 | 81 | 38 | 12 | 4 | 0.3 |
| 1364107 | 84 | 55 | 23 | 9 | 0.5 |
| 1364116 | 78 | 56 | 15 | 6 | 0.4 |
| 1364257 | 83 | 62 | 16 | 15 | 0.5 |

TABLE 37

Dose-dependent reduction of human PLP1 RNA in SK-MEL-28 cells by modified oligonucleotides

| Compound ID | PLP1 (% UTC) | | | | IC$_{50}$ (µM) |
|---|---|---|---|---|---|
| | 94 nM | 375 nM | 1500 nM | 6000 nM | |
| 1362490 | 76 | 39 | 15 | 3 | 0.3 |
| 1362519 | 77 | 51 | 24 | 7 | 0.4 |
| 1362535 | 77 | 56 | 28 | 5 | 0.5 |
| 1362591 | 111 | 72 | 31 | 8 | 0.9 |
| 1362611 | 77 | 41 | 14 | 5 | 0.3 |
| 1362723 | 94 | 60 | 28 | 13 | 0.7 |
| 1362784 | 88 | 57 | 20 | 10 | 0.5 |
| 1362948 | 68 | 41 | 9 | 4 | 0.2 |
| 1363557 | 97 | 75 | 38 | 7 | 0.9 |
| 1363602 | 80 | 52 | 16 | 4 | 0.4 |
| 1363633 | 81 | 58 | 31 | 8 | 0.5 |
| 1363678 | 73 | 61 | 30 | 11 | 0.5 |
| 1364125 | 68 | 42 | 14 | 4 | 0.2 |
| 1363121 | 89 | 70 | 36 | 11 | 0.8 |

TABLE 38

Dose-dependent reduction of human PLP1 RNA in SK-MEL-28 cells by modified oligonucleotides

| Compound ID | PLP1 (% UTC) | | | | IC$_{50}$ (µM) |
|---|---|---|---|---|---|
| | 94 nM | 375 nM | 1500 nM | 6000 nM | |
| 1362490 | 86 | 54 | 18 | 8 | 0.5 |
| 1362497 | 110 | 86 | 50 | 18 | 1.5 |

TABLE 38-continued

Dose-dependent reduction of human PLP1 RNA in SK-MEL-28 cells by modified oligonucleotides

| Compound ID | PLP1 (% UTC) | | | | IC$_{50}$ (µM) |
|---|---|---|---|---|---|
| | 94 nM | 375 nM | 1500 nM | 6000 nM | |
| 1362712 | 77 | 46 | 21 | 13 | 0.4 |
| 1362892 | 91 | 86 | 56 | 30 | 2.2 |
| 1362970 | 91 | 61 | 26 | 10 | 0.7 |
| 1363102 | 91 | 85 | 45 | 20 | 1.3 |
| 1363392 | 77 | 53 | 26 | 14 | 0.5 |
| 1363393 | 74 | 72 | 37 | 13 | 0.7 |
| 1363517 | 97 | 81 | 36 | 18 | 1.1 |
| 1363696 | 77 | 52 | 26 | 13 | 0.5 |
| 1363701 | 89 | 75 | 49 | 21 | 1.2 |
| 1363850 | 102 | 76 | 36 | 13 | 1.0 |
| 1363121 | 76 | 48 | 22 | 8 | 0.4 |

TABLE 39

Dose-dependent reduction of human PLP1 RNA in SK-MEL-28 cells by modified oligonucleotides

| Compound ID | PLP1 (% UTC) | | | | IC$_{50}$ (µM) |
|---|---|---|---|---|---|
| | 94 nM | 375 nM | 1500 nM | 6000 nM | |
| 1362490 | 83 | 47 | 22 | 13 | 0.4 |
| 1362659 | 98 | 76 | 46 | 15 | 1.2 |
| 1362749 | 84 | 49 | 22 | 6 | 0.4 |
| 1362790 | 102 | 76 | 46 | 41 | 2.2 |
| 1362813 | 114 | 82 | 47 | 13 | 1.3 |
| 1362842 | 106 | 96 | 57 | 35 | 2.8 |
| 1362927 | 89 | 72 | 36 | 10 | 0.8 |
| 1363022 | 104 | 85 | 44 | 14 | 1.3 |
| 1363235 | 91 | 68 | 43 | 17 | 1.0 |
| 1363330 | 83 | 91 | 37 | 16 | 1.1 |
| 1363415 | 87 | 72 | 59 | 16 | 1.3 |
| 1363474 | 103 | 77 | 30 | 9 | 0.9 |
| 1363485 | 80 | 50 | 13 | 4 | 0.4 |
| 1363627 | 95 | 86 | 66 | 15 | 1.7 |

TABLE 39-continued

Dose-dependent reduction of human PLP1 RNA in SK-MEL-28 cells by modified oligonucleotides

| Compound ID | PLP1 (% UTC) | | | | IC$_{50}$ (µM) |
|---|---|---|---|---|---|
| | 94 nM | 375 nM | 1500 nM | 6000 nM | |
| 1363724 | 107 | 89 | 49 | 9 | 1.3 |
| 1363801 | 85 | 73 | 29 | 10 | 0.7 |
| 1363802 | 80 | 65 | 26 | 9 | 0.6 |
| 1363940 | 88 | 72 | 30 | 13 | 0.8 |

Example 4: Design of Modified Oligonucleotides Complementary to Human PLP1 Nucleic Acid Modified oligonucleotides complementary to a human PLP1 nucleic acid were designed, as described in the table below. "Start site" indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence. Each modified oligonucleotide listed in the tables below is 100% complementary to SEQ ID NO: 1 (described herein above), to SEQ ID NO: 2 (described herein above), or to both. 'N/A' indicates that the modified oligonucleotide is not 100% complementary to that particular target nucleic acid sequence.

The modified oligonucleotides in Table 40 are 6-10-4 MOE gapmers. The gapmers are 20 nucleosides in length, wherein the sugar motif for the gapmers is (from 5' to 3'): eeeeeedddddddddddeeee; wherein each 'd' represents a 2'-β-D-deoxyribosyl sugar moiety, and each 'e' represents a 2'-MOE sugar moiety. The gapmers have an internucleoside linkage motif of (from 5' to 3'): sooooossssssssssssoss; wherein each "s" represents a phosphorothioate internucleoside linkage, and each "o" represents a phosphodiester internucleoside linkage. Each cytosine residue is a 5-methyl cytosine.

TABLE 40

6-10-4 MOE gapmers with mixed PO/PS internucleoside linkages complementary to human PLP1

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | SEQ ID No. |
|---|---|---|---|---|---|---|
| 1523584 | 2225 | 2244 | 18704 | 18723 | TCTCCAGACATTTCTGATGC | 934 |
| 1523586 | 2227 | 2246 | 18706 | 18725 | ATTCTCCAGACATTTCTGAT | 2146 |
| 1523587 | 2228 | 2247 | 18707 | 18726 | TATTCTCCAGACATTTCTGA | 2147 |
| 1523588 | 2495 | 2514 | 18974 | 18993 | ATGTGATCTATATCAGGAGA | 1772 |
| 1523589 | 2496 | 2515 | 18975 | 18994 | TATGTGATCTATATCAGGAG | 2148 |
| 1523590 | 2497 | 2516 | 18976 | 18995 | TTATGTGATCTATATCAGGA | 1693 |
| 1523591 | 1996 | 2015 | 18475 | 18494 | AGAGGGCCATCTCAGGTTAC | 2149 |
| 1523592 | 1998 | 2017 | 18477 | 18496 | CCAGAGGGCCATCTCAGGTT | 993 |
| 1523593 | 1999 | 2018 | 18478 | 18497 | ACCAGAGGGCCATCTCAGGT | 881 |
| 1523594 | 3024 | 3043 | 19503 | 19522 | TTGCAATTCTATATCAGAAA | 2144 |
| 1523595 | 3025 | 3044 | 19504 | 19523 | ATTGCAATTCTATATCAGAA | 2010 |
| 1523596 | 2695 | 2714 | 19174 | 19193 | CAACTCTTTACAACAAAAGA | 630 |

TABLE 40-continued 6-10-4 MOE gapmers with mixed PO/PS internucleoside linkages complementary to human PLP1

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | SEQ ID No. |
|---|---|---|---|---|---|---|
| 1523597 | 2696 | 2715 | 19175 | 19194 | ACAACTCTTTACAACAAAAG | 556 |
| 1523598 | 2698 | 2717 | 19177 | 19196 | ACACAACTCTTTACAACAAA | 411 |
| 1523599 | 3028 | 3047 | 19507 | 19526 | AAAATTGCAATTCTATATCA | 1780 |
| 1523600 | 3029 | 3048 | 19508 | 19527 | TAAAATTGCAATTCTATATC | 1708 |
| 1523601 | 2667 | 2686 | 19146 | 19165 | ACAAATCTTTCCTTCAATTA | 682 |
| 1523602 | 2669 | 2688 | 19148 | 19167 | GTACAAATCTTTCCTTCAAT | 2150 |
| 1523603 | 2670 | 2689 | 19149 | 19168 | AGTACAAATCTTTCCTTCAA | 545 |
| 1523604 | N/A | N/A | 9198 | 9217 | AGATGTTCATCTCTTCACAA | 2151 |
| 1523605 | N/A | N/A | 9199 | 9218 | CAGATGTTCATCTCTTCACA | 1124 |
| 1523606 | N/A | N/A | 9200 | 9219 | TCAGATGTTCATCTCTTCAC | 2152 |
| 1523607 | N/A | N/A | 9201 | 9220 | ATCAGATGTTCATCTCTTCA | 2153 |
| 1523608 | N/A | N/A | 9202 | 9221 | CATCAGATGTTCATCTCTTC | 2145 |
| 1523609 | N/A | N/A | 9203 | 9222 | GCATCAGATGTTCATCTCTT | 1050 |
| 1523610 | 1382 | 1401 | 17861 | 17880 | CCTCCATTCCTTTGTGACTT | 1499 |
| 1523611 | 1383 | 1402 | 17862 | 17881 | GCCTCCATTCCTTTGTGACT | 1451 |
| 1523612 | 1384 | 1403 | 17863 | 17882 | AGCCTCCATTCCTTTGTGAC | 2154 |
| 1523613 | 1385 | 1404 | 17864 | 17883 | GAGCCTCCATTCCTTTGTGA | 2155 |

Example 5: Activity of Modified Oligonucleotides Complementary to Human PLP1 in Transgenic Mice Modified oligonucleotides selected from the examples above were tested in a human BAC wild type PLP1 transgenic mouse model. A bacterial artificial chromosome (BAC) subclone carrying the human Plp1 gene, including down- and up-stream regulatory elements was identified. Full gene sequencing confirmed the presence of the human genomic region corresponding to current NCBI refseq assembly GRCh38.p13, ChrX sequence NC_000023.11 at position 103776506 . . . 103792619. The BAC subclone was introduced via pronuclear injection into the Taconic Biosciences C57BL/6N Tac ES cell line. Line C57BL/6 NTac-Tg (PLP1)1483Tac-17235 was generated and used in these experiments. Human Plp1 mRNA expression was found in the brain and spinal cord.

Treatment

The PLP1 transgenic mice were divided into groups of 2 mice each. Each mouse received a single intracerebroventricular (ICV) bolus of 100 μg of modified oligonucleotide. A group of 3-5 mice received PBS as a negative control.

RNA Analysis

Two weeks post treatment, mice were sacrificed and RNA was extracted from cortical brain tissue, spinal cord, and/or cerebellum for RTPCR analysis to measure the amount of PLP1 RNA using human primer probe set RTS48932 (forward sequence TGCACCAGTCATCAGCTATTC, designated herein as SEQ ID NO: 14; reverse sequence AGACTGAAATCTGGGAGCTATTC, designated herein as SEQ ID NO: 15; probe sequence AGGTCTCAAACTCTTTCTGCCTGTCC designated herein as SEQ ID NO: 16). Results are presented as percent human PLP1 RNA relative to PBS control, normalized to mouse GAPDH. GAPDH was amplified using primer probe set mGapdh_LTS00102 (forward sequence GGCAAATTCAACGGCACAGT, designated herein as SEQ ID NO: 17; reverse sequence GGGTCTCGCTCCTGGAAGAT, designated herein as SEQ ID NO: 18; probe sequence AAGGCCGAGAATGGGAAGCTTGTCATC, designated herein as SEQ ID NO: 19).

As shown in the tables below, treatment with modified oligonucleotides resulted in reduction of PLP1 RNA in comparison to the PBS control (% control).

TABLE 41

Reduction of human PLP1 RNA in transgenic mice by modified oligonucleotides

| Compound ID | PLP1 RNA (% control) | |
|---|---|---|
| | Spinal Cord | Cortex |
| PBS | 100 | 100 |
| 1362445 | 43 | 50 |
| 1362473 | 69 | 71 |

TABLE 41-continued

Reduction of human PLP1 RNA in transgenic mice by modified oligonucleotides

| Compound ID | PLP1 RNA (% control) | |
|---|---|---|
| | Spinal Cord | Cortex |
| 1362556 | 63 | 66 |
| 1362712 | 25 | 36 |

TABLE 42

Reduction of human PLP1 RNA in transgenic mice by modified oligonucleotides

| Compound ID | PLP1 RNA (% control) | |
|---|---|---|
| | Spinal Cord | Cortex |
| PBS | 100 | 100 |
| 1362445 | 22 | 50 |
| 1362449 | 43 | 61 |
| 1362458 | 27 | 33 |
| 1362468 | 33 | 59 |

TABLE 43

Reduction of human PLP1 RNA in transgenic mice by modified oligonucleotides

| Compound ID | PLP1 RNA (% control) | | | | |
|---|---|---|---|---|---|
| | Spinal Cord | Cortex | Cerebellum | Brain Stem | Hippocampus |
| PBS | 100 | 100 | 100 | 100 | 100 |
| 1362928 | 24 | 49 | 38 | 25 | 29 |
| 1363102 | 65 | 60 | 70 | 52 | 36 |
| 1363410 | 54 | 74 | 65 | 47 | 67 |
| 1363485 | 27 | 30 | 39 | 26 | 16 |
| 1363486 | 86 | 98 | 92 | 71 | 62 |
| 1363565 | 54 | 74 | 39 | 46 | 43 |

TABLE 44

Reduction of human PLP1 RNA in transgenic mice by modified oligonucleotides

| Compound ID | PLP1 RNA (% control) | |
|---|---|---|
| | Spinal Cord | Cortex |
| PBS | 100 | 100 |
| 1362500 | 59 | 100 |
| 1362517 | 50 | 91 |
| 1362602 | 44 | 45 |
| 1362641 | 57 | 70 |
| 1362749 | 69 | 85 |
| 1362784 | 52 | 93 |
| 1362805 | 54 | 63 |
| 1362842 | 34 | 43 |
| 1362892 | 33 | 41 |
| 1362987 | 52 | 63 |
| 1362996 | 73 | 115 |

TABLE 45

Reduction of human PLP1 RNA in transgenic mice by modified oligonucleotides

| Compound ID | PLP1 RNA (% control) | |
|---|---|---|
| | Spinal Cord | Cortex |
| PBS | 100 | 100 |
| 1362649 | 39 | 42 |
| 1363866 | 57 | 43 |
| 1363013 | 34 | 49 |
| 1363146 | 69 | 57 |

TABLE 46

Reduction of human PLP1 RNA in transgenic mice by modified oligonucleotides

| Compound ID | PLP1 RNA (% control) | |
|---|---|---|
| | Spinal Cord | Cortex |
| PBS | 100 | 100 |
| 1363184 | 68 | 58 |
| 1363235 | 29 | 48 |
| 1363255 | 63 | 58 |
| 1363257 | 50 | 50 |
| 1363391 | 69 | 57 |
| 1363398 | 41 | 39 |
| 1363429 | 70 | 48 |
| 1363452 | 81 | 57 |
| 1363493 | 80 | 56 |
| 1363544 | 53 | 92 |
| 1363550 | 79 | 82 |
| 1363557 | 49 | 34 |
| 1363583 | 93 | 69 |

TABLE 47

Reduction of human PLP1 RNA in transgenic mice by modified oligonucleotides

| Compound ID | PLP1 RNA (% control) | |
|---|---|---|
| | Spinal Cord | Cortex |
| PBS | 100 | 100 |
| 1362612 | 50 | 46 |
| 1363591 | 31 | 42 |
| 1363734 | 35 | 54 |
| 1363736 | 49 | 67 |
| 1363762 | 33 | 51 |
| 1363801 | 50 | 67 |
| 1363940 | 24 | 46 |
| 1363993 | 64 | 107 |
| 1364073 | 31 | 51 |
| 1364116 | 29 | 52 |
| 1364182 | 35 | 63 |
| 1523588 | 5 | 35 |
| 1523589 | 37 | 31 |
| 1523590 | 17 | 46 |
| 1523591 | 42 | 17 |
| 1523592 | 43 | 51 |
| 1523593 | 8 | 31 |
| 1523608 | 25 | 42 |

TABLE 48

Reduction of human PLP1 RNA in transgenic mice by modified oligonucleotides

| Compound ID | PLP1 RNA (% control) Spinal Cord | Cortex |
|---|---|---|
| PBS | 100 | 100 |
| 1523601 | 29 | 35 |
| 1523602 | 11 | 16 |
| 1523603 | 14 | 35 |
| 1523604 | 28 | 35 |
| 1523605 | 32 | 34 |
| 1523606 | 50 | 31 |
| 1523607 | 24 | 29 |
| 1523609 | 14 | 28 |
| 1523610 | 43 | 41 |
| 1523611 | 66 | 40 |
| 1523612 | 35 | 30 |

TABLE 49

Reduction of human PLP1 RNA in transgenic mice by modified oligonucleotides

| Compound ID | PLP1 RNA (% control) Spinal Cord | Cortex |
|---|---|---|
| PBS | 100 | 100 |
| 1363627 | 23 | 63 |
| 1523584 | 12 | 39 |
| 1523586 | 39 | 55 |
| 1523587 | 41 | 53 |
| 1523594 | 33 | 47 |
| 1523595 | 45 | 41 |
| 1523596 | 69 | 71 |
| 1523597 | 63 | 81 |
| 1523598 | 11 | 37 |
| 1523599 | 80 | 78 |
| 1523600 | 59 | 75 |
| 1523613 | 64 | 78 |

Example 6: Potency of Modified Oligonucleotides Complementary to Human PLP1 in Transgenic Mice Modified oligonucleotides selected from the examples above were tested in a human BAC wild type PLP1 transgenic mouse model (described herein above).

Treatment

The PLP1 transgenic mice were divided into groups of 4 mice each. Each mouse received a single intracerebroventricular (ICV) bolus of modified oligonucleotide at the doses indicated in the table below. A group of 4 mice received PBS as a negative control.

RNA Analysis

Two weeks post treatment, mice were sacrificed and RNA was extracted from spinal cord and cortical brain tissue for RTPCR analysis to measure the amount of PLP1 RNA using human primer probe sets RTS48932 (described herein above) and RTS48933 (forward sequence CCCTAACTCAGCCAACCTTAC, designated herein as SEQ ID NO: 5; reverse sequence CACCCTGTTTCTCTTCCCTAAC, designated herein as SEQ ID NO: 6; probe sequence AGGGAGCGTAGAATCTGTGTAGACGA, designated herein as SEQ ID NO: 7). Results are presented as percent human PLP1 RNA relative to PBS control, normalized to mouse GAPDH. GAPDH was amplified using primer probe set mGapdh_LTS00102 (described herein above).

Dose response and tissue concentration response data were analyzed using Microsoft Excel (v14.4) and GraphPad Prism software (v 8.2.0, San Diego, Calif.). $ED_{50}$ values were calculated from log transformed dose and individual animal Plp1 mRNA levels using custom equation Motulsky: Agonist vs response—Variable slope (four parameters) Y=Bottom+(Top-Bottom)/(1+(10^log EC50/X)^HillSlope), with the following constraints: bottom >0, top=100, HillSlope <−1 and >−2.

As shown in the table below, treatment with modified oligonucleotides resulted in dose-responsive reduction of PLP1 RNA in comparison to the PBS control.

TABLE 50

Reduction of human PLP1 RNA in transgenic mice by modified oligonucleotides

| Compound ID | Dose (µg) | PLP1 RNA (% control) RTS48932 Spinal Cord | $ED_{50}$ (µg) | Cortex | $ED_{50}$ (µg) | PLP1 RNA (% control) RTS48933 Spinal Cord | $ED_{50}$ (µg) | Cortex | $ED_{50}$ (µg) |
|---|---|---|---|---|---|---|---|---|---|
| PBS | N/A | 100 | N/A | 100 | N/A | 100 | N/A | 100 | N/A |
| 1363235 | 10 | 101 | 86 | 92 | 65 | 102 | 82 | 96 | 60 |
|  | 30 | 97 |  | 70 |  | 88 |  | 68 |  |
|  | 100 | 44 |  | 39 |  | 45 |  | 41 |  |
|  | 300 | 14 |  | 15 |  | 14 |  | 16 |  |
| 1523605 | 10 | 91 | 35 | 84 | 35 | 93 | 44 | 86 | 37 |
|  | 30 | 55 |  | 63 |  | 57 |  | 66 |  |
|  | 100 | 39 |  | 29 |  | 42 |  | 30 |  |
|  | 300 | 17 |  | 19 |  | 17 |  | 20 |  |
| 1523608 | 10 | 92 | 33 | 91 | 76 | 97 | 37 | 92 | 73 |
|  | 30 | 53 |  | 65 |  | 56 |  | 66 |  |
|  | 100 | 30 |  | 44 |  | 31 |  | 48 |  |
|  | 300 | 9 |  | 14 |  | 9 |  | 15 |  |

Example 7: Dose-Dependent Inhibition of Human PLP1 in SK-MEL-28 Cells by Modified Oligonucleotides Modified oligonucleotides selected from the examples above were tested at various doses in SK-MEL-28 cells (American Type Culture Collection). Cultured SK-MEL-28 cells at a density of 20,000 cells per well were transfected using electroporation with concentrations of modified oligonucleotides as specified in the tables below. After a treatment period of approximately 24 hours, total RNA was isolated from the cells and PLP1 RNA levels were measured by quantitative real-time RTPCR. PLP1 RNA levels were measured by quantitative real-time RTPCR using human primer-probe set RTS35092, described in Example 1 above. PLP1 RNA levels were normalized to human GAPDH, amplified using primer probe set RTS104 (forward sequence GAAGGTGAAGGTCGGAGTC, designated herein as SEQ ID NO: 8; reverse sequence GAAGATGGTGATGGGATTTC, designated herein as SEQ ID NO: 9; probe sequence CAAGCTTCCCGTTCTCAGCC, designated herein as SEQ ID NO: 10).

Reduction of PLP1 RNA is presented in the table below as percent PLP1 RNA relative to the amount in untreated control cells (% UTC). The half maximal inhibitory concentration ($IC_{50}$) of each modified oligonucleotide was calculated using GraphPad Prism 6 software and is also presented in the table below. $IC_{50}$ values were calculated from dose and PLP1 RNA levels by least squares fit to equation: log(inhibitor) vs. normalized response—Variable slope, $Y=100/(1+10\wedge((Log\ IC50-X)*HillSlope))$.

TABLE 51

Dose-dependent reduction of human PLP1 RNA in SK-MEL-28 cells by modified oligonucleotides

| Compound No. | 5.24 nM | 13.11 nM | 32.77 nM | 81.92 nM | 205 nM | 512 nM | 1280 nM | 3200 nM | 8000 nM | 20000 nM | $IC_{50}$ (µm) |
|---|---|---|---|---|---|---|---|---|---|---|---|
| 1363235 | 109 | 102 | 104 | 101 | 91 | 77 | 56 | 47 | 21 | 11 | 2.14 |
| 1523601 | 110 | 103 | 100 | 102 | 99 | 94 | 83 | 57 | 34 | 15 | 4.46 |
| 1523605 | 105 | 101 | 106 | 101 | 92 | 87 | 76 | 52 | 40 | 18 | 4.19 |
| 1523608 | 103 | 95 | 97 | 95 | 92 | 84 | 68 | 45 | 29 | 22 | 3.01 |

The invention claimed is:

1. A modified oligonucleotide according to the following chemical structure:

(SEQ ID NO: 1124)

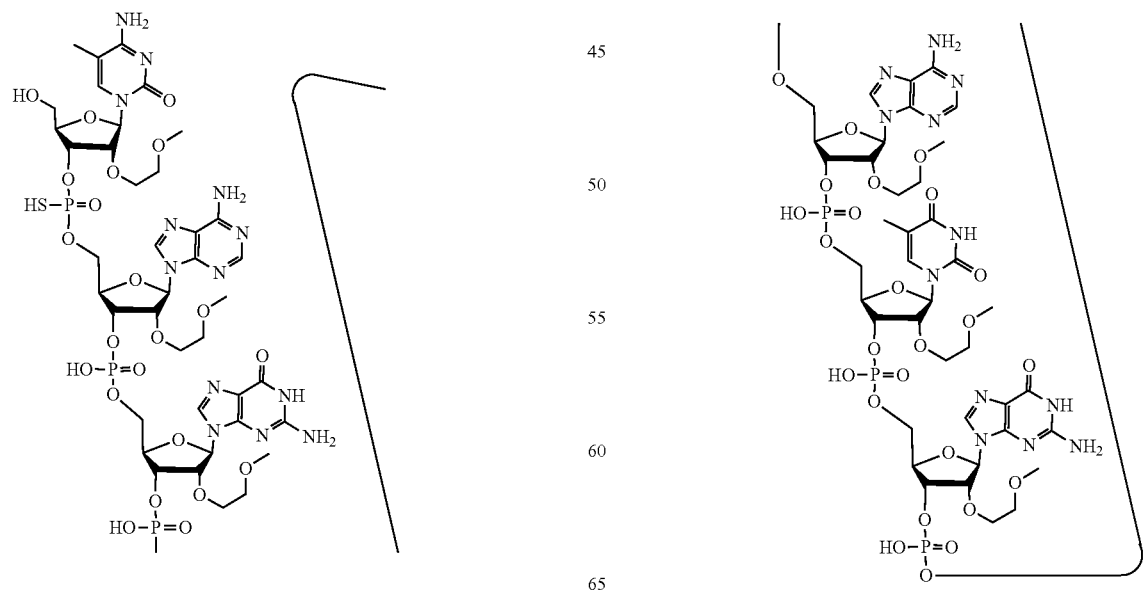

955
-continued
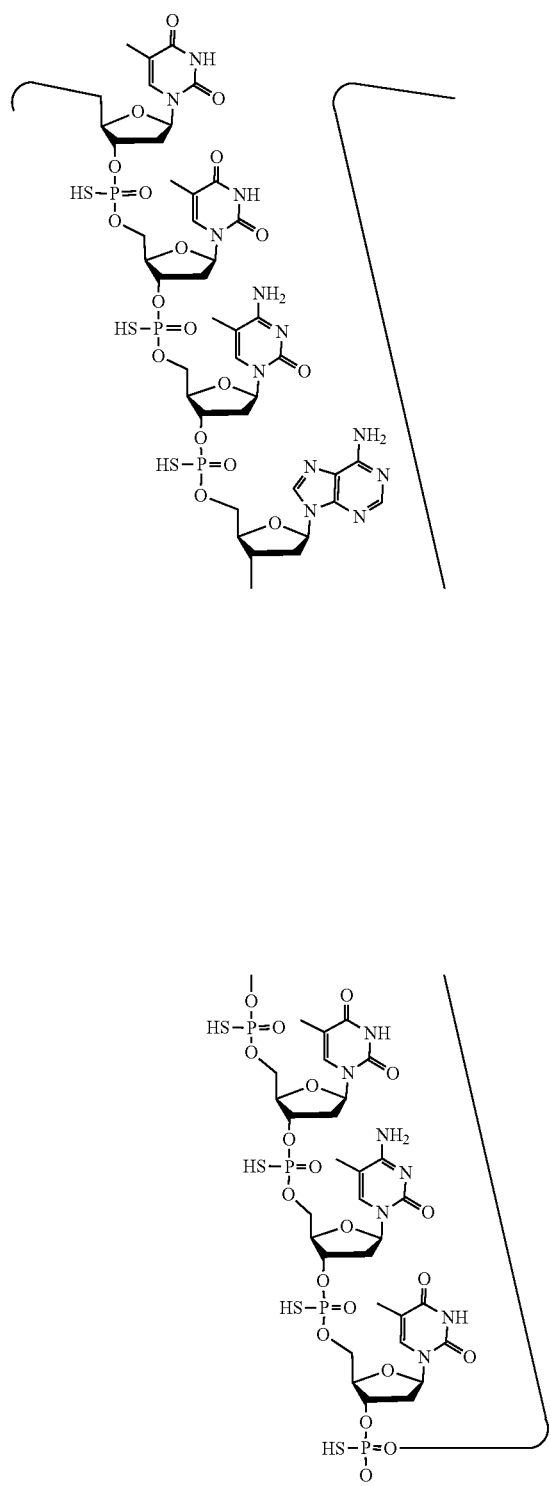
956
-continued
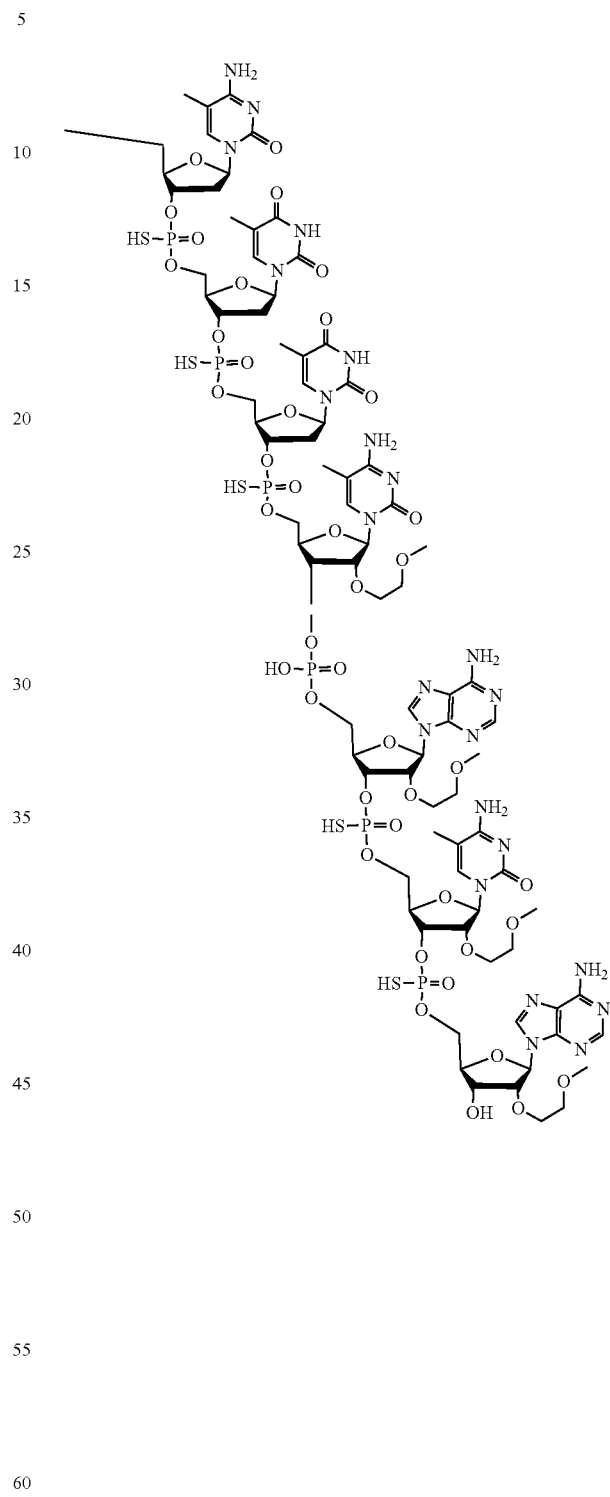
or a salt thereof.
2. The modified oligonucleotide of claim 1, which is the sodium salt or the potassium salt.
3. A modified oligonucleotide according to the following chemical structure:

(SEQ ID NO: 1124)

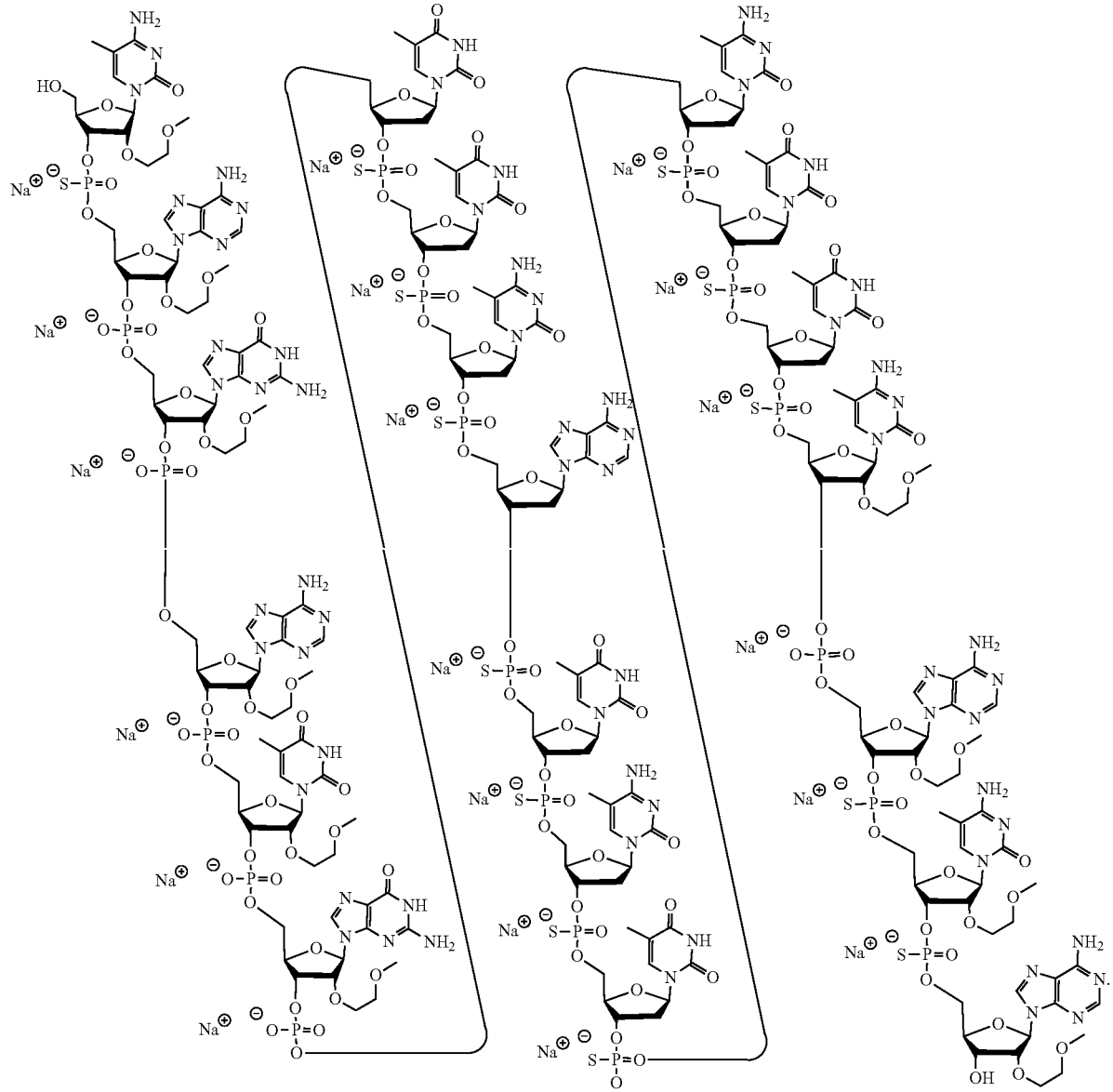

4. An oligomeric compound comprising a modified oligonucleotide according to the following chemical notation:

(SEQ ID NO: 1124)
$^{m}C_{es}A_{eo}G_{eo}A_{eo}T_{eo}G_{eo}T_{ds}T_{ds}{}^{m}C_{ds}A_{ds}T_{ds}{}^{m}C_{ds}T_{ds}{}^{m}C_{ds}T_{ds}$
$T_{ds}{}^{m}C_{eo}A_{es}{}^{m}C_{es}A_{e}$, wherein:
A=an adenine nucleobase,
$^{m}$C=a 5-methylcytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

5. A population of modified oligonucleotides of claim 1, wherein all of the phosphorothioate internucleoside linkages of the modified oligonucleotide are stereorandom.

6. A pharmaceutical composition comprising the modified oligonucleotide of claim 1, and a pharmaceutically acceptable diluent.

7. The pharmaceutical composition of claim 6, wherein the pharmaceutically acceptable diluent is artificial cerebrospinal fluid or phosphate-buffered saline (PBS).

8. The pharmaceutical composition of claim 7, wherein the pharmaceutical composition consists essentially of the modified oligonucleotide and artificial cerebrospinal fluid.

9. The pharmaceutical composition of claim 7, wherein the pharmaceutical composition consists essentially of the modified oligonucleotide and PBS.

10. A method comprising administering to a subject the modified oligonucleotide of claim 1.

11. A method of treating Pelizaeus-Merzbacher disease (PMD), comprising administering to a subject with PMD a therapeutically effective amount of the modified oligonucleotide of claim 1, thereby treating the PMD.

12. The method of claim 11, wherein the PMD is any of connatal PMD, classic PMD, or transitional PMD.

13. The method of claim 11, wherein administering the modified oligonucleotide reduces hypotonia, nystagmus, optic atrophy, respiratory distress, motor delays, spasticity, ataxia, seizures, or choreiform movements, or delays death in the subject.

14. A method of reducing expression of PLP1 in a cell comprising contacting the cell with the modified oligonucleotide of claim 1.

15. The method of claim 14, wherein the cell is an oligodendrocyte or an oligodendrocyte progenitor cell.

16. The method of claim 11, wherein the subject is human.

17. The method of claim 14, wherein the cell is a human cell.

18. A method comprising administering to a subject the pharmaceutical composition of claim 6.

19. A method of treating Pelizaeus-Merzbacher disease (PMD), comprising administering to a subject with PMD a therapeutically effective amount of the pharmaceutical composition of claim 6, thereby treating the PMD.

20. The method of claim 19, wherein the PMD is any of connatal PMD, classic PMD, or transitional PMD.

21. The method of claim 19, wherein administering the pharmaceutical composition reduces hypotonia, nystagmus, optic atrophy, respiratory distress, motor delays, spasticity, ataxia, seizures, or choreiform movements, or delays death in the subject.

22. The method of claim 19, wherein the subject is human.

23. A pharmaceutical composition comprising the modified oligonucleotide of claim 3, and a pharmaceutically acceptable diluent.

24. The pharmaceutical composition of claim 23, wherein the pharmaceutically acceptable diluent is artificial cerebrospinal fluid or phosphate-buffered saline (PBS).

25. The pharmaceutical composition of claim 24, wherein the pharmaceutical composition consists essentially of the modified oligonucleotide and artificial cerebrospinal fluid.

26. The pharmaceutical composition of claim 24, wherein the pharmaceutical composition consists essentially of the modified oligonucleotide and PBS.

27. A method comprising administering to a subject the modified oligonucleotide of claim 3.

28. A method of treating Pelizaeus-Merzbacher disease (PMD), comprising administering to a subject with PMD a therapeutically effective amount of the modified oligonucleotide of claim 3, thereby treating the PMD.

29. A method of reducing expression of PLP1 in a cell comprising contacting the cell with the modified oligonucleotide of claim 3.

30. A method comprising administering to a subject the pharmaceutical composition of claim 23.

31. A method of treating Pelizaeus-Merzbacher disease (PMD), comprising administering to a subject with PMD a therapeutically effective amount of the pharmaceutical composition of claim 23, thereby treating the PMD.

32. A pharmaceutical composition comprising the oligomeric compound of claim 4, and a pharmaceutically acceptable diluent.

33. The pharmaceutical composition of claim 32, wherein the pharmaceutically acceptable diluent is artificial cerebrospinal fluid or phosphate-buffered saline (PBS).

34. A method comprising administering to a subject the oligomeric compound of claim 4.

35. A method of treating Pelizaeus-Merzbacher disease (PMD), comprising administering to a subject with PMD a therapeutically effective amount of the oligomeric compound of claim 4, thereby treating the PMD.

36. A method comprising administering to a subject the pharmaceutical composition of claim 32.

37. A method of treating Pelizaeus-Merzbacher disease (PMD), comprising administering to a subject with PMD a therapeutically effective amount of the pharmaceutical composition of claim 32, thereby treating the PMD.

38. A pharmaceutical composition comprising the population of modified oligonucleotides of claim 5, and a pharmaceutically acceptable diluent.

39. The pharmaceutical composition of claim 38, wherein the pharmaceutically acceptable diluent is artificial cerebrospinal fluid or phosphate-buffered saline (PBS).

40. A method comprising administering to a subject the population of modified oligonucleotides of claim 5.

41. A method of treating Pelizaeus-Merzbacher disease (PMD), comprising administering to a subject with PMD a therapeutically effective amount of the population of modified oligonucleotides of claim 5, thereby treating the PMD.

42. A method of reducing expression of PLP1 in a cell comprising contacting the cell with the population of modified oligonucleotides of claim 5.

43. A method comprising administering to a subject the pharmaceutical composition of claim 38.

44. A method of treating Pelizaeus-Merzbacher disease (PMD), comprising administering to a subject with PMD a therapeutically effective amount of the pharmaceutical composition of claim 38, thereby treating the PMD.

45. A pharmaceutical composition comprising the modified oligonucleotide of claim 2, and a pharmaceutically acceptable diluent.

46. The pharmaceutical composition of claim 45, wherein the pharmaceutically acceptable diluent is artificial cerebrospinal fluid or phosphate-buffered saline (PBS).

47. A population of modified oligonucleotides of claim 2, wherein all of the phosphorothioate internucleoside linkages of the modified oligonucleotide are stereorandom.

48. A population of modified oligonucleotides of claim 3, wherein all of the phosphorothioate internucleoside linkages of the modified oligonucleotide are stereorandom.

49. A population of oligomeric compounds of claim 4, wherein all of the phosphorothioate internucleoside linkages of the modified oligonucleotide are stereorandom.

50. A pharmaceutical composition comprising the population of modified oligonucleotides of claim 47, and a pharmaceutically acceptable diluent.

51. The pharmaceutical composition of claim 50, wherein the pharmaceutically acceptable diluent is artificial cerebrospinal fluid or phosphate-buffered saline (PBS).

52. A pharmaceutical composition comprising the population of modified oligonucleotides of claim 48, and a pharmaceutically acceptable diluent.

53. The pharmaceutical composition of claim 52, wherein the pharmaceutically acceptable diluent is artificial cerebrospinal fluid or phosphate-buffered saline (PBS).

54. A pharmaceutical composition comprising the population of oligomeric compounds of claim 49, and a pharmaceutically acceptable diluent.

55. The pharmaceutical composition of claim 54, wherein the pharmaceutically acceptable diluent is artificial cerebrospinal fluid or phosphate-buffered saline (PBS).

56. The method of claim 10, wherein the subject has Pelizaeus-Merzbacher disease (PMD).

57. The method of claim 27, wherein the subject has Pelizaeus-Merzbacher disease (PMD).

58. The method of claim 34, wherein the subject has Pelizaeus-Merzbacher disease (PMD).

59. The method of claim 56, wherein the subject has connatal PMD, classic PMD, or transitional PMD.

60. The method of claim 57, wherein the subject has connatal PMD, classic PMD, or transitional PMD.

61. The method of claim 58, wherein the subject has connatal PMD, classic PMD, or transitional PMD.

* * * * *

UNITED STATES PATENT AND TRADEMARK OFFICE
CERTIFICATE OF CORRECTION

Page 1 of 3

PATENT NO. : 11,732,263 B2
APPLICATION NO. : 17/362567
DATED : August 22, 2023
INVENTOR(S) : Berit Elissa Powers It is certified that error appears in the above-identified patent and that said Letters Patent is hereby corrected as shown below:

In the Specification

Column 13, Line 43, should read -- $G_{es}{}^mC_{eo}A_{eo}T_{eo}{}^mC_{eo}A_{ds}G_{ds}A_{ds}T_{ds}G_{ds}T_{ds}$ --

In Columns 31 and 32, the structure should read:

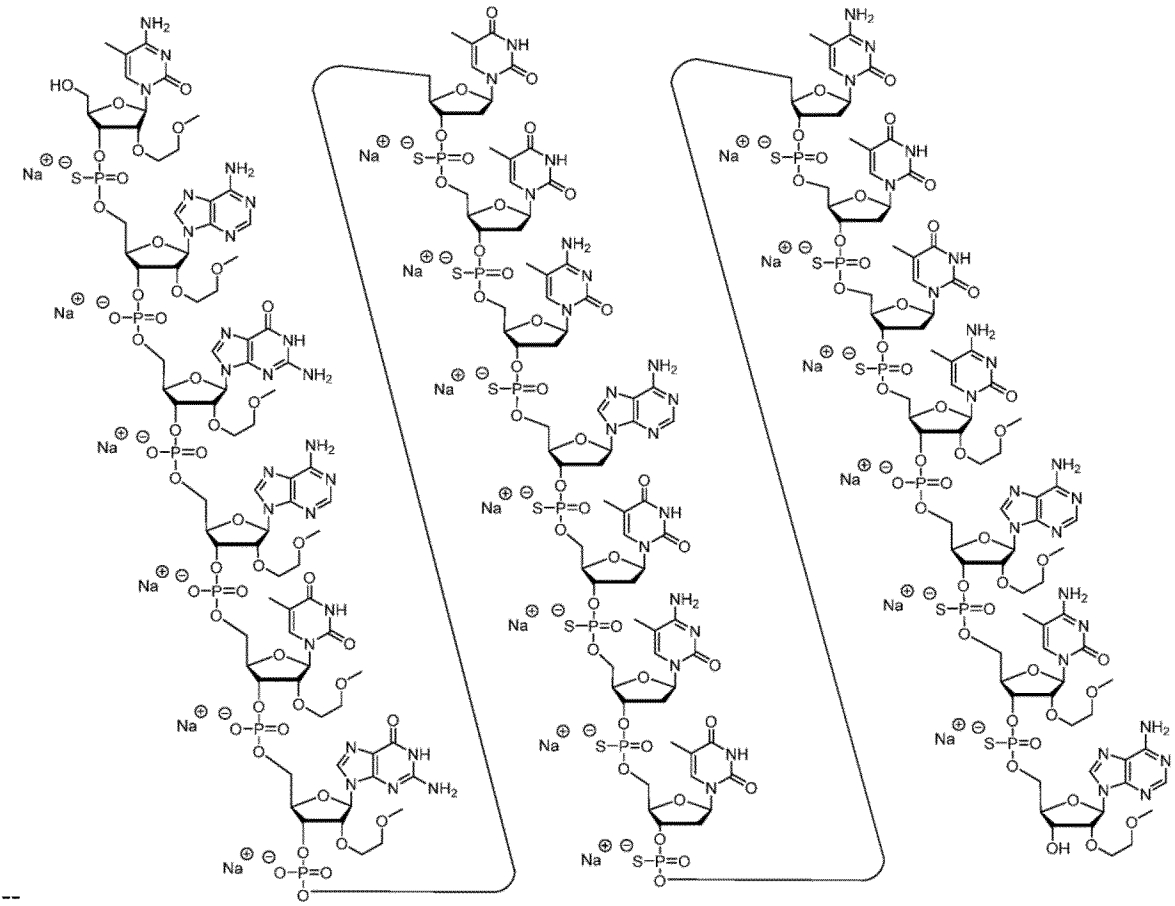

--

Signed and Sealed this
Twelfth Day of December, 2023

*Katherine Kelly Vidal*

Katherine Kelly Vidal
*Director of the United States Patent and Trademark Office*

CERTIFICATE OF CORRECTION (continued)
U.S. Pat. No. 11,732,263 B2

Column 68, Line 66, delete "PGP-122 DNA"

Column 72, Line 57, delete "PGP-123 DNA"

Column 84, Line 5, should read -- $T_{ds}T_{ds}{}^mC_{ds}A_{ds}T_{ds}{}^mC_{eo}T_{eo}{}^mC_{es}T_{es}T_e$, --

In the Claims

Claim 1, Columns 953-956, the structure should read:

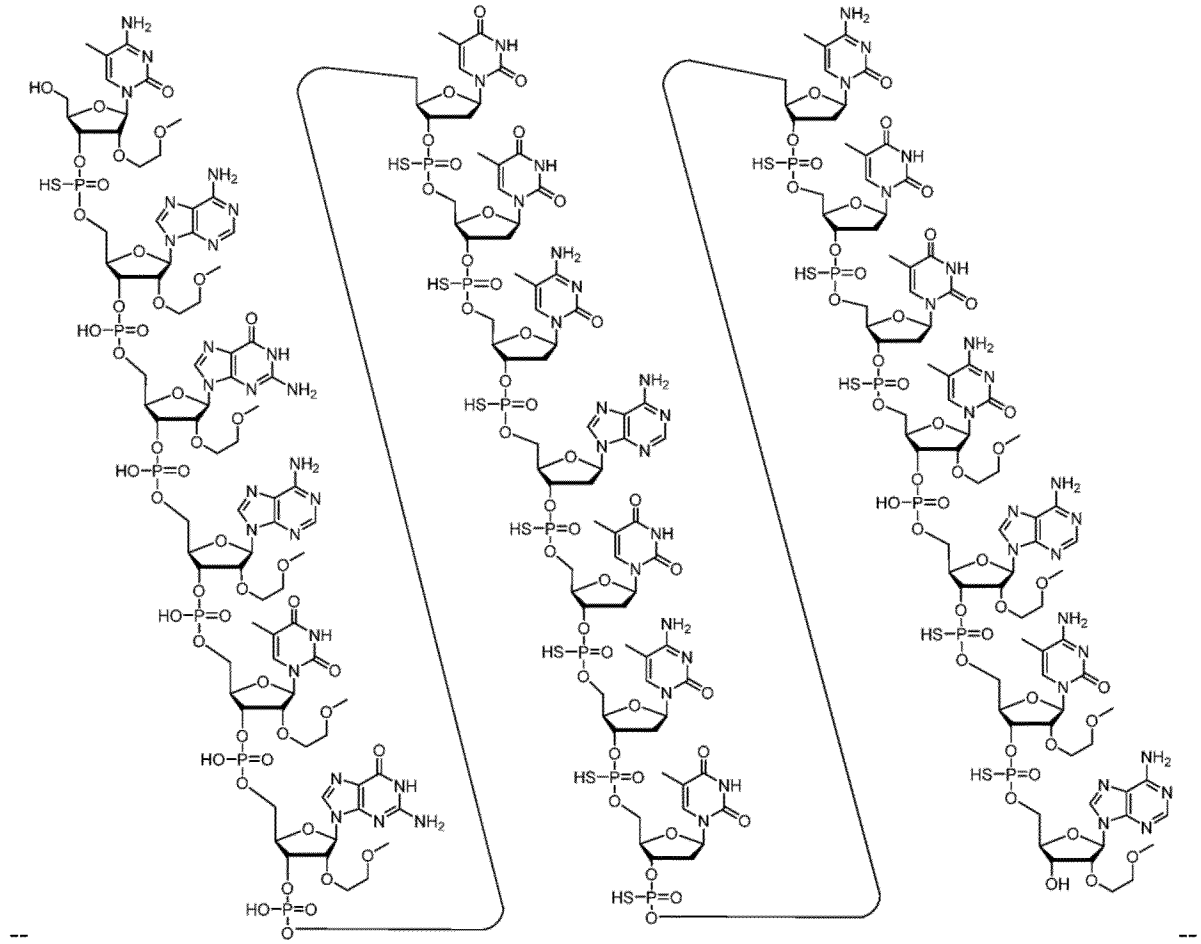

CERTIFICATE OF CORRECTION (continued)
U.S. Pat. No. 11,732,263 B2

Claim 3, Columns 957-958, the structure should read:

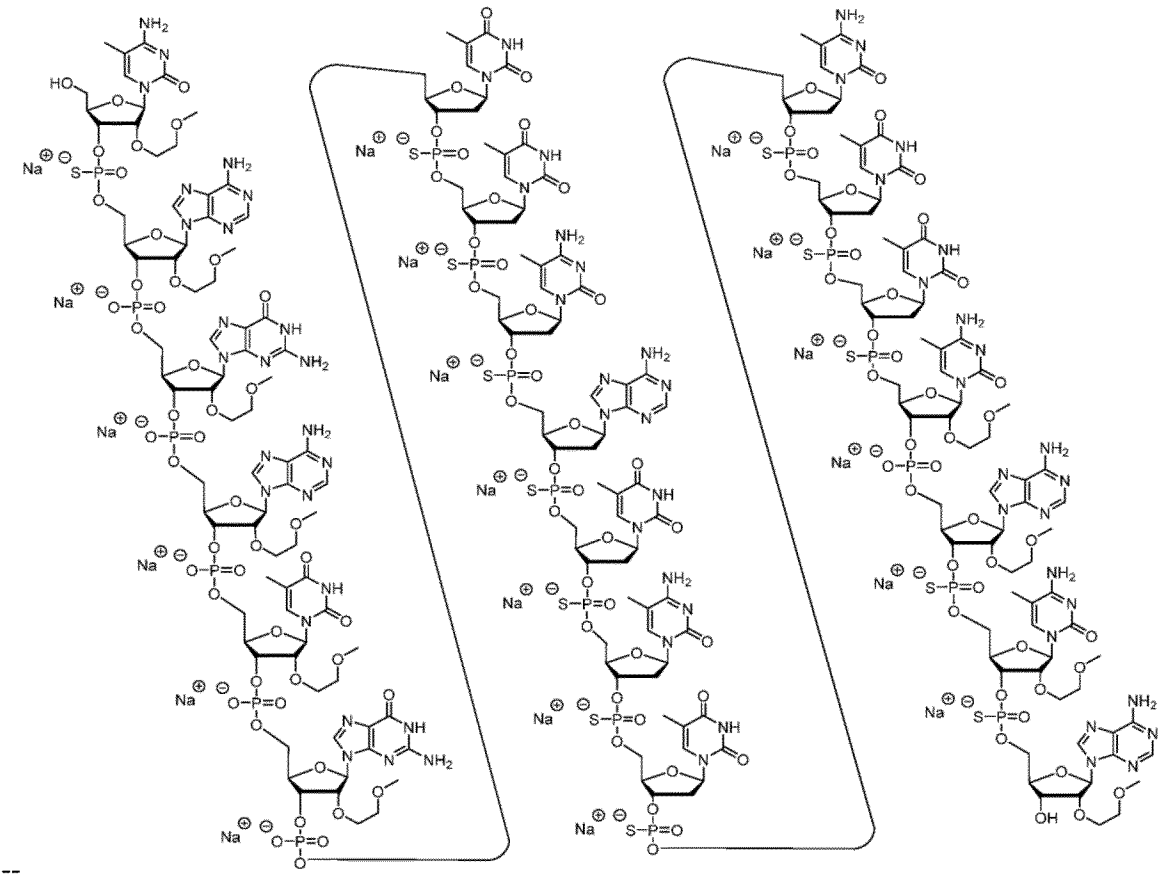

--

SEQUENCE LISTING

```
<160> NUMBER OF SEQ ID NOS: 2155

<210> SEQ ID NO 1
<211> LENGTH: 3152
<212> TYPE: DNA
<213> ORGANISM: Homo sapiens

<400> SEQUENCE: 1
acttcatggc ttctcacgct tgtgctgcat atcccacacc aattagaccc aaggatcagt      60
tggaagtttc caggacatct tcattttatt tccaccctca atccacattt ccagatgtct     120
ctgcagcaaa gcgaaattcc aggagaagag gacaaagata ctcagagaga aaaagtaaaa     180
gaccgaagaa ggaggctgga gagaccagga tccttccagc tgaacaaagt cagccacaaa     240
gcagactagc cagccggcta caattggagt cagagtccca aagacatggg cttgttagag     300
tgctgtgcaa gatgtctggt aggggccccc tttgcttccc tggtggccac tggattgtgt     360
ttctttgggg tggcactgtt ctgtggctgt ggacatgaag ccctcactgg cacagaaaag     420
ctaattgaga cctatttctc caaaaactac caagactatg agtatctcat caatgtgatc     480
catgccttcc agtatgtcat ctatggaact gcctctttct tcttccttta tgggccctc      540 ctgctggctg agggcttcta caccaccggc gcagtcaggc agatctttgg cgactacaag     600
accaccatct gcggcaaggg cctgagcgca acggtaacag ggggccagaa ggggagggt      660 tccagaggcc aacatcaagc tcattctttg gagcgggtgt gtcattgttt gggaaaatgg     720
ctaggacatc ccgacaagtt tgtgggcatc acctatgccc tgaccgttgt gtggctcctg     780
gtgtttgcct gctctgctgt gcctgtgtac atttacttca cacctggac cacctgccag     840 tctattgcct tccccagcaa gacctctgcc agtataggca gtctctgtgc tgatgccaga     900
atgtatggtg ttctcccatg gaatgctttc cctggcaagg tttgtggctc caaccttctg     960
```

-continued

```
tccatctgca aaacagctga gttccaaatg accttccacc tgtttattgc tgcatttgtg    1020
ggggctgcag ctacactggt ttccctgctc accttcatga ttgctgccac ttacaacttt    1080
gccgtcctta aactcatggg ccgaggcacc aagttctgat cccccgtaga aatccccctt    1140
tctctaatag cgaggctcta accacacagc tacaatgct gcgtctccca tcttaactct     1200
ttgcctttgc caccaactgg ccctcttctt acttgatgag tgtaacaaga aaggagagtc    1260
ttgcagtgat taaggtctct ctttggactc tcccctctta tgtacctctt ttagtcattt    1320
tgcttcatag ctggttcctg ctagaaatgg gaaatgccta agaagatgac ttcccaactg    1380
caagtcacaa aggaatggag gctctaattg aattttcaag catctcctga ggatcagaaa    1440
gtaatttctt ctcaaagggt acttccactg atggaaacaa agtggaagga aagatgctca    1500
ggtacagaga aggaatgtct ttggtcctct tgccatctat aggggccaaa tatattctct    1560
ttggtgtaca aaatggaatt cattctggtc tctctattac cactgaagat agaagaaaaa    1620
agaatgtcag aaaaacaata agagcgtttg cccaaatctg cctattgcag ctgggagaag    1680
ggggtcaaag caaggatctt tcacccacag aaagagagca ctgaccccga tggcgatgga    1740
ctactgaagc cctaactcag ccaaccttac ttacagcata agggagcgta gaatctgtgt    1800
agacgaaggg ggcatctggc cttacacctc gttaggaag agaaacaggg tgttgtcagc     1860
atcttctcac tcccttctcc ttgataacag ctaccatgac aaccctgtgg tttccaagga    1920
gctgagaata gaaggaaact agcttacatg agaacagact ggcctgagga gcagcagttg    1980
ctggtggcta atggtgtaac ctgagatggc cctctggtag acacaggata gataactctt    2040
tggatagcat gtcttttttt ctgttaatta gttgtgtact ctggcctctg tcatatcttc    2100
acaatggtgc tcatttcatg gggtattatc cattcagtca tcgtaggtga tttgaaggtc    2160
ttgatttgtt ttagaatgat gcacatttca tgtattccag tttgtttatt acttatttgg    2220
ggttgcatca gaaatgtctg gagaataatt ctttgattat gactgttttt taaactagga    2280
aaattggaca ttaagcatca caaatgatat taaaaattgg ctagttgaat ctattgggat    2340
tttctacaag tattctgcct ttgcagaaac agatttggtg aatttgaatc tcaatttgag    2400
taatctgatc gttcttttcta gctaatggaa aatgatttta cttagcaatg ttatcttggt    2460
gtgttaagag ttaggtttaa cataaaggtt atttttctcct gatatagatc acataacaga    2520
atgcaccagt catcagctat tcagttggta agcttccagg aaaaaggaca ggcagaaaga    2580
gtttgagacc tgaatagctc ccagatttca gtcttttcct gtttttgtta actttgggtt    2640
aaaaaaaaaa aaagtctgat tggtttaat tgaaggaaag atttgtacta cagttctttt    2700
gttgtaaaga gttgtgttgt tcttttcccc caaagtggtt tcagcaatat ttaaggagat    2760
gtaagagctt tacaaaaaga cacttgatac ttgttttcaa accagtatac aagataagct    2820
tccaggctgc atagaaggag gagagggaaa atgttttgta agaaaccaat caagataaag    2880
gacagtgaag taatccgtac cttgtgtttt gttttgattt aataacataa caaataacca    2940 accccttccct gaaaacctca catgcataca tacacatata tacacacaca aagagagtta   3000
atcaactgaa agtgtttcct tcatttctga tatagaattg caattttaac acacataaag    3060
gataaacttt tagaaactta tcttacaaag tgtattttat aaaattaaag aaaataaaat    3120
taagaatgtt ctcaatcaaa aaaaaaaaaa aa                                   3152
```

<210> SEQ ID NO 2
<211> LENGTH: 22000
<212> TYPE: DNA
<213> ORGANISM: Homo sapiens

<400> SEQUENCE: 2

```
tcctccccca gcccccggct gttgttgctc agggcaaagg ctctctattc acacatttt      60
tcacagcaga acaacctccc aagcaacttc caagcaataa gagtctggag acaggcattc    120
tctagagatg gctctggtct ttgcttgcta ggtgccattg ggaaaattgt ctcagtatcc    180
catcagtcaa attgaacaaa taacattggt tccccagaaa taatactagt tttatttcta    240
cttttgctcag aaatcacatc aaacaagcat cctccctgca ggggcaaccc tgcaaaagct   300
ggccaagttt ttatgttggt ggaggtgggt tctgtggaca gcttgtttct tcacattgct    360
agtagctatg tggtgctcct caggcattct ttagctgaga tttttcatgt gattatttg     420
gcttccaggc tactctttac tccatcccaa gccacgggca tctccccctc acaaatacac    480
cccatggcct gcccctatcc atcctcccat tgttccttga accttcagga aaggcagaag    540
atcaccctcc actctctacc cctgtctgcc agctcaaagt atgtgacatc tctggccctc    600
agccctcggt tctcttggcc agaaaggcat agtctagcca atcggcatga agttgggtgt    660
ggaaagttct agccacagta cataggacat aatatactgc ctgcctgcca gccagccagt    720
cttctatgcc agggctagga aagctgcctt ccaaaatttg gtctgggaag acattatcct    780
gggaatgaga agcaaagcct cagctctaga agcccaaata atagcagatg acccaggctt    840
tcactggtac gcgcttctct cttcccttt atgttcttct ctgtgctcag ggagaagttg     900
gccactagat tgggcacttg atcccttatc tagtttttcc tgggagaaat tcactggact    960
tctctgagtt ttagagttca gtctacacaa tgaagcaagg agaacccact tgatctgtgg   1020
ccttcaataa tctgatacta tgggatcata gagcagagag tggaggtaat attcaagtgt   1080
tttcgagtta tttgcaagaa agctgcacag tcaaaccaag ccatgatcaa gggggcccag   1140
attctctgag gtaccatcag aattgcatga agcaaactgt ttacgagttt tatacaatcc   1200
tgcattgttc ccacaggcac ccagtacagg cagcaggctg caccaagaag gctggcagtg   1260
cctcttgagg aatcccttgg cagtgcagga gcctagctgg actcaagaat attttgccaa   1320
gggcacccag cagaaccaat ggaagcagaa tcacagaaat aggtgggggt atgtagataa   1380
aaatgggctc tggaggacct gggaagatac cctatgaggt ctgtagggag ccctcaggaa   1440
aggtctgctg acgaggtact gaggcagagt gtcgggatgt acagagcaat gagaacacac   1500
tagattctag ggagttggga accttaaggc actgggatga gtgagacacg gtcacctggc   1560
tgggtccctt ttctggccct gggcataaga acaagcataa gaacaaggcg aagacaggga   1620
atgtggagag agaaaaagga aacagagaca gacacataga gagaaacaga gacagagaca   1680
ggtaacagag acaaagagat tgagacttgg ggagaggata gaatgaatat taaggcaatg   1740
gagatggaag aaaggagaag agaaatgtgt gttaagggaa tgtggttgat aaattggtat   1800
ctgtgggttt attgggaaca catattttct ttccagtaga gttgctgtcc ccagagctgc   1860
tgctgagaac tcaggggaag cttttgtgaga gggctcagtc tgagtgatgt cccctgtgtg   1920
gagagctgtc tcatctattc gagctgtgaa ggatcatttg cctcatcctc taaatctgaa   1980
ctcccaaagt ttgggctcac tcctgccatc tgatgagctg aggagacaca tttggcgatt   2040
tcttgctctt ggtcctcccc cttctccagg gccattccga cagtgaccat ccagaagttt   2100
attgctggct caatcctaca gttgagcttc caaagcaggc atagtctgtg gctggcgagc   2160
agggctgggg agggcgaggg gctctaggac ccttttccat cagtcacatg gccttagtct   2220
cgtctgctct ggaaagctac tattataccg ttttgcaagg ggcagcattt ccagagatcc   2280
```

```
tttttcttg gggctgatac aagagcaaag gatctagagt tctagtactc taagcaagcc    2340
tcaaacggtg caggatttgg ccccagtggg cccacagggg catctgccaa agactcgtcc    2400
atttcctaac agcagagccc aagccagtaa catgtccaaa gtcacagccc aaagagaaaa    2460
ctgtaagaca caatcttgcc tttctcccac cccaggaagg tactagtctc tgctcagtat    2520
ctccctcctc ttctctcctc tcccaaggca aaatcacagg aaaagttcca ggagaccata    2580
ccttccttct ccggagtctt ccaacaggtg cccctcttat tatatgccag ccagttgttt    2640
taaaggccat ccatgggagg acaccggcct ctaggtcaag ggagctgtga agggagacag    2700
gactgacaag gagcccagac agacactgtt taagattcac ctgttctaga aaaccttccc    2760
aggctgatcc catctagcag tgggcattta ataccttca cagtctttag aaatagctta    2820
ttgctaaggc aggttttata tagtatttcc ctgttttgc tgcttagcca ttttttgtctt    2880 accgcttctt tctctgtggc aaggactata tttcgtttct tctctccacc ctcactgcca    2940
cctgctgctt cactctaacc cactccctgc ctcttgtctg cctggcttaa gctctctgat    3000
gaagatatta cactctcagg atagaatact gactacctga ttcccagatc gtgttcttga    3060
cttgtctcga agtcgattat ccttcttgga aatcacccac atcttcaacg ctggcctttt    3120 cttaaccta gtctgtgaac ttgcataggt cttgcccact tctgggtctt tattattgta    3180
gctataaaat tattacaatt ctagcctccc ccagcctaat cacaatctgt tcatcgaatt    3240
gacagcctgc attttgtctt catgcagttg aaactgagaa ggatttggag gaaattatct    3300
taaaagacaa ttttttcttc tctattgtgt tcgtagagct gggggtgggg gtggggagg     3360 aacgcttatt ttccaaggaa tcgggagggg aaaggtggag agggccaagg gcagctagga    3420
gtgatgtggg gagctggagc agattcggaa ggactttggg agctaatatc taggtttttg    3480
actctgagcc cctgttgggg ctctcacttc atggcttctc acgcttgtgc tgcatatccc    3540
acaccaatta gacccaagga tcagttggaa gtttccagga catcttcatt ttatttccac    3600
cctcaatcca catttccaga tgtctctgca gcaaagcgaa attccaggca agccttaggg    3660 aaaaaggaa aaacaaagaa aatgaaacaa ttggcagtga aaggcagaaa gagaagatgg    3720
agcccttaga gaagggagta tccctgagta ggtggggaaa aggggaggag aagggaggag    3780
gagaggagga ggaaagcagg cctgtccctt taagggggtt ggctgtcaat cagaaagccc    3840
ttttcattgc aggagaagag gacaaagata ctcagagaga aaaagtaaaa gaccgaagaa    3900
ggaggctgga gagaccagga tccttccagc tgaacaaagt cagccacaaa gcagactagc    3960
cagccggcta caattggagt cagagtccca aagacatggg taagtttcaa aaactttagc    4020
attgaagatt caagaggaca caggaattca caagagaatt tccaactttg gggttcgggg    4080
gttccatggt ttaaatgagt cgtgttttgg cacttgtttt cttttttaaat tccttaacat    4140 tcagttagat taactccttc tccgctgtac taagcatgat gctttattac caaagaattc    4200
cagcagcacg tggagagtcc cacagatctc tggagagagt gcccagctgg atggatgtgg    4260
tcatgtgtcc tcctaccccc tcacttccct ctatcttctc ttttcccttg gttccaaggc    4320
cctggcaacg gttgggtcag cttgccctcc tggttctgct ggaggccact gagcactgtc    4380
tagccctcag atgtacaaaa taactgcttg cttgatgcaa actttgaacc atgtttggca    4440
ttaataggaa gctgggatc gggcaagctg gactcaggct tggctatggc tgaggaggcc    4500
attctcaggt tcaggaaatg aaagtaaagt cctcaatggc ttgaccatgg gaaacagata    4560
tgggtaggag tgtgtgtgtg tatgtgcata tgtgcatgtg tgtgcacata tagggttgat    4620
catttctagc aaatatcaca gacacagctt tcctgaaggc tctttgctgt gacaaggagg    4680
```

```
atgctgggac attagggctc ttgctaagtt ggctgagtat tgagggcttt tctaggttcc    4740
gtgaacaaag acagaagcta tgaagttctg gtggtagttt ctactcagag taatgtgtgc    4800
agagcacaag ggtctttgtc cctattggac tccacagagt cctgtagaca ttgctaacat    4860
ttggcaaaac aaagatagca gcttaaacac atcctaaatg aaatgagact cagttgcccc    4920
atgtattccc tatcaaatgt agcatccagt agacaacatc cacagagatc aatttgcaat    4980
tatactgagc tggttcagcc tttaggttgt ttcatcatga aacacagaga gaacactttg    5040
aagcatgtgt tcaggtaaaa caggagggag agcactggac agggagtcgg aaaaatcaga    5100
ttcaaatccc agatctgcta cttatgaact atgtgacctt ggacaggtca ctgaatcacc    5160
acttcctcat ctggaaaatg gggacagcaa taactacttt gtctactttc agggttgtga    5220
gaatcaagta acaataatgt caaagtcctt tgaaaatggg caagatctat aacaactgta    5280
aatcatgata atacctacta ttagacaata atgtgtatac aggcgaactc ttcctctttc    5340
cagggtggtt gggttttctt tgcgtgcttg ggtcagaatc atttgaccaa ttatgtgtga    5400
ccagatgaga ggtgaatgtt ggaggaactc aattcctgcc ctgggtaaca tcaggaatcc    5460
tatctaatgt cagccgagct gactggatag gttgtgcatt aaaaacagag agggagtaaa    5520
gaaggatgtt gaatattact tcctcagggg atgaaatccc tgaggaaagg caggaacaaa    5580
taaagtgacc acagggacaa ttgcctgtta tggaggctgg gtggtttcct ccagaggaag    5640
agtgccacag ataagggcac gattgaggat gcacattggg tcccaggtcc taagggtgga    5700
cgatacttgg gccaggtaca tatgatggag cagccactga gttttcattt attcaataac    5760
agagtatcta aagtactttg aattatagat catctctaac aaggtactgg actgccacta    5820
cttctgatgt ggagtgcact gctgttcaac aattgcagta aacacattgt atcatggaat    5880
ccgggattgg aaggaacttt agaagttgtc tgagccaacc ttcaatgcgg gattcatttt    5940
tacaacaacc aattaaatgt tcgtacagcc tctgcttaat cacctccagg aacagggaac    6000
ttactacttc aaccatatag aatcccttag gattggaagc aaggaggaac actgattcag    6060
tagtgtctgc acaaaagatt tatggggaaa atgatagctc attaattttt gccttgattt    6120 ggaagggaa tgttccaagt gagtctttgg gataatgatg gaaccagaaa ggagcaaaag    6180
agcagtagct gattattctc tgctctgaaa cacaatgcca ttattgaaca gcaaaacatt    6240
gtctgcaagc ctgttgtcgt ctgagaacag tggctgttac cctggtaacc agactgtgat    6300
gcctccatcc aaaagtggct gtttgccaag cagtgtagtt ttggctggct tgcagtaagt    6360
gggtgtagcc caggcaaaaa gtgtggcggc agagcggggg tccagttta taaaatgccc    6420 gaagactaac tgagtcccat caaaatggca agaatgcccc aagaatacca ggagccaaaa    6480 ataaccaga tccagccag catgttcacc tagtcttcct ggagacactg actaaaataa    6540
tcaagtgcag ccttctctac ctcacttctc cctttggccg tgcagagcca gaggagttct    6600
tggaaagcca ggcagtttga aggtctacc ctgcttagg gggccttggg cttggctctg    6660
agctaggaaa gccagaagtt tacttaacag gctgacaact ggaactgctc tctcagagcg    6720
atctgagtaa taacaacctc aaccctggga ggtgggtggg aggggaaata tagtctccaa    6780
acccattaag gtagaactcc agccagtaac atcactttcc cccattgctt ttgtctatcg    6840
tcctgaagcc ttgaaagcca tccctgggt acaggtcttt gtcttgaaag aaagcaacag    6900
tagaaatgcc ttccctgccc acagcacttc aggtctaaag aagaccaagt gaggacagtg    6960
acatgatcag gaagggtcac agcagccatg gtaggtgaat ggagcagctt ttccttcctt    7020
```

```
tcctgctttc agagcctact cagtgccaaa cttacatcaa aagctcagca agtactgatt    7080
gattaatccc tcttgcctac ggcaaaatgg ccctgagggc tatctctcag ctctgcactg    7140
gcctctgagc tgtctgccag gcagggctct agaaaagagt cccaaggaag agaataaggt    7200
tccccaaatc agcttcacac tgcaacaagg agagaggagg aaatggtggg agactgacct    7260
gaggaacaag gtatggctac tattgtctct agtaccagtt acttcccttt catcttccca    7320
ttcgtgggca aggtggagac aatgtgccaa ggataagttt taacaatcaa agtcctacct    7380
cagcttccca atgcttgcac ataaattgga atgtgtacat cattcattct gtctctctct    7440
gtgtgtgtgt gtgtgtgtgt gtgtgtgtgc gcgtctgaag aggagtgggg agtataggaa    7500
acaagatagt ccagatgctg ttgccgtggt aatactaaat cgtgtccaaa gaggaggctg    7560
agattccttt ttagttaacc ttgtccacat gatttgacta tccagcaggc ttggattccc    7620
aggccccaga gacttcggga ctgttttcca gcacttgaat gtggtatata agtgctgata    7680
tcaaaaggga tatgtaggaa agacaagatt ataggcaggg cattgtctga ccaggacgag    7740
gcccgaagca aaagtctttg tttgtctctg gcacctcttg ataattgttg ttttactcct    7800
agaacccacc cactgatccc catccatccc tagtaccagt cacggctgct ctagcatttc    7860
ggccttgtca actactgcag gccctgatca aggaggcctc tgttcatggg gtaaggttaa    7920
ggggtgggtt ctgggaggag ggtaagactg tagtgcagat tcgagaccta gggaggtggg    7980
gccagtttct cactcaatga gcctgcctgt tgtttagctc tattgtatag ggttcttcta    8040
tctctccctt tgtcagctgg attcaaggga caggctggga attgtgcagg gtacaattgg    8100
tctctttcta ccattccttt cgatgaaagc ccttcctctc cttcctttga tgagttccca    8160
gattcacact gaatttccat catggagctg tccttgagg cgggcccagg gcatgggaaa    8220
ggagggaggg agggttggga gctcttggtg cctgcttaaa gagacagcat caggatcaac    8280
acagtccctt gatgaacctg gatctgtgta agtcacattg gttctgttga tctctgtcag    8340
accgctgtga gagcgctggt gagaagggc ttaaagttgg agtatcaact atcacagatt    8400
gattagactt gttttgggag tttgtataca aatgtagcca accatgacat gatctttcc    8460 ctttgcttac attttgccca cacaacttcg ttatatccat tttaacactt gcttataggt    8520
agctttagat tttgattcac agacatatgt ttgttcaccc caacaggatt tcaagtttc    8580 taaagaaagg gactggcctt ttaattccct tctgtttctc ctaatgtcta tgtcactgct    8640
agtgtgctta attcttgtac tgaattcaca taaacagaaa tgaaagaaaa acactggagg    8700
gggtcattat ttttctctat gacctttcat caaagtcagg tggcttaatc tgactgagtt    8760
gcattgagaa atgttattac tatatggttc ttttatgcca actctctcat ctcgcagtct    8820
gtacttagac tggaaatgtg agaatgtctc ttgagagagc caaggaactt ctcccctaga    8880
atctcttcca gccttcttga atcaaactca caccctttca accaggaggg gttctgaaat    8940
ggagagcttt tggctttagg ctattgttca cacatacccca agggacattt cttggactgt    9000
gaaaaatcaa agggagccca atggatcttt tctcagaatg ctttgattgt caactacttt    9060
gatgaaaaaa taatttcttg caggctctga gttttttctca gttagaatct aaaatctgat    9120
tcttgcttgg acagactgac tgagattctt cacttctgct gaacttaaat gccccaaag    9180 caaacatttc atctaggttg tgaagagatg aacatctgat gcttatgctg atattactga    9240 attgttttata gcttaatagt gatagattta tctaaagtca tttatttcag actttacatt    9300
agaaactcat taaagcctac ttctttcttg tcccttgctt tgagctgtag tggagcagaa    9360
aaggggatgc taagttattc aagttctaag aaaatagagg aaaaatggat gtaaaaagaa    9420
```

```
aggctatgat ctggtgactc agaattgctc ctaaggctta gccatttatc acccagtaag    9480
aacacaatcc atgacactct caggttattt ggatgatgat tgagggatca gatacactca    9540
agaggatgtt tccctctcat ctttgcaacc ctagaggtgg catcacctaa cgcttaaagt    9600
ggagttctct tttggctagc aagagttcaa gttcctccat ccctgaccat acctgcacaa    9660
gcacttagcc cttcccagat gaaaatgctg ggatgagtga gtaggcccaa gatggtcact    9720
tgctagggtg gatggctctt cttaccctcg gctaaacaaa cagtcctgcc attgttccct    9780
gagtctgacc ccctccccac ccccggctg caggcccctg tggaatacca atcaggctcc    9840
tgagatctca ggaaagaaca aggcttcttt gtccggggga gctatggagg gctctgtcca    9900
agccctgacc ctgtgctggg gagaaaggga acagtggggt cactgacctt cttctccccc    9960
catccccagg cttcagagac tttcttact agaaaagtct aagagtttgg gggtggggag   10020
gagttggata ggcagagaag gaaaatggca gtactgttta cttctaagct ccttttcttg   10080
acttataggc tgaatctagt atcttaacct gttgagaaag aggaagatca atttctggaa   10140
tgttttctga gaacaacaat cgatttcagt tgttgtgttt ttctctgtgg tatacatgtg   10200
tgtatgtgca catttgtaca catgcatgca tgtgcgtgtg cacacacaca gacacaccca   10260
tgggccagct ctgaaaagac actcttccca agcacgtttg caaagttcat gctgagtaaa   10320
ctcagcctcc actcacagca gcacagctac agattgcttc ttatagaggc caagtttcct   10380
ggcagcaatg ctttagttct tggaaaagga agttctgctc caaatgttag ctgcttactt   10440
tgtttggctt gggcttctga ggctcatctt tggtgtgaca ctctttgaag gccaagaaag   10500
ggctgtcatt tcaggggatg gtgggtaata ggactcactc cttttgtgtc tctgagaaca   10560
gaggcaaatg cctctacctc gattttccca tgacagagat aatttgatct ttccaaatct   10620
gttcacactg atgcaattca gccatgtaaa tcactaggta ttcatgctct ctgggctaaa   10680
aacaaactgt aactaatgtt aacagaatca ggaaaaggag tcccttttcc ctggtaccct   10740
atagaaaagt gagtgtggct tggagaaatg cttgaataca aaaatccaag cctaagtaat   10800
taatacaatt tattttttatt gtacaagctg tcacaacctg cttattcaaa aatagcagct   10860
tcccagtaca tttgctgagt atttgtgtgt gtgcatgtgt atactgtgtt tatagatata   10920
taaaatcagt gggtatatat acatatattt atatatatac atacatatga attaagacat   10980
ttttttctgaa gagcttaaca ttctcatttc ttctacattt tagggatctg gccgagaggc   11040
cagaggaagc cattctttc ctcatctagt cagtcatcta cttggcattt gctaaggttc   11100
actccatatg acatcttaga gcatgggact agtacttgga acacagctgc tttcagagcc   11160
tgtgacttct tgtgtgcctc tcctgtttct cagcaacact ggcatagggc ctgggatacc   11220
aggtctgggg atctcaggga ctcttagcac tttaagacac atgtgttccc aggccctggt   11280
gtgttcctct agtgccagaa agatgtttca tgctttgctg actttgtata aagtctgttt   11340
gtagctgttt tgacagaatc tcagcgtata actgaggggtg gggacattag ccaagctgca   11400
ttataggagg acaaaactgc catacaaagt gtccaaaatc attaagcctg cattttatt   11460
attgggagta atatcaaacc tcctattttc caattttcat ttcttgtcct gtgctagctc   11520
catcctgttt ggactgctcc tcccatatgt aaactaagaa gaatcaagca ttctttgcaa   11580
caaatacaca cgatgctcaa aaatgtccag gagcatccaa tttccaaagt ttcctccacc   11640
tggaatgctc ttcatgctaa aatcctgtct gacaatacca gcatctctgg cctgcactca   11700
tcccttcctg gaactccaag tgcatttacc ctctgttacc acttacttgg ctgcctgaat   11760
```

```
tgttagttga aaatattagg tctacttagc taattcttcc tcaggaaatt aaagactccc   11820
atatggcaga gtctgtgtct tttctctctt catatcccgt ataacaccca gcataatgct   11880
gggcatatag tgagtattcc ataaatagtt gatgaatgac taaaataagc aagcaaacaa   11940
acagactaga acaataagaa agaagggact gatttcataa tctctctggc ttgctatttg   12000
aattgctgaa ttattattat ttattaaata tttttaaat tctggcaata aaaggtaagg    12060
atttattttc tttctttctt tttttttttc ttgagacaga gtctcgctct tactgcccag   12120
gctggagtac aatggcgcaa tcttggctca cggcaacctc cgcctcctcc tgggtttaac   12180
agattctcct gtctcagcct cctgagtagc tgggattaca ggcatacgcc catgcccggc   12240
taattttttgt atttttagta gagacggggt tttgccatgt tggccaggct ggtcttgaac   12300
tcctgacctc atgtgatcca cctgcctcag cctcccaaag tgctgggatt acaggcatga   12360
gccaccgtgc ccggccaaag atttattttc aagaatgaaa caaagtaagg attctgggtc   12420
aatctcacat gctgaaagcc aaaacctcta gccgctcctg cttttttgact tcggagtgcc   12480
cactatctcc gagcctgtga gcacagggcc tggcagaggg gtttgagtgg catgagctac   12540
ctactggatg tgcctgactg tttccccttc ttcttcccca ggcttgttag agtgctgtgc   12600
aagatgtctg gtaggggccc cctttgcttc cctggtggcc actggattgt gtttctttgg   12660
ggtggcactg ttctgtggct gtggacatga agccctcact ggcacagaaa agctaattga   12720
gacctatttc tccaaaaact accaagacta tgagtatctc atcaatgtgt aagtacctgc   12780
cctcccacac agacccatct tttttttccc tctctccatc ctggagatag agaactcttc   12840
agtaccttag taactagcag gggactgggg tggagccaga ccggattccc gagtcttccc   12900
tctgtgcaga tctctcctgc tccacattcg aagcccattc agaaaggagg gtctgcctg    12960
cctgcctgtc agccctccc acccccgccc ccttgttttc ttacacgtgt tctgacttct   13020
gctaggtgtg gttcatattg cccaagttgg agcctccagc gtagtaggta tggagaagcc   13080
aagggaggca ctaagcctct cctgttccta gaacaagtta ggctcctgtt ccttcaccca   13140
cctttcttct tgtctagctc cctactcctg tgagttagca tgtctgaagg gtggggcagg   13200
gagagtaggt ccctggttct ccaggtccca gggtaagcaa ggtgtggcgg gaggggcata   13260
tgtttctggt cacatacacc ctgtcttcac ttatttcaac aaagataagg tgaaagcatg   13320
caggaggaac ctggtgattc ctctagaaaa tccctagcct tgttaaggtg ctcgctctgg   13380
tgtataccctc acttatgtcg ggaaagaagc caggtcttca attaataaga ttccctggtc   13440
tcgtttgtct acctgttaat gcaggatcca tgccttccag tatgtcatct atggaactgc   13500
ctctttcttc ttccttatg gggccctcct gctggctgag ggcttctaca ccaccggcgc    13560
agtcaggcag atctttggcg actacaagac caccatctgc ggcaagggcc tgagcgcaac   13620
ggtaacaggg ggccagaagg ggaggggttc cagaggccaa catcaagctc attctttgga   13680
gcgggtgtgt cattgttggg gaaaatggct aggacatccc gacaaggtga tcatcctcag   13740
gattttgtgg caataacaag gggtggggga aaattgggcg cgagtctgtg gcctcgtccc   13800
cacccaaggc tgggtcctct ctaggggcct ggcatttgag tgaggaagcg atggctgcag   13860
ccgaacgaga aggtcaggaa gaacgtggtg cccagctggc ttagcctcac ctttcaaagg   13920
ttccctaagc aaatttcttc tcaaaacaga aagcatgagt tttgtgggat gctttgtaca   13980
atcagaccat ttctaagcca tctgttggta tccctttgtt cccttcctag taggtaccac   14040
aagagtggat ctaactggac aagagtctaa atgctgctc atgtgattga gacttgggca    14100
cctgatctga gagggaggat ggataataaa aattaaataa ttaactccaa ggtgaaattt   14160
```

```
acaatgttct gggatcctgc acagttcgag gtcccagagg gaattggagt agatctgcat   14220
gttgaatgtt ttattgcctg agggttatcc atgctttgag tgaggtgcac atttgttttc   14280
agtctctgga gttaaagatc ctttggcggc tgaacatgtg tgggttccag caatgtcttt   14340
ttgtggccag cagttagctt agaaaggttt tgtatctgaa atttttaatct cctattggct   14400
ttgttcaatg gctagggaac aaaaatgttc ctatggcaag gaacatgttc taagctcagc   14460
ctaaggcaca aaatggcacg actttctttc aagatctgtt ttgatttctt tacaccttat   14520
ctgcccaaaa acatcctctg aagcctctct aacccaggga tcctcctcac tcttccccta   14580
cccattcccc ccaccctccg ttatactggg gccagttatc tagtagatac tgccaattac   14640
ccttggcaga ggtgccctgc tcactaattt catttgaagg agagccctgg aacctggttt   14700
taatgtctgg cacacgccac tccaggatct cccagtttgt gtttctacat ctgcaggctg   14760
atgctgattt ctaaccaccc catgtcaatc attttagttt gtgggcatca cctatgccct   14820
gaccgttgtg tggctcctgg tgtttgcctg ctctgctgtg cctgtgtaca tttacttcaa   14880
cacctggacc acctgccagt ctattgcctt ccccagcaag acctctgcca gtataggcag   14940
tctctgtgct gatgccagaa tgtatggtga gttagggtac gggtgctttg gctctcctac   15000
ccactatgga agcactatat atttggttat tttcttagtg taaggagggt ggtgattatg   15060
agaaaaatat aagatgatga atgattgggt cttagtttat taatccttcc ctactgaaac   15120
cagagaggtt tcttccccgg gaagggaact tggaagtggt gggagttttc ttggccattc   15180
acattggcct actctagttg actgctgttc acaaccccaa agcagcacat ttcaataaca   15240
aacacaaggt ttcaccactg ttcaatacca ccttctcttt tttgtaaacc tgtagaaaag   15300
aggatcctga ttgttggtag aatccaactt tacagccagg ataattagag atggaagaag   15360
ggctctgggg gaaagtctcc atgtggcccc gtaactccat aaagcttacc ctgcttgctt   15420
tttgtgtctt acttaggtgt tctcccatgg aatgctttcc ctgcaaggt ttgtggctcc   15480
aaccttctgt ccatctgcaa aacagctgag gtgagtgggt tatttgggtt attttacaag   15540
ggagtagcta ataccataca aattacaccc atggccttca attttaagga ctgaaagttt   15600
cccttttgctg gattttgaat tagccgattg ccttctacaa catgttggct aagtgtgcct   15660
gagccaatga gcatagaagg taaaacacct gttttctcta gagttgcata gaaagacttc   15720
ctttccaacc cttcccctct taaaagagaa gtttgtagct ttaggtaaag atagagccta   15780
atggcaaaat ccccccacatg aaaatttttca ttcctttagt taaaaaccat atcaagaaaa   15840
tgggctgtgc acagaggcat tcataggttt tatgaaaaca ttttcaattt ggaacttctt   15900
tatctcaaat gagaggtaaa ataagtacat ttgaaaggga agcactgta ttgagaacag   15960
atattatata caaatgaggc aggggaataa aagtaaatcc gggggagaca ggcagtaaat   16020
tatttctttg acagcaaaat gttgacttta aattttgggc ccctgggcac aactgtaggg   16080
aaccagttaa ttatttttgga gtactgtact atttcatgac tattctgtga tctgggtgtt   16140
aatgggccag gtgctatggt gtacactgaa gactgggagg cccacattta gggaagtgaa   16200
aacttagtta gagatgtgga attagcacac aagaaagata tcaacacatt cagaaagctg   16260
tattcatgat ttacagtgga gcatattact gctgttgcaa gaaacagttc ttcctctttc   16320
attttcctgc agttccaaat gaccttccac ctgtttattg ctgcatttgt gggggctgca   16380
gctacactgg tttccctggt gagttgactt tgaatgatct tggcaagtaa ataggcctga   16440
gatagtgtgg gtacagctat tctgaaaggc aagaaggtag actgcttcca tccttgaaat   16500
```

```
gctggaggga agcttctggg aagatagcaa agggtggagg ctccgtactt ctacttgcat   16560
tggcaaggca gaaagacatc acaaattaga tgggaacaag aaaagtggta tgaggaaaga   16620
ggtaagagat tcatagacac gaatgataat atttagtatt tatagaacat gtaatgttgc   16680
caagtacttt gcagtcataa attacggtta attctcaata cattttgatc agatcagtga   16740
caaaacactg aaacatcacg aaacatgact tgctatagcc tggaattcta tatactatca   16800
atatgaatcc actttggata ctctccagtg gatttagtta ctcatatgga aatactggga   16860
ggacctccta acattattag aattgttatg attataatac aatgctatgt cccaggtctt   16920
gctgatagtg ctacagtgcc ctgtgaatgt agtgtgctca ttgtgcagat taaaaaccta   16980
aggcactgaa gggtgaagtg atttatctga agttatttta taagcagtga tcagacaaga   17040
tgagctcaca gaactcctgg cccctactgc tgaggtttcc atacagagtc aagtaatttc   17100
tcaccttgta aaacgaattg attcattaac caggggagag ctctactgca tgatgtggct   17160
gtgtgtctac agcaagcacc ctatgactct aagtcactcg gacatattga tgtggcaaag   17220
cccaaatatt gttcacttcc ctgaggaaaa ctcagtgcta gatcaaacag aggtgtggaa   17280
taaatcttta tgatttgatt ctctgggcct gggccatgag acccatgatg cctcagagac   17340
atcggacttc cagtcaagtg tatatggaga aagccaagcc tgggatgtac tgcttttgc    17400 agagcatggg ttttttcctt atttagttat gattttattt ctacccttcc tcattcccaa   17460
agggatttga ggagggagtg cttttctttc tactctcatt cacattctct cttctgttcc   17520
ctacagctca ccttcatgat tgctgccact tacaactttg ccgtccttaa actcatgggc   17580
cgaggcacca agttctgatc ccccgtagaa atccccctttt ctctaatagc gaggctctaa   17640
ccacacagcc tacaatgctg cgtctcccat cttaactctt tgcctttgcc accaactggc   17700
cctcttctta cttgatgagt gtaacaagaa aggagagtct tgcagtgatt aaggtctctc   17760
tttggactct cccctcttat gtacctcttt tagtcatttt gcttcatagc tggttcctgc   17820
tagaaatggg aaatgcctaa gaagatgact tcccaactgc aagtcacaaa ggaatggagg   17880
ctctaattga attttcaagc atctcctgag gatcagaaag taatttcttc tcaaagggta   17940
cttccactga tggaaacaaa gtggaaggaa agatgctcag gtacagagaa ggaatgtctt   18000
tggtcctctt gccatctata ggggccaaat atattctctt tggtgtacaa aatggaattc   18060
attctggtct ctctattacc actgaagata gaagaaaaaa gaatgtcaga aaaacaataa   18120
gagcgtttgc ccaaatctgc ctattgcagc tgggagaagg gggtcaaagc aaggatcttt   18180
cacccacaga aagagagcac tgaccccgat ggcgatggac tactgaagcc ctaactcagc   18240
caaccttact tacagcataa gggagcgtag aatctgtgta gacgaagggg gcatctggcc   18300
ttacacctcg ttagggaaga gaaacagggt gttgtcagca tcttctcact cccttctcct   18360
tgataacagc taccatgaca accctgtggt ttccaaggag ctgagaatag aaggaaacta   18420
gcttacatga gaacagactg gcctgaggag cagcagttgc tggtggctaa tggtgtaacc   18480
tgagatggcc ctctggtaga cacaggatag ataactcttt ggatagcatg tcttttttc    18540 tgttaattag ttgtgtactc tggcctctgt catatcttca caatggtgct catttcatgg   18600
ggtattatcc attcagtcat cgtaggtgat ttgaaggtct tgatttgttt tagaatgatg   18660
cacatttcat gtattccagt tgttttatta cttatttggg gttgcatcag aaatgtctgg   18720
agaataattc tttgattatg actgtttttt aaactaggaa aattggacat taagcatcac   18780
aaatgatatt aaaaattggc tagttgaatc tattgggatt ttctacaagt attctgcctt   18840
tgcagaaaca gatttggtga atttgaatct caatttgagt aatctgatcg ttcttttctag   18900
```

```
ctaatggaaa atgattttac ttagcaatgt tatcttggtg tgttaagagt taggtttaac   18960
ataaaggtta ttttctcctg atatagatca cataacagaa tgcaccagtc atcagctatt   19020
cagttggtaa gcttccagga aaaaggacag gcagaaagag tttgagacct gaatagctcc   19080
cagatttcag tcttttcctg tttttgttaa ctttgggtta aaaaaaaaaa aagtctgatt   19140
ggtttttaatt gaaggaaaga tttgtactac agttcttttg ttgtaaagag ttgtgttgtt   19200
cttttccccc aaagtggttt cagcaatatt taaggagatg taagagcttt acaaaaagac   19260
acttgatact tgttttcaaa ccagtataca agataagctt ccaggctgca tagaaggagg   19320
agagggaaaa tgttttgtaa gaaaccaatc aagataaagg acagtgaagt aatccgtacc   19380
ttgtgttttg ttttgattta ataacataac aaataaccaa cccttccctg aaaacctcac   19440
atgcatacat acacatatat acacacacaa agagagttaa tcaactgaaa gtgtttcctt   19500
catttctgat atagaattgc aattttaaca cacataaagg ataaactttt agaaacttat   19560
cttacaaagt gtattttata aaattaaaga aaataaaatt aagaatgttc tcaatcaaac   19620
atcgtgtcct ttgagtgaat tgttctattt gacttcacaa tagaaactta ataatcgtac   19680
cttgttcaag gagatcattc attttttcagc tcatccaagt cattctcata acatttctct   19740
gaaataaata gtatatgaat agattacttc tactttttata gttgaagaca ctaagaaata   19800
gaagcaaagt aatttgccca aagaaatcca gtaagtacat gtctgagctt gtgttaaaac   19860
gcagatattg aaaccaattt attgcctact taaaggtttc ttttctcttc gaagttgggt   19920
ttcagaatgt tcagagtcaa ctatggttac tttttcaata ccttagtggt gccccagtcc   19980
ccggtgcatt tagatttaag ttattgttac cttctcttta aattgtttgg atattccagt   20040
aatgatccct tagtaattca tacgtgacta atatttagtt ttatttggat agtactggat   20100
ggaaggttta gtacttaaag gacagagcag gtatggaaag ggcaacgtaa atgtaaacag   20160
gctgtggcag ggcagtacta aaataaaatta gtgacaccta ccaccctgga tggccagcct   20220
actagcccac cggggacata gcattaaagc cctttcacaa ccctaggtta gaatttggca   20280
cccttggaca gcactctgat gaccagctta aagaaagctg tcttaaaatc atttcattgc   20340
cccatagttg cagctggcaa atgactggag agaaaggaat ctttagctgg agggatgaca   20400
agtcagtcat cagttaagga gctccattca aaagcagttt caatttaatt tcctgatttc   20460
tgcttaacca caattaatat tctgcaagcg agtctggttg aacgacttta agacataaag   20520
aataaaaata tgacagggac ttattttaag acactgcaaa caaggacaca gcaccatatt   20580
ttggagaatt gattcagggt tctacagagt gattgtattt ttgcctcaga ggaaccgaaa   20640
gccagttccc aagaaagcta tgttttccat ctgcccttat ttggctctgc ctctgggatg   20700
aatctataga tggagtttct aggctctcag aagctgagag catctccagt ctatcaattg   20760
aacccattgt tcttagctct cccacacacc ataaacctcc ttttttctaa ctgaaagagc   20820
tctctttgtg ctgagatcag ccgaagatca agatgcagca gtataaacaa gaaacatttt   20880
cttacagcac cagttgtatt gcttttccta tcttcagggt cagtactgag tgcagttatg   20940
caggacgtgg aagctgcagc tttgtccaga gcaacatttg ttcattcctt aattcgttct   21000
gtgaacattc attgagaaac tactaagtat tgtgttaaac cccaggaagt tcaagttgg    21060
gggcagtgtg ggtagaaagg tgatcaagac cagatcttac actcaaggat ctctctcaga   21120
ttcagccata gcagacaggt cttccacggt aaactggagt ggaggcaagg agtgtgcaaa   21180
aggcagtctg atcggctgac tccagtgggc atctgaattc tcccctcagt atgtgggagg   21240
```

```
ggtgggtgtt aagggccttg acttcacgtg gctctgggtt tttagggcat ggatacaaac    21300
aaaacttcaa tttagagtcc tgacaacttg tgacttgctc tttctgtgtc accctgcttc    21360
ttgccttaca tgtgacagca tttatgcaca cactggctca atgcatgtgc gtgcttccac    21420
ccactcaatc atttggggag tcagagggca catgaatcaa gattgatata aacacaagct    21480
attcagtctg gccttttgtc tctatccagg ctaagtctga gaagccaagg aagggtaatg    21540
taagatataa catatcaaaa ctgcacttgt atccccctaaa tttatacaac aacaacaaaa   21600
aagataccaa gtccttctct gtttggatttt ccttaactgt gaacacaggt agtgtggcta   21660
ttttgacatt aacagttaac ttcatgaata ttaagtaaca aataaaagaa atactcatta    21720
ttatatttac gaaatcaata cttggccatt cctacatcaa taagcaggta aggacttcaa    21780
gtcaatattt atatattggg aaagattttc ctcgttcact cacttgtttg aaagacgcaa    21840
acatactctt cattatattt gttgtcccac aaagtttggt gtctatgtgc tcctgttctg    21900
agactccttg aattgattga ctttattcta aaggaaaata tcagataagg taatgagtgt    21960
tttactgatt atggatcagt ccaaagaaat ccagtcttaa                          22000
```

<210> SEQ ID NO 3

<400> SEQUENCE: 3

000

<210> SEQ ID NO 4

<400> SEQUENCE: 4

000

<210> SEQ ID NO 5
<211> LENGTH: 21
<212> TYPE: DNA
<213> ORGANISM: Artificial sequence
<220> FEATURE:
<223> OTHER INFORMATION: Primer

<400> SEQUENCE: 5

```
ccctaactca gccaacctta c                                              21
```

<210> SEQ ID NO 6
<211> LENGTH: 22
<212> TYPE: DNA
<213> ORGANISM: Artificial sequence
<220> FEATURE:
<223> OTHER INFORMATION: Primer

<400> SEQUENCE: 6

```
caccctgttt ctcttcccta ac                                             22
```

<210> SEQ ID NO 7
<211> LENGTH: 26
<212> TYPE: DNA
<213> ORGANISM: Artificial sequence
<220> FEATURE:
<223> OTHER INFORMATION: Probe

<400> SEQUENCE: 7

```
agggagcgta gaatctgtgt agacga                                         26
```

<210> SEQ ID NO 8
<211> LENGTH: 19

```
<212> TYPE: DNA
<213> ORGANISM: Artificial sequence
<220> FEATURE:
<223> OTHER INFORMATION: Primer

<400> SEQUENCE: 8
gaaggtgaag gtcggagtc                                                   19

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
gaagatggtg atgggatttc                                                  20

<210> SEQ ID NO 10
<211> LENGTH: 20
<212> TYPE: DNA
<213> ORGANISM: Artificial sequence
<220> FEATURE:
<223> OTHER INFORMATION: Probe

<400> SEQUENCE: 10
caagcttccc gttctcagcc                                                  20

<210> SEQ ID NO 11
<211> LENGTH: 22
<212> TYPE: DNA
<213> ORGANISM: Artificial sequence
<220> FEATURE:
<223> OTHER INFORMATION: Primer

<400> SEQUENCE: 11
ctgatgccag aatgtatggt gt                                               22

<210> SEQ ID NO 12
<211> LENGTH: 21
<212> TYPE: DNA
<213> ORGANISM: Artificial sequence
<220> FEATURE:
<223> OTHER INFORMATION: Primer

<400> SEQUENCE: 12
aggtggaagg tcatttggaa c                                                21

<210> SEQ ID NO 13
<211> LENGTH: 24
<212> TYPE: DNA
<213> ORGANISM: Artificial sequence
<220> FEATURE:
<223> OTHER INFORMATION: Probe

<400> SEQUENCE: 13
tgcagatgga cagaaggttg gagc                                             24

<210> SEQ ID NO 14
<211> LENGTH: 21
<212> TYPE: DNA
<213> ORGANISM: Artificial sequence
<220> FEATURE:
<223> OTHER INFORMATION: Primer

<400> SEQUENCE: 14
```

```
tgcaccagtc atcagctatt c                                              21

<210> SEQ ID NO 15
<211> LENGTH: 23
<212> TYPE: DNA
<213> ORGANISM: Artificial sequence
<220> FEATURE:
<223> OTHER INFORMATION: Primer

<400> SEQUENCE: 15
agactgaaat ctgggagcta ttc                                            23

<210> SEQ ID NO 16
<211> LENGTH: 26
<212> TYPE: DNA
<213> ORGANISM: Artificial sequence
<220> FEATURE:
<223> OTHER INFORMATION: Probe

<400> SEQUENCE: 16
aggtctcaaa ctctttctgc ctgtcc                                         26

<210> SEQ ID NO 17
<211> LENGTH: 20
<212> TYPE: DNA
<213> ORGANISM: Artificial sequence
<220> FEATURE:
<223> OTHER INFORMATION: Primer

<400> SEQUENCE: 17
ggcaaattca acggcacagt                                                20

<210> SEQ ID NO 18
<211> LENGTH: 20
<212> TYPE: DNA
<213> ORGANISM: Artificial sequence
<220> FEATURE:
<223> OTHER INFORMATION: Primer

<400> SEQUENCE: 18
gggtctcgct cctggaagat                                                20

<210> SEQ ID NO 19
<211> LENGTH: 27
<212> TYPE: DNA
<213> ORGANISM: Artificial sequence
<220> FEATURE:
<223> OTHER INFORMATION: Probe

<400> SEQUENCE: 19
aaggccgaga atgggaagct tgtcatc                                        27

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
agccaacccc cttaaaggga                                                20

<210> SEQ ID NO 21
<211> LENGTH: 20
<212> TYPE: DNA
<213> ORGANISM: Artificial sequence
```

```
<220> FEATURE:
<223> OTHER INFORMATION: Synthetic oligonucleotide

<400> SEQUENCE: 21
tctgattgac agccaacccc                                                     20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
ccggctggct agtctgcttt                                                     20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
tccaattgta gccggctggc                                                     20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
ccctaccaga catcttgcac                                                     20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
gccggtggtg tagaagccct                                                     20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
tctgcctgac tgcgccggtg                                                     20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
tagtcgccaa agatctgcct                                                     20
```

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
atggtggtct tgtagtcgcc                                           20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
ccttgccgca gatggtggtc                                           20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
aggcccttgc cgcagatggt                                           20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
cgttgcgctc aggcccttgc                                           20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
tgttaccgtt gcgctcaggc                                           20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
cccctgttac cgttgcgctc                                           20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 34
atgttggcct ctggaacccc                                              20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
acaatgacac acccgctcca                                              20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
tgtcgggatg tcctagccat                                              20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
agccacacaa cggtcagggc                                              20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
ggtggtccag gtgttgaagt                                              20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
gcattccatg ggagaacacc                                              20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
cagaacttgg tgcctcggcc                                              20

<210> SEQ ID NO 41
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
gggatcagaa cttggtgcct                                                   20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
gctgtgtggt tagagcctcg                                                   20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
ggagacgcag cattgtaggc                                                   20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
ggcccctata gatggcaaga                                                   20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
cagtagtcca tcgccatcgg                                                   20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
agggcttcag tagtccatcg                                                   20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
```
ggttggctga gttagggctt                                              20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
ccttatgctg taagtaaggt                                              20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
acgctccctt atgctgtaag                                              20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
ttctacgctc ccttatgctg                                              20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
tacacagatt ctacgctccc                                              20

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
tgtaaggcca gatgccccct                                              20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
tctcttccct aacgaggtgt                                              20

<210> SEQ ID NO 54
<211> LENGTH: 20
<212> TYPE: DNA

-continued

```
<213> ORGANISM: Artificial sequence
<220> FEATURE:
<223> OTHER INFORMATION: Synthetic oligonucleotide

<400> SEQUENCE: 54
aggttacacc attagccacc                                                   20

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
gtgtctacca gagggccatc                                                   20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
ccaatagatt caactagcca                                                   20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
ggagctattc aggtctcaaa                                                   20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
tacggattac ttcactgtcc                                                   20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
acacaaggta cggattactt                                                   20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
tccttgggtc taattggtgt                                                   20
```

-continued

<210> SEQ ID NO 61
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 61
tcgctttgct gcagagacat                                             20

<210> SEQ ID NO 62
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 62 tgggcccct tgatcatggc                                              20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 63
gctccctaca gacctcatag                                             20

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64
ggtcctagag cccctcgccc                                             20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 65
cctgccttag caataagcta                                             20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
aacctagata ttagctccca                                             20

<210> SEQ ID NO 67
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 67
gcccgatccc cagcttccta                                           20

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
gttgttatag atcttgccca                                           20

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
tgcacaacct atccagtcag                                           20

<210> SEQ ID NO 70
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 70
ccaatcccgg attccatgat                                           20

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
gttgaagtag taagttccct                                           20

<210> SEQ ID NO 72
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 72
gccgccacac tttttgcctg                                           20

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
agggccattt tgccgtaggc                                           20

```
<210> SEQ ID NO 74
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 74
cgatttagta ttaccacggc                                               20

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 75
gatatcagca cttatatacc                                               20

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 76
accaattgta ccctgcacaa                                               20

<210> SEQ ID NO 77
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 77
ttaagccctt ctcaccagcg                                               20

<210> SEQ ID NO 78
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 78
ccattgggct ccctttgatt                                               20

<210> SEQ ID NO 79
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 79
gtgcttgtgc aggtatggtc                                               20

<210> SEQ ID NO 80
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 80
tccaccctag caagtgacca                                               20

<210> SEQ ID NO 81
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 81
gagtcctatt acccaccatc                                               20

<210> SEQ ID NO 82
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 82
aggagtgagt cctattaccc                                               20

<210> SEQ ID NO 83
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 83
ccctcagtta tacgctgaga                                               20

<210> SEQ ID NO 84
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 84
aggaggtttg atattactcc                                               20

<210> SEQ ID NO 85
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 85
accttgctta ccctgggacc                                               20

<210> SEQ ID NO 86
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 86
accttgtcgg gatgtcctag                                               20

<210> SEQ ID NO 87
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 87
actcgcgccc aattttcccc                                               20

<210> SEQ ID NO 88
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 88
cgaggccaca gactcgcgcc                                               20

<210> SEQ ID NO 89
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 89
ccagttagat ccactcttgt                                               20

<210> SEQ ID NO 90
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 90
ggtgcccaag tctcaatcac                                               20

<210> SEQ ID NO 91
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 91
tctactagat aactggcccc                                               20

<210> SEQ ID NO 92
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 92
cccgtaccct aactcaccat                                               20

<210> SEQ ID NO 93
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 93
```
ggtattagct actcccttgt                                                    20

<210> SEQ ID NO 94
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 94
ccattaggct ctatctttac                                                    20

<210> SEQ ID NO 95
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 95
tcagtgtaca ccatagcacc                                                    20

<210> SEQ ID NO 96
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 96
aagtacggag cctccaccct                                                    20

<210> SEQ ID NO 97
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 97
cagtagagct ctcccctggt                                                    20

<210> SEQ ID NO 98
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 98
cagccaaccc ccttaaaggg                                                    20

<210> SEQ ID NO 99
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 99
ttctgattga cagccaaccc                                                    20

<210> SEQ ID NO 100
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 100
tagccggctg gctagtctgc                                                    20

<210> SEQ ID NO 101
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 101
actccaattg tagccggctg                                                    20

<210> SEQ ID NO 102
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 102
gcccctacca gacatcttgc                                                    20

<210> SEQ ID NO 103
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 103
gactgcgccg gtggtgtaga                                                    20

<210> SEQ ID NO 104
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 104
gatctgcctg actgcgccgg                                                    20

<210> SEQ ID NO 105
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 105
gtagtcgcca aagatctgcc                                                    20

<210> SEQ ID NO 106
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 106
gatggtggtc ttgtagtcgc                                                    20

<210> SEQ ID NO 107
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 107
cccttgccgc agatggtggt                                              20

<210> SEQ ID NO 108
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 108
cgctcaggcc cttgccgcag                                              20

<210> SEQ ID NO 109
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 109
taccgttgcg ctcaggccct                                              20

<210> SEQ ID NO 110
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 110
ctgttaccgt tgcgctcagg                                              20

<210> SEQ ID NO 111
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 111
ccccctgtta ccgttgcgct                                              20

<210> SEQ ID NO 112
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 112
gatgttggcc tctggaaccc                                              20

<210> SEQ ID NO 113
<211> LENGTH: 20
<212> TYPE: DNA
<213> ORGANISM: Artificial sequence
<220> FEATURE:
<223> OTHER INFORMATION: Synthetic oligonucleotide -continued

<400> SEQUENCE: 113
ccaaacaatg acacacccgc                                               20

<210> SEQ ID NO 114
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 114
ttgtcgggat gtcctagcca                                               20

<210> SEQ ID NO 115
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 115
ggagccacac aacggtcagg                                               20

<210> SEQ ID NO 116
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 116
gcctatactg gcagaggtct                                               20

<210> SEQ ID NO 117
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 117
ccatgagttt aaggacggca                                               20

<210> SEQ ID NO 118
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 118
tcagaacttg gtgcctcggc                                               20

<210> SEQ ID NO 119
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 119
ggttagagcc tcgctattag                                               20

<210> SEQ ID NO 120

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 120
cgcagcattg taggctgtgt                                                   20

<210> SEQ ID NO 121
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 121
gagttaagat gggagacgca                                                   20

<210> SEQ ID NO 122
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 122
tttggcccct atagatggca                                                   20

<210> SEQ ID NO 123
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 123
tcagtagtcc atcgccatcg                                                   20

<210> SEQ ID NO 124
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 124
gttagggctt cagtagtcca                                                   20

<210> SEQ ID NO 125
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 125
gctgtaagta aggttggctg                                                   20

<210> SEQ ID NO 126
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 126
```
cccttatgct gtaagtaagg                                    20

<210> SEQ ID NO 127
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 127
tacgctccct tatgctgtaa                                    20

<210> SEQ ID NO 128
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 128
cagattctac gctcccttat                                    20

<210> SEQ ID NO 129
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 129
ctacacagat tctacgctcc                                    20

<210> SEQ ID NO 130
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 130
gtgtaaggcc agatgccccc                                    20

<210> SEQ ID NO 131
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 131
ttctcttccc taacgaggtg                                    20

<210> SEQ ID NO 132
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 132
tcaggttaca ccattagcca                                    20

<210> SEQ ID NO 133
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 133
tgtgtctacc agagggccat                                               20

<210> SEQ ID NO 134
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 134
cccaatagat tcaactagcc                                               20

<210> SEQ ID NO 135
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 135
gggagctatt caggtctcaa                                               20

<210> SEQ ID NO 136
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 136
gtacggatta cttcactgtc                                               20

<210> SEQ ID NO 137
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 137
tgggatatgc agcacaagcg                                               20

<210> SEQ ID NO 138
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 138
atccttgggt ctaattggtg                                               20

<210> SEQ ID NO 139
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 139
ggaatttcgc tttgctgcag                                               20
```

<210> SEQ ID NO 140
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 140
ctgggccccc ttgatcatgg                                               20

<210> SEQ ID NO 141
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 141
gctctgtaca tcccgacact                                               20

<210> SEQ ID NO 142
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 142
ctgccccttg caaaacggta                                               20

<210> SEQ ID NO 143
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 143
aggtagtcag tattctatcc                                               20

<210> SEQ ID NO 144
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 144
gcctggaatt tcgctttgct                                               20

<210> SEQ ID NO 145
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 145
agcttgcccg atccccagct                                               20

<210> SEQ ID NO 146
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 146
agttgttata gatcttgccc                                                20

<210> SEQ ID NO 147
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 147
cgtgccctta tctgtggcac                                                20

<210> SEQ ID NO 148
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 148
aagttccttc caatcccgga                                                20

<210> SEQ ID NO 149
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 149
gcttgcagac aatgttttgc                                                20

<210> SEQ ID NO 150
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 150
actcagttag tcttcgggca                                                20

<210> SEQ ID NO 151
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 151
gggactcttt tctagagccc                                                20

<210> SEQ ID NO 152
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 152
gacacgattt agtattacca                                                20

-continued

```
<210> SEQ ID NO 153
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 153
gcagtagttg acaaggccga                                              20

<210> SEQ ID NO 154
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 154
agaccaattg taccctgcac                                              20

<210> SEQ ID NO 155
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 155
gatactccaa ctttaagccc                                              20

<210> SEQ ID NO 156
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 156
gagtcaccag atcatagcct                                              20

<210> SEQ ID NO 157
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 157
ttgggcctac tcactcatcc                                              20

<210> SEQ ID NO 158
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 158
gcaggactgt ttgtttagcc                                              20

<210> SEQ ID NO 159
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 159
tgagtcctat tacccaccat                                                    20

<210> SEQ ID NO 160
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 160
cctctcggcc agatccctaa                                                    20

<210> SEQ ID NO 161
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 161
agcttggcta atgtccccac                                                    20

<210> SEQ ID NO 162
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 162
cgggaatccg gtctggctcc                                                    20

<210> SEQ ID NO 163
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 163
acaccttgct taccctggga                                                    20

<210> SEQ ID NO 164
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 164
gaggatgatc accttgtcgg                                                    20

<210> SEQ ID NO 165
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 165
gactcgcgcc caattttccc                                                    20

<210> SEQ ID NO 166
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 166
ggacgaggcc acagactcgc                                              20

<210> SEQ ID NO 167
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 167
gtccagttag atccactctt                                              20

<210> SEQ ID NO 168
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 168
cctctgggac ctcgaactgt                                              20

<210> SEQ ID NO 169
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 169
ggtgatgccc acaaactaaa                                              20

<210> SEQ ID NO 170
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 170
acccgtaccc taactcacca                                              20

<210> SEQ ID NO 171
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 171
gtatggtatt agctactccc                                              20

<210> SEQ ID NO 172
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 172
```
ccccggattt acttttattc 20

<210> SEQ ID NO 173
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 173
gtcttcagtg tacaccatag 20

<210> SEQ ID NO 174
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 174
accgtaattt atgactgcaa 20

<210> SEQ ID NO 175
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 175
tccgagtgac ttagagtcat 20

<210> SEQ ID NO 176
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 176
tgattgacag ccaaccccct 20

<210> SEQ ID NO 177
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 177
gctggctagt ctgctttgtg 20

<210> SEQ ID NO 178
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 178
ttgtagccgg ctggctagtc 20

<210> SEQ ID NO 179
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 179
gactccaatt gtagccggct					20

<210> SEQ ID NO 180
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 180
gggcccctac cagacatctt					20

<210> SEQ ID NO 181
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 181
gcctgactgc gccggtggtg					20

<210> SEQ ID NO 182
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 182
gtcgccaaag atctgcctga					20

<210> SEQ ID NO 183
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 183
ggtcttgtag tcgccaaaga					20

<210> SEQ ID NO 184
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 184
gcagatggtg gtcttgtagt					20

<210> SEQ ID NO 185
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 185
gcccttgccg cagatggtgg					20

<210> SEQ ID NO 186
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 186
gcgctcaggc ccttgccgca                                             20

<210> SEQ ID NO 187
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 187
ttaccgttgc gctcaggccc                                             20

<210> SEQ ID NO 188
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 188
cctgttaccg ttgcgctcag                                             20

<210> SEQ ID NO 189
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 189 ctggcccect gttaccgttg                                             20

<210> SEQ ID NO 190
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 190
ccgctccaaa gaatgagctt                                             20

<210> SEQ ID NO 191
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 191
cgggatgtcc tagccatttt                                             20

<210> SEQ ID NO 192
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 192
gcataggtga tgcccacaaa                                              20

<210> SEQ ID NO 193
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 193
ccaggagcca cacaacggtc                                              20

<210> SEQ ID NO 194
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 194
tgcctatact ggcagaggtc                                              20

<210> SEQ ID NO 195
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 195
ggtgcctcgg cccatgagtt                                              20

<210> SEQ ID NO 196
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 196
gatcagaact tggtgcctcg                                              20

<210> SEQ ID NO 197
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 197
gtgtggttag agcctcgcta                                              20

<210> SEQ ID NO 198
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 198
acgcagcatt gtaggctgtg                                              20

<210> SEQ ID NO 199
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 199
agtggaagta ccctttgaga                                               20

<210> SEQ ID NO 200
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 200
tgcaataggc agatttgggc                                               20

<210> SEQ ID NO 201
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 201
gcttcagtag tccatcgcca                                               20

<210> SEQ ID NO 202
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 202
agttagggct tcagtagtcc                                               20

<210> SEQ ID NO 203
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 203
tgctgtaagt aaggttggct                                               20

<210> SEQ ID NO 204
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 204
gctcccttat gctgtaagta                                               20

<210> SEQ ID NO 205
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 205
```

-continued ctacgctccc ttatgctgta                                              20

<210> SEQ ID NO 206
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 206
acagattcta cgctccctta                                              20

<210> SEQ ID NO 207
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 207
tctacacaga ttctacgctc                                              20

<210> SEQ ID NO 208
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 208
ggtgtaaggc cagatgcccc                                              20

<210> SEQ ID NO 209
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 209
ggttgtcatg gtagctgtta                                              20

<210> SEQ ID NO 210
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 210
ctcaggttac accattagcc                                              20

<210> SEQ ID NO 211
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 211
gactgaatgg ataataccccc                                             20

<210> SEQ ID NO 212
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 212
gatgactggt gcattctgtt                                               20

<210> SEQ ID NO 213
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 213
cggattactt cactgtcctt                                               20

<210> SEQ ID NO 214
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 214
ggtacggatt acttcactgt                                               20

<210> SEQ ID NO 215
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 215
ggtgtgggat atgcagcaca                                               20

<210> SEQ ID NO 216
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 216
gatccttggg tctaattggt                                               20

<210> SEQ ID NO 217
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 217
aagtgcccaa tctagtggcc                                               20

<210> SEQ ID NO 218
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 218
atctacatac ccccacctat                                               20

<210> SEQ ID NO 219
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 219
ggtgaccgtg tctcactcat                                               20

<210> SEQ ID NO 220
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 220
tactagaact ctagatcctt                                               20

<210> SEQ ID NO 221
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 221
ccaagaagga taatcgactt                                               20

<210> SEQ ID NO 222
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 222
cgactcattt aaaccatgga                                               20

<210> SEQ ID NO 223
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 223
ccagctcagt ataattgcaa                                               20

<210> SEQ ID NO 224
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 224
taggattcct gatgttaccc                                               20

<210> SEQ ID NO 225
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 225
cctgggaccc aatgtgcatc                                        20

<210> SEQ ID NO 226
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 226
gtacgaacat ttaattggtt                                        20

<210> SEQ ID NO 227
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 227
gttctcagac gacaacaggc                                        20

<210> SEQ ID NO 228
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 228
tgttattact cagatcgctc                                        20

<210> SEQ ID NO 229
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 229
gtagccatac cttgttcctc                                        20

<210> SEQ ID NO 230
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 230
gctggatagt caaatcatgt                                        20

<210> SEQ ID NO 231
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 231
aacccacccc ttaaccttac                                        20

```
<210> SEQ ID NO 232
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 232
tgggcccgcc tcaaggacca                                               20

<210> SEQ ID NO 233
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 233
ccagtctaag tacagactgc                                               20

<210> SEQ ID NO 234
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 234
agtgtatctg atccctcaat                                               20

<210> SEQ ID NO 235
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 235
atcttgggcc tactcactca                                               20

<210> SEQ ID NO 236
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 236
tcccccggac aaagaagcct                                               20

<210> SEQ ID NO 237
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 237
agtgagtcct attacccacc                                               20

<210> SEQ ID NO 238
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 238
tccaagtact agtcccatgc                                              20

<210> SEQ ID NO 239
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 239
gaggtttgat attactccca                                              20

<210> SEQ ID NO 240
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 240
gcaatatgaa ccacacctag                                              20

<210> SEQ ID NO 241
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 241
cgccacacct tgcttaccct                                              20

<210> SEQ ID NO 242
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 242
ccaccccttg ttattgccac                                              20

<210> SEQ ID NO 243
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 243
cagactcgcg cccaattttc                                              20

<210> SEQ ID NO 244
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 244
ggtctgattg tacaaagcat                                              20

<210> SEQ ID NO 245
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 245
tgtccagtta gatccactct                                                   20

<210> SEQ ID NO 246
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 246
cgccaaagga tctttaactc                                                   20

<210> SEQ ID NO 247
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 247
cgtaccctaa ctcaccatac                                                   20

<210> SEQ ID NO 248
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 248
cacccgtacc ctaactcacc                                                   20

<210> SEQ ID NO 249
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 249
tgtatggtat tagctactcc                                                   20

<210> SEQ ID NO 250
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 250
ctgtctcccc cggatttact                                                   20

<210> SEQ ID NO 251
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 251
```
tacccacact atctcaggcc                                                20

<210> SEQ ID NO 252
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 252
gcacactaca ttcacagggc                                                20

<210> SEQ ID NO 253
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 253
ccacatcaat atgtccgagt                                                20

<210> SEQ ID NO 254
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 254
ctgattgaca gccaacccc                                                 20

<210> SEQ ID NO 255
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 255
ggctggctag tctgctttgt                                                20

<210> SEQ ID NO 256
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 256
ccaattgtag ccggctggct                                                20

<210> SEQ ID NO 257
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 257
tgactccaat tgtagccggc                                                20

<210> SEQ ID NO 258
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 258
ccggtggtgt agaagccctc					20

<210> SEQ ID NO 259
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 259
tgcctgactg cgccggtggt					20

<210> SEQ ID NO 260
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 260
agtcgccaaa gatctgcctg					20

<210> SEQ ID NO 261
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 261
ggtggtcttg tagtcgccaa					20

<210> SEQ ID NO 262
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 262
ccgcagatgg tggtcttgta					20

<210> SEQ ID NO 263
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 263
ggcccttgcc gcagatggtg					20

<210> SEQ ID NO 264
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 264
ttgcgctcag gcccttgccg					20

```
<210> SEQ ID NO 265
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 265
gttaccgttg cgctcaggcc                                           20

<210> SEQ ID NO 266
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 266
ccctgttacc gttgcgctca                                           20

<210> SEQ ID NO 267
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 267
cttctggccc cctgttaccg                                           20

<210> SEQ ID NO 268
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 268
acccgctcca aagaatgagc                                           20

<210> SEQ ID NO 269
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 269
tcgggatgtc ctagccattt                                           20

<210> SEQ ID NO 270
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 270
ccacacaacg gtcagggcat                                           20

<210> SEQ ID NO 271
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 271
accaggagcc acacaacggt                                              20

<210> SEQ ID NO 272
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 272
gagactgcct atactggcag                                              20

<210> SEQ ID NO 273
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 273
aacttggtgc ctcggcccat                                              20

<210> SEQ ID NO 274
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 274
ggatcagaac ttggtgcctc                                              20

<210> SEQ ID NO 275
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 275
tgtgtggtta gagcctcgct                                              20

<210> SEQ ID NO 276
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 276
gagacgcagc attgtaggct                                              20

<210> SEQ ID NO 277
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 277
tcagtggaag tacccttga                                               20

<210> SEQ ID NO 278
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 278
aagatccttg ctttgacccc                                              20

<210> SEQ ID NO 279
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 279
ggcttcagta gtccatcgcc                                              20

<210> SEQ ID NO 280
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 280
gagttagggc ttcagtagtc                                              20

<210> SEQ ID NO 281
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 281
atgctgtaag taaggttggc                                              20

<210> SEQ ID NO 282
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 282
cgctccctta tgctgtaagt                                              20

<210> SEQ ID NO 283
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 283
tctacgctcc cttatgctgt                                              20

<210> SEQ ID NO 284
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 284
```

```
acacagattc tacgctccct                                              20

<210> SEQ ID NO 285
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 285
gtctacacag attctacgct                                              20

<210> SEQ ID NO 286
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 286
ccctaacgag gtgtaaggcc                                              20

<210> SEQ ID NO 287
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 287
agggttgtca tggtagctgt                                              20

<210> SEQ ID NO 288
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 288
agggccatct caggttacac                                              20

<210> SEQ ID NO 289
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 289
gaccttcaaa tcacctacga                                              20

<210> SEQ ID NO 290
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 290
cctggaagct taccaactga                                              20

<210> SEQ ID NO 291
<211> LENGTH: 20
<212> TYPE: DNA
```

```
<213> ORGANISM: Artificial sequence
<220> FEATURE:
<223> OTHER INFORMATION: Synthetic oligonucleotide

<400> SEQUENCE: 291
acggattact tcactgtcct                                              20

<210> SEQ ID NO 292
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 292
aggtacggat tacttcactg                                              20

<210> SEQ ID NO 293
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 293
ggtctaattg gtgtgggata                                              20

<210> SEQ ID NO 294
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 294
cgctttgctg cagagacatc                                              20

<210> SEQ ID NO 295
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 295
tcattgtgta gactgaactc                                              20

<210> SEQ ID NO 296
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 296
cctcataggg tatcttccca                                              20

<210> SEQ ID NO 297
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 297
atcgccaaat gtgtctcctc                                              20
```

<210> SEQ ID NO 298
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 298
ggtatggtct cctggaactt                                              20

<210> SEQ ID NO 299
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 299
gctcccaaag tccttccgaa                                              20

<210> SEQ ID NO 300
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 300
ggctagacag tgctcagtgg                                              20

<210> SEQ ID NO 301
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 301
ggtgattcag tgacctgtcc                                              20

<210> SEQ ID NO 302
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 302
acctatccag tcagctcggc                                              20

<210> SEQ ID NO 303
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 303
gtccagtacc ttgttagaga                                              20

<210> SEQ ID NO 304
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 304
gcagaggctg tacgaacatt                                           20

<210> SEQ ID NO 305
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 305
gctacaccca cttactgcaa                                           20

<210> SEQ ID NO 306
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 306
gagttctacc ttaatgggtt                                           20

<210> SEQ ID NO 307
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 307
cactcctctt cagacgcgca                                           20

<210> SEQ ID NO 308
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 308
agtgctggaa aacagtcccg                                           20

<210> SEQ ID NO 309
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 309
ggtctcgaat ctgcactaca                                           20

<210> SEQ ID NO 310
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 310
tcaagggact gtgttgatcc                                           20

```
<210> SEQ ID NO 311
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 311
ggtatgtgtg aacaatagcc                                               20

<210> SEQ ID NO 312
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 312
tgagtgtatc tgatccctca                                               20

<210> SEQ ID NO 313
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 313
ccctagcaag tgaccatctt                                               20

<210> SEQ ID NO 314
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 314
ccatagctcc cccggacaaa                                               20

<210> SEQ ID NO 315
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 315
ggagtgagtc ctattaccca                                               20

<210> SEQ ID NO 316
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 316
gtgttccaag tactagtccc                                               20

<210> SEQ ID NO 317
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 317
ggaggtttga tattactccc                                          20

<210> SEQ ID NO 318
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 318
ctccatacct actacgctgg                                          20

<210> SEQ ID NO 319
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 319
ccagagcgag caccttaaca                                          20

<210> SEQ ID NO 320
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 320
gcgcccaatt ttcccccacc                                          20

<210> SEQ ID NO 321
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 321
gaggccacag actcgcgccc                                          20

<210> SEQ ID NO 322
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 322
agttagatcc actcttgtgg                                          20

<210> SEQ ID NO 323
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 323
ttgtccagtt agatccactc                                          20

<210> SEQ ID NO 324
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 324
tgttccctag ccattgaaca                                                 20

<210> SEQ ID NO 325
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 325
ccgtacccta actcaccata                                                 20

<210> SEQ ID NO 326
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 326
gtaggccaat gtgaatggcc                                                 20

<210> SEQ ID NO 327
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 327
ttgtatggta ttagctactc                                                 20

<210> SEQ ID NO 328
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 328
tggcccatta acacccagat                                                 20

<210> SEQ ID NO 329
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 329
gtacggagcc tccacccttt                                                 20

<210> SEQ ID NO 330
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 330
```
agtagagctc tcccctggtt                                              20

<210> SEQ ID NO 331
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 331
agtccgatgt ctctgaggca                                              20

<210> SEQ ID NO 332
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 332
gctccctttg atttttcaca                                              20

<210> SEQ ID NO 333
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 333
tctatatcag gagaaaataa                                              20

<210> SEQ ID NO 334
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 334
tccttctatt ctcagctcct                                              20

<210> SEQ ID NO 335
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 335
catggtagct gttatcaagg                                              20

<210> SEQ ID NO 336
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 336
cattagctag aaagaacgat                                              20

<210> SEQ ID NO 337
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 337
catgaataca gctttctgaa                                                   20

<210> SEQ ID NO 338
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 338
aagatatgac agaggccaga                                                   20

<210> SEQ ID NO 339
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 339
tcaagtaaga agagggccag                                                   20

<210> SEQ ID NO 340
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 340
agattcagcc tataagtcaa                                                   20

<210> SEQ ID NO 341
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 341
caattcagta atatcagcat                                                   20

<210> SEQ ID NO 342
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 342
ttatctatcc tgtgtctacc                                                   20

<210> SEQ ID NO 343
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 343
caatttttaa tatcatttgt                                                   20
```

<210> SEQ ID NO 344
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 344
tcttacaaaa cattttccct                                              20

<210> SEQ ID NO 345
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 345
tttctgcaaa ggcagaatac                                              20

<210> SEQ ID NO 346
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 346
gaaaatccca atagattcaa                                              20

<210> SEQ ID NO 347
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 347
cattctaaaa caaatcaaga                                              20

<210> SEQ ID NO 348
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 348
ctaacaattc aggcagccaa                                              20

<210> SEQ ID NO 349
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 349
tgtagacaca cagccacatc                                              20

<210> SEQ ID NO 350
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 350
cctttgagaa gaaattactt                                               20

<210> SEQ ID NO 351
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 351
ttaatcactg caagactctc                                               20

<210> SEQ ID NO 352
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 352
tcagcaagac ctgggacata                                               20

<210> SEQ ID NO 353
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 353
ccatgatgga aattcagtgt                                               20

<210> SEQ ID NO 354
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 354
aacacaactc tttacaacaa                                               20

<210> SEQ ID NO 355
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 355
tcaccttatc tttgttgaaa                                               20

<210> SEQ ID NO 356
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 356
agtggcagca atcatgaagg                                               20

<210> SEQ ID NO 357
```

-continued

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 357
tctgagtaga aactaccacc                                                    20

<210> SEQ ID NO 358
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 358
atgctgacaa caccctgttt                                                    20

<210> SEQ ID NO 359
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 359
gccacactca cttttctata                                                    20

<210> SEQ ID NO 360
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 360
tgagcatctt tccttccact                                                    20

<210> SEQ ID NO 361
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 361
tagatggcaa gaggaccaaa                                                    20

<210> SEQ ID NO 362
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 362
ttgtatactg gtttgaaaac                                                    20

<210> SEQ ID NO 363
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 363
```
aaagctctta catctcctta        20

<210> SEQ ID NO 364
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 364
gataacattg ctaagtaaaa        20

<210> SEQ ID NO 365
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 365
tttgattgag aacattctta        20

<210> SEQ ID NO 366
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 366
tcacatagtt cataagtagc        20

<210> SEQ ID NO 367
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 367
caaatcacct acgatgactg        20

<210> SEQ ID NO 368
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 368
cattccaatt tatgtgcaag        20

<210> SEQ ID NO 369
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 369
tcaaagaatt attctccaga        20

<210> SEQ ID NO 370
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 370
ctcaaattga gattcaaatt                                               20

<210> SEQ ID NO 371
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 371
actttcagtt gattaactct                                               20

<210> SEQ ID NO 372
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 372
ccaattttcc cccaccccctt                                              20

<210> SEQ ID NO 373
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 373
gcctcgctat tagagaaagg                                               20

<210> SEQ ID NO 374
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 374
tgactaaaag aggtacataa                                               20

<210> SEQ ID NO 375
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 375
ccaacaatca ggatcctctt                                               20

<210> SEQ ID NO 376
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 376
gttccaagta ctagtcccat                                               20

<210> SEQ ID NO 377
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 377
ctaagctaac tgctggccac                                          20

<210> SEQ ID NO 378
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 378
ttcctagttt aaaaaacagt                                          20

<210> SEQ ID NO 379
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 379
ttgaacagca gtgcactcca                                          20

<210> SEQ ID NO 380
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 380
ttttgtacac caaagagaat                                          20

<210> SEQ ID NO 381
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 381
gcaacattac atgttctata                                          20

<210> SEQ ID NO 382
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 382
cttattttag tcattcatca                                          20

<210> SEQ ID NO 383
<211> LENGTH: 20
<212> TYPE: DNA
<213> ORGANISM: Artificial sequence
<220> FEATURE:

-continued

<223> OTHER INFORMATION: Synthetic oligonucleotide

<400> SEQUENCE: 383
aacaaaacac aaggtacgga                                               20

<210> SEQ ID NO 384
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 384
tgcagttggg aagtcatctt                                               20

<210> SEQ ID NO 385
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 385
gtagtacaaa tctttccttc                                               20

<210> SEQ ID NO 386
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 386
tttaacccaa agttaacaaa                                               20

<210> SEQ ID NO 387
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 387 atacccatg aaatgagcac                                                20

<210> SEQ ID NO 388
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 388
tgcttgaaaa ttcaattaga                                               20

<210> SEQ ID NO 389
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 389
cagtacaaga attaagcaca                                               20

-continued

```
<210> SEQ ID NO 390
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 390
gcaaagagtt aagatgggag                                                   20

<210> SEQ ID NO 391
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 391
accattagcc accagcaact                                                   20

<210> SEQ ID NO 392
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 392
tctgggagct attcaggtct                                                   20

<210> SEQ ID NO 393
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 393
aagtttctaa aagtttatcc                                                   20

<210> SEQ ID NO 394
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 394
ctatcttcag tggtaataga                                                   20

<210> SEQ ID NO 395
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 395
ggtgttttac cttctatgct                                                   20

<210> SEQ ID NO 396
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 396
ccccttctcc cagctgcaat                                              20

<210> SEQ ID NO 397
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 397
agcttaccaa ctgaatagct                                              20

<210> SEQ ID NO 398
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 398
gcaattctat atcagaaatg                                              20

<210> SEQ ID NO 399
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 399
ttgatgtaag tttggcactg                                              20

<210> SEQ ID NO 400
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 400
tagcaggaac cagctatgaa                                              20

<210> SEQ ID NO 401
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 401
cccaaataag taataaacaa                                              20

<210> SEQ ID NO 402
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 402
caatgttttg ctgttcaata                                              20

<210> SEQ ID NO 403
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 403
actaattaac agaaaaaaag                                                  20

<210> SEQ ID NO 404
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 404
agataggatt cctgatgtta                                                  20

<210> SEQ ID NO 405
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 405
gttaaaccta actcttaaca                                                  20

<210> SEQ ID NO 406
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 406
tcagttagtc ttcgggcatt                                                  20

<210> SEQ ID NO 407
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 407
taatcactgc aagactctcc                                                  20

<210> SEQ ID NO 408
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 408
tccaatttat gtgcaagcat                                                  20

<210> SEQ ID NO 409
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 409
```
ctatatcagg agaaaataac                                               20

<210> SEQ ID NO 410
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 410
ttgctgttca ataatggcat                                               20

<210> SEQ ID NO 411
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 411
acacaactct ttacaacaaa                                               20

<210> SEQ ID NO 412
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 412
gataggattc ctgatgttac                                               20

<210> SEQ ID NO 413
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 413
acatagttca taagtagcag                                               20

<210> SEQ ID NO 414
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 414
cacagattct acgctccctt                                               20

<210> SEQ ID NO 415
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 415
gttgaaataa gtgaagacag                                               20

<210> SEQ ID NO 416
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 416
tagtacaaat ctttccttca                                                   20

<210> SEQ ID NO 417
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 417
acaaaacaca aggtacggat                                                   20

<210> SEQ ID NO 418
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 418
ataacattgc taagtaaaat                                                   20

<210> SEQ ID NO 419
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 419
cctgtgtcta ccagagggcc                                                   20

<210> SEQ ID NO 420
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 420
ccttctccca gctgcaatag                                                   20

<210> SEQ ID NO 421
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 421
cagcaagacc tgggacatag                                                   20

<210> SEQ ID NO 422
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 422
gaacagcagt gcactccaca                                                   20
```

<210> SEQ ID NO 423
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 423
agcaggaacc agctatgaag                                                 20

<210> SEQ ID NO 424
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 424
caaagaatta ttctccagac                                                 20

<210> SEQ ID NO 425
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 425
tgattgagaa cattcttaat                                                 20

<210> SEQ ID NO 426
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 426
cccttgttat tgccacaaaa                                                 20

<210> SEQ ID NO 427
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 427
cttacaaaac attttccctc                                                 20

<210> SEQ ID NO 428
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 428
ttaaacctaa ctcttaacac                                                 20

<210> SEQ ID NO 429
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 429
tttgtacacc aaagagaata                                              20

<210> SEQ ID NO 430
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 430
atcttcagtg gtaatagaga                                              20

<210> SEQ ID NO 431
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 431
ctgagtagaa actaccacca                                              20

<210> SEQ ID NO 432
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 432
tcctcatacc acttttcttg                                              20

<210> SEQ ID NO 433
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 433
caagtaagaa gagggccagt                                              20

<210> SEQ ID NO 434
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 434
tcaaattgag attcaaattc                                              20

<210> SEQ ID NO 435
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 435
caattctata tcagaaatga                                              20

<210> SEQ ID NO 436
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 436
cagttgggaa gtcatcttct                                              20

<210> SEQ ID NO 437
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 437
gcttaccaac tgaatagctg                                              20

<210> SEQ ID NO 438
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 438
agatatgaca gaggccagag                                              20

<210> SEQ ID NO 439
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 439
tagctgttat caaggagaag                                              20

<210> SEQ ID NO 440
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 440
agatggcaag aggaccaaag                                              20

<210> SEQ ID NO 441
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 441
gtggcagcaa tcatgaaggt                                              20

<210> SEQ ID NO 442
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 442
```

```
gactaaaaga ggtacataag                                          20

<210> SEQ ID NO 443
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 443
aattcagtaa tatcagcata                                          20

<210> SEQ ID NO 444
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 444
atgaatacag ctttctgaat                                          20

<210> SEQ ID NO 445
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 445
agtttctaaa agtttatcct                                          20

<210> SEQ ID NO 446
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 446
tcctagttta aaaaacagtc                                          20

<210> SEQ ID NO 447
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 447
gcattttata aaactggacc                                          20

<210> SEQ ID NO 448
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 448
attctaaaac aaatcaagac                                          20

<210> SEQ ID NO 449
<211> LENGTH: 20
<212> TYPE: DNA
```

<213> ORGANISM: Artificial sequence
<220> FEATURE:
<223> OTHER INFORMATION: Synthetic oligonucleotide

<400> SEQUENCE: 449
ttgagaagaa attactttct                                               20

<210> SEQ ID NO 450
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 450
actgccattt tccttctctg                                               20

<210> SEQ ID NO 451
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 451
caaagagtta agatgggaga                                               20

<210> SEQ ID NO 452
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 452
gcactgagta ggctctgaaa                                               20

<210> SEQ ID NO 453
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 453
tgttattgaa atgtgctgct                                               20

<210> SEQ ID NO 454
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 454
gtgttttacc ttctatgctc                                               20

<210> SEQ ID NO 455
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 455
attagctaga aagaacgatc                                               20

<210> SEQ ID NO 456
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 456
ccattagcca ccagcaactg                                           20

<210> SEQ ID NO 457
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 457
ccaagtacta gtcccatgct                                           20

<210> SEQ ID NO 458
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 458
ttaacccaaa gttaacaaaa                                           20

<210> SEQ ID NO 459
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 459
tgctgacaac accctgtttc                                           20

<210> SEQ ID NO 460
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 460
cctcgctatt agagaaaggg                                           20

<210> SEQ ID NO 461
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 461
ccaaataagt aataaacaaa                                           20

<210> SEQ ID NO 462
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 462
gcttgaaaat tcaattagag                                       20

<210> SEQ ID NO 463
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 463
gtacaagaat taagcacact                                       20

<210> SEQ ID NO 464
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 464
ttctgcaaag gcagaatact                                       20

<210> SEQ ID NO 465
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 465
aaatcaccta cgatgactga                                       20

<210> SEQ ID NO 466
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 466
cctttgattt ttcacagtcc                                       20

<210> SEQ ID NO 467
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 467
agctcttaca tctccttaaa                                       20

<210> SEQ ID NO 468
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 468
aaaatcccaa tagattcaac                                       20

```
<210> SEQ ID NO 469
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 469
tgtatactgg tttgaaaaca                                                   20

<210> SEQ ID NO 470
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 470
tggaaattca gtgtgaatct                                                   20

<210> SEQ ID NO 471
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 471
taccccatga aatgagcacc                                                   20

<210> SEQ ID NO 472
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 472
ccttctattc tcagctcctt                                                   20

<210> SEQ ID NO 473
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 473
gaacccacac atgttcagcc                                                   20

<210> SEQ ID NO 474
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 474
taacaattca ggcagccaag                                                   20

<210> SEQ ID NO 475
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 475
gtagacacac agccacatca                                              20

<210> SEQ ID NO 476
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 476
ctaattaaca gaaaaaaga                                               20

<210> SEQ ID NO 477
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 477
aatttttaat atcatttgtg                                              20

<210> SEQ ID NO 478
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 478
ttctgttaac attagttaca                                              20

<210> SEQ ID NO 479
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 479
gcatctttcc ttccactttg                                              20

<210> SEQ ID NO 480
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 480
attttagtca ttcatcaact                                              20

<210> SEQ ID NO 481
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 481
ctttcagttg attaactctc                                              20

<210> SEQ ID NO 482
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 482
ccaatttatg tgcaagcatt                                          20

<210> SEQ ID NO 483
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 483
tgtacaccaa agagaatata                                          20

<210> SEQ ID NO 484
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 484
ctacccatat ctgtttccca                                          20

<210> SEQ ID NO 485
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 485
gctgacaaca ccctgtttct                                          20

<210> SEQ ID NO 486
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 486
acagcagtgc actccacatc                                          20

<210> SEQ ID NO 487
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 487
ggcagcaatc atgaaggtga                                          20

<210> SEQ ID NO 488
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 488
```
ctgagtaggc tctgaaagca                                          20

<210> SEQ ID NO 489
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 489
taaacctaac tcttaacaca                                          20

<210> SEQ ID NO 490
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 490
tctattctca gctccttgga                                          20

<210> SEQ ID NO 491
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 491
tttccttcca ctttgtttcc                                          20

<210> SEQ ID NO 492
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 492
taactaagtt ttcacttccc                                          20

<210> SEQ ID NO 493
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 493
tgcaagtaga agtacggagc                                          20

<210> SEQ ID NO 494
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 494
tcagtaatat cagcataagc                                          20

<210> SEQ ID NO 495
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 495
aagtaagaag agggccagtt                                              20

<210> SEQ ID NO 496
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 496
gtatactggt ttgaaaacaa                                              20

<210> SEQ ID NO 497
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 497
aaagagttaa gatgggagac                                              20

<210> SEQ ID NO 498
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 498
ccactgttcc ctttctcccc                                              20

<210> SEQ ID NO 499
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 499
ctgtgtctac cagagggcca                                              20

<210> SEQ ID NO 500
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 500
caagtactag tcccatgctc                                              20

<210> SEQ ID NO 501
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 501
gtttctaaaa gtttatcctt                                              20
```

<210> SEQ ID NO 502
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 502
aacattgcta agtaaaatca                                           20

<210> SEQ ID NO 503
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 503
agattctacg ctcccttatg                                           20

<210> SEQ ID NO 504
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 504
cttctcccag ctgcaatagg                                           20

<210> SEQ ID NO 505
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 505
acattagtta cagtttgttt                                           20

<210> SEQ ID NO 506
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 506
agctgttatc aaggagaagg                                           20

<210> SEQ ID NO 507
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 507
catagttcat aagtagcaga                                           20

<210> SEQ ID NO 508
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 508
gttattgaaa tgtgctgctt                                              20

<210> SEQ ID NO 509
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 509
caggcagcca agtaagtggt                                              20

<210> SEQ ID NO 510
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 510
gatggcaaga ggaccaaaga                                              20

<210> SEQ ID NO 511
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 511
caaattgaga ttcaaattca                                              20

<210> SEQ ID NO 512
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 512
actaaaagag gtacataaga                                              20

<210> SEQ ID NO 513
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 513
ccaaaggatc tttaactcca                                              20

<210> SEQ ID NO 514
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 514
gcaggaacca gctatgaagc                                              20

<210> SEQ ID NO 515
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 515
aattctatat cagaaatgaa                                               20

<210> SEQ ID NO 516
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 516
ttagtcattc atcaactatt                                               20

<210> SEQ ID NO 517
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 517
ttctaataat gttaggaggt                                               20

<210> SEQ ID NO 518
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 518
accccatgaa atgagcacca                                               20

<210> SEQ ID NO 519
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 519
caaaacacaa ggtacggatt                                               20

<210> SEQ ID NO 520
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 520
ccttctatgc tcattggctc                                               20

<210> SEQ ID NO 521
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 521
```
ggattcctga tgttacccag                                          20

<210> SEQ ID NO 522
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 522
tgttcaataa tggcattgtg                                          20

<210> SEQ ID NO 523
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 523
tgttattgcc acaaaatcct                                          20

<210> SEQ ID NO 524
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 524
ttacaaaaca ttttccctct                                          20

<210> SEQ ID NO 525
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 525
gatatgacag aggccagagt                                          20

<210> SEQ ID NO 526
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 526
cattagccac cagcaactgc                                          20

<210> SEQ ID NO 527
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 527
gccacacttt ttgcctgggc                                          20

<210> SEQ ID NO 528
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 528
tgagaagaaa ttactttctg                                           20

<210> SEQ ID NO 529
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 529
taacccaaag ttaacaaaaa                                           20

<210> SEQ ID NO 530
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 530
aaagaattat tctccagaca                                           20

<210> SEQ ID NO 531
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 531
ttagctagaa agaacgatca                                           20

<210> SEQ ID NO 532
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 532
atttttaata tcatttgtga                                           20

<210> SEQ ID NO 533
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 533
ttctaaaaca aatcaagacc                                           20

<210> SEQ ID NO 534
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 534
tatatcagga gaaaataacc                                           20

<210> SEQ ID NO 535
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 535
gagaccaatt gtaccctgca                                              20

<210> SEQ ID NO 536
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 536
cctagtttaa aaaacagtca                                              20

<210> SEQ ID NO 537
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 537
cttgaaaatt caattagagc                                              20

<210> SEQ ID NO 538
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 538
cttcagtagt ccatcgccat                                              20

<210> SEQ ID NO 539
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 539
ctgaagagtt ctctatctcc                                              20

<210> SEQ ID NO 540
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 540
gattgagaac attcttaatt                                              20

<210> SEQ ID NO 541
<211> LENGTH: 20
<212> TYPE: DNA
<213> ORGANISM: Artificial sequence
<220> FEATURE:

```
<223> OTHER INFORMATION: Synthetic oligonucleotide

<400> SEQUENCE: 541
gctcttacat ctccttaaat                                              20

<210> SEQ ID NO 542
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 542
aatcacctac gatgactgaa                                              20

<210> SEQ ID NO 543
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 543
ctttgatttt tcacagtcca                                              20

<210> SEQ ID NO 544
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 544
agttgggaag tcatcttctt                                              20

<210> SEQ ID NO 545
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 545
agtacaaatc tttccttcaa                                              20

<210> SEQ ID NO 546
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 546
tagacacaca gccacatcat                                              20

<210> SEQ ID NO 547
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 547
tacaagaatt aagcacacta                                              20
```

<210> SEQ ID NO 548
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 548
taattaacag aaaaaaagac                                               20

<210> SEQ ID NO 549
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 549
aaatcccaat agattcaact                                               20

<210> SEQ ID NO 550
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 550
aatcactgca agactctcct                                               20

<210> SEQ ID NO 551
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 551
tcttcagtgg taatagagag                                               20

<210> SEQ ID NO 552
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 552
ataagtaata aacaaactgg                                               20

<210> SEQ ID NO 553
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 553
tctgcaaagg cagaatactt                                               20

<210> SEQ ID NO 554
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 554
ttaccaactg aatagctgat                                           20

<210> SEQ ID NO 555
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 555
cagttgatta actctctttg                                           20

<210> SEQ ID NO 556
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 556
acaactcttt acaacaaaag                                           20

<210> SEQ ID NO 557
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 557
tctaaaacaa atcaagacct                                           20

<210> SEQ ID NO 558
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 558
aacccaaagt taacaaaaac                                           20

<210> SEQ ID NO 559
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 559
ccttccactt tgtttccatc                                           20

<210> SEQ ID NO 560
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 560
tatactggtt tgaaaacaag                                           20

<210> SEQ ID NO 561
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 561
ctattctcag ctccttggaa                                              20

<210> SEQ ID NO 562
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 562
ttcagtagtc catcgccatc                                              20

<210> SEQ ID NO 563
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 563
aaattgagat tcaaattcac                                              20

<210> SEQ ID NO 564
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 564
tgtctaccag agggccatct                                              20

<210> SEQ ID NO 565
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 565
ctgcaaaggc agaatacttg                                              20

<210> SEQ ID NO 566
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 566
aatcccaata gattcaacta                                              20

<210> SEQ ID NO 567
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 567
```
taccaactga atagctgatg                                          20

<210> SEQ ID NO 568
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 568
tgtgcaagca ttgggaagct                                          20

<210> SEQ ID NO 569
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 569
gggtaagaag agccatccac                                          20

<210> SEQ ID NO 570
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 570
caatcatgaa ggtgagctgt                                          20

<210> SEQ ID NO 571
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 571
gctccattca cctaccatgg                                          20

<210> SEQ ID NO 572
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 572
tagctagaaa gaacgatcag                                          20

<210> SEQ ID NO 573
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 573
ccccatgaaa tgagcaccat                                          20

<210> SEQ ID NO 574
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 574
ctagtttaaa aaacagtcat                                                20

<210> SEQ ID NO 575
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 575
ctaaaagagg tacataagag                                                20

<210> SEQ ID NO 576
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 576
attagccacc agcaactgct                                                20

<210> SEQ ID NO 577
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 577
cttcagtggt aatagagaga                                                20

<210> SEQ ID NO 578
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 578
gccaagtaga tgactgacta                                                20

<210> SEQ ID NO 579
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 579
gattctacgc tcccttatgc                                                20

<210> SEQ ID NO 580
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 580
ctgacaacac cctgtttctc                                                20
```

<210> SEQ ID NO 581
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 581
ttgtcagaca ggattttagc                                          20

<210> SEQ ID NO 582
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 582
tgtttcccat ggtcaagcca                                          20

<210> SEQ ID NO 583
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 583
tgtcccttga atccagctga                                          20

<210> SEQ ID NO 584
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 584
atcacctacg atgactgaat                                          20

<210> SEQ ID NO 585
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 585
attgagaaca ttcttaattt                                          20

<210> SEQ ID NO 586
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 586
gagctattca ggtctcaaac                                          20

<210> SEQ ID NO 587
<211> LENGTH: 20
<212> TYPE: DNA
<213> ORGANISM: Artificial sequence
<220> FEATURE:
<223> OTHER INFORMATION: Synthetic oligonucleotide -continued

```
<400> SEQUENCE: 587
acattgctaa gtaaaatcat                                              20

<210> SEQ ID NO 588
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 588
cccatgagtt taaggacggc                                              20

<210> SEQ ID NO 589
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 589
acagaaaaaa agacatgcta                                              20

<210> SEQ ID NO 590
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 590
atatcaggag aaaataacct                                              20

<210> SEQ ID NO 591
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 591
ttgaaaattc aattagagcc                                              20

<210> SEQ ID NO 592
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 592
gcagagaata atcagctact                                              20

<210> SEQ ID NO 593
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 593
atggcaagag gaccaaagac                                              20

<210> SEQ ID NO 594
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 594
tgatttttca cagtccaaga                                              20

<210> SEQ ID NO 595
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 595
tttttaatat catttgtgat                                              20

<210> SEQ ID NO 596
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 596
ctgatgttac ccagggcagg                                              20

<210> SEQ ID NO 597
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 597
ggatctttaa ctccagagac                                              20

<210> SEQ ID NO 598
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 598
cactccacat cagaagtagt                                              20

<210> SEQ ID NO 599
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 599
gtacaccaaa gagaatatat                                              20

<210> SEQ ID NO 600
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 600
```
agttcataag tagcagatct                                              20

<210> SEQ ID NO 601
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 601
gttgattaac tctctttgtg                                              20

<210> SEQ ID NO 602
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 602
ttgccacaaa atcctgagga                                              20

<210> SEQ ID NO 603
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 603
aagaattatt ctccagacat                                              20

<210> SEQ ID NO 604
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 604
atatgacaga ggccagagta                                              20

<210> SEQ ID NO 605
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 605
tctaaaagtt tatcctttat                                              20

<210> SEQ ID NO 606
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 606
gctgttatca aggagaaggg                                              20

<210> SEQ ID NO 607
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 607
aaacctaact cttaacacac                                          20

<210> SEQ ID NO 608
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 608
aactaagttt tcacttccct                                          20

<210> SEQ ID NO 609
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 609
caggaaccag ctatgaagca                                          20

<210> SEQ ID NO 610
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 610
agtaataaac aaactggaat                                          20

<210> SEQ ID NO 611
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 611
gttgggaagt catcttctta                                          20

<210> SEQ ID NO 612
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 612
aaaacacaag gtacggatta                                          20

<210> SEQ ID NO 613
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 613
aaattatctc tgtcatggga                                          20
```

```
<210> SEQ ID NO 614
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 614
attctatatc agaaatgaag                                           20

<210> SEQ ID NO 615
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 615
tacaaaacat tttccctctc                                           20

<210> SEQ ID NO 616
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 616
agaagcttcc ctccagcatt                                           20

<210> SEQ ID NO 617
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 617
agtaagaaga gggccagttg                                           20

<210> SEQ ID NO 618
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 618
ccaccacttc caagttccct                                           20

<210> SEQ ID NO 619
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 619
ccacactttt tgcctgggct                                           20

<210> SEQ ID NO 620
<211> LENGTH: 20
<212> TYPE: DNA
<213> ORGANISM: Artificial sequence
<220> FEATURE:
```

<223> OTHER INFORMATION: Synthetic oligonucleotide

<400> SEQUENCE: 620
ccagctgcaa taggcagatt                                                  20

<210> SEQ ID NO 621
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 621
tacaaatctt tccttcaatt                                                  20

<210> SEQ ID NO 622
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 622
caagaattaa gcacactagc                                                  20

<210> SEQ ID NO 623
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 623
gagaagaaat tactttctga                                                  20

<210> SEQ ID NO 624
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 624
aagagttaag atgggagacg                                                  20

<210> SEQ ID NO 625
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 625
agacacacag ccacatcatg                                                  20

<210> SEQ ID NO 626
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 626
tcatcaacta tttatggaat                                                  20

```
<210> SEQ ID NO 627
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 627
cagtaatatc agcataagca                                               20

<210> SEQ ID NO 628
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 628
agttctctat ctccaggatg                                               20

<210> SEQ ID NO 629
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 629
tcactgcaag actctccttt                                               20

<210> SEQ ID NO 630
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 630
caactcttta caacaaaaga                                               20

<210> SEQ ID NO 631
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 631
ctcttacatc tccttaaata                                               20

<210> SEQ ID NO 632
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 632
ataatgttag gaggtcctcc                                               20

<210> SEQ ID NO 633
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 633
tctatgctca ttggctcagg     20

<210> SEQ ID NO 634
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 634
tgagaacatt cttaatttta     20

<210> SEQ ID NO 635
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 635
cttccacttt gtttccatca     20

<210> SEQ ID NO 636
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 636
tcagacagga ttttagcatg     20

<210> SEQ ID NO 637
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 637
actaagtttt cacttcccta     20

<210> SEQ ID NO 638
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 638
gagaataatc agctactgct     20

<210> SEQ ID NO 639
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 639
gtctcgaatc tgcactacag     20

<210> SEQ ID NO 640
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 640
tggcaagagg accaaagaca                                             20

<210> SEQ ID NO 641
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 641
tgattaactc tctttgtgtg                                             20

<210> SEQ ID NO 642
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 642
acaaaacatt ttccctctcc                                             20

<210> SEQ ID NO 643
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 643
taaaagaggt acataagagg                                             20

<210> SEQ ID NO 644
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 644
ctaaaacaaa tcaagacctt                                             20

<210> SEQ ID NO 645
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 645
cttacatctc cttaaatatt                                             20

<210> SEQ ID NO 646
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 646
```
cagctgcaat aggcagattt                                          20

<210> SEQ ID NO 647
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 647
aggtagaggc atttgcctct                                          20

<210> SEQ ID NO 648
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 648
gcttggcttt ctccatatac                                          20

<210> SEQ ID NO 649
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 649
aattgagatt caaattcacc                                          20

<210> SEQ ID NO 650
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 650
caagcattgg gaagctgagg                                          20

<210> SEQ ID NO 651
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 651
tcataagtag cagatctggg                                          20

<210> SEQ ID NO 652
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 652
tgcaaaggca gaatacttgt                                          20

<210> SEQ ID NO 653
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 653
tgaaaattca attagagcct                                           20

<210> SEQ ID NO 654
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 654
cagaaaaaaa gacatgctat                                           20

<210> SEQ ID NO 655
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 655
agagttaaga tgggagacgc                                           20

<210> SEQ ID NO 656
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 656
atgttgtaga aggcaatcgg                                           20

<210> SEQ ID NO 657
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 657
ttttaatatc atttgtgatg                                           20

<210> SEQ ID NO 658
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 658
tatgacagag gccagagtac                                           20

<210> SEQ ID NO 659
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 659
ctgttatcaa ggagaaggga                                           20
```

```
<210> SEQ ID NO 660
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 660
acctctctgg tttcagtagg                                               20

<210> SEQ ID NO 661
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 661
tatcaggaga aaataacctt                                               20

<210> SEQ ID NO 662
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 662
cactgcaaga ctctcctttc                                               20

<210> SEQ ID NO 663
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 663
cccatgaaat gagcaccatt                                               20

<210> SEQ ID NO 664
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 664
gacacacagc cacatcatgc                                               20

<210> SEQ ID NO 665
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 665
tctaccagag ggccatctca                                               20

<210> SEQ ID NO 666
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 666
agctattcag gtctcaaact                                          20

<210> SEQ ID NO 667
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 667
agctagaaag aacgatcaga                                          20

<210> SEQ ID NO 668
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 668
cccatggtca agccattgag                                          20

<210> SEQ ID NO 669
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 669
cctcactcaa agcatggata                                          20

<210> SEQ ID NO 670
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 670
agtaatatca gcataagcat                                          20

<210> SEQ ID NO 671
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 671
aaacacaagg tacggattac                                          20

<210> SEQ ID NO 672
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 672
acccaaagtt aacaaaaaca                                          20

<210> SEQ ID NO 673
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 673
ggcaggaatt gagttcctcc                                               20

<210> SEQ ID NO 674
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 674
atcaactatt tatggaatac                                               20

<210> SEQ ID NO 675
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 675
gtaataaaca aactggaata                                               20

<210> SEQ ID NO 676
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 676
aagaattaag cacactagca                                               20

<210> SEQ ID NO 677
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 677
agaattattc tccagacatt                                               20

<210> SEQ ID NO 678
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 678
ctaaaagttt atcctttatg                                               20

<210> SEQ ID NO 679
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 679
```
gtaagaagag ggccagttgg                                        20

<210> SEQ ID NO 680
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 680
agaagaaatt actttctgat                                        20

<210> SEQ ID NO 681
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 681
tcacctacca tggctgctgt                                        20

<210> SEQ ID NO 682
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 682
acaaatcttt ccttcaatta                                        20

<210> SEQ ID NO 683
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 683
atcccaatag attcaactag                                        20

<210> SEQ ID NO 684
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 684
tagtttaaaa aacagtcata                                        20

<210> SEQ ID NO 685
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 685
accaactgaa tagctgatga                                        20

<210> SEQ ID NO 686
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 686
aacacaatcc agtggccacc                                                 20

<210> SEQ ID NO 687
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 687
tcacctacga tgactgaatg                                                 20

<210> SEQ ID NO 688
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 688
tcacagtcca agaaatgtcc                                                 20

<210> SEQ ID NO 689
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 689
ggtatggtca gggatggagg                                                 20

<210> SEQ ID NO 690
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 690
catgagttta aggacggcaa                                                 20

<210> SEQ ID NO 691
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 691
gccacaaaat cctgaggatg                                                 20

<210> SEQ ID NO 692
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 692
aggaaccagc tatgaagcaa                                                 20
```

-continued

<210> SEQ ID NO 693
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 693
tgacaacacc ctgtttctct                                               20

<210> SEQ ID NO 694
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 694
gccagccaaa actacactgc                                               20

<210> SEQ ID NO 695
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 695
cattgctaag taaaatcatt                                               20

<210> SEQ ID NO 696
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 696
ttcagtggta atagagagac                                               20

<210> SEQ ID NO 697
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 697
aacctaactc ttaacacacc                                               20

<210> SEQ ID NO 698
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 698
ttagccacca gcaactgctg                                               20

<210> SEQ ID NO 699
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 699
tattctcagc tccttggaaa                                              20

<210> SEQ ID NO 700
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 700
ttgggaagtc atcttcttag                                              20

<210> SEQ ID NO 701
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 701
actctttaca acaaaagaac                                              20

<210> SEQ ID NO 702
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 702
cctccagcat ttcaaggatg                                              20

<210> SEQ ID NO 703
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 703
ttctatatca gaaatgaagg                                              20

<210> SEQ ID NO 704
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 704
tgtcttaatt catatgtatg                                              20

<210> SEQ ID NO 705
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 705
ggattcatat tgatagtata                                              20

```
<210> SEQ ID NO 706
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 706
tacaccaaag agaatatatt                                              20

<210> SEQ ID NO 707
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 707
actccacatc agaagtagtg                                              20

<210> SEQ ID NO 708
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 708
atactggttt gaaaacaagt                                              20

<210> SEQ ID NO 709
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 709
gctgcaatag gcagatttgg                                              20

<210> SEQ ID NO 710
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 710
gaattgagtt cctccaacat                                              20

<210> SEQ ID NO 711
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 711
acagccactt ttggatggag                                              20

<210> SEQ ID NO 712
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 712
acctacgatg actgaatgga                                          20

<210> SEQ ID NO 713
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 713
attgagattc aaattcacca                                          20

<210> SEQ ID NO 714
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 714
ctattcaggt ctcaaactct                                          20

<210> SEQ ID NO 715
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 715
tgttgtagaa ggcaatcggc                                          20

<210> SEQ ID NO 716
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 716
ggttccctac agttgtgccc                                          20

<210> SEQ ID NO 717
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 717
ggaagtcatc ttcttaggca                                          20

<210> SEQ ID NO 718
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 718
tcccaataga ttcaactagc                                          20

<210> SEQ ID NO 719
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 719
caaatctttc cttcaattaa                                              20

<210> SEQ ID NO 720
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 720
tgatagtata tagaattcca                                              20

<210> SEQ ID NO 721
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 721
cacactagca gtgacataga                                              20

<210> SEQ ID NO 722
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 722
gagaacattc ttaattttat                                              20

<210> SEQ ID NO 723
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 723
atcaggagaa aataaccttt                                              20

<210> SEQ ID NO 724
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 724
gacaacaccc tgtttctctt                                              20

<210> SEQ ID NO 725
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 725
```
attgctaagt aaaatcattt                                                    20

<210> SEQ ID NO 726
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 726
tctgcactac agtcttaccc                                                    20

<210> SEQ ID NO 727
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 727
ttacatctcc ttaaatattg                                                    20

<210> SEQ ID NO 728
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 728
cccaaagtta acaaaaacag                                                    20

<210> SEQ ID NO 729
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 729
ccatggtcaa gccattgagg                                                    20

<210> SEQ ID NO 730
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 730
aacacaaggt acggattact                                                    20

<210> SEQ ID NO 731
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 731
gaaaaaaaga catgctatcc                                                    20

<210> SEQ ID NO 732
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 732
ccatgaaatg agcaccattg                                               20

<210> SEQ ID NO 733
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 733
taaaagttta tcctttatgt                                               20

<210> SEQ ID NO 734
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 734
tccacatcag aagtagtggc                                               20

<210> SEQ ID NO 735
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 735
actgcaagac tctcctttct                                               20

<210> SEQ ID NO 736
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 736
gaagaaatta ctttctgatc                                               20

<210> SEQ ID NO 737
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 737
aaacacagta tacacatgca                                               20

<210> SEQ ID NO 738
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 738
gctagaaaga acgatcagat                                               20
```

<210> SEQ ID NO 739
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 739
tgttatcaag gagaagggag                                         20

<210> SEQ ID NO 740
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 740
gaataatcag ctactgctct                                         20

<210> SEQ ID NO 741
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 741
gacaggattt tagcatgaag                                         20

<210> SEQ ID NO 742
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 742
gaaaattcaa ttagagcctc                                         20

<210> SEQ ID NO 743
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 743
tcttctttag acctgaagtg                                         20

<210> SEQ ID NO 744
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 744
ttctcagctc cttggaaacc                                         20

<210> SEQ ID NO 745
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 745
agttaagatg ggagacgcag                                              20

<210> SEQ ID NO 746
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 746
tccactttgt ttccatcagt                                              20

<210> SEQ ID NO 747
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 747
gtgtatgtat gcatgtgagg                                              20

<210> SEQ ID NO 748
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 748
aaaagaggta cataagaggg                                              20

<210> SEQ ID NO 749
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 749
tcctgtttta cctgaacaca                                              20

<210> SEQ ID NO 750
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 750
taataaacaa actggaatac                                              20

<210> SEQ ID NO 751
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 751
ccagcatttc aaggatggaa                                              20

<210> SEQ ID NO 752
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 752
agacccaatc attcatcatc                                                   20

<210> SEQ ID NO 753
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 753
gggtcagtgc tctctttctg                                                   20

<210> SEQ ID NO 754
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 754
aagaagaggg ccagttggtg                                                   20

<210> SEQ ID NO 755
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 755
ctctttacaa caaaagaact                                                   20

<210> SEQ ID NO 756
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 756
caactgaata gctgatgact                                                   20

<210> SEQ ID NO 757
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 757
aggaacttga actcttgcta                                                   20

<210> SEQ ID NO 758
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 758
```
atgacagagg ccagagtaca                                          20

<210> SEQ ID NO 759
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 759
tcagtggtaa tagagagacc                                          20

<210> SEQ ID NO 760
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 760
agtttaaaaa acagtcataa                                          20

<210> SEQ ID NO 761
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 761
tttaatatca tttgtgatgc                                          20

<210> SEQ ID NO 762
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 762
tctatatcag aaatgaagga                                          20

<210> SEQ ID NO 763
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 763
acacacagcc acatcatgca                                          20

<210> SEQ ID NO 764
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 764
ctaccagagg gccatctcag                                          20

<210> SEQ ID NO 765
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 765
tactggtttg aaaacaagta                                                    20

<210> SEQ ID NO 766
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 766
taaaacaaat caagaccttc                                                    20

<210> SEQ ID NO 767
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 767
tcaactattt atggaatact                                                    20

<210> SEQ ID NO 768
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 768
atgagtttaa ggacggcaaa                                                    20

<210> SEQ ID NO 769
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 769
ggcaagagga ccaaagacat                                                    20

<210> SEQ ID NO 770
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 770
gtatgtgtga acaatagcct                                                    20

<210> SEQ ID NO 771
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 771
cactcaaagc atggataacc                                                    20
```

<210> SEQ ID NO 772
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 772 aaaacattt ccctctcctc                                            20

<210> SEQ ID NO 773
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 773
cacaatccag tggccaccag                                           20

<210> SEQ ID NO 774
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 774
gaattattct ccagacattt                                           20

<210> SEQ ID NO 775
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 775
ggaaccagct atgaagcaaa                                           20

<210> SEQ ID NO 776
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 776
gcaaaggcag aatacttgta                                           20

<210> SEQ ID NO 777
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 777
acctaactct taacacacca                                           20

<210> SEQ ID NO 778
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 778
tctccatata cacttgactg                                               20

<210> SEQ ID NO 779
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 779
gctgccagga aacttggcct                                               20

<210> SEQ ID NO 780
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 780
ccacaaaatc ctgaggatga                                               20

<210> SEQ ID NO 781
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 781
gtaatatcag cataagcatc                                               20

<210> SEQ ID NO 782
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 782
taaaacttat ccttggcaca                                               20

<210> SEQ ID NO 783
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 783
acaccaaaga gaatatattt                                               20

<210> SEQ ID NO 784
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 784
tagccaccag caactgctgc                                               20

```
<210> SEQ ID NO 785
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 785
cagcatttca aggatggaag                                         20

<210> SEQ ID NO 786
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 786
gttatcaagg agaagggagt                                         20

<210> SEQ ID NO 787
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 787
cctgttttac ctgaacacat                                         20

<210> SEQ ID NO 788
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 788
aaaaaaagac atgctatcca                                         20

<210> SEQ ID NO 789
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 789
ctaactctta acacaccaag                                         20

<210> SEQ ID NO 790
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 790
atatcagcat aagcatcaga                                         20

<210> SEQ ID NO 791
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 791
ttatccttgg cacattgtct					20

<210> SEQ ID NO 792
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 792
caaaggcaga atacttgtag					20

<210> SEQ ID NO 793
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 793
gaaccagcta tgaagcaaaa					20

<210> SEQ ID NO 794
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 794
ccaaagttaa caaaaacagg					20

<210> SEQ ID NO 795
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 795
gtttaaaaaa cagtcataat					20

<210> SEQ ID NO 796
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 796
aacacagtat acacatgcac					20

<210> SEQ ID NO 797
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 797
tcaggagaaa ataaccttta					20

<210> SEQ ID NO 798
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 798
ttaatatcat ttgtgatgct                                              20

<210> SEQ ID NO 799
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 799
ccactttgtt tccatcagtg                                              20

<210> SEQ ID NO 800
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 800
taccagaggg ccatctcagg                                              20

<210> SEQ ID NO 801
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 801
ctatatcaga aatgaaggaa                                              20

<210> SEQ ID NO 802
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 802
taaacaaact ggaatacatg                                              20

<210> SEQ ID NO 803
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 803
actggtttga aaacaagtat                                              20

<210> SEQ ID NO 804
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 804
```
cacacagcca catcatgcag                                               20

<210> SEQ ID NO 805
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 805
tggtcaagcc attgaggact                                               20

<210> SEQ ID NO 806
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 806
gttccctaca gttgtgccca                                               20

<210> SEQ ID NO 807
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 807
ttgagattca aattcaccaa                                               20

<210> SEQ ID NO 808
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 808
gatagtatat agaattccag                                               20

<210> SEQ ID NO 809
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 809
cctaccagac atcttgcaca                                               20

<210> SEQ ID NO 810
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 810
caccaaagag aatatatttg                                               20

<210> SEQ ID NO 811
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 811
aagaaattac tttctgatcc                                               20

<210> SEQ ID NO 812
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 812
tattcaggtc tcaaactctt                                               20

<210> SEQ ID NO 813
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 813
tgacagaggc cagagtacac                                               20

<210> SEQ ID NO 814
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 814
tctcagctcc ttggaaacca                                               20

<210> SEQ ID NO 815
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 815
cttcttagtt tacatatggg                                               20

<210> SEQ ID NO 816
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 816
ttaattttat aaaatacact                                               20

<210> SEQ ID NO 817
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 817
aaatctttcc ttcaattaaa                                               20
```

<210> SEQ ID NO 818
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 818
cagccacttt tggatggagg                                           20

<210> SEQ ID NO 819
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 819
gttaagatgg gagacgcagc                                           20

<210> SEQ ID NO 820
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 820
ctagaaagaa cgatcagatt                                           20

<210> SEQ ID NO 821
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 821
gtgaacaata gcctaaagcc                                           20

<210> SEQ ID NO 822
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 822
gacccaatca ttcatcatct                                           20

<210> SEQ ID NO 823
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 823
ctgcaatagg cagatttggg                                           20

<210> SEQ ID NO 824
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 824
attattctcc agacatttct                                           20

<210> SEQ ID NO 825
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 825
gaacttgaac tcttgctagc                                           20

<210> SEQ ID NO 826
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 826
cagtggtaat agagagacca                                           20

<210> SEQ ID NO 827
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 827
aaaacaaatc aagaccttca                                           20

<210> SEQ ID NO 828
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 828
atgaaatgag caccattgtg                                           20

<210> SEQ ID NO 829
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 829
cactacagtc ttaccctcct                                           20

<210> SEQ ID NO 830
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 830
aaacattttc cctctcctcc                                           20

<210> SEQ ID NO 831
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 831
tctttacaac aaaagaactg                                           20

<210> SEQ ID NO 832
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 832
aaaagtttat cctttatgtg                                           20

<210> SEQ ID NO 833
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 833
gggagagtcc aaagagagac                                           20

<210> SEQ ID NO 834
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 834
ctttctgtgg gtgaaagatc                                           20

<210> SEQ ID NO 835
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 835
tgcaagactc tcctttcttg                                           20

<210> SEQ ID NO 836
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 836
cactagcagt gacatagaca                                           20

<210> SEQ ID NO 837
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 837
```
cacatcagaa gtagtggcag                                               20

<210> SEQ ID NO 838
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 838
gtatgtatgc atgtgaggtt                                               20

<210> SEQ ID NO 839
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 839
tccatataca cttgactgga                                               20

<210> SEQ ID NO 840
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 840
acaccctgtt tctcttccct                                               20

<210> SEQ ID NO 841
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 841
gttgtagaag gcaatcggct                                               20

<210> SEQ ID NO 842
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 842
gccaccagca actgctgctc                                               20

<210> SEQ ID NO 843
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 843
ttctatatgg ttgaagtagt                                               20

<210> SEQ ID NO 844
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 844
acatctcctt aaatattgct                                              20

<210> SEQ ID NO 845
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 845
gagttcctcc aacattcacc                                              20

<210> SEQ ID NO 846
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 846
tgagtttaag gacggcaaag                                              20

<210> SEQ ID NO 847
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 847
aaaattcaat tagagcctcc                                              20

<210> SEQ ID NO 848
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 848
agaagagggc cagttggtgg                                              20

<210> SEQ ID NO 849
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 849
tcatcttctt aggcatttcc                                              20

<210> SEQ ID NO 850
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 850
gcaagaggac caaagacatt                                              20
```

<210> SEQ ID NO 851
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 851
aactgaatag ctgatgactg                                        20

<210> SEQ ID NO 852
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 852
actcaaagca tggataaccc                                        20

<210> SEQ ID NO 853
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 853
tgctaagtaa aatcattttc                                        20

<210> SEQ ID NO 854
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 854
cctacgatga ctgaatggat                                        20

<210> SEQ ID NO 855
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 855
gccaggaaac ttggcctcta                                        20

<210> SEQ ID NO 856
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 856
caactattta tggaatactc                                        20

<210> SEQ ID NO 857
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 857
ttctttagac ctgaagtgct                                               20

<210> SEQ ID NO 858
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 858
acacagccac atcatgcagt                                               20

<210> SEQ ID NO 859
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 859
ccatatacac ttgactggaa                                               20

<210> SEQ ID NO 860
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 860
tcttgtagtc gccaaagatc                                               20

<210> SEQ ID NO 861
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 861
tcagcataag catcagatgt                                               20

<210> SEQ ID NO 862
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 862
ggagagtcca aagagagacc                                               20

<210> SEQ ID NO 863
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 863
caggagaaaa taacctttat                                               20

-continued

```
<210> SEQ ID NO 864
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 864
aagactctcc tttcttgtta                                        20

<210> SEQ ID NO 865
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 865
tatatcagaa atgaaggaaa                                        20

<210> SEQ ID NO 866
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 866
ccatgaacag aggcctcctt                                        20

<210> SEQ ID NO 867
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 867
aaacaaatca agaccttcaa                                        20

<210> SEQ ID NO 868
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 868
actttgtttc catcagtgga                                        20

<210> SEQ ID NO 869
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 869
ccaccagcaa ctgctgctcc                                        20

<210> SEQ ID NO 870
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 870
gaaattactt tctgatcctc					20

<210> SEQ ID NO 871
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 871
acttgaactc ttgctagcca					20

<210> SEQ ID NO 872
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 872
cccaatcatt catcatctta					20

<210> SEQ ID NO 873
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 873
tcccttatgc tgtaagtaag					20

<210> SEQ ID NO 874
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 874
ctaccagaca tcttgcacag					20

<210> SEQ ID NO 875
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 875
ttattctcca gacatttctg					20

<210> SEQ ID NO 876
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 876
caaagttaac aaaaacagga					20

<210> SEQ ID NO 877
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 877
cctgaagtgc tgtgggcagg                                              20

<210> SEQ ID NO 878
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 878
tttaaaaaac agtcataatc                                              20

<210> SEQ ID NO 879
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 879
accaaagaga atatatttgg                                              20

<210> SEQ ID NO 880
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 880
gcatttcaag gatggaagca                                              20

<210> SEQ ID NO 881
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 881
accagagggc catctcaggt                                              20

<210> SEQ ID NO 882
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 882
acatcagaag tagtggcagt                                              20

<210> SEQ ID NO 883
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 883
```

-continued

```
accagctatg aagcaaaatg                                            20

<210> SEQ ID NO 884
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 884
aaaaaagaca tgctatccaa                                            20

<210> SEQ ID NO 885
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 885
aaattcaatt agagcctcca                                            20

<210> SEQ ID NO 886
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 886
gaagagggcc agttggtggc                                            20

<210> SEQ ID NO 887
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 887
gacagaggcc agagtacaca                                            20

<210> SEQ ID NO 888
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 888
agtttactca gcatgaactt                                            20

<210> SEQ ID NO 889
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 889
caagaggacc aaagacattc                                            20

<210> SEQ ID NO 890
<211> LENGTH: 20
<212> TYPE: DNA
<213> ORGANISM: Artificial sequence
```

<220> FEATURE:
<223> OTHER INFORMATION: Synthetic oligonucleotide

<400> SEQUENCE: 890
taatatcatt tgtgatgctt        20

<210> SEQ ID NO 891
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 891
tctttccttc aattaaaacc        20

<210> SEQ ID NO 892
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 892
taactcttaa cacaccaaga        20

<210> SEQ ID NO 893
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 893
ccacttttgg atggaggcat        20

<210> SEQ ID NO 894
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 894
ctttacaaca aagaactgt        20

<210> SEQ ID NO 895
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 895
tgagattcaa attcaccaaa        20

<210> SEQ ID NO 896
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 896
ccctacagtt gtgcccaggg        20

<210> SEQ ID NO 897
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 897
gctaagtaaa atcattttcc                                              20

<210> SEQ ID NO 898
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 898
tatgtatgca tgtgaggttt                                              20

<210> SEQ ID NO 899
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 899
gggaattaaa aggccagtcc                                              20

<210> SEQ ID NO 900
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 900
cacaaggtac ggattacttc                                              20

<210> SEQ ID NO 901
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 901
ctggtttgaa aacaagtatc                                              20

<210> SEQ ID NO 902
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 902
tcttagttta catatgggag                                              20

<210> SEQ ID NO 903
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 903
aaacaaactg gaatacatga                                          20

<210> SEQ ID NO 904
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 904
tagtatatag aattccaggc                                          20

<210> SEQ ID NO 905
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 905
ttgttgtaaa aatgaatccc                                          20

<210> SEQ ID NO 906
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 906
aagtttatcc tttatgtgtg                                          20

<210> SEQ ID NO 907
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 907
ctacgatgac tgaatggata                                          20

<210> SEQ ID NO 908
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 908
attttataaa atacactttg                                          20

<210> SEQ ID NO 909
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 909
tcctccaaca ttcacctctc                                          20

<210> SEQ ID NO 910

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 910
actgaatagc tgatgactgg                                          20

<210> SEQ ID NO 911
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 911
gtttctcttc cctaacgagg                                          20

<210> SEQ ID NO 912
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 912 aacatttttcc ctctcctcct                                         20

<210> SEQ ID NO 913
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 913
tagaaagaac gatcagatta                                          20

<210> SEQ ID NO 914
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 914
caggtctcaa actctttctg                                          20

<210> SEQ ID NO 915
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 915
catctcctta aatattgctg                                          20

<210> SEQ ID NO 916
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 916
```
gaaggcaatc ggctaattca                                              20

<210> SEQ ID NO 917
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 917
aaaggcagaa tacttgtaga                                              20

<210> SEQ ID NO 918
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 918
cttggcacat tgtctccacc                                              20

<210> SEQ ID NO 919
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 919
tccatttcag aacccctcct                                              20

<210> SEQ ID NO 920
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 920
agtggtaata gagagaccag                                              20

<210> SEQ ID NO 921
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 921
tcagctcctt ggaaaccaca                                              20

<210> SEQ ID NO 922
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 922
ttatcaagga gaagggagtg                                              20

<210> SEQ ID NO 923
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 923
aactatttat ggaatactca                                                  20

<210> SEQ ID NO 924
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 924
tttctgtggg tgaaagatcc                                                  20

<210> SEQ ID NO 925
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 925
tcttcttagg catttcccat                                                  20

<210> SEQ ID NO 926
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 926
gcacacacac aaatactcag                                                  20

<210> SEQ ID NO 927
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 927
agcatggata accctcaggc                                                  20

<210> SEQ ID NO 928
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 928
ctgttttacc tgaacacatg                                                  20

<210> SEQ ID NO 929
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 929
gagtttaagg acggcaaagt                                                  20
```

<210> SEQ ID NO 930
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 930
ttaagatggg agacgcagca                                               20

<210> SEQ ID NO 931
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 931
tgaaatgagc accattgtga                                               20

<210> SEQ ID NO 932
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 932
ccatagccaa gcctgagtcc                                               20

<210> SEQ ID NO 933
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 933
ctttccttca attaaaacca                                               20

<210> SEQ ID NO 934
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 934
tctccagaca tttctgatgc                                               20

<210> SEQ ID NO 935
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 935
gaaatgagca ccattgtgaa                                               20

<210> SEQ ID NO 936
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 936
gactctcctt tcttgttaca                                      20

<210> SEQ ID NO 937
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 937
agtatataga attccaggct                                      20

<210> SEQ ID NO 938
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 938
agttaacaaa aacaggaaaa                                      20

<210> SEQ ID NO 939
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 939
tacacttgac tggaagtccg                                      20

<210> SEQ ID NO 940
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 940
aagatgggag acgcagcatt                                      20

<210> SEQ ID NO 941
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 941
aaggcagaat acttgtagaa                                      20

<210> SEQ ID NO 942
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 942
gcatgtgagg ttttcaggga                                      20

```
<210> SEQ ID NO 943
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 943
cacacacaaa tactcagcaa                                              20

<210> SEQ ID NO 944
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 944
tggtttgaaa acaagtatca                                              20

<210> SEQ ID NO 945
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 945
ccatttcaga acccctcctg                                              20

<210> SEQ ID NO 946
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 946
aatatcattt gtgatgctta                                              20

<210> SEQ ID NO 947
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 947
atttcaagga tggaagcagt                                              20

<210> SEQ ID NO 948
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 948
caaagtactt tagatactct                                              20

<210> SEQ ID NO 949
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 949
ccaaagagaa tatatttggc                                               20

<210> SEQ ID NO 950
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 950
caatagattc aactagccaa                                               20

<210> SEQ ID NO 951
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 951
ggtctcaaac tctttctgcc                                               20

<210> SEQ ID NO 952
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 952
tctccttaaa tattgctgaa                                               20

<210> SEQ ID NO 953
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 953
tcctcctata atgcagcttg                                               20

<210> SEQ ID NO 954
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 954
acgatgactg aatggataat                                               20

<210> SEQ ID NO 955
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 955
cctttatgtg tgttaaaatt                                               20

<210> SEQ ID NO 956
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 956
ataaaataca ctttgtaaga                                                    20

<210> SEQ ID NO 957
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 957
aaggcaatcg gctaattcaa                                                    20

<210> SEQ ID NO 958
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 958
gtggtaatag agagaccaga                                                    20

<210> SEQ ID NO 959
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 959
aagagggcca gttggtggca                                                    20

<210> SEQ ID NO 960
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 960
gcaaaatgta agcaaaggga                                                    20

<210> SEQ ID NO 961
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 961
aaattacttt ctgatcctca                                                    20

<210> SEQ ID NO 962
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 962
```
agtttaagga cggcaaagtt                                        20

<210> SEQ ID NO 963
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 963
ttgtatataa tatctgttct                                        20

<210> SEQ ID NO 964
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 964
tttacaacaa aagaactgta                                        20

<210> SEQ ID NO 965
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 965
ttttggatgg aggcatcaca                                        20

<210> SEQ ID NO 966
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 966
gcatggataa ccctcaggca                                        20

<210> SEQ ID NO 967
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 967
agaaagaacg atcagattac                                        20

<210> SEQ ID NO 968
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 968
aacaaatcaa gaccttcaaa                                        20

<210> SEQ ID NO 969
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 969
agctccttgg aaaccacagg          20

<210> SEQ ID NO 970
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 970
aacaaactgg aatacatgaa          20

<210> SEQ ID NO 971
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 971
ccaacattca cctctcatct          20

<210> SEQ ID NO 972
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 972
aggagaaaat aacctttatg          20

<210> SEQ ID NO 973
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 973
aactcttaac acaccaagat          20

<210> SEQ ID NO 974
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 974
tgaatagctg atgactggtg          20

<210> SEQ ID NO 975
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 975
ctttgtttcc atcagtggaa          20

<210> SEQ ID NO 976
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 976
aacaacaatt atcaagaggt                                           20

<210> SEQ ID NO 977
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 977
cagaggccag agtacacaac                                           20

<210> SEQ ID NO 978
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 978
caccagcaac tgctgctcct                                           20

<210> SEQ ID NO 979
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 979
tatcagaaat gaaggaaaca                                           20

<210> SEQ ID NO 980
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 980
gcaataggca gatttgggca                                           20

<210> SEQ ID NO 981
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 981
caatcattca tcatcttata                                           20

<210> SEQ ID NO 982
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 982
gagagtccaa agagagacct                                                    20

<210> SEQ ID NO 983
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 983
ccctctcctc cttctatgca                                                    20

<210> SEQ ID NO 984
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 984
gaaagtgatg ttactggctg                                                    20

<210> SEQ ID NO 985
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 985
tgttgtaaaa atgaatcccg                                                    20

<210> SEQ ID NO 986
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 986
acaaggtacg gattacttca                                                    20

<210> SEQ ID NO 987
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 987
accagacatc ttgcacagca                                                    20

<210> SEQ ID NO 988
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 988
ccagctatga agcaaaatga                                                    20

<210> SEQ ID NO 989
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 989
ttaaaaaaca gtcataatca                                              20

<210> SEQ ID NO 990
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 990
ctaagtaaaa tcattttcca                                              20

<210> SEQ ID NO 991
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 991
cttcttaggc atttcccatt                                              20

<210> SEQ ID NO 992
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 992
tctgtgggtg aaagatcctt                                              20

<210> SEQ ID NO 993
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 993
ccagagggcc atctcaggtt                                              20

<210> SEQ ID NO 994
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 994
ttttacctga acacatgctt                                              20

<210> SEQ ID NO 995
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 995
```
cgccaaagat ctgcctgact                                              20

<210> SEQ ID NO 996
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 996
gctagccaaa agagaactcc                                              20

<210> SEQ ID NO 997
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 997
tgtctgatca ctgcttataa                                              20

<210> SEQ ID NO 998
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 998
taagcatcag atgttcatct                                              20

<210> SEQ ID NO 999
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 999
ggaatactca ctatatgccc                                              20

<210> SEQ ID NO 1000
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1000
atcaaggaga agggagtgag                                              20

<210> SEQ ID NO 1001
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1001
aaaaagacat gctatccaaa                                              20

<210> SEQ ID NO 1002
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 1002
tcagcatgaa ctttgcaaac                                              20

<210> SEQ ID NO 1003
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1003
catagccaag cctgagtcca                                              20

<210> SEQ ID NO 1004
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1004
aagaggacca aagacattcc                                              20

<210> SEQ ID NO 1005
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1005
gagattcaaa ttcaccaaat                                              20

<210> SEQ ID NO 1006
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1006
gggaagtaac tggtactaga                                              20

<210> SEQ ID NO 1007
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1007
aattcaatta gagcctccat                                              20

<210> SEQ ID NO 1008
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1008
cctctcctcc ttctatgcag                                              20
```

<210> SEQ ID NO 1009
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1009
ggtgtgagtt tgattcaaga                                                 20

<210> SEQ ID NO 1010
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1010
aaaagacatg ctatccaaag                                                 20

<210> SEQ ID NO 1011
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1011
acaaatcaag accttcaaat                                                 20

<210> SEQ ID NO 1012
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1012
gtatataata tctgttctca                                                 20

<210> SEQ ID NO 1013
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1013
agattcaaat tcaccaaatc                                                 20

<210> SEQ ID NO 1014
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1014
catgtgaggt tttcagggaa                                                 20

<210> SEQ ID NO 1015
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 1015
caaagagaat atatttggcc                    20

<210> SEQ ID NO 1016
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1016
agagggccag ttggtggcaa                    20

<210> SEQ ID NO 1017
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1017
ggtttgaaaa caagtatcaa                    20

<210> SEQ ID NO 1018
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1018
tcaaggagaa gggagtgaga                    20

<210> SEQ ID NO 1019
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1019
caaggtacgg attacttcac                    20

<210> SEQ ID NO 1020
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1020
taagtaaaat cattttccat                    20

<210> SEQ ID NO 1021
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1021
actcttaaca caccaagata                    20

```
<210> SEQ ID NO 1022
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1022
atcatttgtg atgcttaatg                                                  20

<210> SEQ ID NO 1023
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1023
gtttgcatca agcaagcagt                                                  20

<210> SEQ ID NO 1024
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1024
ttacaacaaa agaactgtag                                                  20

<210> SEQ ID NO 1025
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1025
tttgtttcca tcagtggaag                                                  20

<210> SEQ ID NO 1026
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1026
gttgtaaaaa tgaatcccgc                                                  20

<210> SEQ ID NO 1027
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1027
acacacaaat actcagcaaa                                                  20

<210> SEQ ID NO 1028
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 1028
gtgatgttac tggctggagt                                                    20

<210> SEQ ID NO 1029
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1029
caataggcag atttgggcaa                                                    20

<210> SEQ ID NO 1030
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1030
tcggctaatt caaaatccag                                                    20

<210> SEQ ID NO 1031
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1031
tcaaggatgg aagcagtcta                                                    20

<210> SEQ ID NO 1032
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1032
cagacatctt gcacagcact                                                    20

<210> SEQ ID NO 1033
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1033
aaaatacact ttgtaagata                                                    20

<210> SEQ ID NO 1034
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1034
tcttccctaa cgaggtgtaa                                                    20

<210> SEQ ID NO 1035
<211> LENGTH: 20
```

-continued

```
<212> TYPE: DNA
<213> ORGANISM: Artificial sequence
<220> FEATURE:
<223> OTHER INFORMATION: Synthetic oligonucleotide

<400> SEQUENCE: 1035
gaatactcac tatatgccca                                               20

<210> SEQ ID NO 1036
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1036
gctccttgga aaccacaggg                                               20

<210> SEQ ID NO 1037
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1037
agatcaggtg cccaagtctc                                               20

<210> SEQ ID NO 1038
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1038
caacaattat caagaggtgc                                               20

<210> SEQ ID NO 1039
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1039
taaaaaacag tcataatcaa                                               20

<210> SEQ ID NO 1040
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1040
aaatgagcac cattgtgaag                                               20

<210> SEQ ID NO 1041
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1041
```
tggtaataga gagaccagaa                                           20

<210> SEQ ID NO 1042
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1042
cagctatgaa gcaaaatgac                                           20

<210> SEQ ID NO 1043
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1043
agaggccaga gtacacaact                                           20

<210> SEQ ID NO 1044
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1044
attcaattag agcctccatt                                           20

<210> SEQ ID NO 1045
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1045
agagtccaaa gagagacctt                                           20

<210> SEQ ID NO 1046
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1046
tacctgaaca catgcttcaa                                           20

<210> SEQ ID NO 1047
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1047
ctccagacat ttctgatgca                                           20

<210> SEQ ID NO 1048
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 1048
agatgggaga cgcagcattg                                              20

<210> SEQ ID NO 1049
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1049
agtactttag atactctgtt                                              20

<210> SEQ ID NO 1050
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1050
gcatcagatg ttcatctctt                                              20

<210> SEQ ID NO 1051
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1051
aaatcgattg ttgttctcag                                              20

<210> SEQ ID NO 1052
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1052
tctcaaactc tttctgcctg                                              20

<210> SEQ ID NO 1053
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1053
agcacagaga ctgcctatac                                              20

<210> SEQ ID NO 1054
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1054
cgatgactga atggataata                                              20
```

<210> SEQ ID NO 1055
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1055
gccaaagatc tgcctgactg                                               20

<210> SEQ ID NO 1056
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1056
gaaagaacga tcagattact                                               20

<210> SEQ ID NO 1057
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1057
aattactttc tgatcctcag                                               20

<210> SEQ ID NO 1058
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1058
gtatatagaa ttccaggcta                                               20

<210> SEQ ID NO 1059
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1059
cagagggcca tctcaggtta                                               20

<210> SEQ ID NO 1060
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1060
gaatagctga tgactggtgc                                               20

<210> SEQ ID NO 1061
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1061
ctctcctttc ttgttacact                                              20

<210> SEQ ID NO 1062
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1062
ggagaaaata acctttatgt                                              20

<210> SEQ ID NO 1063
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1063
aaactggaat acatgaaatg                                              20

<210> SEQ ID NO 1064
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1064
tcctataatg cagcttggct                                              20

<210> SEQ ID NO 1065
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1065
aatagattca actagccaat                                              20

<210> SEQ ID NO 1066
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1066
ctttatgtgt gttaaaattg                                              20

<210> SEQ ID NO 1067
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1067
ctccttaaat attgctgaaa                                              20

<210> SEQ ID NO 1068

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1068
caacattcac ctctcatctg                                                    20

<210> SEQ ID NO 1069
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1069
gccaaaagag aactccactt                                                    20

<210> SEQ ID NO 1070
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1070
atcagaaatg aaggaaacac                                                    20

<210> SEQ ID NO 1071
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1071
aggcagaata cttgtagaaa                                                    20

<210> SEQ ID NO 1072
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1072
ctgtgggtga aagatccttg                                                    20

<210> SEQ ID NO 1073
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1073
tagagacaat agtagccata                                                    20

<210> SEQ ID NO 1074
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1074
```
acttcagata aatcacttca                                               20

<210> SEQ ID NO 1075
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1075
acttgactgg aagtccgatg                                               20

<210> SEQ ID NO 1076
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1076
gttaacaaaa acaggaaaag                                               20

<210> SEQ ID NO 1077
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1077
agaggaccaa agacattcct                                               20

<210> SEQ ID NO 1078
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1078
gctacatttg tatacaaact                                               20

<210> SEQ ID NO 1079
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1079
gtttaaggac ggcaaagttg                                               20

<210> SEQ ID NO 1080
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1080
ggatggaggc atcacagtct                                               20

<210> SEQ ID NO 1081
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 1081
ttatgctgta agtaaggttg                                                 20

<210> SEQ ID NO 1082
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1082
accagcaact gctgctcctc                                                 20

<210> SEQ ID NO 1083
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1083
tccttcaatt aaaaccaatc                                                 20

<210> SEQ ID NO 1084
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1084
ttcttaggca tttcccattt                                                 20

<210> SEQ ID NO 1085
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1085
acatcttgca cagcactcta                                                 20

<210> SEQ ID NO 1086
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1086
ctgtatacac attattgtct                                                 20

<210> SEQ ID NO 1087
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1087
caaggagaag ggagtgagaa                                                 20
```

<210> SEQ ID NO 1088
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1088
ctttcttgtt acactcatca                                            20

<210> SEQ ID NO 1089
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1089
gtttgaaaac aagtatcaag                                            20

<210> SEQ ID NO 1090
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1090
tagctgatga ctggtgcatt                                            20

<210> SEQ ID NO 1091
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1091
tccttaaata ttgctgaaac                                            20

<210> SEQ ID NO 1092
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1092
cgattgttgt tctcagaaaa                                            20

<210> SEQ ID NO 1093
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1093
aactggaata catgaaatgt                                            20

<210> SEQ ID NO 1094
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 1094
acatttgtat acaaactccc                                              20

<210> SEQ ID NO 1095
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1095
cctctgtttg atctagcact                                              20

<210> SEQ ID NO 1096
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1096
ccttcaatta aaaccaatca                                              20

<210> SEQ ID NO 1097
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1097
tccaggctat agcaagtcat                                              20

<210> SEQ ID NO 1098
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1098
tttaaggacg gcaaagttgt                                              20

<210> SEQ ID NO 1099
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1099
cacacaaata ctcagcaaat                                              20

<210> SEQ ID NO 1100
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1100
agggccagtt ggtggcaaag                                              20

```
<210> SEQ ID NO 1101
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1101
ttatgtgtgt taaaattgca                                               20

<210> SEQ ID NO 1102
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1102
cctataatgc agcttggcta                                               20

<210> SEQ ID NO 1103
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1103
acctgaacac atgcttcaaa                                               20

<210> SEQ ID NO 1104
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1104
tgaaaactca gtggctgctc                                               20

<210> SEQ ID NO 1105
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1105
atagattcaa ctagccaatt                                               20

<210> SEQ ID NO 1106
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1106
aaagacatgc tatccaaaga                                               20

<210> SEQ ID NO 1107
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 1107
aaagagaata tatttggccc                                               20

<210> SEQ ID NO 1108
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1108
gaggccagag tacacaacta                                               20

<210> SEQ ID NO 1109
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1109
gattcaaatt caccaaatct                                               20

<210> SEQ ID NO 1110
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1110
tccagacatt tctgatgcaa                                               20

<210> SEQ ID NO 1111
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1111
cttcagataa atcacttcac                                               20

<210> SEQ ID NO 1112
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1112
tggtcagaca atgccctgcc                                               20

<210> SEQ ID NO 1113
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1113
ggatggaagc agtctacctt                                               20

<210> SEQ ID NO 1114
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 1114
cttaggcatt tcccatttct                                                 20

<210> SEQ ID NO 1115
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1115
tcagaaatga aggaaacact                                                 20

<210> SEQ ID NO 1116
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1116
ttactttctg atcctcagga                                                 20

<210> SEQ ID NO 1117
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1117
gtttccatca gtggaagtac                                                 20

<210> SEQ ID NO 1118
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1118
ggaagggttg gttatttgtt                                                 20

<210> SEQ ID NO 1119
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1119
agagacaata gtagccatac                                                 20

<210> SEQ ID NO 1120
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1120
```

-continued

```
atttgtgatg cttaatgtcc                                             20

<210> SEQ ID NO 1121
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1121
tccttggaaa ccacagggtt                                             20

<210> SEQ ID NO 1122
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1122
tgatccctca atcatcatcc                                             20

<210> SEQ ID NO 1123
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1123
cggctaattc aaaatccagc                                             20

<210> SEQ ID NO 1124
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1124
cagatgttca tctcttcaca                                             20

<210> SEQ ID NO 1125
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1125
cttccctaac gaggtgtaag                                             20

<210> SEQ ID NO 1126
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1126
cccgcattga aggttggctc                                             20

<210> SEQ ID NO 1127
<211> LENGTH: 20
<212> TYPE: DNA
<213> ORGANISM: Artificial sequence
```

```
<220> FEATURE:
<223> OTHER INFORMATION: Synthetic oligonucleotide

<400> SEQUENCE: 1127
aaagaacgat cagattactc                                              20

<210> SEQ ID NO 1128
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1128
atgactgaat ggataatacc                                              20

<210> SEQ ID NO 1129
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1129
tcctccttct atgcagcctg                                              20

<210> SEQ ID NO 1130
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1130
catcacagtc tggttaccag                                              20

<210> SEQ ID NO 1131
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1131
ccagcaactg ctgctcctca                                              20

<210> SEQ ID NO 1132
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1132
gcacagagac tgcctatact                                              20

<210> SEQ ID NO 1133
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1133
acatactgga aggcatggat                                              20
```

<210> SEQ ID NO 1134
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1134
tgtgagtttg attcaagaag                                              20

<210> SEQ ID NO 1135
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1135
ttcaattaga gcctccattc                                              20

<210> SEQ ID NO 1136
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1136
aaggtacgga ttacttcact                                              20

<210> SEQ ID NO 1137
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1137
gagtccaaag agagacctta                                              20

<210> SEQ ID NO 1138
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1138
caaactcttt ctgcctgtcc                                              20

<210> SEQ ID NO 1139
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1139
aaatacactt tgtaagataa                                              20

<210> SEQ ID NO 1140
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 1140
atgggtttgg agactatatt                                              20

<210> SEQ ID NO 1141
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1141
ttaacaaaaa caggaaaaga                                              20

<210> SEQ ID NO 1142
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1142
tacaacaaaa gaactgtagt                                              20

<210> SEQ ID NO 1143
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1143
ggtaatagag agaccagaat                                              20

<210> SEQ ID NO 1144
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1144
ctcttaacac accaagataa                                              20

<210> SEQ ID NO 1145
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1145
aaatgtactt attttacctc                                              20

<210> SEQ ID NO 1146
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1146
agctatgaag caaaatgact                                              20

<210> SEQ ID NO 1147
```

-continued

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1147
aagtaaaatc attttccatt                                              20

<210> SEQ ID NO 1148
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1148
aatgagcacc attgtgaaga                                              20

<210> SEQ ID NO 1149
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1149
aataggcaga tttgggcaaa                                              20

<210> SEQ ID NO 1150
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1150
ctcactatat gcccagcatt                                              20

<210> SEQ ID NO 1151
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1151
gagaaaataa cctttatgtt                                              20

<210> SEQ ID NO 1152
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1152
gcatcaagca agcagttatt                                              20

<210> SEQ ID NO 1153
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1153
```
ggcagaatac ttgtagaaaa                                                    20

<210> SEQ ID NO 1154
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1154
caaatcaaga ccttcaaatc                                                    20

<210> SEQ ID NO 1155
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1155
gatgggagac gcagcattgt                                                    20

<210> SEQ ID NO 1156
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1156
gtgggtgaaa gatccttgct                                                    20

<210> SEQ ID NO 1157
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1157
gaggaccaaa gacattcctt                                                    20

<210> SEQ ID NO 1158
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1158
aaaaaacagt cataatcaaa                                                    20

<210> SEQ ID NO 1159
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1159
ttccctaacg aggtgtaagg                                                    20

<210> SEQ ID NO 1160
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 1160
actgcctata ctggcagagg                                              20

<210> SEQ ID NO 1161
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1161
ctggaataca tgaaatgtgc                                              20

<210> SEQ ID NO 1162
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1162
aaactctttc tgcctgtcct                                              20

<210> SEQ ID NO 1163
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1163
attcaaattc accaaatctg                                              20

<210> SEQ ID NO 1164
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1164
agaaaataac ctttatgtta                                              20

<210> SEQ ID NO 1165
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1165
ttgtatacaa actcccaaaa                                              20

<210> SEQ ID NO 1166
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1166
cagaaatgaa ggaaacactt                                              20
```

<210> SEQ ID NO 1167
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1167
attttgtaca tctgagggct                                               20

<210> SEQ ID NO 1168
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1168
aagaacgatc agattactca                                               20

<210> SEQ ID NO 1169
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1169
tgggtgaaag atccttgctt                                               20

<210> SEQ ID NO 1170
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1170
tgatctagca ctgagttttc                                               20

<210> SEQ ID NO 1171
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1171
gtctggttac cagggtaaca                                               20

<210> SEQ ID NO 1172
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1172
ttcagataaa tcacttcacc                                               20

<210> SEQ ID NO 1173
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 1173
agacatgcta tccaaagagt                                               20

<210> SEQ ID NO 1174
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1174
gctacaaaca gactttatac                                               20

<210> SEQ ID NO 1175
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1175
tgttgttctc agaaaacatt                                               20

<210> SEQ ID NO 1176
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1176
tttccatcag tggaagtacc                                               20

<210> SEQ ID NO 1177
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1177
gggccagttg gtggcaaagg                                               20

<210> SEQ ID NO 1178
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1178
agtttgattc aagaaggctg                                               20

<210> SEQ ID NO 1179
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1179
atgagcacca ttgtgaagat                                               20

```
<210> SEQ ID NO 1180
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1180
ttctgagtca ccagatcata                                          20

<210> SEQ ID NO 1181
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1181
ctgatgactg gtgcattctg                                          20

<210> SEQ ID NO 1182
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1182
ccagtaggta gctcatgcca                                          20

<210> SEQ ID NO 1183
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1183
gctatgaagc aaaatgacta                                          20

<210> SEQ ID NO 1184
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1184
ccaggctata gcaagtcatg                                          20

<210> SEQ ID NO 1185
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1185
tttgaaaaca agtatcaagt                                          20

<210> SEQ ID NO 1186
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 1186
ggcatggatc ctgcattaac                                               20

<210> SEQ ID NO 1187
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1187
actttctgat cctcaggaga                                               20

<210> SEQ ID NO 1188
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1188
tactcagcaa atgtactggg                                               20

<210> SEQ ID NO 1189
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1189
aatacacttt gtaagataag                                               20

<210> SEQ ID NO 1190
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1190
agtccaaaga gagaccttaa                                               20

<210> SEQ ID NO 1191
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1191
ccttctatgc agcctggaag                                               20

<210> SEQ ID NO 1192
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1192
ttaaggacgg caaagttgta                                               20

<210> SEQ ID NO 1193
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 1193
gaagggttgg ttatttgtta                                              20

<210> SEQ ID NO 1194
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1194
tcaattagag cctccattcc                                              20

<210> SEQ ID NO 1195
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1195
tagattcaac tagccaattt                                              20

<210> SEQ ID NO 1196
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1196
ataggcagat ttgggcaaac                                              20

<210> SEQ ID NO 1197
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1197
aagagaatat atttggcccc                                              20

<210> SEQ ID NO 1198
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1198
tttgtgatgc ttaatgtcca                                              20

<210> SEQ ID NO 1199
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1199
```
ggccagagta cacaactaat                                                         20

<210> SEQ ID NO 1200
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1200
gggccatctc aggttacacc                                                         20

<210> SEQ ID NO 1201
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1201
tgtgtgttaa aattgcaatt                                                         20

<210> SEQ ID NO 1202
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1202
agtaaaatca ttttccatta                                                         20

<210> SEQ ID NO 1203
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1203
aaaaacagtc ataatcaaag                                                         20

<210> SEQ ID NO 1204
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1204
aaatcaagac cttcaaatca                                                         20

<210> SEQ ID NO 1205
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1205
tcttaacaca ccaagataac                                                         20

<210> SEQ ID NO 1206
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 1206
acaaaaacag gaaaagactg                                                  20

<210> SEQ ID NO 1207
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1207
ccttggaaac cacagggttg                                                  20

<210> SEQ ID NO 1208
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1208
ggagaaggga gtgagaagat                                                  20

<210> SEQ ID NO 1209
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1209
atgggagacg cagcattgta                                                  20

<210> SEQ ID NO 1210
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1210
ccttaaatat tgctgaaacc                                                  20

<210> SEQ ID NO 1211
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1211
cctgaacaca tgcttcaaag                                                  20

<210> SEQ ID NO 1212
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1212
gaaaactcag tggctgctcc                                                  20
```

```
<210> SEQ ID NO 1213
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1213
gggcatttaa gttcagcaga                                              20

<210> SEQ ID NO 1214
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1214
ttaggcattt cccatttcta                                              20

<210> SEQ ID NO 1215
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1215
tcactatatg cccagcatta                                              20

<210> SEQ ID NO 1216
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1216
gagacaatag tagccatacc                                              20

<210> SEQ ID NO 1217
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1217
gtaatagaga gaccagaatg                                              20

<210> SEQ ID NO 1218
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1218
caactgctgc tcctcaggcc                                              20

<210> SEQ ID NO 1219
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 1219
acttatttta cctctcattt                                              20

<210> SEQ ID NO 1220
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1220
cctgcctata atcttgtctt                                              20

<210> SEQ ID NO 1221
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1221
tgactgaatg gataataccc                                              20

<210> SEQ ID NO 1222
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1222
gtttggagac tatatttccc                                              20

<210> SEQ ID NO 1223
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1223
ttcttgttac actcatcaag                                              20

<210> SEQ ID NO 1224
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1224
ggaagcagtc taccttcttg                                              20

<210> SEQ ID NO 1225
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1225
tgtatacaca ttattgtcta                                              20

<210> SEQ ID NO 1226
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1226
acaacaaaag aactgtagta                                               20

<210> SEQ ID NO 1227
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1227
tgaaggttgg ctcagacaac                                               20

<210> SEQ ID NO 1228
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1228
ggctaattca aaatccagca                                               20

<210> SEQ ID NO 1229
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1229
ccagacattt ctgatgcaac                                               20

<210> SEQ ID NO 1230
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1230
aggaccaaag acattccttc                                               20

<210> SEQ ID NO 1231
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1231
cttcaattaa aaccaatcag                                               20

<210> SEQ ID NO 1232
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1232
```

```
cagaatactt gtagaaaatc                                                    20

<210> SEQ ID NO 1233
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1233
gctaattcaa aatccagcaa                                                    20

<210> SEQ ID NO 1234
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1234
acaagtctaa tcaatctgtg                                                    20

<210> SEQ ID NO 1235
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1235
tcagataaat cacttcaccc                                                    20

<210> SEQ ID NO 1236
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1236
ccagcattat gctgggtgtt                                                    20

<210> SEQ ID NO 1237
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1237
gtaaaatcat tttccattag                                                    20

<210> SEQ ID NO 1238
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1238
gtgtgttaaa attgcaattc                                                    20

<210> SEQ ID NO 1239
<211> LENGTH: 20
<212> TYPE: DNA
```

<213> ORGANISM: Artificial sequence
<220> FEATURE:
<223> OTHER INFORMATION: Synthetic oligonucleotide

<400> SEQUENCE: 1239
tttctgatcc tcaggagatg					20

<210> SEQ ID NO 1240
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1240
ctgcctatac tggcagaggt					20

<210> SEQ ID NO 1241
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1241
tatttgttat gttattaaat					20

<210> SEQ ID NO 1242
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1242
agactttata caaagtcagc					20

<210> SEQ ID NO 1243
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1243
cagacatttc tgatgcaacc					20

<210> SEQ ID NO 1244
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1244
aatcaagacc ttcaaatcac					20

<210> SEQ ID NO 1245
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1245
gaacacatgc ttcaaagtgt					20

<210> SEQ ID NO 1246
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1246
caacaaaaga actgtagtac                                              20

<210> SEQ ID NO 1247
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1247
gtccaaagag agaccttaat                                              20

<210> SEQ ID NO 1248
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1248
cctgtccttt ttcctggaag                                              20

<210> SEQ ID NO 1249
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1249
agaaatgaag gaaacacttt                                              20

<210> SEQ ID NO 1250
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1250
ctgctgctcc tcaggccagt                                              20

<210> SEQ ID NO 1251
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1251
aggcatttcc catttctagc                                              20

<210> SEQ ID NO 1252
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 1252
cttaacacac caagataaca                                               20

<210> SEQ ID NO 1253
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1253
taggcagatt tgggcaaacg                                               20

<210> SEQ ID NO 1254
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1254
ggaccaaaga cattccttct                                               20

<210> SEQ ID NO 1255
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1255
gagaagggag tgagaagatg                                               20

<210> SEQ ID NO 1256
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1256
cacttatata ccacattcaa                                               20

<210> SEQ ID NO 1257
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1257
aactcagtgg ctgctccatc                                               20

<210> SEQ ID NO 1258
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1258
gccagagtac acaactaatt                                               20

```
<210> SEQ ID NO 1259
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1259
tgggagacgc agcattgtag                                                 20

<210> SEQ ID NO 1260
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1260
gcaaatgtac tgggaagctg                                                 20

<210> SEQ ID NO 1261
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1261
cttaaatatt gctgaaacca                                                 20

<210> SEQ ID NO 1262
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1262
tgagtcacca gatcatagcc                                                 20

<210> SEQ ID NO 1263
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1263
tcttgttaca ctcatcaagt                                                 20

<210> SEQ ID NO 1264
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1264
ctatgaagca aaatgactaa                                                 20

<210> SEQ ID NO 1265
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 1265
ggacacatga ccacatccat    20

<210> SEQ ID NO 1266
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1266
ttgagataaa gaagttccaa    20

<210> SEQ ID NO 1267
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1267
gcatttaagt tcagcagaag    20

<210> SEQ ID NO 1268
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1268
gacaatagta gccatacctt    20

<210> SEQ ID NO 1269
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1269
gaaaataacc tttatgttaa    20

<210> SEQ ID NO 1270
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1270
agactatatt tccctccca    20

<210> SEQ ID NO 1271
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1271
gcatggatcc tgcattaaca    20

<210> SEQ ID NO 1272
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 1272
ggccagttgg tggcaaaggc                                               20

<210> SEQ ID NO 1273
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1273
gcagtctacc ttcttgcctt                                               20

<210> SEQ ID NO 1274
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1274
acactttgta agataagttt                                               20

<210> SEQ ID NO 1275
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1275
cttggaaacc acagggttgt                                               20

<210> SEQ ID NO 1276
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1276
tccatcagtg gaagtaccct                                               20

<210> SEQ ID NO 1277
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1277
tgatgactgg tgcattctgt                                               20

<210> SEQ ID NO 1278
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1278
```
caggctatag caagtcatgt				20

<210> SEQ ID NO 1279
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1279
ttcaaattca ccaaatctgt				20

<210> SEQ ID NO 1280
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1280
tgttctcaga aaacattcca				20

<210> SEQ ID NO 1281
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1281
tggaatacat gaaatgtgca				20

<210> SEQ ID NO 1282
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1282
aaaacagtca taatcaaaga				20

<210> SEQ ID NO 1283
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1283
tctggttacc agggtaacag				20

<210> SEQ ID NO 1284
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1284
caattagagc ctccattcct				20

<210> SEQ ID NO 1285
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1285
agattcaact agccaatttt                                               20

<210> SEQ ID NO 1286
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1286
gacatgctat ccaaagagtt                                               20

<210> SEQ ID NO 1287
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1287
aaggacggca aagttgtaag                                               20

<210> SEQ ID NO 1288
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1288
ggttggctca gacaacttct                                               20

<210> SEQ ID NO 1289
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1289
tgagcaccat tgtgaagata                                               20

<210> SEQ ID NO 1290
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1290
gggtgaaaga tccttgcttt                                               20

<210> SEQ ID NO 1291
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1291
gagaagttcc ttggctctct                                               20

<210> SEQ ID NO 1292
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1292
agagaatata tttggcccct                                               20

<210> SEQ ID NO 1293
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1293
gtgatgctta atgtccaatt                                               20

<210> SEQ ID NO 1294
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1294
ttcaattaaa accaatcaga                                               20

<210> SEQ ID NO 1295
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1295
gccatctcag gttacaccat                                               20

<210> SEQ ID NO 1296
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1296
gggataccaa cagatggctt                                               20

<210> SEQ ID NO 1297
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1297
ctagcactga gttttcctca                                               20

<210> SEQ ID NO 1298
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 1298
taatagagag accagaatga                                            20

<210> SEQ ID NO 1299
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1299
caggaaaaga ctgaaatctg                                            20

<210> SEQ ID NO 1300
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1300
ctgtaagtaa ggttggctga                                            20

<210> SEQ ID NO 1301
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1301
gtatacacat tattgtctaa                                            20

<210> SEQ ID NO 1302
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1302
ttgaaaacaa gtatcaagtg                                            20

<210> SEQ ID NO 1303
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1303
cttctatgca gcctggaagc                                            20

<210> SEQ ID NO 1304
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1304
agaatacttg tagaaaatcc                                            20

<210> SEQ ID NO 1305
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1305
cagtaggtag ctcatgccac                                                   20

<210> SEQ ID NO 1306
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1306
agaacgatca gattactcaa                                                   20

<210> SEQ ID NO 1307
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1307
aacaaaagaa ctgtagtaca                                                   20

<210> SEQ ID NO 1308
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1308
ggaatacatg aaatgtgcat                                                   20

<210> SEQ ID NO 1309
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1309
gctgctattt ttgaataagc                                                   20

<210> SEQ ID NO 1310
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1310
tggctcagac aacttctaaa                                                   20

<210> SEQ ID NO 1311
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1311
```
gcactgagtt ttcctcaggg                                          20

<210> SEQ ID NO 1312
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1312
ctgatcctca ggagatgctt                                          20

<210> SEQ ID NO 1313
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1313
ttaaatattg ctgaaaccac                                          20

<210> SEQ ID NO 1314
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1314
gattcaacta gccaattttt                                          20

<210> SEQ ID NO 1315
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1315
cagcagaagt gaagaatctc                                          20

<210> SEQ ID NO 1316
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1316
gactatattt cccctcccac                                          20

<210> SEQ ID NO 1317
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1317
tacacattat tgtctaatag                                          20

<210> SEQ ID NO 1318
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 1318
cctaacgagg tgtaaggcca                                              20

<210> SEQ ID NO 1319
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1319
gaccaaagac attccttctc                                              20

<210> SEQ ID NO 1320
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1320
ctgctcctca ggccagtctg                                              20

<210> SEQ ID NO 1321
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1321
taaaatcatt ttccattagc                                              20

<210> SEQ ID NO 1322
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1322
tcaattaaaa ccaatcagac                                              20

<210> SEQ ID NO 1323
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1323
aggcagattt gggcaaacgc                                              20

<210> SEQ ID NO 1324
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1324
acatgctatc caaagagtta                                              20
```

<210> SEQ ID NO 1325
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1325
tatgaagcaa aatgactaaa                                               20

<210> SEQ ID NO 1326
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1326
cactttgtaa gataagtttc                                               20

<210> SEQ ID NO 1327
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1327
aattagagcc tccattcctt                                               20

<210> SEQ ID NO 1328
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1328
ttaacacacc aagataacat                                               20

<210> SEQ ID NO 1329
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1329
tccaaagaga gaccttaatc                                               20

<210> SEQ ID NO 1330
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1330
gttctcagaa aacattccag                                               20

<210> SEQ ID NO 1331
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 1331
cctgcattaa caggtagaca                                         20

<210> SEQ ID NO 1332
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1332
tttgttatgt tattaaatca                                         20

<210> SEQ ID NO 1333
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1333
ccttcttgcc tttcagaata                                         20

<210> SEQ ID NO 1334
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1334
gactttatac aaagtcagca                                         20

<210> SEQ ID NO 1335
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1335
attgcaaatt gatctctgtg                                         20

<210> SEQ ID NO 1336
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1336
ccagagtaca caactaatta                                         20

<210> SEQ ID NO 1337
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1337
tgtaagtaag gttggctgag                                         20

<210> SEQ ID NO 1338
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1338
ccatcagtgg aagtaccctt                                           20

<210> SEQ ID NO 1339
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1339
gccagttggt ggcaaaggca                                           20

<210> SEQ ID NO 1340
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1340
ggctatagca agtcatgttt                                           20

<210> SEQ ID NO 1341
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1341
tgtgttaaaa ttgcaattct                                           20

<210> SEQ ID NO 1342
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1342
gacacatgac cacatccatc                                           20

<210> SEQ ID NO 1343
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1343
gcaccattgt gaagatatga                                           20

<210> SEQ ID NO 1344
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 1344
cttgttacac tcatcaagta                                                   20

<210> SEQ ID NO 1345
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1345
tgttgaagta aatgtacaca                                                   20

<210> SEQ ID NO 1346
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1346
ggacggcaaa gttgtaagtg                                                   20

<210> SEQ ID NO 1347
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1347
aggaaaagac tgaaatctgg                                                   20

<210> SEQ ID NO 1348
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1348
agaagggagt gagaagatgc                                                   20

<210> SEQ ID NO 1349
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1349
tggaaaccac agggttgtca                                                   20

<210> SEQ ID NO 1350
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1350
aaacagtcat aatcaaagaa                                                   20

<210> SEQ ID NO 1351
<211> LENGTH: 20
```

<212> TYPE: DNA
<213> ORGANISM: Artificial sequence
<220> FEATURE:
<223> OTHER INFORMATION: Synthetic oligonucleotide

<400> SEQUENCE: 1351
gaaaacaagt atcaagtgtc                                              20

<210> SEQ ID NO 1352
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1352
gaaatgaagg aaacactttc                                              20

<210> SEQ ID NO 1353
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1353
ggattacttc actgtccttt                                              20

<210> SEQ ID NO 1354
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1354
ccatctcagg ttacaccatt                                              20

<210> SEQ ID NO 1355
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1355
aaaacctatg aatgcctctg                                              20

<210> SEQ ID NO 1356
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1356
ttggctttca gcatgtgaga                                              20

<210> SEQ ID NO 1357
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1357

```
gcatttccca tttctagcag                                             20

<210> SEQ ID NO 1358
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1358
tgatgcttaa tgtccaattt                                             20

<210> SEQ ID NO 1359
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1359
acaatagtag ccataccttg                                             20

<210> SEQ ID NO 1360
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1360
actgaatgga taatacccca                                             20

<210> SEQ ID NO 1361
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1361
gaatacttgt agaaaatccc                                             20

<210> SEQ ID NO 1362
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1362
gtgaaagatc cttgctttga                                             20

<210> SEQ ID NO 1363
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1363
ctgtcctttt tcctggaagc                                             20

<210> SEQ ID NO 1364
<211> LENGTH: 20
<212> TYPE: DNA
<213> ORGANISM: Artificial sequence
```

```
<220> FEATURE:
<223> OTHER INFORMATION: Synthetic oligonucleotide

<400> SEQUENCE: 1364
atcaagacct tcaaatcacc                                              20

<210> SEQ ID NO 1365
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1365
gaacgatcag attactcaaa                                              20

<210> SEQ ID NO 1366
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1366
aagtctaatc aatctgtgat                                              20

<210> SEQ ID NO 1367
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1367
gagaatatat ttggcccta                                               20

<210> SEQ ID NO 1368
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1368
aaatcacttc acccttcagt                                              20

<210> SEQ ID NO 1369
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1369
aaataacctt tatgttaaac                                              20

<210> SEQ ID NO 1370
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1370
ggataccaac agatggctta                                              20
```

```
<210> SEQ ID NO 1371
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1371
atggtattag ctactccctt                                               20

<210> SEQ ID NO 1372
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1372
tcaaattcac caaatctgtt                                               20

<210> SEQ ID NO 1373
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1373
gacatttctg atgcaacccc                                               20

<210> SEQ ID NO 1374
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1374
ccatcatatg tacctggccc                                               20

<210> SEQ ID NO 1375
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1375
tctatgcagc ctggaagctt                                               20

<210> SEQ ID NO 1376
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1376
ggttaccagg gtaacagcca                                               20

<210> SEQ ID NO 1377
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 1377
gagtctttaa tttcctgagg                                              20

<210> SEQ ID NO 1378
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1378
tcaccagatc atagcctttc                                              20

<210> SEQ ID NO 1379
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1379
acttatatac cacattcaag                                              20

<210> SEQ ID NO 1380
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1380
aatagagaga ccagaatgaa                                              20

<210> SEQ ID NO 1381
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1381
ctctcaagag acattctcac                                              20

<210> SEQ ID NO 1382
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1382
atagagagac cagaatgaat                                              20

<210> SEQ ID NO 1383
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1383
acaaaagaac tgtagtacaa                                              20

<210> SEQ ID NO 1384
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1384
agcagaagtg aagaatctca                                                  20

<210> SEQ ID NO 1385
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1385
tctgcacaat gagcacacta                                                  20

<210> SEQ ID NO 1386
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1386
atttacagtt gttatagatc                                                  20

<210> SEQ ID NO 1387
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1387
tgaatggata atacccccatg                                                 20

<210> SEQ ID NO 1388
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1388
ggaaaccaca gggttgtcat                                                  20

<210> SEQ ID NO 1389
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1389
atctaactga atgttaagga                                                  20

<210> SEQ ID NO 1390
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1390
```

```
gtaagtaagg ttggctgagt                                               20

<210> SEQ ID NO 1391
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1391
actttgtaag ataagtttct                                               20

<210> SEQ ID NO 1392
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1392
ttctcagaaa acattccaga                                               20

<210> SEQ ID NO 1393
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1393
taaatattgc tgaaaccact                                               20

<210> SEQ ID NO 1394
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1394
tagccatacc ttgttcctca                                               20

<210> SEQ ID NO 1395
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1395
cagagtacac aactaattaa                                               20

<210> SEQ ID NO 1396
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1396
gttgaagtaa atgtacacag                                               20

<210> SEQ ID NO 1397
<211> LENGTH: 20
<212> TYPE: DNA
```

```
<213> ORGANISM: Artificial sequence
<220> FEATURE:
<223> OTHER INFORMATION: Synthetic oligonucleotide

<400> SEQUENCE: 1397
tgttacactc atcaagtaag                                                20

<210> SEQ ID NO 1398
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1398
gatgcttaat gtccaatttt                                                20

<210> SEQ ID NO 1399
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1399
tgcaaattga tctctgtgga                                                20

<210> SEQ ID NO 1400
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1400
caaattcacc aaatctgttt                                                20

<210> SEQ ID NO 1401
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1401
tcaagagaca ttctcacatt                                                20

<210> SEQ ID NO 1402
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1402
catgctatcc aaagagttat                                                20

<210> SEQ ID NO 1403
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1403
aaccgtaatt tatgactgca                                                20
```

<210> SEQ ID NO 1404
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1404
ggaaaagact gaaatctggg                                            20

<210> SEQ ID NO 1405
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1405
caattaaaac caatcagact                                            20

<210> SEQ ID NO 1406
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1406
accaaagaca ttccttctct                                            20

<210> SEQ ID NO 1407
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1407
aaaatcattt tccattagct                                            20

<210> SEQ ID NO 1408
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1408
tgaaagatcc ttgctttgac                                            20

<210> SEQ ID NO 1409
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1409
gataccaaca gatggcttag                                            20

<210> SEQ ID NO 1410
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 1410
attcaactag ccaattttta                                               20

<210> SEQ ID NO 1411
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1411
tcatatgtac ctggcccaag                                               20

<210> SEQ ID NO 1412
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1412
caccagatca tagcctttct                                               20

<210> SEQ ID NO 1413
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1413
ctaacgaggt gtaaggccag                                               20

<210> SEQ ID NO 1414
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1414
tcttgccttt cagaatagct                                               20

<210> SEQ ID NO 1415
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1415
atataccaca ttcaagtgct                                               20

<210> SEQ ID NO 1416
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1416
gttaccaggg taacagccac                                               20

```
<210> SEQ ID NO 1417
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1417
aatacttgta gaaaatccca                                              20

<210> SEQ ID NO 1418
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1418
tccaacttta agcccttctc                                              20

<210> SEQ ID NO 1419
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1419
gaatatattt ggcccctata                                              20

<210> SEQ ID NO 1420
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1420
ccaaagagag accttaatca                                              20

<210> SEQ ID NO 1421
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1421
atgaaatgtg catcattcta                                              20

<210> SEQ ID NO 1422
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1422
catctcaggt tacaccatta                                              20

<210> SEQ ID NO 1423
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 1423
acgctcttat tgtttttctg                                               20

<210> SEQ ID NO 1424
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1424
aacagtcata atcaaagaat                                               20

<210> SEQ ID NO 1425
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1425
aaatgaagga aacactttca                                               20

<210> SEQ ID NO 1426
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1426
tgatcctcag gagatgcttg                                               20

<210> SEQ ID NO 1427
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1427
actatatttc ccctcccacc                                               20

<210> SEQ ID NO 1428
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1428
atgaagcaaa atgactaaaa                                               20

<210> SEQ ID NO 1429
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1429
gacggcaaag ttgtaagtgg                                               20

<210> SEQ ID NO 1430
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 1430
cagttggtgg caaaggcaaa                                          20

<210> SEQ ID NO 1431
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1431
agacgcagca ttgtaggctg                                          20

<210> SEQ ID NO 1432
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1432
ctgcattaac aggtagacaa                                          20

<210> SEQ ID NO 1433
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1433
catttcccat ttctagcagg                                          20

<210> SEQ ID NO 1434
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1434
catcagtgga agtacccttt                                          20

<210> SEQ ID NO 1435
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1435
gtgttaaaat tgcaattcta                                          20

<210> SEQ ID NO 1436
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1436
```
acccaaataa cccactcacc                                               20

<210> SEQ ID NO 1437
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1437
gaagggagtg agaagatgct                                               20

<210> SEQ ID NO 1438
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1438
acatttctga tgcaacccca                                               20

<210> SEQ ID NO 1439
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1439
acgatcagat tactcaaatt                                               20

<210> SEQ ID NO 1440
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1440
ctatgcagcc tggaagctta                                               20

<210> SEQ ID NO 1441
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1441
ggctcagaca acttctaaag                                               20

<210> SEQ ID NO 1442
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1442
aaacctatga atgcctctgt                                               20

<210> SEQ ID NO 1443
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1443
caccattgtg aagatatgac                                               20

<210> SEQ ID NO 1444
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1444
gctatttttg aataagcagg                                               20

<210> SEQ ID NO 1445
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1445
tcaagacctt caaatcacct                                               20

<210> SEQ ID NO 1446
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1446
tgactggtgc attctgttat                                               20

<210> SEQ ID NO 1447
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1447
aataaccttt atgttaaacc                                               20

<210> SEQ ID NO 1448
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1448
gaagtgaaca atatttgggc                                               20

<210> SEQ ID NO 1449
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1449
actttataca aagtcagcaa                                               20

<210> SEQ ID NO 1450
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1450
gctttcagca tgtgagattg                                               20

<210> SEQ ID NO 1451
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1451
gcctccattc ctttgtgact                                               20

<210> SEQ ID NO 1452
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1452
aaaacaagta tcaagtgtct                                               20

<210> SEQ ID NO 1453
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1453
tcctcaggcc agtctgttct                                               20

<210> SEQ ID NO 1454
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1454
tctttaattt cctgaggaag                                               20

<210> SEQ ID NO 1455
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1455
tcctttttcc tggaagctta                                               20

<210> SEQ ID NO 1456
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 1456
taacacacca agataacatt                                              20

<210> SEQ ID NO 1457
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1457
gattacttca ctgtcclttta                                             20

<210> SEQ ID NO 1458
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1458
tgttatgtta ttaaatcaaa                                              20

<210> SEQ ID NO 1459
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1459
gttatgttat taaatcaaaa                                              20

<210> SEQ ID NO 1460
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1460
tacaaagtca gcaaagcatg                                              20

<210> SEQ ID NO 1461
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1461
ttgaagtaaa tgtacacagg                                              20

<210> SEQ ID NO 1462
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1462
aattcaccaa atctgtttct                                              20

<210> SEQ ID NO 1463
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1463
cttaatgtcc aattttccta                                             20

<210> SEQ ID NO 1464
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1464
gcattaacag gtagacaaac                                             20

<210> SEQ ID NO 1465
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1465
atctcaggtt acaccattag                                             20

<210> SEQ ID NO 1466
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1466
ctttgtaaga taagtttcta                                             20

<210> SEQ ID NO 1467
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1467
gctacatttg atagggaata                                             20

<210> SEQ ID NO 1468
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1468
aaatcatttt ccattagcta                                             20

<210> SEQ ID NO 1469
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1469
```
aacttctaaa gttccttcca        20

<210> SEQ ID NO 1470
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1470
ccagggttga ggttgttatt        20

<210> SEQ ID NO 1471
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1471
aattaaaacc aatcagactt        20

<210> SEQ ID NO 1472
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1472
gtgccaaaac acgactcatt        20

<210> SEQ ID NO 1473
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1473
ccaactttaa gcccttctca        20

<210> SEQ ID NO 1474
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1474
gaatggataa taccccatga        20

<210> SEQ ID NO 1475
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1475
aacacaccaa gataacattg        20

<210> SEQ ID NO 1476
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 1476
gctcttattg tttttctgac                                          20

<210> SEQ ID NO 1477
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1477
gttacactca tcaagtaaga                                          20

<210> SEQ ID NO 1478
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1478
cgatcagatt actcaaattg                                          20

<210> SEQ ID NO 1479
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1479
tagacctaat attttcaact                                          20

<210> SEQ ID NO 1480
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1480
tgttaaaatt gcaattctat                                          20

<210> SEQ ID NO 1481
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1481
gcatgtgaga ttgacccaga                                          20

<210> SEQ ID NO 1482
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1482
accaacagat ggcttagaaa                                          20
```

<210> SEQ ID NO 1483
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1483
ccgtaattta tgactgcaaa					20

<210> SEQ ID NO 1484
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1484
cattccagaa attgatcttc					20

<210> SEQ ID NO 1485
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1485
aaacaagtat caagtgtctt					20

<210> SEQ ID NO 1486
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1486
attctcacat ttccagtcta					20

<210> SEQ ID NO 1487
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1487
acagtcataa tcaaagaatt					20

<210> SEQ ID NO 1488
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1488
caaagagaga ccttaatcac					20

<210> SEQ ID NO 1489
<211> LENGTH: 20
<212> TYPE: DNA
<213> ORGANISM: Artificial sequence
<220> FEATURE:

```
<223> OTHER INFORMATION: Synthetic oligonucleotide

<400> SEQUENCE: 1489
atacttgtag aaaatcccaa                                          20

<210> SEQ ID NO 1490
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1490
aatatatttg gcccctatag                                          20

<210> SEQ ID NO 1491
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1491
cagtggaagt accctttgag                                          20

<210> SEQ ID NO 1492
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1492
tgaagcaaaa tgactaaaag                                          20

<210> SEQ ID NO 1493
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1493
ttcaactagc caattttaa                                           20

<210> SEQ ID NO 1494
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1494 ataacctta tgttaaacct                                           20

<210> SEQ ID NO 1495
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1495
gaaagatcct tgctttgacc                                          20
```

<210> SEQ ID NO 1496
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1496
tttttcctgg aagcttacca         20

<210> SEQ ID NO 1497
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1497
ttcccatttc tagcaggaac         20

<210> SEQ ID NO 1498
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1498
tggtggcaaa ggcaaagagt         20

<210> SEQ ID NO 1499
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1499
cctccattcc tttgtgactt         20

<210> SEQ ID NO 1500
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1500
gtgaacaata tttgggcttt         20

<210> SEQ ID NO 1501
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1501
atattgctga aaccactttg         20

<210> SEQ ID NO 1502
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 1502
tgcagcctgg aagcttatct                                               20

<210> SEQ ID NO 1503
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1503
aatgaaggaa acactttcag                                               20

<210> SEQ ID NO 1504
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1504
acttcactgt cctttatctt                                               20

<210> SEQ ID NO 1505
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1505
tgctatccaa agagttatct                                               20

<210> SEQ ID NO 1506
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1506
gaaaccacag ggttgtcatg                                               20

<210> SEQ ID NO 1507
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1507
taagtaaggt tggctgagtt                                               20

<210> SEQ ID NO 1508
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1508
tgcacaatga gcacactaca                                               20

<210> SEQ ID NO 1509
<211> LENGTH: 20
```

-continued

<212> TYPE: DNA
<213> ORGANISM: Artificial sequence
<220> FEATURE:
<223> OTHER INFORMATION: Synthetic oligonucleotide

<400> SEQUENCE: 1509
cccaaataac ccactcacct                                              20

<210> SEQ ID NO 1510
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1510
attctgttat gtgatctata                                              20

<210> SEQ ID NO 1511
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1511
ctttcagaat agctgtaccc                                              20

<210> SEQ ID NO 1512
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1512
tataccacat tcaagtgctg                                              20

<210> SEQ ID NO 1513
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1513
taacgaggtg taaggccaga                                              20

<210> SEQ ID NO 1514
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1514
agagtacaca actaattaac                                              20

<210> SEQ ID NO 1515
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1515
caaaagaact gtagtacaaa                                              20

<210> SEQ ID NO 1516
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1516
accttgttcc tcaggtcagt                                              20

<210> SEQ ID NO 1517
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1517
cctatgaatg cctctgtgca                                              20

<210> SEQ ID NO 1518
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1518
acggcaaagt tgtaagtggc                                              20

<210> SEQ ID NO 1519
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1519
ggtaacagcc actgttctca                                              20

<210> SEQ ID NO 1520
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1520
aagggagtga gaagatgctg                                              20

<210> SEQ ID NO 1521
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1521
gaaaagactg aaatctggga                                              20

<210> SEQ ID NO 1522
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 1522
tttacagttg ttatagatct                                               20

<210> SEQ ID NO 1523
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1523
ccaaagacat tccttctctg                                               20

<210> SEQ ID NO 1524
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1524
ctatttttga ataagcaggt                                               20

<210> SEQ ID NO 1525
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1525
accattgtga agatatgaca                                               20

<210> SEQ ID NO 1526
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1526
ggacccaatg tgcatcctca                                               20

<210> SEQ ID NO 1527
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1527
tgaaatgtgc atcattctaa                                               20

<210> SEQ ID NO 1528
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1528
ttttacatcc atttttcctc                                               20
```

<210> SEQ ID NO 1529
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1529
caggccagtc tgttctcatg                                              20

<210> SEQ ID NO 1530
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1530
atcctcagga gatgcttgaa                                              20

<210> SEQ ID NO 1531
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1531
ctgatgcaac cccaaataag                                              20

<210> SEQ ID NO 1532
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1532
tagagagacc agaatgaatt                                              20

<210> SEQ ID NO 1533
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1533
gcagaagtga agaatctcag                                              20

<210> SEQ ID NO 1534
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1534
caagaccttc aaatcaccta                                              20

<210> SEQ ID NO 1535
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1535
tcctcaggtc agtctcccac                                                    20

<210> SEQ ID NO 1536
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1536
gtggaagtac cctttgagaa                                                    20

<210> SEQ ID NO 1537
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1537
aatggataat accccatgaa                                                    20

<210> SEQ ID NO 1538
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1538
cagtctgttc tcatgtaagc                                                    20

<210> SEQ ID NO 1539
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1539
aagaccttca aatcacctac                                                    20

<210> SEQ ID NO 1540
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1540
acttctaaag ttccttccaa                                                    20

<210> SEQ ID NO 1541
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1541
ggttgttatt actcagatcg                                                    20

<210> SEQ ID NO 1542

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1542
gcattgtagg ctgtgtggtt                                              20

<210> SEQ ID NO 1543
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1543
ccattccttt gtgacttgca                                              20

<210> SEQ ID NO 1544
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1544
tctcaggtta caccattagc                                              20

<210> SEQ ID NO 1545
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1545
ccattgtgaa gatatgacag                                              20

<210> SEQ ID NO 1546
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1546
cactgtcctt tatcttgatt                                              20

<210> SEQ ID NO 1547
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1547
tttgtaagat aagtttctaa                                              20

<210> SEQ ID NO 1548
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1548
```
acgaggtgta aggccagatg                                              20

<210> SEQ ID NO 1549
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1549
ggtggcaaag gcaaagagtt                                              20

<210> SEQ ID NO 1550
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1550
aaaagactga aatctgggag                                              20

<210> SEQ ID NO 1551
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1551
tcctcaggag atgcttgaaa                                              20

<210> SEQ ID NO 1552
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1552
tgaagtaaat gtacacaggc                                              20

<210> SEQ ID NO 1553
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1553
accacattca agtgctggaa                                              20

<210> SEQ ID NO 1554
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1554
gctatccaaa gagttatcta                                              20

<210> SEQ ID NO 1555
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 1555
tacactcatc aagtaagaag                                              20

<210> SEQ ID NO 1556
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1556
ggcaaagttg taagtggcag                                              20

<210> SEQ ID NO 1557
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1557
gagtacacaa ctaattaaca                                              20

<210> SEQ ID NO 1558
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1558
taacctttat gttaaaccta                                              20

<210> SEQ ID NO 1559
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1559
taacccactc acctcagctg                                              20

<210> SEQ ID NO 1560
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1560
ttcagaatag ctgtacccac                                              20

<210> SEQ ID NO 1561
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1561
tcaacagaac caatgtgact                                              20
```

<210> SEQ ID NO 1562
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1562
tgttatagat cttgcccatt        20

<210> SEQ ID NO 1563
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1563
tcaactagcc aatttttaat        20

<210> SEQ ID NO 1564
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1564
aatctcagtc agtctgtcca        20

<210> SEQ ID NO 1565
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1565
aaaccacagg gttgtcatgg        20

<210> SEQ ID NO 1566
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1566
ttatgttatt aaatcaaaac        20

<210> SEQ ID NO 1567
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1567
attgctgaaa ccactttggg        20

<210> SEQ ID NO 1568
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 1568
gcagcctgga agcttatctt                                                20

<210> SEQ ID NO 1569
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1569
aagtaaggtt ggctgagtta                                                20

<210> SEQ ID NO 1570
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1570
agggagtgag aagatgctga                                                20

<210> SEQ ID NO 1571
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1571
ttttcctgga agcttaccaa                                                20

<210> SEQ ID NO 1572
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1572
acatccattt ttcctctatt                                                20

<210> SEQ ID NO 1573
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1573
tgaacaatat ttgggctttg                                                20

<210> SEQ ID NO 1574
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1574
acacaccaag ataacattgc                                                20

```
<210> SEQ ID NO 1575
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1575
gaagcaaaat gactaaaaga                                                  20

<210> SEQ ID NO 1576
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1576
tcacatttcc agtctaagta                                                  20

<210> SEQ ID NO 1577
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1577
caaagacatt ccttctctgt                                                  20

<210> SEQ ID NO 1578
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1578
ttaatgtcca attttcctag                                                  20

<210> SEQ ID NO 1579
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1579
acacgactca tttaaaccat                                                  20

<210> SEQ ID NO 1580
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1580
tcctcaggga tttcatcccc                                                  20

<210> SEQ ID NO 1581
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 1581
atatatttgg ccctataga                                              20

<210> SEQ ID NO 1582
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1582
attaaaacca atcagacttt                                             20

<210> SEQ ID NO 1583
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1583
aaaagaactg tagtacaaat                                             20

<210> SEQ ID NO 1584
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1584
gatcagatta ctcaaattga                                             20

<210> SEQ ID NO 1585
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1585
gaaatgtgca tcattctaaa                                             20

<210> SEQ ID NO 1586
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1586
tgtgagattg acccagaatc                                             20

<210> SEQ ID NO 1587
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1587
gcacaatgag cacactacat                                             20

<210> SEQ ID NO 1588
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 1588
gcatgaaaca tctttctggc                                                  20

<210> SEQ ID NO 1589
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1589
tgttatgtga tctatatcag                                                  20

<210> SEQ ID NO 1590
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1590
ctatgaatgc ctctgtgcac                                                  20

<210> SEQ ID NO 1591
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1591
atgaaggaaa cactttcagt                                                  20

<210> SEQ ID NO 1592
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1592
acataagtga ggtatacacc                                                  20

<210> SEQ ID NO 1593
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1593
cccatttcta gcaggaacca                                                  20

<210> SEQ ID NO 1594
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1594
```

-continued attccagaaa ttgatcttcc                                              20

<210> SEQ ID NO 1595
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1595
aaagagagac cttaatcact                                              20

<210> SEQ ID NO 1596
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1596
cgtaatttat gactgcaaag                                              20

<210> SEQ ID NO 1597
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1597
aacaagtatc aagtgtcttt                                              20

<210> SEQ ID NO 1598
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1598
cagtcataat caaagaatta                                              20

<210> SEQ ID NO 1599
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1599
gtaacagcca ctgttctcag                                              20

<210> SEQ ID NO 1600
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1600
atcattttcc attagctaga                                              20

<210> SEQ ID NO 1601
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 1601
agagagacca gaatgaattc                                                    20

<210> SEQ ID NO 1602
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1602
ttgtacaaag catcccacaa                                                    20

<210> SEQ ID NO 1603
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1603
agatccttgc tttgaccccc                                                    20

<210> SEQ ID NO 1604
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1604
caactgagtc tcatttcatt                                                    20

<210> SEQ ID NO 1605
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1605
tcttattgtt tttctgacat                                                    20

<210> SEQ ID NO 1606
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1606
gttaaaattg caattctata                                                    20

<210> SEQ ID NO 1607
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1607
tacttgtaga aaatcccaat                                                    20
```

<210> SEQ ID NO 1608
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1608
tgatgcaacc ccaaataagt                                               20

<210> SEQ ID NO 1609
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1609
tgaataagca ggttgtgaca                                               20

<210> SEQ ID NO 1610
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1610
attcaccaaa tctgtttctg                                               20

<210> SEQ ID NO 1611
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1611
agacctaata ttttcaacta                                               20

<210> SEQ ID NO 1612
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1612
cccaaagttg gaaattctct                                               20

<210> SEQ ID NO 1613
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1613
ttattgtttt tctgacattc                                               20

<210> SEQ ID NO 1614
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1614
atggataata ccccatgaaa                                               20

<210> SEQ ID NO 1615
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1615
tggaagtacc ctttgagaag                                               20

<210> SEQ ID NO 1616
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1616
tctgttctca tgtaagctag                                               20

<210> SEQ ID NO 1617
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1617
gtcataatca aagaattatt                                               20

<210> SEQ ID NO 1618
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1618
gaagtaaatg tacacaggca                                               20

<210> SEQ ID NO 1619
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1619
tatgttatta aatcaaaaca                                               20

<210> SEQ ID NO 1620
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1620
aagagagacc ttaatcactg                                               20

<210> SEQ ID NO 1621

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1621
acctaatatt ttcaactaac                                               20

<210> SEQ ID NO 1622
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1622
aaccacaggg ttgtcatggt                                               20

<210> SEQ ID NO 1623
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1623
ccatttctag caggaaccag                                               20

<210> SEQ ID NO 1624
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1624
cacactacat tcacagggca                                               20

<210> SEQ ID NO 1625
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1625
aacctttatg ttaaacctaa                                               20

<210> SEQ ID NO 1626
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1626
caactagcca atttttaata                                               20

<210> SEQ ID NO 1627
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1627
```
agaccttcaa atcacctacg                                              20

<210> SEQ ID NO 1628
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1628
ccttgctttg accccttct                                               20

<210> SEQ ID NO 1629
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1629
aaagactgaa atctgggagc                                              20

<210> SEQ ID NO 1630
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1630
cctcagggat ttcatcccct                                              20

<210> SEQ ID NO 1631
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1631
gcaaagttgt aagtggcagc                                              20

<210> SEQ ID NO 1632
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1632
acttgtagaa aatcccaata                                              20

<210> SEQ ID NO 1633
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1633
ttaaaattgc aattctatat                                              20

<210> SEQ ID NO 1634
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 1634
aacccactca cctcagctgt                                              20

<210> SEQ ID NO 1635
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1635
atttacttgc caagatcatt                                              20

<210> SEQ ID NO 1636
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1636
cacagcccat tttcttgata                                              20

<210> SEQ ID NO 1637
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1637
ttgtaagata agtttctaaa                                              20

<210> SEQ ID NO 1638
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1638
acaatatttg ggctttgcca                                              20

<210> SEQ ID NO 1639
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1639
caggtcagtc tcccaccatt                                              20

<210> SEQ ID NO 1640
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1640
gcatcccaca aaactcatgc                                              20
```

<210> SEQ ID NO 1641
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1641
ttattgttac ttgattctca                                          20

<210> SEQ ID NO 1642
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1642
ctatccaaag agttatctat                                          20

<210> SEQ ID NO 1643
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1643
aatgtgcatc attctaaaac                                          20

<210> SEQ ID NO 1644
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1644
acagccactg ttctcagacg                                          20

<210> SEQ ID NO 1645
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1645
cattgtaggc tgtgtggtta                                          20

<210> SEQ ID NO 1646
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1646
gttatgtgat ctatatcagg                                          20

<210> SEQ ID NO 1647
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 1647
tgaaggaaac actttcagtt                                           20

<210> SEQ ID NO 1648
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1648
agaaccaatg tgacttacac                                           20

<210> SEQ ID NO 1649
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1649
ggagtgagaa gatgctgaca                                           20

<210> SEQ ID NO 1650
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1650
tgactgcaaa gtacttggca                                           20

<210> SEQ ID NO 1651
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1651
acaagtatca agtgtctttt                                           20

<210> SEQ ID NO 1652
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1652
tttcctggaa gcttaccaac                                           20

<210> SEQ ID NO 1653
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1653
gaataagcag gttgtgacag                                           20

-continued

```
<210> SEQ ID NO 1654
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1654
cattcctttg tgacttgcag                                           20

<210> SEQ ID NO 1655
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1655
atgaaacatc tttctggcac                                           20

<210> SEQ ID NO 1656
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1656
gggaaaagaa caacacaact                                           20

<210> SEQ ID NO 1657
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1657
tttatcttga ttggtttctt                                           20

<210> SEQ ID NO 1658
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1658
cacaccaaga taacattgct                                           20

<210> SEQ ID NO 1659
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1659
aagcaaaatg actaaagag                                            20

<210> SEQ ID NO 1660
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 1660
aagaactgta gtacaaatct                                               20

<210> SEQ ID NO 1661
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1661
gcctggaagc ttatcttgta                                               20

<210> SEQ ID NO 1662
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1662
tgtgtttaag ctgctatctt                                               20

<210> SEQ ID NO 1663
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1663
ttcaccaaat ctgtttctgc                                               20

<210> SEQ ID NO 1664
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1664
taatgtccaa ttttcctagt                                               20

<210> SEQ ID NO 1665
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1665
ccatttttcc tctattttct                                               20

<210> SEQ ID NO 1666
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1666
acactcatca agtaagaaga                                               20

<210> SEQ ID NO 1667
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 1667
cctcaggaga tgcttgaaaa                                          20

<210> SEQ ID NO 1668
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1668
agtacacaac taattaacag                                          20

<210> SEQ ID NO 1669
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1669
tcagtcagtc tgtccaagca                                          20

<210> SEQ ID NO 1670
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1670
cattttccat tagctagaaa                                          20

<210> SEQ ID NO 1671
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1671
atcagattac tcaaattgag                                          20

<210> SEQ ID NO 1672
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1672
cgaggtgtaa ggccagatgc                                          20

<210> SEQ ID NO 1673
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1673
```
aaagacattc cttctctgta                                               20

<210> SEQ ID NO 1674
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1674
ttccagaaat tgatcttcct                                               20

<210> SEQ ID NO 1675
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1675
tctaaagttc cttccaatcc                                               20

<210> SEQ ID NO 1676
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1676
atatttggcc cctatagatg                                               20

<210> SEQ ID NO 1677
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1677
gtggcaaagg caaagagtta                                               20

<210> SEQ ID NO 1678
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1678
gagattgacc cagaatcctt                                               20

<210> SEQ ID NO 1679
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1679
ttaaaaccaa tcagactttt                                               20

<210> SEQ ID NO 1680
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 1680
cataagtgag gtatacacca                                               20

<210> SEQ ID NO 1681
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1681
ttgttattac tcagatcgct                                               20

<210> SEQ ID NO 1682
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1682
acatttccag tctaagtaca                                               20

<210> SEQ ID NO 1683
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1683
cattgtgaag atatgacaga                                               20

<210> SEQ ID NO 1684
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1684
gagagaccag aatgaattcc                                               20

<210> SEQ ID NO 1685
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1685
ccacattcaa gtgctggaaa                                               20

<210> SEQ ID NO 1686
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1686
gatgcaaccc caaataagta                                               20
```

<210> SEQ ID NO 1687
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1687
gtaaggttgg ctgagttagg                                          20

<210> SEQ ID NO 1688
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1688
acactacatt cacagggcac                                          20

<210> SEQ ID NO 1689
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1689
ttgtattaat tacttaggct                                          20

<210> SEQ ID NO 1690
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1690
agattgaccc agaatcctta                                          20

<210> SEQ ID NO 1691
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1691
gccactgttc tcagacgaca                                          20

<210> SEQ ID NO 1692
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1692
ggatagtcaa atcatgtgga                                          20

<210> SEQ ID NO 1693
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1693
ttatgtgatc tatatcagga                                          20

<210> SEQ ID NO 1694
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1694
aagactgaaa tctgggagct                                          20

<210> SEQ ID NO 1695
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1695
tgtaagataa gtttctaaaa                                          20

<210> SEQ ID NO 1696
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1696
ctaaagttcc ttccaatccc                                          20

<210> SEQ ID NO 1697
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1697
gtacacaact aattaacaga                                          20

<210> SEQ ID NO 1698
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1698
ctcaggagat gcttgaaaat                                          20

<210> SEQ ID NO 1699
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1699
gaaggaaaca ctttcagttg                                          20

<210> SEQ ID NO 1700

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1700
attgtgaaga tatgacagag                                               20

<210> SEQ ID NO 1701
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1701
gaggtgtaag gccagatgcc                                               20

<210> SEQ ID NO 1702
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1702
tcaccaaatc tgtttctgca                                               20

<210> SEQ ID NO 1703
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1703
aagtatcaag tgtcttttg                                                20

<210> SEQ ID NO 1704
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1704
agaactgtag tacaaatctt                                               20

<210> SEQ ID NO 1705
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1705
caggttacac cattagccac                                               20

<210> SEQ ID NO 1706
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1706
```
tcagattact caaattgaga                                                20

<210> SEQ ID NO 1707
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1707
accacagggt tgtcatggta                                                20

<210> SEQ ID NO 1708
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1708
taaaattgca attctatatc                                                20

<210> SEQ ID NO 1709
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1709
gtaaatgtac acaggcacag                                                20

<210> SEQ ID NO 1710
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1710
gactgcaaag tacttggcaa                                                20

<210> SEQ ID NO 1711
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1711
gctccactac agctcaaagc                                                20

<210> SEQ ID NO 1712
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1712
ttctcatgta agctagtttc                                                20

<210> SEQ ID NO 1713
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 1713
cttgctttga ccccttctc                                                    20

<210> SEQ ID NO 1714
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1714
catttctagc aggaaccagc                                                   20

<210> SEQ ID NO 1715
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1715
ccaaagttgg aaattctctt                                                   20

<210> SEQ ID NO 1716
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1716
agtgaggtat acaccagagc                                                   20

<210> SEQ ID NO 1717
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1717
tggctgagtt agggcttcag                                                   20

<210> SEQ ID NO 1718
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1718
tttcaactaa caattcaggc                                                   20

<210> SEQ ID NO 1719
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1719
attttccatt agctagaaag                                                   20
```

<210> SEQ ID NO 1720
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1720
agacattcct tctctgtacc                                              20

<210> SEQ ID NO 1721
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1721
acaccaagat aacattgcta                                              20

<210> SEQ ID NO 1722
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1722
tctatcttta cctaaagcta                                              20

<210> SEQ ID NO 1723
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1723
tgttattaaa tcaaaacaaa                                              20

<210> SEQ ID NO 1724
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1724
ggaaaagaac aacacaactc                                              20

<210> SEQ ID NO 1725
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1725
atctctaatt atcctggctg                                              20

<210> SEQ ID NO 1726
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 1726
gaaacatctt tctggcacta					20

<210> SEQ ID NO 1727
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1727
acctttatgt taaacctaac					20

<210> SEQ ID NO 1728
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1728
attgtttttc tgacattctt					20

<210> SEQ ID NO 1729
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1729
agagaccaga atgaattcca					20

<210> SEQ ID NO 1730
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1730
tcataatcaa agaattattc					20

<210> SEQ ID NO 1731
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1731
atgtccaatt ttcctagttt					20

<210> SEQ ID NO 1732
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1732
tatttggccc ctatagatgg					20

```
<210> SEQ ID NO 1733
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1733
cctttgtgac ttgcagttgg                                           20

<210> SEQ ID NO 1734
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1734
tggataatac cccatgaaat                                           20

<210> SEQ ID NO 1735
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1735
aactagccaa tttttaatat                                           20

<210> SEQ ID NO 1736
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1736
ggcaaaggca aagagttaag                                           20

<210> SEQ ID NO 1737
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1737
gagagacctt aatcactgca                                           20

<210> SEQ ID NO 1738
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1738
caatatttgg gctttgccac                                           20

<210> SEQ ID NO 1739
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 1739
cttgtagaaa atcccaatag                                              20

<210> SEQ ID NO 1740
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1740
atgtgcatca ttctaaaaca                                              20

<210> SEQ ID NO 1741
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1741
ggaagtaccc tttgagaaga                                              20

<210> SEQ ID NO 1742
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1742
tacttgccaa gatcattcaa                                              20

<210> SEQ ID NO 1743
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1743
tgttacttga ttctcacaac                                              20

<210> SEQ ID NO 1744
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1744
taaaaccaat cagactttt                                               20

<210> SEQ ID NO 1745
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1745
cactcatcaa gtaagaagag                                              20

<210> SEQ ID NO 1746
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 1746
tcttgattgg tttcttacaa                                            20

<210> SEQ ID NO 1747
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1747
gtgtttaagc tgctatcttt                                            20

<210> SEQ ID NO 1748
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1748
tgaggaagta atattcaaca                                            20

<210> SEQ ID NO 1749
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1749
acaggttaag atactagatt                                            20

<210> SEQ ID NO 1750
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1750
caaagttgta agtggcagca                                            20

<210> SEQ ID NO 1751
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1751
tggaagctta tcttgtatac                                            20

<210> SEQ ID NO 1752
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1752
```

```
tccagtctaa gtacagactg                                              20

<210> SEQ ID NO 1753
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1753
tcccacaaaa ctcatgcttt                                              20

<210> SEQ ID NO 1754
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1754
gctgcacttg attattttag                                              20

<210> SEQ ID NO 1755
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1755
ttcctggaag cttaccaact                                              20

<210> SEQ ID NO 1756
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1756
gagtgagaag atgctgacaa                                              20

<210> SEQ ID NO 1757
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1757
agcaaaatga ctaaagagg                                               20

<210> SEQ ID NO 1758
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1758
tgcaacccca aataagtaat                                              20

<210> SEQ ID NO 1759
<211> LENGTH: 20
<212> TYPE: DNA
<213> ORGANISM: Artificial sequence
```

```
<220> FEATURE:
<223> OTHER INFORMATION: Synthetic oligonucleotide

<400> SEQUENCE: 1759
tatccaaaga gttatctatc                                               20

<210> SEQ ID NO 1760
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1760
tgtccaagca agaatcagat                                               20

<210> SEQ ID NO 1761
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1761
gtgacttaca cagatccagg                                               20

<210> SEQ ID NO 1762
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1762
ccaccatttc ctcctctctc                                               20

<210> SEQ ID NO 1763
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1763
ggttaagata ctagattcag                                               20

<210> SEQ ID NO 1764
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1764
cccacaaaac tcatgctttc                                               20

<210> SEQ ID NO 1765
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1765
ttgtgaagat atgacagagg                                               20
```

<210> SEQ ID NO 1766
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1766
tactgcaatt gttgaacagc                                        20

<210> SEQ ID NO 1767
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1767
gagaccttaa tcactgcaag                                        20

<210> SEQ ID NO 1768
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1768
atttctagca ggaaccagct                                        20

<210> SEQ ID NO 1769
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1769
gcaaaggcaa agagttaaga                                        20

<210> SEQ ID NO 1770
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1770
ccacagggtt gtcatggtag                                        20

<210> SEQ ID NO 1771
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1771
tctgttttta atgcacaacc                                        20

<210> SEQ ID NO 1772
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 1772
atgtgatcta tatcaggaga                                            20

<210> SEQ ID NO 1773
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1773
cataatcaaa gaattattct                                            20

<210> SEQ ID NO 1774
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1774
tgtccaattt tcctagttta                                            20

<210> SEQ ID NO 1775
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1775
cactacattc acagggcact                                            20

<210> SEQ ID NO 1776
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1776
aaatgtacac aggcacagca                                            20

<210> SEQ ID NO 1777
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1777
actagccaat ttttaatatc                                            20

<210> SEQ ID NO 1778
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1778
atcaaaacaa aacacaaggt                                            20

<210> SEQ ID NO 1779
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1779
gtgtcttaaa gtgctaagag                                              20

<210> SEQ ID NO 1780
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1780
aaaattgcaa ttctatatca                                              20

<210> SEQ ID NO 1781
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1781
gaactgtagt acaaatcttt                                              20

<210> SEQ ID NO 1782
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1782
gagaccagaa tgaattccat                                              20

<210> SEQ ID NO 1783
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1783
ggattctacc aacaatcagg                                              20

<210> SEQ ID NO 1784
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1784
ctccactaca gctcaaagca                                              20

<210> SEQ ID NO 1785
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1785
```
taataacatt tctcaatgca                                              20

<210> SEQ ID NO 1786
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1786
accaaatctg tttctgcaaa                                              20

<210> SEQ ID NO 1787
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1787
atccaaagag ttatctatcc                                              20

<210> SEQ ID NO 1788
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1788
tgattggttt cttacaaaac                                              20

<210> SEQ ID NO 1789
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1789
ggaaccttat tctcttcctt                                              20

<210> SEQ ID NO 1790
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1790
caccaagata acattgctaa                                              20

<210> SEQ ID NO 1791
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1791
tgtgcatcat tctaaaacaa                                              20

<210> SEQ ID NO 1792
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 1792
accttcaaat cacctacgat                                                  20

<210> SEQ ID NO 1793
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1793
ggataatacc ccatgaaatg                                                  20

<210> SEQ ID NO 1794
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1794
aggtgtaagg ccagatgccc                                                  20

<210> SEQ ID NO 1795
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1795
acaaagaccc ttgtgctctg                                                  20

<210> SEQ ID NO 1796
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1796
tttttgtaaa gctcttacat                                                  20

<210> SEQ ID NO 1797
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1797
tctttaccta aagctacaaa                                                  20

<210> SEQ ID NO 1798
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1798
tacacaacta attaacagaa                                                  20
```

<210> SEQ ID NO 1799
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1799
ggaagcttat cttgtatact                                              20

<210> SEQ ID NO 1800
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1800
acattccttc tctgtacctg                                              20

<210> SEQ ID NO 1801
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1801
ttcaactaac aattcaggca                                              20

<210> SEQ ID NO 1802
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1802
ggttacacca ttagccacca                                              20

<210> SEQ ID NO 1803
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1803
gcaaaatgac taaaagaggt                                              20

<210> SEQ ID NO 1804
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1804
agactgaaat ctgggagcta                                              20

<210> SEQ ID NO 1805
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 1805
actcatcaag taagaagagg                                              20

<210> SEQ ID NO 1806
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1806
agtacccttt gagaagaaat                                              20

<210> SEQ ID NO 1807
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1807
gcaaccccaa ataagtaata                                              20

<210> SEQ ID NO 1808
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1808
ctgcaaagta cttggcaaca                                              20

<210> SEQ ID NO 1809
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1809
gacttacaca gatccaggtt                                              20

<210> SEQ ID NO 1810
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1810
ctttatgtta aacctaactc                                              20

<210> SEQ ID NO 1811
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1811
aagttgtaag tggcagcaat                                              20

```
<210> SEQ ID NO 1812
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1812
gtaagataag tttctaaaag                                                    20

<210> SEQ ID NO 1813
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1813
gcccctatag atggcaagag                                                    20

<210> SEQ ID NO 1814
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1814
ttgctttgac cccttctcc                                                     20

<210> SEQ ID NO 1815
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1815
ggctgagtta gggcttcagt                                                    20

<210> SEQ ID NO 1816
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1816
cagacgacaa caggcttgca                                                    20

<210> SEQ ID NO 1817
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1817
ttttccatta gctagaaaga                                                    20

<210> SEQ ID NO 1818
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 1818
aaggaaacac tttcagttga                                            20

<210> SEQ ID NO 1819
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1819
acttgccaag atcattcaaa                                            20

<210> SEQ ID NO 1820
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1820
cagattactc aaattgagat                                            20

<210> SEQ ID NO 1821
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1821
ctcatgtaag ctagtttcct                                            20

<210> SEQ ID NO 1822
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1822
tagtcaaatc atgtggacaa                                            20

<210> SEQ ID NO 1823
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1823
ttgtagaaaa tcccaataga                                            20

<210> SEQ ID NO 1824
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1824
gctaaagttt ttgaaactta                                            20

<210> SEQ ID NO 1825
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 1825
gtgaggtata caccagagcg                                                 20

<210> SEQ ID NO 1826
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1826
tcaggagatg cttgaaaatt                                                 20

<210> SEQ ID NO 1827
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1827
agtgagaaga tgctgacaac                                                 20

<210> SEQ ID NO 1828
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1828
aaaaccaatc agactttttt                                                 20

<210> SEQ ID NO 1829
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1829
gttacttgat tctcacaacc                                                 20

<210> SEQ ID NO 1830
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1830
gacccagaat ccttactttg                                                 20

<210> SEQ ID NO 1831
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1831
```
tgtgacttgc agttgggaag								20

<210> SEQ ID NO 1832
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1832
tgtttttctg acattctttt								20

<210> SEQ ID NO 1833
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1833
tccaagcaag aatcagattt								20

<210> SEQ ID NO 1834
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1834
tgtattaatt acttaggctt								20

<210> SEQ ID NO 1835
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1835
gaaaagaaca acacaactct								20

<210> SEQ ID NO 1836
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1836
acttgattat tttagtcagt								20

<210> SEQ ID NO 1837
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1837
tcctggaagc ttaccaactg								20

<210> SEQ ID NO 1838
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 1838
gttgtaagtg gcagcaatca                                                 20

<210> SEQ ID NO 1839
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1839
aaaccaatca gactttttt                                                  20

<210> SEQ ID NO 1840
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1840
ggtatacacc agagcgagca                                                 20

<210> SEQ ID NO 1841
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1841
cacagggttg tcatggtagc                                                 20

<210> SEQ ID NO 1842
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1842
ccttcaaatc acctacgatg                                                 20

<210> SEQ ID NO 1843
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1843 tgttttaat gcacaaccta                                                  20

<210> SEQ ID NO 1844
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1844
tgattatttt agtcagtgtc                                                 20
```

<210> SEQ ID NO 1845
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1845
agattactca aattgagatt					20

<210> SEQ ID NO 1846
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1846
tcaaaacaaa acacaaggta					20

<210> SEQ ID NO 1847
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1847
tctttgggac tctgactcca					20

<210> SEQ ID NO 1848
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1848
tgcatcattc taaaacaaat					20

<210> SEQ ID NO 1849
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1849
aagctacaaa cttctctttt					20

<210> SEQ ID NO 1850
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1850
tgtggttaga gcctcgctat					20

<210> SEQ ID NO 1851
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 1851
aaagaacaac acaactcttt                                               20

<210> SEQ ID NO 1852
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1852
ttaatcaatc agtacttgct                                               20

<210> SEQ ID NO 1853
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1853
caggagatgc ttgaaaattc                                               20

<210> SEQ ID NO 1854
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1854
aactgtagta caaatctttc                                               20

<210> SEQ ID NO 1855
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1855
gttaagatac tagattcagc                                               20

<210> SEQ ID NO 1856
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1856
gattggtttc ttacaaaaca                                               20

<210> SEQ ID NO 1857
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1857
gttacaccat tagccaccag                                               20

<210> SEQ ID NO 1858
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1858 acattcttttt ttcttctatc                                              20

<210> SEQ ID NO 1859
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1859
tggaagctta ccaactgaat                                               20

<210> SEQ ID NO 1860
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1860
gtgagaagat gctgacaaca                                               20

<210> SEQ ID NO 1861
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1861
actacattca cagggcactg                                               20

<210> SEQ ID NO 1862
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1862
gattctacca acaatcagga                                               20

<210> SEQ ID NO 1863
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1863
accaagataa cattgctaag                                               20

<210> SEQ ID NO 1864
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1864
```
ataacatttc tcaatgcaac                                                    20

<210> SEQ ID NO 1865
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1865
ggaacctttg aaaggtgagg                                                    20

<210> SEQ ID NO 1866
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1866
agacgacaac aggcttgcag                                                    20

<210> SEQ ID NO 1867
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1867
gaatccttac tttgtttcat                                                    20

<210> SEQ ID NO 1868
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1868
gtaaggccag atgccccctt                                                    20

<210> SEQ ID NO 1869
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1869
aaaccaggtt ccagggctct                                                    20

<210> SEQ ID NO 1870
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1870
tttctagcag gaaccagcta                                                    20

<210> SEQ ID NO 1871
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 1871
gctgagttag ggcttcagta                                              20

<210> SEQ ID NO 1872
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1872
ctcatcaagt aagaagaggg                                              20

<210> SEQ ID NO 1873
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1873
tgtagaaaat cccaatagat                                              20

<210> SEQ ID NO 1874
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1874
ataatcaaag aattattctc                                              20

<210> SEQ ID NO 1875
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1875
gtaccctttg agaagaaatt                                              20

<210> SEQ ID NO 1876
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1876
agacccttgt gctctgcaca                                              20

<210> SEQ ID NO 1877
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1877
tcaactaaca attcaggcag                                              20

<210> SEQ ID NO 1878
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1878
gaatcagatt ttagattcta                                      20

<210> SEQ ID NO 1879
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1879
tctctgtacc tgagcatctt                                      20

<210> SEQ ID NO 1880
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1880
caaccccaaa taagtaataa                                      20

<210> SEQ ID NO 1881
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1881
agaccagaat gaattccatt                                      20

<210> SEQ ID NO 1882
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1882
ttttgtaaag ctcttacatc                                      20

<210> SEQ ID NO 1883
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1883
tttatgttaa acctaactct                                      20

<210> SEQ ID NO 1884
<211> LENGTH: 20
<212> TYPE: DNA
<213> ORGANISM: Artificial sequence
<220> FEATURE:

```
<223> OTHER INFORMATION: Synthetic oligonucleotide

<400> SEQUENCE: 1884
cttggatttt tgtattcaag                                               20

<210> SEQ ID NO 1885
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1885
cccctataga tggcaagagg                                               20

<210> SEQ ID NO 1886
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1886
ctagccaatt tttaatatca                                               20

<210> SEQ ID NO 1887
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1887
caaaggcaaa gagttaagat                                               20

<210> SEQ ID NO 1888
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1888
tttccattag ctagaaagaa                                               20

<210> SEQ ID NO 1889
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1889
ggaaacactt tcagttgatt                                               20

<210> SEQ ID NO 1890
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1890
gaagcttatc ttgtatactg                                               20
```

```
<210> SEQ ID NO 1891
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1891
ccaaatctgt ttctgcaaag                                               20

<210> SEQ ID NO 1892
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1892
tacttgattc tcacaaccct                                               20

<210> SEQ ID NO 1893
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1893
aaattgcaat tctatatcag                                               20

<210> SEQ ID NO 1894
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1894
tgctttgacc cccttctccc                                               20

<210> SEQ ID NO 1895
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1895
gcaaagtact tggcaacatt                                               20

<210> SEQ ID NO 1896
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1896
actgcaattg ttgaacagca                                               20

<210> SEQ ID NO 1897
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 1897
tccactacag ctcaaagcaa                                               20

<210> SEQ ID NO 1898
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1898
gataataccc catgaaatga                                               20

<210> SEQ ID NO 1899
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1899
tgacttagag tcatagggtg                                               20

<210> SEQ ID NO 1900
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1900
aggtcatttg gaactgcagg                                               20

<210> SEQ ID NO 1901
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1901
gtgatctata tcaggagaaa                                               20

<210> SEQ ID NO 1902
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1902
aaaatgacta aaagaggtac                                               20

<210> SEQ ID NO 1903
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1903
gtcaaatcat gtggacaagg                                               20

<210> SEQ ID NO 1904
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 1904
tccaaagagt tatctatcct                                              20

<210> SEQ ID NO 1905
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1905
taagataagt ttctaaaagt                                              20

<210> SEQ ID NO 1906
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1906
gactgaaatc tgggagctat                                              20

<210> SEQ ID NO 1907
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1907
gcacacaaga agtcacaggc                                              20

<210> SEQ ID NO 1908
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1908
tccaattttc ctagtttaaa                                              20

<210> SEQ ID NO 1909
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1909
acacaactaa ttaacagaaa                                              20

<210> SEQ ID NO 1910
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1910
```

```
acttacacag atccaggttc                                               20

<210> SEQ ID NO 1911
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1911
tgtgaagata tgacagaggc                                               20

<210> SEQ ID NO 1912
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1912
gtgacttgca gttgggaagt                                               20

<210> SEQ ID NO 1913
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1913
agaccttaat cactgcaaga                                               20

<210> SEQ ID NO 1914
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1914
tcatgtaagc tagtttcctt                                               20

<210> SEQ ID NO 1915
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1915
caaaacaaaa cacaaggtac                                               20

<210> SEQ ID NO 1916
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1916
caactaacaa ttcaggcagc                                               20

<210> SEQ ID NO 1917
<211> LENGTH: 20
<212> TYPE: DNA
<213> ORGANISM: Artificial sequence
```

```
<220> FEATURE:
<223> OTHER INFORMATION: Synthetic oligonucleotide

<400> SEQUENCE: 1917
gaacctttga aaggtgaggc                                               20

<210> SEQ ID NO 1918
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1918
tagccaattt ttaatatcat                                               20

<210> SEQ ID NO 1919
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1919
cacaactaat taacagaaaa                                               20

<210> SEQ ID NO 1920
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1920
accaggttcc agggctctcc                                               20

<210> SEQ ID NO 1921
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1921
caattgttga acagcagtgc                                               20

<210> SEQ ID NO 1922
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1922
acagggttgt catggtagct                                               20

<210> SEQ ID NO 1923
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1923
tgaaatctgg gagctattca                                               20
```

<210> SEQ ID NO 1924
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1924
tcatcaagta agaagagggc                                               20

<210> SEQ ID NO 1925
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1925
gtagaaaatc ccaatagatt                                               20

<210> SEQ ID NO 1926
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1926
ccactacagc tcaaagcaag                                               20

<210> SEQ ID NO 1927
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1927
acgacaacag gcttgcagac                                               20

<210> SEQ ID NO 1928
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1928
acacagatcc aggttcatca                                               20

<210> SEQ ID NO 1929
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1929
ttccattagc tagaaagaac                                               20

<210> SEQ ID NO 1930
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 1930
ctgagttagg gcttcagtag                                              20

<210> SEQ ID NO 1931
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1931
gaactgtttc ttgcaacagc                                              20

<210> SEQ ID NO 1932
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1932
tgagaagatg ctgacaacac                                              20

<210> SEQ ID NO 1933
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1933
ttggtttctt acaaaacatt                                              20

<210> SEQ ID NO 1934
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1934
gaccttaatc actgcaagac                                              20

<210> SEQ ID NO 1935
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1935
acttagagtc atagggtgct                                              20

<210> SEQ ID NO 1936
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1936
caaagtactt ggcaacatta                                              20

<210> SEQ ID NO 1937
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1937
acttgcagtt gggaagtcat                                              20

<210> SEQ ID NO 1938
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1938
tttgtaaagc tcttacatct                                              20

<210> SEQ ID NO 1939
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1939
gcatcattct aaaacaaatc                                              20

<210> SEQ ID NO 1940
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1940
ccaaagagtt atctatcctg                                              20

<210> SEQ ID NO 1941
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1941
acttgattct cacaaccctg                                              20

<210> SEQ ID NO 1942
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1942
tgtttcctat actccccact                                              20

<210> SEQ ID NO 1943
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1943
```
aagatactag attcagccta    20

<210> SEQ ID NO 1944
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1944
aaatgactaa aagaggtaca    20

<210> SEQ ID NO 1945
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1945
ccaattttcc tagtttaaaa    20

<210> SEQ ID NO 1946
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1946
aaatctgttt ctgcaaaggc    20

<210> SEQ ID NO 1947
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1947
gctttgaccc ccttctccca    20

<210> SEQ ID NO 1948
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1948
gtgaagatat gacagaggcc    20

<210> SEQ ID NO 1949
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1949
gattactcaa attgagattc    20

<210> SEQ ID NO 1950
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 1950
tctaccaaca atcaggatcc                                                    20

<210> SEQ ID NO 1951
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1951
ttatcttgta tactggtttg                                                    20

<210> SEQ ID NO 1952
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1952
tacattcaca gggcactgta                                                    20

<210> SEQ ID NO 1953
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1953 tttttcttc tatcttcagt                                                     20

<210> SEQ ID NO 1954
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1954
caattgtagc cggctggcta                                                    20

<210> SEQ ID NO 1955
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1955
tctgcacaca ttactctgag                                                    20

<210> SEQ ID NO 1956
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1956
ttctagcagg aaccagctat                                                    20

<210> SEQ ID NO 1957
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1957
ttatgttaaa cctaactctt						20

<210> SEQ ID NO 1958
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1958
aaggccagat gcccccttcg						20

<210> SEQ ID NO 1959
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1959
gagatgcttg aaaattcaat						20

<210> SEQ ID NO 1960
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1960
aaccccaaat aagtaataaa						20

<210> SEQ ID NO 1961
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1961
aaaggcaaag agttaagatg						20

<210> SEQ ID NO 1962
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1962
ctgacattag ataggattcc						20

<210> SEQ ID NO 1963
<211> LENGTH: 20
<212> TYPE: DNA
<213> ORGANISM: Artificial sequence
<220> FEATURE:

```
<223> OTHER INFORMATION: Synthetic oligonucleotide

<400> SEQUENCE: 1963
gaaacacttt cagttgatta                                              20

<210> SEQ ID NO 1964
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1964
cacacaagaa gtcacaggct                                              20

<210> SEQ ID NO 1965
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1965
gtggttagag cctcgctatt                                              20

<210> SEQ ID NO 1966
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1966 tacccttga gaagaaatta                                               20

<210> SEQ ID NO 1967
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1967 ataataccc atgaaatgag                                               20

<210> SEQ ID NO 1968
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1968
actgtagtac aaatctttcc                                              20

<210> SEQ ID NO 1969
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1969
aattgcaatt ctatatcaga                                              20
```

```
<210> SEQ ID NO 1970
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1970
cttcaaatca cctacgatga                                           20

<210> SEQ ID NO 1971
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1971
gaccagaatg aattccattt                                           20

<210> SEQ ID NO 1972
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1972
tcagcaattc aaatagcaag                                           20

<210> SEQ ID NO 1973
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1973
ttacaccatt agccaccagc                                           20

<210> SEQ ID NO 1974
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1974
ttttagtcag tgtctccagg                                           20

<210> SEQ ID NO 1975
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1975
tgtaagctag tttccttcta                                           20

<210> SEQ ID NO 1976
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 1976
tgatctatat caggagaaaa					20

<210> SEQ ID NO 1977
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1977
ccctatagat ggcaagagga					20

<210> SEQ ID NO 1978
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1978
aagataagtt tctaaaagtt					20

<210> SEQ ID NO 1979
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1979
taatcaatca gtacttgctg					20

<210> SEQ ID NO 1980
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1980
taatcaaaga attattctcc					20

<210> SEQ ID NO 1981
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1981
ccaagataac attgctaagt					20

<210> SEQ ID NO 1982
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1982
cagattttag attctaactg					20

<210> SEQ ID NO 1983
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 1983
aaccaatcag actttttttt                                            20

<210> SEQ ID NO 1984
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1984
ggttggaaag gaagtctttc                                            20

<210> SEQ ID NO 1985
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1985
gtatacacca gagcgagcac                                            20

<210> SEQ ID NO 1986
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1986
ggaagcttac caactgaata                                            20

<210> SEQ ID NO 1987
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1987
aagaacaaca caactcttta                                            20

<210> SEQ ID NO 1988
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1988
tgtacctgag catctttcct                                            20

<210> SEQ ID NO 1989
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1989
```
ttgtaagtgg cagcaatcat					20

<210> SEQ ID NO 1990
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1990
ggatttttgt attcaagcat					20

<210> SEQ ID NO 1991
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1991
acatttctca atgcaactca					20

<210> SEQ ID NO 1992
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1992
ttactcaaat tgagattcaa					20

<210> SEQ ID NO 1993
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1993
aagctataaa caattcagta					20

<210> SEQ ID NO 1994
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1994
acaccattag ccaccagcaa					20

<210> SEQ ID NO 1995
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1995
ctctccagcc tccttcttcg					20

<210> SEQ ID NO 1996
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 1996
aatctgtttc tgcaaaggca                                                     20

<210> SEQ ID NO 1997
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1997
atcttgtata ctggtttgaa                                                     20

<210> SEQ ID NO 1998
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1998
gtttcttaca aaacatttc                                                      20

<210> SEQ ID NO 1999
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1999
actatcagca agacctggga                                                     20

<210> SEQ ID NO 2000
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2000 taataccca tgaaatgagc                                                      20

<210> SEQ ID NO 2001
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2001
aatgactaaa agaggtacat                                                     20

<210> SEQ ID NO 2002
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2002
cgtctacaca gattctacgc                                                     20
```

<210> SEQ ID NO 2003
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2003
taagctagtt tccttctatt                                           20

<210> SEQ ID NO 2004
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2004
aatcaaagaa ttattctcca                                           20

<210> SEQ ID NO 2005
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2005
caagataaca ttgctaagta                                           20

<210> SEQ ID NO 2006
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2006
acaccagagc gagcacctta                                           20

<210> SEQ ID NO 2007
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2007
aaaacaaaac acaaggtacg                                           20

<210> SEQ ID NO 2008
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2008
tgtaaagctc ttacatctcc                                           20

<210> SEQ ID NO 2009
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 2009
atgatgtaca cattccaatt                                              20

<210> SEQ ID NO 2010
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2010
attgcaattc tatatcagaa                                              20

<210> SEQ ID NO 2011
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2011
acacaagaag tcacaggctc                                              20

<210> SEQ ID NO 2012
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2012
caagggactg tgttgatcct                                              20

<210> SEQ ID NO 2013
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2013
tgtaagtggc agcaatcatg                                              20

<210> SEQ ID NO 2014
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2014
ccagaatgaa ttccattttg                                              20

<210> SEQ ID NO 2015
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2015
accctttgag aagaaattac                                              20

<210> SEQ ID NO 2016
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2016
tctagcagga accagctatg                                              20

<210> SEQ ID NO 2017
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2017
agaacaacac aactctttac                                              20

<210> SEQ ID NO 2018
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2018
tagaaaatcc caatagattc                                              20

<210> SEQ ID NO 2019
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2019
accccaaata agtaataaac                                              20

<210> SEQ ID NO 2020
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2020
catcattcta aaacaaatca                                              20

<210> SEQ ID NO 2021
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2021
ggaagactag gtgaacatgc                                              20

<210> SEQ ID NO 2022
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2022
```
gtttatgtga attcagtaca                                                        20

<210> SEQ ID NO 2023
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2023
gcttcagagg atgtttttgg                                                        20

<210> SEQ ID NO 2024
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2024
attttcctag tttaaaaaac                                                        20

<210> SEQ ID NO 2025
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2025
cttgcagttg ggaagtcatc                                                        20

<210> SEQ ID NO 2026
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2026
tgagttaggg cttcagtagt                                                        20

<210> SEQ ID NO 2027
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2027
tgagaaaaga tccattgggc                                                        20

<210> SEQ ID NO 2028
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2028
tgacattaga taggattcct                                                        20

<210> SEQ ID NO 2029
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 2029
aactaacaat tcaggcagcc                                               20

<210> SEQ ID NO 2030
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2030
tatgttaaac ctaactctta                                               20

<210> SEQ ID NO 2031
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2031
aattgttgaa cagcagtgca                                               20

<210> SEQ ID NO 2032
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2032
gacaacaggc ttgcagacaa                                               20

<210> SEQ ID NO 2033
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2033
gtcatggtag ctgttatcaa                                               20

<210> SEQ ID NO 2034
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2034
ctaccaacaa tcaggatcct                                               20

<210> SEQ ID NO 2035
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2035
gatctatatc aggagaaaat                                               20
```

-continued

<210> SEQ ID NO 2036
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2036
gtaaatcatg aatacagctt                                              20

<210> SEQ ID NO 2037
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2037
ctttgacccc cttctcccag                                              20

<210> SEQ ID NO 2038
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2038
accttaatca ctgcaagact                                              20

<210> SEQ ID NO 2039
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2039
tgaggaagtg gtgattcagt                                              20

<210> SEQ ID NO 2040
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2040
gaaatctggg agctattcag                                              20

<210> SEQ ID NO 2041
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2041
agataagttt ctaaaagttt                                              20

<210> SEQ ID NO 2042
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 2042
aagtacttgg caacattaca                                              20

<210> SEQ ID NO 2043
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2043
caaagagtta tctatcctgt                                              20

<210> SEQ ID NO 2044
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2044
agatgcttga aaattcaatt                                              20

<210> SEQ ID NO 2045
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2045
aaggcaaaga gttaagatgg                                              20

<210> SEQ ID NO 2046
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2046
gtacctgagc atctttcctt                                              20

<210> SEQ ID NO 2047
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2047
cagcaattca aatagcaagc                                              20

<210> SEQ ID NO 2048
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2048
tccattagct agaaagaacg                                              20

<210> SEQ ID NO 2049
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2049
gatttttgta ttcaagcatt                                      20

<210> SEQ ID NO 2050
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2050 tttttaacc caaagttaac                                       20

<210> SEQ ID NO 2051
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2051
gctaagccag ctgggcacca                                      20

<210> SEQ ID NO 2052
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2052
gagaagatgc tgacaacacc                                      20

<210> SEQ ID NO 2053
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2053
agatactaga ttcagcctat                                      20

<210> SEQ ID NO 2054
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2054
gccaattttt aatatcattt                                      20

<210> SEQ ID NO 2055
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 2055
ctgtagtaca aatctttcct                                              20

<210> SEQ ID NO 2056
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2056
tgaagatatg acagaggcca                                              20

<210> SEQ ID NO 2057
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2057
aacactttca gttgattaac                                              20

<210> SEQ ID NO 2058
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2058
tgcacacatt actctgagta                                              20

<210> SEQ ID NO 2059
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2059
ttcaaatcac ctacgatgac                                              20

<210> SEQ ID NO 2060
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2060
acaactaatt aacagaaaaa                                              20

<210> SEQ ID NO 2061
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2061
ttctatcttc agtggtaata                                              20

<210> SEQ ID NO 2062
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 2062
ggaaaggaag tctttctatg                                           20

<210> SEQ ID NO 2063
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2063
catcaagtaa gaagagggcc                                           20

<210> SEQ ID NO 2064
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2064
tcaatcagta cttgctgagc                                           20

<210> SEQ ID NO 2065
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2065
cttagagtca tagggtgctt                                           20

<210> SEQ ID NO 2066
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2066
cctatagatg gcaagaggac                                           20

<210> SEQ ID NO 2067
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2067
gaagcttacc aactgaatag                                           20

<210> SEQ ID NO 2068
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2068
```
acactttcag ttgattaact                                       20

<210> SEQ ID NO 2069
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2069
accaacaatc aggatcctct                                       20

<210> SEQ ID NO 2070
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2070
ccattagcta gaaagaacga                                       20

<210> SEQ ID NO 2071
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2071
atgactaaaa gaggtacata                                       20

<210> SEQ ID NO 2072
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2072
cagaggatgt ttttgggcag                                       20

<210> SEQ ID NO 2073
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2073
ccaattttta atatcatttg                                       20

<210> SEQ ID NO 2074
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2074
gcaattcaaa tagcaagcca                                       20

<210> SEQ ID NO 2075
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 2075
gctgtgttcc aagtactagt                                               20

<210> SEQ ID NO 2076
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2076
caatcagtac ttgctgagct                                               20

<210> SEQ ID NO 2077
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2077
tttgtattca agcatttctc                                               20

<210> SEQ ID NO 2078
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2078
gatactagat tcagcctata                                               20

<210> SEQ ID NO 2079
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2079
aggtcacata gttcataagt                                               20

<210> SEQ ID NO 2080
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2080
aagtggcagc aatcatgaag                                               20

<210> SEQ ID NO 2081
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2081
tcttgtatac tggtttgaaa                                               20
```

<210> SEQ ID NO 2082
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2082
gagtcatagg gtgcttgctg					20

<210> SEQ ID NO 2083
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2083
ctatcagcaa gacctgggac					20

<210> SEQ ID NO 2084
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2084
gctagtttcc ttctattctc					20

<210> SEQ ID NO 2085
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2085
ttgcagttgg gaagtcatct					20

<210> SEQ ID NO 2086
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2086
atgttaaacc taactcttaa					20

<210> SEQ ID NO 2087
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2087
gcattcttgc cattttgatg					20

<210> SEQ ID NO 2088
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 2088
cccaattttc ccccacccct                                               20

<210> SEQ ID NO 2089
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2089
gaagatatga cagaggccag                                               20

<210> SEQ ID NO 2090
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2090
caccattagc caccagcaac                                               20

<210> SEQ ID NO 2091
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2091
tagggcttca gtagtccatc                                               20

<210> SEQ ID NO 2092
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2092
gatgcttgaa aattcaatta                                               20

<210> SEQ ID NO 2093
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2093
aaacaaaaca caaggtacgg                                               20

<210> SEQ ID NO 2094
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2094
aagcttacca actgaatagc                                               20

<210> SEQ ID NO 2095
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2095
tgcaattcta tatcagaaat                                              20

<210> SEQ ID NO 2096
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2096
aaaggaagtc tttctatgca                                              20

<210> SEQ ID NO 2097
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2097 aatacccat gaaatgagca                                               20

<210> SEQ ID NO 2098
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2098
ccttaatcac tgcaagactc                                              20

<210> SEQ ID NO 2099
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2099
agttatctat cctgtgtcta                                              20

<210> SEQ ID NO 2100
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2100
aaatctggga gctattcagg                                              20

<210> SEQ ID NO 2101
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2101
```
tgtagtacaa atctttcctt 20

<210> SEQ ID NO 2102
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2102
tcattctaaa acaaatcaag 20

<210> SEQ ID NO 2103
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2103
tgatgtacac attccaattt 20

<210> SEQ ID NO 2104
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2104
tcatggtagc tgttatcaag 20

<210> SEQ ID NO 2105
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2105
aggcaaagag ttaagatggg 20

<210> SEQ ID NO 2106
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2106
ttcttacaaa acattttccc 20

<210> SEQ ID NO 2107
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2107
gctccatgat ggaaattcag 20

<210> SEQ ID NO 2108
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 2108
ttttaaccca aagttaacaa                                                  20

<210> SEQ ID NO 2109
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2109
tagagcctcg ctattagaga                                                  20

<210> SEQ ID NO 2110
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2110
gaaaagatcc attgggctcc                                                  20

<210> SEQ ID NO 2111
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2111
gtaaagctct tacatctcct                                                  20

<210> SEQ ID NO 2112
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2112
tcaaatcacc tacgatgact                                                  20

<210> SEQ ID NO 2113
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2113
ccccaaataa gtaataaaca                                                  20

<210> SEQ ID NO 2114
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2114
ttgttgaaca gcagtgcact                                                  20
```

<210> SEQ ID NO 2115
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2115
cttgcagaca atgttttgct        20

<210> SEQ ID NO 2116
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2116
ctagcaggaa ccagctatga        20

<210> SEQ ID NO 2117
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2117
gacattagat aggattcctg        20

<210> SEQ ID NO 2118
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2118
tttcctagtt taaaaaacag        20

<210> SEQ ID NO 2119
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2119
caactaatta acagaaaaaa        20

<210> SEQ ID NO 2120
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2120
gatgctgaca acaccctgtt        20

<210> SEQ ID NO 2121
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 2121
atctatatca ggagaaaata                                           20

<210> SEQ ID NO 2122
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2122
cttggcaaca ttacatgttc                                           20

<210> SEQ ID NO 2123
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2123
atcaagtaag aagagggcca                                           20

<210> SEQ ID NO 2124
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2124
ccctttgaga agaaattact                                           20

<210> SEQ ID NO 2125
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2125
agataacatt gctaagtaaa                                           20

<210> SEQ ID NO 2126
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2126
atcaaagaat tattctccag                                           20

<210> SEQ ID NO 2127
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2127
attttgtaca ccaaagagaa                                           20

```
<210> SEQ ID NO 2128
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2128
aacaattcag taatatcagc                                              20

<210> SEQ ID NO 2129
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2129
tacctgagca tctttccttc                                              20

<210> SEQ ID NO 2130
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2130
catgctttca ccttatcttt                                              20

<210> SEQ ID NO 2131
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2131
ctatagatgg caagaggacc                                              20

<210> SEQ ID NO 2132
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2132
atcatgaata cagctttctg                                              20

<210> SEQ ID NO 2133
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2133
agaaaatccc aatagattca                                              20

<210> SEQ ID NO 2134
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 2134
tctatcttca gtggtaatag                                              20

<210> SEQ ID NO 2135
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2135
actaacaatt caggcagcca                                              20

<210> SEQ ID NO 2136
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2136
gataagtttc taaaagttta                                              20

<210> SEQ ID NO 2137
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2137
tgtgaattca gtacaagaat                                              20

<210> SEQ ID NO 2138
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2138
gtttctgcaa aggcagaata                                              20

<210> SEQ ID NO 2139
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2139
```
gaacaacaca actctttaca                                              20

<210> SEQ ID NO 2140
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2140
cacacattac tctgagtaga                                              20

<210> SEQ ID NO 2141
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2141
tgaccccctt ctcccagctg                                              20

<210> SEQ ID NO 2142
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2142
tctctgagta tctttgtcct                                              20

<210> SEQ ID NO 2143
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2143
tactcaaatt gagattcaaa                                              20

<210> SEQ ID NO 2144
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2144
ttgcaattct atatcagaaa                                              20

<210> SEQ ID NO 2145
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2145
catcagatgt tcatctcttc                                              20

<210> SEQ ID NO 2146
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 2146
attctccaga catttctgat                                              20

<210> SEQ ID NO 2147
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2147
tattctccag acatttctga                                              20

<210> SEQ ID NO 2148
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2148
tatgtgatct atatcaggag                                              20

<210> SEQ ID NO 2149
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2149
agagggccat ctcaggttac                                              20

<210> SEQ ID NO 2150
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2150
gtacaaatct ttccttcaat                                              20

<210> SEQ ID NO 2151
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2151
agatgttcat ctcttcacaa                                              20

<210> SEQ ID NO 2152
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 2152
tcagatgttc atctcttcac                                                    20

<210> SEQ ID NO 2153
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2153
atcagatgtt catctcttca                                                    20

<210> SEQ ID NO 2154
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2154
agcctccatt cctttgtgac                                                    20

<210> SEQ ID NO 2155
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2155
gagcctccat tcctttgtga                                                    20
```